US012503475B2

(12) United States Patent
Lefker et al.

(10) Patent No.: US 12,503,475 B2
(45) Date of Patent: Dec. 23, 2025

(54) BICYCLIC-HETEROCYCLE DERIVATIVES AND THEIR USES AS OREXIN-2 RECEPTOR AGONISTS

(71) Applicant: Centessa Pharmaceuticals (UK) Limited, Altrincham (GB)

(72) Inventors: Bruce Lefker, Swampscott, MA (US); Karl Gibson, Sandwich (GB); Matthew Spendiff, Cambridge (GB); Paul Humphries, Santa Clara, CA (US); Sarah Bucknell, Cambridge (GB); Wojciech Zawodny, Cambridge (GB); Roderick Alan Porter, Hertfordshire (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 429 days.

(21) Appl. No.: 18/024,216

(22) PCT Filed: Sep. 3, 2021

(86) PCT No.: PCT/US2021/049021

§ 371 (c)(1),
(2) Date: Mar. 1, 2023

(87) PCT Pub. No.: WO2022/051596

PCT Pub. Date: Mar. 10, 2022

(65) Prior Publication Data

US 2023/0271973 A1 Aug. 31, 2023

Related U.S. Application Data

(60) Provisional application No. 63/074,216, filed on Sep. 3, 2020.

(51) Int. Cl.

| | |
|---|---|
| ***C07D 487/10*** | (2006.01) |
| ***C07D 209/54*** | (2006.01) |
| ***C07D 221/20*** | (2006.01) |
| ***C07D 403/06*** | (2006.01) |
| ***C07D 405/06*** | (2006.01) |
| ***C07D 405/14*** | (2006.01) |
| ***C07D 413/06*** | (2006.01) |

(52) U.S. Cl.

CPC ......... *C07D 487/10* (2013.01); *C07D 209/54* (2013.01); *C07D 221/20* (2013.01); *C07D 403/06* (2013.01); *C07D 405/06* (2013.01); *C07D 405/14* (2013.01); *C07D 413/06* (2013.01)

(58) Field of Classification Search

CPC .. C07D 487/10; C07D 209/54; C07D 221/20; C07D 403/06; C07D 405/06; C07D 405/14; C07D 413/06; C07D 209/02

See application file for complete search history.

(56) References Cited

U.S. PATENT DOCUMENTS

| | | | |
|---|---|---|---|
| 4,522,811 | A | 6/1985 | Eppstein et al. |
| 5,763,263 | A | 6/1998 | Dehlinger |
| 8,871,794 | B2 | 10/2014 | Yanagisawa |
| 2010/0074863 | A1 | 3/2010 | Or et al. |
| 2020/0255403 | A1 | 8/2020 | Bogen et al. |
| 2021/0155636 | A1 | 5/2021 | Pennington et al. |
| 2023/0331720 | A1 | 10/2023 | Lefker et al. |
| 2024/0239744 | A1 | 7/2024 | Christopher |
| 2024/0360175 | A1 | 10/2024 | O'Boyle et al. |

(Continued)

FOREIGN PATENT DOCUMENTS

| | | | |
|---|---|---|---|
| WO | WO-2008076415 | A1 | 6/2008 |
| WO | WO-2008128121 | A1 | 10/2008 |
| WO | WO-2009070689 | A1 | 6/2009 |

(Continued)

OTHER PUBLICATIONS

Chemical Abstracts Service. CAS Registry: 70693-62-8, PubChem SID: 117687804. ABBLIS Chemicals: pp. 1-5. STN Entry Date Apr. 12, 2011. Retrieved Nov. 7, 2024. Retrieved from: https://pubchem.ncbi.nlm.nih.gov/substance/117687804.

(Continued)

*Primary Examiner* — Laura L Stockton
(74) *Attorney, Agent, or Firm* — WILSON SONSINI GOODRICH & ROSATI

(57) ABSTRACT

The present disclosure relates to compounds of Formula (I'):

(I)

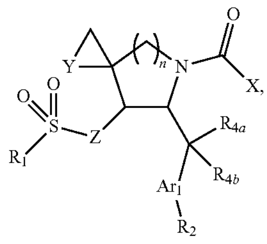

and to their prodrugs, pharmaceutically acceptable salts, pharmaceutical compositions, methods of use, and methods for their preparation. The compounds disclosed herein are useful for modulating orexin receptor activity and may be used in the treatment of disorders in which orexin receptor activity is implicated, such as narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anaesthesia.

20 Claims, No Drawings

(56) References Cited

U.S. PATENT DOCUMENTS

2025/0100968 A1 3/2025 Ott et al.

FOREIGN PATENT DOCUMENTS

| | | | |
|---|---|---|---|
| WO | WO-2011006960 | A1 | 1/2011 |
| WO | WO-2011073376 | A1 | 6/2011 |
| WO | WO-2012117219 | A1 | 9/2012 |
| WO | WO-2013052845 | A1 | 4/2013 |
| WO | WO-2013092893 | A1 | 6/2013 |
| WO | WO-2015078949 | A1 | 6/2015 |
| WO | WO-2016021629 | A1 | 2/2016 |
| WO | WO-2016022464 | A1 | 2/2016 |
| WO | WO-2017135306 | A1 | 8/2017 |
| WO | WO-2018164191 | A1 | 9/2018 |
| WO | WO-2018164192 | A1 | 9/2018 |
| WO | WO-2019027058 | A1 | 2/2019 |
| WO | WO-2020004536 | A1 | 1/2020 |
| WO | WO-2020122092 | A1 | 6/2020 |
| WO | WO-2020122093 | A1 | 6/2020 |
| WO | WO-2020158958 | A1 | 8/2020 |
| WO | WO-2020167706 | A1 | 8/2020 |
| WO | WO-2021048821 | A1 | 3/2021 |
| WO | WO-2021048822 | A1 | 3/2021 |
| WO | WO-2021065893 | A1 | 4/2021 |
| WO | WO-2021107023 | A1 | 6/2021 |
| WO | WO-2021108628 | A1 | 6/2021 |
| WO | WO-2021137982 | A1 | 7/2021 |
| WO | WO-2022051583 | A1 | 3/2022 |
| WO | WO-2022051596 | A1 | 3/2022 |
| WO | WO-2022207935 | A1 | 10/2022 |
| WO | WO-2023017180 | A1 | 2/2023 |
| WO | WO-2023167865 | A1 | 9/2023 |
| WO | WO-2023167925 | A1 | 9/2023 |

OTHER PUBLICATIONS

Li, Kangnan. et al. Diastereoselective and Enantiospecific Synthesis of 1,3-Diamines via 2-Azaallyl Anion Benzylic Ring-Opening of Aziridines. Organic Letters 19(16):4239-4242 (2017).

Tanaka, Kouichi. et al. Reductive Amination of Ketonic Compounds Catalyzed by Cp*Ir(III) Complexes Bearing a Picolinamidato Ligand. The Journal of Organic Chemistry 84(17):10962-10977 (2019).

Baykal, S. et al. Decreased serum orexin A levels in drug-naive children with attention deficit and hyperactivity disorder. Neurol Sci. Mar. 2019;40(3):593-602. doi: 10.1007/s10072-018-3692-8. Epub Jan. 7, 2019.

Black, S.W. et al. Challenges in the development of therapeutics for narcolepsy. Prog. Neurobiol., 2017; 152:89-113.

Boss, C. et. al. Orexin research: patent news from 2016. Expert Opinion on Therapeutic Patents, vol. 27, No. 10, Jun. 28, 2017, pp. 1123-1133.

Calva, C.B. et al. Intranasal administration of orexin peptides: Mechanisms and therapeutic potential for age-related cognitive dysfunction. Brain Res. Mar. 15, 2020;1731:145921. doi: 10.1016/j.brainres.2018.08.024. Epub Aug. 24, 2018; 9 pages.

Cheong, R.Y. et al. The Role of Hypothalamic Pathology for Non-Motor Features of Huntington's Disease. J Huntingtons Dis. 2019;8(4):375-391. doi: 10.3233/JHD-190372.

Database STN, CAS, File Registry, RN 1422063-50-0, "Methanesulfonamide, N-[(2R,3S)-2-(phenylmethyl)-3-pyrrolidinyl]-, rel-" (CA Index Name), Supplier WuXi AppTec Co., Ltd. American Chemical Society, CAS; entered STN: Feb. 28, 2013; 3 printed pages.

De Lecea, L. et al. The hypocretins: hypothalamus-specific peptides with neuroexcitatory activity. Proc Natl Acad Sci USA. Jan. 1998;95:322-7.

Funato, H. et al. Enhanced orexin receptor-2 signaling prevents diet-induced obesity and improves leptin sensitivity. Cell Metab. Jan. 7, 2009;9(1):64-76. doi: 10.1016/j.cmet.2008.10.010.

Hara, J. et al. Genetic ablation of orexin neurons in mice results in narcolepsy, hypophagia, and obesity. Neuron. May 2001;30(2):345-54. doi: 10.1016/s0896-6273(01)00293-8.

Hasegawa, E. et al. Orexin neurons suppress narcolepsy via 2 distinct efferent pathways. J Clin Invest. Feb. 2014;124(2):604-16. doi: 10.1172/JCI71017. Epub Jan. 2, 2014.

Irukayama-Tomobe, Y. et al. Nonpeptide orexin type-2 receptor agonist ameliorates narcolepsy-cataplexy symptoms in mouse models. PNAS, May 30, 2017;114(22):5731-6.

Kelz, M.B. et al. An essential role for orexins in emergence from general anesthesia. Proc Natl Acad Sci U S A. Jan. 29, 2008;105(4):1309-14. doi: 10.1073/pnas.0707146105. Epub Jan. 14, 2008.

Liu, M.F. et al. Orexin-A Exerts Neuroprotective Effects via OX1R in Parkinson's Disease. Front Neurosci. Nov. 15, 2018;12:835. doi: 10.3389/fnins.2018.00835; 18 pages.

Mahoney, C.E, et al. The neurobiological basis of narcolepsy. Nat Rev Neurosci. Feb. 2019;20(2):83-93. doi: 10.1038/s41583-018-0097-x.

Mieda, M.et al. Orexin peptides prevent cataplexy and improve wakefulness in an orexin neuron-ablated model of narcolepsy in mice. PNAS, Mar. 30, 2004;101:4649-54.

Mignot, E. et al. Sleeping with the hypothalamus: emerging therapeutic targets for sleep disorders. Nat Neurosci. Nov. 2002;5 Suppl:1071-5. doi: 10.1038/nn944.

Mignot, E. Narcolepsy: genetics, immunology, and pathophysiology. In: Kryger M, Roth T, Dement WC, eds. Principles and Practice of Sleep Medicine. 6th ed. Philadelphia, PA: Elsevier; 2017; Chapter 89, pp. 855-872.e7.

Mochizuki, T. et al. Orexin receptor 2 expression in the posterior hypothalamus rescues sleepiness in narcoleptic mice. Proc Natl Acad Sci U S A. Mar. 15, 2011;108(11):4471-6. doi: 10.1073/pnas.1012456108. Epub Feb. 28, 2011.

Modi, H.R., et al. Intranasal post-cardiac arrest treatment with orexin-A facilitates arousal from coma and ameliorates neuroinflammation. PLoS One. Sep. 28, 2017;12(9):e0182707. doi: 10.1371/journal.pone.0182707; 20 pages.

Nishino, S. et al. Hypocretin (orexin) deficiency in human narcolepsy. Lancet. Jan. 1, 2000;355(9197):39-40. doi: 10.1016/S0140-6736(99)05582-8.

Pallais, J.P. et al. Orexin/hypocretinin in multiple sclerosis and experimental autoimmune encephalomyelitis. Neural Regen Res. Jun. 2020;15(6):1039-1040. doi: 10.4103/1673-5374.270310.

Patel, V.H. et al. Functional cardiac orexin receptors: role of orexin-B/orexin 2 receptor in myocardial protection. Clin Sci (Lond). Dec. 13, 20183;132(24):2547-2564. doi: 10.1042/CS20180150.

Peyron, R. et al. Functional imaging of brain responses to pain. A review and meta-analysis (2000). Neurophysiol Clin. Oct. 2000;30(5):263-88. doi: 10.1016/s0987-7053(00)00227-6.

Sakurai, T. et al. Orexins and orexin receptors: a family of hypothalamic neuropeptides and G protein-coupled receptors that regulate feeding behavior. Cell, Feb. 20, 1998;92:573-585.

Tabuchi, S. et al. Conditional ablation of orexin/hypocretin neurons: a new mouse model for the study of narcolepsy and orexin system function. J. Neurosci., May 7, 2014;34(19):6495-6509.

Thannickal, T.C. et al. Reduced number of hypocretin neurons in human narcolepsy. Neuron. Sep. 2000;27(3):469-74. doi: 10.1016/s0896-6273(00)00058-1.

Thomasy, H.E. et al. Hypocretin Mediates Sleep and Wake Disturbances in a Mouse Model of Traumatic Brain Injury. J Neurotrauma. Mar. 1, 2019;36(5):802-814. doi: 10.1089/neu.2018.5810. Epub Oct. 3, 2018.

Um, Y.H. and Lim, H.K. Orexin and Alzheimer's Disease: A New Perspective. Psychiatry Investig. Jul. 2020;17(7):621-626. doi: 10.30773/pi.2020.0136. Epub Jun. 11, 2020.

Wei, W, et al. Orexin regulates bone remodeling via a dominant positive central action and a subordinate negative peripheral action. Cell Metab. Jun. 3, 2014;19(6):927-40. doi: 10.1016/j.cmet.2014.03.016. Epub May 1, 2014.

Yukitake, H. et al. TAK-925, an orexin 2 receptor-selective agonist, shows robust wake-promoting effects in mice. Pharmacol Biochem Behav, 2019;187:172794, 10 pages.

PCT/EP2022/058817 International Search Report and Written Opinion dated Aug. 3, 2022.

(56) References Cited

OTHER PUBLICATIONS

PCT/US2021/049003 International Search Report and Written Opinion dated Nov. 11, 2021.
PCT/US2021/049021 International Search Report and Written Opinion dated Nov. 11, 2021.
PCT/US2023/014139 International Search Report and Written Opinion dated May 30, 2023.
PCT/US2023/014275 International Search Report and Written Opinion dated Jun. 15, 2023.

BICYCLIC-HETEROCYCLE DERIVATIVES AND THEIR USES AS OREXIN-2 RECEPTOR AGONISTS

RELATED APPLICATIONS

This application is a U.S. National Phase Application, filed under U.S.C. § 371 (c), of International Application No. PCT/US2021/049021, filed Sep. 3, 2021, which claims priority to and benefit of U.S. Provisional Application No. 63/074,216, filed Sep. 3, 2020, both of which are incorporated herein by reference in their entirety.

BACKGROUND

The present disclosure relates to small molecule, potent agonists of the orexin-2 receptor (OX2R), designed for the treatment of narcolepsy and other disorders associated with orexin insufficiency and/or excessive sleepiness. Narcolepsy afflicts 1 in 2000 individuals worldwide. Onset may occur during adolescence for a lifelong duration and debilitating impact on quality of life. Narcolepsy Type 1 (NT1) is caused by the loss of neurons in the brain which produce orexin neuropeptides. There is no known cure, and currently approved treatments are symptomatic. Thus, development of pharmacotherapeutics to restore lost orexin signaling is critically important for treatment of the root cause of NT1.

In narcolepsy Type 1 (NT1), the sole population of neurons that produce orexin A and B (also known as hypocretin-1 and 2) peptides are destroyed by an immune mechanism which causes arousal state boundary dysfunction. Mouse models of narcolepsy type 1 recapitulate the loss of orexin neurons and the two cardinal symptoms observed in NT1 patients, specifically excessive daytime sleepiness and cataplexy. Common symptoms of narcolepsy type 1 and type 2 may include excessive daytime sleepiness, disturbed nighttime sleep, and inappropriately timed rapid-eye-movement (REM) sleep, as well as sleep paralysis and hypnopompic/hypnogogic hallucinations. Cataplexy is the intrusion of sudden, reversible loss of muscle tone (the atonia of REM sleep) into wakefulness in response to emotional stimuli and is pathognomonic of NT1.

The two predominant symptoms of narcolepsy type 1, excessive daytime sleepiness and cataplexy, can be reduced by re-activation of orexin neurotransmission at OX2R in mouse models. Reversal of cataplexy-like events and sleep/wake fragmentation has been achieved by genetic, focal restoration of OX2R signaling in the dorsal raphe nucleus of the pons and the tuberomammillary nucleus of the hypothalamus, respectively, in mice that otherwise lack orexin receptors in those regions. Intracerebroventricular (ICV) administration of orexin A (OXA) has been shown to increase time spent awake and decreases cataplexy-like behavior in orexin-neuron ablated mice. Selective OX2R agonist, YNT-185 administered intraperitoneally or ICV, modestly increases wakefulness in wild type (WT) and orexin ligand-deficient mice, and decrease sleep-onset REM periods and cataplexy-like events in an NT1 mouse model. Subcutaneous administration of the selective OX2R agonist TAK-925 modestly increased wakefulness in WT mice, but not in OX2R-knockout mice. Brain penetrant and stable OX2R agonists that are bioavailable after alternative routes of administration (including but not limited to oral, intranasal, transmucosal, and transdermal) and that bind with high affinity for potent excitation of arousal-state regulating neurons will provide an improvement to current therapeutics for patients with NT1. In fact, initial clinical studies reported with TAK-925 showed both substantial levels of increased wakefulness and trends for decreasing cataplexy in individuals with NT1. Activation of the OX1R is implicated in regulation of mood and reward behaviors, and may also contribute to arousal.

Orexin receptor agonists may also be useful in other indications marked by some degree of orexin neurodegeneration and excessive daytime sleepiness, such as Parkinson's disease, Alzheimer's disease, Huntington's disease, multiple sclerosis, and traumatic brain injury. Because stimulation of OX2R promotes wakefulness in orexin-intact animals, orexin receptor agonists may treat excessive daytime sleepiness in patients with normal levels of orexin, including narcolepsy type 2, idiopathic hypersomnia, or sleep apnea. Similarly, orexin receptor agonists may confer wake-promoting benefits in disorders of recurrent hypersomnia, such as Klein-Levin syndrome, or inappropriately timed sleep (i.e., circadian rhythm sleep disorders), such as delayed- or advanced-sleep phase disorder, shift work disorder, and jet lag disorder. The abnormal daytime sleepiness, sleep onset REM periods, and cataplexy-like symptoms of rare genetic disorders (e.g., ADCA-DN, Coffin-Lowry syndrome, Moebius syndrome, Norrie disease, Niemann-Pick disease type C, and Prader-Willi syndrome) could be alleviated with orexin receptor agonists. Other indications in which orexin receptor agonists have been suggested to confer benefits include attention deficit hyperactivity disorder, age-related cognitive dysfunction, metabolic syndrome and obesity, osteoporosis, cardiac failure, coma, and emergence from anesthesia.

The disclosure arises from a need to provide further compounds for the modulation of orexin receptor activity in the brain, including activation of the orexin-2 receptor, with improved therapeutic potential. In particular, compounds with improved physicochemical, pharmacological and pharmaceutical properties to existing compounds are desirable.

SUMMARY

In some aspects, the present disclosure provides a compound of Formula (I'''):

(I''')

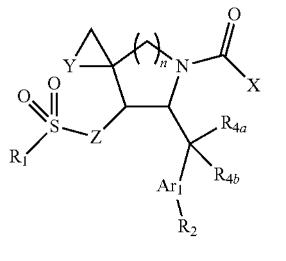

or a pharmaceutically acceptable salt thereof, wherein:

X is $—C(R_{X1})_3$, $—OR_{X2}$, or $—N(R_{X2})_2$;

Y is a $—(C(R_Y)_2)_m—$, $—O—(C(R_Y)_2)_m—$, $—(C(R_Y)_2)_m—O—$, $—N(R_Y)—(C(R_Y)_2)_m—$, or $—(C(R_Y)_2)_m—N(R_Y)—$;

Z is —O— or $—NR_Z—$;

each $R_{X1}$ independently is H, halogen, —CN, —OH, $—NH_2$, $—NH(C_1$-$C_6$ alkyl), $—N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, $C_3$-$C_6$ cycloalkyl, or 3- to 7-membered heterocycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—($CH_2$)$_2$—O$C_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

In some aspects, the present disclosure provides a compound obtainable by, or obtained by, a method for preparing a compound as described herein (e.g., a method comprising one or more steps described in Scheme 1).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-82).

In some aspects, the present disclosure provides a method of modulating orexin receptor activity (e.g., in vitro or in vivo), comprising contacting a cell with an effective amount of a compound of the present disclosure or a pharmaceutically acceptable salt thereof.

In some aspects, the present disclosure provides a method of modulating orexin-2 receptor activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating orexin receptor activity (e.g., in vitro or in vivo).

In some aspects, the present disclosure provides a compound of the present disclosure or a pharmaceutically acceptable salt thereof for use in modulating orexin-2 receptor activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for modulating orexin receptor activity (e.g., in vitro or in vivo).

In some aspects, the present disclosure provides use of a compound of the present disclosure or a pharmaceutically acceptable salt thereof in the manufacture of a medicament for modulating orexin-2 receptor activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

The present disclosure relates to spiroheterocyclic derivatives, prodrugs, and pharmaceutically acceptable salts thereof, which may modulate orexin-2 receptor activity and are accordingly useful in methods of treatment of the human or animal body. The present disclosure also relates to processes for the preparation of these compounds, to pharmaceutical compositions comprising them and to their use in the treatment of disorders in which the orexin-2 receptor is implicated, such as a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

Definitions

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_2$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, I-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a RM, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or $—O^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following scheme as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons. New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic scheme described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models used herein.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers, both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing the appearance of clinical symptoms of the state or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al, *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., EDMO (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4- toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient, the severity of the condition to be treated; the route of administration; the renal and hepatic function of the patient, and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic scheme described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure provides a compound of Formula (I'''):

(I''')

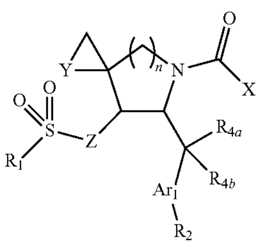

or a pharmaceutically acceptable salt thereof, wherein:

X is —$C(R_{X1})_3$, —$OR_{X2}$, or —$N(R_{X2})_2$;

Y is a —$(C(R_Y)_2)_m$—, —O—$(C(R_Y)_2)_m$—, —$(C(R_Y)_2)_m$—O—, —$N(R_Y)$—$(C(R_Y)_2)_m$—, or —$(C(R_Y)_2)_m$—$N(R_Y)$—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, $C_3$-$C_6$ cycloalkyl, or 3- to 7-membered heterocycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—$(CH_2)_2$—$OC_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

In some aspects, the present disclosure provides a compound of Formula (I''):

(I'')

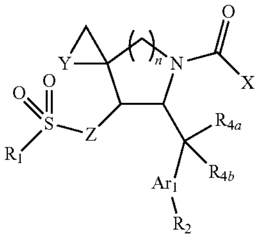

or a pharmaceutically acceptable salt thereof, wherein:

X is —$C(R_{X1})_3$, —$OR_{X2}$, or —$N(R_{X2})_2$;

Y is a —$(C(R_Y)_2)_m$—, —O—$(C(R_Y)_2)_m$—, —$(C(R_Y)_2)_m$—O—, —$N(R_Y)$—$(C(R_Y)_2)_m$—, or —$(C(R_Y)_2)_m$—$N(R_Y)$—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, or $C_3$-$C_6$ cycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—$(CH_2)_2$—$OC_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

In some aspects, the present disclosure provides a compound of Formula (I'):

(I')

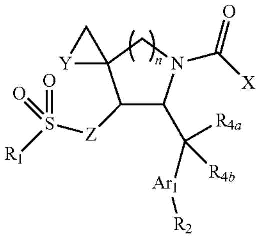

or a pharmaceutically acceptable salt thereof, wherein:

X is —$C(R_{X1})_3$, —$OR_{X2}$, or —$N(R_{X2})_2$;

Y is a —$(C(R_Y)_2)_m$—, —O—$(C(R_Y)_2)_m$—, —$(C(R_Y)_2)_m$—O—, —$N(R_Y)$—$(C(R_Y)_2)_m$—, or —$(C(R_Y)_2)_m$—$N(R_Y)$—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl; $Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —S($C_1$-$C_6$ alkyl), —S($C_1$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

In some aspects, the present disclosure provides a compound of Formula (I):

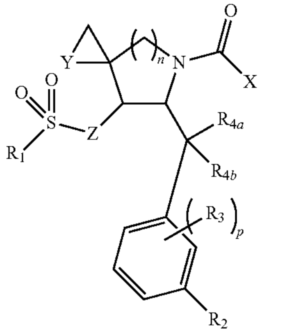

(I)

or a pharmaceutically acceptable salt thereof, wherein:

X is —$C(R_{X1})_3$, —$OR_{X2}$, or —$N(R_{X2})_2$;

Y is a —$(C(R_Y)_2)_m$—, —O—$(C(R_Y)_2)_m$—, —$(C(R_Y)_2)_m$—O—, —$N(R_Y)$—$(C(R_Y)_2)_m$—, or —$(C(R_Y)_2)_m$—$N(R_Y)$—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0, 1, 2, 3, or 4.

In some aspects, the present disclosure provides a compound of Formula (II):

(II)

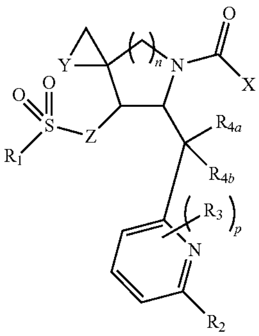

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —N$R_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0, 1, 2, or 3.

In some aspects, the present disclosure provides a compound of Formula (111):

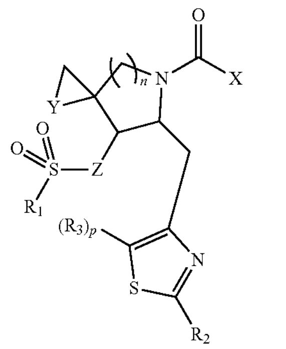

(III)

or a pharmaceutically acceptable salt thereof, wherein:

X is —$C(R_{X1})_3$, —$OR_{X2}$, or —$N(R_{X2})_2$;

Y is a —$(C(R_Y)_2)_m$—, —O—$(C(R_Y)_2)_m$—, —$(C(R_Y)_2)_m$—O—, —$N(R_Y)$—$(C(R_Y)_2)_m$—, or —$(C(R_Y)_2)_m$—$N(R_Y)$—,

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_2$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0 or 1.

In some aspects, the present disclosure provides a compound of Formula (I') or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some aspects, the present disclosure provides a compound of Formula (I') or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy.

In some aspects, the present disclosure provides a compound of Formula (I') or a pharmaceutically acceptable salt thereof, wherein:

Z is —NH—; and $R_1$ is $C_1$-$C_6$ alkyl.

In some aspects, the present disclosure provides a compound of Formula (I) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some aspects, the present disclosure provides a compound of Formula (I) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy.

In some aspects, the present disclosure provides a compound of Formula (I) or a pharmaceutically acceptable salt thereof, wherein:

Z is —NH—; and $R_1$ is $C_1$-$C_6$ alkyl.

In some aspects, the present disclosure provides a compound of Formula (II) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some aspects, the present disclosure provides a compound of Formula (U) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy.

In some aspects, the present disclosure provides a compound of Formula (II) or a pharmaceutically acceptable salt thereof, wherein:

Z is —NH—; and $R_1$ is $C_1$-$C_6$ alkyl.

In some aspects, the present disclosure provides a compound of Formula (III) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some aspects, the present disclosure provides a compound of Formula (III) or a pharmaceutically acceptable salt thereof, wherein:

Z is —$NR_Z$—; and $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy.

In some aspects, the present disclosure provides a compound of Formula (III) or a pharmaceutically acceptable salt thereof, wherein:

Z is —NH—; and $R_1$ is $C_1$-$C_6$ alkyl.

It is understood that, for a compound of Formula (I''), (I'), (I), (II), or (III), X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4b}$, n, m, or p can each be, where applicable, selected from the groups described herein, and any group described herein for any of X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4b}$, n, m, or p can be combined, where applicable, with any group described herein for one or more of the remainder of X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4a}$, n, m, or p.

In some embodiments, X is —C($R_{X1}$)$_3$, —$OR_{X2}$, or —N($R_{X2}$)$_2$.

In some embodiments, X is —$OR_{X2}$ or —N($R_{X2}$)$_2$.

In some embodiments, X is —C($R_{X1}$)$_3$. In some embodiments, X is —$OR_{X2}$. In some embodiments, X is —N($R_{X2}$)$_2$.

In some embodiments, X is

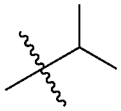, 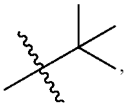, —O(methyl),

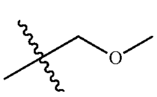, 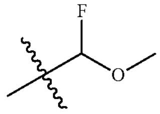, 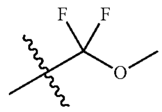,

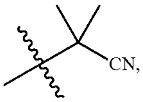, 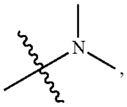, 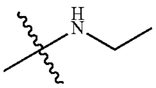, 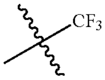,

-continued

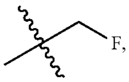 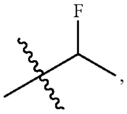, 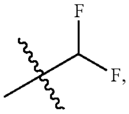 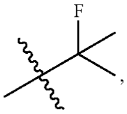,

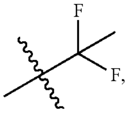 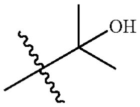, 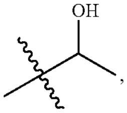, 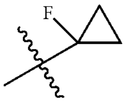,

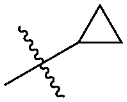, 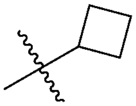, 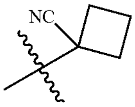,

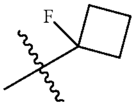, 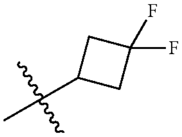, 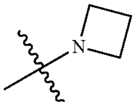,

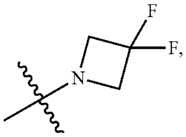 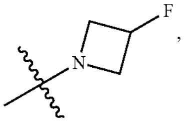, or 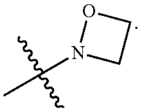

In some embodiments, X is

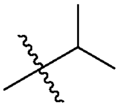 or 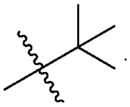

In some embodiments, X is —O(methyl).

In some embodiments, X is

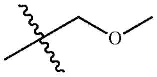, 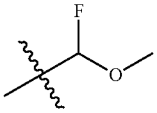, 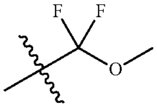, or 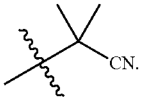

In some embodiments, X is

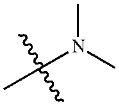 or 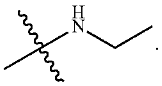

In some embodiments, X is

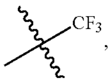, 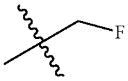, 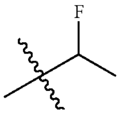, 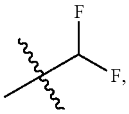

-continued

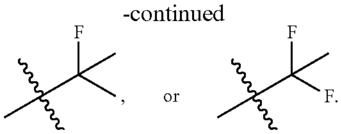

, or

In some embodiments, X is

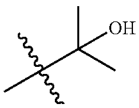 or 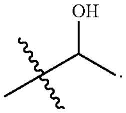

In some embodiments, X is

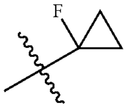 or 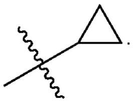

In some embodiments, X is

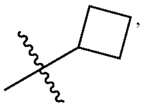, 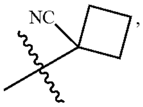, 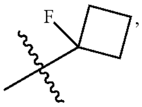, or 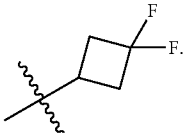

In some embodiments, X is

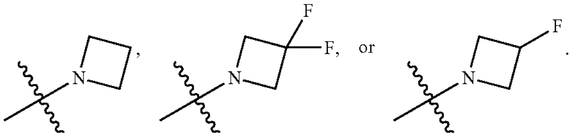 [SMILES: *N1CCC1 ; *N1CC(F)(F)C1 ; *N1CC(F)C1]

, or

In some embodiments, X is

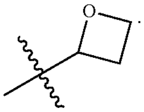 [SMILES: *C1CCO1]

In some embodiments, Y is $-(C(R_Y)_2)_m-$, $-O-(C(R_Y)_2)_m-$, $-(C(R_Y)_2)_m-O-$, $-N(R_Y)-(C(R_Y)_2)_m-$, or $-(C(R_Y)_2)_m-N(R_Y)-$.

In some embodiments, Y is $-O-(C(R_Y)_2)_m-$, $-(C(R_Y)_2)_m-O-$, $-N(R_Y)-(C(R_Y)_2)_m-$, or $-(C(R_Y)_2)_m-N(R_Y)-$.

In some embodiments, Y is $-(C(R_Y)_2)_m-$.

In some embodiments, Y is $-O-(C(R_Y)_2)_m-$ or $-(C(R_Y)_2)_m-O-$.

In some embodiments, Y is $-O-(C(R_Y)_2)_m-$. In some embodiments, Y is $-(C(R_Y)_2)_m-O-$.

In some embodiments, Y is —N($R_Y$)—(C($R_Y$)$_2$)$_m$— or —(C($R_Y$)$_2$)$_m$—N($R_Y$)—.

In some embodiments, Y is —N($R_Y$)—(C($R_Y$)$_2$)$_m$—. In some embodiments, Y is —(C($R_Y$)$_2$)$_m$—N($R_Y$)—.

In some embodiments, Y is —$CH_2$—, —$CF_2$—, —$CH_2$—O—, —O—$CH_2$—, —$CH_2$—NH—, —NH—$CH_2$—, —$CH_2$—N($CH_2CF_3$)—, or —N($CH_2$—$CF_3$)—$CH_2$—.

In some embodiments, Y is —$CH_2$—.

In some embodiments, Y is —$CH_2$—O— or —O—$CH_2$.

In some embodiments, Y is —$CH_2$—NH—, —NH—$CH_2$—, —$CH_2$—N($CH_2CF_3$)—, or —N($CH_2$—$CF_3$)—$CH_2$—.

In some embodiments, Y is —$CH_2$—NH— or —NH—$CH_2$—.

In some embodiments, Y is —$CH_2$—N($CH_2CF_3$)— or —N($CH_2$—$CF_3$)—$CH_2$—.

In some embodiments, Z is —O— or —$NR_Z$—.

In some embodiments, Z is —O—. In some embodiments, Z is —$NR_Z$—.

In some embodiments, Z is —NH—.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, $C_3$-$C_7$ cycloalkyl, or 3- to 7-membered heterocycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, or $C_3$-$C_7$ cycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_3$-$C_7$ cycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_3$-$C_7$ cycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_7$ cycloalkyl, or 3- to 7-membered heterocycloalkyl.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, or $C_3$-$C_7$ cycloalkyl.

In some embodiments, each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is H.

In some embodiments, each $R_{X1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is halogen, —CN, —OH, —$NH_2$, —NH($C_1$-$C_6$ alkyl), or —N($C_1$-$C_6$ alkyl)$_2$.

In some embodiments, each $R_{X1}$ independently is halogen.

In some embodiments, each $R_{X1}$ independently is F, Cl, Br, or I. In some embodiments, each $R_{X1}$ independently is F, Cl, or Br. In some embodiments, each $R_{X1}$ independently is F or Cl.

In some embodiments, each $R_{X1}$ independently is F. In some embodiments, each $R_{X1}$ independently is $C_1$. In some embodiments, each $R_{X1}$ independently is Br. In some embodiments, each $R_{X1}$ independently is I.

In some embodiments, each $R_{X1}$ independently is —CN.

In some embodiments, each $R_{X1}$ independently is —OH.

In some embodiments, each $R_{X1}$ independently is —$NH_2$, —NH($C_1$-$C_6$ alkyl), or —N($C_1$-$C_6$ alkyl)$_2$.

In some embodiments, each $R_{X1}$ independently is —$NH_2$.

In some embodiments, each $R_{X1}$ independently is —NH($C_1$-$C_6$ alkyl).

In some embodiments, each $R_{X1}$ independently is —NH(methyl). In some embodiments, each $R_{X1}$ independently is —NH(ethyl). In some embodiments, each $R_{X1}$ independently is —NH(propyl). In some embodiments, each $R_{X1}$ independently is —NH(butyl). In some embodiments, each $R_{X1}$ independently is —NH(pentyl). In some embodiments, each $R_{X1}$ independently is —NH(hexyl).

In some embodiments, each $R_{X1}$ independently is —N($C_1$-$C_6$ alkyl)$_2$.

In some embodiments, each $R_{X1}$ independently is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X1}$ independently is $C_1$-$C_6$ alkyl, $C_2$-$C_6$ alkenyl, or $C_2$-$C_6$ alkynyl.

In some embodiments, each $R_{X1}$ independently is $C_1$-$C_6$ alkyl.

In some embodiments, each $R_{X1}$ independently is methyl. In some embodiments, each $R_{X1}$ independently is ethyl. In some embodiments, each $R_{X1}$ independently is propyl. In some embodiments, each $R_{X1}$ independently is butyl. In some embodiments, each $R_{X1}$ independently is pentyl. In some embodiments, each $R_{X1}$ independently is hexyl. In some embodiments, each $R_{X1}$ independently is isopropyl. In some embodiments, each $R_{X1}$ independently is isobutyl. In some embodiments, each $R_{X1}$ independently is isopentyl. In some embodiments, each $R_{X1}$ independently is isohexyl. In some embodiments, each $R_{X1}$ independently is secbutyl. In some embodiments, each $R_{X1}$ independently is secpentyl. In some embodiments, each $R_{X1}$ independently is sechexyl. In some embodiments, each $R_{X1}$ independently is tertbutyl.

In some embodiments, each $R_{X1}$ independently is $C_2$-$C_6$ alkenyl.

In some embodiments, each $R_{X1}$ independently is $C_2$ alkenyl. In some embodiments, each $R_{X1}$ independently is $C_3$ alkenyl. In some embodiments, each $R_{X1}$ independently is $C_4$ alkenyl. In some embodiments, each $R_{X1}$ independently is $C_5$ alkenyl. In some embodiments, each $R_{X1}$ independently is $C_6$ alkenyl.

In some embodiments, each $R_{X1}$ independently is $C_2$-$C_6$ alkynyl.

In some embodiments, each $R_{X1}$ independently is $C_2$ alkynyl. In some embodiments, each $R_{X1}$ independently is $C_3$ alkynyl. In some embodiments, each $R_{X1}$ independently is $C_4$ alkynyl. In some embodiments, each $R_{X1}$ independently is $C_5$ alkynyl. In some embodiments, each $R_{X1}$ independently is $C_6$ alkynyl.

In some embodiments, each $R_{X1}$ independently is $C_1$-$C_6$ haloalkyl or $C_1$-$C_6$ alkoxy.

In some embodiments, each $R_{X1}$ independently is $C_1$-$C_6$ haloalkyl.

In some embodiments, each $R_{X1}$ independently is halomethyl. In some embodiments, each $R_{X1}$ independently is haloethyl. In some embodiments, each $R_{X1}$ independently is halopropyl. In some embodiments, each $R_{X1}$ independently is halobutyl. In some embodiments, each $R_{X1}$ independently is halopentyl. In some embodiments, each $R_{X1}$ independently is halohexyl.

In some embodiments, each $R_{X1}$ independently is $C_1$-$C_6$ alkoxy.

In some embodiments, each $R_{X1}$ independently is methoxy. In some embodiments, each $R_{X1}$ independently is ethoxy. In some embodiments, each $R_{X1}$ independently is propoxy. In some embodiments, each $R_{X1}$ independently is butoxy. In some embodiments, each $R_{X1}$ independently is pentoxy. In some embodiments, each $R_{X1}$ independently is hexoxy.

In some embodiments, each $R_{X1}$ independently is $C_1$-$C_6$ alkyl-$C_1$-$C_6$ alkoxy.

In some embodiments, each $R_{X1}$ independently is $C_1$ alkyl-$C_1$-$C_6$ alkoxy. In some embodiments, each $R_{X1}$ independently is $C_2$ alkyl-$C_1$-$C_6$ alkoxy. In some embodiments, each $R_{X1}$ independently is $C_3$ alkyl-$C_1$-$C_6$ alkoxy. In some embodiments, each $R_{X1}$ independently is $C_4$ alkyl-$C_1$-$C_6$ alkoxy. In some embodiments, each $R_{X1}$ independently is $C_5$ alkyl-$C_1$-$C_6$ alkoxy. In some embodiments, each $R_{X1}$ independently is $C_6$ alkyl-$C_1$-$C_6$ alkoxy.

In some embodiments, each $R_{X1}$ independently is $C_1$-$C_6$ alkyl-$C_1$ alkoxy. In some embodiments, each $R_{X1}$ independently is $C_1$-$C_6$ alkyl-$C_2$ alkoxy. In some embodiments, each $R_{X1}$ independently is $C_1$-$C_6$ alkyl-$C_3$ alkoxy. In some embodiments, each $R_{X1}$ independently is $C_1$-$C_6$ alkyl-$C_4$ alkoxy. In some embodiments, each $R_{X1}$ independently is $C_1$-$C_6$ alkyl-$C_5$ alkoxy. In some embodiments, each $R_{X1}$ independently is $C_1$-$C_6$ alkyl-$C_6$ alkoxy.

In some embodiments, each $R_{X1}$ independently is $C_3$-$C_6$ cycloalkyl.

In some embodiments, each $R_{X1}$ independently is $C_3$ cycloalkyl. In some embodiments, each $R_{X1}$ independently is $C_4$ cycloalkyl. In some embodiments, each $R_{X1}$ independently is $C_5$ cycloalkyl. In some embodiments, each $R_{X1}$ independently is $C_6$ cycloalkyl.

In some embodiments, each $R_{X1}$ independently is 3- to 7-membered heterocycloalkyl.

In some embodiments, each $R_{X1}$ independently is 3-membered heterocycloalkyl. In some embodiments, each $R_{X1}$ independently is 4-membered heterocycloalkyl. In some embodiments, each $R_{X1}$ independently is 5-membered heterocycloalkyl. In some embodiments, each $R_{X1}$ independently is 6-membered heterocycloalkyl. In some embodiments, each $R_{X1}$ independently is 7-membered heterocycloalkyl.

In some embodiments, two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$-$C_7$ cycloalkyl or 3- to 7-membered heterocycloalkyl.

In some embodiments, two $R_{X1}$ together with the atom to which they are attached form a $C_3$-$C_7$ cycloalkyl.

In some embodiments, two $R_{X1}$ together with the atom to which they are attached form a $C_3$-$C_7$ cycloalkyl optionally substituted with one or more oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$-$C_7$ cycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$-$C_7$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$ cycloalkyl.

In some embodiments, two $R_{X1}$ together with the atom to which they are attached form a $C_3$ cycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_3$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_4$ cycloalkyl.

In some embodiments, two $R_{X1}$ together with the atom to which they are attached form a $C_4$ cycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_4$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_5$ cycloalkyl.

In some embodiments, two $R_{X1}$ together with the atom to which they are attached form a $C_5$ cycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_5$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_6$ cycloalkyl.

In some embodiments, two $R_{X1}$ together with the atom to which they are attached form a $C_6$ cycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_6$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_7$ cycloalkyl.

In some embodiments, two $R_{X1}$ together with the atom to which they are attached form a $C_7$ cycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a $C_7$ cycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3- to 7-membered heterocycloalkyl.

In some embodiments, two $R_{X1}$ together with the atom to which they are attached form a 3- to 7-membered heterocycloalkyl optionally substituted with one or more oxo, halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3- to 7-membered heterocycloalkyl substituted with one or more oxo, halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3- to 7-membered heterocycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3- to 7-membered heterocycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3-membered heterocycloalkyl.

In some embodiments, two $R_{X1}$ together with the atom to which they are attached form a 3-membered heterocycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 3-membered heterocycloalkyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form an oxetanyl.

In some embodiments, two $R_{X1}$ together with the atom to which they are attached form an oxetanyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form an oxetanyl substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 4-membered heterocycloalkyl.

In some embodiments, two $R_{X1}$ together with the atom to which they are attached form a 4-membered heterocycloalkyl optionally substituted with one or more halogen, —CN, —OH, —NH$_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 4-membered heterocycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 5-membered heterocycloalkyl.

In some embodiments, two $R_{X1}$ together with the atom to which they are attached form a 5-membered heterocycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 5-membered heterocycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 6-membered heterocycloalkyl.

In some embodiments, two $R_{X1}$ together with the atom to which they are attached form a 6-membered heterocycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 6-membered heterocycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 7-membered heterocycloalkyl.

In some embodiments, two $R_{X1}$ together with the atom to which they are attached form a 7-membered heterocycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X1}$ together with the atom to which they are attached form a 7-membered heterocycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_4$-$C_{10}$ cycloalkyl.

In some embodiments, three $R_{X1}$ together with the atom to which they are attached form a $C_4$-$C_{10}$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_4$-$C_{10}$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_4$ cycloalkyl.

In some embodiments, three $R_{X1}$ together with the atom to which they are attached form a $C_4$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_4$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_5$ cycloalkyl.

In some embodiments, three $R_{X1}$ together with the atom to which they are attached form a $C_5$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_5$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_6$ cycloalkyl.

In some embodiments, three $R_{X1}$ together with the atom to which they are attached form a $C_6$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_6$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_7$ cycloalkyl.

In some embodiments, three $R_{X1}$ together with the atom to which they are attached form a $C_7$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_7$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_8$ cycloalkyl.

In some embodiments, three $R_{X1}$ together with the atom to which they are attached form a $C_8$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_8$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_9$ cycloalkyl.

In some embodiments, three $R_{X1}$ together with the atom to which they are attached form a $C_9$ cycloalkyl optionally substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_9$ cycloalkyl substituted with one or more halogen, —CN, —OH, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_{10}$ cycloalkyl.

In some embodiments, three $R_{X1}$ together with the atom to which they are attached form a $C_{10}$ cycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, three $R_{X1}$ together with the atom to which they are attached form a $C_{10}$ cycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X2}$ independently is H, $C_1$-$C_6$ alkyl, $C_2$-$C_6$ alkenyl, $C_2$-$C_6$ alkynyl, or $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X2}$ independently is H, $C_1$-$C_6$ alkyl, $C_2$-$C_6$ alkenyl, $C_2$-$C_6$ alkynyl, $C_1$-$C_6$ haloalkyl, or two $R_{X2}$ together with the atom to which they are attached form a 3-to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is H, $C_1$-$C_6$ alkyl, $C_2$-$C_6$ alkenyl, $C_2$-$C_6$ alkynyl, or $C_1$-$C_6$ haloalkyl.

In some embodiments, each $R_{X2}$ independently is H.

In some embodiments, each $R_{X2}$ independently is $C_1$-$C_6$ alkyl, $C_2$-$C_6$ alkenyl, $C_2$-$C_6$ alkynyl, or $C_1$-$C_6$ haloalkyl.

In some embodiments, each $R_{X2}$ independently is $C_1$-$C_6$ alkyl, $C_2$-$C_6$ alkenyl, $C_2$-$C_6$ alkynyl, or $C_1$-$C_6$ haloalkyl, wherein the alkyl, alkenyl, alkynyl, or haloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_1$-$C_6$ alkyl, $C_2$-$C_6$ alkenyl, or $C_2$-$C_6$ alkynyl.

In some embodiments, each $R_{X2}$ independently is $C_1$-$C_6$ alkyl, $C_2$-$C_6$ alkenyl, or $C_2$-$C_6$ alkynyl, wherein the alkyl, alkenyl, or alkynyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_1$-$C_6$ alkyl.

In some embodiments, each $R_{X2}$ independently is $C_1$-$C_6$ alkyl optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_1$-$C_6$ alkyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is methyl. In some embodiments, each $R_{X2}$ independently is ethyl. In some embodiments, each $R_{X2}$ independently is propyl. In some embodiments, each $R_{X2}$ independently is butyl. In some embodiments, each $R_{X2}$ independently is pentyl. In some embodiments, each $R_{X2}$ independently is hexyl. In some embodiments, each $R_{X2}$ independently is isopropyl. In some embodiments, each $R_{X2}$ independently is isobutyl. In some embodiments, each $R_{X2}$ independently is isopentyl. In some embodiments, each $R_{X2}$ independently is isohexyl. In some embodiments, each $R_{X2}$ independently is secbutyl. In some embodiments, each $R_{X2}$ independently is secpentyl. In some embodiments, each $R_{X2}$ independently is sechexyl. In some embodiments, each $R_{X2}$ independently is tertbutyl.

In some embodiments, each $R_{X2}$ independently is $C_2$-$C_6$ alkenyl.

In some embodiments, each $R_{X2}$ independently is $C_2$-$C_6$ alkenyl optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_2$-$C_6$ alkenyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_2$ alkenyl. In some embodiments, each $R_{X2}$ independently is $C_3$ alkenyl. In some embodiments, each $R_{X2}$ independently is $C_4$ alkenyl. In some embodiments, each $R_{X2}$ independently is $C_5$ alkenyl. In some embodiments, each $R_{X2}$ independently is $C_6$ alkenyl.

In some embodiments, each $R_{X2}$ independently is $C_2$-$C_6$ alkynyl.

In some embodiments, each $R_{X2}$ independently is $C_2$-$C_6$ alkynyl optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_2$-$C_6$ alkynyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_2$ alkynyl. In some embodiments, each $R_{X2}$ independently is $C_3$ alkynyl. In some embodiments, each $R_{X2}$ independently is $C_4$ alkynyl. In some embodiments, each $R_{X2}$ independently is $C_5$ alkynyl. In some embodiments, each $R_{X2}$ independently is $C_6$ alkynyl.

In some embodiments, each $R_{X2}$ independently is $C_1$-$C_6$ haloalkyl.

In some embodiments, each $R_{X2}$ independently is $C_1$-$C_6$ haloalkyl optionally substituted with one or more halogen, —CN, —OH, $C_1$-$C_6$, alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_1$-$C_6$ haloalkyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is halomethyl. In some embodiments, each $R_{X2}$ independently is haloethyl. In some embodiments, each $R_{X2}$ independently is halopropyl. In some embodiments, each $R_{X2}$ independently is halobutyl. In some embodiments, each $R_{X2}$ independently is halopentyl. In some embodiments, each $R_{X2}$ independently is halohexyl.

In some embodiments, each $R_{X2}$ independently is $C_3$-$C_6$ cycloalkyl.

In some embodiments, each $R_{X2}$ independently is $C_3$-$C_6$ cycloalkyl optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_3$-$C_6$ cycloalkyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is $C_3$ cycloalkyl. In some embodiments, each $R_{X2}$ independently is $C_4$ cycloalkyl. In some embodiments, each $R_{X2}$ independently is $C_5$ cycloalkyl. In some embodiments, each $R_{X2}$ independently is $C_6$ cycloalkyl.

In some embodiments, each $R_{X2}$ independently is a 3- to 7-membered heterocycloalkyl.

In some embodiments, each $R_{X2}$ independently is a 3- to 7-membered heterocycloalkyl optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is a 3- to 7-membered heterocycloalkyl substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl.

In some embodiments, each $R_{X2}$ independently is a 3-membered heterocycloalkyl. In some embodiments, each $R_{X2}$ independently is a 4-membered heterocycloalkyl. In some embodiments, each $R_{X2}$ independently is a 5-membered heterocycloalkyl. In some embodiments, each $R_{X2}$ independently is a 6-membered heterocycloalkyl. In some embodiments, each $R_{X2}$ independently is a 7-membered heterocycloalkyl.

In some embodiments, two $R_{X2}$ together with the atom to which they are attached form a 3- to 7-membered heterocycloalkyl.

In some embodiments, two $R_{X2}$ together with the atom to which they are attached form a 3- to 7-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 3- to 7-membered heterocycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 3-membered heterocycloalkyl.

In some embodiments, two $R_{X2}$ together with the atom to which they are attached form a 3-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 3-membered heterocycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 4-membered heterocycloalkyl.

In some embodiments, two $R_{X2}$ together with the atom to which they are attached form a 4-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 4-membered heterocycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 5-membered heterocycloalkyl.

In some embodiments, two $R_{X2}$ together with the atom to which they are attached form a 5-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 5-membered heterocycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 6-membered heterocycloalkyl.

In some embodiments, two $R_{X2}$ together with the atom to which they are attached form a 6-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 6-membered heterocycloalkyl substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 7-membered heterocycloalkyl.

In some embodiments, two $R_{X2}$ together with the atom to which they are attached form a 7-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, two $R_{X2}$ together with the atom to which they are attached form a 7-membered heterocycloalkyl substituted with one or more halogen, —CN, —OH, —$NH_2$—, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, each $R_Y$ independently is H.

In some embodiments, each $R_Y$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, each $R_Y$ independently is halogen, —CN, —OH, —$NH_2$, —NH($C_1$-$C_6$ alkyl), or —N($C_1$-$C_6$ alkyl)$_2$.

In some embodiments, each $R_Y$ independently is halogen.

In some embodiments, each $R_Y$ independently is F, Cl, Br, or I. In some embodiments, each $R_Y$ independently is F, Cl, or Br. In some embodiments, each $R_Y$ independently is F or Cl.

In some embodiments, each $R_Y$ independently is F. In some embodiments, each $R_Y$ independently is $C_1$. In some embodiments, each $R_Y$ independently is Br. In some embodiments, each $R_Y$ independently is 1.

In some embodiments, each $R_Y$ independently is —CN, —OH, —$NH_2$, —NH($C_1$-$C_6$ alkyl), or —N($C_1$-$C_6$ alkyl)$_2$.

In some embodiments, each $R_Y$ independently is —CN.

In some embodiments, each $R_Y$ independently is —OH.

In some embodiments, each $R_Y$ independently is —$NH_2$, —NH($C_1$-$C_6$ alkyl), or —N($C_1$-$C_6$ alkyl)$_2$.

In some embodiments, each $R_Y$ independently is —$NH_2$.

In some embodiments, each $R_Y$ independently is —NH ($C_1$-$C_6$ alkyl).

In some embodiments, each $R_Y$ independently is —NH (methyl). In some embodiments, each $R_Y$ independently is —NH(ethyl). In some embodiments, each $R_Y$ independently is —NH(propyl). In some embodiments, each $R_Y$ independently is —NH(butyl). In some embodiments, each $R_Y$ independently is —NH(pentyl). In some embodiments, each $R_Y$ independently is —NH(hexyl).

In some embodiments, each $R_Y$ independently is —N($C_1$-$C_6$ alkyl)$_2$.

In some embodiments, each $R_Y$ independently is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, each $R_Y$ independently is $C_1$-$C_6$ alkyl, $C_2$-$C_6$ alkenyl, or $C_2$-$C_6$ alkynyl.

In some embodiments, each $R_Y$ independently is $C_1$-$C_6$ alkyl.

In some embodiments, each $R_Y$ independently is methyl. In some embodiments, each $R_Y$ independently is ethyl. In some embodiments, each $R_Y$ independently is propyl. In some embodiments, each $R_Y$ independently is butyl. In some embodiments, each $R_Y$ independently is pentyl. In some embodiments, each $R_Y$ independently is hexyl. In some embodiments, each $R_Y$ independently is isopropyl. In some embodiments, each $R_Y$ independently is isobutyl. In some embodiments, each $R_Y$ independently is isopentyl. In some embodiments, each $R_Y$ independently is isohexyl. In some embodiments, each $R_Y$ independently is secbutyl. In some embodiments, each $R_Y$ independently is secpentyl. In some embodiments, each $R_Y$ independently is sechexyl. In some embodiments, each $R_Y$ independently is tertbutyl.

In some embodiments, each $R_Y$ independently is $C_2$-$C_6$ alkenyl.

In some embodiments, each $R_Y$ independently is $C_2$ alkenyl. In some embodiments, each $R_Y$ independently is $C_3$ alkenyl. In some embodiments, each $R_Y$ independently is $C_4$ alkenyl. In some embodiments, each $R_Y$ independently is $C_5$ alkenyl. In some embodiments, each $R_Y$ independently is $C_6$ alkenyl.

In some embodiments, each $R_Y$ independently is $C_2$-$C_6$ alkynyl.

In some embodiments, each $R_Y$ independently is $C_2$ alkynyl. In some embodiments, each $R_Y$ independently is $C_3$ alkynyl. In some embodiments, each $R_Y$ independently is $C_4$ alkynyl. In some embodiments, each $R_Y$ independently is $C_5$ alkynyl. In some embodiments, each $R_Y$ independently is $C_6$ alkynyl.

In some embodiments, each $R_Y$ independently is $C_1$-$C_6$ haloalkyl or $C_{1-6}$ alkoxy.

In some embodiments, each $R_Y$ independently is $C_1$-$C_6$ haloalkyl.

In some embodiments, each $R_Y$ independently is halomethyl. In some embodiments, each $R_Y$ independently is haloethyl. In some embodiments, each $R_Y$ independently is halopropyl. In some embodiments, each $R_Y$ independently is halobutyl. In some embodiments, each $R_Y$ independently is halopentyl. In some embodiments, each $R_Y$ independently is halohexyl.

In some embodiments, each $R_Y$ independently is $C_{1-6}$ alkoxy.

In some embodiments, each $R_Y$ independently is methoxy. In some embodiments, each $R_Y$ independently is ethoxy. In some embodiments, each $R_Y$ independently is propoxy. In some embodiments, each $R_Y$ independently is butoxy. In some embodiments, each $R_Y$ independently is pentoxy. In some embodiments, each $R_Y$ independently is hexoxy.

In some embodiments, each $R_Z$ is H, $C_1$-$C_6$ alkyl, $C_2$-$C_6$ alkenyl, $C_2$-$C_6$ alkynyl, or $C_1$-$C_6$ haloalkyl.

In some embodiments, $R_Z$ is H.

In some embodiments, $R_Z$ is $C_1$-$C_6$ alkyl, $C_2$-$C_6$ alkenyl, $C_2$-$C_6$ alkynyl, or $C_1$-$C_6$ haloalkyl.

In some embodiments, $R_Z$ is $C_1$-$C_6$ alkyl, $C_2$-$C_6$ alkenyl, or $C_2$-$C_6$ alkynyl.

In some embodiments, $R_Z$ is $C_1$-$C_6$ alkyl.

In some embodiments, $R_Z$ is methyl. In some embodiments, $R_Z$ is ethyl. In some embodiments, $R_Z$ is propyl. In some embodiments, $R_Z$ is butyl. In some embodiments, $R_Z$ is pentyl. In some embodiments, $R_Z$ is hexyl. In some embodiments, $R_Z$ is isopropyl. In some embodiments, $R_Z$ is isobutyl. In some embodiments, $R_Z$ is isopentyl. In some embodiments, $R_Z$ is isohexyl. In some embodiments, $R_Z$ is secbutyl. In some embodiments, $R_Z$ is secpentyl. In some embodiments, $R_Z$ is sechexyl. In some embodiments, $R_Z$ is tertbutyl.

In some embodiments, $R_Z$ is $C_2$-$C_6$ alkenyl.

In some embodiments, $R_Z$ is $C_2$ alkenyl. In some embodiments, $R_Z$ is $C_3$ alkenyl. In some embodiments, $R_Z$ is $C_4$ alkenyl. In some embodiments, $R_Z$ is $C_5$ alkenyl. In some embodiments, $R_Z$ is $C_6$ alkenyl.

In some embodiments, $R_Z$ is $C_2$-$C_6$ alkynyl.

In some embodiments, $R_Z$ is $C_2$ alkynyl. In some embodiments, $R_Z$ is $C_3$ alkynyl. In some embodiments, $R_Z$ is $C_4$ alkynyl. In some embodiments, $R_Z$ is $C_5$ alkynyl. In some embodiments, $R_Z$ is $C_6$ alkynyl.

In some embodiments, $R_Z$ is $C_1$-$C_6$ haloalkyl.

In some embodiments, $R_Z$ is halomethyl. In some embodiments, $R_Z$ is haloethyl. In some embodiments, $R_Z$ is halopropyl. In some embodiments, $R_Z$ is halobutyl. In some embodiments, $R_Z$ is halopentyl. In some embodiments, $R_Z$ is halohexyl.

In some embodiments, $Ar_1$ is $C_6$-$C_{10}$ aryl or 5- to 10-membered heteroaryl.

In some embodiments, $Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$.

In some embodiments, $Ar_1$ is $C_6$-$C_{10}$ aryl.

In some embodiments, $Ar_1$ is $C_6$-$C_{10}$ aryl optionally substituted with one or more $R_3$.

In some embodiments, $Ar_1$ is $C_6$-$C_{10}$ aryl (e.g., phenyl) substituted with one or more $R_3$.

In some embodiments, $Ar_1$ is $C_6$-$C_{10}$ aryl (e.g., phenyl) substituted with one $R_3$. In some embodiments, $Ar_1$ is $C_6$-$C_{10}$ aryl (e.g., phenyl) substituted with two $R_3$. In some embodiments, $Ar_1$ is $C_6$-$C_{10}$ aryl (e.g., phenyl) substituted with three $R_3$.

In some embodiments, $Ar_1$ is $C_6$ aryl (e.g., phenyl).

In some embodiments, $Ar_1$ is $C_6$ aryl (e.g., phenyl) optionally substituted with one or more $R_3$.

In some embodiments, $Ar_1$ is $C_6$ aryl (e.g., phenyl) substituted with one or more $R_3$.

In some embodiments, $Ar_1$ is $C_6$ aryl (e.g., phenyl) substituted with one $R_3$. In some embodiments, $Ar_1$ is $C_6$ aryl (e.g., phenyl) substituted with two $R_3$. In some embodiments, $Ar_1$ is $C_6$ aryl (e.g., phenyl) substituted with three $R_3$.

In some embodiments, $Ar_1$ is phenyl.

In some embodiments, $Ar_1$ is phenyl optionally substituted with one or more $R_3$.

In some embodiments, $Ar_1$ is phenyl substituted with one or more $R_3$.

In some embodiments, $Ar_1$ is phenyl substituted with one $R_3$. In some embodiments, $Ar_1$ is phenyl substituted with two $R_3$. In some embodiments, $Ar_1$ is phenyl substituted with three $R_3$.

In some embodiments, $Ar_1$ is phenyl optionally substituted with one or more halo (e.g., F, Cl, or Br).

In some embodiments, $Ar_1$ is phenyl substituted with one or more halo (e.g., F, Cl, or Br).

In some embodiments, $Ar_1$ is phenyl substituted with one halo (e.g., F, Cl, or Br). In some embodiments, $Ar_1$ is phenyl substituted with two halo (e.g., F, Cl, or Br). In some embodiments, $Ar_1$ is phenyl substituted with three halo (e.g., F, Cl, or Br).

In some embodiments, $Ar_1$ is $C_8$ aryl.

In some embodiments, $Ar_1$ is $C_8$ aryl optionally substituted with one or more $R_3$.

In some embodiments, $Ar_1$ is $C_8$ aryl (e.g., phenyl) substituted with one or more $R_3$.

In some embodiments, $Ar_1$ is $C_8$ aryl (e.g., phenyl) substituted with one $R_3$. In some embodiments, $Ar_1$ is $C_8$ aryl (e.g., phenyl) substituted with two $R_3$. In some embodiments, $Ar_1$ is $C_8$ aryl (e.g., phenyl) substituted with three $R_3$.

In some embodiments, $Ar_1$ is $C_{10}$ aryl.

In some embodiments, $Ar_1$ is $C_{10}$ aryl optionally substituted with one or more $R_3$.

In some embodiments, $Ar_1$ is $C_{10}$ aryl (e.g., phenyl) substituted with one or more $R_3$.

In some embodiments, $Ar_1$ is $C_{10}$ aryl (e.g., phenyl) substituted with one $R_3$. In some embodiments, $Ar_1$ is $C_{10}$ aryl (e.g., phenyl) substituted with two $R_3$. In some embodiments, $Ar_1$ is $C_{10}$ aryl (e.g., phenyl) substituted with three $R_3$.

In some embodiments, $Ar_1$ is 5- to 10-membered heteroaryl.

In some embodiments, $Ar_1$ is 5- to 10-membered heteroaryl optionally substituted with one or more $R_3$.

In some embodiments, $Ar_1$ is 5- to 10-membered heteroaryl substituted with one or more $R_3$.

In some embodiments, $Ar_1$ is 5- to 10-membered heteroaryl substituted with one $R_3$. In some embodiments, $Ar_1$ is 5- to 10-membered heteroaryl substituted with two $R_3$. In some embodiments, $Ar_1$ is 5- to 10-membered heteroaryl substituted with three $R_3$.

In some embodiments, $Ar_1$ is 5-membered heteroaryl.

In some embodiments, $Ar_1$ is 5-membered heteroaryl optionally substituted with one or more $R_3$.

In some embodiments, $Ar_1$ is 5-membered heteroaryl substituted with one or more $R_3$.

In some embodiments, $Ar_1$ is 5-membered heteroaryl substituted with one $R_3$. In some embodiments, $Ar_1$ is 5-membered heteroaryl substituted with two $R_3$. In some embodiments, $Ar_1$ is 5-membered heteroaryl substituted with three $R_3$.

In some embodiments, $Ar_1$ is thiazolyl.

In some embodiments, $Ar_1$ is thiazolyl optionally substituted with one or more $R_3$.

In some embodiments, $Ar_1$ is thiazolyl substituted with one or more $R_3$.

In some embodiments, $Ar_1$ is thiazolyl substituted with one $R_3$. In some embodiments, $Ar_1$ is thiazolyl substituted with two $R_3$. In some embodiments, $Ar_1$ is thiazolyl substituted with three $R_3$.

In some embodiments, $Ar_1$ is 6-membered heteroaryl.

In some embodiments, $Ar_1$ is 6-membered heteroaryl optionally substituted with one or more $R_3$.

In some embodiments, $Ar_1$ is 6-membered heteroaryl substituted with one or more $R_3$.

In some embodiments, $Ar_1$ is 6-membered heteroaryl substituted with one $R_3$. In some embodiments, $Ar_1$ is 6-membered heteroaryl substituted with two $R_3$. In some embodiments, $Ar_1$ is 6-membered heteroaryl substituted with three $R_3$.

In some embodiments, $Ar_1$ is pyridyl.

In some embodiments, $Ar_1$ is pyridyl optionally substituted with one or more $R_3$.

In some embodiments, $Ar_1$ is pyridyl substituted with one or more $R_3$.

In some embodiments, $Ar_1$ is pyridyl substituted with one $R_3$. In some embodiments, $Ar_1$ is pyridyl substituted with two $R_3$. In some embodiments, $Ar_1$ is pyridyl substituted with three $R_3$.

In some embodiments, $Ar_1$ is 7-membered heteroaryl.

In some embodiments, $Ar_1$ is 7-membered heteroaryl optionally substituted with one or more $R_3$.

In some embodiments, $Ar_1$ is 7-membered heteroaryl substituted with one or more $R_3$.

In some embodiments, $Ar_1$ is 7-membered heteroaryl substituted with one $R_3$. In some embodiments, $Ar_1$ is 7-membered heteroaryl substituted with two $R_3$. In some embodiments, $Ar_1$ is 7-membered heteroaryl substituted with three $R_3$.

In some embodiments, $Ar_1$ is 8-membered heteroaryl.

In some embodiments, $Ar_1$ is 8-membered heteroaryl optionally substituted with one or more $R_3$.

In some embodiments, $Ar_1$ is 8-membered heteroaryl substituted with one or more $R_3$.

In some embodiments, $Ar_1$ is 8-membered heteroaryl substituted with one $R_3$. In some embodiments, $Ar_1$ is 8-membered heteroaryl substituted with two $R_3$. In some embodiments, $Ar_1$ is 8-membered heteroaryl substituted with three $R_3$.

In some embodiments, $Ar_1$ is 9-membered heteroaryl.

In some embodiments, $Ar_1$ is 9-membered heteroaryl optionally substituted with one or more $R_3$.

In some embodiments, $Ar_1$ is 9-membered heteroaryl substituted with one or more $R_3$.

In some embodiments, $Ar_1$ is 9-membered heteroaryl substituted with one $R_3$. In some embodiments, $Ar_1$ is 9-membered heteroaryl substituted with two $R_3$. In some embodiments, $Ar_1$ is 9-membered heteroaryl substituted with three $R_3$.

In some embodiments, $Ar_1$ is 10-membered heteroaryl.

In some embodiments, $Ar_1$ is 10-membered heteroaryl optionally substituted with one or more $R_3$.

In some embodiments, $Ar_1$ is 10-membered heteroaryl substituted with one or more $R_3$.

In some embodiments, $Ar_1$ is 10-membered heteroaryl substituted with one $R_3$. In some embodiments, $Ar_1$ is 10-membered heteroaryl substituted with two $R_3$. In some embodiments, $Ar_1$ is 10-membered heteroaryl substituted with three $R_3$.

In some embodiments, $R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some embodiments, $R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), or —S($C_6$-$C_{10}$ aryl).

In some embodiments, $R_1$ is —$NH_2$, —NH($C_1$-$C_6$ alkyl), —N($C_1$-$C_6$ alkyl)$_2$, —S($C_1$-$C_6$ alkyl), or —S($C_6$-$C_{10}$ aryl).

In some embodiments, $R_1$ is —$NH_2$, —NH($C_1$-$C_6$ alkyl), or —N($C_1$-$C_6$ alkyl)$_2$, or —N($C_1$-$C_6$ alkyl)($C_3$-$C_{10}$ cycloalkyl).

In some embodiments, $R_1$ is —$NH_2$, —NH($C_1$-$C_6$ alkyl), or —N($C_1$-$C_6$ alkyl)$_2$.

In some embodiments, $R_1$ is —$NH_2$.

In some embodiments, $R_1$ is —NH($C_1$-$C_6$ alkyl).

In some embodiments, $R_1$ is —NH(methyl). In some embodiments, $R_1$ is —NH(ethyl). In some embodiments, $R_1$ is —NH(propyl). In some embodiments, $R_1$ is —NH(butyl). In some embodiments, $R_1$ is —NH(pentyl). In some embodiments, $R_1$ is —NH(hexyl).

In some embodiments, $R_1$ is —N($C_1$-$C_6$ alkyl)$_2$.

In some embodiments, $R_1$ is —N($C_1$-$C_6$ alkyl)($C_3$-$C_{10}$ cycloalkyl).

In some embodiments, $R_1$ is —N($C_1$-$C_6$ alkyl)($C_3$ cycloalkyl). In some embodiments, $R_1$ is —N($C_1$-$C_6$ alkyl)($C_4$ cycloalkyl). In some embodiments, $R_1$ is —N($C_1$-$C_6$ alkyl)($C_5$ cycloalkyl). In some embodiments, $R_1$ is —N($C_1$-$C_6$ alkyl)($C_6$ cycloalkyl). In some embodiments, $R_1$ is —N($C_1$-$C_6$ alkyl)($C_7$ cycloalkyl). In some embodiments, $R_1$ is —N($C_1$-$C_6$ alkyl)($C_8$ cycloalkyl). In some embodiments, $R_1$ is —N($C_1$-$C_6$ alkyl)($C_9$ cycloalkyl). In some embodiments, $R_1$ is —N($C_1$-$C_6$ alkyl)($C_{10}$ cycloalkyl).

In some embodiments, $R_1$ is —S($C_1$-$C_6$ alkyl) or —S($C_6$-$C_{10}$ aryl).

In some embodiments, $R_1$ is —S($C_1$-$C_6$ alkyl).

In some embodiments, $R_1$ is —S(methyl). In some embodiments, $R_1$ is —S(ethyl). In some embodiments, $R_1$ is —S(propyl). In some embodiments, $R_1$ is —S(butyl). In some embodiments, $R_1$ is —S(heptyl). In some embodiments, $R_1$ is —S(hexyl).

In some embodiments, $R_1$ is —S($C_6$-$C_{10}$ aryl).

In some embodiments, $R_1$ is —S($C_6$ aryl). In some embodiments, $R_1$ is —S($C_8$ aryl). In some embodiments, $R_1$ is —S($C_{10}$ aryl).

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, or alkynyl are optionally substituted with one or more $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, or alkynyl are substituted with one or more $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, or alkynyl are substituted with one $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, or alkynyl are substituted with two $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, wherein the alkyl, alkenyl, or alkynyl are substituted with three $R_{1S}$.

In some embodiments, $R_1$ is $C_1$-$C_6$ alkyl.

In some embodiments, $R_1$ is methyl. In some embodiments, $R_1$ is ethyl. In some embodiments, $R_1$ is propyl. In some embodiments, $R_1$ is butyl. In some embodiments, $R_1$ is pentyl. In some embodiments, $R_1$ is hexyl. In some embodiments, $R_1$ is isopropyl. In some embodiments, $R_1$ is isobutyl. In some embodiments, $R_1$ is isopentyl. In some embodiments, $R_1$ is isohexyl. In some embodiments, $R_1$ is secbutyl. In some embodiments, $R_1$ is secpentyl. In some embodiments, $R_1$ is sechexyl. In some embodiments, $R_1$ is tertbutyl.

In some embodiments, $R_1$ is $C_1$-$C_6$ alkyl optionally substituted with one or more $R_{1S}$.

In some embodiments, $R_1$ is $C_1$-$C_6$ alkyl substituted with one or more $R_{1S}$.

In some embodiments, $R_1$ is $C_1$-$C_6$ alkyl substituted with one $R_{1S}$.

In some embodiments, $R_1$ is $C_1$-$C_6$ alkyl substituted with two $R_{1S}$.

In some embodiments, $R_1$ is $C_1$-$C_6$ alkyl substituted with three $R_{1S}$.

In some embodiments, $R_1$ is $C_2$-$C_6$ alkenyl.

In some embodiments, $R_1$ is $C_2$ alkenyl. In some embodiments, $R_1$ is $C_3$ alkenyl. In some embodiments, $R_1$ is $C_4$ alkenyl. In some embodiments, $R_1$ is $C_5$ alkenyl. In some embodiments, $R_1$ is $C_6$ alkenyl.

In some embodiments, $R_1$ is $C_2$-$C_6$ alkenyl optionally substituted with one or more $R_{1S}$.

In some embodiments, $R_1$ is $C_2$-$C_6$ alkenyl substituted with one or more $R_{1S}$.

In some embodiments, $R_1$ is $C_2$-$C_6$ alkenyl substituted with one $R_{1S}$.

In some embodiments, $R_1$ is $C_2$-$C_6$ alkenyl substituted with two $R_{1S}$.

In some embodiments, $R_1$ is $C_2$-$C_6$ alkenyl substituted with three $R_{1S}$.

In some embodiments, $R_1$ is $C_2$-$C_6$ alkynyl.

In some embodiments, $R_1$ is $C_2$ alkynyl. In some embodiments, $R_1$ is $C_3$ alkynyl. In some embodiments, $R_1$ is $C_4$ alkynyl. In some embodiments, $R_1$ is $C_5$ alkynyl. In some embodiments, $R_1$ is $C_6$ alkynyl.

In some embodiments, $R_1$ is $C_2$-$C_6$ alkynyl optionally substituted with one or more $R_{1S}$.

In some embodiments, $R_1$ is $C_2$-$C_6$ alkynyl substituted with one or more $R_{1S}$.

In some embodiments, $R_1$ is $C_2$-$C_6$ alkynyl substituted with one $R_{1S}$.

In some embodiments, $R_1$ is $C_2$-$C_6$ alkynyl substituted with two $R_{1S}$.

In some embodiments, $R_1$ is $C_2$-$C_6$ alkynyl substituted with three $R_{1S}$.

In some embodiments, $R_1$ is $C_1$-$C_6$ haloalkyl.

In some embodiments, $R_1$ is halomethyl. In some embodiments, $R_1$ is haloethyl. In some embodiments, $R_1$ is halopropyl. In some embodiments, $R_1$ is halobutyl. In some embodiments, $R_1$ is halopentyl. In some embodiments, $R_1$ is halohexyl.

In some embodiments, $R_1$ is $C_1$-$C_6$ haloalkyl optionally substituted with one or more $R_{1S}$.

In some embodiments, $R_1$ is $C_1$-$C_6$ haloalkyl substituted with one or more $R_{1S}$.

In some embodiments, $R_1$ is $C_1$-$C_6$ haloalkyl substituted with one $R_{1S}$.

In some embodiments, $R_1$ is $C_1$-$C_6$ haloalkyl substituted with two $R_{1S}$.

In some embodiments, $R_1$ is $C_1$-$C_6$ haloalkyl substituted with three $R_{1S}$.

In some embodiments, $R_1$ is $C_1$-$C_6$ alkoxy.

In some embodiments, $R_1$ is methoxy. In some embodiments, $R_1$ is ethoxy. In some embodiments, $R_1$ is propoxy. In some embodiments, $R_1$ is butoxy. In some embodiments, $R_1$ is pentoxy. In some embodiments, $R_1$ is hexoxy.

In some embodiments, $R_1$ is $C_1$-$C_6$ alkoxy optionally substituted with one or more $R_{1S}$.

In some embodiments, $R_1$ is $C_1$-$C_6$ alkoxy substituted with one or more $R_{1S}$.

In some embodiments, $R_1$ is $C_1$-$C_6$ alkoxy substituted with one $R_{1S}$.

In some embodiments, $R_1$ is $C_1$-$C_6$ alkoxy substituted with two $R_{1S}$.

In some embodiments, $R_1$ is $C_1$-$C_6$ alkoxy substituted with three $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are optionally substituted with one or more $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with one or more $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with one $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with two $R_{1S}$.

In some embodiments, $R_1$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with three $R_{1S}$.

In some embodiments, $R_1$ is $C_6$-$C_{10}$ aryl.

In some embodiments, $R_1$ is $C_6$ aryl (e.g., phenyl). In some embodiments, $R_1$ is $C_8$ aryl. In some embodiments, $R_1$ is $C_{10}$ aryl.

In some embodiments, $R_1$ is $C_6$-$C_{10}$ aryl optionally substituted with one or more $R_{1S}$.

In some embodiments, $R_1$ is $C_6$-$C_{10}$ aryl substituted with one or more $R_{1S}$.

In some embodiments, $R_1$ is $C_6$-$C_{10}$ aryl substituted with one $R_{1S}$. In some embodiments, $R_1$ is $C_6$-$C_{10}$ aryl substituted with two $R_{1S}$. In some embodiments, $R_1$ is $C_6$-$C_{10}$ aryl substituted with three $R_{1S}$.

In some embodiments, $R_1$ is 5- to 10-membered heteroaryl.

In some embodiments, $R_1$ is 5-membered heteroaryl. In some embodiments, $R_1$ is 6-membered heteroaryl. In some embodiments, $R_1$ is 7-membered heteroaryl. In some embodiments, $R_1$ is 8-membered heteroaryl. In some embodiments, $R_1$ is 9-membered heteroaryl. In some embodiments, $R_1$ is 10-membered heteroaryl.

In some embodiments, $R_1$ is 5- to 10-membered heteroaryl optionally substituted with one or more $R_{1S}$.

In some embodiments, $R_1$ is 5- to 10-membered heteroaryl substituted with one or more $R_{1S}$.

In some embodiments, $R_1$ is 5- to 10-membered heteroaryl substituted with one $R_{1S}$. In some embodiments, $R_1$ is 5- to 10-membered heteroaryl substituted with two $R_{1S}$. In some embodiments, $R_1$ is 5- to 10-membered heteroaryl substituted with three $R_{1S}$.

In some embodiments, $R_1$ is $C_3$-$C_7$ cycloalkyl.

In some embodiments, $R_1$ is cyclopropyl. In some embodiments, $R_1$ is cyclobutyl. In some embodiments, $R_1$ is cyclopentyl. In some embodiments, $R_1$ is cyclohexyl. In some embodiments, $R_1$ is cycloheptyl.

In some embodiments, $R_1$ is $C_3$-$C_7$ cycloalkyl optionally substituted with one or more $R_{1S}$.

In some embodiments, $R_1$ is $C_3$-$C_7$ cycloalkyl substituted with one or more $R_{1S}$.

In some embodiments, $R_1$ is $C_3$-$C_7$ cycloalkyl substituted with one $R_{1S}$. In some embodiments, $R_1$ is $C_3$-$C_7$ cycloalkyl substituted with two $R_{1S}$. In some embodiments, $R_1$ is $C_3$-$C_7$ cycloalkyl substituted with three $R_{1S}$.

In some embodiments, $R_1$ is 3- to 7-membered heterocycloalkyl.

In some embodiments, $R_1$ is 3-membered heterocycloalkyl. In some embodiments, $R_1$ is 4-membered heterocycloalkyl. In some embodiments, $R_1$ is 5-membered heterocycloalkyl. In some embodiments, $R_1$ is 6-membered heterocycloalkyl. In some embodiments, $R_1$ is 7-membered heterocycloalkyl.

In some embodiments, $R_1$ is 3- to 7-membered heterocycloalkyl optionally substituted with one or more $R_{1S}$.

In some embodiments, $R_1$ is 3- to 7-membered heterocycloalkyl substituted with one or more $R_{1S}$.

In some embodiments, $R_1$ is 3- to 7-membered heterocycloalkyl substituted with one $R_{1S}$. In some embodiments, $R_1$ is 3- to 7-membered heterocycloalkyl substituted with two $R_{1S}$. In some embodiments, $R_1$ is 3- to 7-membered heterocycloalkyl substituted with three $R_{1S}$.

In some embodiments, when $R_1$ is heterocycloalkyl, $R_1$ is bonded via the nitrogen atom.

In some embodiments, $R_1$ is —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl).

In some embodiments, $R_1$ is —O—($C_6$-$C_{10}$ aryl).

In some embodiments, $R_1$ is —O—($C_6$ aryl). In some embodiments, $R_1$ is —O—($C_8$ aryl). In some embodiments, $R_1$ is —O—($C_{10}$ aryl).

In some embodiments, $R_1$ is —O-(5- to 10-membered heteroaryl).

In some embodiments, $R_1$ is —O-(5-membered heteroaryl). In some embodiments, $R_1$ is —O-(6-membered heteroaryl). In some embodiments, $R_1$ is —O-(7-membered heteroaryl). In some embodiments, $R_1$ is —O-(8-membered heteroaryl). In some embodiments, $R_1$ is —O-(9-membered heteroaryl). In some embodiments, $R_1$ is —O-(10-membered heteroaryl).

In some embodiments, $R_1$ is —O—($C_3$-$C_{10}$ cycloalkyl).

In some embodiments, $R_1$ is —O—($C_3$ cycloalkyl). In some embodiments, $R_1$ is —O—($C_4$ cycloalkyl). In some embodiments, $R_1$ is —O—($C_5$ cycloalkyl). In some embodiments, $R_1$ is —O—($C_6$ cycloalkyl). In some embodiments, $R_1$ is —O—($C_7$ cycloalkyl). In some embodiments, $R_1$ is —O—($C_8$ cycloalkyl). In some embodiments, $R_1$ is —O—($C_9$ cycloalkyl). In some embodiments, $R_1$ is —O—($C_{10}$ cycloalkyl).

In some embodiments, $R_1$ is —O-(3- to 7-membered heterocycloalkyl).

In some embodiments, $R_1$ is —O-(3-membered heterocycloalkyl). In some embodiments, $R_1$ is —O-(4-membered heterocycloalkyl). In some embodiments, $R_1$ is —O-(5-membered heterocycloalkyl). In some embodiments, $R_1$ is —O-(6-membered heterocycloalkyl). In some embodiments, $R_1$ is —O-(7-membered heterocycloalkyl).

In some embodiments, $R_1$ is —NH—($C_1$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_1$ is —NH—($C_1$-$C_{10}$ aryl).

In some embodiments, $R_1$ is —NH—($C_6$ aryl). In some embodiments, $R_1$ is —NH—($C_8$ aryl). In some embodiments, $R_1$ is —NH—($C_{10}$ aryl).

In some embodiments, $R_1$ is —NH-(5- to 10-membered heteroaryl).

In some embodiments, $R_1$ is —NH-(5-membered heteroaryl). In some embodiments, $R_1$ is —NH-(6-membered heteroaryl). In some embodiments, $R_1$ is —NH-(7-membered heteroaryl). In some embodiments, $R_1$ is —NH-(8-membered heteroaryl). In some embodiments, $R_1$ is —NH-(9-membered heteroaryl). In some embodiments, $R_1$ is —NH-(10-membered heteroaryl).

In some embodiments, $R_1$ is —NH—($C_3$-$C_{10}$ cycloalkyl).

In some embodiments, $R_1$ is —NH—($C_3$ cycloalkyl). In some embodiments, $R_1$ is —NH—($C_4$ cycloalkyl). In some embodiments, $R_1$ is —NH—$C_5$ cycloalkyl). In some embodiments, $R_1$ is —NH—($C_6$ cycloalkyl). In some embodiments, $R_1$ is —NH—($C_7$ cycloalkyl). In some embodiments, $R_1$ is —NH—($C_8$ cycloalkyl). In some embodiments, $R_1$ is —NH—($C_9$ cycloalkyl). In some embodiments, $R_1$ is —NH—($C_{10}$ cycloalkyl).

In some embodiments, $R_1$ is —NH-(3- to 7-membered heterocycloalkyl).

In some embodiments, $R_1$ is —NH-(3-membered heterocycloalkyl). In some embodiments, $R_1$ is —NH-(4-membered heterocycloalkyl). In some embodiments, $R_1$ is —NH-(5-membered heterocycloalkyl). In some embodiments, $R_1$ is —NH-(6-membered heterocycloalkyl). In some embodiments, $R_1$ is —NH-(7-membered heterocycloalkyl).

In some embodiments, $R_1$ is methyl, isopropyl, ethyl, —$CF_3$, —$CHF_2$, $CH_2F$, —$CF_2CH_3$, —$CF(CH_3)_2$, cyclopropyl, or flurocyclopropyl.

In some embodiments, $R_1$ is methyl, ethyl, —$CF_3$, $CHF_2$, or $CH_2F$.

In some embodiments, $R_1$ is methyl or ethyl.

In some embodiments, $R_1$ is —$CF_3$, $CHF_2$, or $CH_2F$.

In some embodiments, each $R_{1S}$ independently is oxo, halogen, —CN, —OH, —O—$(CH_2)_2$—$OC_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl.

In some embodiments, each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl.

In some embodiments, each $R_{1S}$ independently is oxo, halogen, or —CN.

In some embodiments, each $R_{1S}$ independently is oxo.

In some embodiments, each $R_{1S}$ independently is halogen.

In some embodiments, each $R_{1S}$ independently is F, Cl, Br, or I. In some embodiments, each $R_{1S}$ independently is F, Cl, or Br. In some embodiments, each $R_{1S}$ independently is F or Cl.

In some embodiments, each $R_{1S}$ independently is F. In some embodiments, each $R_{1S}$ independently is $C_1$. In some embodiments, each $R_{1S}$ independently is Br. In some embodiments, each $R_{1S}$ independently is I.

In some embodiments, each $R_{1S}$ independently is —CN.

In some embodiments, each $R_{1S}$ independently is —OH, —O—$(CH_2)_2$—$OC_1$—$C_6$ alkyl, —$NH_2$, —NH($C_1$-$C_6$ alkyl), —N($C_1$-$C_6$ alkyl)$_2$, —S($C_1$-$C_6$ alkyl), or —$SO_2$($C_1$-$C_6$ alkyl).

In some embodiments, each $R_{1S}$ independently is —OH, —$NH_2$, —NH($C_1$-$C_6$ alkyl), —N($C_1$-$C_6$ alkyl)$_2$, —S($C_1$-$C_6$ alkyl), or —$SO_2$($C_1$-$C_6$ alkyl).

In some embodiments, each $R_{1S}$ independently is —OH.

In some embodiments, each $R_{1S}$ independently is —O—$(CH_2)_2$—$OC_1$—$C_6$ alkyl.

In some embodiments, each $R_{1S}$ independently is —$NH_2$, —NH($C_1$-$C_6$ alkyl), —N($C_1$-$C_6$ alkyl)$_2$, —S($C_1$-$C_6$ alkyl), or —$SO_2$($C_1$-$C_6$ alkyl).

In some embodiments, each $R_{1S}$ independently is —$NH_2$, —NH($C_1$-$C_6$ alkyl), or —N($C_1$-$C_6$ alkyl)$_2$.

In some embodiments, each $R_{1S}$ independently is —$NH_2$.

In some embodiments, each $R_{1S}$ independently is —NH ($C_1$-$C_6$ alkyl).

In some embodiments, each $R_{1S}$ independently is —NH (methyl). In some embodiments, each $R_{1S}$ independently is —NH(ethyl). In some embodiments, each $R_{1S}$ independently is —NH(propyl). In some embodiments, each $R_{1S}$ independently is —NH(butyl). In some embodiments, each $R_{1S}$ independently is —NH(pentyl). In some embodiments, each $R_{1S}$ independently is —NH(hexyl).

In some embodiments, each $R_{1S}$ independently is —N($C_1$-$C_6$ alkyl)$_2$.

In some embodiments, each $R_{1S}$ independently is —S($C_1$-$C_6$ alkyl) or —$SO_2$($C_1$-$C_6$ alkyl).

In some embodiments, each $R_{1S}$ independently is —S($C_1$-$C_6$ alkyl).

In some embodiments, each $R_{1S}$ independently is —S(methyl). In some embodiments, each $R_{1S}$ independently is —S(ethyl). In some embodiments, each $R_{1S}$ independently is —S(propyl). In some embodiments, each $R_{1S}$ independently is —S(butyl). In some embodiments, each $R_{1S}$ independently is —S(heptyl). In some embodiments, each $R_{1S}$ independently is —S(hexyl).

In some embodiments, each $R_{1S}$ independently is —$SO_2$ ($C_1$-$C_6$ alkyl).

In some embodiments, each $R_{1S}$ independently is —$SO_2$ (methyl). In some embodiments, each $R_{1S}$ independently is —$SO_2$(ethyl). In some embodiments, each $R_{1S}$ independently is —$SO_2$(propyl). In some embodiments, each $R_{1S}$ independently is —$SO_2$(butyl). In some embodiments, each $R_{2S}$ independently is —$SO_2$(heptyl). In some embodiments, each $R_{1S}$ independently is —$SO_2$(hexyl).

In some embodiments, each $R_{1S}$ independently is $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl.

In some embodiments, each $R_{1S}$ independently is $C_1$-$C_6$ alkyl, $C_2$-$C_6$ alkenyl, $C_2$-$C_6$ alkynyl, or $C_1$-$C_6$ alkoxy.

In some embodiments, each $R_{1S}$ independently is $C_1$-$C_6$ alkyl.

In some embodiments, each $R_{1S}$ independently is methyl. In some embodiments, each $R_{1S}$ independently is ethyl. In some embodiments, each $R_{1S}$ independently is propyl. In some embodiments, each $R_{1S}$ independently is butyl. In some embodiments, each $R_{1S}$ independently is pentyl. In some embodiments, each $R_{1S}$ independently is hexyl. In some embodiments, each $R_{1S}$ independently is isopropyl. In some embodiments, each $R_{1S}$ independently is isobutyl. In some embodiments, each $R_{1S}$ independently is isopentyl. In some embodiments, each $R_{1S}$ independently is isohexyl. In some embodiments, each $R_{1S}$ independently is secbutyl. In some embodiments, each $R_{1S}$ independently is secpentyl. In some embodiments, each $R_{1S}$ independently is sechexyl. In some embodiments, each $R_{1S}$ independently is tertbutyl.

In some embodiments, each $R_{1S}$ independently is $C_2$-$C_6$ alkenyl.

In some embodiments, each $R_{1S}$ independently is $C_2$ alkenyl. In some embodiments, each $R_{1S}$ independently is $C_3$ alkenyl. In some embodiments, each $R_{1S}$ independently is $C_4$ alkenyl. In some embodiments, each $R_{1S}$ independently is $C_5$ alkenyl. In some embodiments, each $R_{1S}$ independently is $C_6$ alkenyl.

In some embodiments, each $R_{1S}$ independently is $C_2$-$C_6$ alkynyl.

In some embodiments, each $R_{1S}$ independently is $C_2$ alkynyl. In some embodiments, each $R_{1S}$ independently is $C_3$ alkynyl. In some embodiments, each $R_{1S}$ independently is $C_4$ alkynyl. In some embodiments, each $R_{1S}$ independently is $C_5$ alkynyl. In some embodiments, each $R_{1S}$ independently is $C_6$ alkynyl.

In some embodiments, each $R_{1S}$ independently is $C_1$-$C_6$ alkoxy.

In some embodiments, each $R_{1S}$ independently is methoxy. In some embodiments, each $R_{1S}$ independently is ethoxy. In some embodiments, each $R_{1S}$ independently is propoxy. In some embodiments, each $R_{1S}$ independently is butoxy. In some embodiments, each $R_{1S}$ independently is pentoxy. In some embodiments, each $R_{1S}$ independently is hexoxy.

In some embodiments, each $R_{1S}$ independently is $C_3$-$C_7$ cycloalkyl or 3- to 7-membered heterocycloalkyl.

In some embodiments, each $R_{1S}$ independently is $C_3$-$C_7$ cycloalkyl.

In some embodiments, each $R_{1S}$ independently is cyclopropyl. In some embodiments, each $R_{1S}$ independently is cyclobutyl. In some embodiments, each $R_{1S}$ independently is cyclopentyl. In some embodiments, each $R_{1S}$ independently is cyclohexyl. In some embodiments, each $R_{1S}$ independently is cycloheptyl. In some embodiments, each $R_{1S}$ independently is cyclooctyl.

In some embodiments, each $R_{1S}$ independently is 3- to 7-membered heterocycloalkyl.

In some embodiments, each $R_{1S}$ independently is 3-membered heterocycloalkyl. In some embodiments, each $R_{1S}$ independently is 4-membered heterocycloalkyl. In some embodiments, each $R_{1S}$ independently is 5-membered heterocycloalkyl. In some embodiments, each $R_{1S}$ independently is 6-membered heterocycloalkyl. In some embodiments, each $R_{1S}$ independently is 7-membered heterocycloalkyl.

In some embodiments, $R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$.

In some embodiments, $R_2$ is halogen or —CN.

In some embodiments, $R_2$ is halogen.

In some embodiments, $R_2$ is F, Cl, Br, or I. In some embodiments, $R_2$ is F, Cl, or Br. In some embodiments, $R_2$ is F or Cl.

In some embodiments, $R_2$ is F. In some embodiments, $R_2$ is $C_1$. In some embodiments, $R_2$ is Br. In some embodiments, $R_2$ is I.

In some embodiments, $R_2$ is —CN.

In some embodiments, $R_2$ is —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_2$ is —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_1$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$.

In some embodiments, $R_2$ is —OH.

In some embodiments, $R_2$ is —$NH_2$, —NH($C_1$-$C_6$ alkyl), —N($C_1$-$C_6$ alkyl)$_2$, —S($C_1$-$C_6$ alkyl), or —S($C_6$-$C_{10}$ aryl).

In some embodiments, $R_2$ is —$NH_2$, —NH($C_1$-$C_6$ alkyl), or —N($C_1$-$C_6$ alkyl)$_2$.

In some embodiments, $R_2$ is —$NH_2$.

In some embodiments, $R_2$ is —NH($C_1$-$C_6$ alkyl).

In some embodiments, $R_2$ is —NH(methyl). In some embodiments, $R_2$ is —NH(ethyl). In some embodiments, $R_2$ is —NH(propyl). In some embodiments, $R_2$ is —NH(butyl). In some embodiments, $R_2$ is —NH(pentyl). In some embodiments, $R_2$ is —NH(hexyl).

In some embodiments, $R_2$ is —N($C_1$-$C_6$ alkyl)$_2$.

In some embodiments, $R_2$ is —SH, —S($C_1$-$C_6$ alkyl), —$SO_2$($C_1$-$C_6$ alkyl), —S($C_6$-$C_{10}$ aryl), or —$SO_2$($C_6$-$C_{10}$ aryl).

In some embodiments, $R_2$ is —SH.

In some embodiments, $R_2$ is —S($C_1$-$C_6$ alkyl) or —S($C_6$-$C_{10}$ aryl).

In some embodiments, $R_2$ is —S($C_1$-$C_6$ alkyl).

In some embodiments, $R_2$ is —S(methyl). In some embodiments, $R_2$ is —S(ethyl). In some embodiments, $R_2$ is —S(propyl). In some embodiments, $R_2$ is —S(butyl). In some embodiments, $R_2$ is —S(heptyl). In some embodiments, $R_2$ is —S(hexyl).

In some embodiments, $R_2$ is —S($C_6$-$C_{10}$ aryl).

In some embodiments, $R_2$ is —S($C_6$ aryl). In some embodiments, $R_2$ is —S($C_8$ aryl). In some embodiments, $R_2$ is —S($C_{10}$ aryl).

In some embodiments, $R_2$ is —$SO_2$($C_1$-$C_6$ alkyl) or —$SO_2$($C_6$-$C_{10}$ aryl).

In some embodiments, $R_2$ is —$SO_2$($C_1$-$C_6$ alkyl).

In some embodiments, $R_2$ is —$SO_2$(methyl). In some embodiments, $R_2$ is —$SO_2$(ethyl). In some embodiments, $R_2$ is —$SO_2$(propyl). In some embodiments, $R_2$ is —$SO_2$(butyl). In some embodiments, $R_2$ is —$SO_2$(heptyl). In some embodiments, $R_2$ is —$SO_2$(hexyl).

In some embodiments, $R_2$ is —$SO_2$($C_6$-$C_{10}$ aryl).

In some embodiments, $R_2$ is —$SO_2$($C_6$ aryl). In some embodiments, $R_2$ is —$SO_2$($C_8$ aryl). In some embodiments, $R_2$ is —$SO_2$($C_{10}$ aryl).

In some embodiments, $R_2$ is $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_2$ is $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$.

In some embodiments, $R_2$ is $C_1$-$C_6$ alkyl, $C_2$-$C_6$ alkenyl, $C_1$-$C_6$ haloalkyl, or $C_1$-$C_6$ alkoxy.

In some embodiments, $R_2$ is $C_1$-$C_6$ alkyl, $C_2$-$C_6$ alkenyl, $C_1$-$C_6$ haloalkyl, or $C_1$-$C_6$ alkoxy, wherein the alkyl or alkenyl are optionally substituted with one or more $R_{2S}$.

In some embodiments, $R_2$ is $C_1$-$C_6$ alkyl, $C_2$-$C_6$ alkenyl, $C_1$-$C_6$ haloalkyl, or $C_1$-$C_6$ alkoxy, wherein the alkyl or alkenyl are substituted with one or more $R_{2S}$.

In some embodiments, $R_2$ is $C_1$-$C_6$ alkyl, $C_2$-$C_6$ alkenyl, $C_1$-$C_6$ haloalkyl, or $C_1$-$C_6$ alkoxy, wherein the alkyl or alkenyl are substituted with one $R_{2S}$.

In some embodiments, $R_2$ is $C_1$-$C_6$ alkyl, $C_2$-$C_6$ alkenyl, $C_1$-$C_6$ haloalkyl, or $C_1$-$C_6$ alkoxy, wherein the alkyl or alkenyl are substituted with two $R_{2S}$.

In some embodiments, $R_2$ is $C_1$-$C_6$ alkyl, $C_2$-$C_6$ alkenyl, $C_1$-$C_6$ haloalkyl, or $C_1$-$C_6$ alkoxy, wherein the alkyl or alkenyl are substituted with three $R_{2S}$.

In some embodiments, $R_2$ is $C_1$-$C_6$ alkyl.

In some embodiments, $R_2$ is methyl. In some embodiments, $R_2$ is ethyl. In some embodiments, $R_2$ is propyl. In some embodiments, $R_2$ is butyl. In some embodiments, $R_2$ is pentyl. In some embodiments, $R_2$ is hexyl. In some embodiments, $R_2$ is isopropyl. In some embodiments, $R_2$ is isobutyl. In some embodiments, $R_2$ is isopentyl. In some embodiments, $R_2$ is isohexyl. In some embodiments, $R_2$ is secbutyl. In some embodiments, $R_2$ is secpentyl. In some embodiments, $R_2$ is sechexyl. In some embodiments, $R_2$ is tertbutyl.

In some embodiments, $R_2$ is $C_1$-$C_6$ alkyl optionally substituted with one or more $R_{2S}$.

In some embodiments, $R_2$ is $C_1$-$C_6$ alkyl substituted with one or more $R_{2S}$.

In some embodiments, $R_2$ is $C_1$-$C_6$ alkyl substituted with one $R_{2S}$. In some embodiments, $R_2$ is $C_1$-$C_6$ alkyl substituted with two $R_{2S}$. In some embodiments, $R_2$ is $C_1$-$C_6$ alkyl substituted with three $R_{2S}$.

In some embodiments, $R_2$ is $C_2$-$C_6$ alkenyl.

In some embodiments, $R_2$ is $C_2$ alkenyl. In some embodiments, $R_2$ is $C_3$ alkenyl. In some embodiments, $R_2$ is $C_4$ alkenyl. In some embodiments, $R_2$ is $C_5$ alkenyl. In some embodiments, $R_2$ is $C_6$ alkenyl.

In some embodiments, $R_2$ is $C_2$-$C_6$ alkenyl optionally substituted with one or more $R_{2S}$.

In some embodiments, $R_2$ is $C_2$-$C_6$ alkenyl substituted with one or more $R_{2S}$.

In some embodiments, $R_2$ is $C_2$-$C_6$ alkenyl substituted with one $R_{2S}$. In some embodiments, $R_2$ is $C_2$-$C_6$ alkenyl substituted with two $R_{2S}$. In some embodiments, $R_2$ is $C_2$-$C_6$ alkenyl substituted with three $R_{2S}$.

In some embodiments, $R_2$ is $C_1$-$C_6$ haloalkyl.

In some embodiments, $R_2$ is halomethyl. In some embodiments, $R_2$ is haloethyl. In some embodiments, $R_2$ is halopropyl. In some embodiments, $R_2$ is halobutyl. In some embodiments, $R_2$ is halopentyl. In some embodiments, $R_2$ is halohexyl.

In some embodiments, $R_2$ is $C_1$-$C_6$ haloalkyl optionally substituted with one or more $R_{2S}$.

In some embodiments, $R_2$ is $C_1$-$C_6$ haloalkyl substituted with one or more $R_{2S}$.

In some embodiments, $R_2$ is $C_1$-$C_6$ haloalkyl substituted with one $R_{2S}$. In some embodiments, $R_2$ is $C_1$-$C_6$ haloalkyl substituted with two $R_{2S}$. In some embodiments, $R_2$ is $C_1$-$C_6$ haloalkyl substituted with three $R_{2S}$.

In some embodiments, $R_2$ is $C_1$-$C_6$ alkoxy.

In some embodiments, $R_2$ is methoxy. In some embodiments, $R_2$ is ethoxy. In some embodiments, $R_2$ is propoxy. In some embodiments, $R_2$ is butoxy. In some embodiments, $R_2$ is pentoxy. In some embodiments, $R_2$ is hexoxy.

In some embodiments, $R_2$ is $C_1$-$C_6$ alkoxy optionally substituted with one or more $R_{2S}$.

In some embodiments, $R_2$ is $C_1$-$C_6$ alkoxy substituted with one or more $R_{2S}$.

In some embodiments, $R_2$ is $C_1$-$C_6$ alkoxy substituted with one $R_{2S}$. In some embodiments, $R_2$ is $C_1$-$C_6$ alkoxy substituted with two $R_{2S}$. In some embodiments, $R_2$ is $C_1$-$C_6$ alkoxy substituted with three $R_{2S}$.

In some embodiments, $R_2$ is $C_6$-$C_{10}$ aryl, 5- to 10-membered heteroaryl, $C_3$-$C_7$ cycloalkyl, or 3- to 7-membered heterocycloalkyl.

In some embodiments, $R_2$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are optionally substituted with one or more $R_{2S}$.

In some embodiments, $R_2$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with one or more $R_{2S}$.

In some embodiments, $R_2$ is $C_1$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with one $R_{2S}$.

In some embodiments, $R_2$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with two $R_{2S}$.

In some embodiments, $R_2$ is $C_6$-$C_{10}$ aryl, 5- to 10-membered heteroaryl, $C_3$-$C_7$ cycloalkyl, or 3- to 7-membered heterocycloalkyl, wherein the aryl, heteroaryl, cycloalkyl, and heterocycloalkyl are substituted with three $R_{2S}$.

In some embodiments, $R_2$ is $C_6$-$C_{10}$ aryl.

In some embodiments, $R_2$ is $C_6$ aryl (e.g., phenyl). In some embodiments, $R_2$ is $C_8$ aryl. In some embodiments, $R_2$ is $C_{10}$ aryl.

In some embodiments, $R_2$ is $C_6$-$C_{10}$ aryl optionally substituted with one or more $R_{2S}$.

In some embodiments, $R_2$ is $C_6$-$C_{10}$ aryl substituted with one or more $R_{2S}$.

In some embodiments, $R_2$ is $C_6$-$C_{10}$ aryl substituted with one $R_{2S}$. In some embodiments, $R_2$ is $C_6$-$C_{10}$ aryl substituted with two $R_{2S}$. In some embodiments, $R_2$ is $C_6$-$C_{10}$ aryl substituted with three $R_{2S}$.

In some embodiments, $R_2$ is 5- to 10-membered heteroaryl.

In some embodiments, $R_2$ is 5-membered heteroaryl. In some embodiments, $R_2$ is 6-membered heteroaryl. In some embodiments, $R_2$ is 7-membered heteroaryl. In some embodiments, $R_2$ is 8-membered heteroaryl. In some embodiments, $R_2$ is 9-membered heteroaryl. In some embodiments, $R_2$ is 10-membered heteroaryl.

In some embodiments, $R_2$ is 5- to 10-membered heteroaryl optionally substituted with one or more $R_{2S}$.

In some embodiments, $R_2$ is 5- to 10-membered heteroaryl substituted with one or more $R_{2S}$.

In some embodiments, $R_2$ is 5- to 10-membered heteroaryl substituted with one $R_{2S}$. In some embodiments, $R_2$ is 5- to 10-membered heteroaryl substituted with two $R_{2S}$. In some embodiments, $R_2$ is 5- to 10-membered heteroaryl substituted with three $R_{2S}$.

In some embodiments, $R_2$ is $C_3$-$C_7$ cycloalkyl.

In some embodiments, $R_2$ is cyclopropyl. In some embodiments, $R_2$ is cyclobutyl. In some embodiments, $R_2$ is cyclopentyl. In some embodiments, $R_2$ is cyclohexyl. In some embodiments, $R_2$ is cycloheptyl.

In some embodiments, $R_2$ is $C_3$-$C_7$ cycloalkyl optionally substituted with one or more $R_{2S}$.

In some embodiments, $R_2$ is $C_3$-$C_7$ cycloalkyl substituted with one or more $R_{2S}$.

In some embodiments, $R_2$ is $C_3$-$C_7$ cycloalkyl substituted with one $R_{2S}$. In some embodiments, $R_2$ is $C_3$-$C_7$ cycloalkyl substituted with two $R_{2S}$. In some embodiments, $R_2$ is $C_3$-$C_7$ cycloalkyl substituted with three $R_{2S}$.

In some embodiments, $R_2$ is 3- to 7-membered heterocycloalkyl.

In some embodiments, $R_2$ is 3-membered heterocycloalkyl. In some embodiments, $R_2$ is 4-membered heterocycloalkyl. In some embodiments, $R_2$ is 5-membered heterocycloalkyl. In some embodiments, $R_2$ is 6-membered heterocycloalkyl. In some embodiments, $R_2$ is 7-membered heterocycloalkyl.

In some embodiments, $R_2$ is 3- to 7-membered heterocycloalkyl optionally substituted with one or more $R_{2S}$.

In some embodiments, $R_2$ is 3- to 7-membered heterocycloalkyl substituted with one or more $R_{2S}$.

In some embodiments, $R_2$ is 3- to 7-membered heterocycloalkyl substituted with one $R_{2S}$. In some embodiments, $R_2$ is 3- to 7-membered heterocycloalkyl substituted with two $R_{2S}$. In some embodiments, $R_2$ is 3- to 7-membered heterocycloalkyl substituted with three $R_{2S}$.

In some embodiments, $R_2$ is —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_2$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl).

In some embodiments, $R_2$ is —O—($C_6$-$C_{10}$ aryl).

In some embodiments, $R_2$ is —O—($C_6$ aryl). In some embodiments, $R_2$ is —O—($C_8$ aryl). In some embodiments, $R_2$ is —O—($C_{10}$ aryl).

In some embodiments, $R_2$ is —O-(5- to 10-membered heteroaryl).

In some embodiments, $R_2$ is —O-(5-membered heteroaryl). In some embodiments, $R_2$ is —O-(6-membered heteroaryl). In some embodiments, $R_2$ is —O-(7-membered heteroaryl). In some embodiments, $R_2$ is —O-(8-membered heteroaryl). In some embodiments, $R_2$ is —O-(9-membered heteroaryl). In some embodiments, $R_2$ is —O-(10-membered heteroaryl).

In some embodiments, $R_2$ is —O—($C_3$-$C_{10}$ cycloalkyl).

In some embodiments, $R_2$ is —O—($C_3$ cycloalkyl). In some embodiments, $R_2$ is —O—($C_4$ cycloalkyl). In some embodiments, $R_2$ is —O—($C_5$ cycloalkyl). In some embodiments, $R_2$ is —O—($C_6$ cycloalkyl). In some embodiments, $R_2$ is —O—($C_7$ cycloalkyl). In some embodiments, $R_2$ is —O—($C_8$ cycloalkyl). In some embodiments, $R_2$ is —O—($C_9$ cycloalkyl). In some embodiments, $R_2$ is —O—($C_{10}$ cycloalkyl).

In some embodiments, $R_2$ is —O-(3- to 7-membered heterocycloalkyl).

In some embodiments, $R_2$ is —O-(3-membered heterocycloalkyl). In some embodiments, $R_2$ is —O-(4-membered heterocycloalkyl). In some embodiments, $R_2$ is —O-(5-membered heterocycloalkyl). In some embodiments, $R_2$ is —O-(6-membered heterocycloalkyl). In some embodiments, $R_2$ is —O-(7-membered heterocycloalkyl).

In some embodiments, $R_2$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

In some embodiments, $R_2$ is —NH—($C_6$-$C_{10}$ aryl).

In some embodiments, $R_2$ is —NH—($C_6$ aryl). In some embodiments, $R_2$ is —NH—($C_8$ aryl). In some embodiments, $R_2$ is —NH—($C_{10}$ aryl).

In some embodiments, $R_2$ is —NH-(5- to 10-membered heteroaryl).

In some embodiments, $R_2$ is —NH-(5-membered heteroaryl). In some embodiments, $R_2$ is —NH-(6-membered heteroaryl). In some embodiments, $R_2$ is —NH-(7-membered heteroaryl). In some embodiments, $R_2$ is —NH-(8-membered heteroaryl). In some embodiments, $R_2$ is —NH-(9-membered heteroaryl). In some embodiments, $R_2$ is —NH-(10-membered heteroaryl).

In some embodiments, $R_2$ is —NH—($C_3$-$C_{10}$ cycloalkyl).

In some embodiments, $R_2$ is —NH—($C_3$ cycloalkyl). In some embodiments, $R_2$ is —NH—($C_4$ cycloalkyl). In some embodiments, $R_2$ is —NH—($C_5$ cycloalkyl). In some embodiments, $R_2$ is —NH—($C_6$ cycloalkyl). In some embodiments, $R_2$ is —NH—($C_7$ cycloalkyl). In some embodiments, $R_2$ is —NH—($C_8$ cycloalkyl). In some embodiments, $R_2$ is —NH—($C_9$ cycloalkyl). In some embodiments, $R_2$ is —NH—($C_{10}$ cycloalkyl).

In some embodiments, $R_2$ is —NH-(3- to 7-membered heterocycloalkyl).

In some embodiments, $R_2$ is —NH-(3-membered heterocycloalkyl). In some embodiments, $R_2$ is —NH-(4-membered heterocycloalkyl). In some embodiments, $R_2$ is —NH-(5-membered heterocycloalkyl). In some embodiments, $R_2$ is —NH-(6-membered heterocycloalkyl). In some embodiments, $R_2$ is —NH-(7-membered heterocycloalkyl).

In some embodiments, $R_2$ is

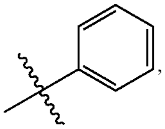, 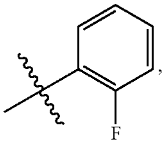, 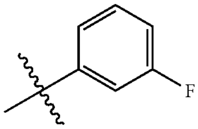,
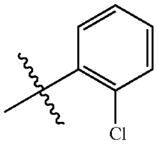, 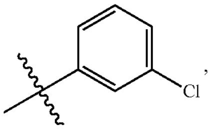, 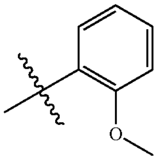,
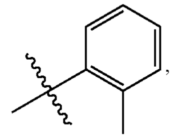, 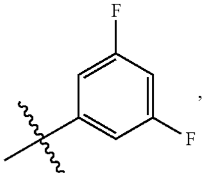, —CN,
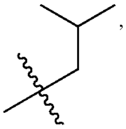, 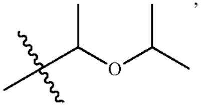, 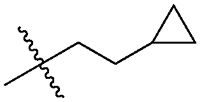,
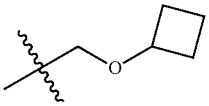, 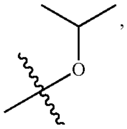, 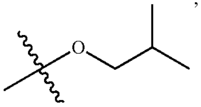,
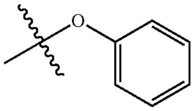, 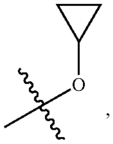, 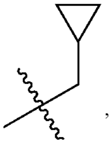,
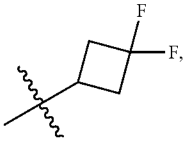 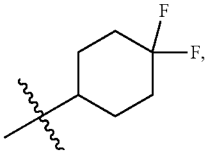
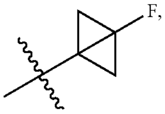 [SMILES: *C12CC1(F)C2] or 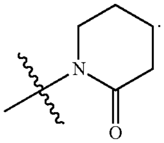.

In some embodiments, $R_2$ is

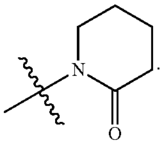.

In some embodiments, $R_2$ is
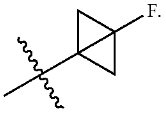
In some embodiments, $R_2$ is
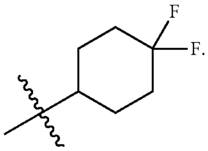 [SMILES: *C1CCC(F)(F)CC1]
In some embodiments, $R_2$ is
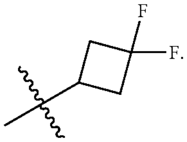 [SMILES: *C1CC(F)(F)C1]
In some embodiments, $R_2$ is
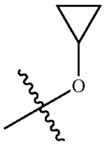 or 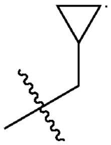
In some embodiments, $R_2$ is —CN
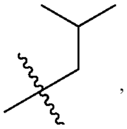, 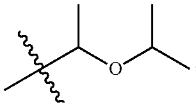, 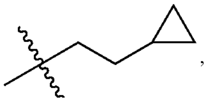, 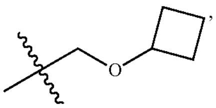, 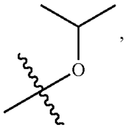, 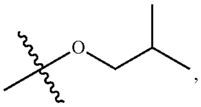, or 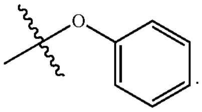
In some embodiments, $R_2$ is
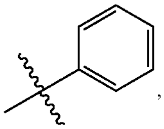, 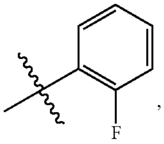, 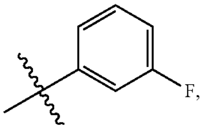
-continued
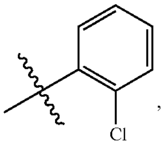, 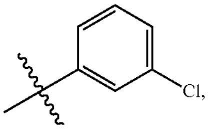, 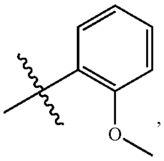, 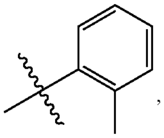, or 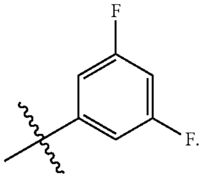
In some embodiments, $R_2$ is
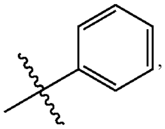, 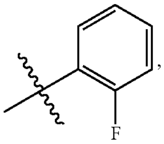, 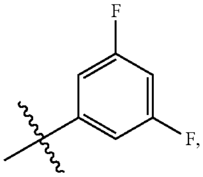, 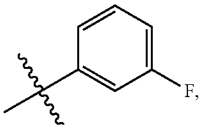, 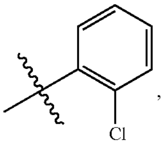, 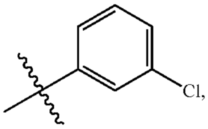, 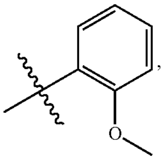, 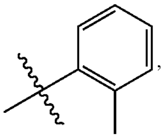, 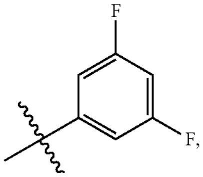, 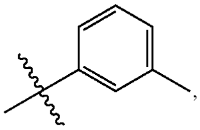,
—CN, 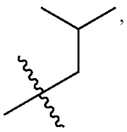, 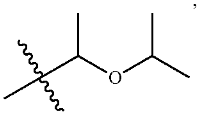, 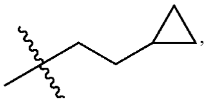, 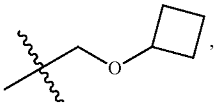, 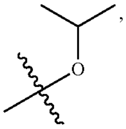, 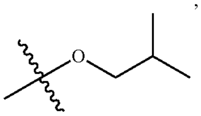, -continued

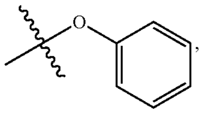,

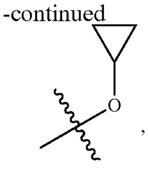,

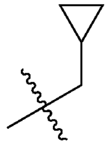,

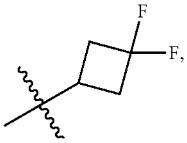,

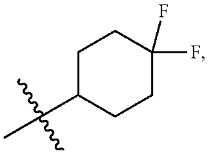,

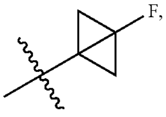, or

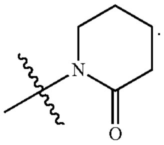.

In some embodiments, each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl.

In some embodiments, each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl.

In some embodiments, each $R_{2S}$ independently is oxo, halogen, or —CN.

In some embodiments, each $R_{2S}$ independently is oxo.

In some embodiments, each $R_{2S}$ independently is halogen.

In some embodiments, each $R_{2S}$ independently is F, Cl, Br, or I. In some embodiments, each $R_{2S}$ independently is F, Cl, or Br. In some embodiments, each $R_{2S}$ independently is F or Cl.

In some embodiments, each $R_{2S}$ independently is F. In some embodiments, each $R_{2S}$ independently is $C_1$. In some embodiments, each $R_{2S}$ independently is Br. In some embodiments, each $R_{2S}$ independently is I.

In some embodiments, each $R_{2S}$ independently is —CN.

In some embodiments, each $R_{2S}$ independently is —OH, —$NH_2$, —NH($C_1$-$C_6$ alkyl), —N($C_1$-$C_6$ alkyl)$_2$, —S($C_1$-$C_6$ alkyl), or —$SO_2$($C_1$-$C_6$ alkyl).

In some embodiments, each $R_{2S}$ independently is —OH.

In some embodiments, each $R_{2S}$ independently is —$NH_2$, —NH($C_1$-$C_6$ alkyl), —N($C_1$-$C_6$ alkyl)$_2$, —S($C_1$-$C_6$ alkyl), or —$SO_2$($C_1$-$C_6$ alkyl).

In some embodiments, each $R_{2S}$ independently is —$NH_2$, —NH($C_1$-$C_6$ alkyl), or —N($C_1$-$C_6$ alkyl)$_2$.

In some embodiments, each $R_{2S}$ independently is —$NH_2$.

In some embodiments, each $R_{2S}$ independently is —NH ($C_1$-$C_6$ alkyl).

In some embodiments, each $R_{2S}$ independently is —NH (methyl). In some embodiments, each $R_{2S}$ independently is —NH(ethyl). In some embodiments, each $R_{2S}$ independently is —NH(propyl). In some embodiments, each $R_{2S}$ independently is —NH(butyl). In some embodiments, each $R_{2S}$ independently is —NH(pentyl). In some embodiments, each $R_{2S}$ independently is —NH(hexyl).

In some embodiments, each $R_{2S}$ independently is —N($C_1$-$C_6$ alkyl)$_2$.

In some embodiments, each $R_{2S}$ independently is —S($C_1$-$C_6$ alkyl) or —$SO_2$($C_1$-$C_6$ alkyl).

In some embodiments, each $R_{2S}$ independently is —S($C_1$-$C_6$ alkyl).

In some embodiments, each $R_{2S}$ independently is —S(methyl). In some embodiments, each $R_{2S}$ independently is —S(ethyl). In some embodiments, each $R_{2S}$ independently is —S(propyl). In some embodiments, each $R_{2S}$ independently is —S(butyl). In some embodiments, each $R_{2S}$ independently is —S(heptyl). In some embodiments, each $R_{2S}$ independently is —S(hexyl).

In some embodiments, each $R_{2S}$ independently is —$SO_2$ ($C_1$-$C_6$ alkyl).

In some embodiments, each $R_{2S}$ independently is —$SO_2$ (methyl). In some embodiments, each $R_{2S}$ independently is —$SO_2$(ethyl). In some embodiments, each $R_{2S}$ independently is —$SO_2$(propyl). In some embodiments, each $R_{2S}$ independently is —$SO_2$(butyl). In some embodiments, each $R_{2S}$ independently is —$SO_2$(heptyl). In some embodiments, each $R_{2S}$ independently is —$SO_2$(hexyl).

In some embodiments, each $R_{2S}$ independently is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl.

In some embodiments, each $R_{2S}$ independently is $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl.

In some embodiments, each $R_{2S}$ independently is $C_1$-$C_6$ alkyl, $C_2$-$C_6$ alkenyl, $C_2$-$C_6$ alkynyl, $C_1$-$C_6$ alkoxy, or $C_1$-$C_6$ haloalkyl.

In some embodiments, each $R_{2S}$ independently is $C_1$-$C_6$ alkyl, $C_2$-$C_6$ alkenyl, $C_2$-$C_6$ alkynyl, or $C_1$-$C_6$ alkoxy.

In some embodiments, each $R_{2S}$ independently is $C_1$-$C_6$ alkyl.

In some embodiments, each $R_{2S}$ independently is methyl. In some embodiments, each $R_{2S}$ independently is ethyl. In some embodiments, each $R_{2S}$ independently is propyl. In some embodiments, each $R_{2S}$ independently is butyl. In some embodiments, each $R_{2S}$ independently is pentyl. In some embodiments, each $R_{2S}$ independently is hexyl. In some embodiments, each $R_{2S}$ independently is isopropyl. In some embodiments, each $R_{2S}$ independently is isobutyl. In some embodiments, each $R_{2S}$ independently is isopentyl. In some embodiments, each $R_{2S}$ independently is isohexyl. In some embodiments, each $R_{2S}$ independently is secbutyl. In some embodiments, each $R_{1S}$ independently is secpentyl. In some embodiments, each $R_{2S}$ independently is sechexyl. In some embodiments, each $R_{2S}$ independently is tertbutyl.

In some embodiments, each $R_{2S}$ independently is $C_2$-$C_6$ alkenyl.

In some embodiments, each $R_{2S}$ independently is $C_2$ alkenyl. In some embodiments, each $R_{2S}$ independently is $C_3$ alkenyl. In some embodiments, each $R_{2S}$ independently is $C_4$ alkenyl. In some embodiments, each $R_{2S}$ independently is $C_5$ alkenyl. In some embodiments, each $R_{2S}$ independently is $C_6$ alkenyl.

In some embodiments, each $R_{2S}$ independently is $C_2$-$C_6$ alkynyl.

In some embodiments, each $R_{2S}$ independently is $C_2$ alkynyl. In some embodiments, each $R_{2S}$ independently is $C_3$ alkynyl. In some embodiments, each $R_{2S}$ independently is $C_4$ alkynyl. In some embodiments, each $R_{2S}$ independently is $C_5$ alkynyl. In some embodiments, each $R_{2S}$ independently is $C_6$ alkynyl.

In some embodiments, each $R_{2S}$ independently is $C_1$-$C_6$ alkoxy.

In some embodiments, each $R_{2S}$ independently is methoxy. In some embodiments, each $R_{2S}$ independently is ethoxy. In some embodiments, each $R_{2S}$ independently is propoxy. In some embodiments, each $R_{2S}$ independently is butoxy. In some embodiments, each $R_{2S}$ independently is pentoxy. In some embodiments, each $R_{2S}$ independently is hexoxy.

In some embodiments, each $R_{2S}$ independently is $C_1$-$C_6$ haloalkyl.

In some embodiments, each $R_{2S}$ independently is $C_1$ haloalkyl. In some embodiments, each $R_{2S}$ independently is $C_2$ haloalkyl. In some embodiments, each $R_{2S}$ independently is $C_3$ haloalkyl. In some embodiments, each $R_{2S}$ independently is $C_4$ haloalkyl. In some embodiments, each $R_{2S}$ independently is $C_5$ haloalkyl. In some embodiments, each $R_{2S}$ independently is $C_6$ haloalkyl.

In some embodiments, each $R_{2S}$ independently is $C_3$-$C_7$ cycloalkyl or 3- to 7-membered heterocycloalkyl.

In some embodiments, each $R_{2S}$ independently is $C_3$-$C_7$ cycloalkyl.

In some embodiments, each $R_{2S}$ independently is cyclopropyl. In some embodiments, each $R_{2S}$ independently is cyclobutyl. In some embodiments, each $R_{2S}$ independently is cyclopentyl. In some embodiments, each $R_{2S}$ independently is cyclohexyl. In some embodiments, each $R_{2S}$ independently is cycloheptyl. In some embodiments, each $R_{2S}$ independently is cyclooctyl.

In some embodiments, each $R_{2S}$ independently is 3- to 7-membered heterocycloalkyl.

In some embodiments, each $R_{2S}$ independently is 3-membered heterocycloalkyl. In some embodiments, each $R_{2S}$ independently is 4-membered heterocycloalkyl. In some embodiments, each $R_{2S}$ independently is 5-membered heterocycloalkyl. In some embodiments, each $R_{2S}$ independently is 6-membered heterocycloalkyl. In some embodiments, each $R_{2S}$ independently is 7-membered heterocycloalkyl.

In some embodiments, each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, each $R_3$ independently is halogen, —CN, —OH, —$NH_2$, —NH($C_1$-$C_6$ alkyl), or —N($C_1$-$C_6$ alkyl)$_2$.

In some embodiments, each $R_3$ independently is halogen.

In some embodiments, each $R_3$ independently is F, Cl, Br, or I. In some embodiments, each $R_3$ independently is F, Cl, or Br. In some embodiments, each $R_3$ independently is F or Cl.

In some embodiments, each $R_3$ independently is F. In some embodiments, each $R_3$ independently is $C_1$. In some embodiments, each $R_3$ independently is Br. In some embodiments, each $R_3$ independently is I.

In some embodiments, each $R_3$ independently is —CN.

In some embodiments, each $R_3$ independently is —OH.

In some embodiments, each $R_3$ independently is —$NH_2$, —NH($C_1$-$C_6$ alkyl), or —N($C_1$-$C_6$ alkyl)$_2$.

In some embodiments, each $R_3$ independently is —$NH_2$.

In some embodiments, each $R_3$ independently is —NH ($C_1$-$C_6$ alkyl).

In some embodiments, each $R_3$ independently is —NH (methyl). In some embodiments, each $R_3$ independently is —NH(ethyl). In some embodiments, each $R_3$ independently is —NH(propyl). In some embodiments, each $R_3$ independently is —NH(butyl). In some embodiments, each $R_3$ independently is —NH(pentyl). In some embodiments, each $R_3$ independently is —NH(hexyl).

In some embodiments, each $R_3$ independently is —N($C_1$-$C_6$ alkyl)$_2$.

In some embodiments, each $R_3$ independently is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, each $R_3$ independently is $C_1$-$C_6$ alkyl, $C_2$-$C_6$ alkenyl, or $C_2$-$C_6$ alkynyl.

In some embodiments, each $R_3$ independently is $C_1$-$C_6$ alkyl.

In some embodiments, each $R_3$ independently is methyl. In some embodiments, each $R_3$ independently is ethyl. In some embodiments, each $R_3$ independently is propyl. In some embodiments, each $R_3$ independently is butyl. In some embodiments, each $R_3$ independently is pentyl. In some embodiments, each $R_3$ independently is hexyl. In some embodiments, each $R_3$ independently is isopropyl. In some embodiments, each $R_3$ independently is isobutyl. In some embodiments, each $R_3$ independently is isopentyl. In some embodiments, each $R_3$ independently is isohexyl. In some embodiments, each $R_3$ independently is secbutyl. In some embodiments, each $R_3$ independently is secpentyl. In some embodiments, each $R_3$ independently is sechexyl. In some embodiments, each $R_3$ independently is tertbutyl.

In some embodiments, each $R_3$ independently is $C_2$-$C_6$ alkenyl.

In some embodiments, each $R_3$ independently is $C_2$ alkenyl. In some embodiments, each $R_3$ independently is $C_3$ alkenyl. In some embodiments, each $R_3$ independently is $C_4$ alkenyl. In some embodiments, each $R_3$ independently is $C_5$ alkenyl. In some embodiments, each $R_3$ independently is $C_6$ alkenyl.

In some embodiments, each $R_3$ independently is $C_2$-$C_6$ alkynyl.

In some embodiments, each $R_3$ independently is $C_2$ alkynyl. In some embodiments, each $R_3$ independently is $C_3$ alkynyl. In some embodiments, each $R_3$ independently is $C_4$ alkynyl. In some embodiments, each $R_3$ independently is $C_5$ alkynyl. In some embodiments, each $R_3$ independently is $C_6$ alkynyl.

In some embodiments, each $R_3$ independently is $C_1$-$C_6$ haloalkyl or $C_{1-6}$ alkoxy.

In some embodiments, each $R_3$ independently is $C_1$-$C_6$ haloalkyl.

In some embodiments, each $R_3$ independently is halomethyl. In some embodiments, each $R_3$ independently is haloethyl. In some embodiments, each $R_3$ independently is halopropyl. In some embodiments, each $R_3$ independently is halobutyl. In some embodiments, each $R_3$ independently is halopentyl. In some embodiments, each $R_3$ independently is halohexyl.

In some embodiments, each $R_3$ independently is $C_{1-6}$ alkoxy.

In some embodiments, each $R_3$ independently is methoxy. In some embodiments, each $R_3$ independently is ethoxy. In some embodiments, each $R_3$ independently is propoxy. In some embodiments, each $R_3$ independently is butoxy. In some embodiments, each $R_3$ independently is pentoxy. In some embodiments, each $R_3$ independently is hexoxy.

In some embodiments, $R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

In some embodiments, $R_{4a}$ is halogen, —CN, —OH, —$NH_2$, —NH($C_1$-$C_6$ alkyl), or —N($C_1$-$C_6$ alkyl)$_2$.

In some embodiments, $R_{4a}$ is halogen.

In some embodiments, $R_{4a}$ is F, Cl, Br, or I. In some embodiments, $R_{4a}$ is F, Cl, or Br. In some embodiments, $R_{4a}$ is F or Cl.

In some embodiments, RU is F. In some embodiments, $R_{4a}$ is $C_1$. In some embodiments, $R_{4a}$ is Br. In some embodiments, $R_{4a}$ is I.

In some embodiments, $R_{4a}$ is —CN.

In some embodiments, $R_{4a}$ is —OH.

In some embodiments, $R_{4a}$ is —$NH_2$, —NH($C_1$-$C_6$ alkyl), or —N($C_1$-$C_6$ alkyl)$_2$.

In some embodiments, $R_{4a}$ is —$NH_2$.

In some embodiments, $R_{4a}$ is —NH($C_1$-$C_6$ alkyl).

In some embodiments, $R_{4a}$ is —NH(methyl). In some embodiments, $R_{4a}$ is —NH(ethyl). In some embodiments, $R_{4a}$ is —NH(propyl). In some embodiments, $R_{4a}$ is —NH (butyl). In some embodiments, $R_{4a}$ is —NH(pentyl). In some embodiments, $R_{4a}$ is —NH(hexyl).

In some embodiments, $R_{4a}$ is —N($C_1$-$C_6$ alkyl)$_2$.

In some embodiments, $R_{4a}$ is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, $R_{4a}$ is H, $C_1$-$C_6$ alkyl, $C_2$-$C_6$ alkenyl, $C_2$-$C_6$ alkynyl, or $C_1$-$C_6$ haloalkyl.

In some embodiments, $R_{4a}$ is H.

In some embodiments, $R_{4a}$ is $C_1$-$C_6$ alkyl, $C_2$-$C_6$ alkenyl, $C_2$-$C_6$ alkynyl, or $C_1$-$C_6$ haloalkyl.

In some embodiments, $R_{4a}$ is $C_1$-$C_6$ alkyl, $C_2$-$C_6$ alkenyl, or $C_2$-$C_6$ alkynyl.

In some embodiments, $R_{4a}$ is $C_1$-$C_6$ alkyl.

In some embodiments, $R_{4a}$ is methyl. In some embodiments, $R_{4a}$ is ethyl. In some embodiments, $R_{4a}$ is propyl. In some embodiments, $R_{4a}$ is butyl. In some embodiments, $R_{4a}$ is pentyl. In some embodiments, $R_{4a}$ is hexyl. In some embodiments, $R_{4a}$ is isopropyl. In some embodiments, $R_{4a}$ is isobutyl. In some embodiments, $R_{4a}$ is isopentyl. In some embodiments, $R_{4a}$ is isohexyl. In some embodiments, Ria is secbutyl. In some embodiments, $R_{4a}$ is secpentyl. In some embodiments, Ria is sechexyl. In some embodiments, $R_{4a}$ is tertbutyl.

In some embodiments, $R_{4a}$ is $C_2$-$C_6$ alkenyl.

In some embodiments, $R_{4a}$ is $C_2$ alkenyl. In some embodiments, $R_{4a}$ is $C_3$ alkenyl. In some embodiments, $R_{4a}$ is $C_4$ alkenyl. In some embodiments, $R_{4a}$ is $C_5$ alkenyl. In some embodiments, $R_{4a}$ is $C_6$ alkenyl.

In some embodiments, $R_{4a}$ is $C_2$-$C_6$ alkynyl.

In some embodiments, $R_{4a}$ is $C_2$ alkynyl. In some embodiments, $R_{4a}$ is $C_3$ alkynyl. In some embodiments, $R_{4a}$ is $C_4$ alkynyl. In some embodiments, $R_{4a}$ is $C_5$ alkynyl. In some embodiments, $R_{4a}$ is $C_6$ alkynyl.

In some embodiments, $R_{4a}$ is $C_1$-$C_6$ haloalkyl.

In some embodiments, $R_{4a}$ is halomethyl. In some embodiments, $R_{4a}$ is haloethyl. In some embodiments, $R_{4a}$ is halopropyl. In some embodiments, $R_{4a}$ is halobutyl. In some embodiments, $R_{4a}$ is halopentyl. In some embodiments, $R_{4a}$ is halohexyl.

In some embodiments, $R_{4a}$ is $C_{1-6}$ alkoxy.

In some embodiments, $R_{4a}$ is methoxy. In some embodiments, $R_{4a}$ is ethoxy. In some embodiments, $R_{4a}$ is propoxy. In some embodiments, $R_{4a}$ is butoxy. In some embodiments, $R_{4a}$ is pentoxy. In some embodiments, $R_{4a}$ is hexoxy.

In some embodiments, $R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

In some embodiments, $R_{4b}$ is halogen, —CN, —OH, —$NH_2$, —NH($C_1$-$C_6$ alkyl), or —N($C_1$-$C_6$ alkyl)$_2$.

In some embodiments, $R_{4b}$ is halogen.

In some embodiments, $R_{4b}$ is F, Cl, Br, or I. In some embodiments, $R_{4b}$ is F, Cl, or Br. In some embodiments, $R_{4b}$ is F or Cl.

In some embodiments, $R_{4b}$ is F. In some embodiments, $R_{4b}$ is $C_1$. In some embodiments, $R_{4b}$ is Br. In some embodiments, $R_{4b}$ is I.

In some embodiments, $R_{4b}$ is —CN.

In some embodiments, $R_{4b}$ is —OH.

In some embodiments, $R_{4b}$ is —$NH_2$, —NH($C_1$-$C_6$ alkyl), or —N($C_1$-$C_6$ alkyl)$_2$.

In some embodiments, $R_{4b}$ is —$NH_2$.

In some embodiments, $R_{4b}$ is —NH($C_1$-$C_6$ alkyl).

In some embodiments, $R_{4b}$ is —NH(methyl). In some embodiments, $R_{4b}$ is —NH(ethyl). In some embodiments, $R_{4b}$ is —NH(propyl). In some embodiments, $R_{4b}$ is —NH (butyl). In some embodiments, $R_{4b}$ is —NH(pentyl). In some embodiments, $R_{4b}$ is —NH(hexyl).

In some embodiments, $R_{4b}$ is —N($C_1$-$C_6$ alkyl)$_2$.

In some embodiments, $R_{4b}$ is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

In some embodiments, $R_{4b}$ is H, $C_1$-$C_6$, alkyl, $C_2$-$C_6$ alkenyl, $C_2$-$C_6$ alkynyl, or $C_1$-$C_6$ haloalkyl.

In some embodiments, $R_{4b}$ is H.

In some embodiments, $R_{4b}$ is $C_1$-$C_6$ alkyl, $C_2$-$C_6$ alkenyl, $C_2$-$C_6$ alkynyl, or $C_1$-$C_6$ haloalkyl.

In some embodiments, $R_{4b}$ is $C_1$-$C_6$ alkyl, $C_2$-$C_6$ alkenyl, or $C_2$-$C_6$ alkynyl.

In some embodiments, $R_{4b}$ is $C_1$-$C_6$ alkyl.

In some embodiments, $R_{4b}$ is methyl. In some embodiments, $R_{4b}$ is ethyl. In some embodiments, $R_{4b}$ is propyl. In some embodiments, $R_{4b}$ is butyl. In some embodiments, $R_{4b}$ is pentyl. In some embodiments, $R_{4b}$ is hexyl. In some embodiments, $R_{4b}$ is isopropyl. In some embodiments, $R_{4b}$ is isobutyl. In some embodiments, $R_{4b}$ is isopentyl. In some embodiments, $R_{4b}$ is isohexyl. In some embodiments, $R_{4b}$ is secbutyl. In some embodiments, $R_{4b}$ is secpentyl. In some embodiments, $R_{4b}$ is sechexyl. In some embodiments, $R_{4b}$ is tertbutyl.

In some embodiments, $R_{4b}$ is $C_2$-$C_6$ alkenyl.

In some embodiments, $R_{4b}$ is $C_2$ alkenyl. In some embodiments, $R_{4b}$ is $C_3$ alkenyl. In some embodiments, $R_{4b}$ is $C_4$ alkenyl. In some embodiments, $R_{4b}$ is $C_5$ alkenyl. In some embodiments, $R_{4b}$ is $C_6$ alkenyl.

In some embodiments, $R_{4b}$ is $C_2$-$C_6$ alkynyl.

In some embodiments, $R_{4b}$ is $C_2$ alkynyl. In some embodiments, $R_{4b}$ is $C_3$ alkynyl. In some embodiments, $R_{4b}$ is $C_4$ alkynyl. In some embodiments, $R_{4b}$ is $C_5$ alkynyl. In some embodiments, $R_{4b}$ is $C_6$ alkynyl.

In some embodiments, $R_{4b}$ is $C_1$-$C_6$ haloalkyl.

In some embodiments, $R_{4b}$ is halomethyl. In some embodiments, $R_{4b}$ is haloethyl. In some embodiments, $R_{4b}$ is halopropyl. In some embodiments, $R_{4b}$ is halobutyl. In some embodiments, $R_{4b}$ is halopentyl. In some embodiments, $R_{4b}$ is halohexyl.

In some embodiments, $R_{4b}$ is $C_{1-6}$ alkoxy.

In some embodiments, $R_{4b}$ is methoxy. In some embodiments, $R_{4b}$ is ethoxy. In some embodiments, $R_{4b}$ is propoxy. In some embodiments, $R_{4b}$ is butoxy. In some embodiments, $R_{4b}$ is pentoxy. In some embodiments, $R_{4b}$ is hexoxy.

In some embodiments, n is 0, 1, 2, or 3. In some embodiments, n is 0, 1, or 2. In some embodiments, n is 0 or 1.

In some embodiments, n is 0. In some embodiments, n is 1. In some embodiments, n is 2. In some embodiments, n is 3.

In some embodiments, m is 0, 1, 2, 3, 4, or 5. In some embodiments, m is 0, 1, 2, 3, or 4. In some embodiments, m is 0, 1, 2, or 3. In some embodiments, m is 0, 1, or 2. In some embodiments, m is 0 or 1.

In some embodiments, m is 0. In some embodiments, m is 1. In some embodiments, m is 2. In some embodiments, m is 3. In some embodiments, m is 4. In some embodiments, m is 5.

In some embodiments, p is 0, 1, 2, 3, or 4. In some embodiments, p is 0, 1, 2, or 3. In some embodiments, p is 0, 1, or 2. In some embodiments, p is 0 or 1.

In some embodiments, p is 0. In some embodiments, p is 1. In some embodiments, p is 2. In some embodiments, p is 3. In some embodiments, p is 4.

In some embodiments, the compound is of Forula (I-1):

(I-1)

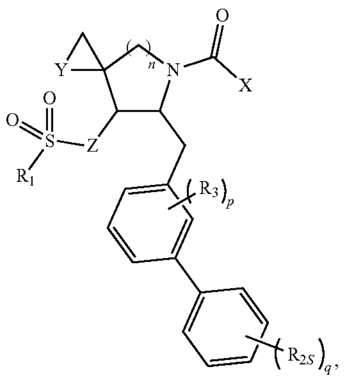

or a prodrug, solvate, or pharmaceutically acceptable salt thereof, wherein q is 0, 1, 3, 4, or 5.

In some embodiments, the compound is of Formula (I-1) or a prodrug, solvate, or pharmaceutically acceptable salt thereof.

In some embodiments, the compound is of Formula (I-1a), (I-1b), or (I-1c):

(I-1a)

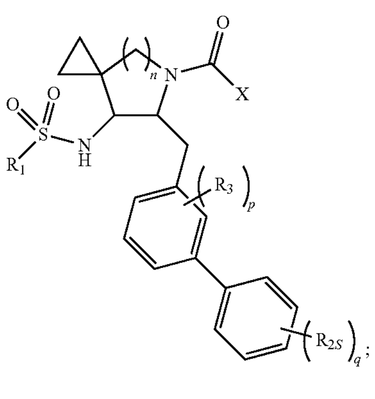

-continued (I-1b)

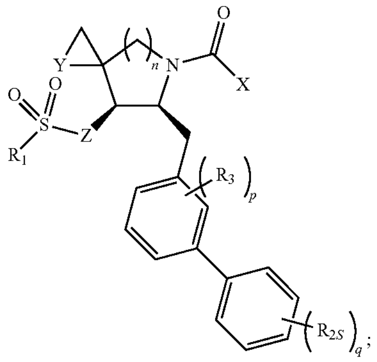

or (I-1c)

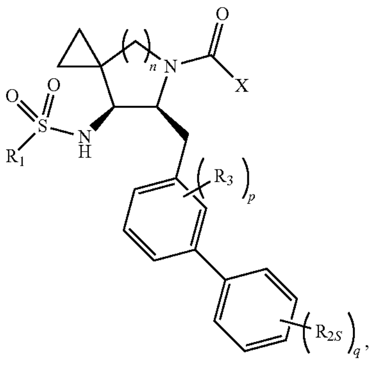

or a prodrug, solvate, or pharmaceutically acceptable salt thereof, wherein q is 0, 1, 2, 3, 4, or 5.

In some embodiments, the compound is of Formula (I-1a) or a prodrug, solvate, or pharmaceutically acceptable salt thereof.

In some embodiments, the compound is of Formula (I-1b) or a prodrug, solvate, or pharmaceutically acceptable salt thereof.

In some embodiments, the compound is of Formula (I-1c) or a prodrug, solvate, or pharmaceutically acceptable salt thereof.

In some embodiments, the compound is of Formula (I-2):

(I-2)

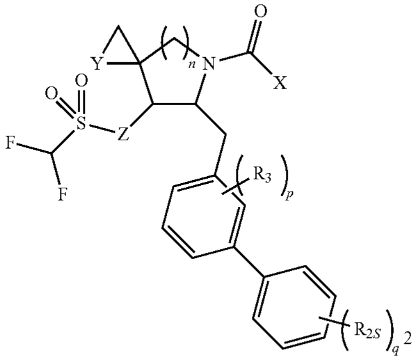

or a prodrug, solvate, or pharmaceutically acceptable salt thereof, wherein q is 0, 1, 2, 3, 4, or 5.

In some embodiments, the compound is of Formula (I-2) or a prodrug, solvate, or pharmaceutically acceptable salt thereof.

In some embodiments, the compound is of Formula (I-2a), (I-2b), or (I-2c):

(I-2a)

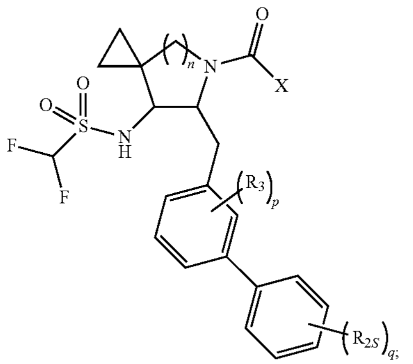

(I-2b)

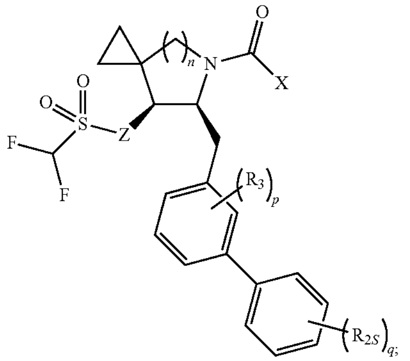

or (I-2c)

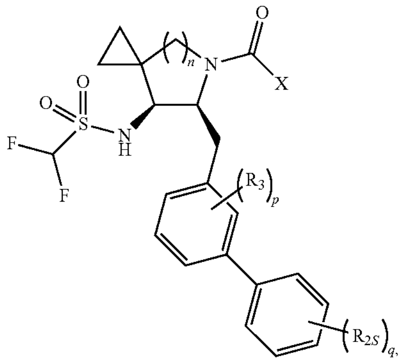

or a prodrug, solvate, or pharmaceutically acceptable salt thereof, wherein q is 0, 1, 2, 3, 4, or 5.

In some embodiments, the compound is of Formula (I-2a) or a prodrug, solvate, or pharmaceutically acceptable salt thereof.

In some embodiments, the compound is of Formula (I-2b) or a prodrug, solvate, or pharmaceutically acceptable salt thereof.

In some embodiments, the compound is of Formula (I-2c) or a prodrug, solvate, or pharmaceutically acceptable salt thereof.

In some embodiments, the compound is of Formula (I-3):

(I-3)

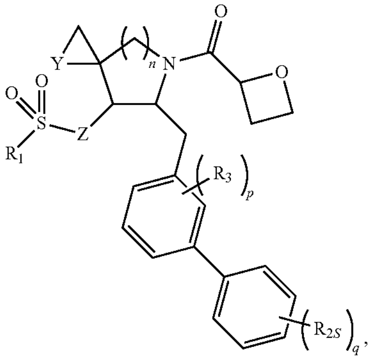

or a prodrug, solvate, or pharmaceutically acceptable salt thereof, wherein q is 0, 1, 2, 3, 4, or 5.

In some embodiments, the compound is of Formula (I-3) or a prodrug, solvate, or pharmaceutically acceptable salt thereof.

In some embodiments, the compound is of Formula (I-3a), (I-3b), or (I-3c):

(I-3a)

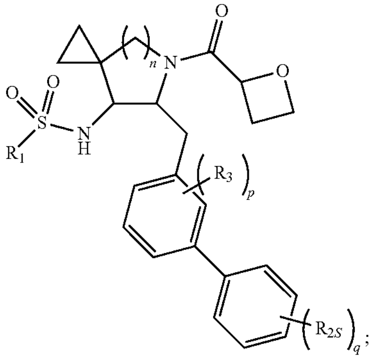

(I-3b)

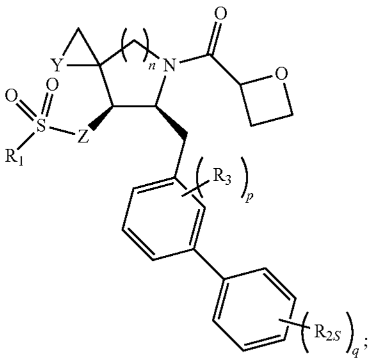

or

-continued (I-3c)

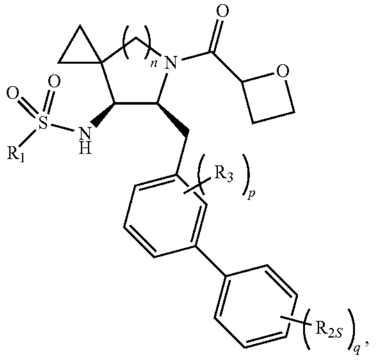

or a prodrug, solvate, or pharmaceutically acceptable salt thereof, wherein q is 0, 1, 2, 3, 4, or 5.

In some embodiments, the compound is of Formula (I-3a) or a prodrug, solvate, or pharmaceutically acceptable salt thereof.

In some embodiments, the compound is of Formula (I-3b) or a prodrug, solvate, or pharmaceutically acceptable salt thereof.

In some embodiments, the compound is of Formula (I-3c) or a prodrug, solvate, or pharmaceutically acceptable salt thereof.

In some embodiments, the compound is of Formula (II-1):

(II-1)

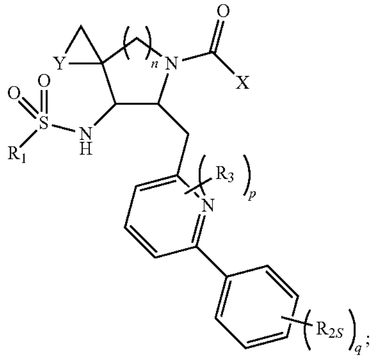

or a prodrug, solvate, or pharmaceutically acceptable salt thereof, wherein q is 0, 1, 2, 3, 4, or 5.

In some embodiments, the compound is of Formula (II-1) or a prodrug, solvate, or pharmaceutically acceptable salt thereof.

In some embodiments, the compound is of Formula (II-1a), (II-1b), or (II-1c):

(II-1a)

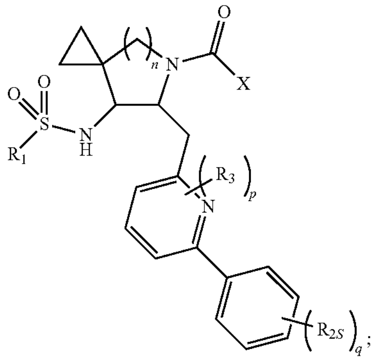

(II-1b)

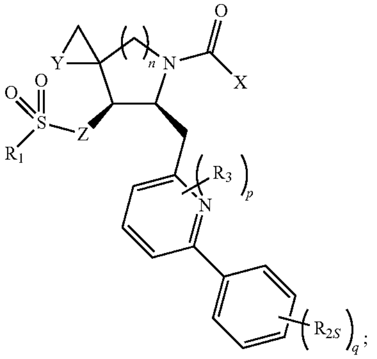

or (II-1c)

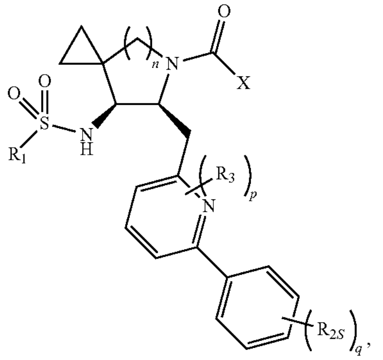

or a prodrug, solvate, or pharmaceutically acceptable salt thereof, wherein q is 0, 1, 2, 3, 4, or 5.

In some embodiments, the compound is of Formula (II-1a) or a prodrug, solvate, or pharmaceutically acceptable salt thereof.

In some embodiments, the compound is of Formula (II-1b) or a prodrug, solvate, or pharmaceutically acceptable salt thereof.

In some embodiments, the compound is of Formula (II-1c) or a prodrug, solvate, or pharmaceutically acceptable salt thereof.

In some embodiments, the compound is of Formula (III-1):

(III-1)

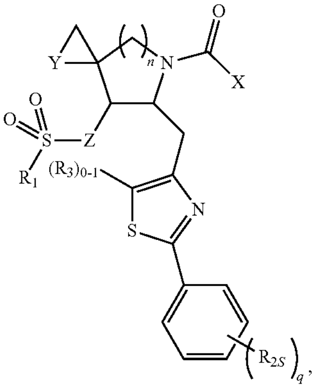

or a prodrug, solvate, or pharmaceutically acceptable salt thereof, wherein q is 0, 1, 2, 3, 4, or 5.

In some embodiments, the compound is of Formula (III-1) or a prodrug, solvate, or pharmaceutically acceptable salt thereof.

In some embodiments, the compound is of Formula (III-1a), (III-1b), or (III-1c):

(III-1a)

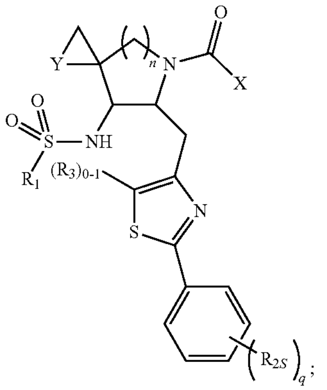

(III-2a)

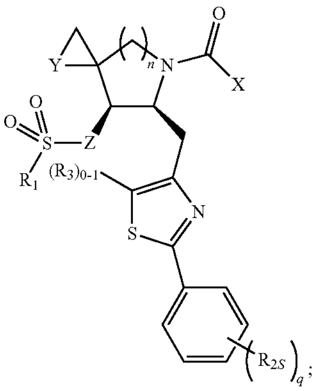

or

-continued (III-3a)

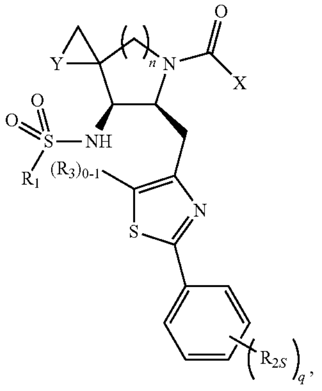

or a prodrug, solvate, or pharmaceutically acceptable salt thereof, wherein q is 0, 1, 2, 3, 4, or 5.

In some embodiments, the compound is of Formula (III-1a) or a prodrug, solvate, or pharmaceutically acceptable salt thereof.

In some embodiments, the compound is of Formula (III-1b) or a prodrug, solvate, or pharmaceutically acceptable salt thereof.

In some embodiments, the compound is of Formula (III-1c) or a prodrug, solvate, or pharmaceutically acceptable salt thereof.

In some embodiments, a compound of Formula (I") is a compound of Formula (I-1), Formula (I-1a), Formula (I-1b), Formula (I-1c), Formula (I-2), Formula (I-2a), Formula (I-2b), Formula (I-2c), Formula (I-3), Formula (I-3a), Formula (I-3b), Formula (I-3c), Formula (II-1), Formula (II-1a), Formula (II-1b), Formula (II-1c), Formula (III-1), Formula (III-1a), Formula (III-1b), or Formula (III-1c) or a prodrug, solvate, or pharmaceutically acceptable salt thereof.

In some embodiments, a compound of Formula (I') is a compound of Formula (I-1), Formula (I-1a), Formula (I-1b), Formula (I-1c), Formula (I-2), Formula (I-2a), Formula (I-2b), Formula (I-2c), Formula (I-3), Formula (I-3a), Formula (I-3b), Formula (I-3c), Formula (II-1), Formula (II-1a), Formula (II-1b), Formula (II-1c), Formula (III-1), Formula (III-1a), Formula (III-1b), or Formula (III-1c) or a prodrug, solvate, or pharmaceutically acceptable salt thereof.

In some embodiments, a compound of Formula (I') is a compound of Formula (I-1), Formula (I-1a), Formula (I-1b), Formula (I-1c), Formula (I-2), Formula (I-2a), Formula (I-2b), Formula (I-2c), Formula (I-3), Formula (I-3a), Formula (I-3b), Formula (I-3c), Formula (II-1), Formula (II-1a), Formula (II-1b), Formula (II-1c), Formula (III-1), Formula (III-1a), Formula (III-1 b), or Formula (III-1c) or a prodrug, solvate, or pharmaceutically acceptable salt thereof.

In some embodiments, a compound of Formula (I) is a compound of Formula (I-1), Formula (I-1a), Formula (I-1b), or Formula (I-1c), or a prodrug, solvate, or pharmaceutically acceptable salt thereof.

In some embodiments, a compound of Formula (II) is a compound of Formula (II-1), Formula (II-1a), Formula (II-1b), or Formula (II-1c), or a prodrug, solvate, or pharmaceutically acceptable salt thereof.

In some embodiments, a compound of Formula (III) is a compound of Formula (III-1), Formula (III-1a), Formula (III-1b), or Formula (III-1c), or a prodrug, solvate, or pharmaceutically acceptable salt thereof.

It is understood that, for a compound of any one of the formulae described herein, X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4b}$, n, m, or p can each be, where applicable, selected from the groups described herein, and any group described herein for any of X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4b}$, n, m, or p can be combined, where applicable, with any group described herein for one or more of the remainder of X, Y, Z, $R_{X1}$, $R_{X2}$, $R_Y$, $R_Z$, $Ar_1$, $R_1$, $R_{1S}$, $R_2$, $R_{2S}$, $R_3$, $R_{4a}$, $R_{4b}$, n, m, or p.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the prodrugs of compounds described in Table 1 and pharmaceutically acceptable salts thereof.

In some embodiments, the compound is selected from the compounds described in Table 1.

In some embodiments, the compound is selected from the compounds described in Table 2 and prodrugs and pharmaceutically acceptable salts thereof.

In some embodiments, the compound is selected from the compounds described in Table 2 and pharmaceutically acceptable salts thereof.

In some embodiments, the compound is selected from the prodrugs of compounds described in Table 2 and pharmaceutically acceptable salts thereof.

In some embodiments, the compound is selected from the compounds described in Table 1.

In some embodiments, the compound is selected from the compounds described in Table 3 and prodrugs and pharmaceutically acceptable salts thereof.

In some embodiments, the compound is selected from the compounds described in Table 3 and pharmaceutically acceptable salts thereof.

In some embodiments, the compound is selected from the prodrugs of compounds described in Table 3 and pharmaceutically acceptable salts thereof.

In some embodiments, the compound is selected from the compounds described in Table 3.

In some embodiments, the compound is selected from the compounds described in Table 4 and prodrugs and pharmaceutically acceptable salts thereof.

In some embodiments, the compound is selected from the compounds described in Table 4 and pharmaceutically acceptable salts thereof.

In some embodiments, the compound is selected from the prodrugs of compounds described in Table 4 and pharmaceutically acceptable salts thereof.

In some embodiments, the compound is selected from the compounds described in Table 4.

In some embodiments, the compound is selected from the compounds described in Table 5 and prodrugs and pharmaceutically acceptable salts thereof.

In some embodiments, the compound is selected from the compounds described in Table 5 and pharmaceutically acceptable salts thereof.

In some embodiments, the compound is selected from the prodrugs of compounds described in Table 5 and pharmaceutically acceptable salts thereof.

In some embodiments, the compound is selected from the compounds described in Table 5.

TABLE 1

| Compound No. | Name | Structure |
|---|---|---|
| 1 | N-(6-([1,1'-biphenyl]-3-ylmethyl)-5-(2-fluoropropanoyl)-5-azaspiro[2.4]heptan-7-yl)methanesulfonamide_cis racemic_isomer 1 | 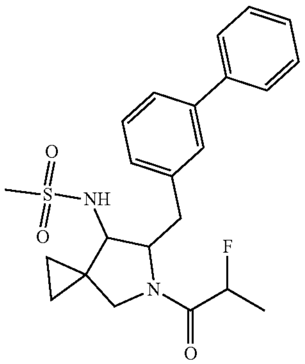 [SMILES: CC(F)C(=O)N1CC2(CC2)C(NS(C)(=O)=O)C1Cc1cccc(-c2ccccc2)c1] |
| 2 | N-(6-([1,1'-biphenyl]-3-ylmethyl)-5-(2-fluoropropanoyl)-5-azaspiro[2.4]heptan-7-yl)methanesulfonamide_cis racemic_isomer 2 | 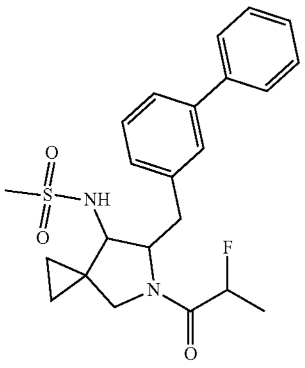 [SMILES: CC(F)C(=O)N1CC2(CC2)C(NS(C)(=O)=O)C1Cc1cccc(-c2ccccc2)c1] |

TABLE 1-continued

| Compound No. | Name | Structure |
| --- | --- | --- |
| 3 | N-(6-([1,1'-biphenyl]-3-lmethyl)-5-(azetidine-1-carbonyl)-5-azaspiro[2.4]heptan-7-ylethanesulfonamide_cis racemic | 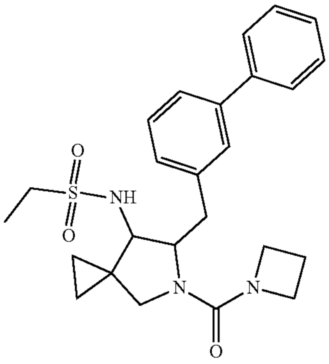 [SMILES: CCS(=O)(=O)NC1C(Cc2cccc(-c3ccccc3)c2)N(C(=O)N2CCC2)CC12CC2] |
| 4 | N-(6-([1,1'-biphenyl]-3-ylmethyl)-5-(2,2,2-trifluoroacetyl)-5-azaspiro[2.4]heptan-7-yl)methanesulfonamide_cis racemic | 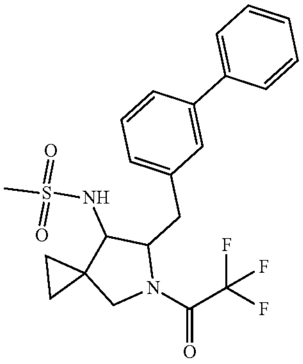 |
| 5 | N-(6-([1,1'-biphenyl]-3-ylmethyl)-5-(2,2-difluoroacetyl)-5-azaspiro[2.4]heptan-7-yl)methanesulfonamide_cis racemic | 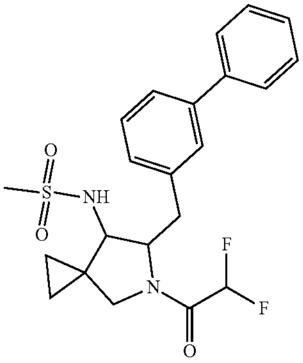 [SMILES: CS(=O)(=O)NC1C(Cc2cccc(-c3ccccc3)c2)N(C(=O)C(F)F)CC12CC2] |
| 6 | methyl 6-([1,1'-biphenyl]-3-ylmethyl)-7-(ethylsulfonamido)-5-azaspiro[2.4]heptane-5-carboxylate_cis racemic | 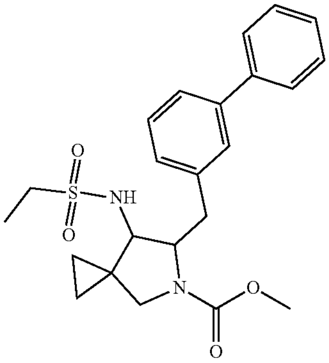 [SMILES: CCS(=O)(=O)NC1C(Cc2cccc(-c3ccccc3)c2)N(C(=O)OC)CC12CC2] |

TABLE 1-continued

| Compound No. | Name | Structure |
| --- | --- | --- |
| 7 | N-(6-([1,1-biphenyl]-3-ylmethyl)-5-isobutyryl-5-azaspiro[2.4]heptan-7-yl)ethanesulfonamide_cis racemic | 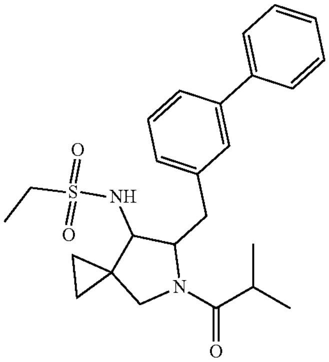 [SMILES: CCS(=O)(=O)NC1C(Cc2cccc(-c3ccccc3)c2)N(C(=O)C(C)C)CC12CC2] |
| 8 | N-(6-((3'-fluoro-[1,1'-biphenyl]-3-yl)methyl)-5-isobutyryl-5-azaspiro[2.4]heptan-7-yl)methanesulfonamide_cis racemic | 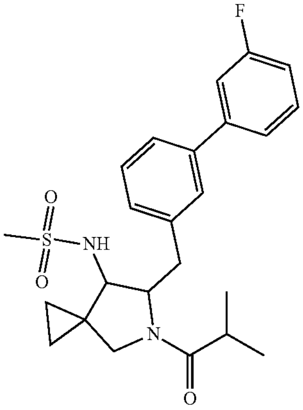 [SMILES: CC(C)C(=O)N1CC2(CC2)C(NS(C)(=O)=O)C1Cc1cccc(-c2cccc(F)c2)c1] |
| 9 | N-(6-([1,1'-biphenyl]-3-ylmethyl)-5-(2,2-difluoropropanoyl)-5-azaspiro[2.4]heptan-7-yl)methanesulfonamide_cis racemic | 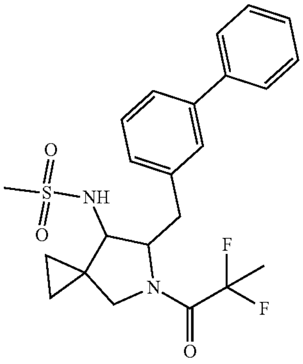 |
| 10 | N-(6-([1,1'-biphenyl]-3-ylmethyl)-5-(3,3-difluoroazetidine-1-carbonyl)-5-azaspiro[2.4]heptan-7-yl)methanesulfonamide_cis racemic | 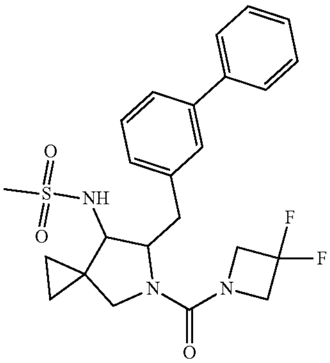 [SMILES: CS(=O)(=O)NC1C(Cc2cccc(-c3ccccc3)c2)N(C(=O)N2CC(F)(F)C2)CC12CC2] |

TABLE 1-continued

| Compound No. | Name | Structure |
|---|---|---|
| 11 | N-(6-([1,1'-biphenyl]-3-ylmethyl)-5-(3-fluoroazetidine-1-carbonyl)-5-azaspiro[2.4]heptan-7-yl)methanesulfonamide_cis racemic | 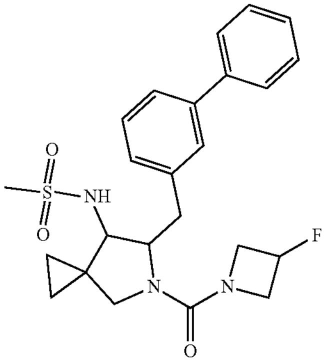 [SMILES: CS(=O)(=O)NC1C(Cc2cccc(-c3ccccc3)c2)N(C(=O)N2CC(F)C2)CC12CC2] |
| 12 | N-(6-([1,1-biphenyl]-3-ylmethyl)-5-(3,3-difluorocyclobutane-1-carbonyl)-5-azaspiro[2.4]heptan-7-yl)methanesulfonamide_cis racemic | 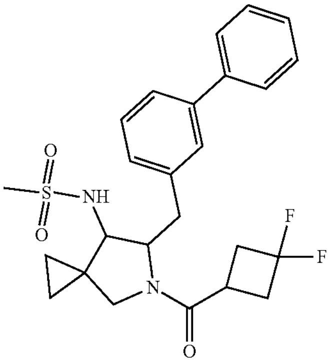 [SMILES: CS(=O)(=O)NC1C(Cc2cccc(-c3ccccc3)c2)N(C(=O)C2CC(F)(F)C2)CC12CC2] |
| 13 | N-(6-([1,1'-biphenyl]-3-ylmethyl)-5-(2-fluoro-2-methylpropanoyl)-5-azaspiro[2.4]heptan-7-yl)methanesulfonamide_cis racemic | 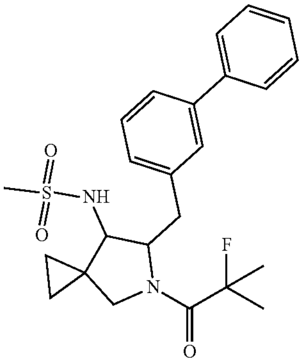 [SMILES: CC(C)(F)C(=O)N1CC2(CC2)C(NS(C)(=O)=O)C1Cc1cccc(-c2ccccc2)c1] |
| 14 | methyl 5-([1,1'-biphenyl]-3-ylmethyl)-4-(methylsulfonamido)-6-azaspiro[2.5]octane-6-carboxylate_cis racemic | 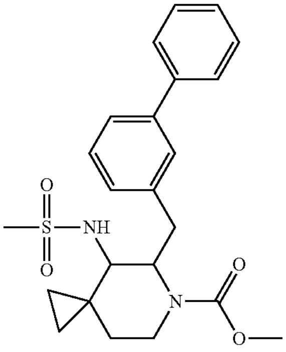 |

TABLE 1-continued

| Compound No. | Name | Structure |
|---|---|---|
| 15 | N-(6-([1,1'-biphenyl]-3-ylmethyl)-5-isobutyryl-5-azaspiro[2.4]heptan-7-yl)methanesulfonamide_cis racemic | 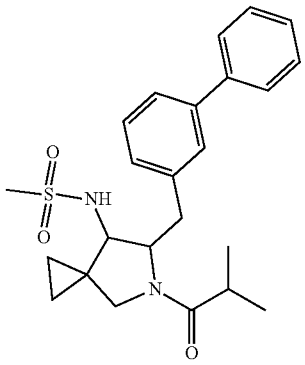 [SMILES: CC(C)C(=O)N1CC2(CC2)C(NS(C)(=O)=O)C1Cc1cccc(-c2ccccc2)c1] |
| 16 | N-((6R,7R)-6-([1,1'-biphenyl]-3-ylmethyl)-5-isobutyryl-5-azaspiro[2.4]heptan-7-yl)methanesulfonamide | 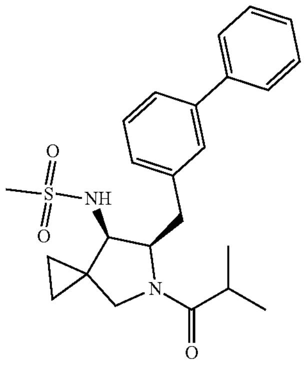 [SMILES: CC(C)C(=O)N1CC2(CC2)[C@@H](NS(C)(=O)=O)[C@H]1Cc1cccc(-c2ccccc2)c1] |
| 17 | N-((6S,7S)-6-([1,1'-biphenyl]-3-ylmethyl)-5-isobutyryl-5-azaspiro[2.4]heptan-7-yl)methanesulfonamide | 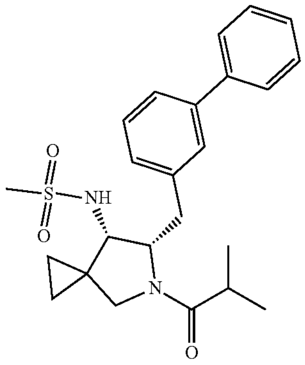 [SMILES: CC(C)C(=O)N1CC2(CC2)[C@H](NS(C)(=O)=O)[C@@H]1Cc1cccc(-c2ccccc2)c1] |
| 18 | N-(5-(azetidine-1-carbonyl)-6-((2-fluoro-[1,1'-biphenyl]-3-yl)methyl)-5-azaspiro[2.4]heptan-7-yl)methanesulfonamide_cis racemic | 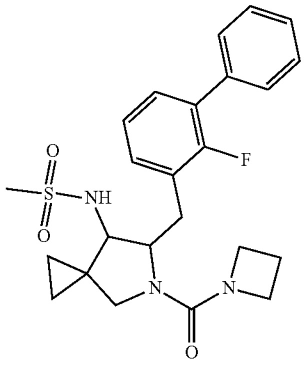 [SMILES: CS(=O)(=O)NC1C(Cc2cccc(-c3ccccc3)c2F)N(C(=O)N2CCC2)CC12CC2] |

TABLE 1-continued

| Compound No. | Name | Structure |
|---|---|---|
| 19 | N-((6R,7R)-6-((2-fluoro-[1,1'-biphenyl]-3-yl)methyl)-5-((S)-oxetane-2-carbonyl)-5-azaspiro[2.4]heptan-7-yl)methanesulfonamide | 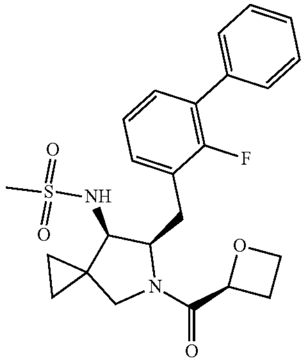 [SMILES: CS(=O)(=O)N[C@H]1[C@@H](Cc2cccc(-c3ccccc3)c2F)N(C(=O)[C@@H]2CCO2)CC12CC2] |
| 20 | N-((6S,7S)-6-((2-fluoro-[1,1'-biphenyl]-3-yl)methyl)-5-((S)-oxetane-2-carbonyl)-5-azaspiro[2.4]heptan-7-yl)methanesulfonamide | 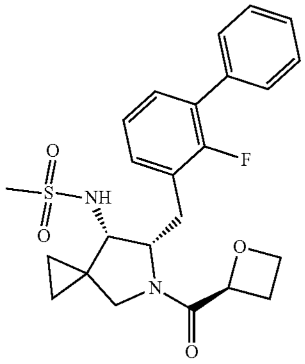 [SMILES: CS(=O)(=O)N[C@@H]1[C@H](Cc2cccc(-c3ccccc3)c2F)N(C(=O)[C@@H]2CCO2)CC12CC2] |
| 21 | N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide | 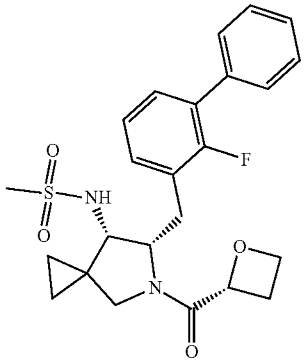 [SMILES: CS(=O)(=O)N[C@@H]1[C@H](Cc2cccc(-c3ccccc3)c2F)N(C(=O)[C@H]2CCO2)CC12CC2] |
| 22 | N-((6R,7R)-6-((2-fluoro-[1,1'-biphenyl]-3-yl)methyl)-5-((R)-oxetane-2-carbonyl)-5-azaspiro[2.4]heptan-7-yl)methanesulfonamide | 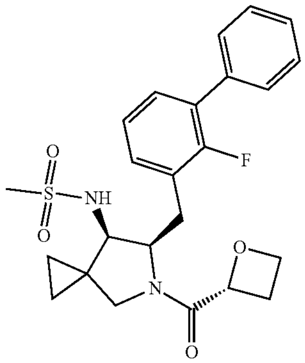 [SMILES: CS(=O)(=O)N[C@H]1[C@@H](Cc2cccc(-c3ccccc3)c2F)N(C(=O)[C@H]2CCO2)CC12CC2] |

TABLE 1-continued

| Compound No. | Name | Structure |
|---|---|---|
| 23 | N-(6-(2,3'-difluoro-[1,1'-biphenyl]-3-yl)methyl)-5-pivaloyl-5-azaspiro[2.4]heptan-7-yl)methanesulfonamide_cis racemic | 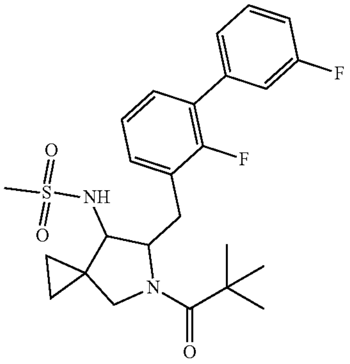 [SMILES: CC(C)(C)C(=O)N1CC2(CC2)C(NS(C)(=O)=O)C1Cc1cccc(-c2cccc(F)c2)c1F] |
| 24 | N-(6-((2,3'-difluoro-[1,1'-biphenyl]-3-yl)methyl)-5-(2,2-difluoropropanoyl)-5-azaspiro[2.4]heptan-7-yl)methanesulfonamide_cis racemic | 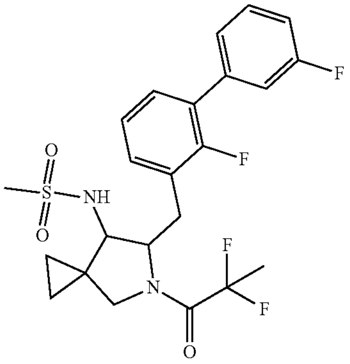 [SMILES: CC(F)(F)C(=O)N1CC2(CC2)C(NS(C)(=O)=O)C1Cc1cccc(-c2cccc(F)c2)c1F] |
| 25 | N-(5-(azetidine-1-carbonyl)-6-((2,3'-difluoro-[1,1'-biphenyl]-3-yl)methyl)-5-azaspiro[2.4]heptan-7-yl)methanesulfonamide_cis racemic | 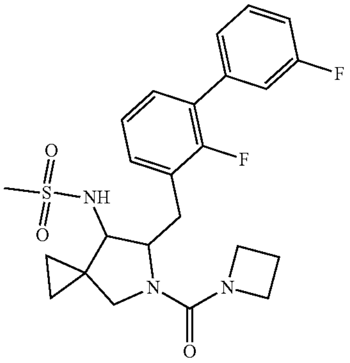 [SMILES: CS(=O)(=O)NC1C(Cc2cccc(-c3cccc(F)c3)c2F)N(C(=O)N2CCC2)CC12CC2] |
| 26 | N-((6R,7R)-5-(azetidine-1-carbonyl)-6-((2,3'-difluoro-[1,1'-biphenyl]-3-yl)methyl)-5-azaspiro[2.4]heptan-7-yl)methanesulfonamide | 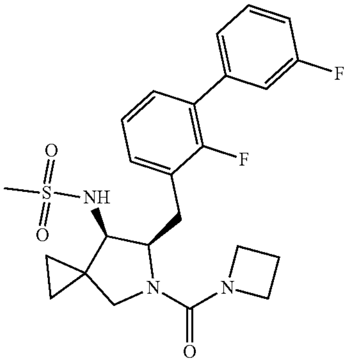 [SMILES: CS(=O)(=O)N[C@H]1[C@@H](Cc2cccc(-c3cccc(F)c3)c2F)N(C(=O)N2CCC2)CC12CC2] |

TABLE 1-continued

| Compound No. | Name | Structure |
|---|---|---|
| 27 | N-((6S,7S)-5-(azetidine-1-carbonyl)-6-((2,3'-difluoro-[1,1'-biphenyl]-3-yl)methyl)-5-azaspiro[2.4]heptan-7-yl)methanesulfonamide | 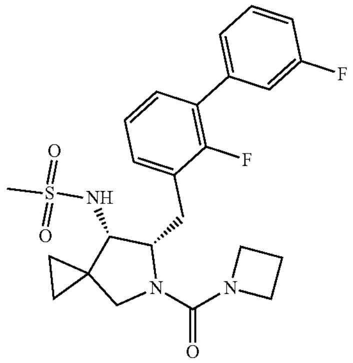 [SMILES: CS(=O)(=O)N[C@@H]1[C@H](Cc2cccc(-c3cccc(F)c3)c2F)N(C(=O)N2CCC2)CC12CC2] |
| 28 | N-(5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide_cis racemic | 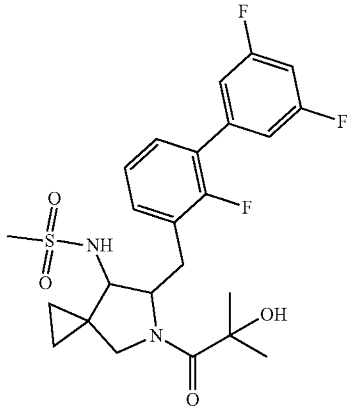 [SMILES: CC(C)(O)C(=O)N1CC2(CC2)C(NS(C)(=O)=O)C1Cc1cccc(-c2cc(F)cc(F)c2)c1F] |
| 29 | N-(5-(cyclobutanecarbonyl)-6-((2,3',5'-trifluoro-[1,1'-biphenyl]-3-yl)methyl)-5-azaspiro[2.4]heptan-7-yl)methanesulfonamide_cis racemic | 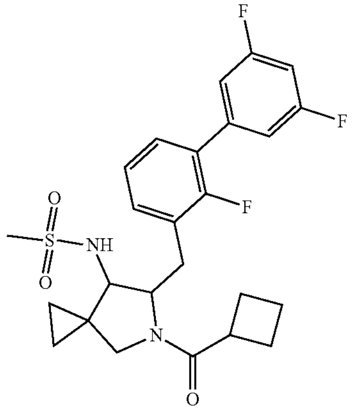 [SMILES: CS(=O)(=O)NC1C(Cc2cccc(-c3cc(F)cc(F)c3)c2F)N(C(=O)C2CCC2)CC12CC2] |
| 30 | N-(5-(azetidine-1-carbonyl)-6-((2,3',5'-trifluoro-[1,1'-biphenyl]-3-yl)methyl)-5-azaspiro[2.4]heptan-7-yl)methanesulfonamide_cis racemic | 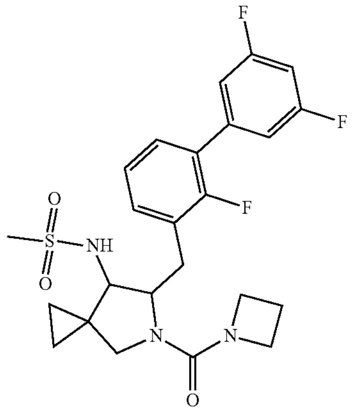 [SMILES: CS(=O)(=O)NC1C(Cc2cccc(-c3cc(F)cc(F)c3)c2F)N(C(=O)N2CCC2)CC12CC2] |

TABLE 1-continued
| Compound No. | Name | Structure |
|---|---|---|
| 31 | N-((6R,7R)-5-(azetidine-1-carbonyl)-6-((2,3',5'-trifluoro-[1,1'-biphenyl]-3-yl)methyl)-5-azaspiro[2.4]heptan-7-yl)methanesulfonamide | 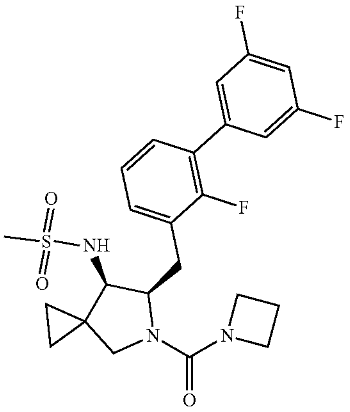 [SMILES: CS(=O)(=O)N[C@H]1[C@@H](Cc2cccc(-c3cc(F)cc(F)c3)c2F)N(C(=O)N2CCC2)CC12CC2] |
| 32 | N-((6S,7S)-5-(azetidine-1-carbonyl)-6-((2,3',5'-trifluoro-[1,1'-biphenyl]-3-yl)methyl)-5-azaspiro[2.4]heptan-7-yl)methanesulfonamide | 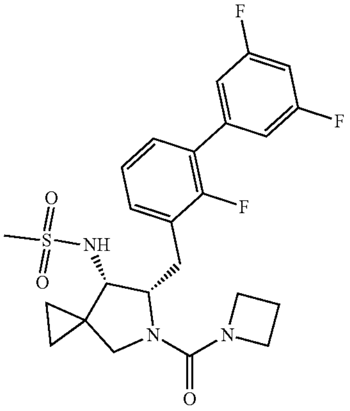 [SMILES: CS(=O)(=O)N[C@@H]1[C@H](Cc2cccc(-c3cc(F)cc(F)c3)c2F)N(C(=O)N2CCC2)CC12CC2] |
| 33 | N-((6S,7S)-5-(cyclobutanecarbonyl)-6-((2,3',5'-trifluoro-[1,1'-biphenyl]-3-yl)methyl)-5-azaspiro[2.4]heptan-7-yl)methanesulfonamide | 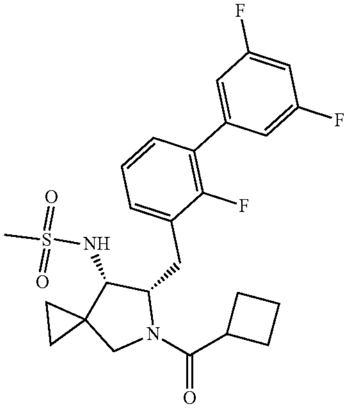 [SMILES: CS(=O)(=O)N[C@@H]1[C@H](Cc2cccc(-c3cc(F)cc(F)c3)c2F)N(C(=O)C2CCC2)CC12CC2] |

TABLE 1-continued

| Compound No. | Name | Structure |
|---|---|---|
| 34 | N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide | 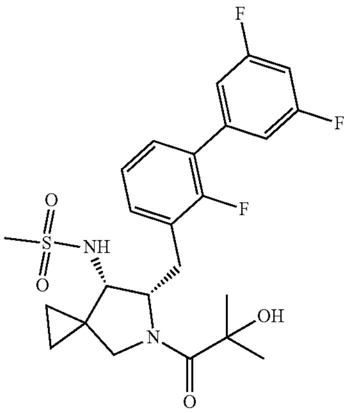 [SMILES: CC(C)(O)C(=O)N1CC2(CC2)[C@H](NS(C)(=O)=O)[C@@H]1Cc1cccc(-c2cc(F)cc(F)c2)c1F] |
| 35 | N-((6S,7S)-5-(azetidine-1-carbonyl)-6-((2-fluoro-[1,1'-biphenyl]-3-yl)methyl)-5-azaspiro[2.4]heptan-7-yl)methanesulfonamide | 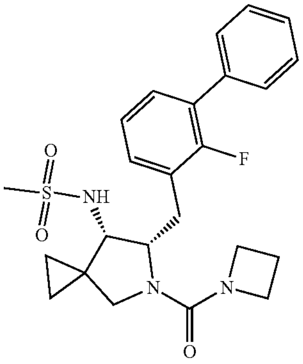 [SMILES: CS(=O)(=O)N[C@@H]1[C@H](Cc2cccc(-c3ccccc3)c2F)N(C(=O)N2CCC2)CC12CC2] |
| 36 | N-(6-([1,1'-biphenyl]-3-ylmethyl)-5-isobutyryl-5-azaspiro[2.4]heptan-7-yl)-1-fluoromethanesulfonamide_cis racemic | 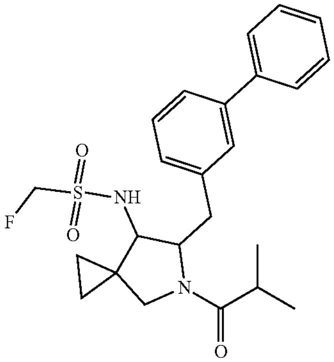 [SMILES: CC(C)C(=O)N1CC2(CC2)C(NS(=O)(=O)CF)C1Cc1cccc(-c2ccccc2)c1] |
| 37 | N-(6-([1,1'-biphenyl]-3-ylmethyl)-5-((R)-2-hydroxybutanoyl)-5-azaspiro[2.4]heptan-7-yl)methanesulfonamide_cis racemic | 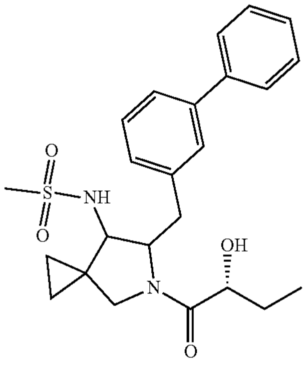 [SMILES: CC[C@@H](O)C(=O)N1CC2(CC2)C(NS(C)(=O)=O)C1Cc1cccc(-c2ccccc2)c1] |

TABLE 1-continued

| Compound No. | Name | Structure |
|---|---|---|
| 38 | N-ethyl-6-((2-fluoro-[1,1'-biphenyl]-3-yl)methyl)-7-(methylsulfonamido)-5-azaspiro[2.4]heptane-5-carboxamide_cis racemic | 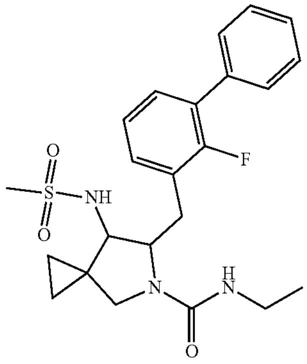 [SMILES: CCNC(=O)N1CC2(CC2)C(NS(C)(=O)=O)C1Cc1cccc(-c2ccccc2)c1F] |
| 39 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)methanesulfonamide | 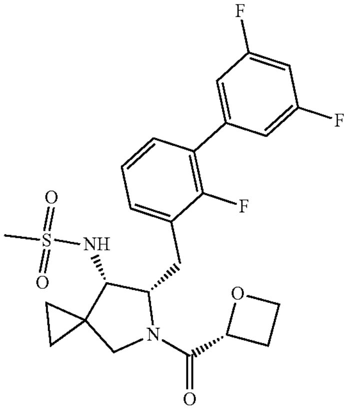 [SMILES: CS(=O)(=O)N[C@@H]1[C@H](Cc2cccc(-c3cc(F)cc(F)c3)c2F)N(C(=O)[C@H]2CCO2)CC12CC2] |
| 40 | N-((6S,7S)-6-((2'-fluoro-[1,1'-biphenyl]-3-yl)methyl)-5-((R)-oxetane-2-carbonyl)-5-azaspiro[2.4]heptan-7-yl)methanesulfonamide | 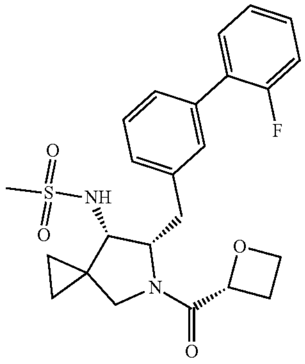 [SMILES: CS(=O)(=O)N[C@@H]1[C@H](Cc2cccc(-c3ccccc3F)c2)N(C(=O)[C@H]2CCO2)CC12CC2] |
| 41 | N-((6S,7S)-6-([1,1'-biphenyl]-3-ylmethyl)-5-((R)-oxetane-2-carbonyl)-5-azaspiro[2.4]heptan-7-ylethanesulfonamide | 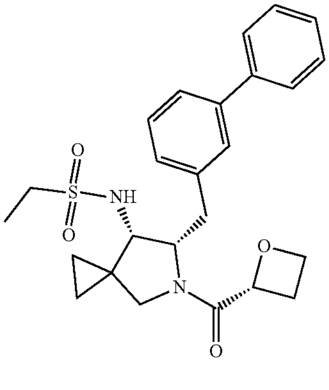 [SMILES: CCS(=O)(=O)N[C@@H]1[C@H](Cc2cccc(-c3ccccc3)c2)N(C(=O)[C@H]2CCO2)CC12CC2] |

TABLE 1-continued

| Compound No. | Name | Structure |
|---|---|---|
| 42 | N-((6S,7S)-6-([1,1'-biphenyl]-3-ylmethyl)-5-((R)-oxetane-2-carbonyl)-5-azaspiro[2.4]heptan-7-yl)cyclopropanesulfonamide | 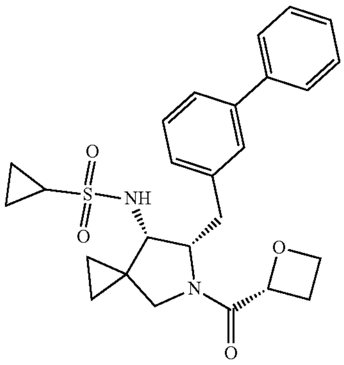 [SMILES: O=C([C@H]1CCO1)N1CC2(CC2)[C@H](NS(=O)(=O)C2CC2)[C@@H]1Cc1cccc(-c2ccccc2)c1] |
| 43 | N-((6S,7S)-6-([1,1'-biphenyl]-3-ylmethyl)-5-((S)-3,3,3-trifluoro-2-hydroxypropanoyl)-5-azaspiro[2.4]heptan-7-yl)methanesulfonamide | 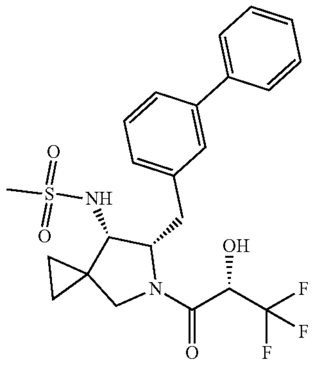 [SMILES: CS(=O)(=O)N[C@@H]1[C@H](Cc2cccc(-c3ccccc3)c2)N(C(=O)[C@H](O)C(F)(F)F)CC12CC2] |
| 44 | N-ethyl-6-((2-methoxy-[1,1'-biphenyl]-3-yl)methyl)-7-(methylsulfonamido)-5-azaspiro[2.4]heptane-5-carboxamide_cis racemic | 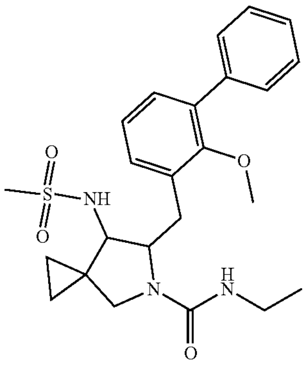 [SMILES: CCNC(=O)N1CC2(CC2)C(NS(C)(=O)=O)C1Cc1cccc(-c2ccccc2)c1OC] |
| 45 | N-(6-((2-fluoro-[1,1'-biphenyl]-3-yl)methyl)-5-(3-fluoroazetidine-1-carbonyl)-5-azaspiro[2.4]heptan-7-yl)methanesulfonamide_cis racemic | 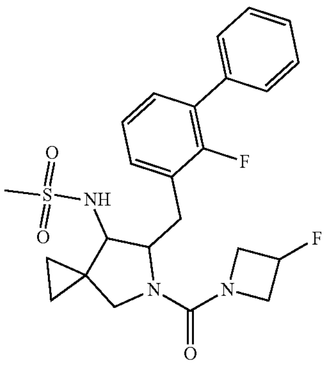 [SMILES: CS(=O)(=O)NC1C(Cc2cccc(-c3ccccc3)c2F)N(C(=O)N2CC(F)C2)CC12CC2] |

TABLE 1-continued

| Compound No. | Name | Structure |
|---|---|---|
| 46 | N-(6-((2-fluoro-[1,1'-biphenyl]-3-yl)methyl)-5-(3-methoxyazetidine-1-carbonyl)-5-azaspiro[2.4]heptan-7-yl)methanesulfonamide_cis racemic | 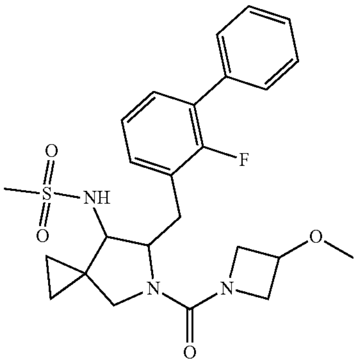 |
| 47 | N-((6S,7S)-6-([1,1'-biphenyl]-3-ylmethyl)-5-(2-cyanooxetane-2-carbonyl)-5-azaspiro[2.4]heptan-7-yl)methanesulfonamide | 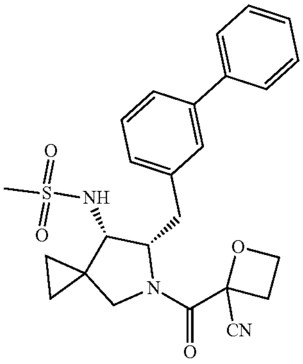 [SMILES: CS(=O)(=O)N[C@@H]1[C@H](Cc2cccc(-c3ccccc3)c2)N(C(=O)C2(C#N)CCO2)CC12CC2] |
| 48 | N-((6S,7S)-6-([1,1'-biphenyl]-3-ylmethyl)-5-((R)-oxetane-2-carbonyl)-5-azaspiro[2.4]heptan-7-yl)-1-fluoromethanesulfonamide | 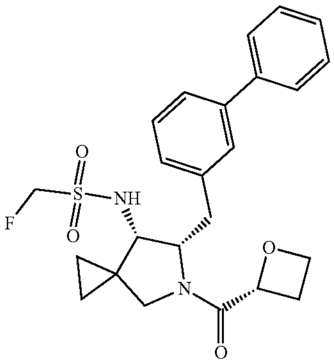 [SMILES: O=C([C@H]1CCO1)N1CC2(CC2)[C@H](NS(=O)(=O)CF)[C@@H]1Cc1cccc(-c2ccccc2)c1] |
| 49 | N-(6-([1,1'-biphenyl]-3-ylmethyl)-5-((1r,3r)-3-fluorocyclobutane-1-carbonyl)-5-azaspiro[2.4]heptan-7-yl)methanesulfonamide_cis racemic | 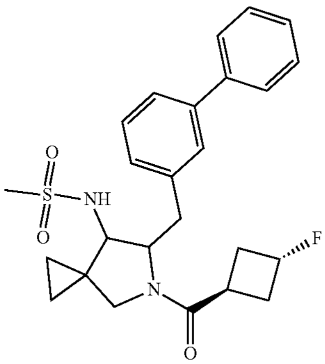 [SMILES: CS(=O)(=O)NC1C(Cc2cccc(-c3ccccc3)c2)N(C(=O)[C@H]2C[C@H](F)C2)CC12CC2] |

TABLE 1-continued

| Compound No. | Name | Structure |
|---|---|---|
| 50 | N-(6-((2-fluoro-[1,1'-biphenyl]-3-yl)methyl)-5-(1-hydroxycyclobutane-1-carbonyl)-5-azaspiro[2.4]heptan-7-yl)methanesulfonamide_cis racemic | 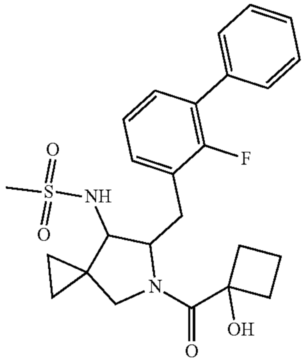 [SMILES: CS(=O)(=O)NC1C(Cc2cccc(-c3ccccc3)c2F)N(C(=O)C2(O)CCC2)CC12CC2] |
| 51 | N-(6-((3'-fluoro-[1,1'-biphenyl]-3-yl)methyl)-5-(1-hydroxycyclobutane-1-carbonyl)-5-zaspiro[2.4]heptan-7-yl)methanesulfonamide_cis racemic | 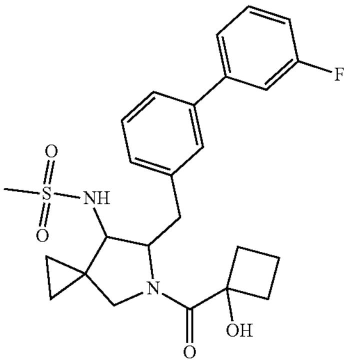 [SMILES: CS(=O)(=O)NC1C(Cc2cccc(-c3cccc(F)c3)c2)N(C(=O)C2(O)CCC2)CC12CC2] |
| 52 | N-ethyl-7-(ethylsulfonamido)-6-((2-fluoro-[1,1'-biphenyl]-3-yl)methyl)-5-azaspiro[2.4]heptane-5-carboxamide_cis racemic | 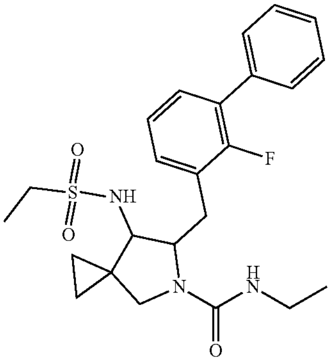 [SMILES: CCNC(=O)N1CC2(CC2)C(NS(=O)(=O)CC)C1Cc1cccc(-c2ccccc2)c1F] |
| 53 | N-((6S,7S)-6-((2-fluoro-[1,1'-biphenyl]-3-yl)methyl)-5-((R)-oxetane-2-carbonyl)-5-azaspiro[2.4]heptan-7-yl)ethanesulfonamide | 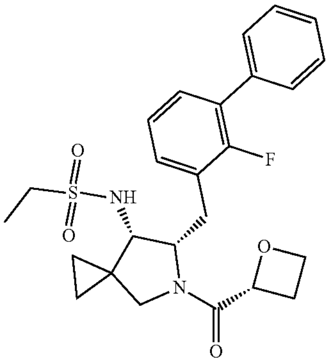 [SMILES: CCS(=O)(=O)N[C@@H]1[C@H](Cc2cccc(-c3ccccc3)c2F)N(C(=O)[C@H]2CCO2)CC12CC2] |

TABLE 1-continued

| Compound No. | Name | Structure |
|---|---|---|
| 54 | (6S,7S)-N-ethyl-6-((2-methoxy-[1,1'-biphenyl]-3-yl)methyl)-7-(methylsulfonamido)-5-azaspiro[2.4]heptane-5-carboxamide | 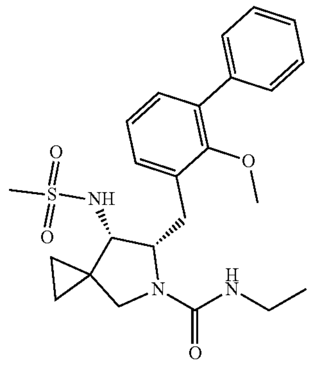 [SMILES: CCNC(=O)N1CC2(CC2)[C@H](NS(C)(=O)=O)[C@@H]1Cc1cccc(-c2ccccc2)c1OC] |
| 55 | N-((6S,7S)-6-([1,1'-biphenyl]-3-ylmethyl)-5-((R)-oxetane-2-carbonyl)-5-azaspiro[2.4]heptan-7-yl)methanesulfonamide | 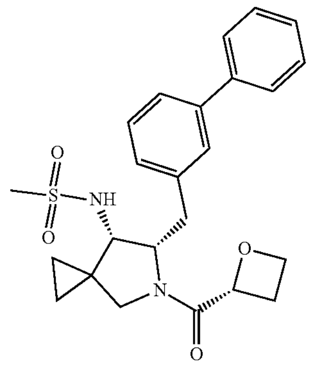 [SMILES: CS(=O)(=O)N[C@@H]1[C@H](Cc2cccc(-c3ccccc3)c2)N(C(=O)[C@H]2CCO2)CC12CC2] |
| 56 | N-((6S,7S)-6-((2-fluoro-[1,1'-biphenyl]-3-yl)methyl)-5-((S)-3,3,3-trifluoro-2-hydroxypropanoyl)-5-azaspiro[2.4]heptan-7-yl)methanesulfonamide | 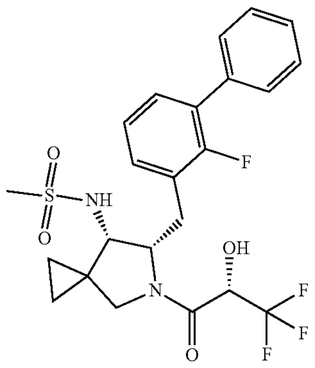 [SMILES: CS(=O)(=O)N[C@@H]1[C@H](Cc2cccc(-c3ccccc3)c2F)N(C(=O)[C@H](O)C(F)(F)F)CC12CC2] |
| 57 | N-(6-([1,1'-biphenyl]-3-ylmethyl)-5-(3-methylazetidine-1-carbonyl)-5-azaspiro[2.4]heptan-7-yl)methanesulfonamide_cis racemic | 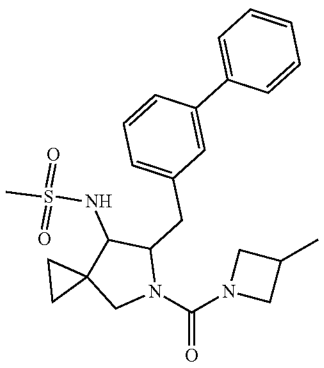 |

TABLE 1-continued

| Compound No. | Name | Structure |
| --- | --- | --- |
| 58 | N-((6S,7S)-6-([1,1'-biphenyl]-3-ylmethyl)-5-((S)-3,3,3-trifluoro-2-hydroxypropanoyl)-5-azaspiro[2.4]heptan-7-yl)ethanesulfonamide | 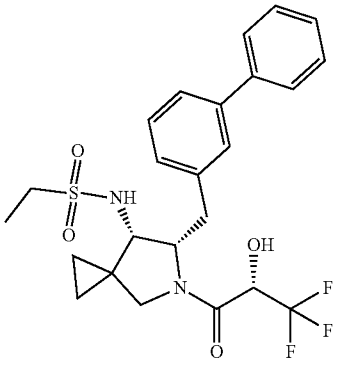 [SMILES: CCS(=O)(=O)N[C@@H]1[C@H](Cc2cccc(-c3ccccc3)c2)N(C(=O)[C@H](O)C(F)(F)F)CC12CC2] |
| 59 | N-((6S,7S)-6-((2,5-difluoro-[1,1'-biphenyl]-3-yl)methyl)-5-((R)-oxetane-2-carbonyl)-5-azaspiro[2.4]heptan-7-yl)methanesulfonamide | 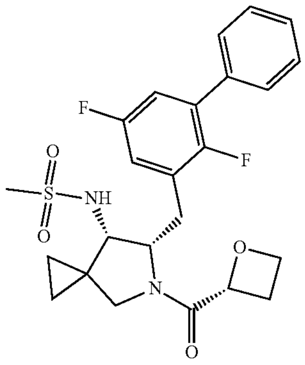 [SMILES: CS(=O)(=O)N[C@@H]1[C@H](Cc2cc(F)cc(-c3ccccc3)c2F)N(C(=O)[C@H]2CCO2)CC12CC2] |
| 60 | N-((6S,7S)-6-([1,1'-biphenyl]-3-ylmethyl)-5-(1-methoxycyclopropane-1-carbonyl)-5-azaspiro[2.4]heptan-7-yl)methanesulfonamide | 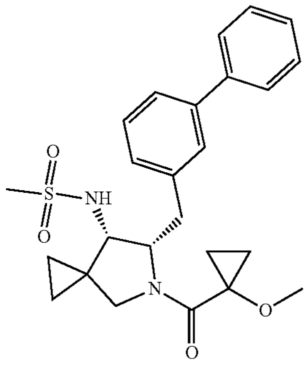 |
| 61 | N-((6S,7S)-6-([1,1'-biphenyl]-3-ylmethyl)-5-((R)-2-cyclopropyl-2-hydroxyacetyl)-5-azaspiro[2.4]heptan-7-yl)methanesulfonamide | 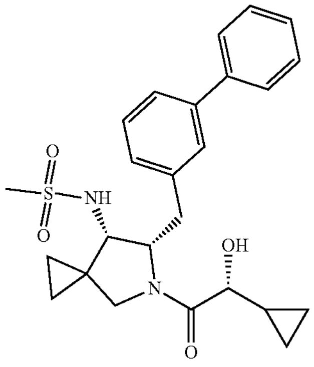 [SMILES: CS(=O)(=O)N[C@@H]1[C@H](Cc2cccc(-c3ccccc3)c2)N(C(=O)[C@H](O)C2CC2)CC12CC2] |

TABLE 1-continued

| Compound No. | Name | Structure |
| --- | --- | --- |
| 62 | N-((6S,7S)-6-([1,1'-biphenyl]-3-ylmethyl)-5-((S)-3-fluoro-2-hydroxypropanoyl)-5-azaspiro[2.4]heptan-7-yl)methanesulfonamide | 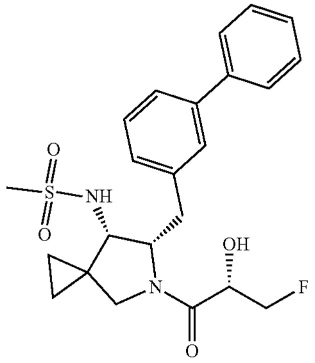 [SMILES: CS(=O)(=O)N[C@@H]1[C@H](Cc2cccc(-c3ccccc3)c2)N(C(=O)[C@H](O)CF)CC12CC2] |
| 63 | N-((6S,7S)-6-([1,1'-biphenyl]-3-ylmethyl)-5-((R)-2-hydroxy-3-methoxypropanoyl)-5-azaspiro[2.4]heptan-7-yl)methanesulfonamide | 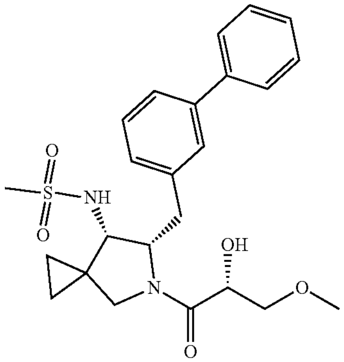 |
| 64 | N-((6S,7S)-6-((2-fluoro-[1,1'-biphenyl]-3-yl)methyl)-5-((R)-oxetane-2-carbonyl)-5-azaspiro[2.4]heptan-7-yl)-N,N-dimethylsulfuric diamide | 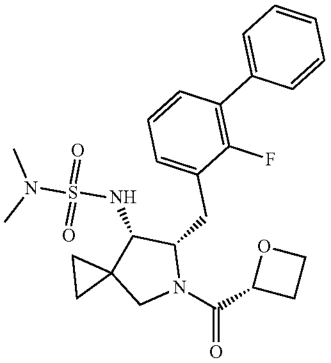 [SMILES: CN(C)S(=O)(=O)N[C@@H]1[C@H](Cc2cccc(-c3ccccc3)c2F)N(C(=O)[C@H]2CCO2)CC12CC2] |
| 65 | N-((6S,7S)-6-((2-fluoro-[1,1'-biphenyl]-3-yl)methyl)-5-((R)-oxetane-2-carbonyl)-5-azaspiro[2.4]heptan-7-yl)-N-methylsulfuric diamide | 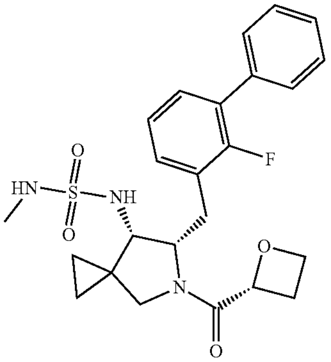 [SMILES: CNS(=O)(=O)N[C@@H]1[C@H](Cc2cccc(-c3ccccc3)c2F)N(C(=O)[C@H]2CCO2)CC12CC2] |

TABLE 1-continued

| Compound No. | Name | Structure |
|---|---|---|
| 66 | N-(6-([1,1'-biphenyl]-3-ylmethyl)-5-(bicyclo[1.1.0]butane-1-carbonyl)-5-azaspiro[2.4]heptan-7-yl)methanesulfonamide_cis racemic | 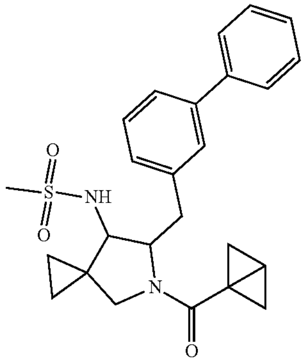 [SMILES: CS(=O)(=O)NC1C(Cc2cccc(-c3ccccc3)c2)N(C(=O)C23CC2C3)CC12CC2] |
| 67 | N-((6S,7S)-6-((2,3'-difluoro-[1,1'-biphenyl]-3-yl)methyl)-5-((R)-oxetane-2-carbonyl)-5-azaspiro[2.4]heptan-7-yl)methanesulfonamide | 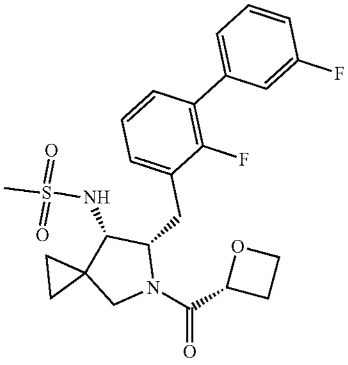 [SMILES: CS(=O)(=O)N[C@@H]1[C@H](Cc2cccc(-c3cccc(F)c3)c2F)N(C(=O)[C@H]2CCO2)CC12CC2] |
| 68 | N-((6S,7S)-6-((2-fluoro-[1,1'-biphenyl]-3-yl)methyl)-5-(1-hydroxycyclobutane-1-carbonyl)-5-azaspiro[2.4]heptan-7-yl)methanesulfonamide | 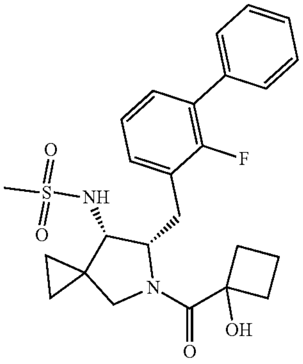 [SMILES: CS(=O)(=O)N[C@@H]1[C@H](Cc2cccc(-c3ccccc3)c2F)N(C(=O)C2(O)CCC2)CC12CC2] |
| 69 | N-((6S,7S)-6-((2-fluoro-[1,1'-biphenyl]-3-yl)methyl)-5-((R)-oxetane-2-carbonyl)-5-azaspiro[2.4]heptan-7-yl)cyclopropanesulfonamide | 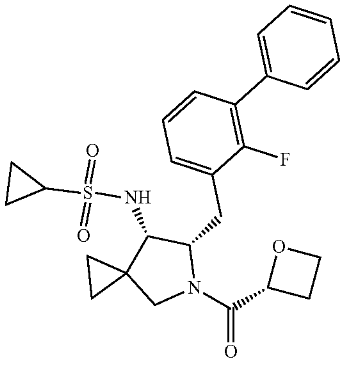 [SMILES: O=C([C@H]1CCO1)N1CC2(CC2)[C@H](NS(=O)(=O)C2CC2)[C@@H]1Cc1cccc(-c2ccccc2)c1F] |

TABLE 1-continued

| Compound No. | Name | Structure |
| --- | --- | --- |
| 70 | N-((6S,7S)-6-([1,1'-biphenyl]-3-ylmethyl)-5-((S)-3,3-difluoro-2-hydroxypropanoyl)-5-azaspiro[2.4]heptan-7-yl)methanesulfonamide | 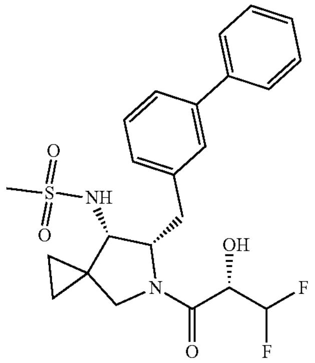 [SMILES: CS(=O)(=O)N[C@@H]1[C@H](Cc2cccc(-c3ccccc3)c2)N(C(=O)[C@H](O)C(F)F)CC12CC2] |
| 71 | N-((6S,7S)-6-([1,1'-biphenyl]-3-ylmethyl)-5-((R)-oxetane-2-carbonyl)-5-azaspiro[2.4]heptan-7-yl)-N-methylsulfuric diamide | 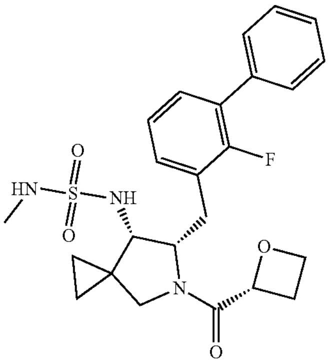 [SMILES: CNS(=O)(=O)N[C@@H]1[C@H](Cc2cccc(-c3ccccc3)c2F)N(C(=O)[C@H]2CCO2)CC12CC2] |
| 72 | N-((6S,7S)-6-([1,1'-biphenyl]-3-ylmethyl)-5-((R)-oxetane-2-carbonyl)-5-azaspiro[2.4]heptan-7-yl)-1-methyl-1H-pyrazole-3-sulfonamide | 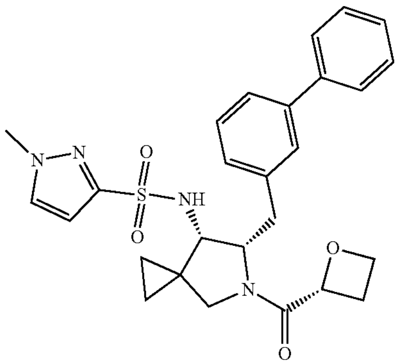 [SMILES: Cn1ccc(S(=O)(=O)N[C@@H]2[C@H](Cc3cccc(-c4ccccc4)c3)N(C(=O)[C@H]3CCO3)CC23CC3)n1] |
| 73 | N-(6S,7S)-6-([1,1'-biphenyl]-3-ylmethyl)-5-((R)-oxetane-2-carbonyl)-5-azaspiro[2.4]heptan-7-yl)-1-cyanomethanesulfonamide | 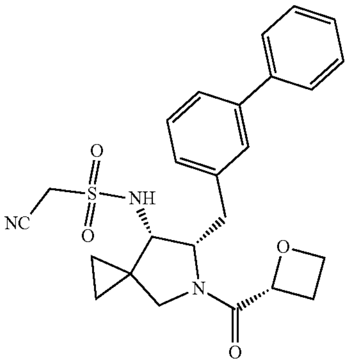 [SMILES: N#CCS(=O)(=O)N[C@@H]1[C@H](Cc2cccc(-c3ccccc3)c2)N(C(=O)[C@H]2CCO2)CC12CC2] |

TABLE 1-continued

| Compound No. | Name | Structure |
|---|---|---|
| 74 | N-((6S,7S)-6-([1,1'-biphenyl]-3-ylmethyl)-5-((R)-oxetane-2-carbonyl)-5-azaspiro[2.4]heptan-7-yl)-2-(2-methoxyethoxy)ethane-1-sulfonamide | 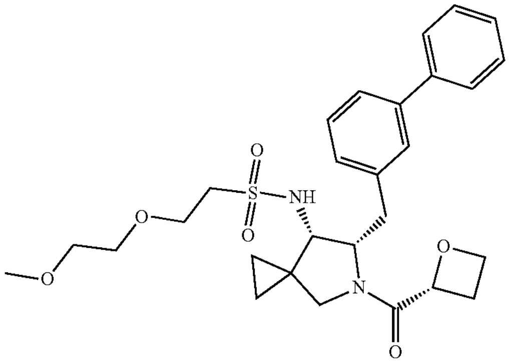 [SMILES: COCCOCCS(=O)(=O)N[C@@H]1[C@H](Cc2cccc(-c3ccccc3)c2)N(C(=O)[C@H]2CCO2)CC12CC2] |
| 75 | N-((6S,7S)-6-([1,1'-biphenyl]-3-ylmethyl)-5-((R)-oxetane-2-carbonyl)-5-azaspiro[2.4]heptan-7-yl)-1H-imidazole-4-sulfonamide | 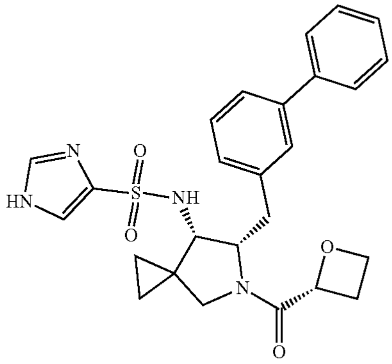 [SMILES: O=C([C@H]1CCO1)N1CC2(CC2)[C@H](NS(=O)(=O)c2c[nH]cn2)[C@@H]1Cc1cccc(-c2ccccc2)c1] |
| 76 | N-((6S,7S)-6-([1,1'-biphenyl]-3-ylmethyl)-5-((R)-oxetane-2-carbonyl)-5-azaspiro[2.4]heptan-7-yl)azetidine-1-sulfonamide | 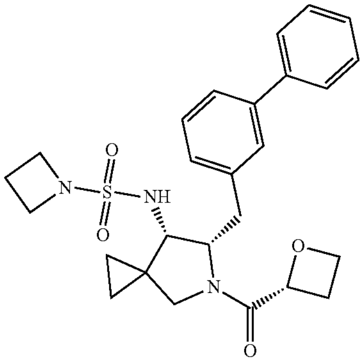 [SMILES: O=C([C@H]1CCO1)N1CC2(CC2)[C@H](NS(=O)(=O)N2CCC2)[C@@H]1Cc1cccc(-c2ccccc2)c1] |
| 77 | N-((6S,7S)-6-([1,1'-biphenyl]-3-ylmethyl)-5-((R)-oxetane-2-carbonyl)-5-azaspiro[2.4]heptan-7-yl)oxetane-3-sulfonamide | 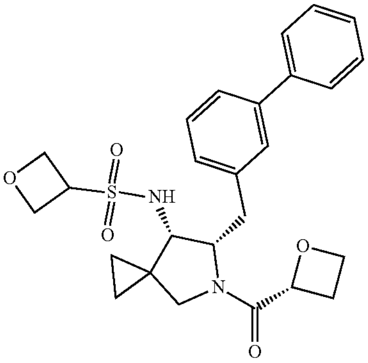 [SMILES: O=C([C@H]1CCO1)N1CC2(CC2)[C@H](NS(=O)(=O)C2COC2)[C@@H]1Cc1cccc(-c2ccccc2)c1] |

TABLE 1-continued

| Compound No. | Name | Structure |
|---|---|---|
| 78 | N-((6S,7S)-6-([1,1'-biphenyl]-3-ylmethyl)-5-((R)-oxetane-2-carbonyl)-5-azaspiro[2.4]heptan-7-yl)-N-methyl-N-ethylsulfuric diamide | 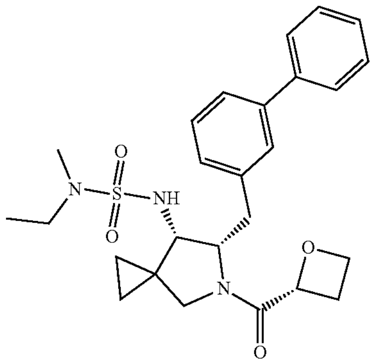 [SMILES: CCN(C)S(=O)(=O)N[C@@H]1[C@H](Cc2cccc(-c3ccccc3)c2)N(C(=O)[C@H]2CCO2)CC12CC2] |
| 79 | (6S,7S)-6-((2-fluoro-[1,1'-biphenyl]-3-yl)methyl)-N-(3-fluoropropyl)-7-(methylsulfonamido)-5-azaspiro[2.4]heptane-5-carboxamide | 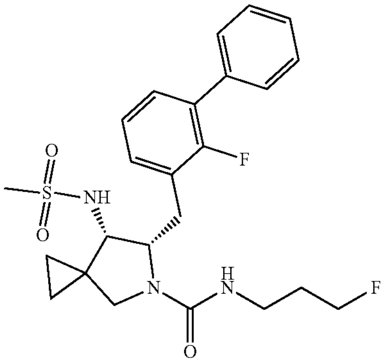 [SMILES: CS(=O)(=O)N[C@@H]1[C@H](Cc2cccc(-c3ccccc3)c2F)N(C(=O)NCCCF)CC12CC2] |
| 80 | N-((6S,7S)-6-((2-fluoro-[1,1'-biphenyl]-3-yl)methyl)-5-((S)-2-(fluoromethyl)azetidine-1-carbonyl)-5-azaspiro[2.4]heptan-7-yl)methanesulfonamide | 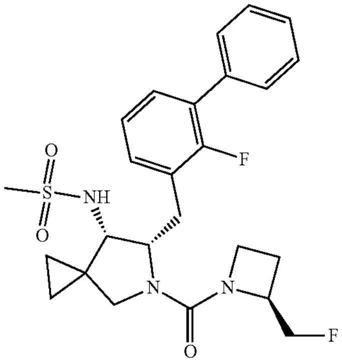 [SMILES: CS(=O)(=O)N[C@@H]1[C@H](Cc2cccc(-c3ccccc3)c2F)N(C(=O)N2CC[C@H]2CF)CC12CC2] |
| 81 | (6S,7S)-N-(2,2-difluoroethyl)-6-((2-fluoro-[1,1'-biphenyl]-3-yl)methyl)-N-methyl-7-(methylsulfonamido)-5-azaspiro[2.4]heptane-5-carboxamide | 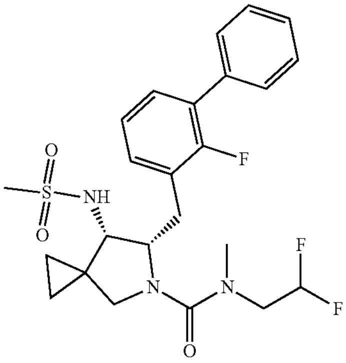 [SMILES: CN(CC(F)F)C(=O)N1CC2(CC2)[C@H](NS(C)(=O)=O)[C@@H]1Cc1cccc(-c2ccccc2)c1F] |

TABLE 1-continued

| Compound No. | Name | Structure |
|---|---|---|
| 82 | (6S,7S)-6-((2-fluoro-[1,1'-biphenyl]-3-yl)methyl)-N-(2-fluoroethyl)-N-methyl-7-(methylsulfonamido)-5-azaspiro[2.4]heptane-5-carboxamide | 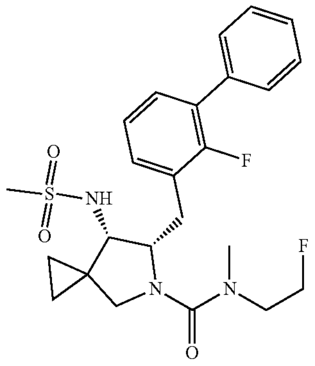 [SMILES: CN(CCF)C(=O)N1CC2(CC2)[C@H](NS(C)(=O)=O)[C@@H]1Cc1cccc(-c2ccccc2)c1F] |
| 83 | (6S,7S)-N-(3,3-difluorocyclobutyl)-6-((2-fluoro-[1,1'-biphenyl]-3-yl)methyl)-7-(methylsulfonamido)-5-azaspiro[2.4]heptane-5-carboxamide | 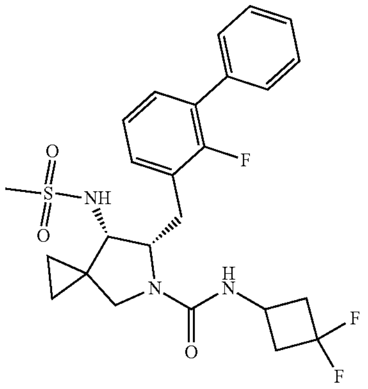 [SMILES: CS(=O)(=O)N[C@@H]1[C@H](Cc2cccc(-c3ccccc3)c2F)N(C(=O)NC2CC(F)(F)C2)CC12CC2] |
| 84 | (6S,7S)-6-((2-fluoro-[1,1'-biphenyl]-3-yl)methyl)-N-((S)-2-fluoropropyl)-7-(methylsulfonamido)-5-azaspiro[2.4]heptane-5-carboxamide | 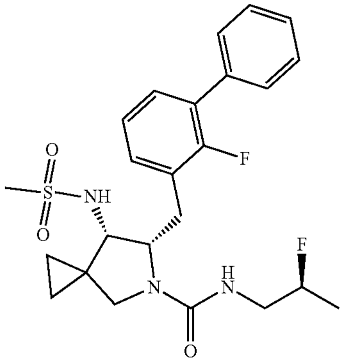 [SMILES: C[C@H](F)CNC(=O)N1CC2(CC2)[C@H](NS(C)(=O)=O)[C@@H]1Cc1cccc(-c2ccccc2)c1F] |
| 85 | 6S,7S)-6-((2-fluoro-[1,1'-biphenyl]-3-yl)methyl)-N-isopropyl-7-(methylsulfonamido)-5-azaspiro[2.4]heptane-5-carboxamide | 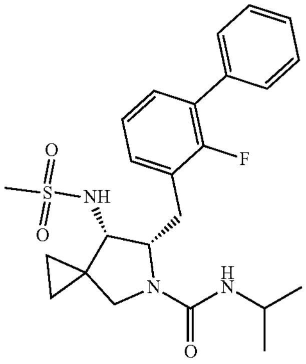 [SMILES: CC(C)NC(=O)N1CC2(CC2)[C@H](NS(C)(=O)=O)[C@@H]1Cc1cccc(-c2ccccc2)c1F] |

TABLE 1-continued

| Compound No. | Name | Structure |
|---|---|---|
| 86 | (6S,7S)-6-((2-fluoro-[1,1'-biphenyl]-3-yl)methyl)-N-(2-fluoroethyl)-7-(methylsulfonamido)-5-azaspiro[2.4]heptane-5-carboxamide | 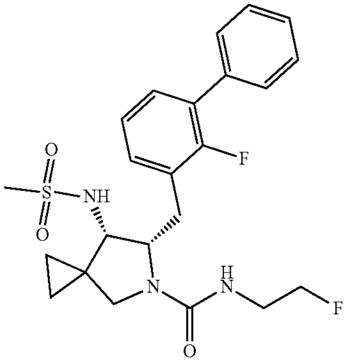 [SMILES: CS(=O)(=O)N[C@@H]1[C@H](Cc2cccc(-c3ccccc3)c2F)N(C(=O)NCCF)CC12CC2] |
| 87 | N-((6S,7S)-5-(3,3-difluoroazetidine-1-carbonyl)-6-((2-fluoro-[1,1'-biphenyl]-3-yl)methyl)-5-azaspiro[2.4]heptan-7-yl)methanesulfonamide | 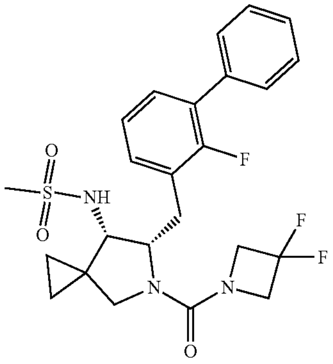 [SMILES: CS(=O)(=O)N[C@@H]1[C@H](Cc2cccc(-c3ccccc3)c2F)N(C(=O)N2CC(F)(F)C2)CC12CC2] |
| 88 | (6S,7S)-N-ethyl-6-((2-fluoro-[1,1'-biphenyl]-3-yl)methyl)-N-methyl-7-(methylsulfonamido)-5-azaspiro[2.4]heptane-5-carboxamide | 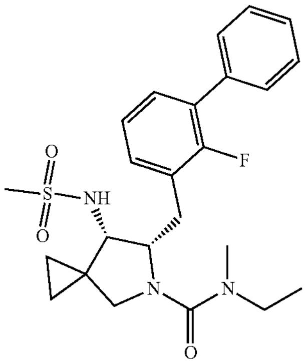 [SMILES: CCN(C)C(=O)N1CC2(CC2)[C@H](NS(C)(=O)=O)[C@@H]1Cc1cccc(-c2ccccc2)c1F] |
| 89 | (6S,7S)-N-ethyl-7-(ethylsulfonamido)-6-(2-fluoro-[1,1'-biphenyl]-3-yl)methyl)-5-azaspiro[2.4]heptane-5-carboxamide | 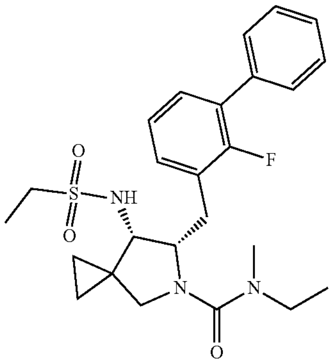 [SMILES: CCN(C)C(=O)N1CC2(CC2)[C@H](NS(=O)(=O)CC)[C@@H]1Cc1cccc(-c2ccccc2)c1F] |

TABLE 1-continued

| Compound No. | Name | Structure |
|---|---|---|
| 90 | N-(6-((2-fluoro-[1,1'-biphenyl]-3-yl)methyl)-5-((1r,3r)-3-fluorocyclobutane-1-carbonyl)-5-azaspiro[2.4]heptan-7-yl)methanesulfonamide_cis racemic | 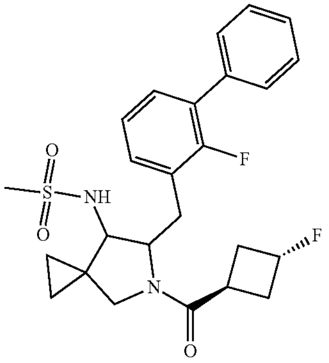 [SMILES: CS(=O)(=O)NC1C(Cc2cccc(-c3ccccc3)c2F)N(C(=O)[C@H]2C[C@H](F)C2)CC12CC2] |
| 91 | N-(6-((2-fluoro-[1,1'-biphenyl]-3-yl)methyl)-5-((1s,3s)-3-fluorocyclobutane-1-carbonyl)-5-azaspiro[2.4]heptan-7-yl)methanesulfonamide_cis racemic | 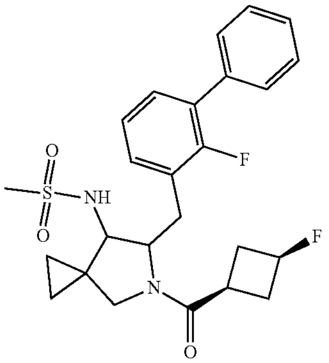 [SMILES: CS(=O)(=O)NC1C(Cc2cccc(-c3ccccc3)c2F)N(C(=O)[C@H]2C[C@@H](F)C2)CC12CC2] |
| 92 | N-(5-(cyclobutanecarbonyl)-6-((2-fluoro-[1,1'-biphenyl]-3-yl)methyl)-5-azaspiro[2.4]heptan-7-yl)-N,N-dimethylsulfuric diamide_cis racemic | 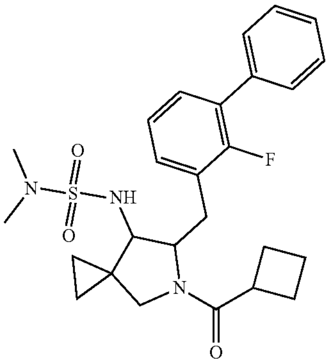 [SMILES: CN(C)S(=O)(=O)NC1C(Cc2cccc(-c3ccccc3)c2F)N(C(=O)C2CCC2)CC12CC2] |
| 93 | 1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide | 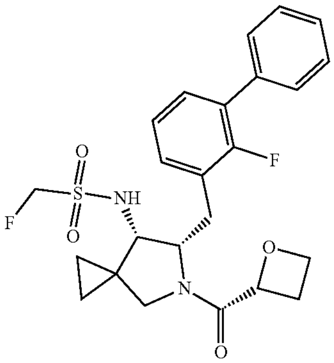 |

TABLE 1-continued

| Compound No. | Name | Structure |
|---|---|---|
| 94 | N-((6S,7S)-6-([1,1'-biphenyl]-3-ylmethyl)-5-((S)-3,3,3-trifluoro-2-hydroxypropanoyl)-5-azaspiro[2.4]heptan-7-yl)-1-fluoromethanesulfonamide | 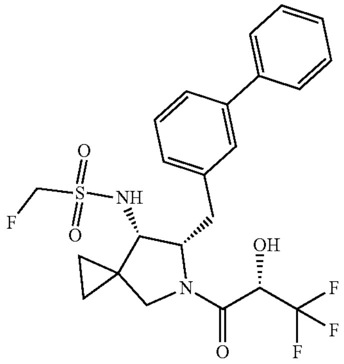 [SMILES: O=C([C@H](O)C(F)(F)F)N1CC2(CC2)[C@H](NS(=O)(=O)CF)[C@@H]1Cc1cccc(-c2ccccc2)c1] |
| 95 | N-((6S,7S)-6-([1,1'-biphenyl]-3-ylmethyl)-5-((R)-oxetane-2-carbonyl)-5-azaspiro[2.4]heptan-7-yl)-N.N-dimethylsulfuric diamide | 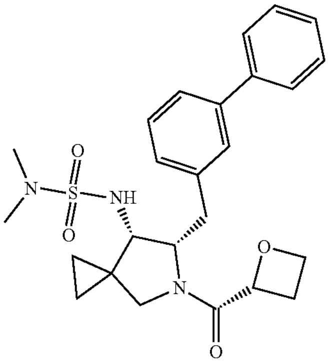 |
| 96 | N-((6S,7S)-6-([1,1'-biphenyl]-3-ylmethyl)-5-((R)-oxetane-2-carbonyl)-5-azaspiro[2.4]heptan-7-yl)pyrrolidine-1-sulfonamide | 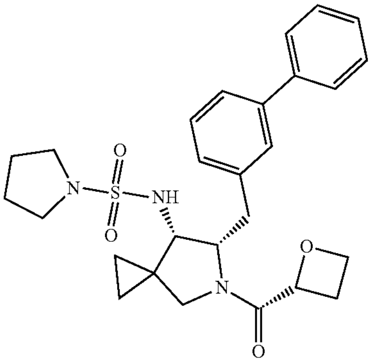 |
| 97 | N-((6S,7S)-6-([1,1'-biphenyl]-3-ylmethyl)-5-(R)-oxetane-2-carbonyl)-5-azaspiro[2.4]heptan-7-yl)-N-methyl-N-cyclopropyl-sulfonamide | 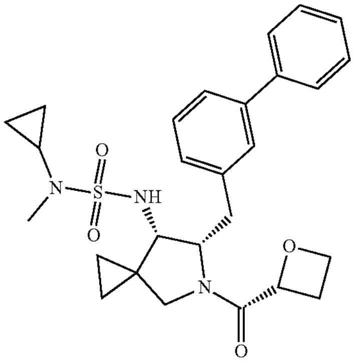 |

TABLE 1-continued

| Compound No. | Name | Structure |
|---|---|---|
| 98 | 1-fluoro-N-((6S,7S)-6-((2-fluoro-[1,1'-biphenyl]-3-yl)methyl)-5-((S)-3,3,3-trifluoro-2-hydroxypropanoyl)-5-azaspiro[2.4]heptan-7-yl)methanesulfonamide | 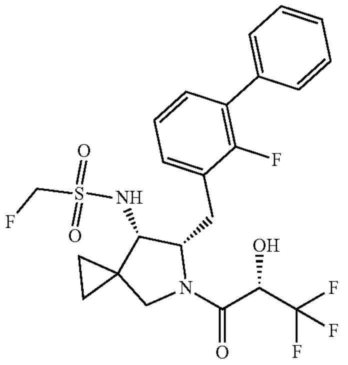 [SMILES: O=C([C@H](O)C(F)(F)F)N1CC2(CC2)[C@H](NS(=O)(=O)CF)[C@@H]1Cc1cccc(-c2ccccc2)c1F] |
| 99 | (6S,7S)-6-((2-fluoro-[1,1'-biphenyl]-3-yl)methyl)-7-(methylsulfonamido)-N-(2,2,2-trifluoroethyl)-5-azaspiro[2.4]heptane-5-carboxamide | 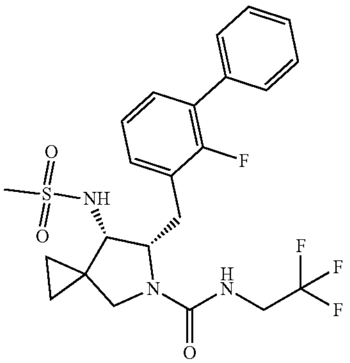 [SMILES: CS(=O)(=O)N[C@@H]1[C@H](Cc2cccc(-c3ccccc3)c2F)N(C(=O)NCC(F)(F)F)CC12CC2] |
| 100 | (6S,7S)-6-((2-fluoro-[1,1'-biphenyl]-3-yl)methyl)-N-((1-methoxycyclopropyl)methyl)-7-(methylsulfonamido)-5-azaspiro[2.4]heptane-5-carboxamide | 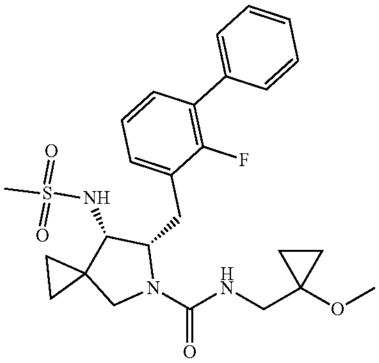 |
| 101 | (6S,7S)-6-((2-fluoro-[1,1'-biphenyl]-3-yl)methyl)-N-((R)-1-fluoropropan-2-yl)-7-(methylsulfonamido)-5-azaspiro[2.4]heptane-5-carboxamide | 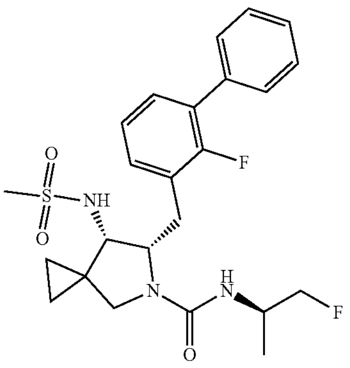 [SMILES: C[C@H](CF)NC(=O)N1CC2(CC2)[C@H](NS(C)(=O)=O)[C@@H]1Cc1cccc(-c2ccccc2)c1F] |

TABLE 1-continued

| Compound No. | Name | Structure |
|---|---|---|
| 102 | N-((6S,7S)-6-((2-fluoro-[1,1'-biphenyl]-3-yl)methyl)-5-((S)-2-(methoxymethyl)azetidine-1-carbonyl)-5-azaspiro[2.4]heptan-7-yl)methanesulfonamide | 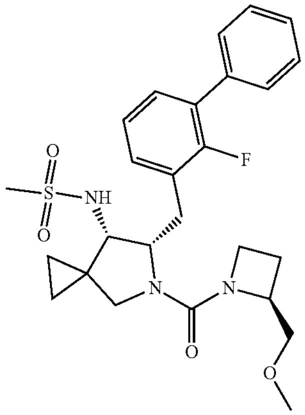 [SMILES: COC[C@@H]1CCN1C(=O)N1CC2(CC2)[C@H](NS(C)(=O)=O)[C@@H]1Cc1cccc(-c2ccccc2)c1F] |
| 103 | N-((6S,7S)-6-((2-fluoro-[1,1'-biphenyl]-3-yl)methyl)-5-((R)-2-(methoxymethyl)azetidine-1-carbonyl)-5-azaspiro[2.4]heptan-7-yl)methanesulfonamide | 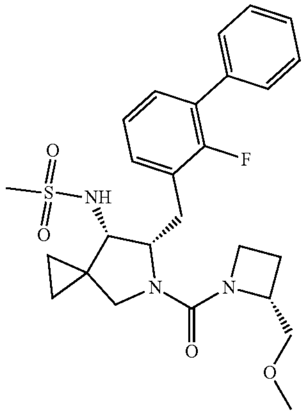 [SMILES: COC[C@H]1CCN1C(=O)N1CC2(CC2)[C@H](NS(C)(=O)=O)[C@@H]1Cc1cccc(-c2ccccc2)c1F] |
| 104 | (6S,7S)-6-((2-fluoro-[1,1'-biphenyl]-3-yl)methyl)-N-((1-fluorocyclopropyl)methyl)-7-(methylsulfonamido)-5-azaspiro[2.4]heptane-5-carboxamide | 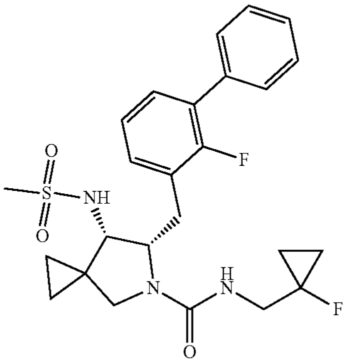 [SMILES: CS(=O)(=O)N[C@@H]1[C@H](Cc2cccc(-c3ccccc3)c2F)N(C(=O)NCC2(F)CC2)CC12CC2] |
| 105 | 1-fluoro-N-(6-((2-fluoro-[1,1'-biphenyl]-3-yl)methyl)-5-(3-fluoroazetidine-1-carbonyl)-5-azaspiro[2.4]heptan-7-yl)methanesulfonamide_cis racemic | 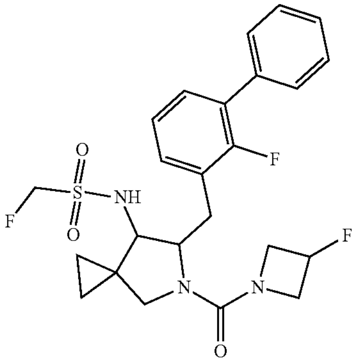 [SMILES: O=C(N1CC(F)C1)N1CC2(CC2)C(NS(=O)(=O)CF)C1Cc1cccc(-c2ccccc2)c1F] |

TABLE 1-continued

| Compound No. | Name | Structure |
|---|---|---|
| 106 | N-(5-5(cyclobutanecarbonyl)-6-((2-fluoro-[1,1'-biphenyl]-3-yl)methyl)-5-azaspiro[2.4]heptan-7-yl)-1-fluoromethanesulfonamide_cis racemic | 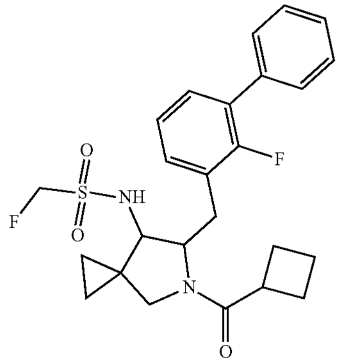 [SMILES: O=C(C1CCC1)N1CC2(CC2)C(NS(=O)(=O)CF)C1Cc1cccc(-c2ccccc2)c1F] |
| 107 | N-((6S,7S)-6-((2,2'-difluoro-[1,1'-biphenyl]-3-yl)methyl)-5-((R)-oxetane-2-carbonyl)-5-azaspiro[2.4]heptan-7-yl)methanesulfonamide | 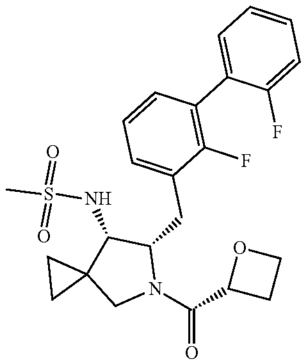 |
| 108 | 1-fluoro-N-(6-((2-fluoro-[1,1'-biphenyl]-3-yl)methyl)-5-(1-hydroxycyclobutane-1-carbonyl)-5-azaspiro[2.4]heptan-7-yl)methanesulfonamide_cis racemic | 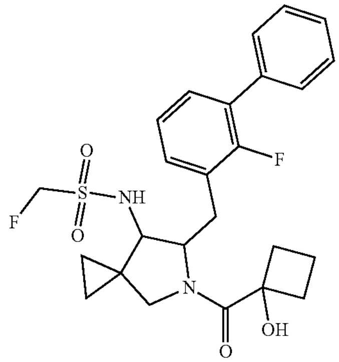 [SMILES: O=C(N1CC2(CC2)C(NS(=O)(=O)CF)C1Cc1cccc(-c2ccccc2)c1F)C1(O)CCC1] |
| 109 | N-ethyl-6-((2-fluoro-[1,1'-biphenyl]-3-yl)methyl)-7-((fluoromethyl)sulfonamido)-5-azaspiro[2.4]heptane-5-carboxamide_cis racemic | 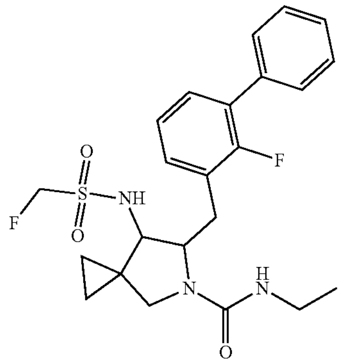 [SMILES: CCNC(=O)N1CC2(CC2)C(NS(=O)(=O)CF)C1Cc1cccc(-c2ccccc2)c1F] |

TABLE 1-continued

| Compound No. | Name | Structure |
|---|---|---|
| 110 | (6S,7S)-6-((2-fluoro-[1,1'-biphenyl]-3-yl)methyl)-N,N-dimethyl-7-(methylsulfonamido)-5-azaspiro[2.4]heptane-5-carboxamide | 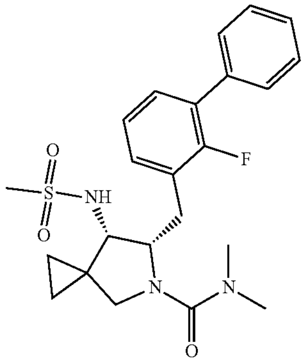 [SMILES: CN(C)C(=O)N1CC2(CC2)[C@H](NS(C)(=O)=O)[C@@H]1Cc1cccc(-c2ccccc2)c1F] |
| 111 | (6S,7S)-6-((2-fluoro-[1,1'-biphenyl]-3-yl)methyl)-7-(methylsulfonamido)-N-propyl-5-.azaspiro[2.4]heptane-5-carboxamide | 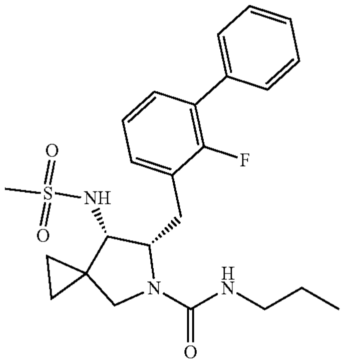 [SMILES: CCCNC(=O)N1CC2(CC2)[C@H](NS(C)(=O)=O)[C@@H]1Cc1cccc(-c2ccccc2)c1F] |
| 112 | (6S,7S)-N-(2,2-difluoroethyl)-6-((2-fluoro-[1,1'-biphenyl]-3-yl)methyl)-7-(methylsulfonamido)-5-azaspiro[2.4]heptane-5-carboxamide | 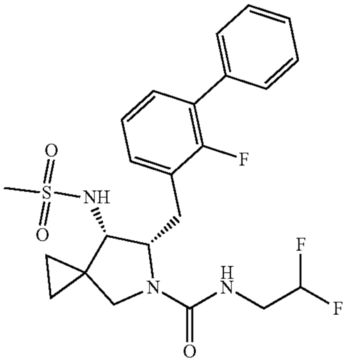 [SMILES: CS(=O)(=O)N[C@@H]1[C@H](Cc2cccc(-c3ccccc3)c2F)N(C(=O)NCC(F)F)CC12CC2] |
| 113 | N-((6S,7S)-6-([1,1'-biphenyl]-3-ylmethyl)-5-(bicyclo[1.1.0]butane-1-carbonyl)-5-azaspiro[2.4]heptan-7-yl)methanesulfonamide | 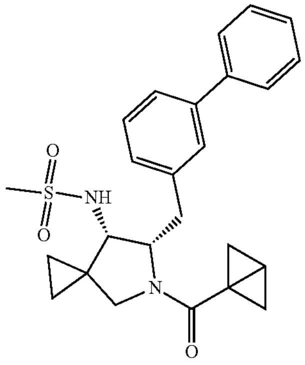 [SMILES: CS(=O)(=O)N[C@@H]1[C@H](Cc2cccc(-c3ccccc3)c2)N(C(=O)C23CC2C3)CC12CC2] |

TABLE 1-continued

| Compound No. | Name | Structure |
|---|---|---|
| 114 | N-((6S,7S)-6-([1,1'-biphenyl]-3-ylmethyl)-5-((R)-oxetane-2-carbonyl)-5-azaspiro[2.4]heptan-7-yl)propane-2-sulfonamide | 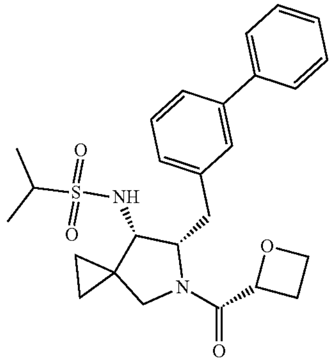 |
| 115 | N-((6S,7S)-6-([1,1'-biphenyl]-3-ylmethyl)-5-((R)-oxetane-2-carbonyl)-5-azaspiro[2.4]heptan-7-yl)-1,1-difluoromethanesulfonamide | 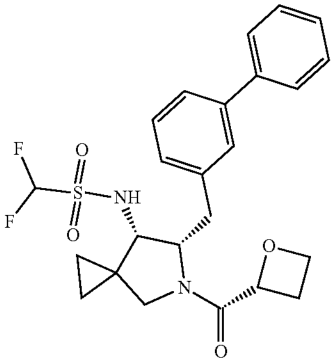 |
| 116 | N-((6S,7S)-5-(azetidine-1-carbonyl)-6-((2-fluoro-[1,1'-biphenyl]-3-yl)methyl)-5-azaspiro[2.4]heptan-7-yl)-N,N-dimethylsulfuric diamide | 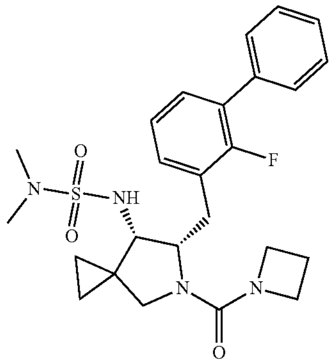 [SMILES: CN(C)S(=O)(=O)N[C@@H]1[C@H](Cc2cccc(-c3ccccc3)c2F)N(C(=O)N2CCC2)CC12CC2] |
| 117 | N-((6S,7S)-6-((2-fluoro-[1,1'-biphenyl]-3-yl)methyl)-5-(3-fluoroazetidine-1-carbonyl)-5-azaspiro[2.4]heptan-7-yl)-N,N-dimethylsulfuric diamide | 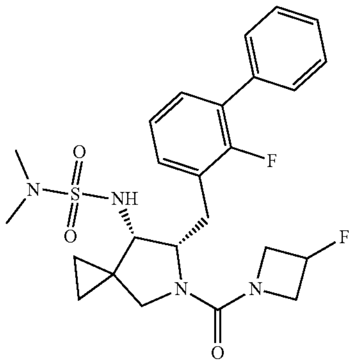 [SMILES: CN(C)S(=O)(=O)N[C@@H]1[C@H](Cc2cccc(-c3ccccc3)c2F)N(C(=O)N2CC(F)C2)CC12CC2] |

TABLE 1-continued

| Compound No. | Name | Structure |
|---|---|---|
| 118 | N-((6S,7S)-6-((2-fluoro-[1,1'-biphenyl]-3-yl)methyl)-5-(3-methoxyazetidine-1-carbonyl)-5-azaspiro[2.4]heptan-7-yl)-N,N-dimethylsulfuric diamide | 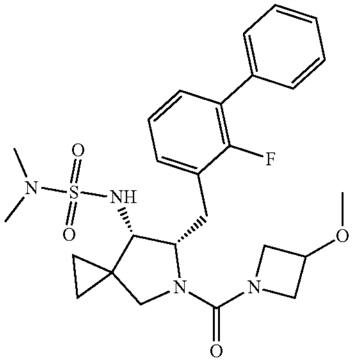 |
| 119 | N-((6S,7S)-6-((2-fluoro-[1,1'-biphenyl]-3-yl)methyl)-5-((S)-3,3,3-trifluoro-2-hydroxypropanoyl)-5-azaspiro[2.4]heptan-7-yl)-N,N-dimethylsulfuric diamide | 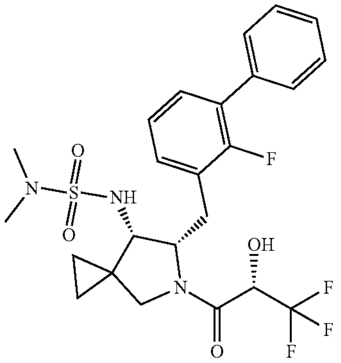 [SMILES: CN(C)S(=O)(=O)N[C@@H]1[C@H](Cc2cccc(-c3ccccc3)c2F)N(C(=O)[C@H](O)C(F)(F)F)CC12CC2] |
| 120 | N-((6S,7S)-6-((2-fluoro-[1,1'-biphenyl]-3-yl)methyl)-5-(1-hydroxycyclobutane-1-carbonyl)-5-azaspiro[2.4]heptan-7-yl)-N,N-dimethylsulfuric diamide | 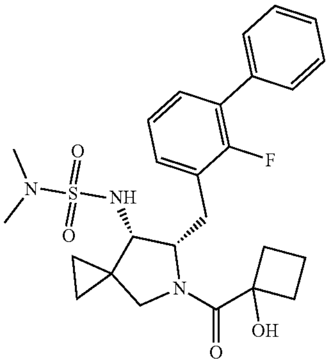 [SMILES: CN(C)S(=O)(=O)N[C@@H]1[C@H](Cc2cccc(-c3ccccc3)c2F)N(C(=O)C2(O)CCC2)CC12CC2] |
| 121 | (6S,7S)-7-((N,N-dimethylsulfamoyl)amino)-N-ethyl-6-(2-fluoro-[1,1'-biphenyl]-3-yl)methyl)-5-azaspiro[2.4]heptane-5-carboxamide | 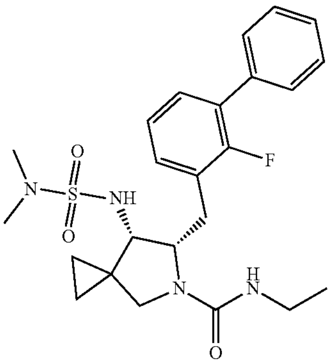 [SMILES: CCNC(=O)N1CC2(CC2)[C@H](NS(=O)(=O)N(C)C)[C@@H]1Cc1cccc(-c2ccccc2)c1F] |

TABLE 1-continued

| Compound No. | Name | Structure |
|---|---|---|
| 122 | N-((6S,7S)-5-((R)-oxetane-2-carbonyl)-6-((2,3',5-trifluoro-[1,1'-biphenyl]-3-yl)methyl)-5-azaspiro[2.4]heptan-7-yl)methanesulfonamide | 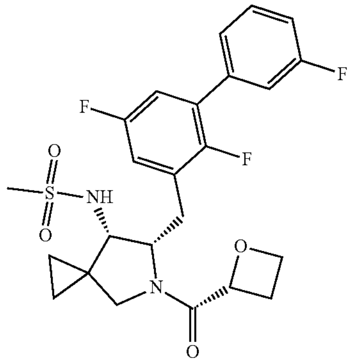 |
| 123 | 1-fluoro-N-((6S,7S)-5-((R)-oxetane-2-carbonyl)-6-((2,3',5-trifluoro-[1,1'-biphenyl]-3-yl)methyl)-5-azaspiro[2.4]heptan-7-yl)methanesulfonamide | 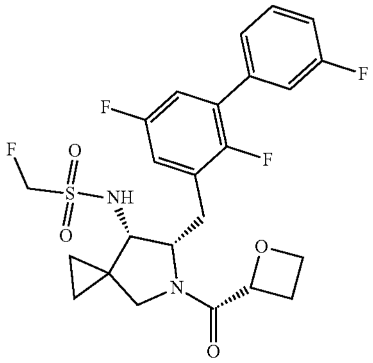 |
| 124 | 1-fluoro-N-((6S,7S)-5-((R)-oxetane-2-carbonyl)-6-((2,3',5-trifluoro-[1,1'-biphenyl]-3-yl)methyl)-5-azaspiro[2.4]heptan-7-yl)-N,N-dimethylsulfuric diamide | 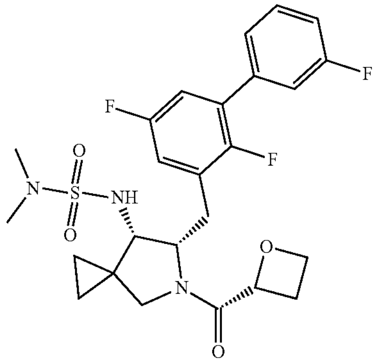 |
| 125 | N-((6S,7S)-5-((R)-2-cyclopropyl-2-hydroxyacetyl)-6-((2-fluoro-[1,1'-biphenyl]-3-yl)methyl)-5-azaspiro[2.4]heptan-7-yl)-N,N-dimethylsulfuric diamide | 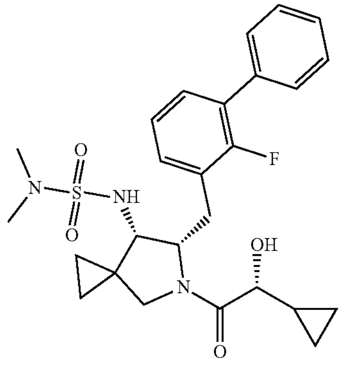 [SMILES: CN(C)S(=O)(=O)N[C@@H]1[C@H](Cc2cccc(-c3ccccc3)c2F)N(C(=O)[C@H](O)C2CC2)CC12CC2] |

TABLE 1-continued

| Compound No. | Name | Structure |
|---|---|---|
| 126 | N-((6S,7S)-6-((2,3'-difluoro-[1,1'-biphenyl]-3-yl)methyl)-5-((R)-oxetane-2-carbonyl)-5-azaspiro[2.4]heptan-7-yl)-N,N-dimethylsulfuric diamide | 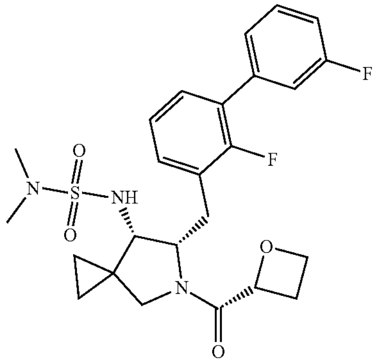 |
| 127 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)-N,N-dimethylsulfuric diamide | 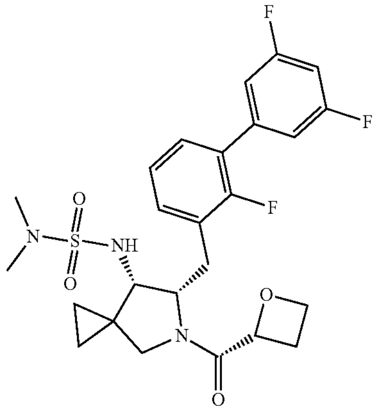 |
| 128 | 1-fluoro-N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)methanesulfonamide | 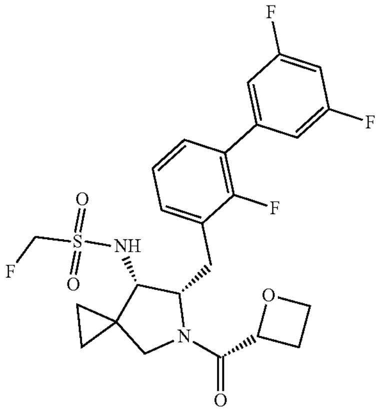 |
| 129 | N-((6S,7S)-6-(2,3'-difluoro-[1,1'-biphenyl]-3-yl)methyl)-5-((R)-oxetane-2-carbonyl)-5-azaspiro[2.4]heptan-7-yl)ethanesulfonamide | 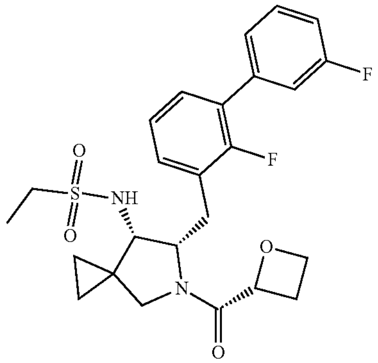 |

TABLE 1-continued

| Compound No. | Name | Structure |
|---|---|---|
| 130 | N-(6S,7S)-6-(2,2-difluoro-[1,1'-biphenyl]-3-yl)methyl)-5-((R)-oxetane-2-carbonyl)-5-azaspiro[2.4]heptan-7-yl)ethanesulfonamide | 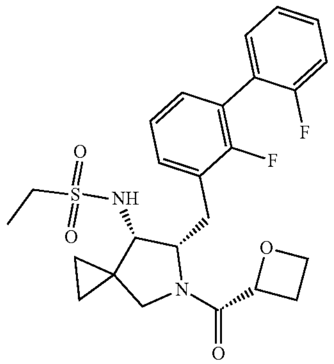 |
| 131 | N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)methanesulfonamide | 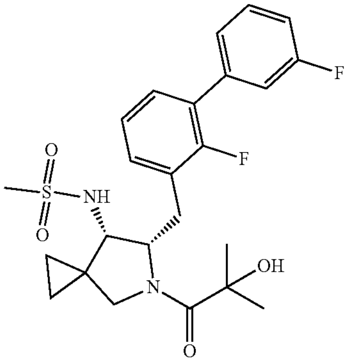 [SMILES: CC(C)(O)C(=O)N1CC2(CC2)[C@H](NS(C)(=O)=O)[C@@H]1Cc1cccc(-c2cccc(F)c2)c1F] |
| 132 | N-((6S,7S)-6-((2,3'-difluoro-[1,1'-biphenyl]-3-yl)methyl)-5-((R)-oxetane-2-carbonyl)-5-azaspiro[2.4]heptan-7-yl)-1-fluoromethanesulfonamide | 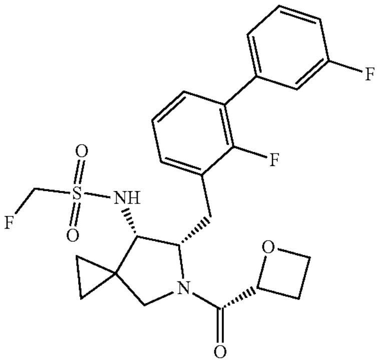 |
| 133 | N-((6S,7S)-5-((R)-2-cyclopropyl-2-hydroxyacetyl)-6-((2-fluoro-[1,1'-biphenyl]-3-yl)methyl)-5-azaspiro[2.4]heptan-7-yl)-1-fluoromethanesulfonamide | 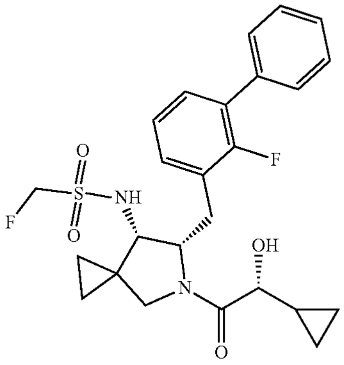 [SMILES: O=C([C@H](O)C1CC1)N1CC2(CC2)[C@H](NS(=O)(=O)CF)[C@@H]1Cc1cccc(-c2ccccc2)c1F] |

TABLE 1-continued

| Compound No. | Name | Structure |
|---|---|---|
| 134 | 1-fluoro-N-((6S,7S)-6-((2-fluoro-[1,1'-biphenyl]-3-yl)methyl)-5-(2-hydroxy-2-methylpropanoyl)-5-azaspiro[2.4]heptan-7-yl)methanesulfonamide | 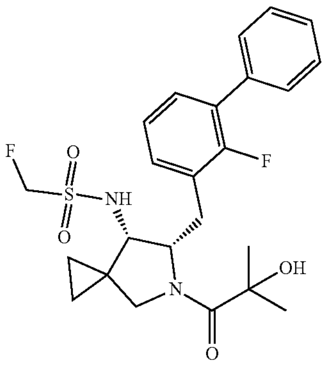 [SMILES: CC(C)(O)C(=O)N1CC2(CC2)[C@H](NS(=O)(=O)CF)[C@@H]1Cc1cccc(-c2ccccc2)c1F] |
| 135 | N-((6S,7S)-5-(azetidine-1-carbonyl)-6-((2-fluoro-[1,1'-biphenyl]-3-yl)methyl)-5-azaspiro[2.4]heptan-7-yl)-1-fluoromethanesulfonamide | 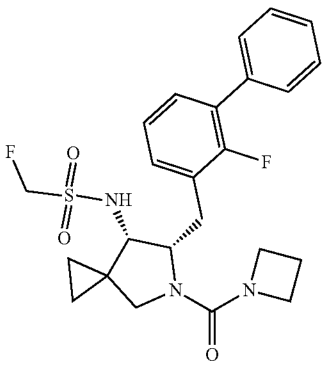 [SMILES: O=C(N1CCC1)N1CC2(CC2)[C@H](NS(=O)(=O)CF)[C@@H]1Cc1cccc(-c2ccccc2)c1F] |
| 136 | 1-fluoro-N-((6S,7S)-6-((2-fluoro-[1,1'-biphenyl]-3-yl)methyl)-5-(3-methoxyazetidine-1-carbonyl)-5-azaspiro[2.4]heptan-7-yl)methanesulfonamide | 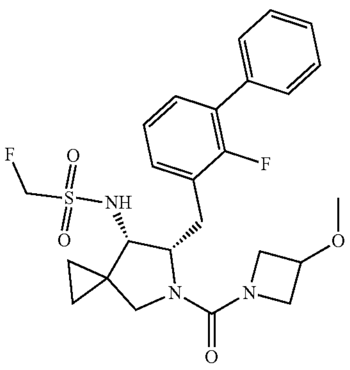 [SMILES: COC1CN(C(=O)N2CC3(CC3)[C@H](NS(=O)(=O)CF)[C@@H]2Cc2cccc(-c3ccccc3)c2F)C1] |
| 137 | N-((6S,7S)-6-((2,2'-difluoro-[1,1'-biphenyl]-3-yl)methyl)-5-((R)-oxetane-2-carbonyl)-5-azaspiro[2.4]heptan-7-yl)-1-fluoromethanesulfonamide | 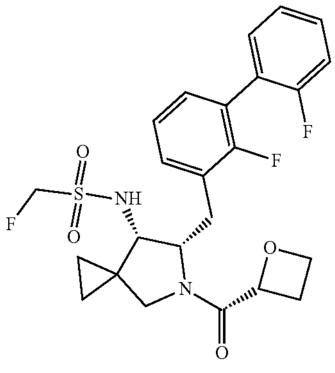 |

TABLE 1-continued

| Compound No. | Name | Structure |
|---|---|---|
| 138 | N-((6S,7S)-6-((2-fluoro-[1,1'-biphenyl]-3-yl)methyl)-5-(2-hydroxy-2-methylpropanoyl)-5-azaspiro[2.4]heptan-7-yl)-N,N-dimethylsulfuric diamide | 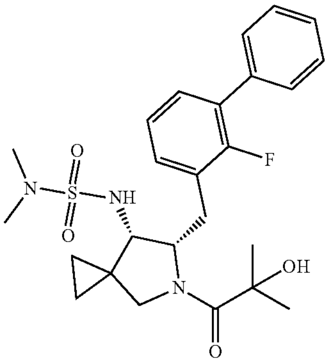 [SMILES: CN(C)S(=O)(=O)N[C@@H]1[C@H](Cc2cccc(-c3ccccc3)c2F)N(C(=O)C(C)(C)O)CC12CC2] |
| 139 | (6S,7S)-7-((N,N-dimethylsulfamoyl)amino)-6-((2-fluoro-[1,1'-biphenyl]-3-yl)methyl)-N,N-dimethyl-5-azaspiro[2.4]heptane-5-carboxamide | 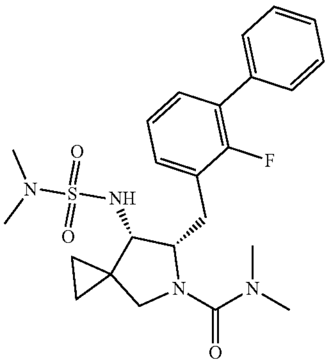 [SMILES: CN(C)C(=O)N1CC2(CC2)[C@H](NS(=O)(=O)N(C)C)[C@@H]1Cc1cccc(-c2ccccc2)c1F] |
| 140 | N-((6S,7S)-6-((2,2'-difluoro-[1,1'-biphenyl]-3-yl)methyl)-5-((R)-oxetane-2-carbonyl)-5-azaspiro[2.4]heptan-7-yl)-N,N-dimethylsulfuric diamide | 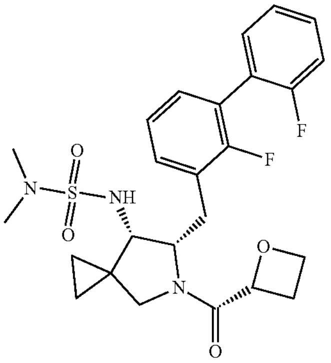 |
| 141 | N-((6S,7S)-5-((R)-oxetane-2-carbonyl)-6-((2,2',5'-trifluoro-[1,1'-biphenyl]-3-yl)methyl)-5-azaspiro[2.4]heptan-7-yl)methanesulfonamide | 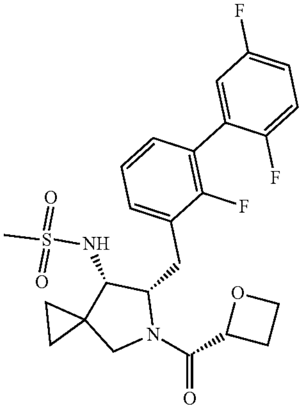 |

TABLE 1-continued

| Compound No. | Name | Structure |
|---|---|---|
| 142 | N-((6S,7S)-5-((R)-oxetane-2-carbonyl)-6-((2,2',3'-trifluoro-[1,1'-biphenyl]-3-yl)methyl)-5-azaspiro[2.4]heptan-7-yl)methanesulfonamide | 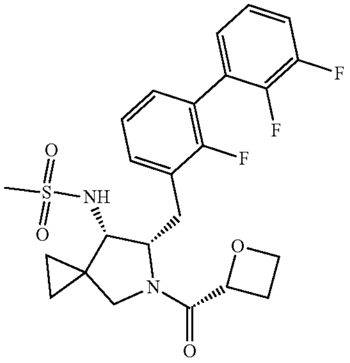 |
| 143 | N-((6S,7S)-5-((R)-2-cyclopropyl-2-hydroxyacetyl)-6-((2-fluoro-[1,1'-biphenyl]-3-yl)methyl)-5-azaspiro[2.4]heptan-7-yl)methanesulfonamide | 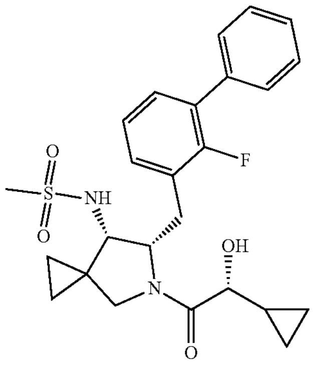 [SMILES: CS(=O)(=O)N[C@@H]1[C@H](Cc2cccc(-c3ccccc3)c2F)N(C(=O)[C@H](O)C2CC2)CC12CC2] |
| 144 | 1,1-difluoro-N-(6S,7S)-6-((2-fluoro-[1,1'-biphenyl]-3-yl)methyl)-5-((R)-oxetane-2-carbonyl)-5-azaspiro[2.4]heptan-7-yl)methanesulfonamide | 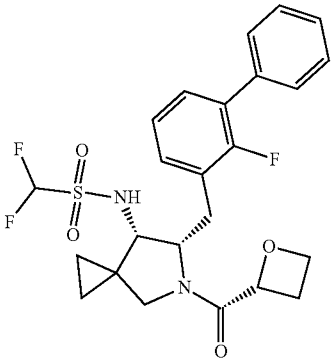 |
| 145 | N-((6S,7S)-6-((2,5-difluoro-[1,1'-biphenyl]-3-yl)methyl)-5-((R)-oxetane-2-carbonyl)-5-azaspiro[2.4]heptan-7-yl)-1-fluoromethanesulfonamide | 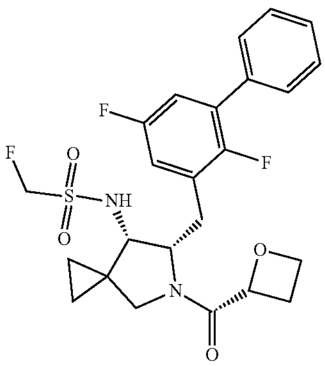 |

TABLE 1-continued

| Compound No. | Name | Structure |
|---|---|---|
| 146 | N-((6S,7S)-6-((2,5-difluoro-[1,1'-biphenyl]-3-yl)methyl)-5-((R)-oxetane-2-carbonyl)-5-azaspiro[2.4]heptan-7-yl)ethanesulfonamide | 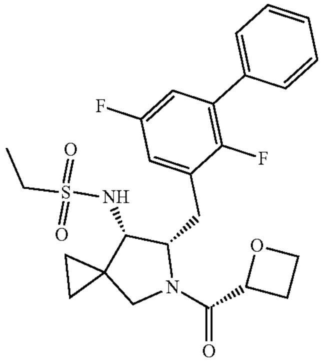 |
| 147 | N-((6S,7S)-5-((R)-oxetane-2-carbonyl)-6-((2,3',5-trifluoro-[1,1'-biphenyl]-3-yl)methyl)-5-azaspiro[2.4]heptan-7-yl)ethanesulfonamide | 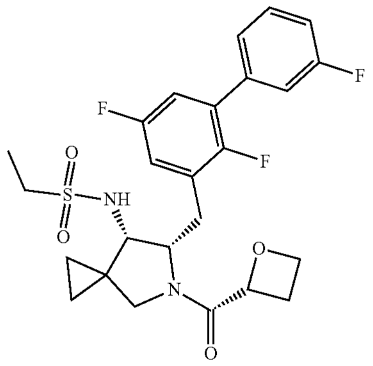 |
| 148 | 1-fluoro-N-((6S,7S)-5-((R)-oxetane-2-carbonyl)-6-((2,2',5-trifluoro-[1,1'-biphenyl]-3-yl)methyl)-5-azaspiro[2.4]heptan-7-yl)methanesulfonamide | 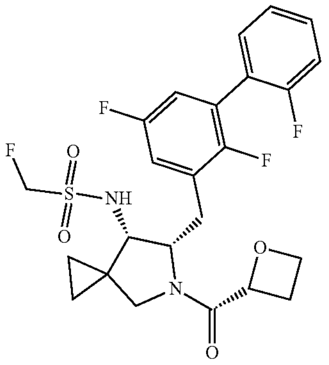 |
| 149 | N-((6S,7S)-5-((R)-oxetane-2-carbonyl)-6-((2,2',5-trifluoro-[1,1'-biphenyl]-3-yl)methyl)-5-azaspiro[2.4]heptan-7-yl)ethanesulfonamide | 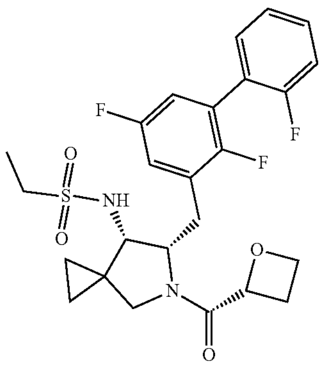 |

TABLE 1-continued

| Compound No. | Name | Structure |
|---|---|---|
| 150 | N-((6S,7S)-5-((S)-3,3-difluoro-2-hydroxypropanoyl)-6-((2-fluoro-[1,1'-biphenyl]-3-yl)methyl)-5-azaspiro[2.4]heptan-7-yl)-1-fluoromethanesulfonamide | 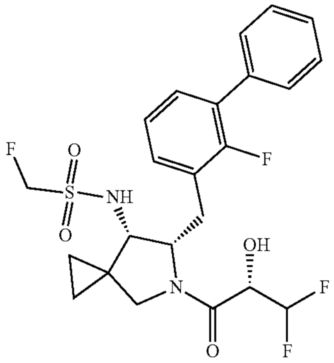 [SMILES: O=C([C@H](O)C(F)F)N1CC2(CC2)[C@H](NS(=O)(=O)CF)[C@@H]1Cc1cccc(-c2ccccc2)c1F] |
| 151 | N-((6S,7S)-5-(azetidine-1-carbonyl)-6-((2,5-difluoro-[1,1'-biphenyl]-3-yl)methyl)-5-azaspiro[2.4]heptan-7-yl)methanesulfonamide | 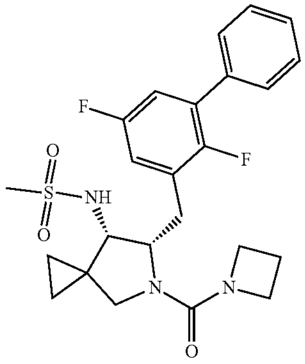 [SMILES: CS(=O)(=O)N[C@@H]1[C@H](Cc2cc(F)cc(-c3ccccc3)c2F)N(C(=O)N2CCC2)CC12CC2] |
| 152 | 1-fluoro-[1,1'-biphenyl]-3-yl)methyl)-5-((S)-2-fluoropropanoyl)-5-azaspiro[2.4]heptan-7-yl)methanesulfonamide | 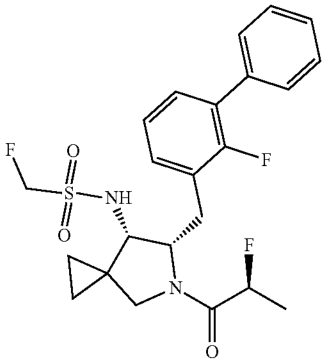 [SMILES: C[C@H](F)C(=O)N1CC2(CC2)[C@H](NS(=O)(=O)CF)[C@@H]1Cc1cccc(-c2ccccc2)c1F] |
| 153 | 1-fluoro-N-((6S,7S)-5-((S)-3-fluoro-2-hydroxypropanoyl)-6-((2-fluoro-[1,1'-biphenyl]-3-yl)methyl)-5-azaspiro[2.4]heptan-7-yl)methanesulfonamide | 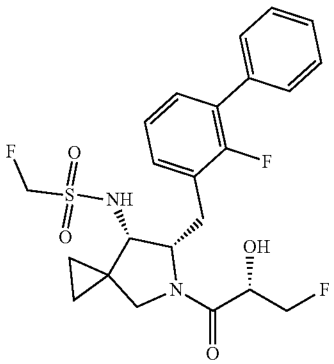 [SMILES: O=C([C@H](O)CF)N1CC2(CC2)[C@H](NS(=O)(=O)CF)[C@@H]1Cc1cccc(-c2ccccc2)c1F] |

TABLE 1-continued

| Compound No. | Name | Structure |
|---|---|---|
| 154 | N-((6S,7S)-6-((2,3'-difluoro-[1,1'-biphenyl]-3-yl)methyl)-5-((R)-oxetane-2-carbonyl)-5-azaspiro[2.4]heptan-7-yl)-1,1-difluoromethanesulfonamide | 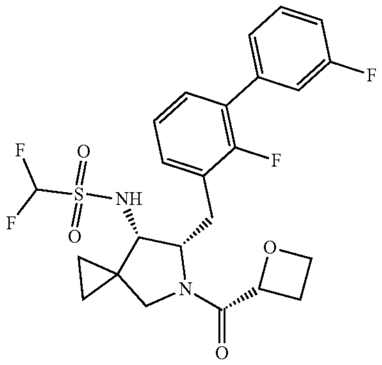 |
| 155 | N-((6S,7S)-6-((2,5-difluoro-[1,1'-biphenyl]-3-yl)methyl)-5-((R)-oxetane-2-carbonyl)-5-azaspiro[2.4]heptan-7-yl)-1,1-difluoromethanesulfonamide | 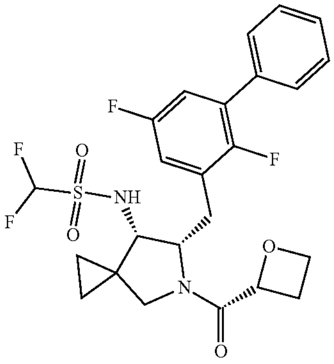 |
| 156 | N-((6S,7S)-6-((2-fluoro-[1,1'-biphenyl]-3-yl)methyl)-5-((R)-oxetane-2-carbonyl)-5-azaspiro[2.4]heptan-7-yl)-N,N-dimethylsulfuric diamide-$d_6$ | 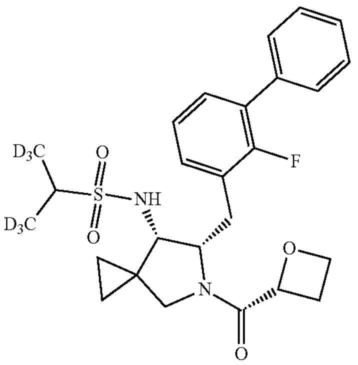 |
| 157 | (6S,7S)-6-((2-fluoro-[1,1'-biphenyl]-3-yl)methyl)-N-((1-fluorocyclopropyl)methyl)-7-((fluoromethyl)sulfonamido)-5-azaspiro[2.4]heptane-5-carboxamide | 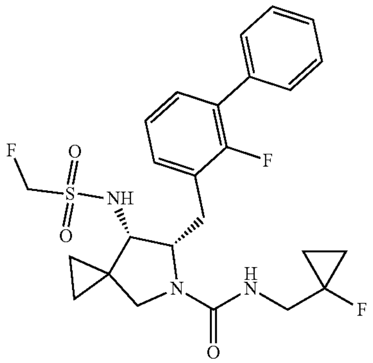 [SMILES: O=C(NCC1(F)CC1)N1CC2(CC2)[C@H](NS(=O)(=O)CF)[C@@H]1Cc1cccc(-c2ccccc2)c1F] |

TABLE 1-continued

| Compound No. | Name | Structure |
|---|---|---|
| 158 | (6S,7S)-6-(2-fluoro-[1,1'-biphenyl]-3-yl)methyl)-7-((fluoromethyl)sulfonamido)-N-((R)-1-fluoropropan-2-yl)-5-azaspiro[2.4]heptane-5-carboxamide | 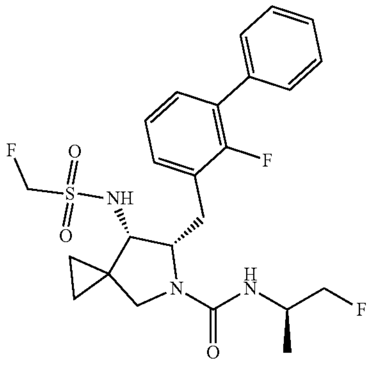 [SMILES: C[C@H](CF)NC(=O)N1CC2(CC2)[C@H](NS(=O)(=O)CF)[C@@H]1Cc1cccc(-c2ccccc2)c1F] |
| 159 | 1,1-difluoro-N-((6S,7S)-6-(2-fluoro-3'-methyl-[1,1'-biphenyl]-3-yl)methyl)-5-((R)-oxetane-2-carbonyl)-5-azaspiro[2.4]heptan-7-yl)methanesulfonamide | 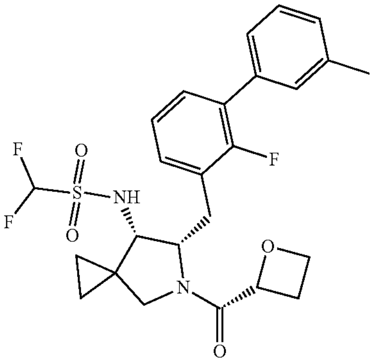 |
| 160 | 1,1-difluoro-N-((6S,7S)-6-((2-fluoro-[1,1'-biphenyl]-3-yl)methyl)-5-((S)-2-fluoropropanoyl)-5-azaspiro[2.4]heptan-7-yl)methanesulfonamide | 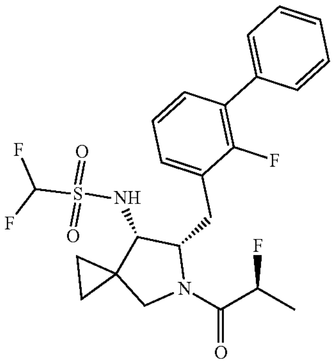 [SMILES: C[C@H](F)C(=O)N1CC2(CC2)[C@H](NS(=O)(=O)C(F)F)[C@@H]1Cc1cccc(-c2ccccc2)c1F] |
| 161 | N-((6S,7S)-6-((3'-chloro-2-fluoro-[1,1'-biphenyl]-3-yl)methyl)-5-((R)-oxetane-2-carbonyl)-5-azaspiro[2.4]heptan-7-yl)methanesulfonamide | 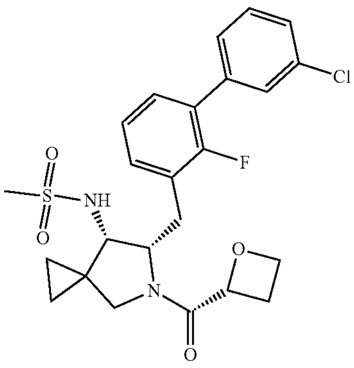 |

TABLE 1-continued

| Compound No. | Name | Structure |
|---|---|---|
| 162 | N-((6S,7S)-6-((2-fluoro-[1,1'-biphenyl]-3-yl)methyl)-5-((R)-oxetane-2-carbonyl)-5-azaspiro[2.4]heptan-7-yl)propane-2-sulfonamide | 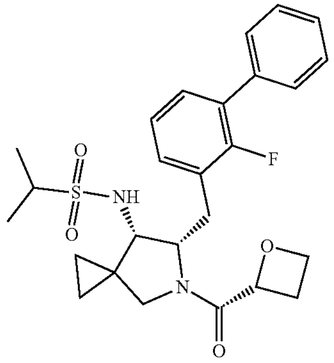 |
| 163 | N-((6S,7S)-6-((2,2'-difluoro-[1,1'-biphenyl]-3-yl)methyl)-5-((R)-oxetane-2-carbonyl)-5-azaspiro[2.4]heptan-7-yl)-1,1-difluoromethanesulfonamide | 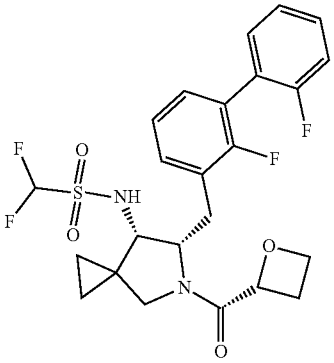 |
| 164 | N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)-1,1-difluoromethanesulfonamide | 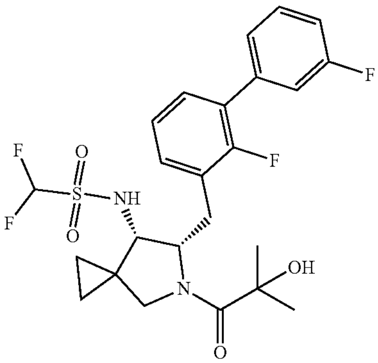 [SMILES: CC(C)(O)C(=O)N1CC2(CC2)[C@H](NS(=O)(=O)C(F)F)[C@@H]1Cc1cccc(-c2cccc(F)c2)c1F] |
| 165 | (6S,7S)-N-(2,2-difluoroethyl)-7-((difluoromethyl)sulfonamido)-6-((2-fluoro-[1,1'-biphenyl]-3-yl)methyl)-5-azaspiro[2.4]heptane-5-carboxamide | 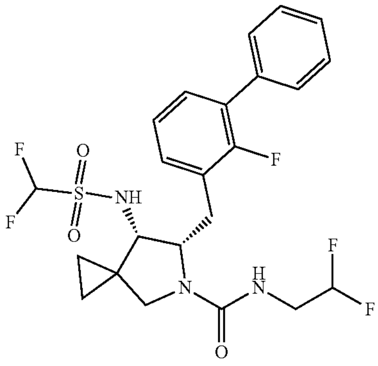 [SMILES: O=C(NCC(F)F)N1CC2(CC2)[C@H](NS(=O)(=O)C(F)F)[C@@H]1Cc1cccc(-c2ccccc2)c1F] |

TABLE 1-continued

| Compound No. | Name | Structure |
|---|---|---|
| 166 | (6S,7S)-7-((difluoromethyl)sulfonamido)-6-((2-fluoro-[1,1'-biphenyl]-3-yl)methyl)-N-((1-fluorocyclopropyl)methyl)-5-azaspiro[2.4]heptane-5-carboxamide | 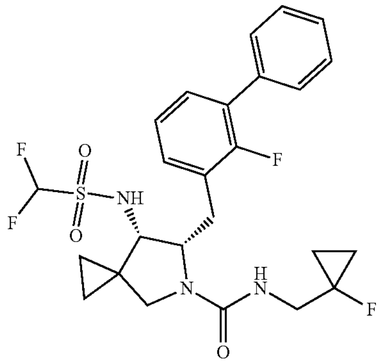 [SMILES: O=C(NCC1(F)CC1)N1CC2(CC2)[C@H](NS(=O)(=O)C(F)F)[C@@H]1Cc1cccc(-c2ccccc2)c1F] |
| 167 | 1,1,1-trifluoro-N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide | 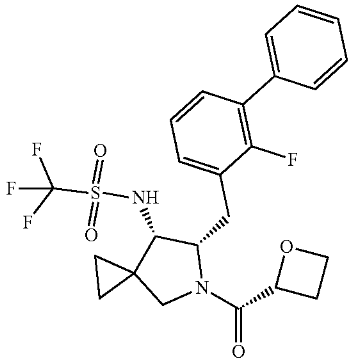 |
| 168 | 1-fluoro-N-((6S,7S)-5-((R)-oxetane-2-carbonyl)-6-((2,2',3'-trifluoro-[1,1'-biphenyl]-3-yl)methyl)-5-azaspiro[2.4]heptan-7-yl)methanesulfonamide | 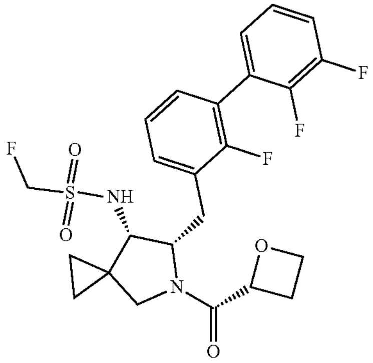 |
| 169 | 1-fluoro-N-((6S,7S)-5-((R)-oxetane-2-carbonyl)-6-((2,2',5'-trifluoro-[1,1'-biphenyl]-3-yl)methyl)-5-azaspiro[2.4]heptan-7-yl)methanesulfonamide | 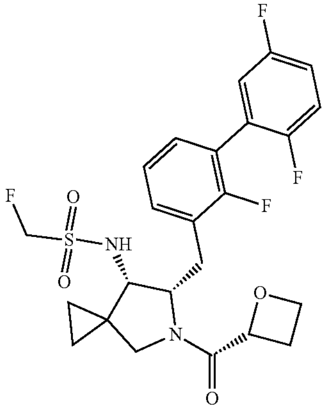 |

TABLE 1-continued

| Compound No. | Name | Structure |
|---|---|---|
| 170 | N-((6S,7S)-5-((S)-2-cyclopropyl-2-hydroxyacetyl)-6-((2-fluoro-[1,1'-biphenyl]-3-yl)methyl)-5-azaspiro[2.4]heptan-7-yl)-1,1-difluoromethanesulfonamide | 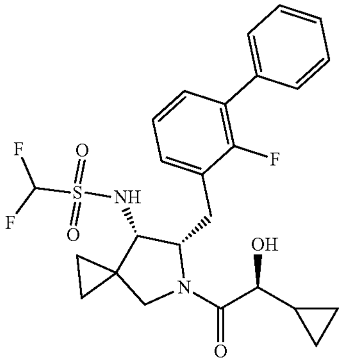 [SMILES: O=C([C@@H](O)C1CC1)N1CC2(CC2)[C@H](NS(=O)(=O)C(F)F)[C@@H]1Cc1cccc(-c2ccccc2)c1F] |
| 171 | 1,1-difluoro-N-((6S,7S)-5-((R)-oxetane-2-carbonyl)-6-((2,2',5'-trifluoro-[1,1'-biphenyl]-3-yl)methyl)-5-azaspiro[2.4]heptan-7-yl)methanesulfonamide | 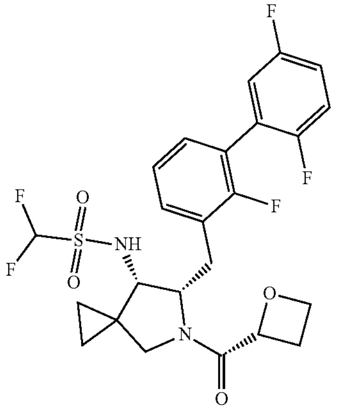 |
| 172 | 1,1-difluoro-N-((6S,7S)-5-((R)-oxetane-2-carbonyl)-6-(2,2,3-trifluoro-[1,1'-biphenyl]-3-yl)methyl)-5-azaspiro[2.4]heptan-7-yl)methanesulfonamide | 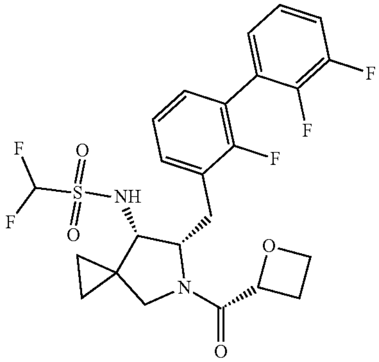 |
| 173 | 1,1-difluoro-N-((6S,7S)-6-((2-fluoro-[1,1'-biphenyl]-3-yl-2',3',4',5',6'-d5)methyl)-5-((R)-oxetane-2-carbonyl)-5-azaspiro[2.4]heptan-7-yl)methanesulfonamide | 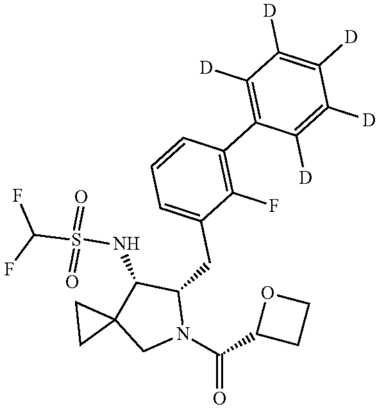 |

TABLE 1-continued

| Compound No. | Name | Structure |
|---|---|---|
| 174 | 1,1-difluoro-N-((6S,7S)-5-((S)-3-fluoro-2-hydroxypropanoyl)-6-((2-fluoro-[1,1'-biphenyl]-3-yl)methyl)-5-azaspiro[2.4]heptan-7-yl)methanesulfonamide | 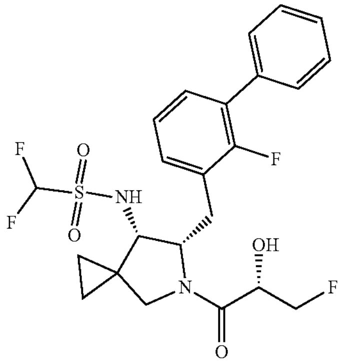 [SMILES: O=C([C@H](O)CF)N1CC2(CC2)[C@H](NS(=O)(=O)C(F)F)[C@@H]1Cc1cccc(-c2ccccc2)c1F] |
| 175 | 1,1-difluoro-N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)methanesulfonamide | 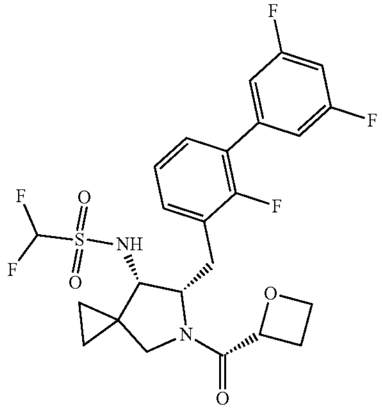 |
| 176 | 1,1-difluoro-N-((6S,7S)-5-((R)-oxetane-2-carbonyl)-6-((2,3',5-trifluoro-[1,1'-biphenyl]-3-yl)methyl)-5-azaspiro[2.4]heptan-7-yl)methanesulfonamide | 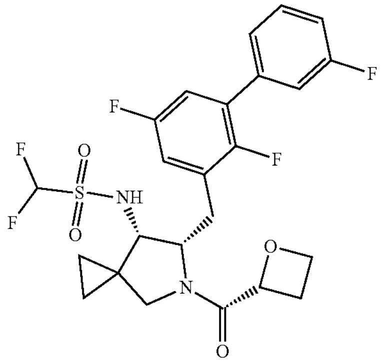 |
| 177 | N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)-1-fluoromethanesulfonamide | 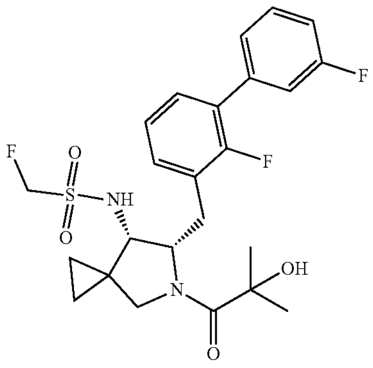 [SMILES: CC(C)(O)C(=O)N1CC2(CC2)[C@H](NS(=O)(=O)CF)[C@@H]1Cc1cccc(-c2cccc(F)c2)c1F] |

TABLE 1-continued

| Compound No. | Name | Structure |
| --- | --- | --- |
| 178 | N-((6S,7S)-5-((S)-3-fluoro-2-hydroxypropanoyl)-6-((2-fluoro-[1,1'-biphenyl]-3-yl)methyl)-5-azaspiro[2.4]heptan-7-ylethanesulfonamide | 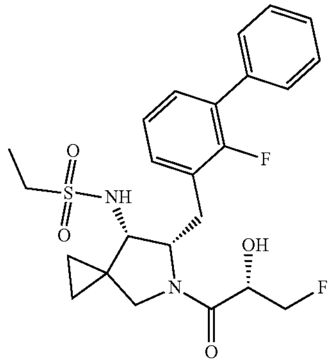 [SMILES: CCS(=O)(=O)N[C@@H]1[C@H](Cc2cccc(-c3ccccc3)c2F)N(C(=O)[C@H](O)CF)CC12CC2] |
| 179 | N-((6S,7S)-6-((2,3'-difluoro-[1,1'-biphenyl]-3-yl)methyl)-5-(2,2-difluoropropanoyl)-5-azaspiro[2.4]heptan-7-yl)-1-fluoromethanesulfonamide | 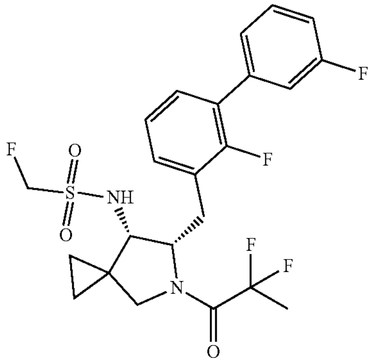 [SMILES: CC(F)(F)C(=O)N1CC2(CC2)[C@H](NS(=O)(=O)CF)[C@@H]1Cc1cccc(-c2cccc(F)c2)c1F] |
| 180 | 1-fluoro-N-((6S,7S)-6-((2-fluoro-[1,1'-biphenyl]-3-yl)methyl)-5-(1-methoxycyclopropane-1-carbonyl)-5-azaspiro[2.4]heptan-7-yl)methanesulfonamide | 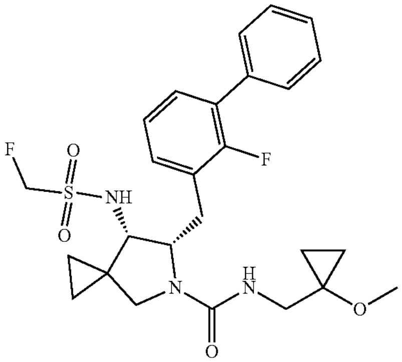 [SMILES: COC1(CNC(=O)N2CC3(CC3)[C@H](NS(=O)(=O)CF)[C@@H]2Cc2cccc(-c3ccccc3)c2F)CC1] |
| 181 | N-((6S,7S)-5-(1-cyanocyclobutane-1-carbonyl)-6-((2-fluoro-[1,1'-biphenyl]-3-yl)methyl)-5-azaspiro[2.4]heptan-7-yl)-1-fluoromethanesulfonamide | 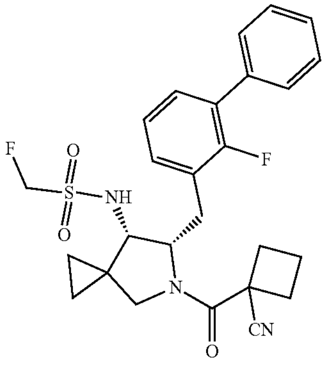 [SMILES: N#CC1(C(=O)N2CC3(CC3)[C@H](NS(=O)(=O)CF)[C@@H]2Cc2cccc(-c3ccccc3)c2F)CCC1] |

TABLE 1-continued

| Compound No. | Name | Structure |
| --- | --- | --- |
| 182 | 1,1-difluoro-N-((6S,7S)-6-((2-fluoro-[1,1'-biphenyl]-3-yl)methyl)-5-((1r,3r)-3-fluorocyclobutane-1-carbonyl)-5-azaspiro[2.4]heptan-7-yl)methanesulfonamide | 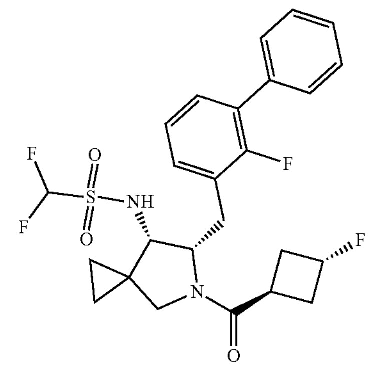 [SMILES: O=C([C@H]1C[C@H](F)C1)N1CC2(CC2)[C@H](NS(=O)(=O)C(F)F)[C@@H]1Cc1cccc(-c2ccccc2)c1F] |
| 183 | 1,1-difluoro-N-((6S,7S)-6-((2-fluoro-[1,1'-biphenyl]-3-yl)methyl)-5-((S)-2-hydroxy-3-methoxypropanoyl)-5-azaspiro[2.4]heptan-7-yl)methanesulfonamide | 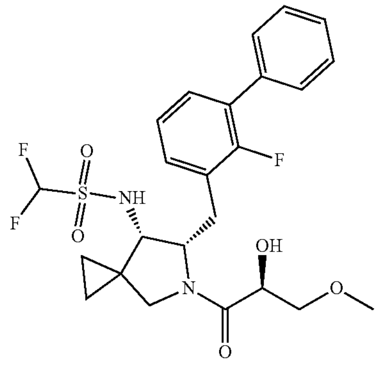 |
| 184 | N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)ethanesulfonamide | 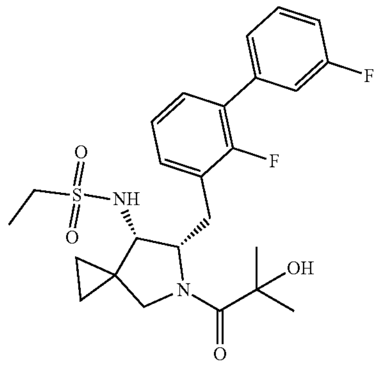 [SMILES: CCS(=O)(=O)N[C@@H]1[C@H](Cc2cccc(-c3cccc(F)c3)c2F)N(C(=O)C(C)(C)O)CC12CC2] |
| 185 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)ethanesulfonamide | 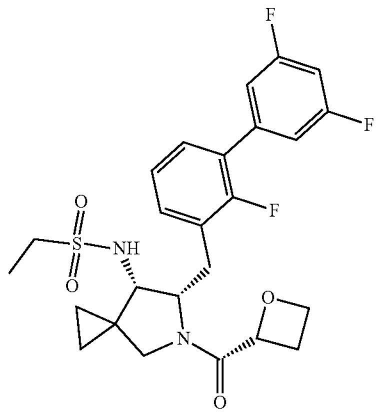 |

TABLE 1-continued

| Compound No. | Name | Structure |
|---|---|---|
| 186 | (6S,7S)-N-((1-cyanocyclopropyl)methyl)-6-((2-fluoro-[1,1'-biphenyl]-3-yl)methyl)-7-((fluoromethyl)sulfonamido)-5-azaspiro[2.4]heptane-5-carboxamide | 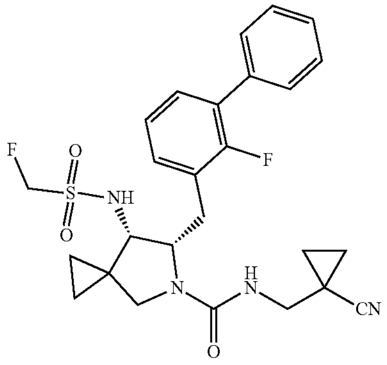 [SMILES: N#CC1(CNC(=O)N2CC3(CC3)[C@H](NS(=O)(=O)CF)[C@@H]2Cc2cccc(-c3ccccc3)c2F)CC1] |
| 187 | (6S,7S)-N-(2,2-difluoroethyl)-6-((2-fluoro-[1,1'-biphenyl]-3-yl)methyl)-7-((fluoromethyl)sulfonamido)-5-azaspiro[2.4]heptane-5-carboxamide | 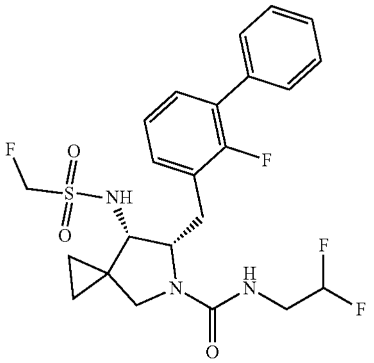 [SMILES: O=C(NCC(F)F)N1CC2(CC2)[C@H](NS(=O)(=O)CF)[C@@H]1Cc1cccc(-c2ccccc2)c1F] |
| 188 | 1-fluoro-N-(6S,7S)-6-((2-fluoro-[1,1'-biphenyl]-3-yl)methyl)-5-((1r,3r)-3-fluorocyclobutane-1-carbonyl)-5-azaspiro[2.4]heptan-7-yl)methanesulfonamide | 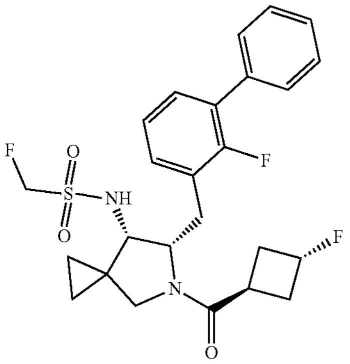 [SMILES: O=C([C@H]1C[C@H](F)C1)N1CC2(CC2)[C@H](NS(=O)(=O)CF)[C@@H]1Cc1cccc(-c2ccccc2)c1F] |
| 189 | 1-fluoro-N-(6S,7S)-6-((2-fluoro-[1,1'-biphenyl]-3-yl)methyl)-5-((1s,3s)-3-fluorocyclobutane-1-carbonyl)-5-azaspiro[2.4]heptan-7-yl)methanesulfonamide | 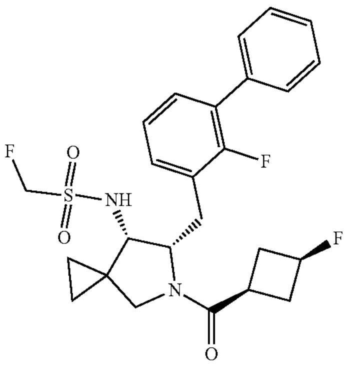 [SMILES: O=C([C@H]1C[C@@H](F)C1)N1CC2(CC2)[C@H](NS(=O)(=O)CF)[C@@H]1Cc1cccc(-c2ccccc2)c1F] |

TABLE 1-continued

| Compound No. | Name | Structure |
|---|---|---|
| 190 | N-((6S,7S)-6-((2,5-difluoro-[1,1'-biphenyl]-3-yl)methyl)-5-((S)-3-fluoro-2-hydroxypropanoyl)-5-azaspiro[2.4]heptan-7-yl)-1-fluoromethanesulfonamide | 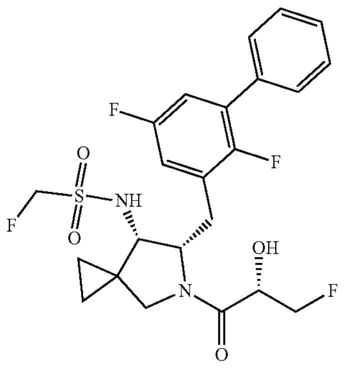 [SMILES: O=C([C@H](O)CF)N1CC2(CC2)[C@H](NS(=O)(=O)CF)[C@@H]1Cc1cc(F)cc(-c2ccccc2)c1F] |
| 191 | (6S,7S)-6-((2,5-difluoro-[1,1'-biphenyl]-3-yl)methyl)-N-(2,2-difluoroethyl)-7-((fluoromethyl)sulfonamido)-5-azaspiro[2.4]heptane-5-carboxamide | 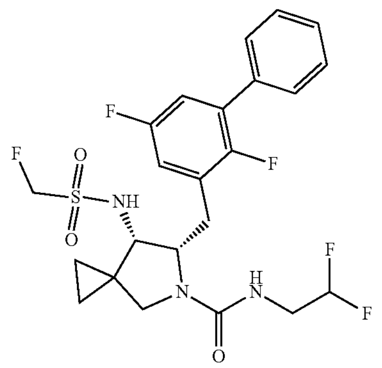 [SMILES: O=C(NCC(F)F)N1CC2(CC2)[C@H](NS(=O)(=O)CF)[C@@H]1Cc1cc(F)cc(-c2ccccc2)c1F] |
| 192 | 1-fluoro-N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide | 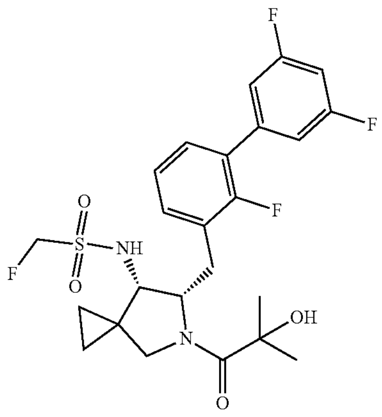 [SMILES: CC(C)(O)C(=O)N1CC2(CC2)[C@H](NS(=O)(=O)CF)[C@@H]1Cc1cccc(-c2cc(F)cc(F)c2)c1F] |
| 193 | (S)-1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethane-1-sulfonamide | 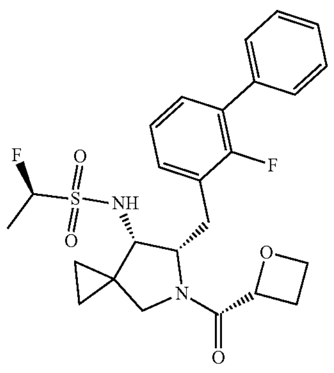 |

TABLE 1-continued

| Compound No. | Name | Structure |
|---|---|---|
| 194 | (R)-1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethane-1-sulfonamide | 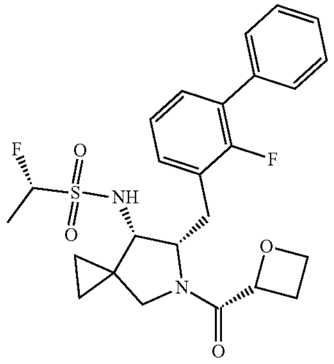 |
| 195 | 1,1-difluoro-N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide | 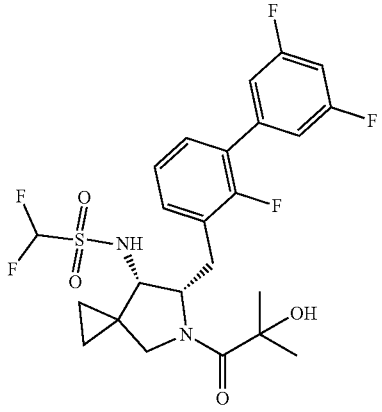 [SMILES: CC(C)(O)C(=O)N1CC2(CC2)[C@H](NS(=O)(=O)C(F)F)[C@@H]1Cc1cccc(-c2cc(F)cc(F)c2)c1F] |
| 196 | N-((6S,7S)-6-((3'-(difluoromethyl)-2-fluoro-[1,1'-biphenyl]-3-yl)methyl)-5-((R)-oxetane-2-carbonyl)-5-azaspiro[2.4]heptan-7-yl)-1-fluoromethanesulfonamide | 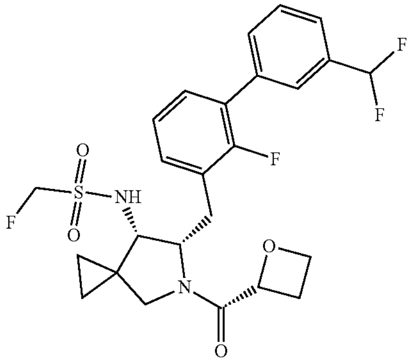 |
| 197 | 1-fluoro-N-((6S,7S)-6-((2-fluoro-3'-(trifluoromethyl)-[1,1'-biphenyl]-3-yl)methyl)-5-((R)-oxetane-2-carbonyl)-5-azaspiro[2.4]heptan-7-yl)methanesulfonamide | 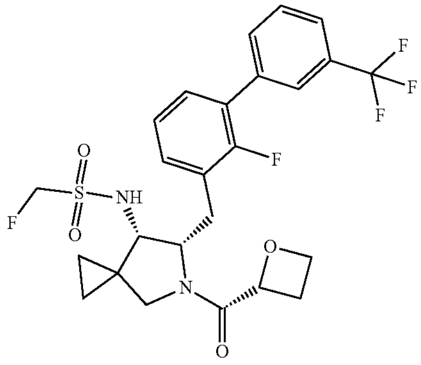 |

TABLE 1-continued

| Compound No. | Name | Structure |
|---|---|---|
| 198 | N-((6S,7S)-5-((R)-3,3-difluoro-2-hydroxypropanoyl)-6-((2-fluoro-[1,1'-biphenyl]-3-yl)methyl)-5-azaspiro[2.4]heptan-7-yl)-1,1-difluoromethanesulfonamide | 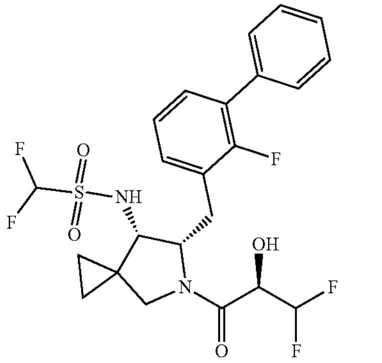 [SMILES: O=C([C@@H](O)C(F)F)N1CC2(CC2)[C@H](NS(=O)(=O)C(F)F)[C@@H]1Cc1cccc(-c2ccccc2)c1F] |
| 199 | 1,1-difluoro-N-((6S,7S)-6-((2-fluoro-3'-(methyl-d3)-[1,1'-biphenyl]-3-yl)methyl)-5-((R)-oxetane-2-carbonyl)-5-azaspiro[2.4]heptan-7-yl)methanesulfonamide | 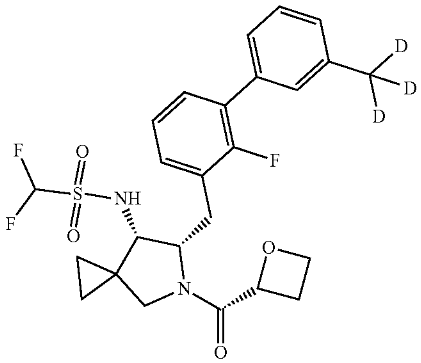 |
| 200 | (6S,7S)-7-((difluoromethyl)sulfonamido)-6-((2-fluoro-[1,1'-biphenyl]-3-yl)methyl)-N-(2,2,2-trifluoroethyl)-5-azaspiro[2.4]heptane-5-carboxamide | 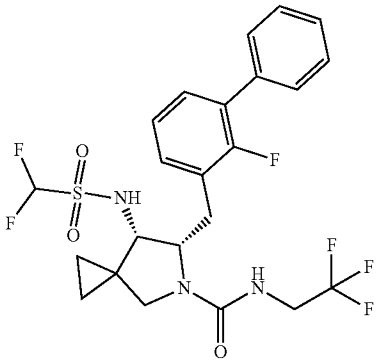 [SMILES: O=C(NCC(F)(F)F)N1CC2(CC2)[C@H](NS(=O)(=O)C(F)F)[C@@H]1Cc1cccc(-c2ccccc2)c1F] |
| 201 | 1,1-difluoro-N-((6S,7S)-6-((2-fluoro-[1,1'-biphenyl]-3-yl)methyl)-5-((1s,3s)-3-fluorocyclobutane-1-carbonyl)-5-azaspiro[2.4]heptan-7-yl)methanesulfonamide | 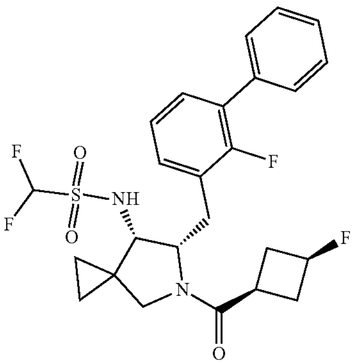 [SMILES: O=C([C@H]1C[C@@H](F)C1)N1CC2(CC2)[C@H](NS(=O)(=O)C(F)F)[C@@H]1Cc1cccc(-c2ccccc2)c1F] |

TABLE 1-continued

| Compound No. | Name | Structure |
|---|---|---|
| 202 | 1-fluoro-N-((6S,7S)-6-((2-fluoro-[1,1'-biphenyl]-3-yl)methyl)-5-((R)-2-methyloxetane-2-carbonyl)-5-azaspiro[2.4]heptan-7-yl)methanesulfonamide | 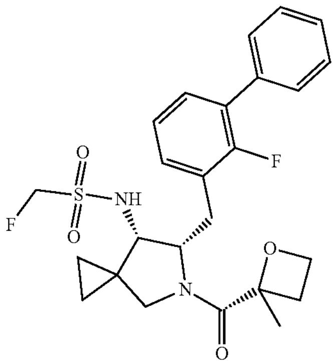 |
| 203 | 1-fluoro-N-((6S,7S)-6-((2-fluoro-[1,1'-biphenyl]-3-yl)methyl)-5-((S)-2-methyloxetane-2-carbonyl)-5-azaspiro[2.4]heptan-7-yl)methanesulfonamide | 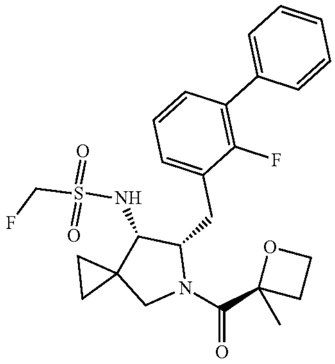 [SMILES: C[C@@]1(C(=O)N2CC3(CC3)[C@H](NS(=O)(=O)CF)[C@@H]2Cc2cccc(-c3ccccc3)c2F)CCO1] |
| 204 | (E)-2-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethene-1-sulfonamide | 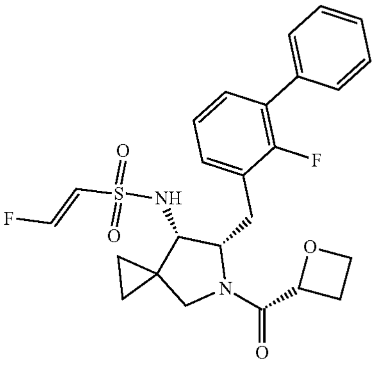 |
| 205 | (6S,7S)-6-((2-fluoro-[1,1'-biphenyl]-3-yl)methyl)-7-(fluoromethyl)sulfonamido)-N-((S)-2-fluoropropyl)-5-azaspiro[2.4]heptane-5-carboxamide | 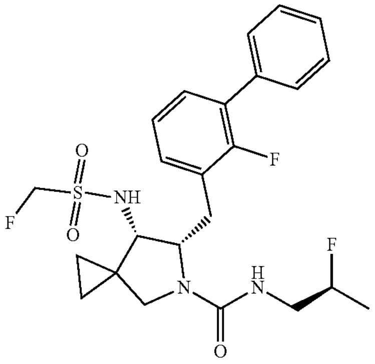 [SMILES: C[C@H](F)CNC(=O)N1CC2(CC2)[C@H](NS(=O)(=O)CF)[C@@H]1Cc1cccc(-c2ccccc2)c1F] |

TABLE 1-continued

| Compound No. | Name | Structure |
|---|---|---|
| 206 | (6S,7S)-6-((2-fluoro-[1,1'-biphenyl]-3-yl)methyl)-7-((fluoromethyl)sulfonamido)-N-((R)-2-fluoropropyl)-5-azaspiro[2.4]heptane-5-carboxamide | 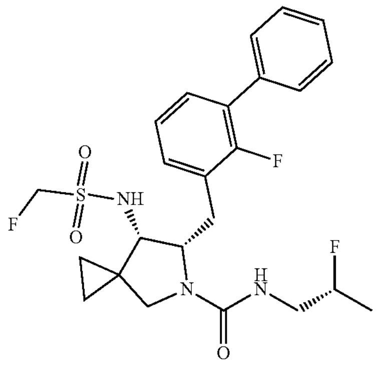 [SMILES: C[C@@H](F)CNC(=O)N1CC2(CC2)[C@H](NS(=O)(=O)CF)[C@@H]1Cc1cccc(-c2ccccc2)c1F] |
| 207 | (6S,7S)-7-((difluoromethyl)sulfonamido)-6-((2-fluoro-[1,1'-biphenyl]-3-yl)methyl)-N-(2-fluoroethyl)-5-azaspiro[2.4]heptane-5-carboxamide | 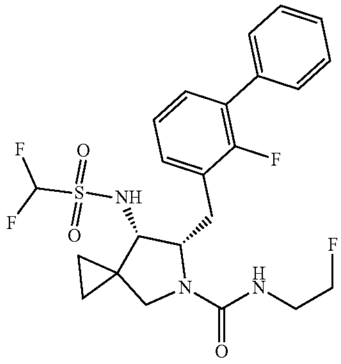 [SMILES: O=C(NCCF)N1CC2(CC2)[C@H](NS(=O)(=O)C(F)F)[C@@H]1Cc1cccc(-c2ccccc2)c1F] |
| 208 | (6S,7S)-6-((2,5-difluoro-[1,1'-biphenyl]-3-yl)methyl)-7-((fluoromethyl)sulfonamido)-N-(2,2,2-trifluoroethyl)-5-azaspiro[2.4]heptane-5-carboxamide | 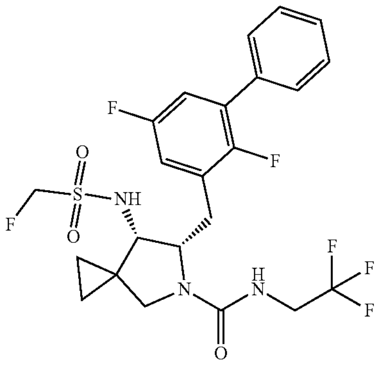 [SMILES: O=C(NCC(F)(F)F)N1CC2(CC2)[C@H](NS(=O)(=O)CF)[C@@H]1Cc1cc(F)cc(-c2ccccc2)c1F] |
| 209 | (6S,7S)-6-((2-fluoro-[1,1'-biphenyl]-3-yl)methyl)-7-((fluoromethyl)sulfonamido)-N-((R)-1,1,1-trifluoropropan-2-yl)-5-azaspiro[2.4]heptane-5-carboxamide | 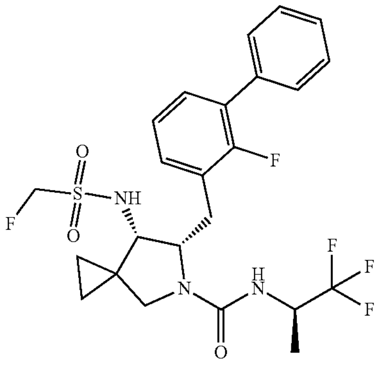 [SMILES: C[C@@H](NC(=O)N1CC2(CC2)[C@H](NS(=O)(=O)CF)[C@@H]1Cc1cccc(-c2ccccc2)c1F)C(F)(F)F] |

TABLE 1-continued

| Compound No. | Name | Structure |
| --- | --- | --- |
| 210 | 1-fluoro-N-((6S,7S)-5-(2-hydroxy-2-methylpropanoyl)-6-((2,3',5-trifluoro-[1,1'-biphenyl]-3-yl)methyl)-5-azaspiro[2.4]heptan-7-yl)methanesulfonamide | 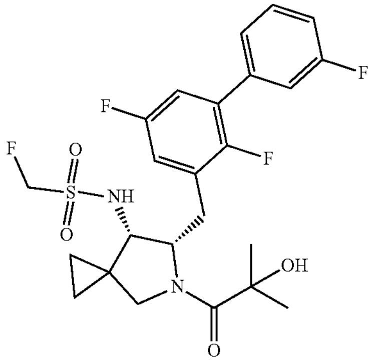 [SMILES: CC(C)(O)C(=O)N1CC2(CC2)[C@H](NS(=O)(=O)CF)[C@@H]1Cc1cc(F)cc(-c2cccc(F)c2)c1F] |
| 211 | (6S,7S)-6-((2-fluoro-[1,1'-biphenyl]-3-yl)methyl)-7-((fluoromethyl)sulfonamido)-N-(2,2,2-trifluoroethyl)-5-azaspiro[2.4]heptane-5-carboxamide | 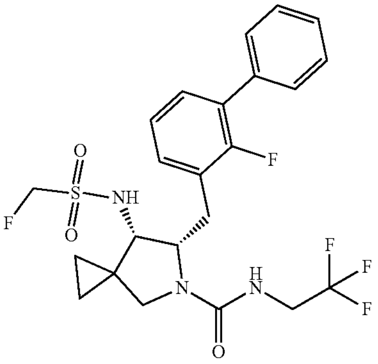 [SMILES: O=C(NCC(F)(F)F)N1CC2(CC2)[C@H](NS(=O)(=O)CF)[C@@H]1Cc1cccc(-c2ccccc2)c1F] |
| 212 | (6S,7S)-7-((difluoromethyl)sulfonamido)-6-((2-fluoro-[1,1'-biphenyl]-3-yl)methyl)-N-((R)-I-fluoropropan-2-yl)-5-azaspiro[2.4]heptane-5-carboxamide | 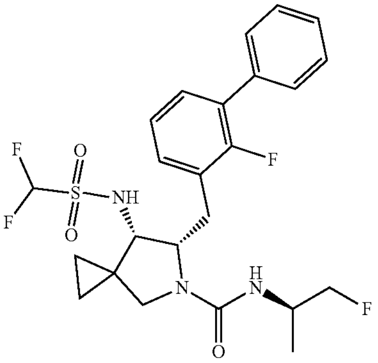 [SMILES: C[C@H](CF)NC(=O)N1CC2(CC2)[C@H](NS(=O)(=O)C(F)F)[C@@H]1Cc1cccc(-c2ccccc2)c1F] |
| 213 | 1,1-difluoro-N-((6S,7S)-6-((3'-fluoro-[1,1'-biphenyl]-3-yl)methyl)-5-((R)-oxetane-2-carbonyl)-5-azaspiro[2.4]heptan-7-yl)methanesulfonamide | 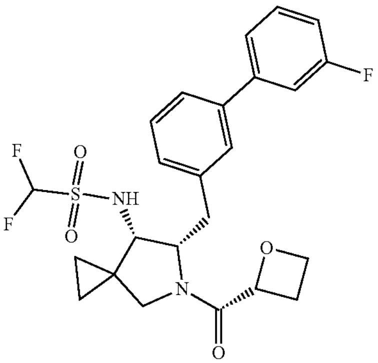 |

TABLE 1-continued

| Compound No. | Name | Structure |
| --- | --- | --- |
| 214 | N-((6S,7S)-6-((3',5'-difluoro-[1,1'-biphenyl]-3-yl)methyl)-5-((R)-oxetane-2-carbonyl)-5-azaspiro[2.4]heptan-7-yl)-1,1-difluoromethanesulfonamide | 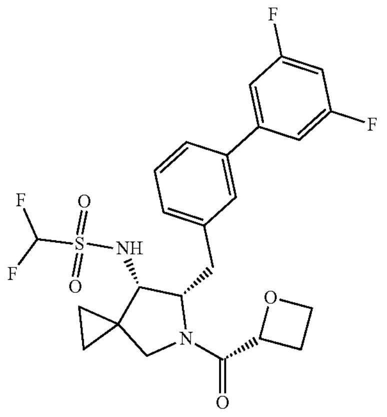 |
| 215 | (6S,7S)-7-((difluoromethyl)sulfonamido)-6-((2-fluoro-[1,1'-biphenyl]-3-yl)methyl)-N-((1-methoxycyclopropyl)methyl)-5-azaspiro[2.4]heptane-5-carboxamide | 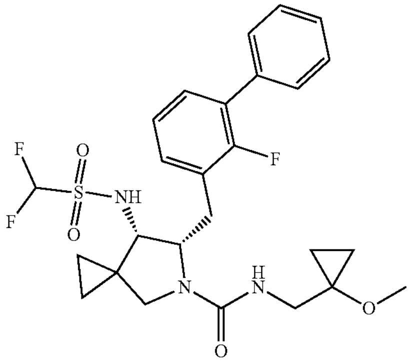 [SMILES: COC1(CNC(=O)N2CC3(CC3)[C@H](NS(=O)(=O)C(F)F)[C@@H]2Cc2cccc(-c3ccccc3)c2F)CC1] |
| 216 | (6S,7S)-6-(2,5-difluoro-[1,1'-biphenyl]-3-yl)methyl)-7-((difluoromethyl)sulfonamido)-N-((S)-1-fluoroethyl)-5-azaspiro[2.4]heptane-5-carboxamide | 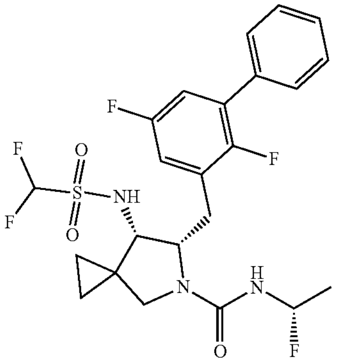 [SMILES: C[C@H](F)NC(=O)N1CC2(CC2)[C@H](NS(=O)(=O)C(F)F)[C@@H]1Cc1cc(F)cc(-c2ccccc2)c1F] |
| 217 | 1-fluoro-N-((6S,7S)-5-((R)-oxetane-2-carbonyl)-6-((2,2',3',5-tetrafluoro-[1,1'-biphenyl]-3-yl)methyl)-5-azaspiro[2.4]heptan-7-yl)methanesulfonamide | 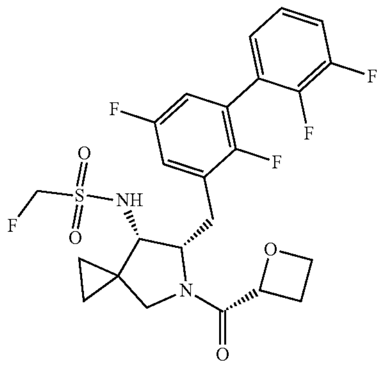 |

TABLE 1-continued

| Compound No. | Name | Structure |
|---|---|---|
| 218 | 1-fluoro-N-((6S,7S)-5-((R)-oxetane-2-carbonyl)-6-((2,2',5,5'-tetrafluoro-[1,1'-biphenyl]-3-yl)methyl)-5-azaspiro[2.4]heptan-7-yl)methanesulfonamide | 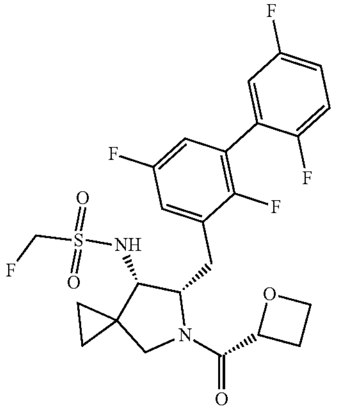 |
| 219 | (6S,7S)-N-((R)-1,1-difluoropropan-2-yl)-6-((2-fluoro-[1,1'-biphenyl]-3-yl)methyl)-7-((fluoromethyl)sulfonamido)-5-azaspiro[2.4]heptane-5-carboxamide | 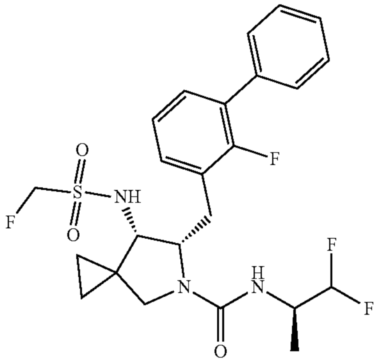 [SMILES: C[C@@H](NC(=O)N1CC2(CC2)[C@H](NS(=O)(=O)CF)[C@@H]1Cc1cccc(-c2ccccc2)c1F)C(F)F] |
| 220 | 1,1-difluoro-N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)methanesulfonamide | 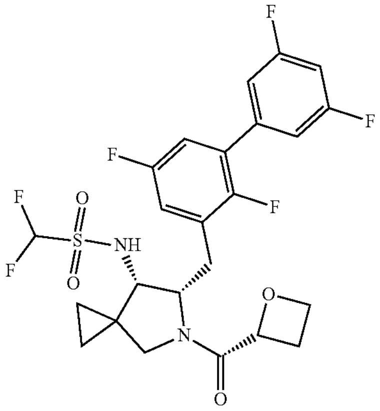 |
| 221 | 1,1-difluoro-N-((6S,7S)-5-((S)-3-fluoro-2-hydroxypropanoyl)-6-((2,3',5,5'-tetrafluoro-[1,1'-biphenyl]-3-yl)methyl)-5-azaspiro[2.4]heptan-7-yl)methanesulfonamide | 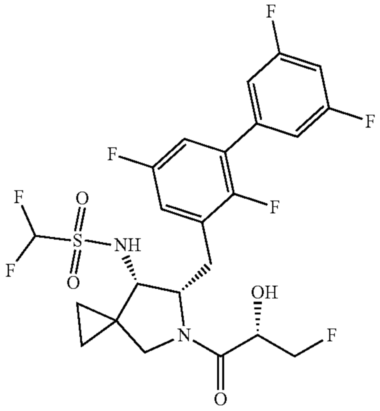 [SMILES: O=C([C@H](O)CF)N1CC2(CC2)[C@H](NS(=O)(=O)C(F)F)[C@@H]1Cc1cc(F)cc(-c2cc(F)cc(F)c2)c1F] |

TABLE 1-continued

| Compound No. | Name | Structure |
| --- | --- | --- |
| 222 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)propane-2-sulfonamide | 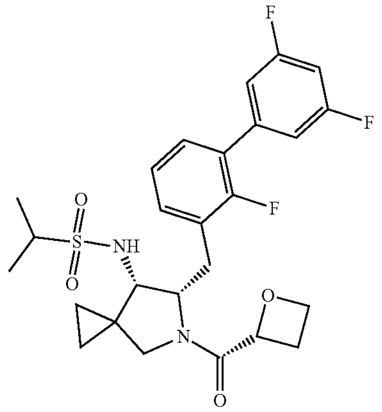 |
| 223 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)cyclopropanesulfonamide | 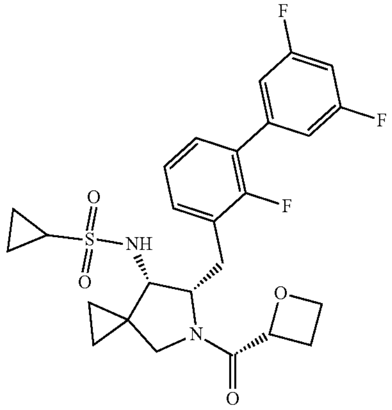 |
| 224 | 1-fluoro-N-((6S,7S)-5-((S)-2-fluoro-3-methoxypropanoyl)-6-((2-fluoro-[1,1'-biphenyl]-3-yl)methyl)-5-azaspiro[2.4]heptan-7-yl)methanesulfonamide | 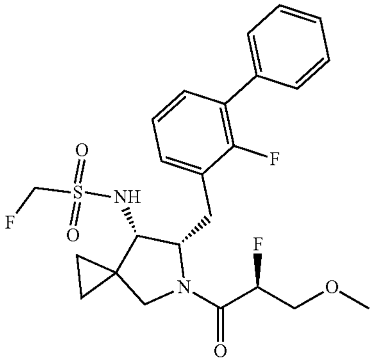 [SMILES: COC[C@H](F)C(=O)N1CC2(CC2)[C@H](NS(=O)(=O)CF)[C@@H]1Cc1cccc(-c2ccccc2)c1F] |
| 225 | N-((6S,7S)-5-((R)-2-cyanooxetane-2-carbonyl)-6-((2-fluoro-[1,1'-biphenyl]-3-yl)methyl)-5-azaspiro[2.4]heptan-7-yl)-1-fluoromethanesulfonamide | 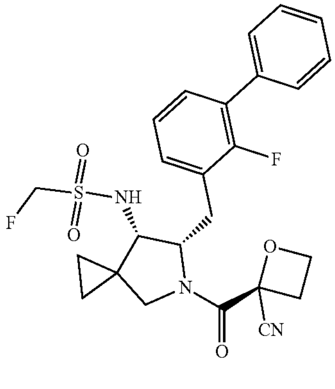 [SMILES: N#C[C@@]1(C(=O)N2CC3(CC3)[C@H](NS(=O)(=O)CF)[C@@H]2Cc2cccc(-c3ccccc3)c2F)CCO1] |

TABLE 1-continued

| Compound No. | Name | Structure |
| --- | --- | --- |
| 226 | N-((6S,7S)-5-((S)-2-cyanooxetane-2-carbonyl)-6-((2-fluoro-[1,1'-biphenyl]-3-yl)methyl)-5-azaspiro[2.4]heptan-7-yl)-1-fluoromethanesulfonamide | 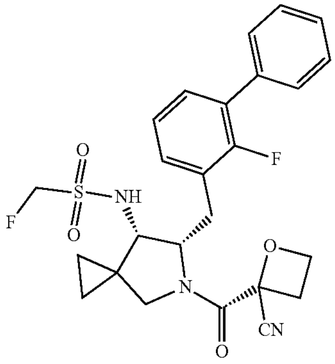 |
| 227 | 1-fluoro-N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)methanesulfonamide | 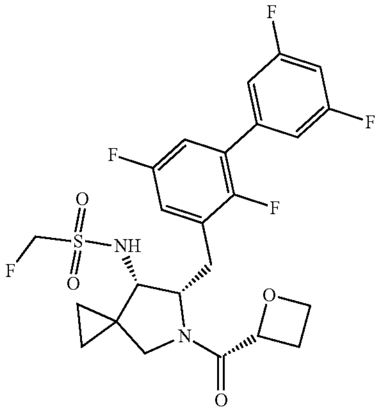 |
| 228 | (6S,7S)-6-(2,5-difluoro-[1,1'-biphenyl]-3-yl)methyl)-N-((1-fluorocyclopropyl)methyl)-7-((fluoromethyl)sulfonamido)-5-azaspiro[2.4]heptane-5-carboxamide | 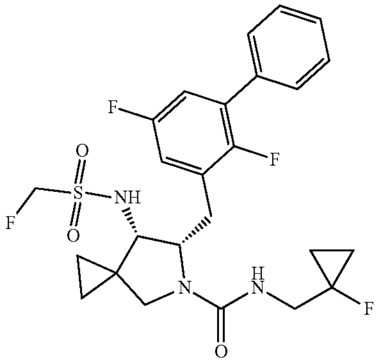 [SMILES: O=C(NCC1(F)CC1)N1CC2(CC2)[C@H](NS(=O)(=O)CF)[C@@H]1Cc1cc(F)cc(-c2ccccc2)c1F] |
| 229 | 1-fluoro-N-((6S,7S)-6-((2-fluoro-3'-(methyl-$d_3$)-[1,1'-biphenyl]-3-yl)methyl)-5-((R)-oxetane-2-carbonyl)-5-azaspiro[2.4]heptan-7-yl)methanesulfonamide | 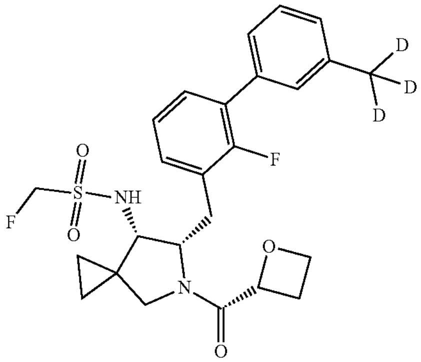 |

TABLE 1-continued

| Compound No. | Name | Structure |
|---|---|---|
| 230 | N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)cyclopropanesulfonamide | 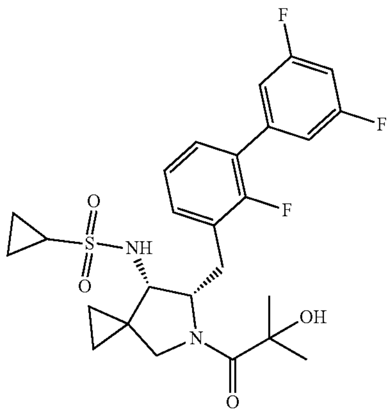 [SMILES: CC(C)(O)C(=O)N1CC2(CC2)[C@H](NS(=O)(=O)C2CC2)[C@@H]1Cc1cccc(-c2cc(F)cc(F)c2)c1F] |
| 231 | N-((6S,7S)-5-(1-cyanocyclobutane-1-carbonyl)-6-((2,3',5'-trifluoro-[1,1'-biphenyl]-3-yl)methyl)-5-azaspiro[2.4]heptan-7-yl)-1-fluoromethanesulfonamide | 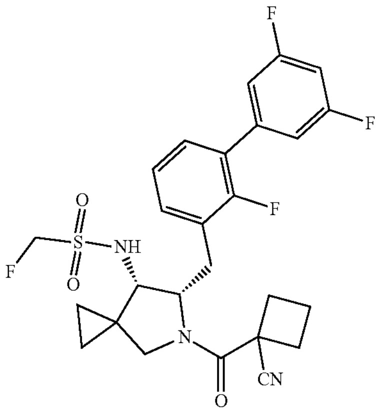 [SMILES: N#CC1(C(=O)N2CC3(CC3)[C@H](NS(=O)(=O)CF)[C@@H]2Cc2cccc(-c3cc(F)cc(F)c3)c2F)CCC1] |
| 232 | 1-fluoro-N-((6S,7S)-5-((S)-2-fluoropropanoyl)-6-((2,3',5'-trifluoro-[1,1'-biphenyl]-3-yl)methyl)-5-azaspiro[2.4]heptan-7-yl)methanesulfonamide | 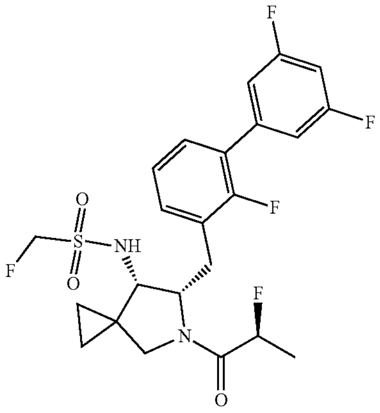 [SMILES: C[C@H](F)C(=O)N1CC2(CC2)[C@H](NS(=O)(=O)CF)[C@@H]1Cc1cccc(-c2cc(F)cc(F)c2)c1F] |

TABLE 1-continued

| Compound No. | Name | Structure |
|---|---|---|
| 233 | 1-fluoro-N-((6S,7S)-5-((R)-2-fluoropropanoyl)-6-((2,3',5'-trifluoro-[1,1'-biphenyl]-3-yl)methyl)-5-azaspiro[2.4]heptan-7-yl)methanesulfonamide | 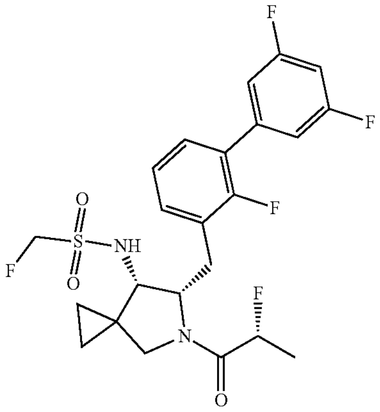 [SMILES: C[C@@H](F)C(=O)N1CC2(CC2)[C@H](NS(=O)(=O)CF)[C@@H]1Cc1cccc(-c2cc(F)cc(F)c2)c1F] |
| 234 | N-((6S,7S)-5-((S)-3,3-difluoro-2-hydroxy-2-methylpropanoyl)-6-(2-fluoro-[1,1'-biphenyl]-3-yl)methyl)-5-azaspiro[2.4]heptan-7-yl)-1-fluoromethanesulfonamide | 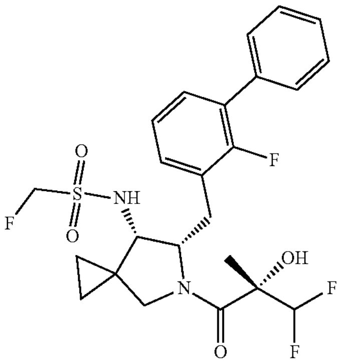 [SMILES: C[C@](O)(C(=O)N1CC2(CC2)[C@H](NS(=O)(=O)CF)[C@@H]1Cc1cccc(-c2ccccc2)c1F)C(F)F] |
| 235 | (6S,7S)-7-((difluoromethyl)sulfonamido)-N-((1-fluorocyclopropyl)methyl)-6-((2,3',5'-trifluoro-[1,1'-biphenyl]-3-yl)methyl)-5-azaspiro[2.4]heptane-5-carboxamide | 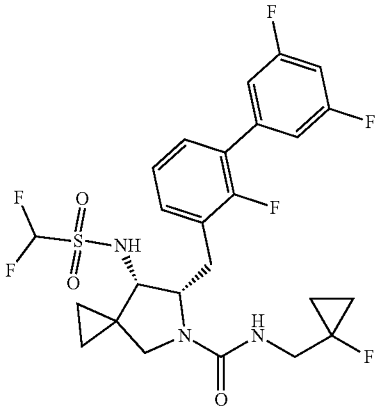 [SMILES: O=C(NCC1(F)CC1)N1CC2(CC2)[C@H](NS(=O)(=O)C(F)F)[C@@H]1Cc1cccc(-c2cc(F)cc(F)c2)c1F] |

TABLE 2

| Compound No | Name | Structure |
|---|---|---|
| 236 | N-(6-((3',5'-difluoro-[1,1'-biphenyl]-3-yl)methyl)-5-((R)-oxetane-2-carbonyl)-5-azaspiro[2.4]heptan-7-yl)methanesulfonamide | 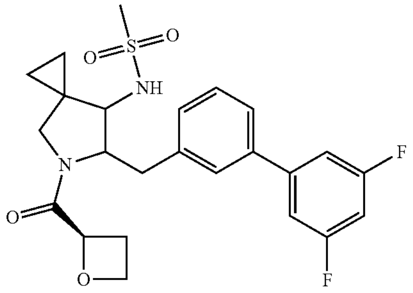 [SMILES: CS(=O)(=O)NC1C(Cc2cccc(-c3cc(F)cc(F)c3)c2)N(C(=O)[C@H]2CCO2)CC12CC2] |
| 237 | N-(6-((3',5'-difluoro-[1,1'-biphenyl]-3-yl)methyl)-5-((R)-2-hydroxypropanoyl)-5-azaspiro[2.4]heptan-7-yl)methanesulfonamide | 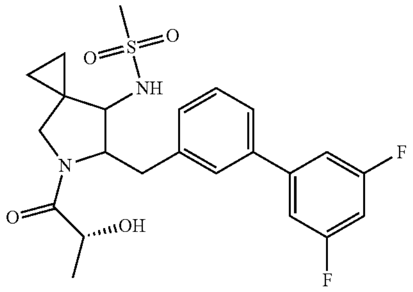 [SMILES: C[C@@H](O)C(=O)N1CC2(CC2)C(NS(C)(=O)=O)C1Cc1cccc(-c2cc(F)cc(F)c2)c1] |
| 238 | N-(5-((R)-2-hydroxypropanoyl)-6-((2,3',5'-trifluoro-[1,1'-biphenyl]-3-yl)methyl)-5-azaspiro[2.4]heptan-7-yl)methanesulfonamide | 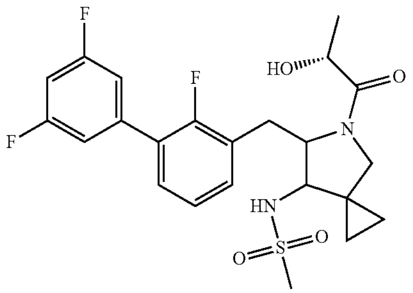 [SMILES: C[C@@H](O)C(=O)N1CC2(CC2)C(NS(C)(=O)=O)C1Cc1cccc(-c2cc(F)cc(F)c2)c1F] |
| 239 | N-(5-(1-fluorocyclopropane-1-carbonyl)-6-((2,3',5'-trifluoro-[1,1'-biphenyl-3-yl)methyl)-5-azaspiro[2.4]heptan-7-yl)methanesulfonamide | 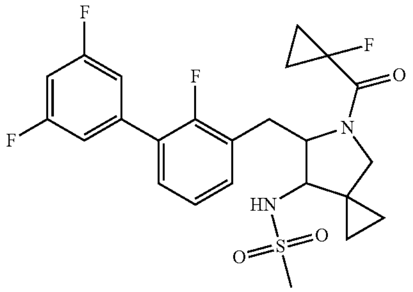 [SMILES: CS(=O)(=O)NC1C(Cc2cccc(-c3cc(F)cc(F)c3)c2F)N(C(=O)C2(F)CC2)CC12CC2] |
| 240 | N-(6-((3',5'-difluoro-[1,1'-biphenyl]-3-yl)methyl)-5-(1-fluorocyclopropane-1-carbonyl)-5-azaspiro[2.4]heptan-7-yl)methanesulfonamide | 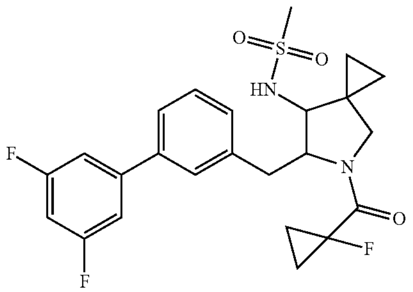 [SMILES: CS(=O)(=O)NC1C(Cc2cccc(-c3cc(F)cc(F)c3)c2)N(C(=O)C2(F)CC2)CC12CC2] |

TABLE 2-continued

| Compound No | Name | Structure |
|---|---|---|
| 241 | N-(5-(cyclopropanecarbonyl)-6-((2,3',5'-trifluoro-[1,1'-biphenyl]-3-yl)methyl)-5-azaspiro[2.4]heptan-7-yl)methanesulfonamide | 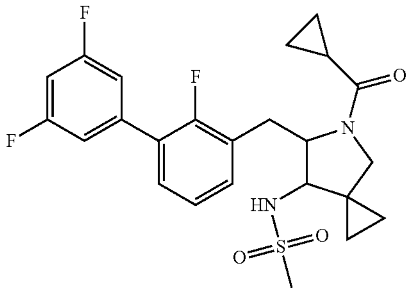 [SMILES: CS(=O)(=O)NC1C(Cc2cccc(-c3cc(F)cc(F)c3)c2F)N(C(=O)C2CC2)CC12CC2] |
| 242 | N-(5-(cyclopropanecarbonyl)-6-((3',5'-difluoro-[1,1'-biphenyl]-3-yl)methyl)-5-azaspiro[2.4]heptan-7-yl)methanesulfonamide | 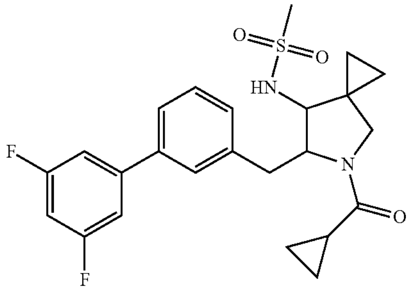 [SMILES: CS(=O)(=O)NC1C(Cc2cccc(-c3cc(F)cc(F)c3)c2)N(C(=O)C2CC2)CC12CC2] |
| 243 | N-(6-((2'-fluoro-[1,1'-biphenyl]-3-yl)methyl)-5-isobutyryl-5-azaspiro[2.4]heptan-7-yl)methanesulfonamide | 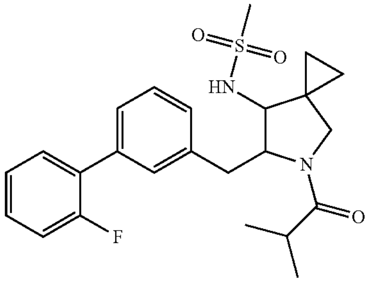 [SMILES: CC(C)C(=O)N1CC2(CC2)C(NS(C)(=O)=O)C1Cc1cccc(-c2ccccc2F)c1] |
| 244 | N-(6-((2'-chloro-[1,1'-biphenyl]-3-yl)methyl)-5-isobutyryl-5-azaspiro[2.4]heptan-7-yl)methanesulfonamide | 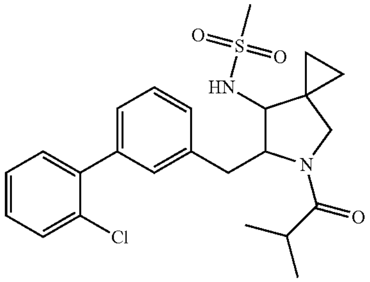 [SMILES: CC(C)C(=O)N1CC2(CC2)C(NS(C)(=O)=O)C1Cc1cccc(-c2ccccc2Cl)c1] |
| 245 | N-(6-((3',5'-difluoro-[1,1'-biphenyl]-3-yl)methyl)-5-azaspiro[2.4]heptan-7-yl)methanesulfonamide | 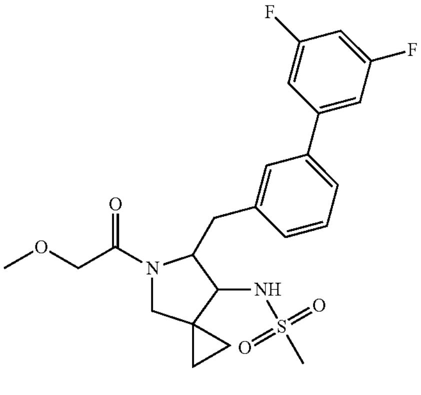 [SMILES: COCC(=O)N1CC2(CC2)C(NS(C)(=O)=O)C1Cc1cccc(-c2cc(F)cc(F)c2)c1] |

TABLE 2-continued

| Compound No | Name | Structure |
|---|---|---|
| 246 | N-(7-([1,1'-biphenyl]-3-ylmethyl)-6-isobutyryl-2-(2,2,2-trifluoroethyl)-2,6-diazaspiro[3.4]octan-8-yl)methanesulfonamide | 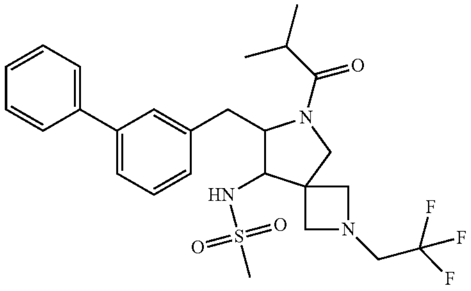 [SMILES: CC(C)C(=O)N1CC2(CN(CC(F)(F)F)C2)C(NS(C)(=O)=O)C1Cc1cccc(-c2ccccc2)c1] |
| 247 | N-(5-(2-methoxyacetyl)-6-((2,3',5'-trifluoro-[1,1'-biphenyl]-3-yl)methyl)-5-azaspiro[2.4]heptan-7-yl)methanesulfonamide (2-methoxyacetyl)-5- | 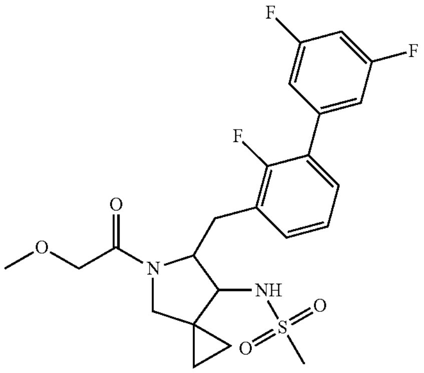 [SMILES: COCC(=O)N1CC2(CC2)C(NS(C)(=O)=O)C1Cc1cccc(-c2cc(F)cc(F)c2)c1F] |
| 248 | N-(6-((3',5'-difluoro-[1,1'-biphenyl]-3-yl)methyl)-5-(2-fluoro-2-methoxyacetyl)-5-azaspiro[2.4]heptan-7-yl)methanesulfonamide | 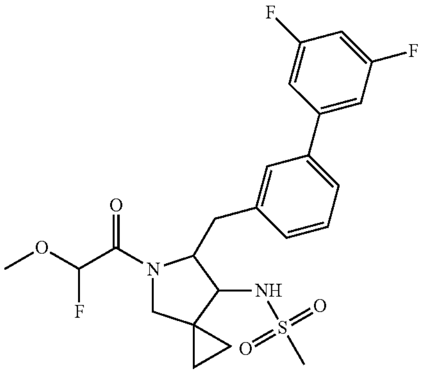 [SMILES: COC(F)C(=O)N1CC2(CC2)C(NS(C)(=O)=O)C1Cc1cccc(-c2cc(F)cc(F)c2)c1] |
| 249 | N-(5-(2-fluoro-2-methoxyacetyl)-6-((2,3',5'-trifluoro-[1,1'-biphenyl]-3-yl)methyl)-5-azaspiro[2.4]heptan-7-yl)methanesulfonamide | 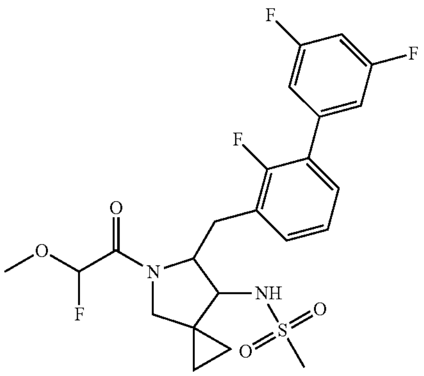 [SMILES: COC(F)C(=O)N1CC2(CC2)C(NS(C)(=O)=O)C1Cc1cccc(-c2cc(F)cc(F)c2)c1F] |

TABLE 2-continued

| Compound No | Name | Structure |
|---|---|---|
| 250 | N-(5-(2,2-difluoro-2-methoxyacetyl)-6-((3',5'-difluoro-[1,1'-biphenyl]-3-yl)methyl)-5-azaspiro[2.4]heptan-7-yl)methanesulfonamide | 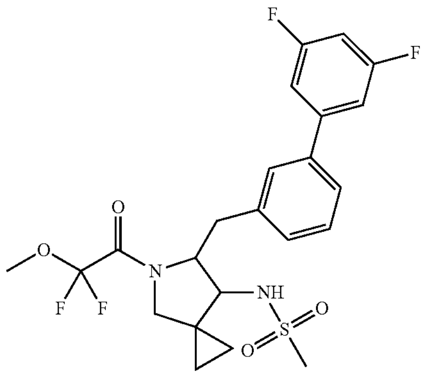 [SMILES: COC(F)(F)C(=O)N1CC2(CC2)C(NS(C)(=O)=O)C1Cc1cccc(-c2cc(F)cc(F)c2)c1] |
| 251 | N-(5-(2,2-difluoro-2-methoxyacetyl)-6-((2,3',5'-trifluoro-[1,1'-biphenyl]-3-yl)methyl)-5-azaspiro[2.4]heptan-7-yl)methanesulfonamide | 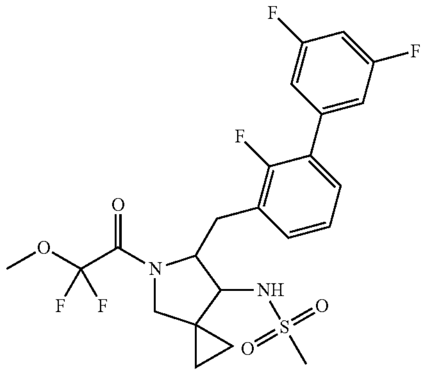 [SMILES: COC(F)(F)C(=O)N1CC2(CC2)C(NS(C)(=O)=O)C1Cc1cccc(-c2cc(F)cc(F)c2)c1F] |
| 252 | N-(6-([1,1'-biphenyl]-3-ylmethyl)-5-(1-cyanocyclobutane-1-carbonyl)-5-azaspiro[2.4]heptan-7-yl)methanesulfonamide | 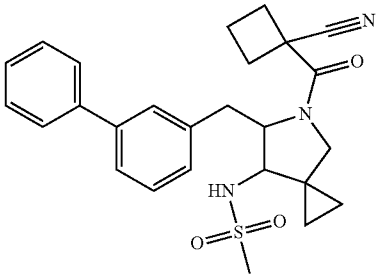 [SMILES: CS(=O)(=O)NC1C(Cc2cccc(-c3ccccc3)c2)N(C(=O)C2(C#N)CCC2)CC12CC2] |
| 253 | N-(6-([1,1'-biphenyl]-3-ylmethyl)-5-(2-cyano-2-methylpropanoyl)-5-azaspiro[2.4]heptan-7-yl)methanesulfonamide | 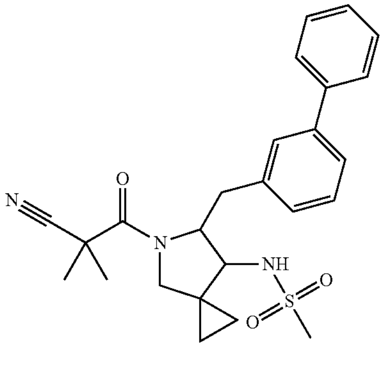 [SMILES: CC(C)(C#N)C(=O)N1CC2(CC2)C(NS(C)(=O)=O)C1Cc1cccc(-c2ccccc2)c1] |

TABLE 2-continued

| Compound No | Name | Structure |
|---|---|---|
| 254 | N-(5-(2-fluoro-2-methylpropanoyl)-6-((2,3',5'-trifluoro-[1,1'-biphenyl]-3-yl)methyl)-5-azaspiro[2.4]heptan-7-yl)methanesulfonamide | 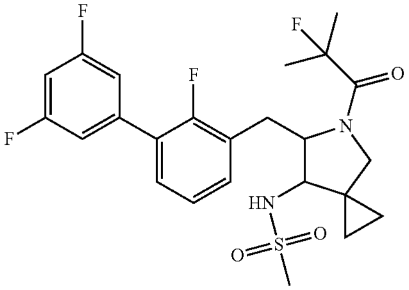 [SMILES: CC(C)(F)C(=O)N1CC2(CC2)C(NS(C)(=O)=O)C1Cc1cccc(-c2cc(F)cc(F)c2)c1F] |
| 255 | N-(6-((3',5'-difluoro-[1,1'-biphenyl]-3-yl)methyl)-5-(2-fluoro-2-methylpropanoyl)-5-azaspiro[2.4]heptan-7-yl)methanesulfonamide | 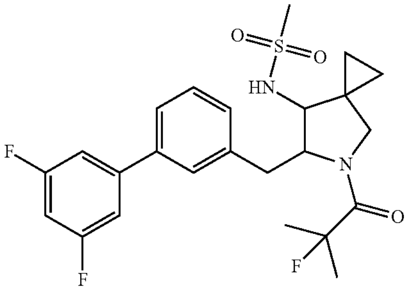 [SMILES: CC(C)(F)C(=O)N1CC2(CC2)C(NS(C)(=O)=O)C1Cc1cccc(-c2cc(F)cc(F)c2)c1] |
| 256 | N-(7-([1,1'-biphenyl]-3-ylmethyl)-6-isobutyryl-2,6-diazaspiro[3.4]octan-8-yl)methanesulfonamide | 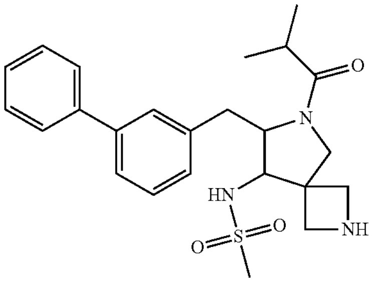 [SMILES: CC(C)C(=O)N1CC2(CNC2)C(NS(C)(=O)=O)C1Cc1cccc(-c2ccccc2)c1] |
| 257 | N-(7-([1,1'-biphenyl]-3-ylmethyl)-6-isobutyryl-1,6-diazaspiro[3.4]octan-8-yl)methanesulfonamide | 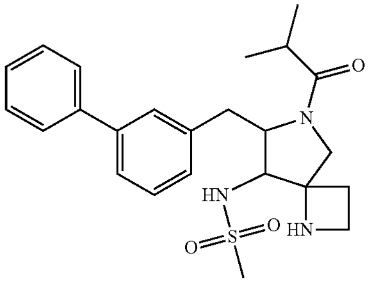 [SMILES: CC(C)C(=O)N1CC2(CCN2)C(NS(C)(=O)=O)C1Cc1cccc(-c2ccccc2)c1] |
| 258 | N-(5-isobutyryl-6-((2'-methoxy-[1,1'-biphenyl]-3-yl)methyl)-5-azaspiro[2.4]heptan-7-yl)methanesulfonamide | 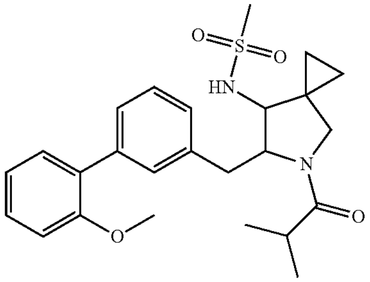 [SMILES: COc1ccccc1-c1cccc(CC2C(NS(C)(=O)=O)C3(CC3)CN2C(=O)C(C)C)c1] |

TABLE 2-continued

| Compound No | Name | Structure |
|---|---|---|
| 259 | N-(6-(3-cyclopropoxybenzyl)-5-isobutyry1-5-azaspiro[2.4]heptan-7-yl)methanesulfonamide | 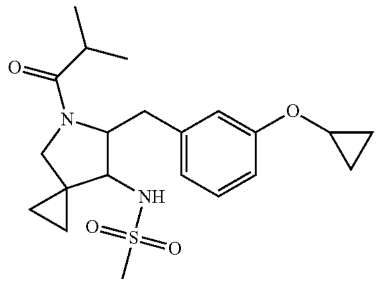 [SMILES: CC(C)C(=O)N1CC2(CC2)C(NS(C)(=O)=O)C1Cc1cccc(OC2CC2)c1] |
| 260 | N-(6-(3-(cyclopropylmethyl) benzyl)-5-isobutyryl-5-azaspiro[2.4]heptan-7-yl)methanesulfonamide | 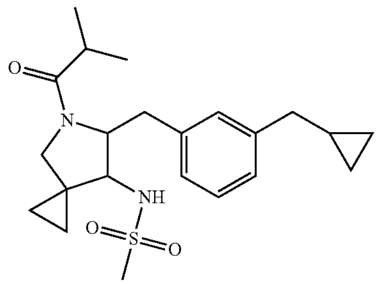 |
| 261 | N-(5-isobutyryl-6-(3-isopropoxybenzyl)-5-azaspiro[2.4]heptan-7-yl)methanesulfonamide | 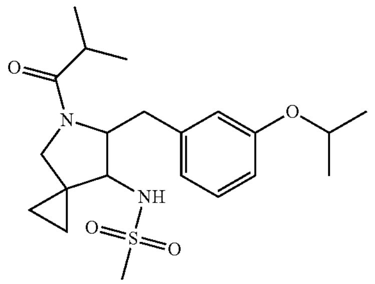 [SMILES: CC(C)Oc1cccc(CC2C(NS(C)(=O)=O)C3(CC3)CN2C(=O)C(C)C)c1] |
| 262 | N-(6-(3-isobutylbenzyl)-5-isobutyryl-5-azaspiro[2.4]heptan-7-yl)methanesulfonamide | 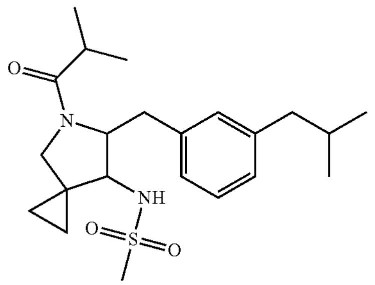 [SMILES: CC(C)Cc1cccc(CC2C(NS(C)(=O)=O)C3(CC3)CN2C(=O)C(C)C)c1] |
| 263 | N-(5-isobutyryl-6-((2,3',5'-trifluoro-[1,1'-biphenyl]-3-yl)methyl)-5-azaspiro[2.4]heptan-7-yl)methanesulfonamide | 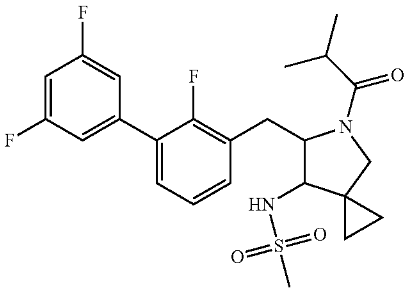 [SMILES: CC(C)C(=O)N1CC2(CC2)C(NS(C)(=O)=O)C1Cc1cccc(-c2cc(F)cc(F)c2)c1F] |

TABLE 2-continued

| Compound No | Name | Structure |
|---|---|---|
| 264 | N-(5-isobutyryl-6-((2'-methyl-[1,1'-biphenyl]-3-yl)methyl)-5-azaspiro[2.4]heptan-7-yl)methanesulfonamide | 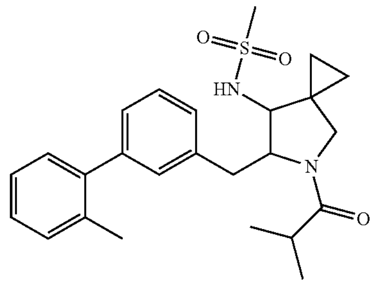 [SMILES: Cc1ccccc1-c1cccc(CC2C(NS(C)(=O)=O)C3(CC3)CN2C(=O)C(C)C)c1] |
| 265 | N-(6-(3-(3,3-difluorocyclobutyl) benzyl)-5-isobutyryl-5-azaspiro[2.4]heptan-7-yl)methanesulfonamide | 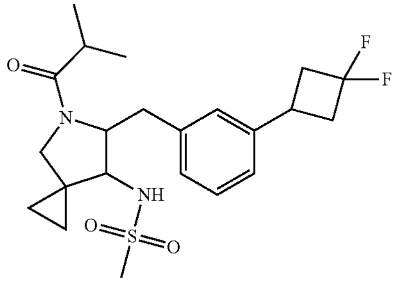 [SMILES: CC(C)C(=O)N1CC2(CC2)C(NS(C)(=O)=O)C1Cc1cccc(C2CC(F)(F)C2)c1] |
| 266 | N-(6-(3-(4,4-difluorocyclohexyl) benzyl)-5-isobutyryl-5-azaspiro[2.4]heptan-7-yl)methanesulfonamide | 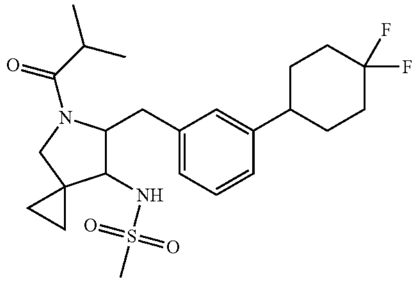 [SMILES: CC(C)C(=O)N1CC2(CC2)C(NS(C)(=O)=O)C1Cc1cccc(C2CCC(F)(F)CC2)c1] |
| 267 | N-(5-propionyl-6-((2,3',5'-trifluoro-[1,1'-biphenyl]-3-yl)methyl)-5-azaspiro[2.4]heptan-7-yl)methanesulfonamide | 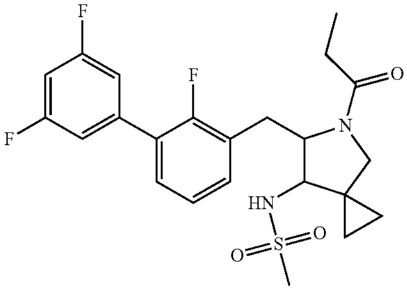 |
| 268 | N-(6-(1-([1,1'-biphenyl]-3-yl)ethyl)-5-isobutyryl-5-azaspiro[2.4]heptan-7-yl)methanesulfonamide | 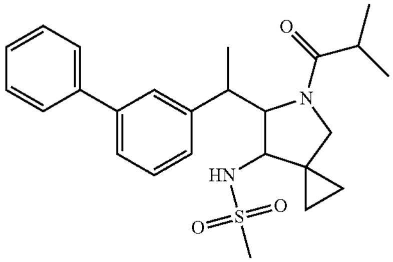 [SMILES: CC(C)C(=O)N1CC2(CC2)C(NS(C)(=O)=O)C1C(C)c1cccc(-c2ccccc2)c1] |

TABLE 2-continued

| Compound No | Name | Structure |
|---|---|---|
| 269 | N-(5-isobutyryl-6-(3-(1-isopropoxyethyl)benzyl)-5-azaspiro[2.4]heptan-7-yl)methanesulfonamide | 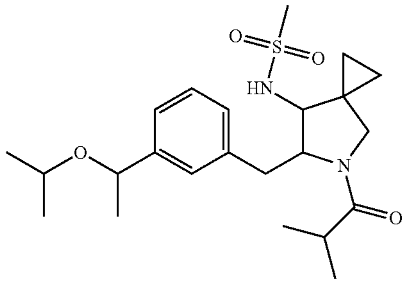 [SMILES: CC(C)OC(C)c1cccc(CC2C(NS(C)(=O)=O)C3(CC3)CN2C(=O)C(C)C)c1] |
| 270 | N-(5-([1,1'-biphenyl]-3-ylmethyl)-6-isobutyryl-6-azaspiro[2.5]octan-4-yl)methanesulfonamide | 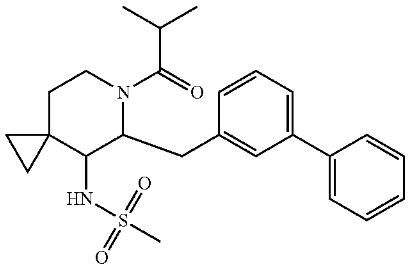 [SMILES: CC(C)C(=O)N1CCC2(CC2)C(NS(C)(=O)=O)C1Cc1cccc(-c2ccccc2)c1] |
| 271 | methyl 7-(methylsulfonamido)-6-((2,3',5'-trifluoro-[1,1'-biphenyl]-3-yl)methyl)-5-azaspiro[2.4]heptane-5-carboxylate | 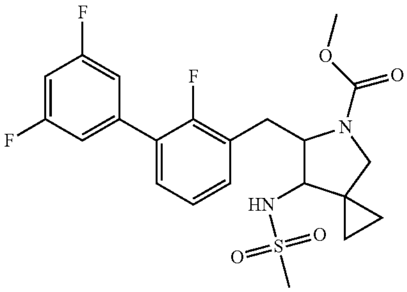 [SMILES: COC(=O)N1CC2(CC2)C(NS(C)(=O)=O)C1Cc1cccc(-c2cc(F)cc(F)c2)c1F] |
| 272 | methyl 6-((3',5'-difluoro-[1,1'-biphenyl]-3-yl)methyl)-7-(methylsulfonamido)-5-azaspiro[2.4]heptane-5-carboxylate | 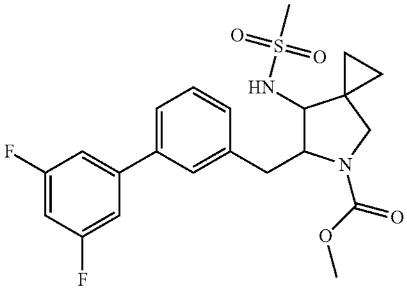 [SMILES: COC(=O)N1CC2(CC2)C(NS(C)(=O)=O)C1Cc1cccc(-c2cc(F)cc(F)c2)c1] |
| 273 | N-(5-(2,2-difluoropropanoyl)-6-((2,3',5'-trifluoro-[1,1'-biphenyl]-3-yl)methyl)-5-azaspiro[2.4]heptan-7-yl)methanesulfonamide | 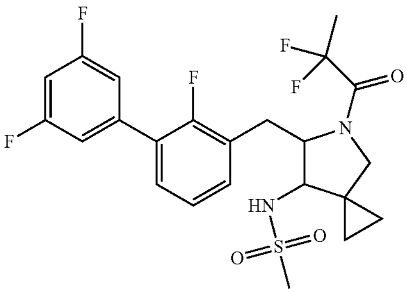 [SMILES: CC(F)(F)C(=O)N1CC2(CC2)C(NS(C)(=O)=O)C1Cc1cccc(-c2cc(F)cc(F)c2)c1F] |

TABLE 2-continued

| Compound No | Name | Structure |
|---|---|---|
| 274 | N-(6-((3',5'-difluoro-[1,1'-biphenyl]-3-yl)methyl)-5-(2,2-difluoropropanoyl)-5-azaspiro[2.4]heptan-7-yl)methanesulfonamide | 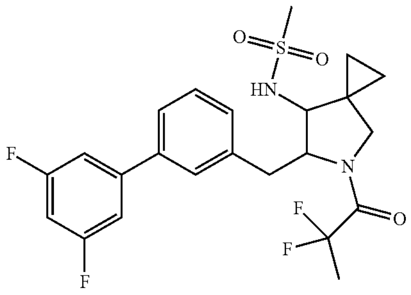 [SMILES: CC(F)(F)C(=O)N1CC2(CC2)C(NS(C)(=O)=O)C1Cc1cccc(-c2cc(F)cc(F)c2)c1] |
| 275 | N-(5-isobutyryl-6-(4-phenoxybenzyl)-5-azaspiro[2.4]heptan-7-yl)methanesulfonamide | 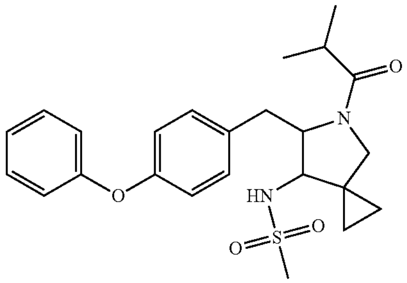 [SMILES: CC(C)C(=O)N1CC2(CC2)C(NS(C)(=O)=O)C1Cc1ccc(Oc2ccccc2)cc1] |
| 276 | 6-([1,1'-biphenyl]-3-ylmethyl)-N,N-dimethyl-7-(methylsulfonamido)-5-azaspiro[2.4]heptane-5-carboxamide | 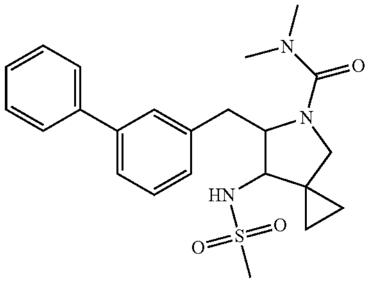 [SMILES: CN(C)C(=O)N1CC2(CC2)C(NS(C)(=O)=O)C1Cc1cccc(-c2ccccc2)c1] |
| 277 | N-(6-([1,1'-biphenyl]-3-ylmethyl)-5-(1-fluorocyclobutane-1-carbonyl)-5-azaspiro[2.4]heptan-7-yl)methanesulfonamide | 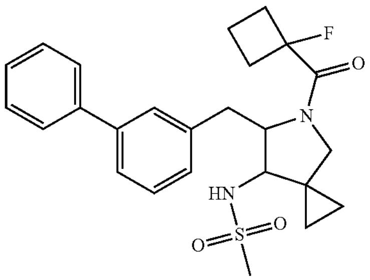 [SMILES: CS(=O)(=O)NC1C(Cc2cccc(-c3ccccc3)c2)N(C(=O)C2(F)CCC2)CC12CC2] |
| 278 | N-(6-([1,1'-biphenyl]-3-ylmethyl)-5-isobutyryl-5-azaspiro[2.4]heptan-7-yl)-1,1,1-trifluoromethane-sulfonamide | 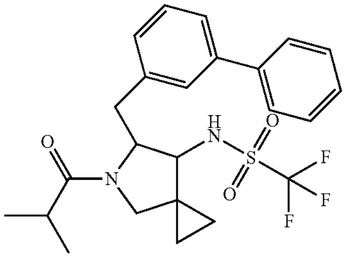 [SMILES: CC(C)C(=O)N1CC2(CC2)C(NS(=O)(=O)C(F)(F)F)C1Cc1cccc(-c2ccccc2)c1] |

TABLE 2-continued

| Compound No | Name | Structure |
|---|---|---|
| 279 | N-(6-([1,1'-biphenyl]-3-ylmethyl)-5-isobutyryl-5-azaspiro[2.4]heptan-7-yl)-1,1-difluoromethane-sulfonamide | 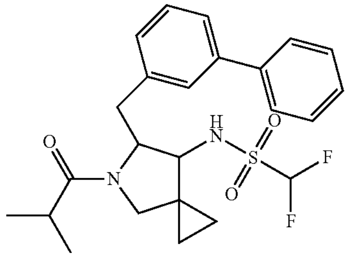 [SMILES: CC(C)C(=O)N1CC2(CC2)C(NS(=O)(=O)C(F)F)C1Cc1cccc(-c2ccccc2)c1] |
| 280 | N-(6-([1,1'-biphenyl]-3-ylmethyl)-5-(2-fluoroacetyl)-5-azaspiro[2.4]heptan-7-yl)methanesulfonamide | 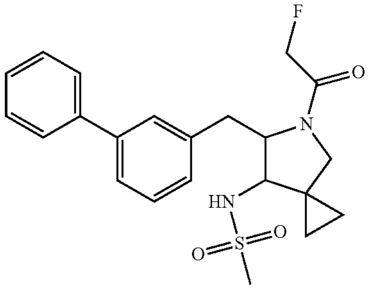 [SMILES: CS(=O)(=O)NC1C(Cc2cccc(-c3ccccc3)c2)N(C(=O)CF)CC12CC2] |
| 281 | N-(6-(3-cyano-2-fluorobenzyl)-5-isobutyryl-5-azaspiro[2.4]heptan-7-yl)methanesulfonamide | 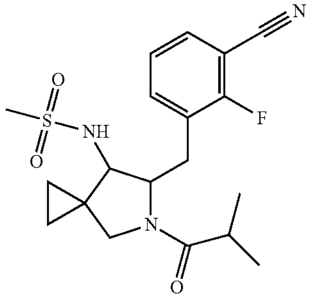 [SMILES: CC(C)C(=O)N1CC2(CC2)C(NS(C)(=O)=O)C1Cc1cccc(C#N)c1F] |
| 282 | N-(6-(3-(2-cyclopropylethyl)benzyl)-5-isobutyryl-5-azaspiro[2.4]heptan-7-yl)methanesulfonamide | 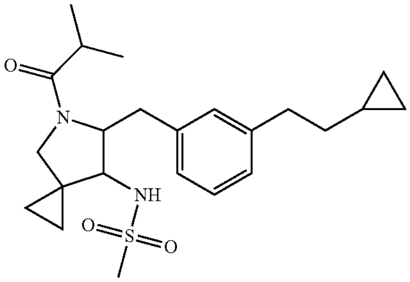 [SMILES: CC(C)C(=O)N1CC2(CC2)C(NS(C)(=O)=O)C1Cc1cccc(CCC2CC2)c1] |
| 283 | N-(6-(3-(cyclobutoxymethyl)benzyl)-5-isobutyryl-5-azaspiro[2.4]heptan-7-yl)methanesulfonamide | 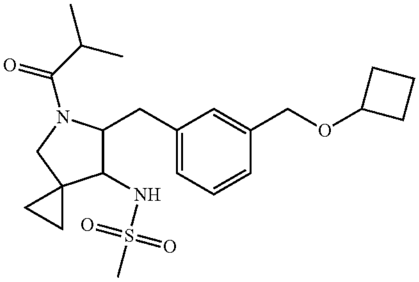 [SMILES: CC(C)C(=O)N1CC2(CC2)C(NS(C)(=O)=O)C1Cc1cccc(COC2CCC2)c1] |

TABLE 2-continued

| Compound No | Name | Structure |
|---|---|---|
| 284 | N-(6-(3-isobutoxybenzyl)-5-isobutyryl-5-azaspiro[2.4]heptan-7-yl)methanesulfonamide | 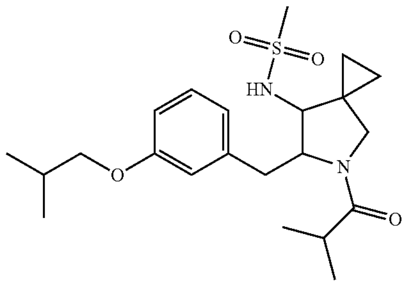 [SMILES: CC(C)COc1cccc(CC2C(NS(C)(=O)=O)C3(CC3)CN2C(=O)C(C)C)c1] |
| 285 | N-(5-(azetidine-1-carbonyl)-6-(3-(2-cyclopropylethyl)benzyl)-5-azaspiro[2.4]heptan-7-yl)methanesulfonamide | 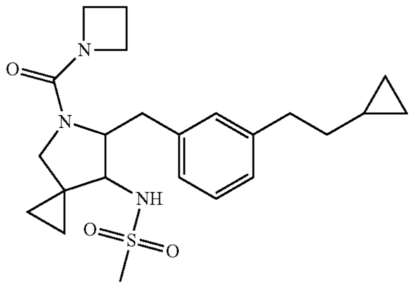 [SMILES: CS(=O)(=O)NC1C(Cc2cccc(CCC3CC3)c2)N(C(=O)N2CCC2)CC12CC2] |
| 286 | N-(5-isobutyryl-6-(3-(2-oxopiperidin-1-yl)benzyl)-5-azaspiro[2.4]heptan-7-yl)methanesulfonamide | 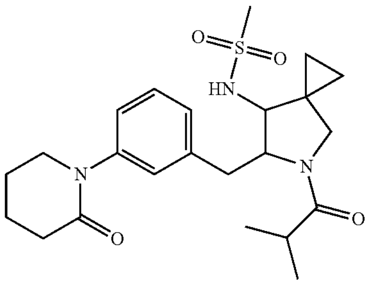 [SMILES: CC(C)C(=O)N1CC2(CC2)C(NS(C)(=O)=O)C1Cc1cccc(N2CCCCC2=O)c1] |
| 287 | N-(7-([1,1'-biphenyl]-3-ylmethyl)-6-isobutyryl-2-oxa-6-azaspiro[3.4]octan-8-yl)methanesulfonamide | 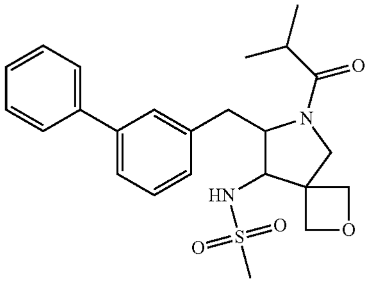 [SMILES: CC(C)C(=O)N1CC2(CCO2)C(NS(C)(=O)=O)C1Cc1cccc(-c2ccccc2)c1] |
| 288 | N-(7-([1,1'-biphenyl]-3-ylmethyl)-6-isobutyryl-1-oxa-6-azaspiro[3.4]octan-8-yl)methanesulfonamide | 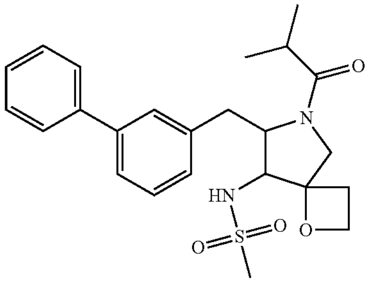 |

TABLE 2-continued

| Compound No | Name | Structure |
| --- | --- | --- |
| 289 | N-(7-([1,1'-biphenyl]-3-ylmethyl)-6-isobutyryl-6-azaspiro[3.4]octan-8-yl)methanesulfonamide | 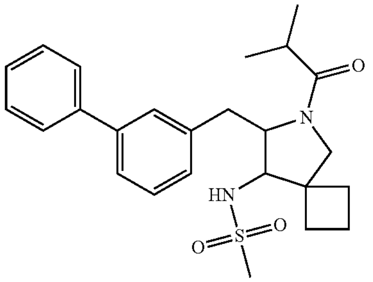 |
| 290 | N-(5-(cyclobutanecarbonyl)-6-((3'-fluoro-[1,1'-biphenyl]-3-yl)methyl)-5-azaspiro[2.4]heptan-7-yl)ethanesulfonamide | 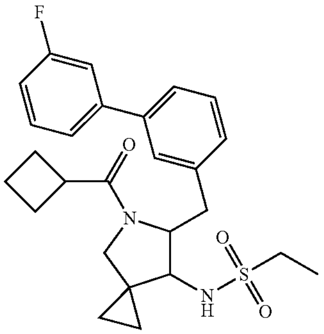 [SMILES: CCS(=O)(=O)NC1C(Cc2cccc(-c3cccc(F)c3)c2)N(C(=O)C2CCC2)CC12CC2] |
| 291 | 6-([1,1'-biphenyl]-3-ylmethyl)-N-ethyl-7-(ethylsulfonamido)-5-azaspiro[2.4]heptane-5-carboxamide | 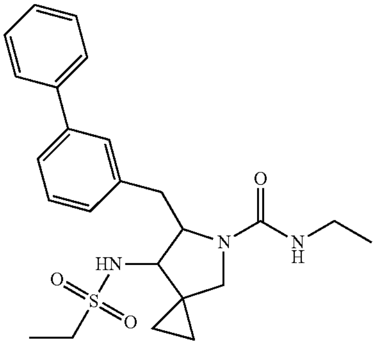 [SMILES: CCNC(=O)N1CC2(CC2)C(NS(=O)(=O)CC)C1Cc1cccc(-c2ccccc2)c1] |
| 292 | N-(6-(3-(3-fluorobicyclo[1.1.0]butan-1-yl)benzyl)-5-isobutyryl-5-azaspiro[2.4]heptan-7-yl)methanesulfonamide | 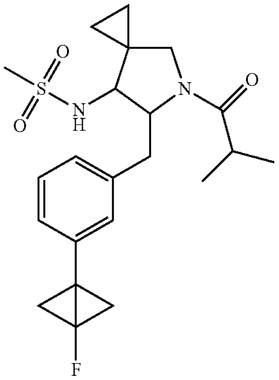 [SMILES: CC(C)C(=O)N1CC2(CC2)C(NS(C)(=O)=O)C1Cc1cccc(C23CC2(F)C3)c1] |

TABLE 2-continued

| Compound No | Name | Structure |
|---|---|---|
| 293 | N-(5-(2-hydroxy-2-methylpropanoyl)-6-((2,3',5'-trifluoro-[1,1'-biphenyl]-3-yl)methyl)-5-azaspiro[2.4]heptan-7-yl)ethanesulfonamide | 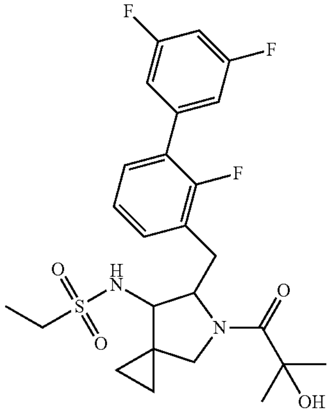 [SMILES: CCS(=O)(=O)NC1C(Cc2cccc(-c3cc(F)cc(F)c3)c2F)N(C(=O)C(C)(C)O)CC12CC2] |

TABLE 3

| Compound No. | Name | Structure |
|---|---|---|
| 294 | N-((6S,7S)-6-((2,3'-difluoro-[1,1'-biphenyl]-3-yl)methyl)-5-(2,2-difluoropropanoyl)-5-azaspiro[2.4]heptan-7-yl)methanesulfonamide | 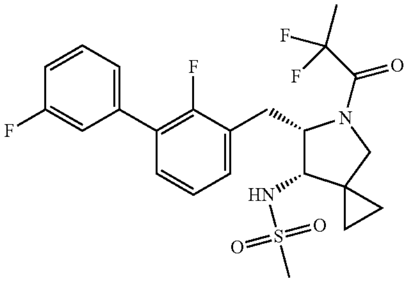 [SMILES: CC(F)(F)C(=O)N1CC2(CC2)[C@H](NS(C)(=O)=O)[C@@H]1Cc1cccc(-c2cccc(F)c2)c1F] |
| 295 | N-6-([1,1'-bipbenyl]-3-ylmethyl)-5-(1-cyanocyclobutane-1-carbonyl)-5-azaspiro[2.4]heptan-7-yl)methanesulfonamide_cis racemic | 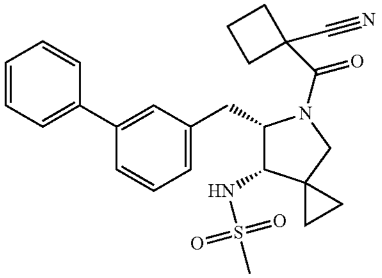 [SMILES: CS(=O)(=O)N[C@@H]1[C@H](Cc2cccc(-c3ccccc3)c2)N(C(=O)C2(C#N)CCC2)CC12CC2] |
| 296 | 6-((3',5'-difluoro-[1,1'-biphenyl]-3-yl)methyl)-N,N-dimethyl-7-(methylsulfonamido)-5-azaspiro[2.4]heptane-5-carboxamide_cis racemic | 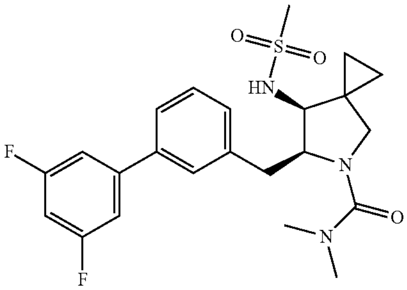 [SMILES: CN(C)C(=O)N1CC2(CC2)[C@H](NS(C)(=O)=O)[C@@H]1Cc1cccc(-c2cc(F)cc(F)c2)c1] |

TABLE 3-continued

| Compound No. | Name | Structure |
|---|---|---|
| 297 | N-6-((2'-fluoro-[1,1'-biphenyl]-3-yl)methyl)-5-isobutyryl-5-azaspiro[2.4]heptan-7-yl)methanesulfonamide_cis racemic | 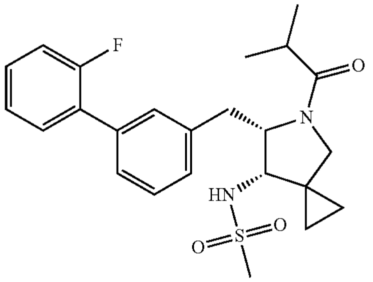 [SMILES: CC(C)C(=O)N1CC2(CC2)[C@H](NS(C)(=O)=O)[C@@H]1Cc1cccc(-c2ccccc2F)c1] |
| 298 | N-6-([1,1'-biphenyl]-3-ylmethyl)-5-(1-hydroxycyclobutane-1-carbonyl)-5-azaspiro[2.4]heptan-7-yl)methanesulfonamide_cis racemic | 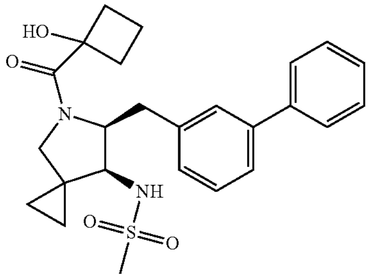 [SMILES: CS(=O)(=O)N[C@@H]1[C@H](Cc2cccc(-c3ccccc3)c2)N(C(=O)C2(O)CCC2)CC12CC2] |
| 299 | N-((6S,7S)-6-([1,1'-biphenyl]-3-ylmethyl)-5-((S)-3,3,3-trifluoro-2-hydroxypropanoyl)-5-azaspiro[2.4]heptan-7-yl)methanesulfonamide | 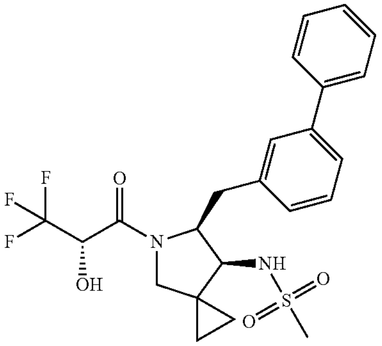 [SMILES: CS(=O)(=O)N[C@@H]1[C@H](Cc2cccc(-c3ccccc3)c2)N(C(=O)[C@H](O)C(F)(F)F)CC12CC2] |
| 300 | N-6-([1,1'-biphenyl]-3-ylmethyl)-5-((R)-2-hydroxybutanoyl)-5-azaspiro[2.4]heptan-7-yl)methanesulfonamide_cis racemic | 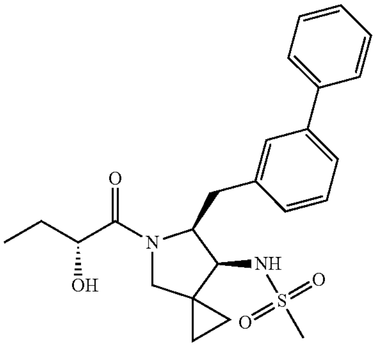 [SMILES: CC[C@@H](O)C(=O)N1CC2(CC2)[C@H](NS(C)(=O)=O)[C@@H]1Cc1cccc(-c2ccccc2)c1] |

TABLE 3-continued

| Compound No. | Name | Structure |
|---|---|---|
| 301 | N-(-6-([1,1'-biphenyl]-3-ylmethyl)-5-((R)-2-hydroxybutanoyl)-5-azaspiro[2.4]heptan-7-yl)methanesulfonamide_cis racemic | 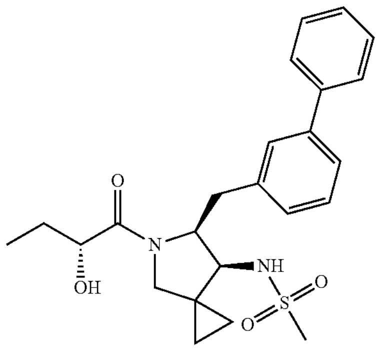 [SMILES: CC[C@@H](O)C(=O)N1CC2(CC2)[C@H](NS(C)(=O)=O)[C@@H]1Cc1cccc(-c2ccccc2)c1] |
| 302 | N-(-6-([1,1'-biphenyl]-3-ylmethyl)-5-(cyclobutanecarbonyl)-5-azaspiro[2.4]heptan-7-yl)methanesulfonamide_cis racemic | 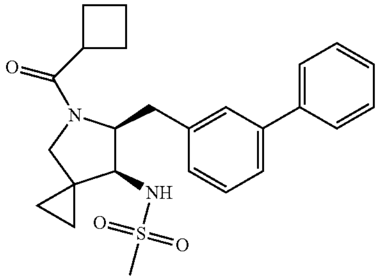 [SMILES: CS(=O)(=O)N[C@@H]1[C@H](Cc2cccc(-c3ccccc3)c2)N(C(=O)C2CCC2)CC12CC2] |
| 303 | 6-([1,1'-biphenyl]-3-ylmethyl)-N-ethyl-7-(methylsulfonamido)-5-azaspiro[2.4]heptane-5-carboxamide_cis racemic | 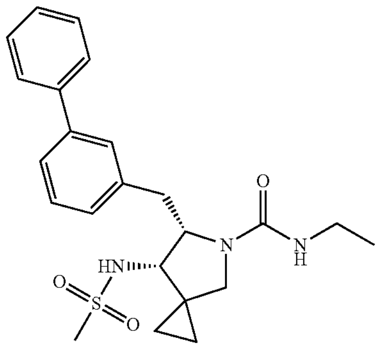 [SMILES: CCNC(=O)N1CC2(CC2)[C@H](NS(C)(=O)=O)[C@@H]1Cc1cccc(-c2ccccc2)c1] |
| 304 | N-(6-(([1,1'-biphenyl]-3-yl)methyl)-5-isopropyl-2-carbonyl)-5-azaspiro[2.4]heptan-7-yl)-N,N-dimethylsulfuric diamide_cis racemic | 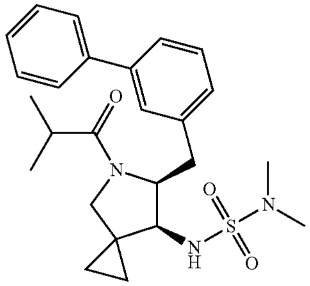 [SMILES: CC(C)C(=O)N1CC2(CC2)[C@H](NS(=O)(=O)N(C)C)[C@@H]1Cc1cccc(-c2ccccc2)c1] |
| 305 | N-(6S,7S)-6-((3'-fluoro-[1,1'-biphenyl]-3-yl)methyl)-5-((R)-oxetane-2-carbonyl)-5-azaspiro[2.4]heptan-7-yl)methanesulfonamide | 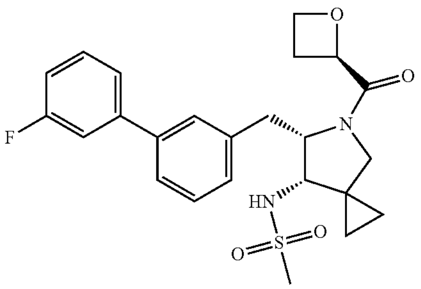 [SMILES: CS(=O)(=O)N[C@@H]1[C@H](Cc2cccc(-c3cccc(F)c3)c2)N(C(=O)[C@H]2CCO2)CC12CC2] |

TABLE 3-continued

| Compound No. | Name | Structure |
| --- | --- | --- |
| 306 | 6-((2-fluoro-[1,1'-biphenyl]-3-yl)methyl)-N-(2-methoxyethyl)-7-(methylsulfonamido)-5-azaspiro[2.4]heptane-5-carboxamide_cis racemic | 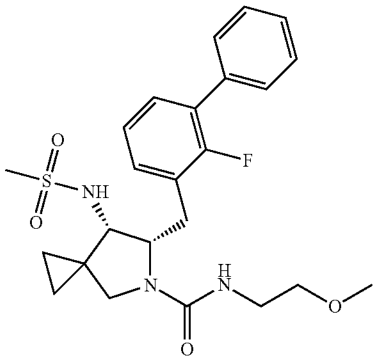 |
| 307 | 6-((2-fluoro-[1,1'-biphenyl]-3-yl)methyl)-N-(2-hydroxyethyl)-7-(methylsulfonamido)-5-azaspiro[2.4]heptane-5-carboxamide_cis racemic | 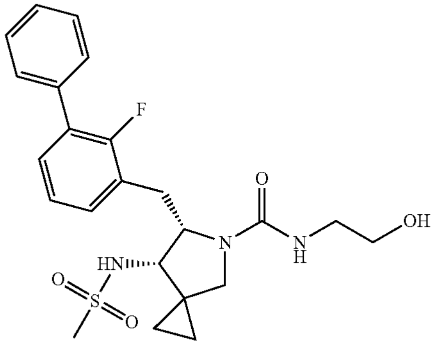 [SMILES: CS(=O)(=O)N[C@@H]1[C@H](Cc2cccc(-c3ccccc3)c2F)N(C(=O)NCCO)CC12CC2] |
| 308 | N-(-6-([1,1'-biphenyl]-3-ylmethyl)-5-((1s,3R)-3-fluorocyclobutane-1-carbonyl)-5-azaspiro[2.4]heptan-7-yl)methanesulfonamide_cis racemic | 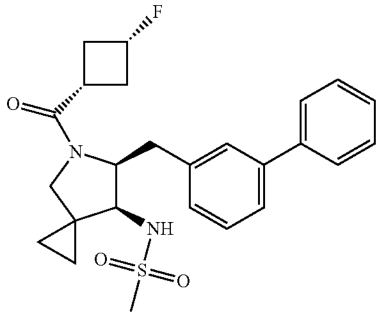 [SMILES: CS(=O)(=O)N[C@@H]1[C@H](Cc2cccc(-c3ccccc3)c2)N(C(=O)[C@H]2C[C@@H](F)C2)CC12CC2] |
| 309 | N-((6S,7S)-6-([1,1'-biphenyl]-3-ylmethyl)-5-((S)-2-cyanopropanoyl)-5-azaspiro[2.4]heptan-7-yl)methanesulfonamide | 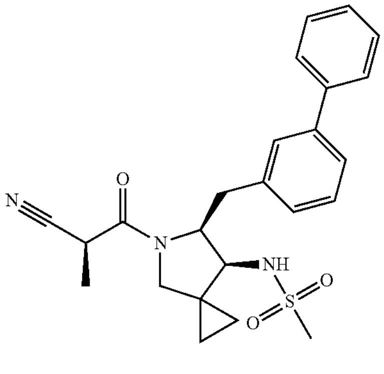 [SMILES: C[C@@H](C#N)C(=O)N1CC2(CC2)[C@H](NS(C)(=O)=O)[C@@H]1Cc1cccc(-c2ccccc2)c1] |

TABLE 3-continued

| Compound No. | Name | Structure |
|---|---|---|
| 310 | N-((6S,7S)-6-([1,1'-biphenyl]-3-ylmethyl)-5-((R)-oxetane-2-carbonyl)-5-azaspiro[2.4]heptan-7-yl)propane-1-sulfonamide | 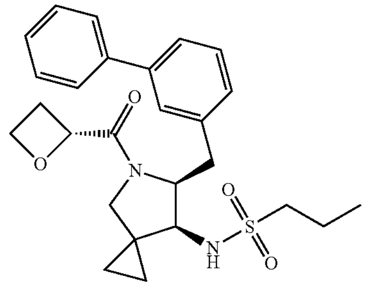 [SMILES: CCCS(=O)(=O)N[C@@H]1[C@H](Cc2cccc(-c3ccccc3)c2)N(C(=O)[C@H]2CCO2)CC12CC2] |
| 311 | (6S,7S)-6-((2-fluoro-[1,1'-biphenyl]-3-yl)methyl)-N-(2-methoxyethyl)-7-(methylsulfonamido)-5-azaspiro[2.4]heptane-5-carboxamide | 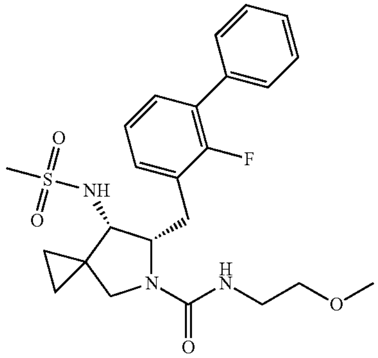 |
| 312 | (1S*,2S*)-N-(6R,7R)-6-([1,1'-biphenyl]-3-ylmethyl)-5-((R)-oxetane-2-carbonyl)-5-azaspiro[2.4]heptan-7-yl)-2-methylcyclopropane-1-sulfonamide | 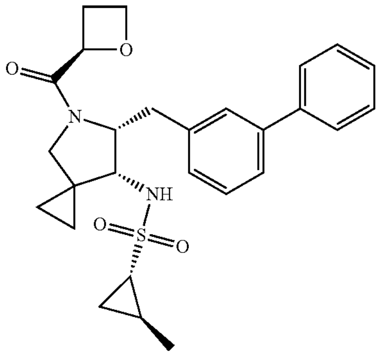 [SMILES: C[C@H]1C[C@@H]1S(=O)(=O)N[C@H]1[C@@H](Cc2cccc(-c3ccccc3)c2)N(C(=O)[C@H]2CCO2)CC12CC2] |
| 313 | N-((6S,7S)-6-((2-fluoro-[1,1'-biphenyl]-3-yl)methyl)-5-((S)-3-methoxypyrrolidine-1-carbonyl)-5-azaspiro[2.4]heptan-7-yl)methanesulfonamide | 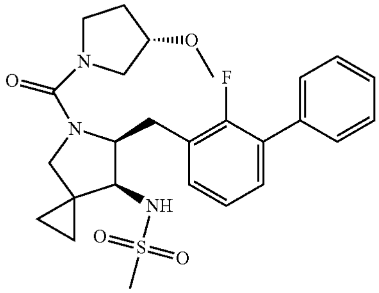 [SMILES: CO[C@H]1CCN(C(=O)N2CC3(CC3)[C@H](NS(C)(=O)=O)[C@@H]2Cc2cccc(-c3ccccc3)c2F)C1] |

TABLE 3-continued

| Compound No. | Name | Structure |
|---|---|---|
| 314 | N-((6S,7S)-6-((2-fluoro-[1,1'-biphenyl]-3-yl)methyl)-5-((R)-2-(fluoromethyl)azetidine-1-carbonyl)-5-azaspiro[2.4]heptan-7-yl)metbanesulfonamide | 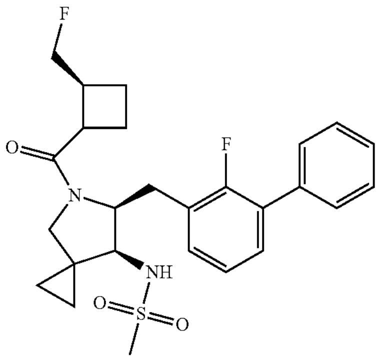 [SMILES: CS(=O)(=O)N[C@@H]1[C@H](Cc2cccc(-c3ccccc3)c2F)N(C(=O)C2CC[C@@H]2CF)CC12CC2] |
| 315 | (6S,7S)-6-((2-fluoro-[1,1'-biphenyl]-3-yl)methyl)-N-(3-fluorocyclobutyl)-7-(methylsulfonamido)-5-azaspiro[2.4]heptane-5-carboxamide | 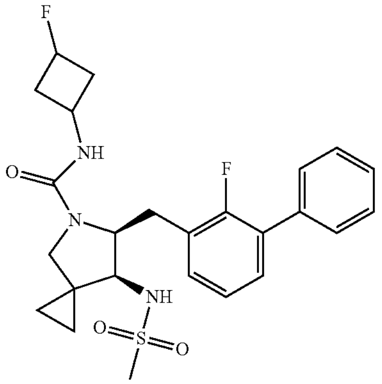 [SMILES: CS(=O)(=O)N[C@@H]1[C@H](Cc2cccc(-c3ccccc3)c2F)N(C(=O)NC2CC(F)C2)CC12CC2] |
| 316 | (6S,7S)-6-(2-fluoro-[1,1'-biphenyl]-3-yl)methyl)-N-((S)-2-methoxypropyl)-N-methyl-7-(methylsulfonamido)-5-azaspiro[2.4]heptane-5-carboxamide | 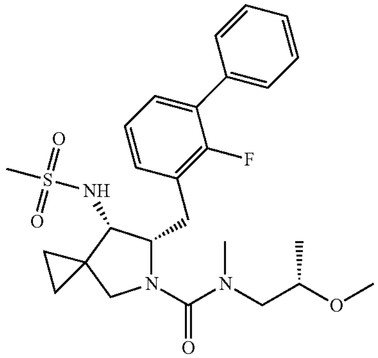 |
| 317 | (6S,7S)-6-((2-fluoro-[1,1'-biphenyl]-3-yl)methyl)-N-((R)-1-methoxypropan-2-yl)-N-methyl-7-(methylsulfonamido)-5-azaspiro[2.4]heptane-5-carboxamide | 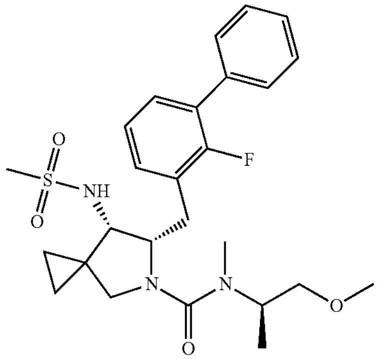 |

TABLE 3-continued

| Compound No. | Name | Structure |
|---|---|---|
| 318 | (6S,7S)-N-((S)-1-cyanopropan-2-yl)-6-((2-fluoro-[1,1'-biphenyl]-3-yl)methyl)-7-(methylsulfonamido)-5-azaspiro[2.4]heptane-5-carboxamide | 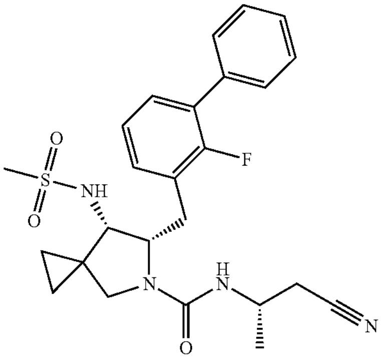 [SMILES: C[C@@H](CC#N)NC(=O)N1CC2(CC2)[C@H](NS(C)(=O)=O)[C@@H]1Cc1cccc(-c2ccccc2)c1F] |
| 319 | (6S,7S)-6-((2-fluoro-[1,1'-biphenyl]-3-yl)methyl)-N-(3-fluorobicyclo[1.1.1]pentan-1-yl)-7-(methylsulfonamido)-5-azaspiro[2.4]heptane-5-carboxamide | 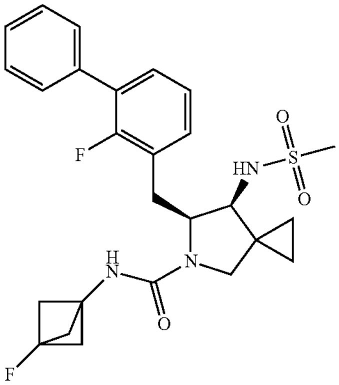 [SMILES: CS(=O)(=O)N[C@@H]1[C@H](Cc2cccc(-c3ccccc3)c2F)N(C(=O)NC23CC(F)(C2)C3)CC12CC2] |
| 320 | (6S,7S)-6-((2-fluoro-[1,1'-biphenyl]-3-yl)methyl)-7-(methylsulfonamido)-N-((S)-3-methyltetrahydrofuran-3-yl)-5-azaspiro[2.4]heptane-5-carboxamide | 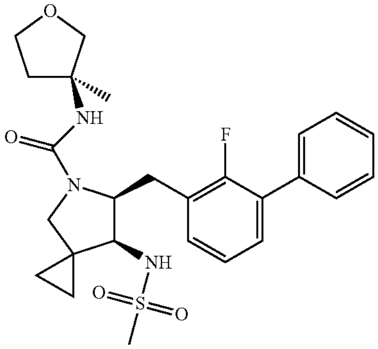 [SMILES: C[C@]1(NC(=O)N2CC3(CC3)[C@H](NS(C)(=O)=O)[C@@H]2Cc2cccc(-c3ccccc3)c2F)CCOC1] |
| 321 | (6S,7S)-6-((2-fluoro-[1,1'-biphenyl]-3-yl)methyl)-N-methyl-7-(methylsulfonamido)-N-((S)-tetrahydrofuran-3-yl)-5-azaspiro[2.4]heptane-5-carboxamide | 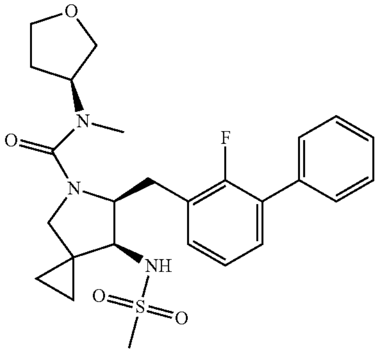 [SMILES: CN(C(=O)N1CC2(CC2)[C@H](NS(C)(=O)=O)[C@@H]1Cc1cccc(-c2ccccc2)c1F)[C@H]1CCOC1] |

TABLE 3-continued

| Compound No. | Name | Structure |
|---|---|---|
| 322 | (6S,7S)-6-((2-fluoro-[1,1'-biphenyl]-3-yl)methyl)-N-((3-methyloxetan-3-yl)methyl)-7-(methylsulfonamido)-5-azaspiro[2.4]heptane-5-carboxamide | 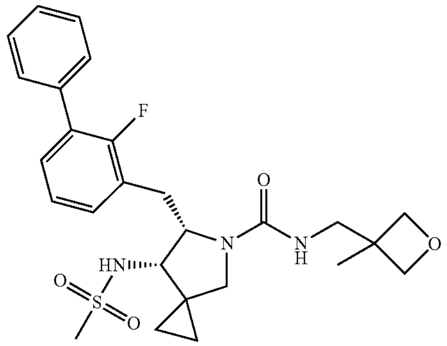 [SMILES: CC1(CNC(=O)N2CC3(CC3)[C@H](NS(C)(=O)=O)[C@@H]2Cc2cccc(-c3ccccc3)c2F)COC1] |
| 323 | (6S,7S)-6-((2-fluoro-[1,1'-biphenyl]-3-yl)methyl)-N-((S)-2-hydroxypropyl)-N-methyl-7-(methylsulfonamido)-5-azaspiro[2.4]heptane-5-carboxamide | 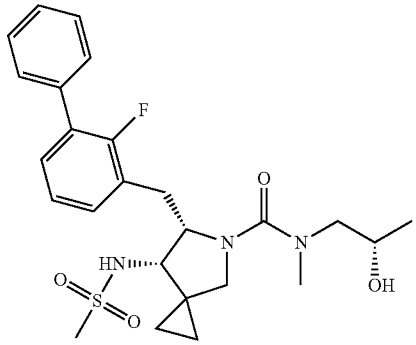 [SMILES: C[C@H](O)CN(C)C(=O)N1CC2(CC2)[C@H](NS(C)(=O)=O)[C@@H]1Cc1cccc(-c2ccccc2)c1F] |
| 324 | (6S,7S)-6-((2-fluoro-[1,1'-biphenyl]-3-yl)methyl)-N-((R)-2-methoxypropyl)-7-(methylsulfonamido)-5-azaspiro[2.4]heptane-5-carboxamide | 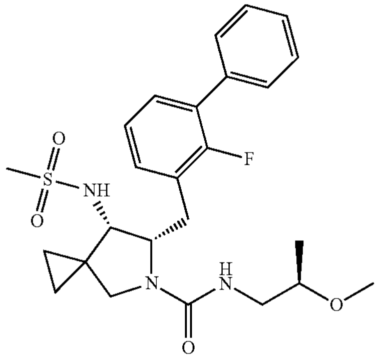 |
| 325 | (6S,7S)-6-((2-fluoro-[1,1'-biphenyl]-3-yl)methyl)-N-((R)-1-methoxypropan-2-yl)-7-(methylsulfonamido)-5-azaspiro[2.4]heptane-5-carboxamide | 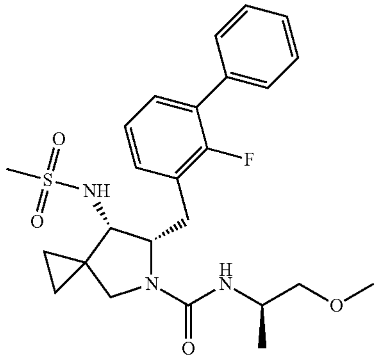 |

TABLE 3-continued

| Compound No. | Name | Structure |
|---|---|---|
| 326 | (6S,7S)-6-((2-fluoro-[1,1'-biphenyl]-3-yl)methyl)-N-(2-methoxyethyl)-N-methyl-7-(methylsulfonamido)-5-azaspiro[2.4]heptane-5-carboxamide | 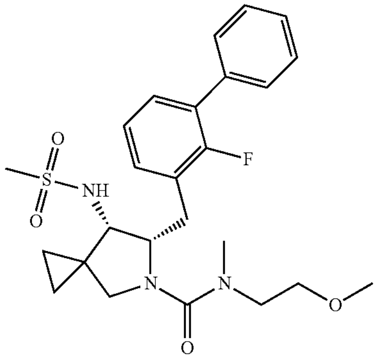 |
| 327 | (6S,7S)-N-(2-cyanoethyl)-6-((2-fluoro-[1,1'-biphenyl]-3-yl)methyl)-N-methyl-7-(methylsulfonamido)-5-azaspiro[2.4]heptane-5-carboxamide | 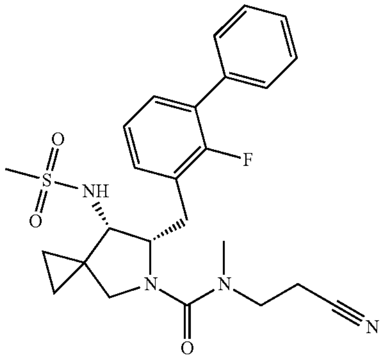 [SMILES: CN(CCC#N)C(=O)N1CC2(CC2)[C@H](NS(C)(=O)=O)[C@@H]1Cc1cccc(-c2ccccc2)c1F] |
| 328 | (6S,7S)-6-((2-fluoro-[1,1'-biphenyl]-3-yl)methyl)-N-((S)-1-methoxypropan-2-yl)-7-(methylsulfonamido)-5-azaspiro[2.4]heptane-5-carboxamide | 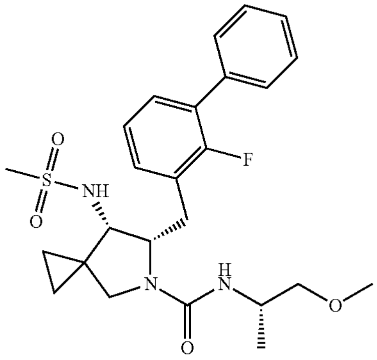 |
| 329 | (6S,7S)-6-((2-fluoro-[1,1'-biphenyl]-3-yl)methyl)-7-(methylsulfonamido)-N-(((S)-tetrahydrofuran-3-yl)methyl)-5-azaspiro[2.4]heptane-5-carboxamide | 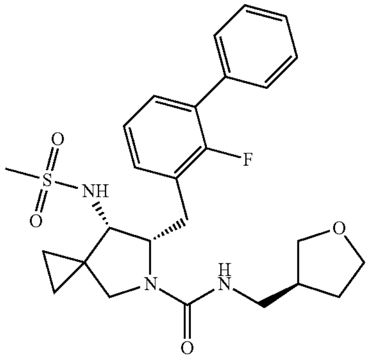 [SMILES: CS(=O)(=O)N[C@@H]1[C@H](Cc2cccc(-c3ccccc3)c2F)N(C(=O)NC[C@@H]2CCOC2)CC12CC2] |

TABLE 3-continued

| Compound No. | Name | Structure |
|---|---|---|
| 330 | (6S,7S)-N-(2-cyanoethyl)-6-((2-fluoro-[1,1'-biphenyl]-3-yl)methyl)-7-(methylsulfonamido)-5-azaspiro[2.4]heptane-5-carboxamide | 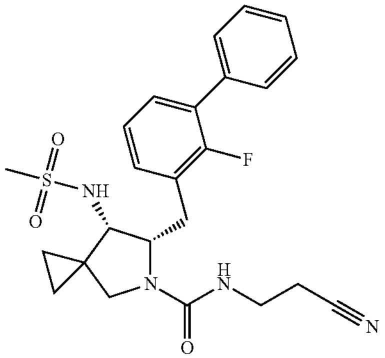 [SMILES: CS(=O)(=O)N[C@@H]1[C@H](Cc2cccc(-c3ccccc3)c2F)N(C(=O)NCCC#N)CC12CC2] |
| 331 | (6S,7S)-6-((2-fluoro-[1,1'-biphenyl]-3-yl)methyl)-7-(methylsulfonamido)-N-(((R)-oxetan-2-yl)methyl)-5-azaspiro[2.4]heptane-5-carboxamide | 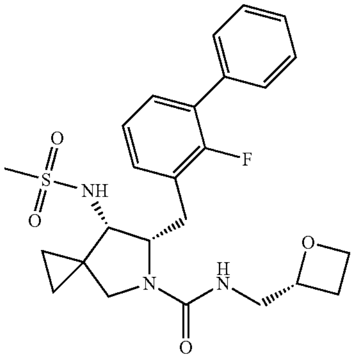 [SMILES: CS(=O)(=O)N[C@@H]1[C@H](Cc2cccc(-c3ccccc3)c2F)N(C(=O)NC[C@H]2CCO2)CC12CC2] |
| 332 | (6S,7S)-N-(cyclopropylmethyl)-6-((2-fluoro-[1,1'-biphenyl]-3-yl)methyl)-N-methyl-7-(methylsulfonamido)-5-azaspiro[2.4]heptane-5-carboxamide | 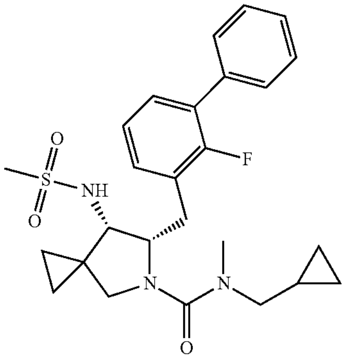 [SMILES: CN(CC1CC1)C(=O)N1CC2(CC2)[C@H](NS(C)(=O)=O)[C@@H]1Cc1cccc(-c2ccccc2)c1F] |
| 333 | (6S,7S)-6-((2-fluoro-[1,1'-biphenyl]-3-yl)methyl)-7-(methylsulfonamido)-N-(((S)-oxetan-2-yl)methyl)-5-azaspiro[2.4]heptane-5-carboxamide | 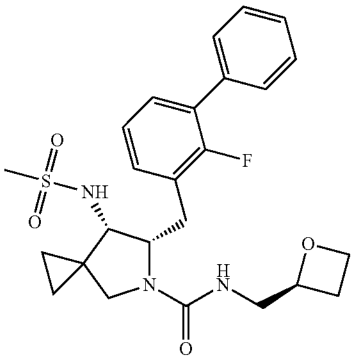 [SMILES: CS(=O)(=O)N[C@@H]1[C@H](Cc2cccc(-c3ccccc3)c2F)N(C(=O)NC[C@@H]2CCO2)CC12CC2] |

TABLE 3-continued

| Compound No. | Name | Structure |
|---|---|---|
| 334 | (6S,7S)-6-((2-fluoro-[1,1'-biphenyl]-3-yl)methyl)-7-(methylsulfonamido)-N-(oxetan-3-ylmethyl)-5-azaspiro[2.4]heptane-5-carboxamide | 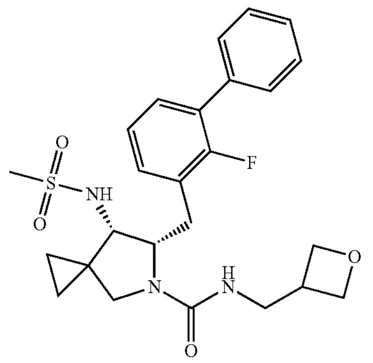 [SMILES: CS(=O)(=O)N[C@@H]1[C@H](Cc2cccc(-c3ccccc3)c2F)N(C(=O)NCC2COC2)CC12CC2] |
| 335 | (6S,7S)-6-((2-fluoro-[1,1'-biphenyl]-3-yl)methyl)-7-(methylsulfonamido)-N-(((R)-tetrahydrofuran-3-yl)methyl)-5-azaspiro[2.4]heptane-5-carboxamide | 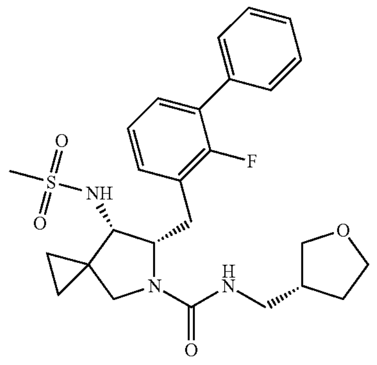 [SMILES: CS(=O)(=O)N[C@@H]1[C@H](Cc2cccc(-c3ccccc3)c2F)N(C(=O)NC[C@H]2CCOC2)CC12CC2] |
| 336 | (6S,7S)-6-((2-fluoro-[1,1'-biphenyl]-3-yl)methyl)-N-((S)-2-methoxypropyl)-7-(methylsulfonamido)-5-azaspiro[2.4]heptane-5-carboxamide | 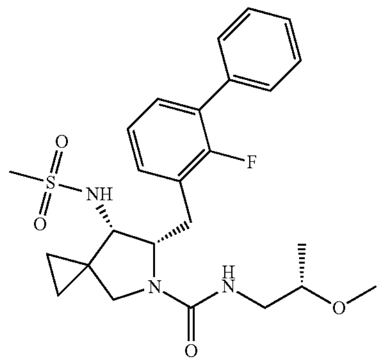 |
| 337 | (6S,7S)-6-((2-fluoro-[1,1'-biphenyl]-3-yl)methyl)-N-((S)-1-fluoropropan-2-yl)-7-(methylsulfonamido)-5-azaspiro[2.4]heptane-5-carboxamide | 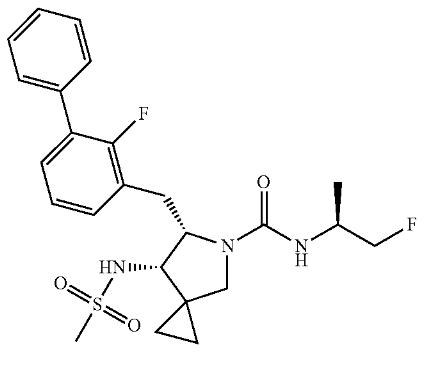 [SMILES: C[C@@H](CF)NC(=O)N1CC2(CC2)[C@H](NS(C)(=O)=O)[C@@H]1Cc1cccc(-c2ccccc2)c1F] |

TABLE 3-continued

| Compound No. | Name | Structure |
|---|---|---|
| 338 | (S)-N-((6S,7S)-6-([1,1'-biphenyl]-3-ylmethyl)-5-((R)-oxetane-2-carbonyl)-5-azaspiro[2.4]heptan-7-yl)-1-cyanoethane-1-sulfonamide | 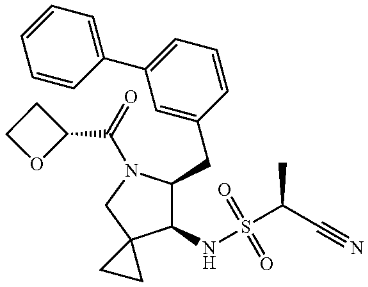 [SMILES: C[C@@H](C#N)S(=O)(=O)N[C@@H]1[C@H](Cc2cccc(-c3ccccc3)c2)N(C(=O)[C@H]2CCO2)CC12CC2] |
| 339 | N-((6S,7S)-5-(3-fluorocyclobutane-1-carbonyl)-6-((2-methoxy-[1,1'-biphenyl]-3-yl)methyl)-5-azaspiro[2.4]heptan-7-yl)methanesulfonamide | 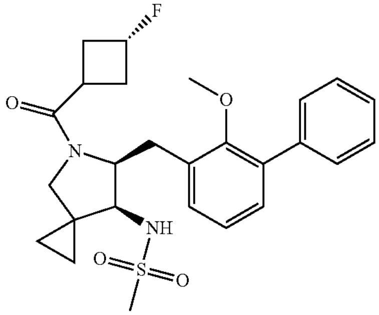 |
| 340 | N-((6S,7S)-5-(3-fluorocyclobutane-1-carbonyl)-6-((2-methoxy-[1,1'-biphenyl]-3-yl)methyl)-5-azaspiro[2.4]heptan-7-yl)methanesulfonamide | 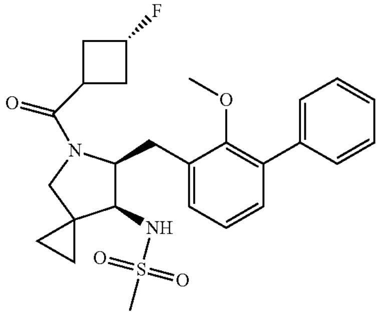 |
| 341 | (6S,7S)-N-(1-cyanoethyl)-6-((2-fluoro-[1,1'-biphenyl]-3-yl)methyl)-7-(methylsulfonamido)-5-azaspiro[2.4]heptane-5-carboxamide | 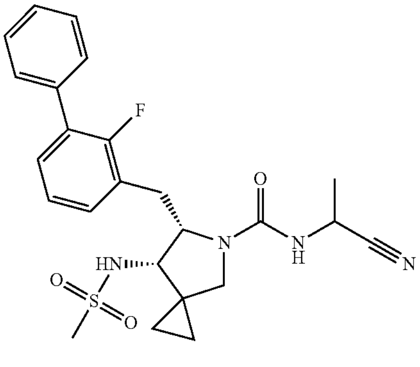 [SMILES: CC(C#N)NC(=O)N1CC2(CC2)[C@H](NS(C)(=O)=O)[C@@H]1Cc1cccc(-c2ccccc2)c1F] |

TABLE 3-continued

| Compound No. | Name | Structure |
|---|---|---|
| 342 | (6S,7S)-6-((2-methoxy-[1,1'-biphenyl]-3-yl)methyl)-7-(methylsulfonamido)-N-propyl-5-azaspiro[2.4]heptane-5-carboxamide | 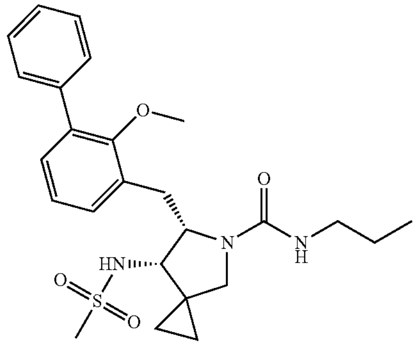 [SMILES: CCCNC(=O)N1CC2(CC2)[C@H](NS(C)(=O)=O)[C@@H]1Cc1cccc(-c2ccccc2)c1OC] |
| 343 | (6S,7S)-6-((2-methoxy-[1,1'-biphenyl]-3-yl)methyl)-7-(methylsulfonamido)-N-(2,2,2-trifluoroethyl)-5-azaspiro[2.4]heptane-5-carboxamide | 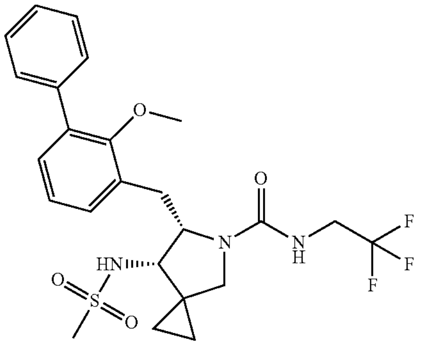 [SMILES: COc1c(C[C@H]2[C@@H](NS(C)(=O)=O)C3(CC3)CN2C(=O)NCC(F)(F)F)cccc1-c1ccccc1] |
| 344 | N-((6S,7S)-6-((2-fluoro-[1,1'-biphenyl]-3-yl)methyl)-5-((R)-2-hydroxy-3-methoxypropanoyl)-5-azaspiro[2.4]heptan-7-yl)ethanesulfonamide | 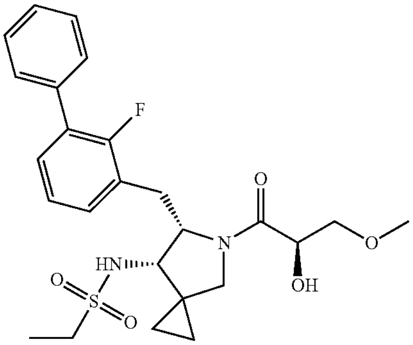 [SMILES: CCS(=O)(=O)N[C@@H]1[C@H](Cc2cccc(-c3ccccc3)c2F)N(C(=O)[C@H](O)COC)CC12CC2] |
| 345 | (6S,7S)-6-((2-fluoro-[1,1'-biphenyl]-3-yl)methyl)-N,N-bis(methyl-d3)-7-(methylsulfonamido)-5-azaspiro[2.4]heptane-5-carboxamide | 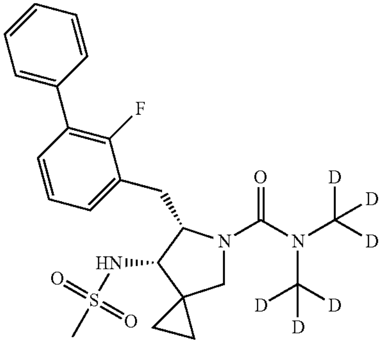 [SMILES: [2H]C([2H])([2H])N(C(=O)N1CC2(CC2)[C@H](NS(C)(=O)=O)[C@@H]1Cc1cccc(-c2ccccc2)c1F)C([2H])([2H])[2H]] |

TABLE 3-continued

| Compound No. | Name | Structure |
|---|---|---|
| 346 | N-((6S,7S)-6-((2-fluoro-[1,1'-biphenyl]-3-yl)methyl)-5-((S)-2-fluoropropanoyl)-5-azaspiro[2.4]heptan-7-yl)methanesulfonamide | 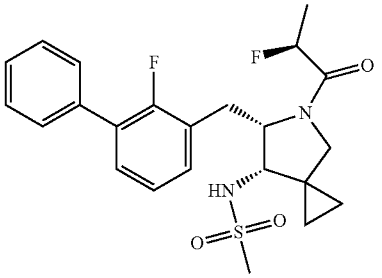 [SMILES: C[C@H](F)C(=O)N1CC2(CC2)[C@H](NS(C)(=O)=O)[C@@H]1Cc1cccc(-c2ccccc2)c1F] |
| 347 | N-((6S,7S)-6-((2,5-difluoro-[1,1'-biphenyl]-3-yl)methyl)-5-((R)-oxetane-2-carbonyl)-5-azaspiro[2.4]heptan-7-yl)-N,N-dimethylsulfuric diamide | 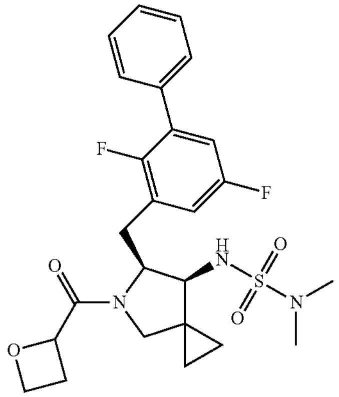 [SMILES: CN(C)S(=O)(=O)N[C@@H]1[C@H](Cc2cc(F)cc(-c3ccccc3)c2F)N(C(=O)C2CCO2)CC12CC2] |
| 348 | N-((6S,7S)-6-((2,5-difluoro-[1,1'-biphenyl]-3-yl-2',3',4',5',6'-d5)methyl)-5-((R)-oxetane-2-carbonyl)-5-azaspiro[2.4]heptan-7-yl)methanesulfonamide | 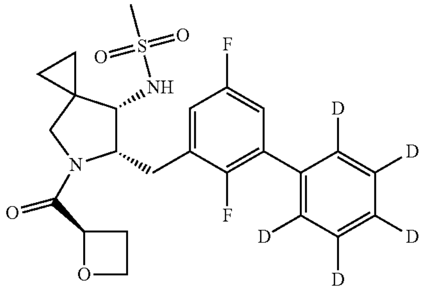 [SMILES: [2H]c1c([2H])c([2H])c(-c2cc(F)cc(C[C@H]3[C@@H](NS(C)(=O)=O)C4(CC4)CN3C(=O)[C@H]3CCO3)c2F)c([2H])c1[2H]] |
| 349 | N-((6S,7S)-6-((2,5-difluoro-[1,1'-biphenyl]-3-yl)methyl)-5-((R)-oxetane-2-carbonyl)-5-azaspiro[2.4]heptan-7-yl)cyclopropanesulfonamide | 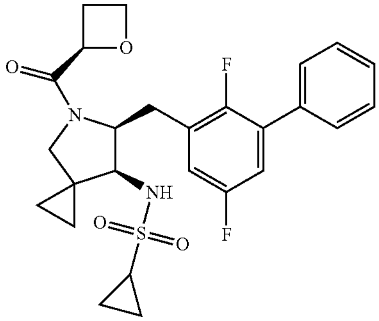 [SMILES: O=C([C@H]1CCO1)N1CC2(CC2)[C@H](NS(=O)(=O)C2CC2)[C@@H]1Cc1cc(F)cc(-c2ccccc2)c1F] |

TABLE 3-continued

| Compound No. | Name | Structure |
|---|---|---|
| 350 | N-((6S,7S)-5-((R)-oxetane-2-carbonyl)-6-((2,2',5-trifluoro-[1,1'-biphenyl]-3-yl)methyl)-5-azaspiro[2.4]heptan-7-yl)methanesulfonamide | 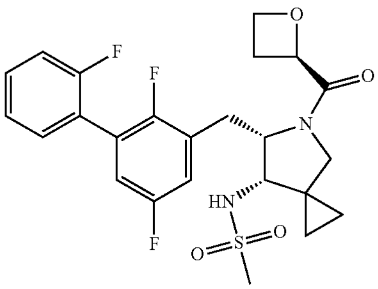 [SMILES: CS(=O)(=O)N[C@@H]1[C@H](Cc2cc(F)cc(-c3ccccc3F)c2F)N(C(=O)[C@H]2CCO2)CC12CC2] |
| 351 | N-((6S,7S)-5-((S)-3,3-difluoro-2-hydroxypropanoyl)-6-((2-fluoro-[1,1'-biphenyl]-3-yl)methyl)-5-azaspiro[2.4]heptan-7-yl)methanesulfonamide | 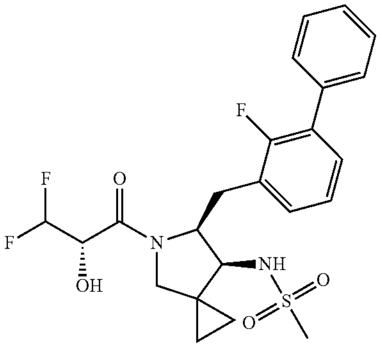 [SMILES: CS(=O)(=O)N[C@@H]1[C@H](Cc2cccc(-c3ccccc3)c2F)N(C(=O)[C@H](O)C(F)F)CC12CC2] |
| 352 | N-((6S,7S)-5-((R)-2-cyclopropyl-2-hydroxyacetyl)-6-((2,5-difluoro-[1,1'-biphenyl]-3-yl)methyl)-5-azaspiro[2.4]heptan-7-yl)methanesulfonamide | 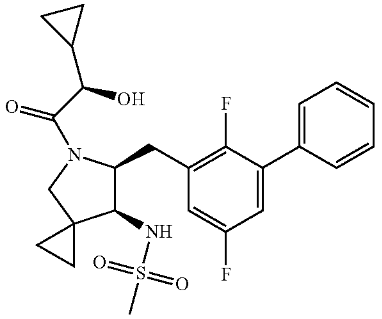 [SMILES: CS(=O)(=O)N[C@@H]1[C@H](Cc2cc(F)cc(-c3ccccc3)c2F)N(C(=O)[C@H](O)C2CC2)CC12CC2] |
| 353 | N-((6S,7S)-5-((S)-3-fluoro-2-hydroxypropanoyl)-6-((2,5-difluoro-[1,1'-biphenyl]-3-yl)methyl)-5-azaspiro[2.4]heptan-7-yl))-N,N-dimethylsulfuric diamide | 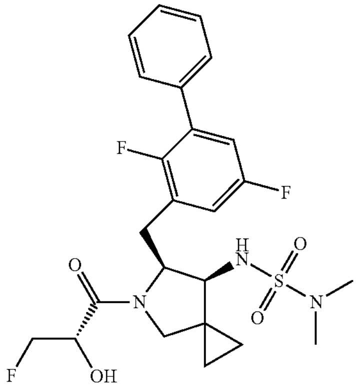 [SMILES: CN(C)S(=O)(=O)N[C@@H]1[C@H](Cc2cc(F)cc(-c3ccccc3)c2F)N(C(=O)[C@H](O)CF)CC12CC2] |

TABLE 3-continued

| Compound No. | Name | Structure |
|---|---|---|
| 354 | (6S,7S)-6-((2,5-difluoro-[1,1'-biphenyl]-3-yl)methyl)-N,N-dimethyl-7-(methylsulfonamido)-5-azaspiro[2.4]heptane-5-carboxamide | 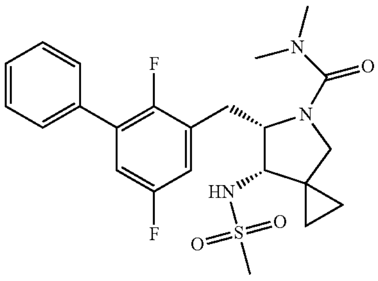 [SMILES: CN(C)C(=O)N1CC2(CC2)[C@H](NS(C)(=O)=O)[C@@H]1Cc1cc(F)cc(-c2ccccc2)c1F] |
| 355 | (6S,7S)-6-((2,5-difluoro-[1,1'-biphenyl]-3-yl)methyl)-N,N-bis(methyl-d3)-7-(methylsulfonamido)-5-azaspiro[2.4]heptane-5-carboxamide | 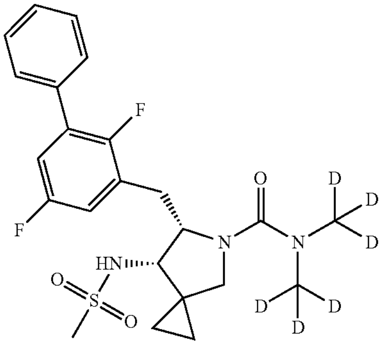 [SMILES: [2H]C([2H])([2H])N(C(=O)N1CC2(CC2)[C@H](NS(C)(=O)=O)[C@@H]1Cc1cc(F)cc(-c2ccccc2)c1F)C([2H])([2H])[2H]] |
| 356 | N-((6S,7S)-6-((2,5-difluoro-[1,1'-biphenyl]-3-yl)methyl)-5-((S)-3-fluoro-2-hydroxypropanoyl)-5-azaspiro[2.4]heptan-7-yl)ethanesulfonamide | 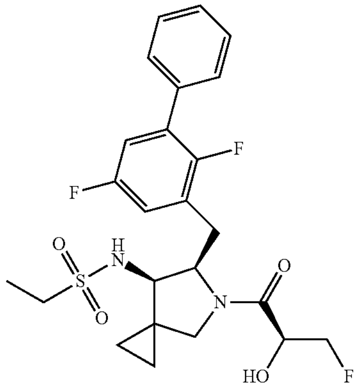 [SMILES: CCS(=O)(=O)N[C@H]1[C@@H](Cc2cc(F)cc(-c3ccccc3)c2F)N(C(=O)[C@H](O)CF)CC12CC2] |
| 357 | (6S,7S)-6-((2-fluoro-[1,1'-biphenyl]-3-yl)methyl)-7-((fluoromethyl)sulfonamido)-N-(2-methoxyethyl)-5-azaspiro[2.4]heptane-5-carboxamide | 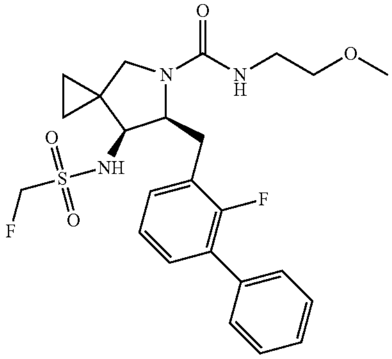 [SMILES: COCCNC(=O)N1CC2(CC2)[C@H](NS(=O)(=O)CF)[C@@H]1Cc1cccc(-c2ccccc2)c1F] |

TABLE 3-continued

| Compound No. | Name | Structure |
|---|---|---|
| 358 | N-((6S,7S)-5-(2-cyanopropanoyl)-6-((2-fluoro-[1,1'-biphenyl]-3-yl)methyl)-5-azaspiro[2.4]heptan-7-yl)methanesulfonamide | 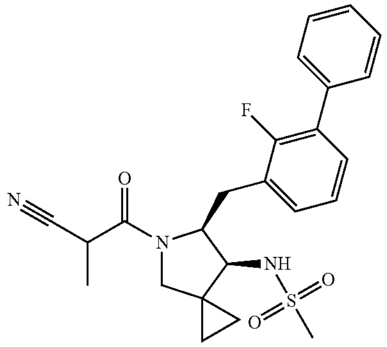 [SMILES: CC(C#N)C(=O)N1CC2(CC2)[C@H](NS(C)(=O)=O)[C@@H]1Cc1cccc(-c2ccccc2)c1F] |
| 359 | N-((6S,7S)-6-(2,5-difluoro-[1,1'-biphenyl]-3-yl-4'-d)methyl)-5-((R)-oxetane-2-carbonyl)-5-azaspiro[2.4]heptan-7-yl)methanesulfonamide | 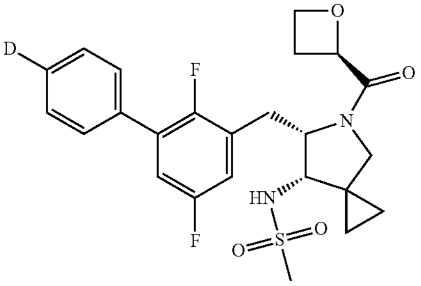 [SMILES: [2H]c1ccc(-c2cc(F)cc(C[C@H]3[C@@H](NS(C)(=O)=O)C4(CC4)CN3C(=O)[C@H]3CCO3)c2F)cc1] |
| 360 | N-((6S,7S)-5-((S)-3,3-difluoro-2-hydroxypropanoyl)-6-((2,5-difluoro-[1,1'-biphenyl]-3-yl)methyl)-5-azaspiro[2.4]heptan-7-yl)-1-fluoromethanesulfonamide | 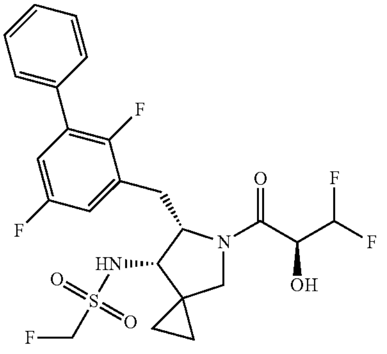 [SMILES: O=C([C@H](O)C(F)F)N1CC2(CC2)[C@H](NS(=O)(=O)CF)[C@@H]1Cc1cc(F)cc(-c2ccccc2)c1F] |
| 361 | N-((6S,7S)-6-((2,2’-difluoro-[1,1'-biphenyl]-3-yl)methyl)-5-(2-hydroxy-2-methylpropanoyl)-5-azaspiro[2.4]heptan-7-yl)methanesulfonamide | 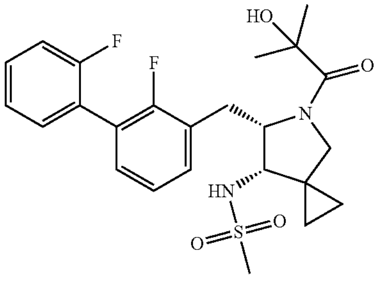 [SMILES: CC(C)(O)C(=O)N1CC2(CC2)[C@H](NS(C)(=O)=O)[C@@H]1Cc1cccc(-c2ccccc2F)c1F] |

TABLE 3-continued

| Compound No. | Name | Structure |
|---|---|---|
| 362 | 1-cyano-N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide | 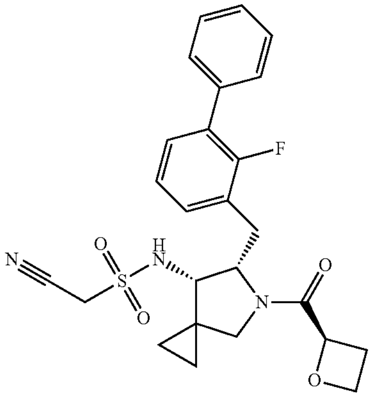 [SMILES: N#CCS(=O)(=O)N[C@@H]1[C@H](Cc2cccc(-c3ccccc3)c2F)N(C(=O)[C@H]2CCO2)CC12CC2] |
| 363 | (6S,7S)-N-(ethyl-d5)-6-((2-methoxy-[1,1'-biphenyl]-3-yl)methyl)-7-(methylsulfonamido)-5-azaspiro[2.4]heptane-5-carboxamide | 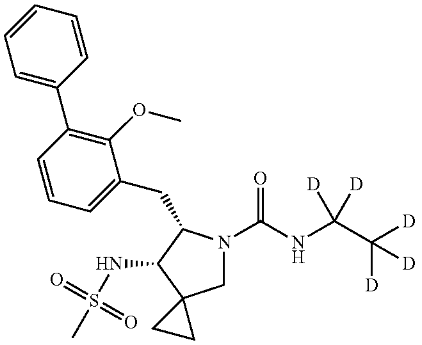 [SMILES: [2H]C([2H])([2H])C([2H])([2H])NC(=O)N1CC2(CC2)[C@H](NS(C)(=O)=O)[C@@H]1Cc1cccc(-c2ccccc2)c1OC] |
| 364 | (6S,7S)-7-((difluoromethyl)sulfonamido)-6-((2-fluoro-[1,1'-biphenyl]-3-yl)methyl)-N-((R)-1-hydroxypropan-2-yl)-5-azaspiro[2.4]heptane-5-carboxamide | 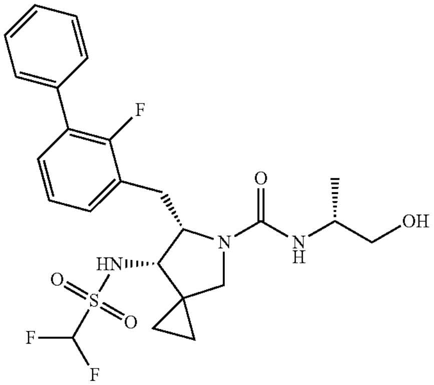 [SMILES: C[C@H](CO)NC(=O)N1CC2(CC2)[C@H](NS(=O)(=O)C(F)F)[C@@H]1Cc1cccc(-c2ccccc2)c1F] |
| 365 | 1-fluoro-N-((6S,7S)-6-((2-fluoro-[1,1'-biphenyl]-3-yl-2',3',4',5',6'-d5)methyl)-5-((R)-oxetane-2-carbonyl)-5-azaspiro[2.4]heptan-7-yl)methanesulfonamide | 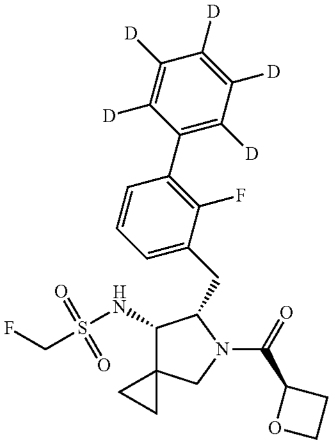 [SMILES: [2H]c1c([2H])c([2H])c(-c2cccc(C[C@H]3[C@@H](NS(=O)(=O)CF)C4(CC4)CN3C(=O)[C@H]3CCO3)c2F)c([2H])c1[2H]] |

TABLE 3-continued

| Compound No. | Name | Structure |
| --- | --- | --- |
| 366 | (6S,7S)-6-((2-fluoro-[1,1'-biphenyl]-3-yl)methyl)-7-((fluoromethyl)sulfonamido)-N-(oxetan-3-ylmethyl)-5-azaspiro[2.4]heptane-5-carboxamide | 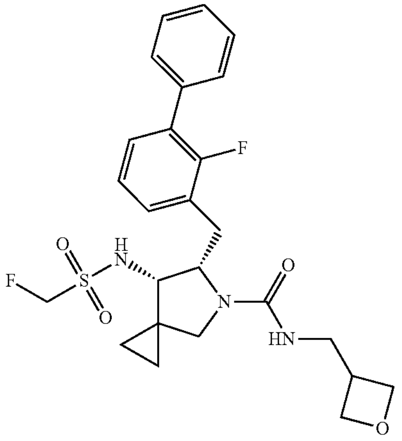 [SMILES: O=C(NCC1COC1)N1CC2(CC2)[C@H](NS(=O)(=O)CF)[C@@H]1Cc1cccc(-c2ccccc2)c1F] |
| 367 | (6S,7S)-6-((2-fluoro-[1,1'-biphenyl]-3-yl)methyl)-N-(2-fluoroethyl)-7-((fluoromethyl)sulfonamido)-5-azaspiro[2.4]heptane-5-carboxamide | 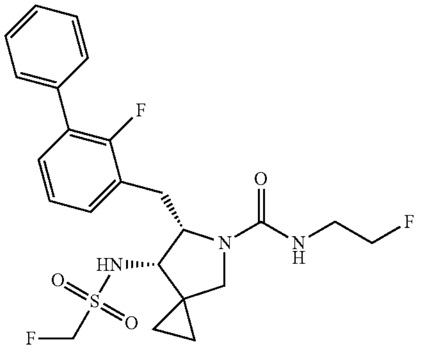 [SMILES: O=C(NCCF)N1CC2(CC2)[C@H](NS(=O)(=O)CF)[C@@H]1Cc1cccc(-c2ccccc2)c1F] |
| 368 | (6S,7S)-7-((difluoromethyl)sulfonamido)-6-((2-fluoro-[1,1'-biphenyl]-3-yl)methyl)-N-(((S)-oxetan-2-yl)methyl)-5-azaspiro[2.4]heptane-5-carboxamide | 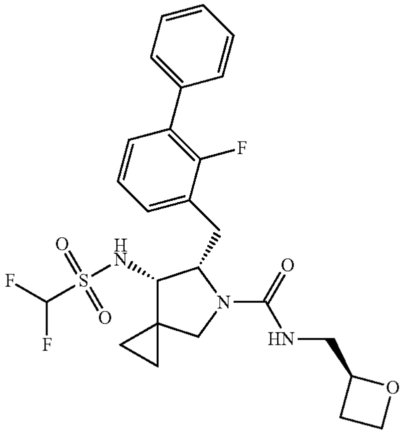 [SMILES: O=C(NC[C@@H]1CCO1)N1CC2(CC2)[C@H](NS(=O)(=O)C(F)F)[C@@H]1Cc1cccc(-c2ccccc2)c1F] |

TABLE 3-continued

| Compound No. | Name | Structure |
|---|---|---|
| 369 | (6S,7S)-N-(1,3-difluoropropan-2-yl)-6-((2-fluoro-[1,1'-biphenyl]-3-yl)methyl)-7-((fluoromethyl)sulfonamido)-5-azaspiro[2.4]heptane-5-carboxamide | 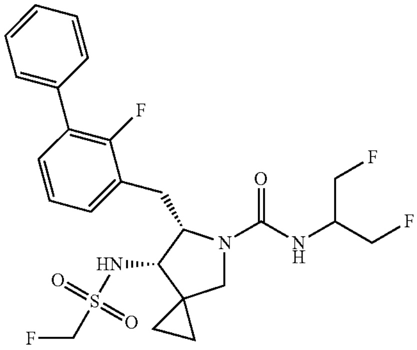 [SMILES: O=C(NC(CF)CF)N1CC2(CC2)[C@H](NS(=O)(=O)CF)[C@@H]1Cc1cccc(-c2ccccc2)c1F] |
| 370 | (6S,7S)-6-((2-fluoro-[1,1'-biphenyl]-3-yl)methyl)-7-((fluoromethyl)sulfonamido)-N-((1-methoxycyclopropyl)methyl)-5-azaspiro[2.4]heptane-5-carboxamide | 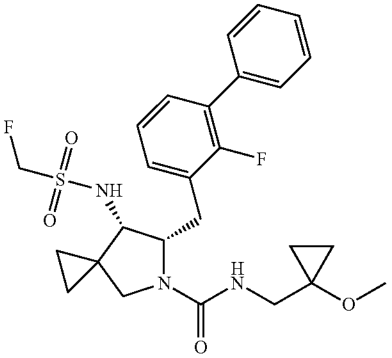 [SMILES: COC1(CNC(=O)N2CC3(CC3)[C@H](NS(=O)(=O)CF)[C@@H]2Cc2cccc(-c3ccccc3)c2F)CC1] |
| 371 | (6S,7S)-6-((2,5-difluoro-[1,1'-biphenyl]-3-yl)methyl)-N-(2-fluoroethyl)-7-((fluoromethyl)sulfonamido)-5-azaspiro[2.4]heptane-5-carboxamide | 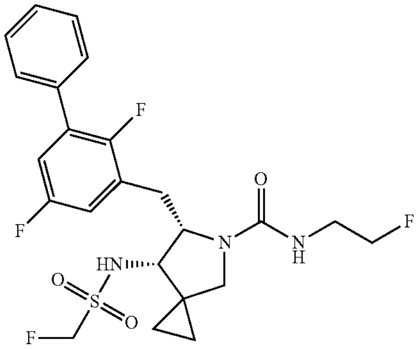 [SMILES: O=C(NCCF)N1CC2(CC2)[C@H](NS(=O)(=O)CF)[C@@H]1Cc1cc(F)cc(-c2ccccc2)c1F] |
| 372 | 1-fluoro-N-((6S,7S)-6-((2-fluoro-[1,1'-biphenyl]-3-yl)methyl)-5-((R)-2-hydroxy-3-methoxypropanoyl)-5-azaspiro[2.4]heptan-7-yl)methanesulfonamide | 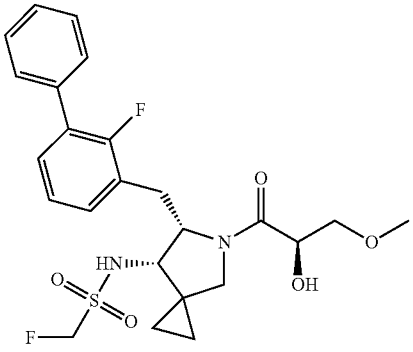 [SMILES: COC[C@@H](O)C(=O)N1CC2(CC2)[C@H](NS(=O)(=O)CF)[C@@H]1Cc1cccc(-c2ccccc2)c1F] |

TABLE 3-continued

| Compound No. | Name | Structure |
|---|---|---|
| 373 | 1-fluoro-N-((6S,7S)-5-((S)-3-fluoro-2-hydroxypropanoyl)-6-((2,3',5,5'-tetrafluoro-[1,1'-biphenyl]-3-yl)methyl)-5-azaspiro[2.4]heptan-7-yl)methanesulfonamide | 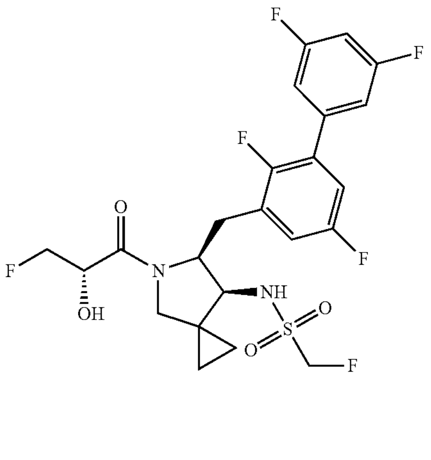 [SMILES: O=C([C@H](O)CF)N1CC2(CC2)[C@H](NS(=O)(=O)CF)[C@@H]1Cc1cc(F)cc(-c2cc(F)cc(F)c2)c1F] |
| 374 | (6S,7S)-6-((2-fluoro-[1,1'-biphenyl]-3-yl)methyl)-7-((fluoromethyl)sulfonamido)-N-(((S)-oxetan-2-yl)methyl)-5-azaspiro[2.4]heptane-5-carboxamide | 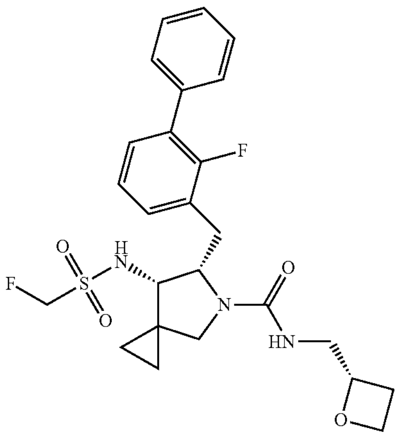 [SMILES: O=C(NC[C@@H]1CCO1)N1CC2(CC2)[C@H](NS(=O)(=O)CF)[C@@H]1Cc1cccc(-c2ccccc2)c1F] |
| 375 | (6S,7S)-6-((2,5-difluoro-[1,1'-biphenyl]-3-yl)methyl)-7-((fluoromethyl)sulfonamido)-N-((R)-1-fluoropropan-2-yl)-5-azaspiro[2.4]heptane-5-carboxamide | 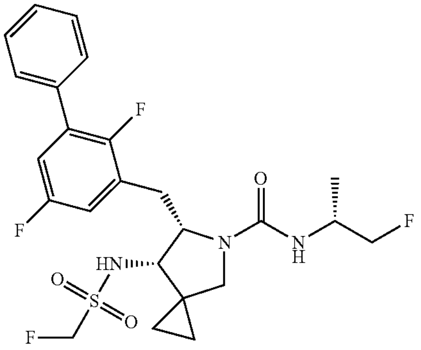 [SMILES: C[C@H](CF)NC(=O)N1CC2(CC2)[C@H](NS(=O)(=O)CF)[C@@H]1Cc1cc(F)cc(-c2ccccc2)c1F] |

TABLE 4

| Compound No. | Name | Structure |
|---|---|---|
| 376 | N-((6S,7S)-6-((2,3'-difluoro-[1,1'-biphenyl]-3-yl)methyl)-5-((S)-2-hydroxy-2-methylbutanoyl)-5-azaspiro[2.4]heptan-7-yl)-1-fluoromethanesulfonamide | 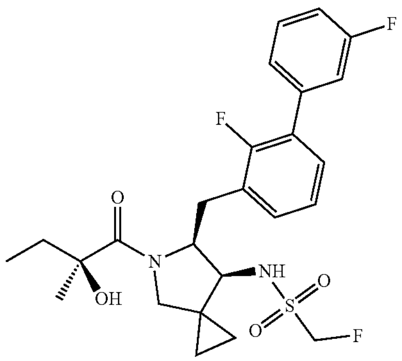 [SMILES: CC[C@](C)(O)C(=O)N1CC2(CC2)[C@H](NS(=O)(=O)CF)[C@@H]1Cc1cccc(-c2cccc(F)c2)c1F] |
| 377 | N-((6S,7S)-5-((S)-2-cyclopropyl-2-hydroxyacetyl)-6-((2,3',5'-trifluoro-[1,1'-biphenyl]-3-yl)methyl)-5-azaspiro[2.4]heptan-7-yl)-1,1-difluoromethanesulfonamide | 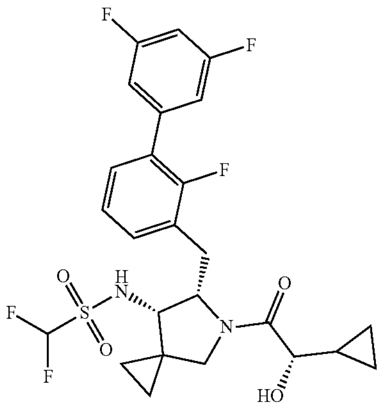 [SMILES: O=C([C@@H](O)C1CC1)N1CC2(CC2)[C@H](NS(=O)(=O)C(F)F)[C@@H]1Cc1cccc(-c2cc(F)cc(F)c2)c1F] |
| 378 | 1,1-difluoro-N-((6S,7S)-5-((R)-2-fluoropropanoyl)-6-((2,3',5'-trifluoro-[1,1'-biphenyl]-3-yl)methyl)-5-azaspiro[2.4]heptan-7-yl)methanesulfonamide | 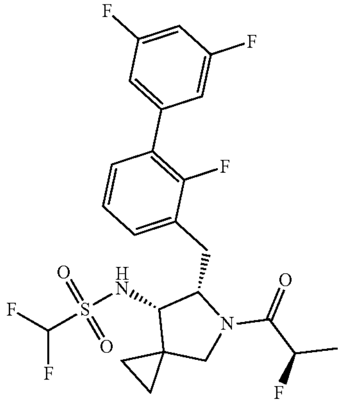 [SMILES: C[C@@H](F)C(=O)N1CC2(CC2)[C@H](NS(=O)(=O)C(F)F)[C@@H]1Cc1cccc(-c2cc(F)cc(F)c2)c1F] |
| 379 | N-((6S,7S)-6-((2,3'-difluoro-[1,1'-biphenyl]-3-yl)methyl)-5-((R)-2-hydroxy-2-methylbutanoyl)-5-azaspiro[2.4]heptan-7-yl)-1-fluoromethanesulfonamide | 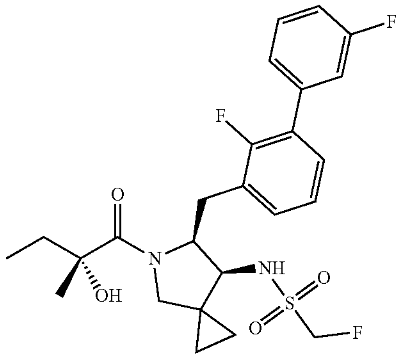 [SMILES: CC[C@@](C)(O)C(=O)N1CC2(CC2)[C@H](NS(=O)(=O)CF)[C@@H]1Cc1cccc(-c2cccc(F)c2)c1F] |

TABLE 4-continued

| Compound No. | Name | Structure |
|---|---|---|
| 380 | N-((6S,7S)-6-((2,3'-difluoro-[1,1'-biphenyl]-3-yl)methyl)-5-((S)-3-fluoro-2-hydroxypropanoyl)-5-azaspiro[2.4]heptan-7-yl)-1,1-difluoromethanesulfonamide | 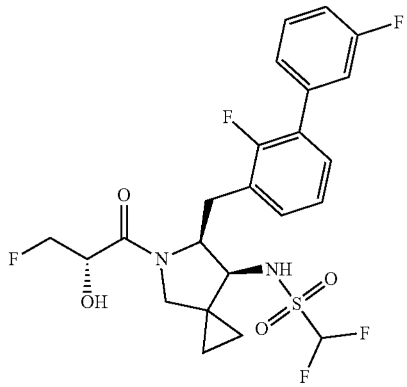 [SMILES: O=C([C@H](O)CF)N1CC2(CC2)[C@H](NS(=O)(=O)C(F)F)[C@@H]1Cc1cccc(-c2cccc(F)c2)c1F] |
| 381 | N-((6S,7S)-5-(1-cyanocyclobutane-1-carbonyl)-6-((2,3',5'-trifluoro-[1,1'-biphenyl]-3-yl)methyl)-5-azaspiro[2.4]heptan-7-yl)-1,1-difluoromethanesulfonamide | 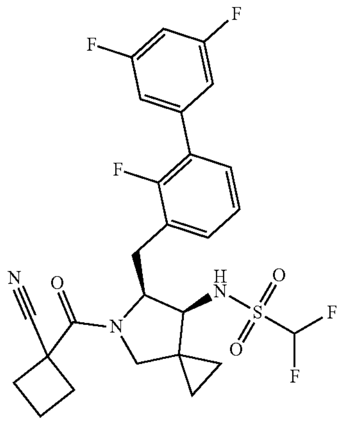 [SMILES: N#CC1(C(=O)N2CC3(CC3)[C@H](NS(=O)(=O)C(F)F)[C@@H]2Cc2cccc(-c3cc(F)cc(F)c3)c2F)CCC1] |
| 382 | (6S,7S)-N-(2,2-difluoroethyl)-7-((difluoromethyl)sulfonamido)-6-((2,3',5'-trifluoro-[1,1'-biphenyl]-3-yl)methyl)-5-azaspiro[2.4]heptane-5-carboxamide | 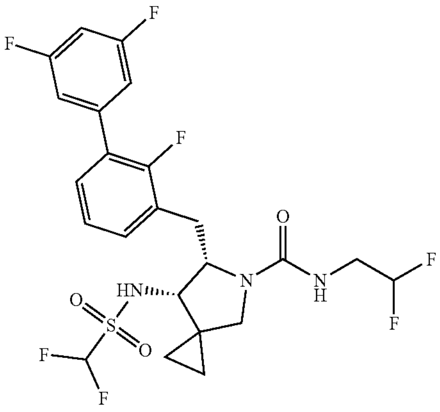 [SMILES: O=C(NCC(F)F)N1CC2(CC2)[C@H](NS(=O)(=O)C(F)F)[C@@H]1Cc1cccc(-c2cc(F)cc(F)c2)c1F] |
| 383 | (6S,7S)-6-((2,5-difluoro-[1,1'-biphenyl]-3-yl)methyl)-7-((difluoromethyl)sulfonamido)-N-(2,2,2-trifluoroethyl)-5-azaspiro[2.4]heptane-5-carboxamide | 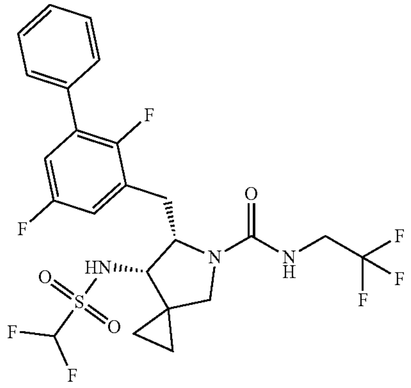 [SMILES: O=C(NCC(F)(F)F)N1CC2(CC2)[C@H](NS(=O)(=O)C(F)F)[C@@H]1Cc1cc(F)cc(-c2ccccc2)c1F] |

TABLE 4-continued

| Compound No. | Name | Structure |
|---|---|---|
| 384 | N-((6S,7S)-5-((S)-2-cyclopropyl-2-hydroxyacetyl)-6-((2,3',5,5'-tetrafluoro-[1,1'-biphenyl]-3-yl)methyl)-5-azaspiro[2.4]heptan-7-yl)-1,1-difluoromethanesulfonamide | 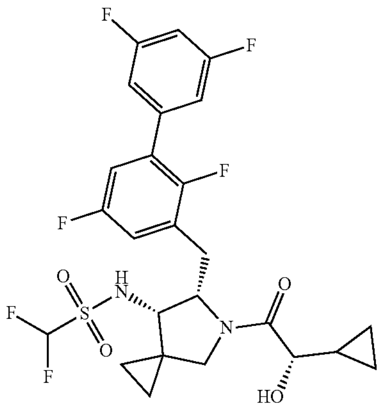 [SMILES: O=C([C@@H](O)C1CC1)N1CC2(CC2)[C@H](NS(=O)(=O)C(F)F)[C@@H]1Cc1cc(F)cc(-c2cc(F)cc(F)c2)c1F] |
| 385 | N-(6S,7S)-5-((S)-2-cyclopropyl-2-hydroxyacetyl)-6-(2,5-difluoro-[1,1'-biphenyl]-3-yl)methyl)-5-azaspiro[2.4]heptan-7-yl)-1,1-difluoromethanesulfonamide | 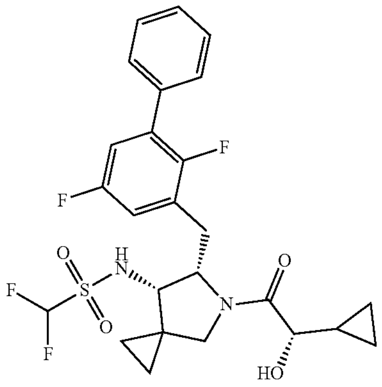 [SMILES: O=C([C@@H](O)C1CC1)N1CC2(CC2)[C@H](NS(=O)(=O)C(F)F)[C@@H]1Cc1cc(F)cc(-c2ccccc2)c1F] |
| 386 | N-((6S,7S)-6-((2-fluoro-[1,1'-biphenyl]-3-yl)methyl)-5-(1-(methoxymethyl)cyclopropane-1-carbonyl)-5-azaspiro[2.4]heptan-7-yl)methanesulfonamide | 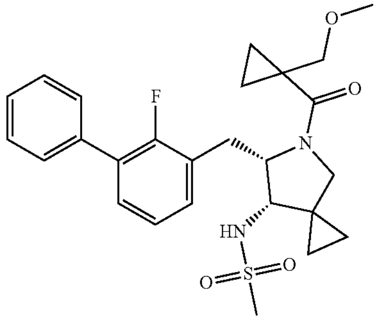 [SMILES: COCC1(C(=O)N2CC3(CC3)[C@H](NS(C)(=O)=O)[C@@H]2Cc2cccc(-c3ccccc3)c2F)CC1] |
| 387 | (6S,7S)-N-(2,2-difluoroethyl)-7-((difluoromethyl)sulfonamido)-biphenyl]-3-yl)methyl)-5-azaspiro[2.4]heptane-5-carboxamide | 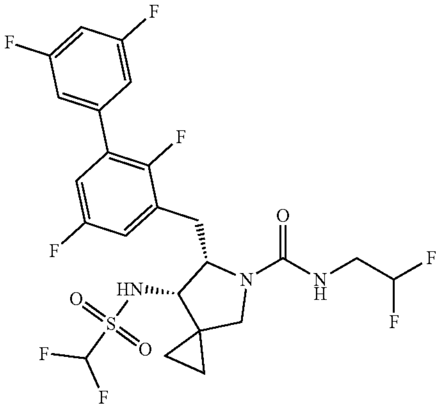 [SMILES: O=C(NCC(F)F)N1CC2(CC2)[C@H](NS(=O)(=O)C(F)F)[C@@H]1Cc1cc(F)cc(-c2cc(F)cc(F)c2)c1F] |

TABLE 4-continued

| Compound No. | Name | Structure |
|---|---|---|
| 388 | (6S,7S)-6-((2,5-difluoro-[1,1'-biphenyl]-3-yl)methyl)-7-((difluoromethyl)sulfonamido)-N-((R)-1-fluoropropan-2-yl)-5-azaspiro[2.4]heptane-5-carboxamide | 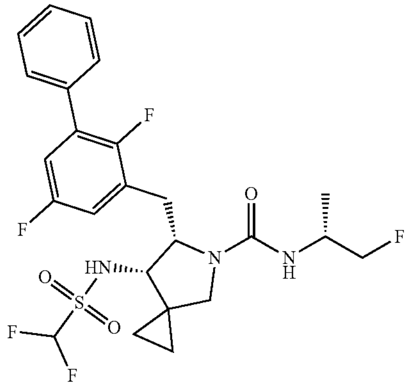 [SMILES: C[C@H](CF)NC(=O)N1CC2(CC2)[C@H](NS(=O)(=O)C(F)F)[C@@H]1Cc1cc(F)cc(-c2ccccc2)c1F] |
| 389 | (6S,7S)-6-((2,5-difluoro-[1,1'-biphenyl]-3-yl)methyl)-N-(2,2-difluoroethyl)-7-((difluoromethyl)sulfonamido)-5-azaspiro[2.4]heptane-5-carboxamide | 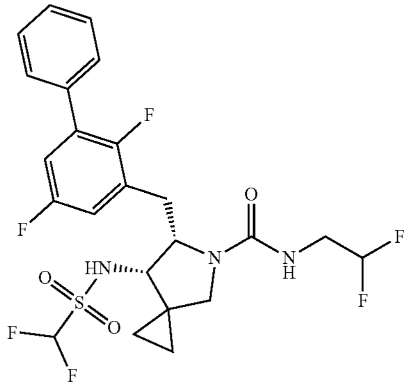 [SMILES: O=C(NCC(F)F)N1CC2(CC2)[C@H](NS(=O)(=O)C(F)F)[C@@H]1Cc1cc(F)cc(-c2ccccc2)c1F] |
| 390 | N-((6S,7S)-6-((2,5-difluoro-[1,1'-biphenyl]-3-yl)methyl)-5-((S)-3-fluoro-2-hydroxypropanoyl)-5-azaspiro[2.4]heptan-7-yl)-1,1-difluoromethanesulfonamide | 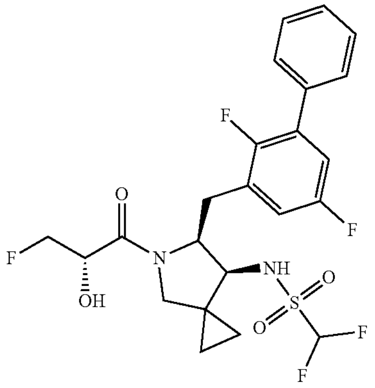 [SMILES: O=C([C@H](O)CF)N1CC2(CC2)[C@H](NS(=O)(=O)C(F)F)[C@@H]1Cc1cc(F)cc(-c2ccccc2)c1F] |
| 391 | 1-fluoro-N-((6S,7S)-5-((S)-3-fluoro-2-hydroxypropanoyl)-6-((2,3',5'-trifluoro-[1,1'-biphenyl]-3-yl)methyl)-5-azaspiro[2.4]heptan-7-yl)methanesulfonamide | 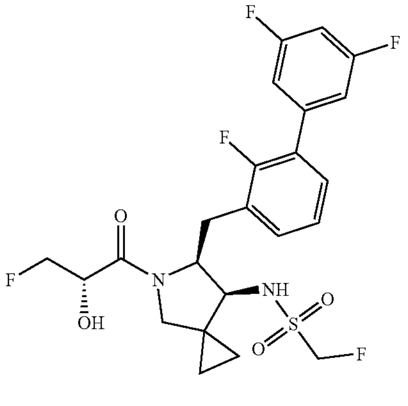 [SMILES: O=C([C@H](O)CF)N1CC2(CC2)[C@H](NS(=O)(=O)CF)[C@@H]1Cc1cccc(-c2cc(F)cc(F)c2)c1F] |

TABLE 4-continued

| Compound No. | Name | Structure |
|---|---|---|
| 392 | 1,1-difluoro-N-((6S,7S)-5-((S)-3-fluoro-2-hydroxypropanoyl)-6-((2,3',5'-trifluoro-[1,1'-biphenyl]-3-yl)methyl)-5-azaspiro[2.4]heptan-7-yl)methanesulfonamide | 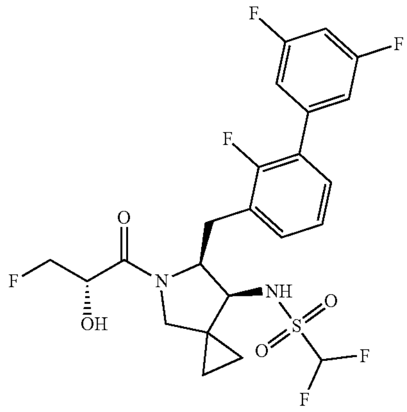 [SMILES: O=C([C@H](O)CF)N1CC2(CC2)[C@H](NS(=O)(=O)C(F)F)[C@@H]1Cc1cccc(-c2cc(F)cc(F)c2)c1F] |
| 393 | 1-fluoro-N-((6S,7S)-5-((S)-2-fluoropropanoyl)-6-((2,3',5-trifluoro-[1,1'-biphenyl]-3-yl)methyl)-5-azaspiro[2.4]heptan-7-yl)methanesulfonamide | 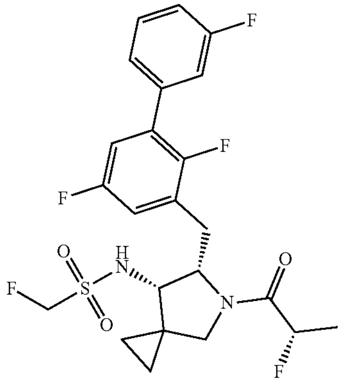 [SMILES: C[C@H](F)C(=O)N1CC2(CC2)[C@H](NS(=O)(=O)CF)[C@@H]1Cc1cc(F)cc(-c2cccc(F)c2)c1F] |
| 394 | 1-fluoro-N-(6S,7S)-5-(R)-2-fluoropropanoyl)-6-((2,3',5-trifluoro-[1,1'-biphenyl]-3-yl)methyl)-5-azaspiro[2.4]heptan-7-yl)methanesulfonamide | 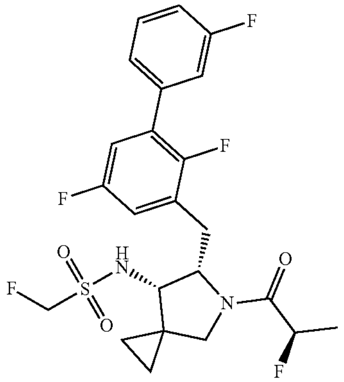 [SMILES: C[C@@H](F)C(=O)N1CC2(CC2)[C@H](NS(=O)(=O)CF)[C@@H]1Cc1cc(F)cc(-c2cccc(F)c2)c1F] |
| 395 | N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)propane-2-sulfonamide | 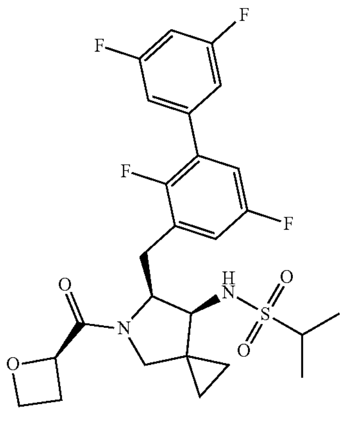 |

TABLE 4-continued

| Compound No. | Name | Structure |
|---|---|---|
| 396 | N-(6S,7S)-6-(2,5-difluoro-[1,1'-biphenyl]-3-yl)methyl)-5-((R)-oxetane-2-carbonyl)-5-azaspiro[2.4]heptan-7-yl)propane-2-sulfonamide | 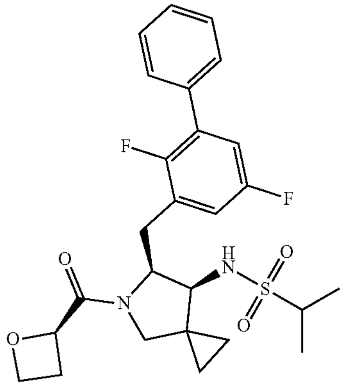 [SMILES: CC(C)S(=O)(=O)N[C@@H]1[C@H](Cc2cc(F)cc(-c3ccccc3)c2F)N(C(=O)[C@H]2CCO2)CC12CC2] |
| 397 | (6S,7S)-N-(ethyl-d5)-7-((fluoromethyl)sulfonamido)-6-((2-(methoxy-d3)-[1,1'-biphenyl]-3-yl)methyl)-5-azaspiro[2.4]heptane-5-carboxamide | 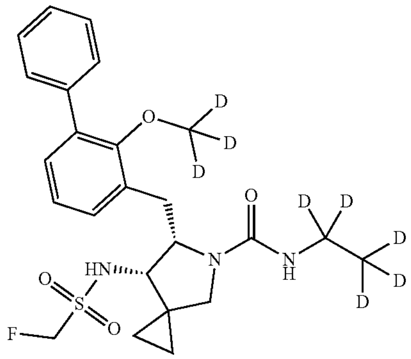 [SMILES: [2H]C([2H])([2H])Oc1c(C[C@H]2[C@@H](NS(=O)(=O)CF)C3(CC3)CN2C(=O)NC([2H])([2H])C([2H])([2H])[2H])cccc1-c1ccccc1] |
| 398 | 2-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)propane-2-sulfonamide | 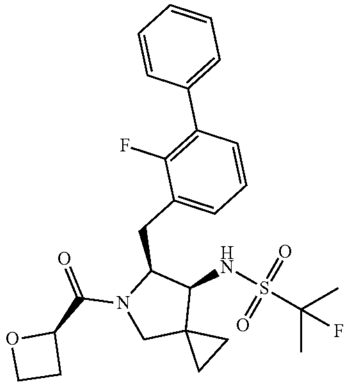 [SMILES: CC(C)(F)S(=O)(=O)N[C@@H]1[C@H](Cc2cccc(-c3ccccc3)c2F)N(C(=O)[C@H]2CCO2)CC12CC2] |
| 399 | N-((6S,7S)-6-methyl-5-((R)-oxetane-2-carbonyl)-5-azaspiro[2.4]heptan-7-yl)-N,N-dimethylsulfamide | 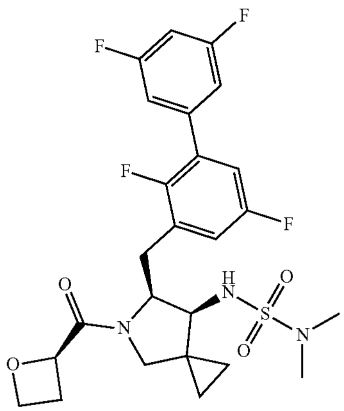 [SMILES: CN(C)S(=O)(=O)N[C@@H]1[C@H](Cc2cc(F)cc(-c3cc(F)cc(F)c3)c2F)N(C(=O)[C@H]2CCO2)CC12CC2] |

TABLE 4-continued

| Compound No. | Name | Structure |
|---|---|---|
| 400 | N-((6S,7S)-6-((2,3'-difluoro-[1,1'-biphenyl]-3-yl)methyl)-5-(3-methoxyazetidine-1-carbonyl)-5-azaspiro[2.4]heptan-7-yl)-1-fluoromethanesulfonamide | 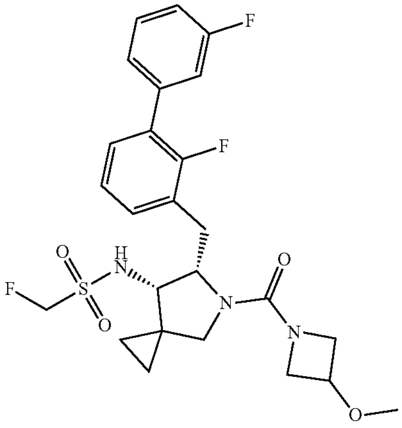 [SMILES: COC1CN(C(=O)N2CC3(CC3)[C@H](NS(=O)(=O)CF)[C@@H]2Cc2cccc(-c3cccc(F)c3)c2F)C1] |
| 401 | 1-fluoro-N-((6S,7S)-6-((2-fluoro-[1,1'-biphenyl]-3-yl)methyl)-5-((R)-tetrahydrofuran-2-carbonyl)-5-azaspiro[2.4]heptan-7-yl)methanesulfonamide | 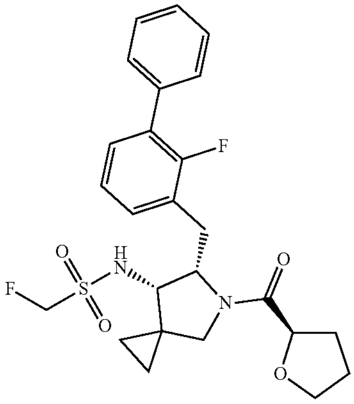 [SMILES: O=C([C@H]1CCCO1)N1CC2(CC2)[C@H](NS(=O)(=O)CF)[C@@H]1Cc1cccc(-c2ccccc2)c1F] |
| 402 | 1-fluoro-N-((6S,7S)-5-(3-methoxyazetidine-1-carbonyl)-6-((2,3',5'-trifluoro-[1,1'-biphenyl]-3-yl)methyl)-5-azaspiro[2.4]heptan-7-yl)methanesulfonamide | 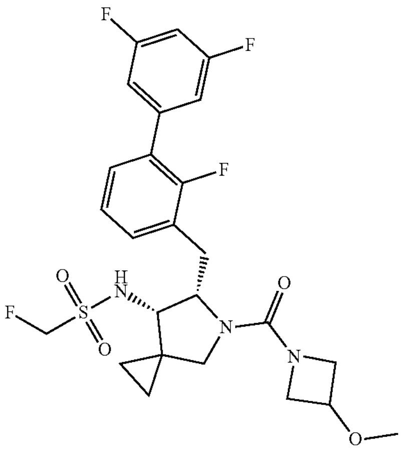 [SMILES: COC1CN(C(=O)N2CC3(CC3)[C@H](NS(=O)(=O)CF)[C@@H]2Cc2cccc(-c3cc(F)cc(F)c3)c2F)C1] |

TABLE 4-continued

| Compound No. | Name | Structure |
|---|---|---|
| 403 | N-((6S,7S)-5-(1-cyanocyclobutane-1-carbonyl)-6-((2-fluoro-[1,l'-bipheny]]-3-yl)methyl)-5-azaspiro[2.4]heptan-7-yl)-1,1-difluoromethanesulfonamide | 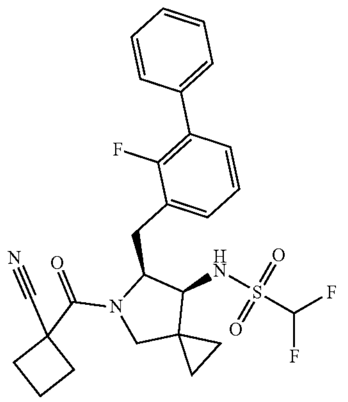 [SMILES: N#CC1(C(=O)N2CC3(CC3)[C@H](NS(=O)(=O)C(F)F)[C@@H]2Cc2cccc(-c3ccccc3)c2F)CCC1] |
| 404 | N-((6S,7S)-6-((2,5-difluoro-[1,1'-biphenyl]-3-yl)methyl)-5-(1-methoxycyclopropane-1-carbonyl)-5-azaspiro[2.4]heptan-7-yl)-1-fluoromethanesulfonamide | 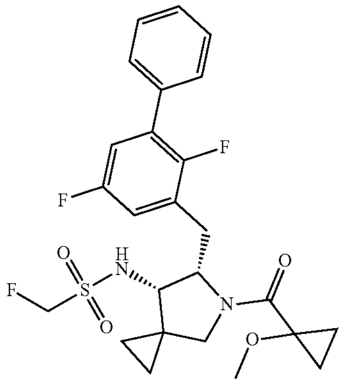 [SMILES: COC1(C(=O)N2CC3(CC3)[C@H](NS(=O)(=O)CF)[C@@H]2Cc2cc(F)cc(-c3ccccc3)c2F)CC1] |
| 405 | N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)cyclopropanesulfonamide | 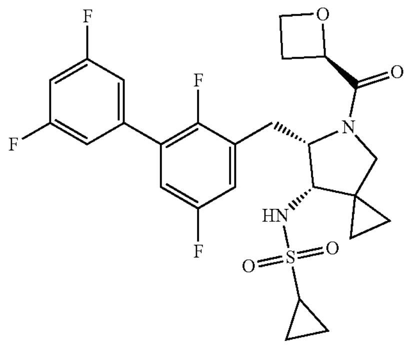 [SMILES: O=C([C@H]1CCO1)N1CC2(CC2)[C@H](NS(=O)(=O)C2CC2)[C@@H]1Cc1cc(F)cc(-c2cc(F)cc(F)c2)c1F] |
| 406 | 1,1-difluoro-N-((6S,7S)-5-((R)-2-fluoropropanoyl)-6-((2,3',5,5'-tetrafluoro-[1,1'-biphenyl]-3-yl)methyl)-5-azaspiro[2.4]heptan-7-yl)methanesulfonamide | 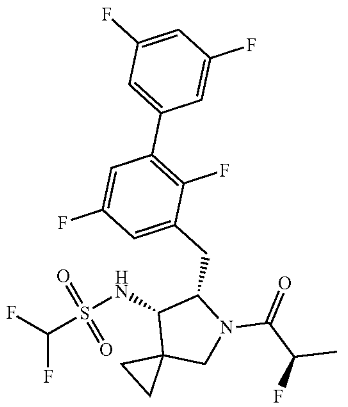 [SMILES: C[C@@H](F)C(=O)N1CC2(CC2)[C@H](NS(=O)(=O)C(F)F)[C@@H]1Cc1cc(F)cc(-c2cc(F)cc(F)c2)c1F] |

TABLE 4-continued

| Compound No. | Name | Structure |
|---|---|---|
| 407 | N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)ethanesulfonamide | 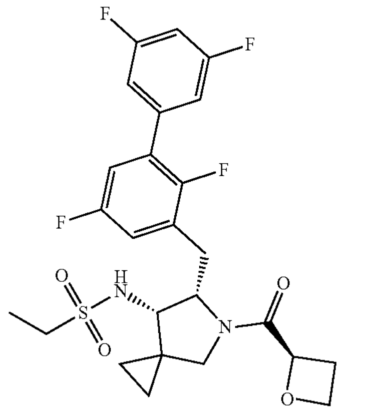 [SMILES: CCS(=O)(=O)N[C@@H]1[C@H](Cc2cc(F)cc(-c3cc(F)cc(F)c3)c2F)N(C(=O)[C@H]2CCO2)CC12CC2] |
| 408 | N-((6S,7S)-5-((S)-2-cyanooxetane-2-carbonyl)-6-((2-fluoro-[1,1'-biphenyl]-3-yl)methyl)-5-azaspiro[2.4]heptan-7-yl)-1,1-difluoromethanesulfonamide | 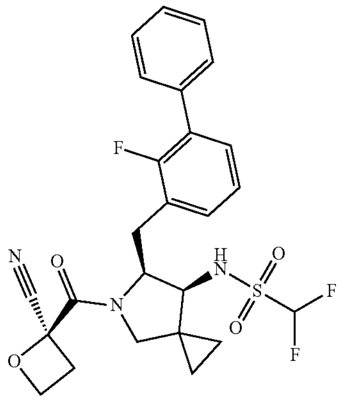 [SMILES: N#C[C@]1(C(=O)N2CC3(CC3)[C@H](NS(=O)(=O)C(F)F)[C@@H]2Cc2cccc(-c3ccccc3)c2F)CCO1] |
| 409 | (6S,7S)-N-(2,2-difluoropropyl)-6-((2-fluoro-[1,1'-bipheny]]-3-yl)methyl)-7-((fluoromethyl)sulfonamido)-5-azaspiro[2.4]heptane-5-carboxamide | 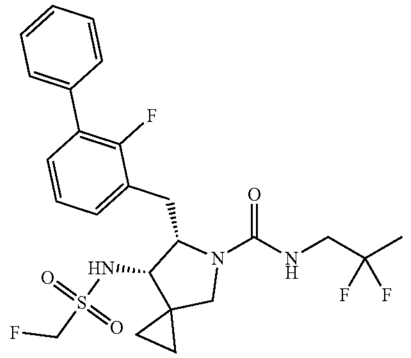 [SMILES: CC(F)(F)CNC(=O)N1CC2(CC2)[C@H](NS(=O)(=O)CF)[C@@H]1Cc1cccc(-c2ccccc2)c1F] |
| 410 | (6S,7S)-N-(2-fluoro-2-methylpropyl)-6-((2-fluoro-[1,1'-biphenyl]-3-yl)methyl)-7-((fluoromethyl)sulfonamido)-5-azaspiro[2.4]heptane-5-carboxamide | 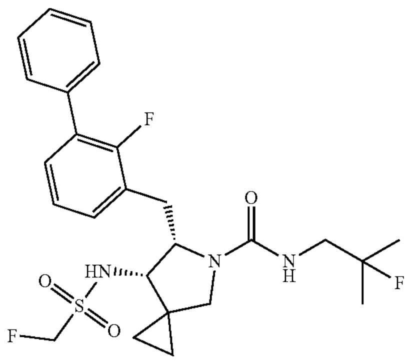 [SMILES: CC(C)(F)CNC(=O)N1CC2(CC2)[C@H](NS(=O)(=O)CF)[C@@H]1Cc1cccc(-c2ccccc2)c1F] |

TABLE 4-continued

| Compound No. | Name | Structure |
|---|---|---|
| 411 | (6S,7S)-N-(2,2-difluoroethyl)-7-((fluoromethyl)sulfonamido)-6-(2,3,5'-trifluoro-[1,1'-biphenyl]-3-yl)methyl)-5-azaspiro[2.4]heptane-5-carboxamide | 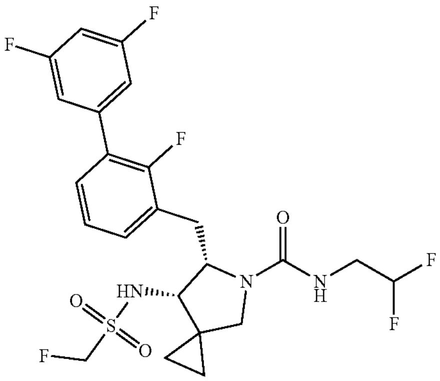 [SMILES: O=C(NCC(F)F)N1CC2(CC2)[C@H](NS(=O)(=O)CF)[C@@H]1Cc1cccc(-c2cc(F)cc(F)c2)c1F] |
| 412 | (6S,7S)-N-((1-fluorocyclopropyl)methyl)-7-((fluoromethyl)sulfonamido)-6-((2,3',5'-trifluoro-[1,1'-biphenyl]-3-yl)methyl)-5-azaspiro[2.4]heptane-5-carboxamide | 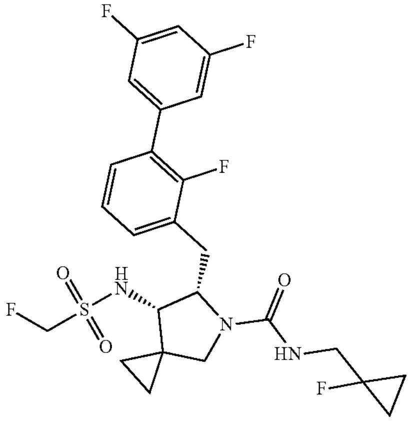 [SMILES: O=C(NCC1(F)CC1)N1CC2(CC2)[C@H](NS(=O)(=O)CF)[C@@H]1Cc1cccc(-c2cc(F)cc(F)c2)c1F] |
| 413 | N-((6S,7S)-5-(1-cyanocyclobutane-1-carbonyl)-6-((2,5-difluoro-[1,1'-biphenyl]-3-yl)methyl)-5-azaspiro[2.4]heptan-7-yl)-1-fluoromethanesulfonamide | 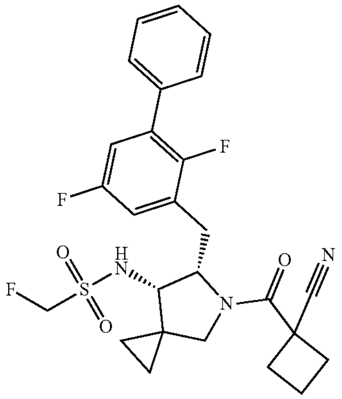 [SMILES: N#CC1(C(=O)N2CC3(CC3)[C@H](NS(=O)(=O)CF)[C@@H]2Cc2cc(F)cc(-c3ccccc3)c2F)CCC1] |
| 414 | 1-fluoro-N-((6S,7S)-5-((R)-2-fluoropropanoyl)-6-((2,3',5,5'-tetrafluoro-[1,1'-biphenyl]-3-yl)methyl)-5-azaspiro[2.4]heptan-7-yl)methanesulfonamide | 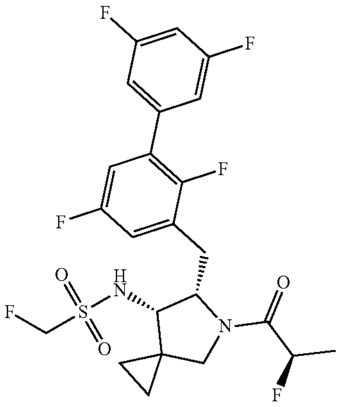 [SMILES: C[C@@H](F)C(=O)N1CC2(CC2)[C@H](NS(=O)(=O)CF)[C@@H]1Cc1cc(F)cc(-c2cc(F)cc(F)c2)c1F] |

TABLE 4-continued

| Compound No. | Name | Structure |
|---|---|---|
| 415 | (6S,7S)-N-((1-fluorocyclopropyl)methyl)-7-((fluoromethyl)sulfonamido)-6-((2,3',5,5'-tetrafluoro-[1,1'-biphenyl]-3-yl)methyl)-5-azaspiro[2.4]heptane-5-carboxamide | 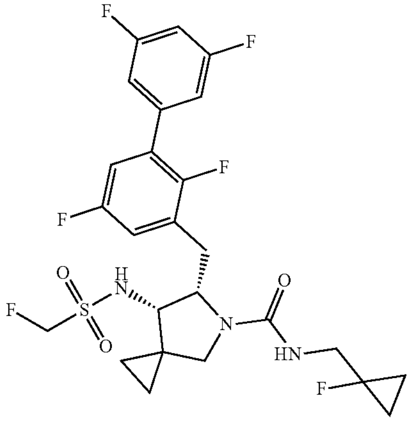 [SMILES: O=C(NCC1(F)CC1)N1CC2(CC2)[C@H](NS(=O)(=O)CF)[C@@H]1Cc1cc(F)cc(-c2cc(F)cc(F)c2)c1F] |
| 416 | (6S,7S)-7-((difluoromethyl)sulfonamido)-N-((1-fluorocyclopropyl)methyl)-6-((2,3',5,5'-tetrafluoro-[1,1'-biphenyl]-3-yl)methyl)-5-azaspiro[2.4]heptane-5-carboxamide | 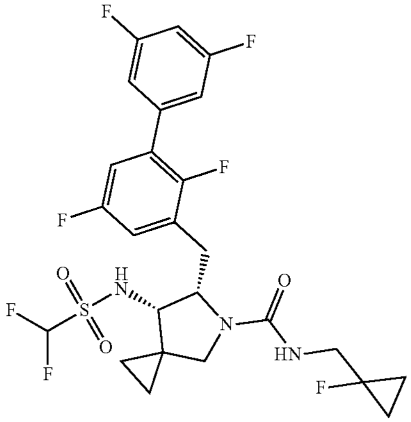 [SMILES: O=C(NCC1(F)CC1)N1CC2(CC2)[C@H](NS(=O)(=O)C(F)F)[C@@H]1Cc1cc(F)cc(-c2cc(F)cc(F)c2)c1F] |
| 417 | (6S,7S)-6-(2,5-difluoro-[1,1'-biphenyl]-3-yl)methyl)-7-((difluoromethyl)sulfonamido)-N-((1-fluorocyclopropylmethyl)-5-azaspiro[2.4]heptane-5-carboxamide | 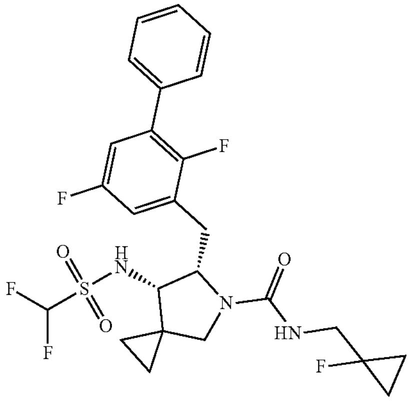 [SMILES: O=C(NCC1(F)CC1)N1CC2(CC2)[C@H](NS(=O)(=O)C(F)F)[C@@H]1Cc1cc(F)cc(-c2ccccc2)c1F] |

TABLE 4-continued

| Compound No. | Name | Structure |
|---|---|---|
| 418 | N-((6S,7S)-6-((2,5-difluoro-[1,1'-bipheny]]-3-yl)methyl)-5-((R)-2-fluoropropanoyl)-5-azaspiro[2.4]heptan-7-yl)-1-fluoromethanesulfonamide | 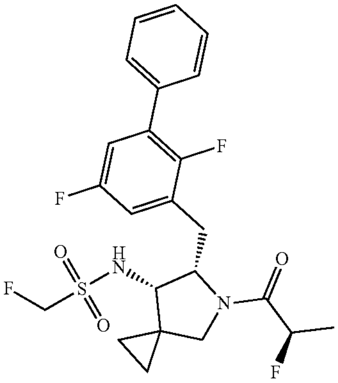 [SMILES: C[C@@H](F)C(=O)N1CC2(CC2)[C@H](NS(=O)(=O)CF)[C@@H]1Cc1cc(F)cc(-c2ccccc2)c1F] |
| 419 | 1-fluoro-N-((6S,7S)-5-(2-hydroxy-2-methylpropanoyl)-6-((2,3',5,5'-tetrafluoro-[1,1'-biphenyl]-3-yl)methyl)-5-azaspiro[2.4]heptan-7-yl)methanesulfonamide | 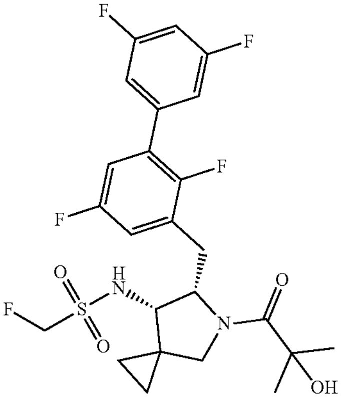 [SMILES: CC(C)(O)C(=O)N1CC2(CC2)[C@H](NS(=O)(=O)CF)[C@@H]1Cc1cc(F)cc(-c2cc(F)cc(F)c2)c1F] |
| 420 | 1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)cyclopropane-1-sulfonamide | 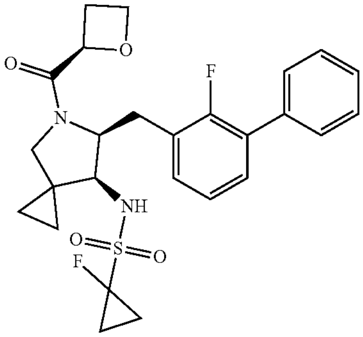 [SMILES: O=C([C@H]1CCO1)N1CC2(CC2)[C@H](NS(=O)(=O)C2(F)CC2)[C@@H]1Cc1cccc(-c2ccccc2)c1F] |

TABLE 5

| Compound No. | Name | Structure |
|---|---|---|
| 421 | 1-fluoro-N-((6S,7S)-6-((2-fluoro-[1,1'-bipheny]]-3-yl)methyl)-5-(3-methoxy-2,2-dimethylpropanoyl)-5-azaspiro[2.4]heptan-7-yl)methanesulfonamide | 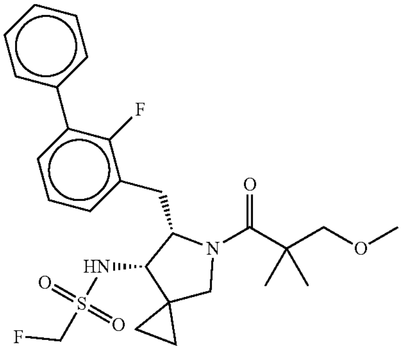 |

TABLE 5-continued

| Compound No. | Name | Structure |
| --- | --- | --- |
| 422 | N-((6S,7S)-5-((R)-2-cyclopropyl-2-hydroxyacetyl)-6-((2,3',5'-trifluoro-[1,1'-biphenyl]-3-yl)methyl)-5-azaspiro[2.4]heptan-7-y])-1-fluoromethanesulfonamide | 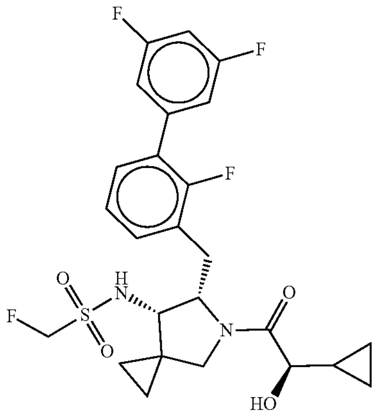 |
| 423 | 1,1-difluoro-N-((6S,7S)-5-(3-methoxyazetidine-1 -carbonyl)-6-((2,3',5'-trifluoro-[1,1'-biphenyl]-3-yl)methyl)-5-azaspiro[2.4]heptan-7-yl)methanesulfonamide | 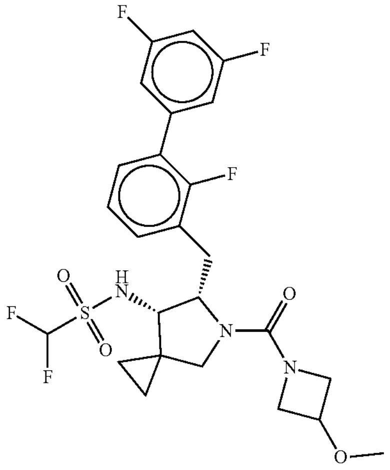 |
| 424 | (65,75)-6-(2,5-difluoro-[1,1'-biphenyl]-3-yl)methyl)-N-(2-fluoro-2-methylpropyl)-7-((fluoromethyl)sulfonamido)-5-azaspiro[2.4]heptane-5-carboxamide | 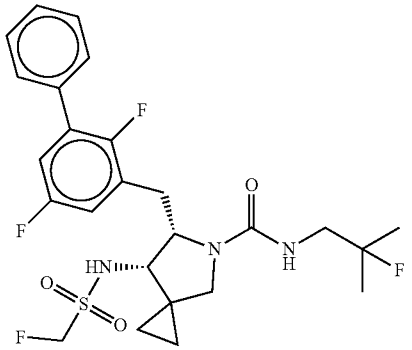 |
| 425 | 1,1-difluoro-N-((6S,7S)-5-((R)-tetrahydrofuran-2-carbonyl)-6-((2,3',5'-trifluoro-[1,1'-biphenyl]-3-yl)methyl)-5-azaspiro[2.4]heptan-7-yl)methanesulfonamide | 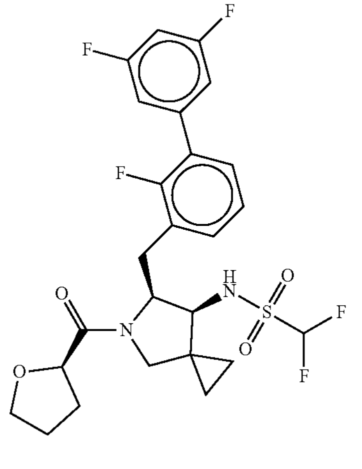 |

TABLE 5-continued

| Compound No. | Name | Structure |
|---|---|---|
| 426 | 1-fluoro-N-((6S,7S)-5-((R)-tetrahydrofuran-2-carbonyl)-6-((2,3',5'-trifluoro-[1,1'-biphenyl]-3-yl)methyl)-5-azaspiro[2.4]heptan-7-yl)methanesulfonamide | 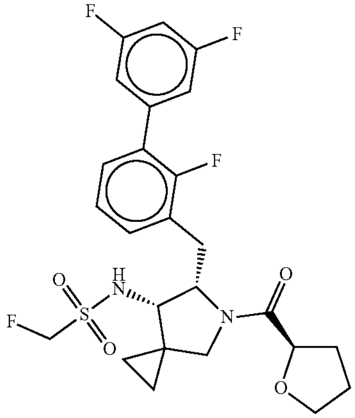 |
| 427 | 1,1-difluoro-N-((6S,7S)-5-(1-(methoxymethyl)cyclopropane-1-carbonyl)-6-((2,3',5'-trifluoro-[1,1'-biphenyl]-3-yl)methyl)-5-azaspiro[2.4]heptan-7-yl)methanesulfonamide | 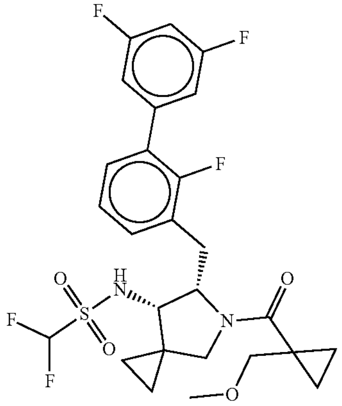 |
| 428 | 1-fluoro-N-((6S,7S)-5-(1-(methoxymethyl)cyclopropane-1-carbonyl)-6-((2,3',5'-trifluoro-[1,1'-biphenyl]-3-yl)methyl)-5-azaspiro[2.4]heptan-7-yl)methanesulfonamide | 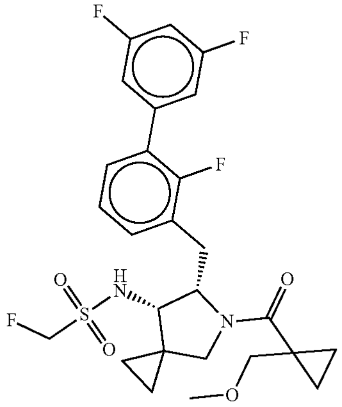 |
| 429 | 1-fluoro-N-((6S,7S)-6-((2-fluoro-[1,1'-bipheny]]-3-yl)methyl)-5-(1-(methoxymethyl)cyclopropane-1-carbonyl)-5-azaspiro[2.4]heptan-7-yl)methanesulfonamide | 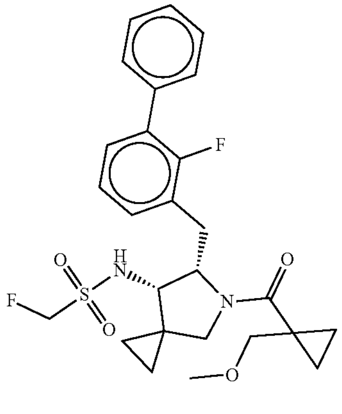 |

TABLE 5-continued

| Compound No. | Name | Structure |
| --- | --- | --- |
| 430 | (6S,7S)-N-((1-fluorocyclopropyl)methyl)-7-((2-methoxyethyl)sulfonamido)-6-((2,3',5'-trifluoro-[1,1'-bipbenyl]-3-yl)methyl)-5-azaspiro[2.4]heptane-5-carboxamide | 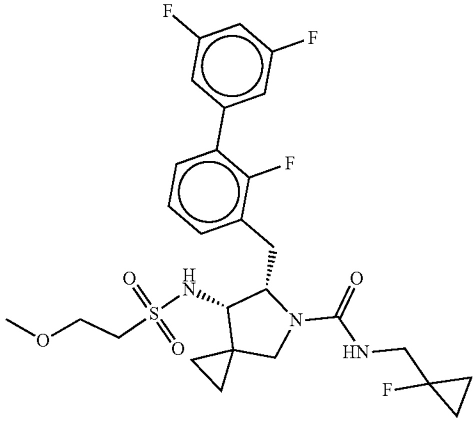 |
| 431 | N-((6S,7S)-5-(2-cyanooxetane-2-carbonyl)-6-((2-fluoro-[1,1'-biphenyl]-3-yl)methyl)-5-azaspiro[2.4]heptan-7-yl)-2-methoxyethane-1-sulfonamide | 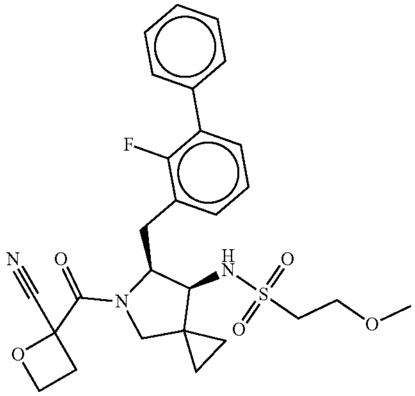 |
| 432 | N-((6S,7S)-5-(2-cyanotetrahydrofuran-2-carbonyl)-6-((2-fluoro-[1,1'-bipbenyl]-3-yl)methyl)-5-azaspiro[2.4]heptan-7-y])-1-fluoromethanesulfonamide | 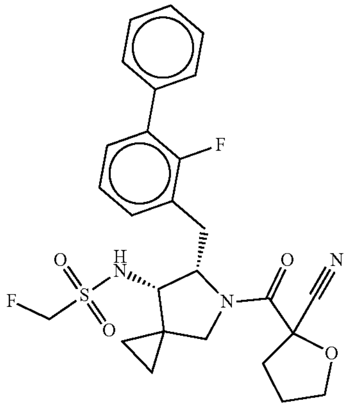 |
| 433 | N-(65,75)-5-(2-cyanopropanoyl)-6-((2,3',5'-trifluoro-[1,1'-bipheny]]-3-yl)methyl)-5-azaspiro[2.4]heptan-7-y])-1,1-difluoromethanesulfonamide | 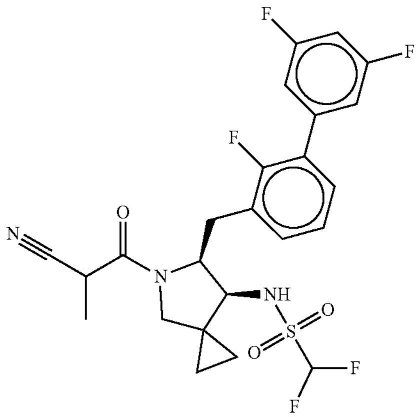 |

TABLE 5-continued

| Compound No. | Name | Structure |
|---|---|---|
| 434 | N-(65,75)-5-(2-cyanopropanoyl)-6-((2,3',5'-trifluoro-[1, 1'-bipheny]]-3-yl)methyl)-5-azaspiro[2.4]heptan-7-yl)-1-fluoromethanesulfonamide | 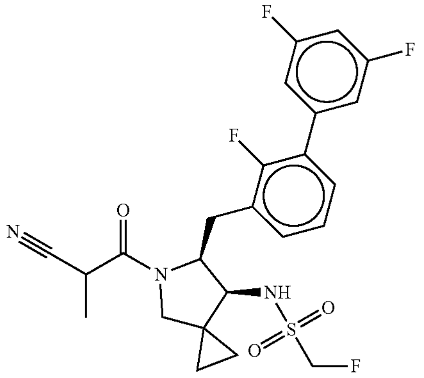 |
| 435 | N-((6S,7S)-5-(2-cyanopropanoyl)-6-((2-fluoro-[1,1'-bipheny]]-3-yl)methyl)-5-azaspiro[2.4]heptan-7-y])-1,1-difluoromethanesulfonamide | 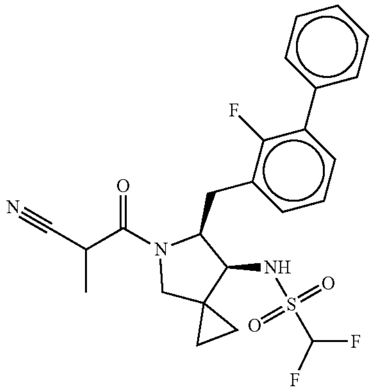 |
| 436 | N-((6S,7S)-5-(2-cyanopropanoyl)-6-((2-fluoro-[1,1'-bipheny]]-3-yl)methyl)-5.azaspiro[2.4]heptan-7-yl)-1-fluoromethanesulfonamide | 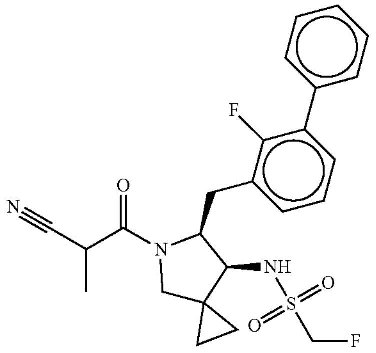 |
| 437 | (68,7S)-7-((difluoromethyl)sulfonamido)-N-((R)-1-fluoropropan-2-yl)-6-((2,3',5'-trifluoro-[1,1'-biphenyl]-3-yl)methyl)-5-azaspiro[2.4]heptane-5-carboxamide | 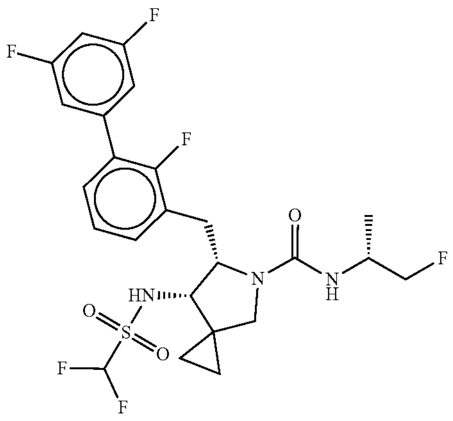 |

TABLE 5-continued

| Compound No. | Name | Structure |
|---|---|---|
| 438 | (6S,7S)-7-((fluoromethyl)sulfonamido)-N-((R)-1-fluoropropan-2-yl)-6-biphenyl[-3-yl)methyl)-5-azaspiro[2.4]heptane-5-carboxamide | 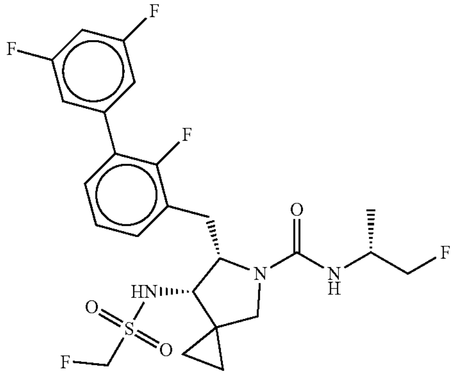 |
| 439 | (6S,7S)-N-(1,1-difluoro-2-methylpropan-2-yl)-6-((2-fluoro-[1,1'-biphenyl]-3-yl)methyl)-7-((fluoromethyl)sulfonamido)-5-azaspiro[2.4]heptane-5-carboxamide | 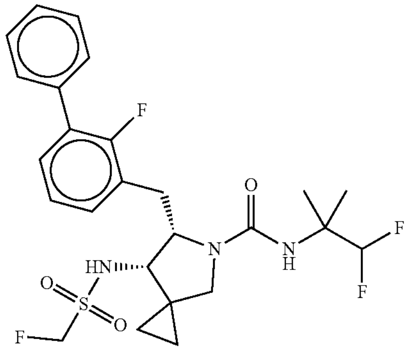 |
| 440 | N-((6S,7S)-5-(3,3-difluoro-2-hydroxy-2-methylpropanoyl)-6-((2,3',5'-trifluoro-[1,1'-biphenyl]-3-yl)methyl)-5-azaspiro[2.4]heptan-7-yl)-1,1-difluoromethanesulfonamide | 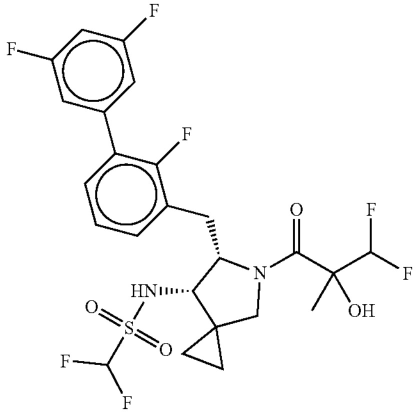 |
| 441 | N-((6S,7S)-5-(3,3-difluoro-2-hydroxy-2-methylpropanoyl)-6-((2,3',5'-trifluoro-[1,1'-biphenyl]-3-yl)methyl)-5-azaspiro[2.4]heptan-7-y])-1-fluoromethanesulfonamide | 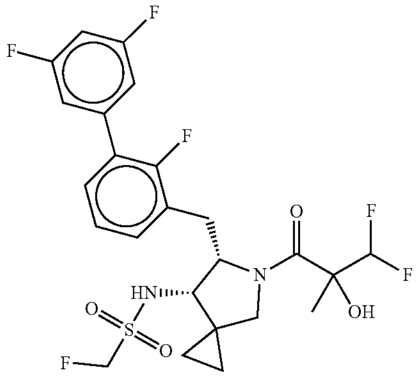 |

TABLE 5-continued

| Compound No. | Name | Structure |
| --- | --- | --- |
| 442 | N-((6S,7S)-5-(3,3-difluoro-2-hydroxy-2-methylpropanoyl)-6-(2-fluoro-[1,1-bipheny]-3-yl)methyl)-5-azaspiro[2.4]heptan-7-yl)-1,1-difluoromethanesulfonamide | 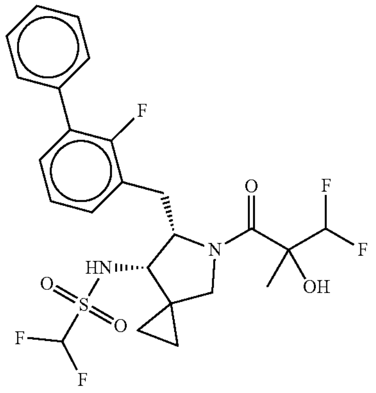 |
| 443 | 1,1-difluoro-N-((6S,7S)-5-(2-fluoro-3-methoxypropanoyl)-6-((2,3',5'-trifluoro-[1,1'-biphenyl]-3-yl)methyl)-5-azaspiro[2.4]heptan-7-yl)methanesulfonamide | 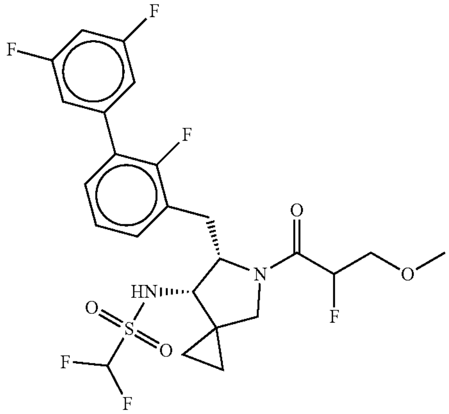 |
| 444 | 1-fluoro-N-((6S,7S)-5-(2-fluoro-3-methoxypropanoyl)-6-((2,3',5'-trifluoro-[1,1'-biphenyl]-3-yl)methyl)-5-azaspiro[2.4]heptan-7-yl)methanesulfonamide | 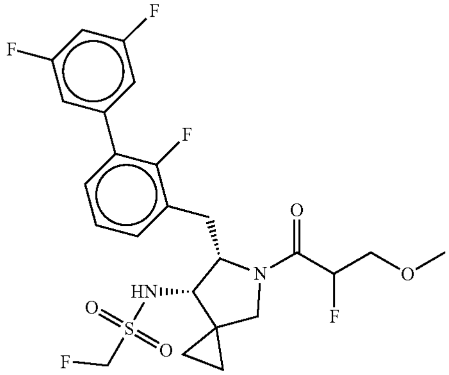 |
| 445 | (65,7S)-7-((difluoromethyl)sulfonamido)-N-((R)-1,1-difluoropropan-2-yl)-6-((2,3',5'-trifluoro-[1,1'-biphenyl]-3-yl)methyl)-5-azaspiro[2.4]heptane-5-carboxamide | 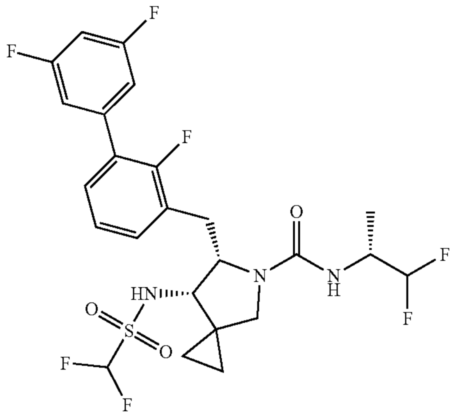 [SMILES: C[C@@H](NC(=O)N1CC2(CC2)[C@H](NS(=O)(=O)C(F)F)[C@@H]1Cc1cccc(-c2cc(F)cc(F)c2)c1F)C(F)F] |

TABLE 5-continued

| Compound No. | Name | Structure |
| --- | --- | --- |
| 446 | (6S,7S)-7-((fluoromethyl)sulfonamido)-N-((R)-1,1-difluoropropan-2-yl)-6-((2,3',5'-trifluoro-[1,1'-biphenyl]-3-yl)methyl)-5-azaspiro[2.4]heptane-5-carboxamide | 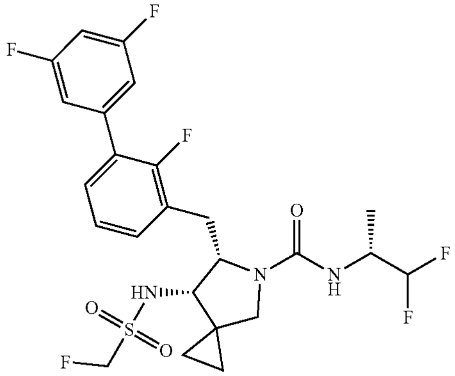 [SMILES: C[C@@H](NC(=O)N1CC2(CC2)[C@H](NS(=O)(=O)CF)[C@@H]1Cc1cccc(-c2cc(F)cc(F)c2)c1F)C(F)F] |
| 447 | N-((6S,7S)-5-(2-cyanooxetane-2-carbonyl)-6-((2,3',5'.trifluoro-[1,1'-biphenyl]-3-yl)methyl)-5-azaspiro[2.4]heptan-7-y])-1,1-difluoromethanesulfonamide | 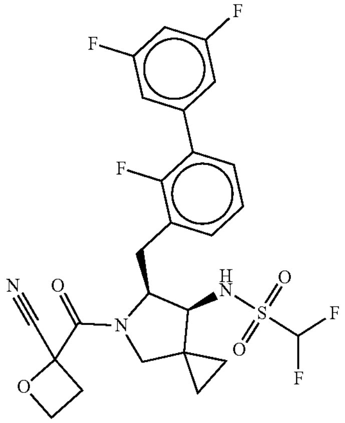 |
| 448 | N-((6S,7S)-5-(2-cyanooxetane-2-carbonyl)-6-((2,3'-difluoro-[1,1'-biphenyl]-3-yl)methyl)-5-azaspiro[2.4]heptan-7-yl)-1,1-difluoromethanesulfonamide | 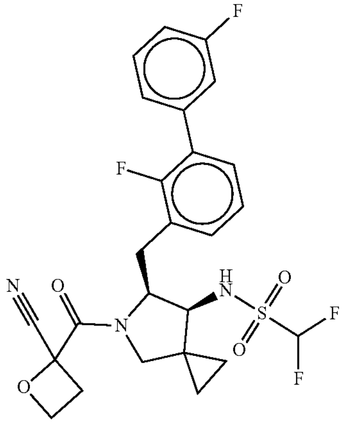 |
| 449 | N-((6S,7S)-5-(2-cyanooxetane-2-carbonyl)-6-((2,3',5'-trifluoro-[1,1'-biphenyl]-3-yl)methyl)-5-azaspiro[2.4]heptan-7-yl)-1-fluoromethanesulfonamide | 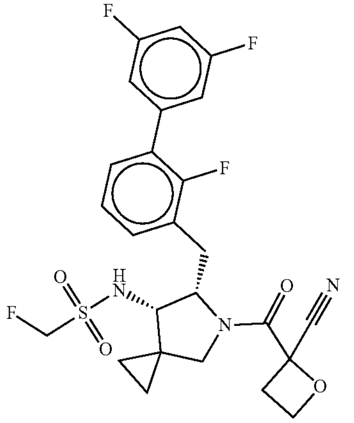 |

TABLE 5-continued

| Compound No. | Name | Structure |
|---|---|---|
| 450 | N-((6S,7S)-5-(2-cyanooxetane-2-carbonyl)-6-((2,3'-difluoro-[1,1'-bipheny]]-3-yl)methyl)-5-azaspiro[2.4]heptan-7-y])-1-fluoromethanesulfonamide | 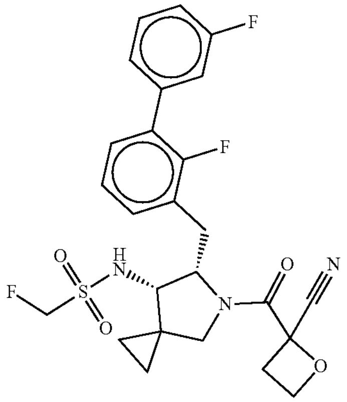 |
| 451 | N-((6S,7S)-5-(1-cyanocyclopropane-1-carbonyl)-6-((2-fluoro-[1,1'-biphenyl]-3-yl)methyl)-5 -. azaspiro[2.4]heptan-7-yl)-1-fluoromethanesulfonamide | 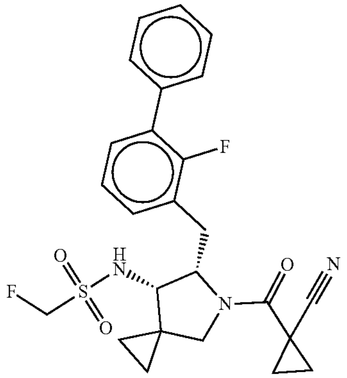 |
| 452 | N-(65,75)-5-((R)-oxetane-2-carbonyl)-6-((2-fluoro-[1,1'-biphenyl]-3-yl)methyl)-5-azaspiro[2.4]heptan-7-yl)-3-methoxycyclobutylsulfonamide | 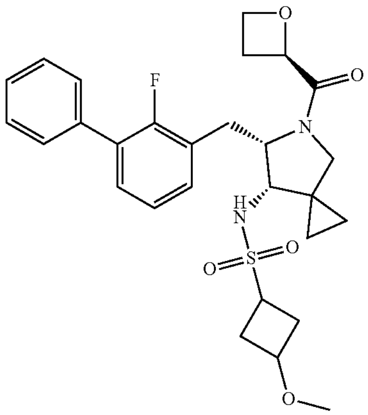 [SMILES: COC1CC(S(=O)(=O)N[C@@H]2[C@H](Cc3cccc(-c4ccccc4)c3F)N(C(=O)[C@H]3CCO3)CC23CC3)C1] |
| 453 | N-((6S,7S)-6-((2,5-difluoro-[1,1'-bipheny]]-3-yl)methyl)-5-(3-methoxyazetidine-1-carbonyl)-5-azaspiro[2.4]heptan-7-y])-1-fluoromethanesulfonamide | 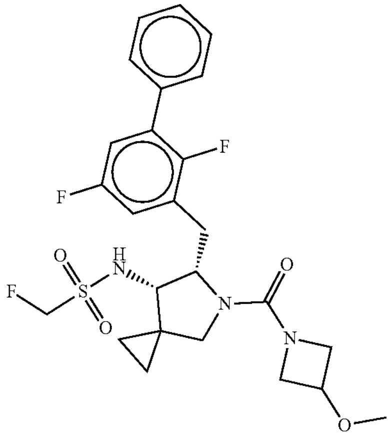 |

TABLE 5-continued

| Compound No. | Name | Structure |
|---|---|---|
| 454 | N-((6S,7S)-5-((R)-oxetane-2-carbonyl)-6-((2,5,3',5'-tetrafluoro-[1,1'-biphenyl]-3-yl)methyl)-5-azaspiro[2.4]heptan-7-y])-1-fluoroethylsulfonamide | 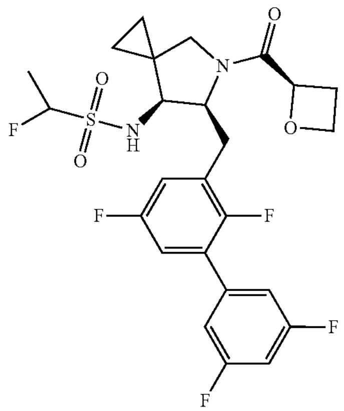 [SMILES: CC(F)S(=O)(=O)N[C@@H]1[C@H](Cc2cc(F)cc(-c3cc(F)cc(F)c3)c2F)N(C(=O)[C@H]2CCO2)CC12CC2] |
| 455 | N-((6S,7S)-5-((R)-oxetane-2-carbonyl)-6-((2,5-difluoro-[1,1'-bipheny]]-3-yl)methyl)-5-azaspiro[2.4]heptan-7-yl)-1-fluoroethylsulfonamide | 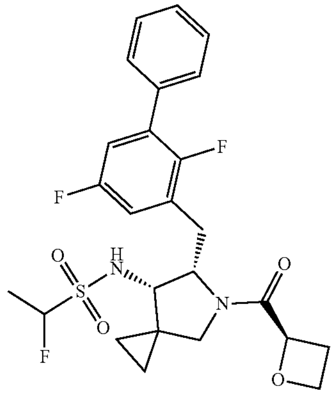 [SMILES: CC(F)S(=O)(=O)N[C@@H]1[C@H](Cc2cc(F)cc(-c3ccccc3)c2F)N(C(=O)[C@H]2CCO2)CC12CC2] |
| 456 | N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)-1-fluoroethylsulfonamide | 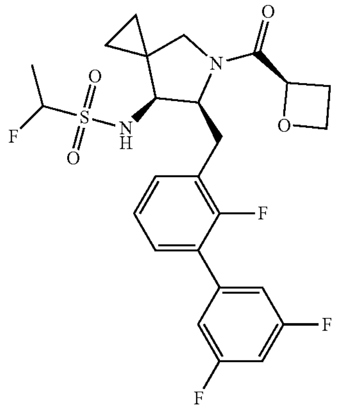 [SMILES: CC(F)S(=O)(=O)N[C@@H]1[C@H](Cc2cccc(-c3cc(F)cc(F)c3)c2F)N(C(=O)[C@H]2CCO2)CC12CC2] |
| 457 | N-((6S,7S)-5-(2-(difluoromethyl)-3,3-difluoro-2-hydroxypropanoyl)-6-((2-fluoro-[1,1'-bipheny]]-3-yl)methyl)-5-azaspiro[2.4]heptan-7-y])-1-fluoromethanesulfonamide | 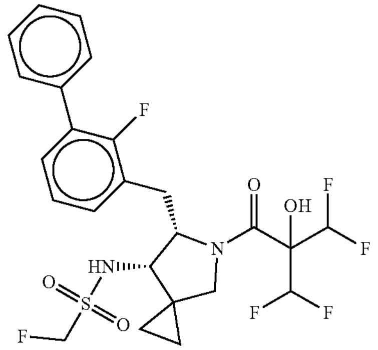 |

TABLE 5-continued

| Compound No. | Name | Structure |
|---|---|---|
| 458 | 1-fluoro-N-((6S,7S)-5-(2-fluoro-3-methoxy-2-methylpropanoyl)-6-((2-fluoro-[1,1'-biphenyl]-3-yl)methyl)-5-azaspiro[2.4]heptan-7-yl)methanesulfonamide | 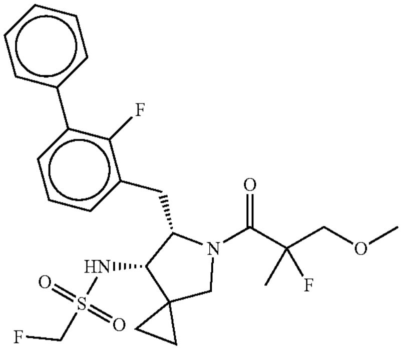 |
| 459 | N-(65,75)-5-(2-(difluoromethyl)-3,3-difluoropropanoyl)-6-((2-fluoro-[1,1'-bipheny]]-3-yl)methyl)-5-azaspiro[2.4]heptan-7-y])-1-fluoromethanesulfonamide | 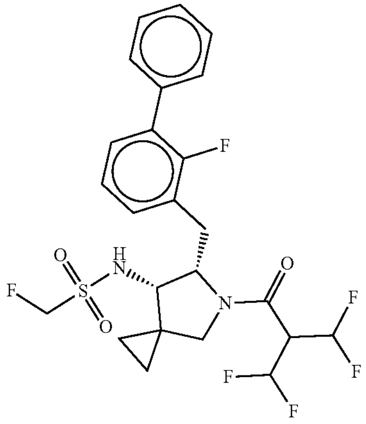 |
| 460 | N-((6S,7S)-6-((2-fluoro-[1,1'-biphenyl]-3-yl)methyl)-5-((R)-2-oxooxazolidine-4-carbonyl)-5-azaspiro[2.4]heptan-7-yl)methanesulfonamide | 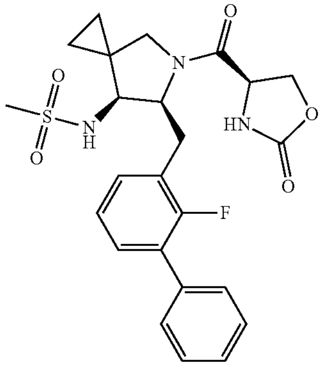 [SMILES: CS(=O)(=O)N[C@@H]1[C@H](Cc2cccc(-c3ccccc3)c2F)N(C(=O)[C@H]2COC(=O)N2)CC12CC2] |
| 461 | N-((6S,7S)-5-((S)-2-cyclopropyl-2-methoxyacetyl)-6-((2-fluoro-[1,1'-bipheny]]-3-yl)methyl)-5-azaspiro[2.4]heptan-7-yl)methanesulfonamide | 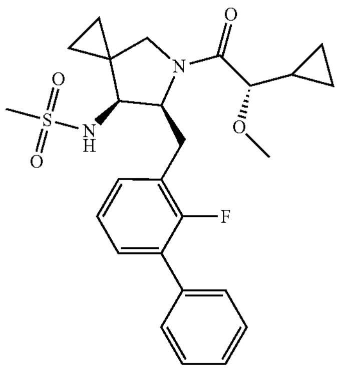 [SMILES: CO[C@H](C(=O)N1CC2(CC2)[C@H](NS(C)(=O)=O)[C@@H]1Cc1cccc(-c2ccccc2)c1F)C1CC1] |

TABLE 5-continued

| Compound No. | Name | Structure |
| --- | --- | --- |
| 462 | N-((65,7S)-5-((S)-2-cyclobutyl-2-hydroxyacetyl)-6-((2-fluoro-[1, 1'-biphenyl]-3-yl)methyl)-5-azaspiro[2.4]heptan-7-yl)methanesulfonamide | 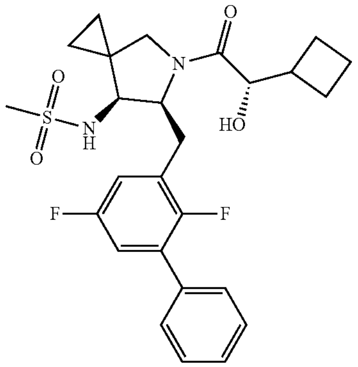 [SMILES: CS(=O)(=O)N[C@@H]1[C@H](Cc2cc(F)cc(-c3ccccc3)c2F)N(C(=O)[C@@H](O)C2CCC2)CC12CC2] |
| 463 | N-((6S,7S)-5-((R)-2-cyclobutyl-2-hydroxyacetyl)-6-((2-fluoro-[1,1'-bipheny]]-3-yl)methyl)-5-azaspiro[2.4]heptan-7-yl)methanesulfonamide | 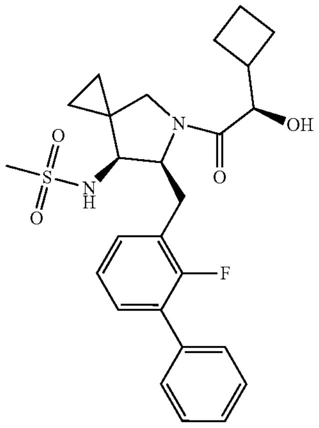 [SMILES: CS(=O)(=O)N[C@@H]1[C@H](Cc2cccc(-c3ccccc3)c2F)N(C(=O)[C@H](O)C2CCC2)CC12CC2] |
| 464 | N-((6S,7S)-5-((S)-2-ethoxypropanoyl)-6-((2-fluoro-[1,1'-bipheny]]-3-yl)methyl)-5-azaspiro[2.4]heptan-7-yl)methanesulfonamide | 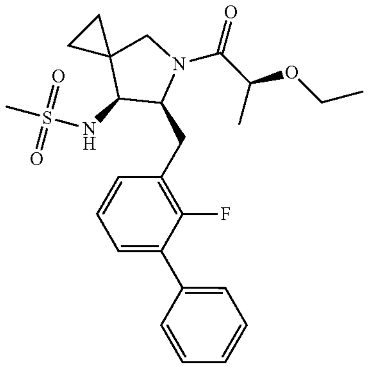 [SMILES: CCO[C@@H](C)C(=O)N1CC2(CC2)[C@H](NS(C)(=O)=O)[C@@H]1Cc1cccc(-c2ccccc2)c1F] |
| 465 | N-((6S,7S)-6-((2-fluoro-[1,1'-biphenyl]-3-yl)methyl)-5-((S)-3-methoxy-2-methylpropanoyl)-5-azaspiro[2.4]heptan-7-yl)methanesulfonamide | 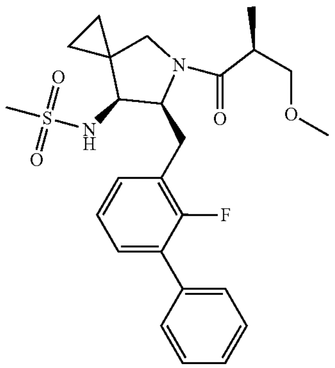 |

TABLE 5-continued

| Compound No. | Name | Structure |
| --- | --- | --- |
| 466 | N-((6S,7S)-6-((2-fluoro-[1,1'-biphenyl]-3-yl)methyl)-5-((S)-3-methoxy-2-methylpropanoyl)-5-azaspiro[2.4]heptan-7-yl)methanesulfonamide | 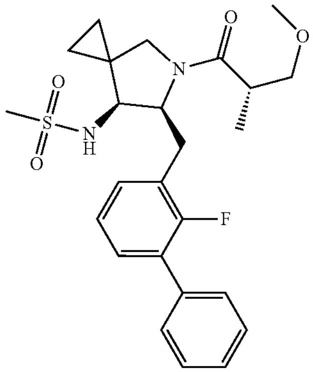 [SMILES: COC[C@H](C)C(=O)N1CC2(CC2)[C@H](NS(C)(=O)=O)[C@@H]1Cc1cccc(-c2ccccc2)c1F] |
| 467 | 1,1-difluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethane-1-sulfonamide | 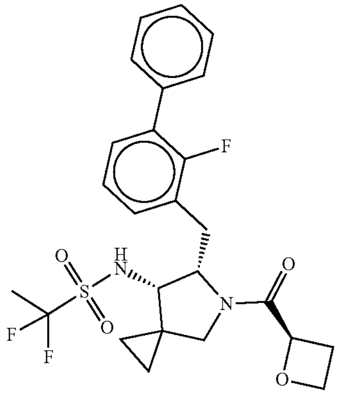 |
| 468 | 1-fluoro-N-((6S,7S)-6-((2-fluoro-[1,1'-biphenyl]-3-yl)methyl)-5-((R)-oxetane-2-carbonyl)-5-azaspiro[2.4]heptan-7-y]-1,1,2,2-d4)methanesulfonamide | 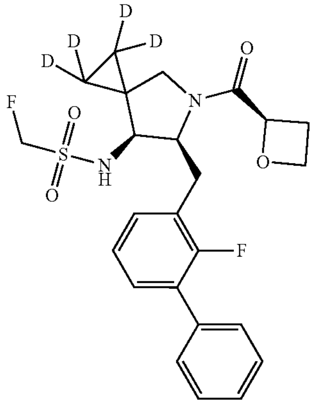 [SMILES: [2H]C1([2H])C([2H])([2H])C12CN(C(=O)[C@H]1CCO1)[C@@H](Cc1cccc(-c3ccccc3)c1F)[C@H]2NS(=O)(=O)CF] |
| 469 | 1,1-difluoro-N-((6S,7S)-5-((R)-oxetane-2-carbonyl-4,4-d2)-6-((2,3',5'-trifluoro-[1,1'-biphenyl]-3-yl)methyl)-5-azaspiro[2.4]heptan-7-yl)methanesulfonamide | 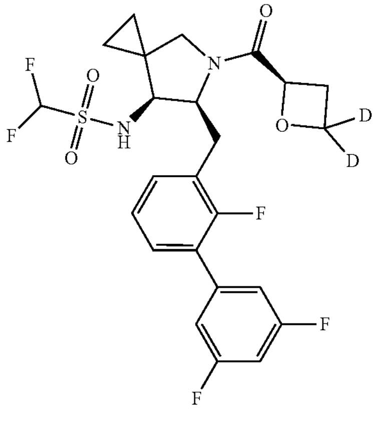 [SMILES: [2H]C1([2H])C[C@H](C(=O)N2CC3(CC3)[C@H](NS(=O)(=O)C(F)F)[C@@H]2Cc2cccc(-c3cc(F)cc(F)c3)c2F)O1] |

TABLE 5-continued

| Compound No. | Name | Structure |
| --- | --- | --- |
| 470 | (R)-2-cyano-N-((6S,7S)-6-((2-fluoro-[1,1'-bipheny]]-3-yl)methyl)-5-((R)-oxetane-2-carbonyl)-5-azaspiro[2.4]heptan-7-yl)propane-1-sulfonamide | 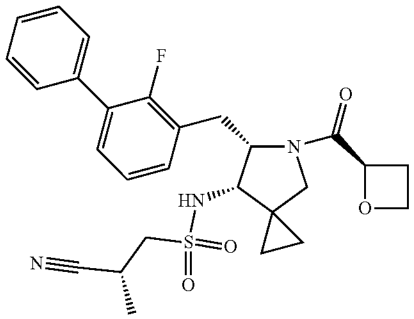 [SMILES: C[C@H](C#N)CS(=O)(=O)N[C@@H]1[C@H](Cc2cccc(-c3ccccc3)c2F)N(C(=O)[C@H]2CCO2)CC12CC2] |
| 471 | N-((6S,7S)-6-((2-fluoro-[1,1'-biphenyl]-3-yl)methyl)-5-(2-((S)-oxetan-2-yl)acetyl)-5-azaspiro[2.4]heptan-7-yl)methanesulfonamide | 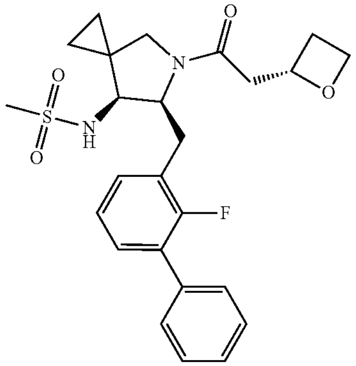 [SMILES: CS(=O)(=O)N[C@@H]1[C@H](Cc2cccc(-c3ccccc3)c2F)N(C(=O)C[C@@H]2CCO2)CC12CC2] |
| 472 | N-((6S,7S)-6-((2-fluoro-[1,1'-biphenyl]-3-yl)methyl)-5-(2-((R)-oxetan-2-yl)acetyl)-5-azaspiro[2.4]heptan-7-yl)methanesulfonamide | 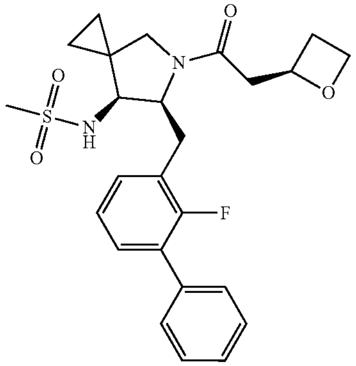 [SMILES: CS(=O)(=O)N[C@@H]1[C@H](Cc2cccc(-c3ccccc3)c2F)N(C(=O)C[C@H]2CCO2)CC12CC2] |
| 473 | 2,2,2-trifluoro-N-((6S,7S)-6-((2-fluoro-[1, 1'-biphenyl]-3-yl)methyl)-5-(oxetane-2-carbonyl)-5-azaspiro[2.4]heptan-7-yl)ethane-1-sulfonamide | 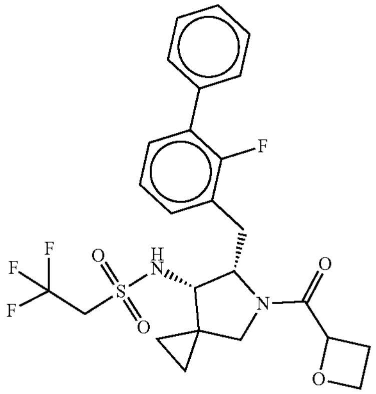 |

TABLE 5-continued

| Compound No. | Name | Structure |
|---|---|---|
| 474 | (6S,7S)-7-((difluoromethyl)sulfonamido)-N-(2,2-difluoropropyl)-6-((2,3',5'-trifluoro-[1,1'-biphenyl]-3-yl)methyl)-5-azaspiro[2.4]heptane-5-carboxamide | 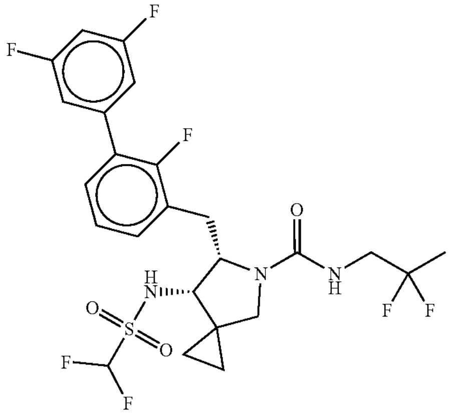 |
| 475 | (6S,7S)-N-(2,2-difluoropropyl)-7-((fluoromethyl)sulfonamido)-6-((2,3',5'-trifluoro-[1,1'-biphenyl]-3-yl)methyl)-5-azaspiro[2.4]heptane-5-carboxamide | 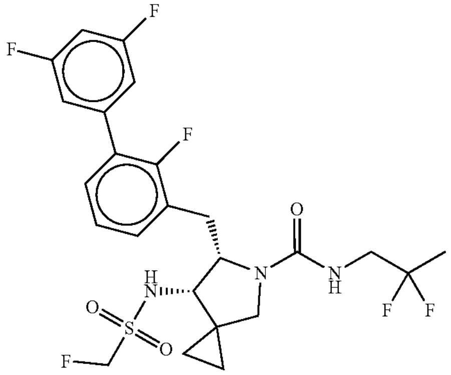 |
| 476 | (6S,7S)-N-(2-fluoro-2-methylpropyl)-7-((fluoromethyl)sulfonamido)-6-((2,3',5'-trifluoro-[1,1'-biphenyl]-3-yl)methyl)-5-azaspiro[2.4]heptane-5-carboxamide | 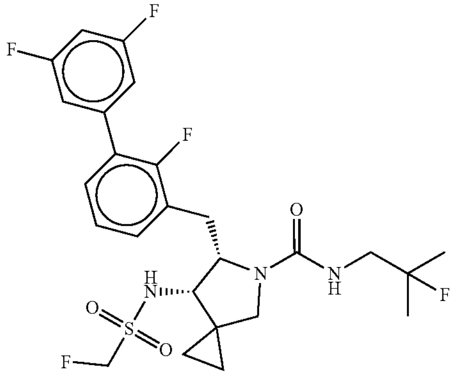 |
| 477 | (6S,7S)-7-((difluoromethyl)sulfonamido)-N-(2-fluoro-2-methylpropyl)-6-((2,3',5'-trifluoro-[1,1'-biphenyl]-3-yl)methyl)-5-azaspiro[2.4]heptane-5-carboxamide | 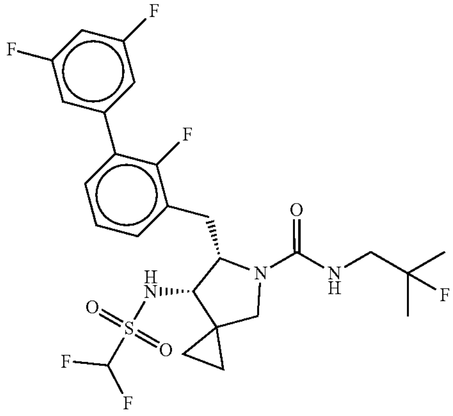 |

TABLE 5-continued

| Compound No. | Name | Structure |
| --- | --- | --- |
| 478 | 1-fluoro-N-((6S,7S)-5-((R)-oxetane-2-carbonyl)-6-((2,3',5'-trifluoro-[1,1'-bipheny]]-3-yl)methyl)-5-azaspiro[2.4]heptan-7-yl)cyclopropane-1-sulfonamide | 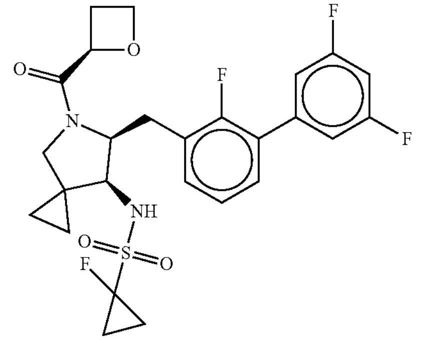 |
| 479 | N-((6S,7S)-5-((S)-3,3-difluoro-2-hydroxy-2-methylpropanoyl)-6-(2,3'-difluoro-[1,1'-biphenyl]-3-yl)methyl)-5-azaspiro[2.4]heptan-7-y])-1-fluoromethanesulfonamide | 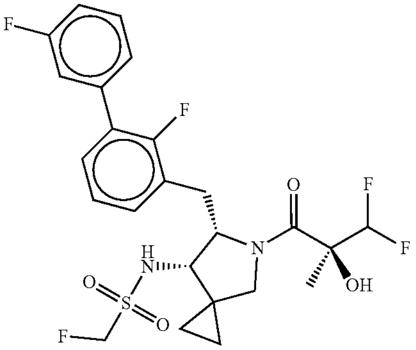 |
| 480 | N-((6S,7S)-5-((S)-2-cyclopropyl-2-hydroxypropanoyl)-6-((2,3'-difluoro-[1,1'-biphenyl]-3-yl)methyl)-5-azaspiro[2.4]heptan-7-yl)-1-fluoromethanesulfonamide | 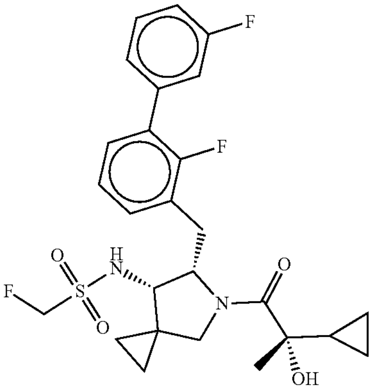 |
| 481 | N-((6S,7S)-5-((R)-2-cyclopropyl-2-hydroxypropanoyl)-6-((2,3'-difluoro-[1, l'-biphenyl]-3-yl)methyl)-5-azaspiro[2.4]heptan-7-y])-1-fluoromethanesulfonamide | 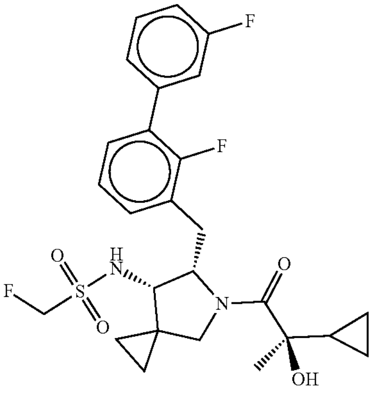 |

TABLE 5-continued

| Compound No. | Name | Structure |
|---|---|---|
| 482 | 1-fluoro-N-((6S,7S)-5-((S)-3-fluoro-2-hydroxy-2-methylpropanoyl)-6-((2-fluoro-[1,1'-biphenyl]-3-yl)methyl)-5-azaspiro[2.4]heptan-7-yl)methanesulfonamide | 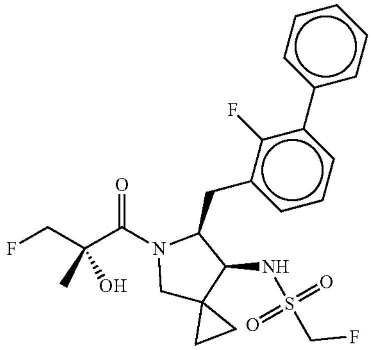 |
| 483 | 1-fluoro-N-((6S,7S)-5-((R)-3-fluoro-2-hydroxy-2-methylpropanoyl)-6-((2-fluoro-[1,1'-bipheny]]-3-yl)methyl)-5-azaspiro[2.4 ]heptan-7-yl)methanesulfonamide | 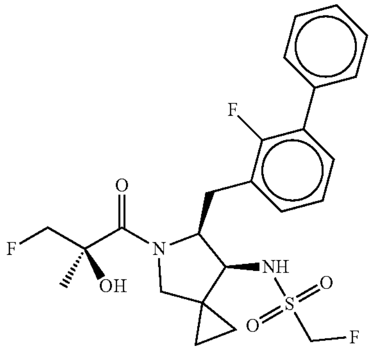 |
| 484 | N-((6S,7S)-5-(3-cyanooxetane-3-carbonyl)-6-((2-fluoro-[1,1'-biphenyl]-3-yl)methyl)-5-azaspiro[2.4]heptan-7-yl)-1-fluoromethanesulfonamide | 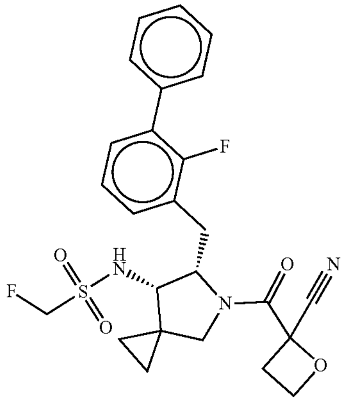 |
| 485 | 1-fluoro-N-((6S,7S)-6-((2-fluoro-[1,1'-bipheny]]-3-yl)methyl)-5-(3-fluorooxetane-3-carbonyl)-5-azaspiro[2.4]heptan-7-yl)methanesulfonamide | 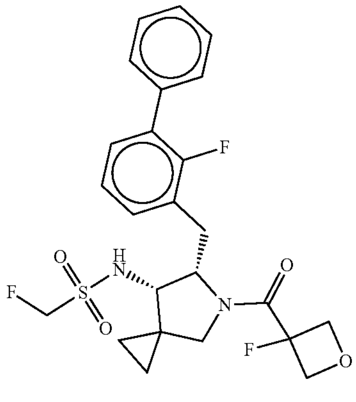 |

In some embodiments, the compound is a pharmaceutically acceptable salt of any one of the compounds described in Table 1.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of prodrugs of the compounds described in Table 1 and pharmaceutically acceptable salts thereof.

In some embodiments, the compound is an isotopic derivative of any one of the compounds described in Table 1.

In some embodiments, the compound is a pharmaceutically acceptable salt of any one of the compounds described in Table 2.

In some embodiments, the compound is an isotopic derivative of any one of the compounds described in Table 2 and prodrugs and pharmaceutically acceptable salts thereof.

In some embodiments, the compound is an isotopic derivative of any one of the compounds described in Table 2 and pharmaceutically acceptable salts thereof.

In some embodiments, the compound is an isotopic derivative of any one of prodrugs of the compounds described in Table 2 and pharmaceutically acceptable salts thereof.

In some embodiments, the compound is an isotopic derivative of any one of the compounds described in Table 2.

In some embodiments, the compound is a pharmaceutically acceptable salt of any one of the compounds described in Table 3.

In some embodiments, the compound is an isotopic derivative of any one of the compounds described in Table 3 and prodrugs and pharmaceutically acceptable salts thereof.

In some embodiments, the compound is an isotopic derivative of any one of the compounds described in Table 3 and pharmaceutically acceptable salts thereof.

In some embodiments, the compound is an isotopic derivative of any one of prodrugs of the compounds described in Table 3 and pharmaceutically acceptable salts thereof.

In some embodiments, the compound is an isotopic derivative of any one of the compounds described in Table 3.

In some embodiments, the compound is a pharmaceutically acceptable salt of any one of the compounds described in Table 4.

In some embodiments, the compound is an isotopic derivative of any one of the compounds described in Table 4 and prodrugs and pharmaceutically acceptable salts thereof.

In some embodiments, the compound is an isotopic derivative of any one of the compounds described in Table 4 and pharmaceutically acceptable salts thereof.

In some embodiments, the compound is an isotopic derivative of any one of prodrugs of the compounds described in Table 4 and pharmaceutically acceptable salts thereof.

In some embodiments, the compound is an isotopic derivative of any one of the compounds described in Table 4.

In some embodiments, the compound is a pharmaceutically acceptable salt of any one of the compounds described in Table 5.

In some embodiments, the compound is an isotopic derivative of any one of the compounds described in Table 5 and prodrugs and pharmaceutically acceptable salts thereof.

In some embodiments, the compound is an isotopic derivative of any one of the compounds described in Table 5 and pharmaceutically acceptable salts thereof.

In some embodiments, the compound is an isotopic derivative of any one of prodrugs of the compounds described in Table 5 and pharmaceutically acceptable salts thereof.

In some embodiments, the compound is an isotopic derivative of any one of the compounds described in Table 5.

In some embodiments, the compound is selected from Compound Nos. 21, 39, 54, 56, 58-59, 64, 67, 69, 93, 95, 98-99, 104, 110, 114-116, 126, 128-129, 131-134, 137, 144-147, 154, 162, 170-171, 175-177, 180-181, 185, 192-195, 206, 220-221, 225-226, 228, 230-231, and 234-235, and pharmaceutically acceptable salts thereof.

In some embodiments, the compound is selected from Compound Nos. 21, 39, 54, 56, 58-59, 64, 67, 69, 93, 95, 98-99, 104, 110, 114-116, 126, 128-129, 131-134, 137, 144-147, 154, 162, 170-171, 175-177, 180-181, 185, 192-195, 206, 220-221, 225-226, 228, 230-231, and 234-235.

In some embodiments, the compound is selected from Compound Nos. 21, 59, 129, 144, 145, 154, and 175, and pharmaceutically acceptable salts thereof.

In some embodiments, the compound is selected from Compound Nos. 21, 59, 129, 144, 145, 154, and 175.

In some embodiments, the compound is selected from Compound Nos. 144, 154, and 175, and pharmaceutically acceptable salts thereof.

In some embodiments, the compound is selected from Compound Nos. 144, 154, and 175.

In some embodiments, the compound is Compound No. 21, and pharmaceutically acceptable salts thereof. In some embodiments, the compound is Compound No. 21.

In some embodiments, the compound is Compound No. 59, and pharmaceutically acceptable salts thereof. In some embodiments, the compound is Compound No. 59.

In some embodiments, the compound is Compound No. 129, and pharmaceutically acceptable salts thereof. In some embodiments, the compound is Compound No. 129.

In some embodiments, the compound is Compound No. 144, and pharmaceutically acceptable salts thereof. In some embodiments, the compound is Compound No. 144.

In some embodiments, the compound is Compound No. 145, and pharmaceutically acceptable salts thereof. In some embodiments, the compound is Compound No. 145.

In some embodiments, the compound is Compound No. 154, and pharmaceutically acceptable salts thereof. In some embodiments, the compound is Compound No. 154.

In some embodiments, the compound is Compound No. 175, and pharmaceutically acceptable salts thereof. In some embodiments, the compound is Compound No. 175.

It is understood that the isotopic derivative can be prepared using any of a variety of art-recognized techniques. For example, the isotopic derivative can generally be prepared by carrying out the procedures disclosed in the Scheme and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I'), Formula (I), Formula (II), or Formula (III) is isotopically enriched with regard to, or labelled with, one or more isotopes as compared to the corresponding compound of Formula (I'), Formula (I), Formula (II), or Formula (III). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognized techniques. For example, the deuterium labeled compound can generally be prepared by carrying out the procedures disclosed in the Scheme and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I'), Formula (I), Formula (II), or Formula (III) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterised by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess orexin modulatory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate: and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess orexin modulatory activity.

It is also to be understood that certain compounds of any one of the Formulae disclosed herein may exhibit polymorphism, and that the disclosure encompasses all such forms, or mixtures thereof, which possess orexin modulatory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I'), Formula (I), Formula (II), or Formula (III) include all such forms. For the avoidance of doubt, where a compound can exist in one of several tautomeric forms, and only one is specifically described or shown, all others are nevertheless embraced by Formula (I'), Formula (I), Formula (II), or Formula (III). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

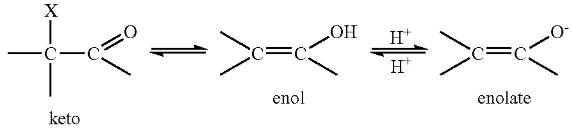

Compounds of any one of the Formulae disclosed herein containing an amine function may also form N-oxides. A reference herein to a compound of Formula (I'), Formula (I), Formula (II), or Formula (III) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of anyone of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Prodrugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of anyone of the Formulae disclosed herein that possesses a hydroxy group is, for example, an in vivo cleavable ester or ether thereof. An in vino cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of anyone of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vitro effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I'), Formula (I), Formula (II), or Formula (III) has been synthesized by any one of the processes defined herein, the processes may then further comprise the additional steps of; (i) removing any protecting groups present; (ii) converting the compound Formula (I'), Formula (I), Formula (II), or Formula (III) into another compound of Formula (I'), Formula (I), Formula (II), or Formula (III); (iii) forming a pharmaceutically acceptable salt, hydrate or solvate thereof; and/or (iv) forming a prodrug thereof.

The resultant compounds of Formula (I'), Formula (I), Formula (II), or Formula (III) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006)(John Wiley & Sons).

General routes for the preparation of a compound of the application are described in Scheme 1 herein.

Compound I, which are compounds of Formula (I'), (I), (II), and (III) wherein Z═NH, can be produced from commercially available and known compounds A, according to the method shown in the following Scheme 1, wherein $P_1$ is a protecting group and X represents various leaving groups known in the art. Examples of the protecting group $P_1$ for an amino group include, but are not limited to, carbamate-type protecting groups such as tertbutyl carbamate and the like. Examples of the leaving group X include halogens, in particular bromine or iodine, or sulfonate esters such as methyl sulfonate.

Scheme 1

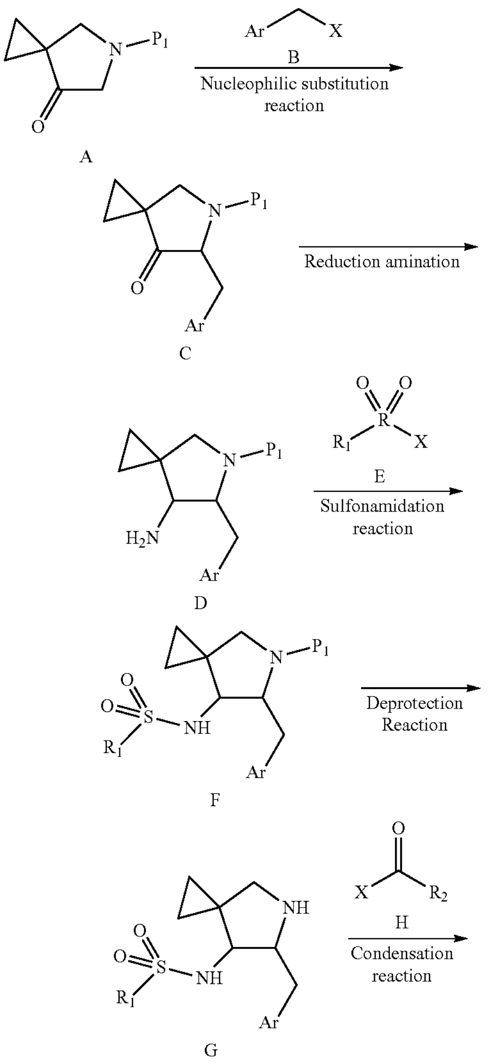

-continued

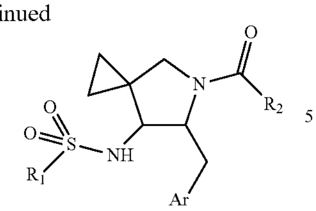

I

Compound C can be produced by subjecting compound A to a nucleophilic substitution reaction with Compound B in the presence of a base. Examples of the base include, but are not limited to, lithium amides and the like. Alternatively Compound C can also be produced by conversion to the corresponding enamine, and then reacting the enamine with Compound B. Examples of the amine that can be used for the enamine formation include, but are not limited to pyrrolidine.

Compound D can be produced by subjecting Compound C to a reductive amination reaction. Examples of the amine used include, but are not limited to, ammonium salts such as ammonium formate and the like. Examples of the reducing agent include, but are not limited to, sodium triacetoxyborohydride, sodium cyanoborohydride, hydrogen and formic acid and the like. In addition, a metal catalyst may be added to the reaction system. Examples of the catalyst to be used include, but are not limited to, iridium catalysts and the like.

Compound F can be produced by subjecting Compound D to a sulfonamidation reaction with Compound E in the presence of a base. Compound E may be commercially available or can be produced from known methods. Examples of the base to be used include, but are not limited to, organic bases such as tertiary alkyl amines such as N,N-diisopropylethylamine and the like.

Compound G can be prepared by subjecting Compound F to a deprotection reaction to remove protecting group $P_1$. The specific deprotection reaction will depend on the choice of protecting group. For example, wherein $P_1$ is tert-butyl carbamate the deprotection can be achieved by treatment with an acid such as hydrochloric acid or trifluoroacetic acid and the like.

Compound I can be prepared by subjecting Compound G and Compound H to a condensation reaction. Examples of Compound H include, but are not limited to, acyl halides such as acid chlorides, alkyl chloroformates, carbamoyl chlorides and the like; activated carboxylic acids such as acid anhydrides, activated esters and the like. Examples of the activating agent for carboxylic acids include, but are not limited to, carbodiimide condensing agents, carbonate ester condensing agents such as 1,1-carbonyldiimidazole (CDI) and the like; benzotriazole-1-yloxy-trisdimethylaminophosphonium salt (BOP reagent), alkyl chloroformates; O-(7-azabenzotriazol-1-yl)-N,N,N',N'-tetramethyluronium hexafluorophosphate (HATU) and the like). When a condensing agent is used, an additive such as 1-hydroxybenzotriazole (HOBt) or dimethylaminopyridine (DMAP) may be added to the reaction system, Compound I obtained by the above-mentioned method can be isolated and purified by a known means (e.g., solvent extraction, phase transfer, crystallization, chromatography and the like).

When Compound I contains optical isomers, stereoisomers and rotamers, these compounds are also included in Compound I, and each can be obtained by a synthesis method or a separation method. For example, when an optical isomer exists in Compound 1, an optical isomer resolved from the compound is also encompassed in Compound 1.

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Despite orexin cell loss and decreased orexin peptides in cerebrospinal fluid in NT1, orexin receptors on post synaptic neurons remain intact as suitable targets for pharmacotherapeutic intervention. The orexin peptides A and B (OXA and OXB) may be cleaved from a single precursor molecule (prepro-orexin) that is produced exclusively in the lateral hypothalamus. Both orexin peptides bind with similar high affinity to OX2R, but the orexin-1 receptor (OX1R) may be preferentially bound by OXA. Postsynaptic excitation of these G-protein coupled orexin receptors may stimulate the release of monoaminergic and cholinergic neurotransmitters that promote wakefulness and inhibitory neurotransmitters that suppress REM sleep atonia.

In some embodiments, the biological assay is described in the Examples herein.

The biological activity of the compounds of the present disclosure may be determined in cells stably expressing either orexin type 2 or orexin type 1 receptor. The activity may be measured in cells (e.g., Chinese hamster ovary (CHO) cells expressing human orexin type 2 receptor (hOX2R) or human orexin type 2 receptor (hOX1R)) dosed with a compound of the present disclosure. The agonist activity of a compound of the present disclosure may be determined by fluorescence value.

Wake-promoting efficacy of the compounds of the present disclosure may be evaluated in a model (e.g., the B6.Cg-Tg (HCRT-MJD)1Stak/J (Atax) mouse model of NT1 and wild type (WT) colony mates). The model (e.g., mouse model) may be monitored for rapid, non-invasive classification of sleep and wakefulness by unsupervised machine learning on physiologically relevant readouts, such as body movement and breath rate, after dosing of a compound of the present disclosure (e.g., oral dosing).

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, tiethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and E-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to treat or prevent an orexin related condition referred to herein, slow its progression and/or reduce the symptoms associated with the condition.

An effective amount of a compound of the present disclosure for use in therapy is an amount sufficient to treat an orexin related condition referred to herein, slow its progression and/or reduce the symptoms associated with the condition.

The size of the dose for therapeutic or prophylactic purposes of a compound of Formula (I'), Formula (I), Formula (II), or Formula (III) will naturally vary according to the nature and severity of the conditions, the age and sex of the animal or patient and the route of administration, according to well-known principles of medicine.

Methods of Use

In some aspects, the present disclosure provides a method of modulating orexin receptor activity (e.g., in vitro or in vivo), comprising contacting a cell with an effective amount of a compound of the present disclosure or a pharmaceutically acceptable salt thereof.

In some aspects, the present disclosure provides a method of modulating orexin-2 receptor activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is associated with an implicated orexin receptor activity. In some embodiments, the disease or disorder is a disease or disorder in which orexin receptor activity is implicated.

In some embodiments, the disease or disorder is associated with an implicated orexin-2 receptor activity. In some embodiments, the disease or disorder is a disease or disorder in which orexin-2 receptor activity is implicated.

In some embodiments, the disease or disorder is narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia.

In some aspects, the present disclosure provides a method of treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing narcolepsy in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a hypersomnia disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating narcolepsy in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a hypersomnia disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating orexin receptor activity (e.g., in vitro or in vivo).

In some aspects, the present disclosure provides a compound of the present disclosure or a pharmaceutically acceptable salt thereof for use in modulating orexin-2 receptor activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating or preventing narcolepsy in a subject in need thereof.

In some aspects, the present disclosure provides a compound of the present disclosure or a pharmaceutically acceptable salt thereof for use in treating or preventing a hypersomnia disorder in a subject in need thereof.

In some aspects, the present disclosure provides a compound of the present disclosure or a pharmaceutically acceptable salt thereof for use in treating or preventing a neurodegenerative disorder in a subject in need thereof.

In some aspects, the present disclosure provides a compound of the present disclosure or a pharmaceutically acceptable salt thereof for use in treating or preventing a symptom of a rare genetic disorder in a subject in need thereof.

In some aspects, the present disclosure provides a compound of the present disclosure or a pharmaceutically acceptable salt thereof for use in treating or preventing a mental health disorder in a subject in need thereof.

In some aspects, the present disclosure provides a compound of the present disclosure or a pharmaceutically acceptable salt thereof for use in treating or preventing a metabolic syndrome in a subject in need thereof.

In some aspects, the present disclosure provides a compound of the present disclosure or a pharmaceutically acceptable salt thereof for use in treating or preventing osteoporosis in a subject in need thereof.

In some aspects, the present disclosure provides a compound of the present disclosure or a pharmaceutically acceptable salt thereof for use in treating or preventing cardiac failure in a subject in need thereof.

In some aspects, the present disclosure provides a compound of the present disclosure or a pharmaceutically acceptable salt thereof for use in treating or preventing coma in a subject in need thereof.

In some aspects, the present disclosure provides a compound of the present disclosure or a pharmaceutically acceptable salt thereof for use in treating or preventing a complication in emergence from anesthesia in a subject in need thereof.

In some aspects, the present disclosure provides a compound of the present disclosure or a pharmaceutically acceptable salt thereof for use in treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating narcolepsy in a subject in need thereof.

In some aspects, the present disclosure provides a compound of the present disclosure or a pharmaceutically acceptable salt thereof for use in treating a hypersomnia disorder in a subject in need thereof.

In some aspects, the present disclosure provides a compound of the present disclosure or a pharmaceutically acceptable salt thereof for use in treating a neurodegenerative disorder in a subject in need thereof.

In some aspects, the present disclosure provides a compound of the present disclosure or a pharmaceutically acceptable salt thereof for use in treating a symptom of a rare genetic disorder in a subject in need thereof.

In some aspects, the present disclosure provides a compound of the present disclosure or a pharmaceutically acceptable salt thereof for use in treating a mental health disorder in a subject in need thereof.

In some aspects, the present disclosure provides a compound of the present disclosure or a pharmaceutically acceptable salt thereof for use in treating a metabolic syndrome in a subject in need thereof.

In some aspects, the present disclosure provides a compound of the present disclosure or a pharmaceutically acceptable salt thereof for use in treating osteoporosis in a subject in need thereof.

In some aspects, the present disclosure provides a compound of the present disclosure or a pharmaceutically acceptable salt thereof for use in treating cardiac failure in a subject in need thereof.

In some aspects, the present disclosure provides a compound of the present disclosure or a pharmaceutically acceptable salt thereof for use in treating coma in a subject in need thereof.

In some aspects, the present disclosure provides a compound of the present disclosure or a pharmaceutically acceptable salt thereof for use in treating a complication in emergence from anesthesia in a subject in need thereof.

In some aspects, the present disclosure provides use of a compound of the present disclosure or a pharmaceutically acceptable salt thereof in the manufacture of a medicament for modulating orexin activity (e.g., in vitro or in vivo).

In some aspects, the present disclosure provides use of a compound of the present disclosure or a pharmaceutically acceptable salt thereof in the manufacture of a medicament for modulating orexin-2 activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating or preventing narcolepsy in a subject in need thereof.

In some aspects, the present disclosure provides use of a compound of the present disclosure or a pharmaceutically acceptable salt thereof in the manufacture of a medicament for treating or preventing a hypersomnia disorder in a subject in need thereof.

In some aspects, the present disclosure provides use of a compound of the present disclosure or a pharmaceutically acceptable salt thereof in the manufacture of a medicament for treating or preventing a neurodegenerative disorder in a subject in need thereof.

In some aspects, the present disclosure provides use of a compound of the present disclosure or a pharmaceutically acceptable salt thereof in the manufacture of a medicament for treating or preventing a symptom of a rare genetic disorder in a subject in need thereof.

In some aspects, the present disclosure provides use of a compound of the present disclosure or a pharmaceutically acceptable salt thereof in the manufacture of a medicament for treating or preventing a mental health disorder in a subject in need thereof.

In some aspects, the present disclosure provides use of a compound of the present disclosure or a pharmaceutically acceptable salt thereof in the manufacture of a medicament for treating or preventing a metabolic syndrome in a subject in need thereof.

In some aspects, the present disclosure provides use of a compound of the present disclosure or a pharmaceutically acceptable salt thereof in the manufacture of a medicament for treating or preventing osteoporosis in a subject in need thereof.

In some aspects, the present disclosure provides use of a compound of the present disclosure or a pharmaceutically acceptable salt thereof in the manufacture of a medicament for treating or preventing cardiac failure in a subject in need thereof.

In some aspects, the present disclosure provides use of a compound of the present disclosure or a pharmaceutically acceptable salt thereof in the manufacture of a medicament for treating or preventing coma in a subject in need thereof.

In some aspects, the present disclosure provides use of a compound of the present disclosure or a pharmaceutically acceptable salt thereof in the manufacture of a medicament for treating or preventing a complication in emergence from anesthesia in a subject in need thereof.

In some aspects, the present disclosure provides use of a compound of the present disclosure or a pharmaceutically acceptable salt thereof in the manufacture of a medicament for treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating narcolepsy in a subject in need thereof.

In some aspects, the present disclosure provides use of a compound of the present disclosure or a pharmaceutically acceptable salt thereof in the manufacture of a medicament for treating a hypersomnia disorder in a subject in need thereof.

In some aspects, the present disclosure provides use of a compound of the present disclosure or a pharmaceutically acceptable salt thereof in the manufacture of a medicament for treating a neurodegenerative disorder in a subject in need thereof.

In some aspects, the present disclosure provides use of a compound of the present disclosure or a pharmaceutically acceptable salt thereof in the manufacture of a medicament for treating a symptom of a rare genetic disorder in a subject in need thereof.

In some aspects, the present disclosure provides use of a compound of the present disclosure or a pharmaceutically acceptable salt thereof in the manufacture of a medicament for treating a mental health disorder in a subject in need thereof.

In some aspects, the present disclosure provides use of a compound of the present disclosure or a pharmaceutically acceptable salt thereof in the manufacture of a medicament for treating a metabolic syndrome in a subject in need thereof.

In some aspects, the present disclosure provides use of a compound of the present disclosure or a pharmaceutically acceptable salt thereof in the manufacture of a medicament for treating osteoporosis in a subject in need thereof.

In some aspects, the present disclosure provides use of a compound of the present disclosure or a pharmaceutically acceptable salt thereof in the manufacture of a medicament for treating cardiac failure in a subject in need thereof.

In some aspects, the present disclosure provides use of a compound of the present disclosure or a pharmaceutically acceptable salt thereof in the manufacture of a medicament for treating coma in a subject in need thereof.

In some aspects, the present disclosure provides use of a compound of the present disclosure or a pharmaceutically acceptable salt thereof in the manufacture of a medicament for treating a complication in emergence from anesthesia in a subject in need thereof.

The present disclosure provides compounds that function as modulators of orexin receptor activity.

In some embodiments, the compounds of the present disclosure are agonists of the orexin receptor.

The present disclosure provides compounds that function as modulators of orexin-2 receptor activity.

In some embodiments, the compounds of the present disclosure are agonists of the orexin-2 receptor.

In some embodiments, the modulation of the orexin receptor is activation of the orexin receptor.

Effectiveness of compounds of the disclosure can be determined by industry-accepted assays/disease models according to standard practices of elucidating the same as described in the art and are found in the current general knowledge.

The present disclosure also provides a method of treating a disease or disorder in which orexin receptor activity is implicated in a patient in need of such treatment, said method comprising administering to said patient a therapeutically effective amount of a compound, or a pharmaceutically acceptable salt thereof, or a pharmaceutical composition as defined herein.

The present disclosure also provides a method of treating a disease or disorder in which orexin-2 receptor activity is implicated in a patient in need of such treatment, said method comprising administering to said patient a therapeutically effective amount of a compound, or a pharmaceutically acceptable salt thereof, or a pharmaceutical composition as defined herein.

In some embodiments, the present disclosure also provides a method for treating a disease or disorder by decreasing excessive sleepiness and/or excessive daytime sleepiness.

In some embodiments, the present disclosure also provides a method for treating a disease or disorder by decreasing excessive sleepiness.

In some embodiments, the present disclosure also provides a method for treating a disease or disorder by decreasing excessive daytime sleepiness.

In some embodiments, the disease or disorder is associated with excessive sleepiness and/or excessive daytime sleepiness.

In some embodiments, the disease or disorder is a primary hypersomnia disorder, neurodegenerative disorder, a symptom of a hypersomnia/neurodegenerative disorder, a symptom of a rare genetic disorder, a mental health disorder, a metabolic syndrome, osteoporosis, cardiac failure, coma, or emergence from anesthesia.

In some embodiments, the disease or disorder is a primary hypersomnia disorder, neurodegenerative disorder, a symptom of a hypersomnia/neurodegenerative disorder, a symptom of a rare genetic disorder, a mental health disorder, a metabolic syndrome, osteoporosis, cardiac failure, coma, or a complication in emergence from anesthesia.

In some embodiments, the excessive daytime sleepiness is associated with a neurodegenerative disorder.

In some embodiments, the neurodegenerative disorder associated with excessive daytime sleepiness is Parkinson's disease, Alzheimer's disease, Huntington's disease, or multiple sclerosis.

In some embodiments, the disease or disorder is a recurrence of hypersomnia.

In some embodiments, the recurrence of hypersomnia is narcolepsy type 1, narcolepsy type 2, or idiopathic hypersomnia.

In some embodiments, the disease or disorder is sleep apnea, traumatic brain injury, age-related cognitive dysfunction, or excessive daytime sleepiness.

In some embodiments, excessive daytime sleepiness is associated with sleep apnea, traumatic brain injury, or age-related cognitive dysfunction.

In some embodiments, the disorder is narcolepsy. In some embodiments, narcolepsy is narcolepsy type 1. In some embodiments, the narcolepsy is narcolepsy type 2.

In some embodiments, the hypersomnia is a symptom of narcolepsy.

In some embodiments, the disease or disorder is a symptom of narcolepsy.

In some embodiments, a symptom of narcolepsy is excessive daytime sleepiness, cataplexy, sleep paralysis, hypnopompic and hynogogic hallucinations, disturbed nighttime sleep, or inappropriately timed rapid-eye-movement (REM) sleep.

In some embodiments, a symptom of narcolepsy is excessive daytime sleepiness.

In some embodiments, the symptom of narcolepsy is cataplexy. In some embodiments, cataplexy is pathognomonic of narcolepsy (e.g., narcolepsy type 1)

In some embodiments, a symptom of narcolepsy is sleep paralysis.

In some embodiments, a symptom of narcolepsy is hypnopompic and hynogogic hallucinations.

In some embodiments, a symptom of narcolepsy is disturbed nighttime sleep.

In some embodiments, a symptom of narcolepsy is inappropriately timed rapid-eye-movement (REM) sleep.

In some embodiments, the neurodegenerative disorder is characterized by cataplexy.

In some embodiments, the neurodegenerative disorder is characterized by excessive daytime sleepiness.

In some embodiments, the neurodegenerative disorder is Parkinson's disease.

In some embodiments, the neurodegenerative disorder is Alzheimer's disease.

In some embodiments, the neurodegenerative disorder is Huntington's disease.

In some embodiments, the neurodegenerative disorder is multiple sclerosis.

In some embodiments, the neurodegenerative disorder is a traumatic brain injury.

In some embodiments, the neurodegenerative disorder is sleep apnea.

In some embodiments, the neurodegenerative disorder is age-related cognitive dysfunction.

In some embodiments, the neurodegenerative disorder is a disorder of recurrent hypersomnia.

In some embodiments, a disorder of recurrent hypersomnia is Klein-Levin syndrome, inappropriately timed sleep, (e.g., delayed- or advanced-sleep phase disorder), shift work disorder, or jet lag disorder.

In some embodiments, the disease or disorder is a symptom of a rare genetic disorder.

In some embodiments, a symptom of a rare genetic disorder is abnormal daytime sleepiness.

In some embodiments, a symptom of a rare genetic disorder is excessive daytime sleepiness.

In some embodiments, a symptom of a rare genetic disorder is sleep onset REM periods.

In some embodiments, a symptom of a rare genetic disorder is characterized by cataplexy-like symptoms.

In some embodiments, a rare genetic disorder is ADCA-DN, Coffin-Lowry syndrome, Moebius syndrome, Norrie disease, Niemann-Pick disease type C, or Prader-Willi syndrome.

In some embodiments, the disease or disorder is a mental health disorder.

In some embodiments, the mental health disorder is attention deficit hyperactivity disorder.

In some embodiments, the mental health disorder is attention deficit disorder.

In some embodiments, the disease or disorder is a metabolic syndrome.

In some embodiments, the metabolic syndrome is obesity.

In some embodiments, the disease or disorder is osteoporosis.

In some embodiments, the disease or disorder is cardiac failure.

In some embodiments, the disease or disorder is a coma.

In some embodiments, the disease or disorder is emergence from anesthesia.

In some embodiments, the disease or disorder is a complication in emergence from anesthesia.

In some embodiments, the disease or disorder is narcolepsy, a hypersomnia disorder, a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia. In some embodiments, the disease or disorder is narcolepsy, idiopathic hypersomnia, or sleep apnea.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I'), Formula (I), Formula (II), or Formula (III) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which orexin activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I'), Formula (I), Formula (II), or Formula (III) and pharmaceutically acceptable salts thereof are also useful as pharmacological tools in the development and standardization of in vitro and in vivo test systems for the evaluation of the effects of modulators of orexin-2 receptor activity in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Exemplary Embodiment No. 1. A compound of Formula (I''):

(I''')

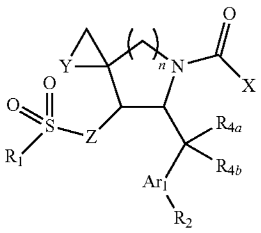

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —N$R_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, $C_3$-$C_6$ cycloalkyl, or 3- to 7-membered heterocycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—($CH_2$)$_2$—O$C_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_1$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

Exemplary Embodiment No. 2. The compound of Exemplary Embodiment 1, wherein the compound is of Formula (I''):

(I'')

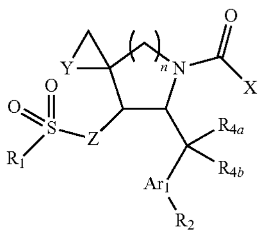

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —N$R_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, or $C_3$-$C_6$ cycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—($CH_2$)$_2$—O$C_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$, alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_1$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

Exemplary Embodiment No. 3. The compound of Exemplary Embodiment 1, wherein the compound is of Formula (I'):

(I')

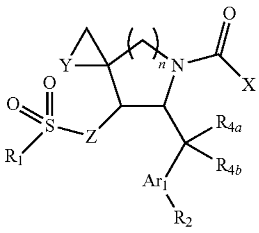

or a pharmaceutically acceptable salt thereof, wherein:

X is —C($R_{X1}$)$_3$, —O$R_{X2}$, or —N($R_{X2}$)$_2$.

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—,

Z is —O— or —N$R_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, or $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl; $Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_1$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3; and m is 0, 1, 2, 3, 4, or 5.

Exemplary Embodiment No. 4. The compound of Exemplary Embodiment 1, wherein the compound is of Formula (I):

(I)

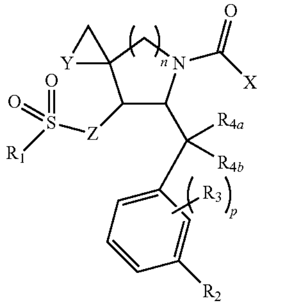

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, or $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{00}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_1$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_0$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0, 1, 2, 3, or 4.

Exemplary Embodiment No. 5. The compound of Exemplary Embodiment 1, wherein the compound is of Formula (II):

(II)

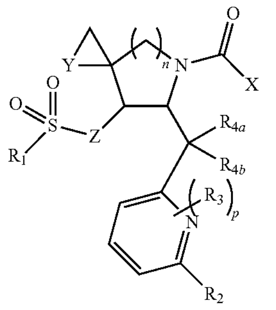

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, or $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0, 1, 2, or 3.

Exemplary Embodiment No. 6. The compound of Exemplary Embodiment 1, wherein the compound is of Formula (III):

(III)

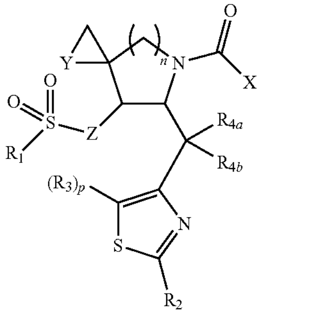

or a pharmaceutically acceptable salt thereof, wherein:

X is —C($R_{X1}$)$_3$, —O$R_{X2}$, or —N($R_{X2}$)$_2$;

Y is a —(C($R_Y$)$_2$)$_m$—, —O—(C($R_Y$)$_2$)$_m$—, —(C($R_Y$)$_2$)$_m$—O—, —N($R_Y$)—(C($R_Y$)$_2$)$_m$—, or —(C($R_Y$)$_2$)$_m$—N($R_Y$)—;

Z is —O— or —N$R_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, or $C_1$-$C_6$ haloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Y$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

n is 0, 1, 2, or 3;

m is 0, 1, 2, 3, 4, or 5; and p is 0 or 1.

Exemplary Embodiment No. 7. The compound of any one of the preceding Exemplary Embodiments, wherein Z is —$NR_Z$—.

Exemplary Embodiment No. 8. The compound of any one of the preceding Exemplary Embodiments, wherein Z is —NH—.

Exemplary Embodiment No. 9. The compound of any one of the preceding Exemplary Embodiments, wherein Z is —NH— and $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy.

Exemplary Embodiment No. 10. The compound of any one of the preceding Exemplary Embodiments, wherein X is —C($R_{X1}$)$_3$ or —N($R_{X2}$)$_2$.

Exemplary Embodiment No. 11. The compound of any one of Exemplary Embodiments 1-9, wherein X is —$OR_{X2}$.

Exemplary Embodiment No. 12. The compound of any one of the preceding Exemplary Embodiments, wherein X is

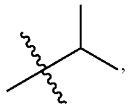, 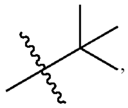, —O(methyl),

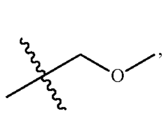, 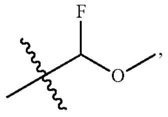, 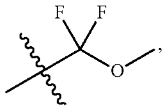,

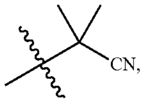, 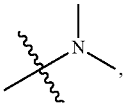, 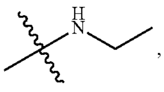,

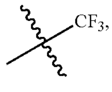, 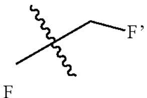, 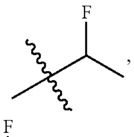, 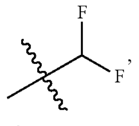,

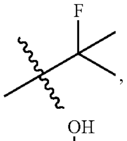, 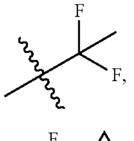, 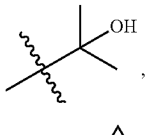,

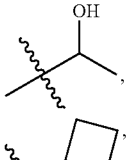, 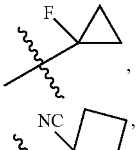, 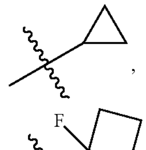,

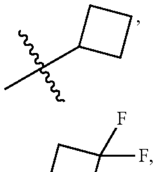, 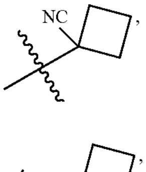, 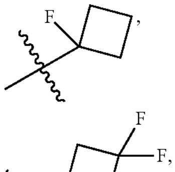,

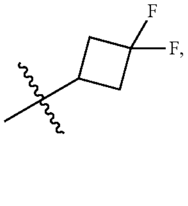, 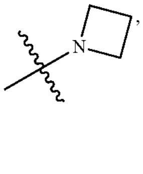, 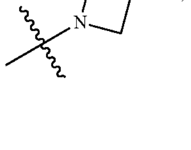,

-continued

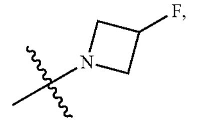 or 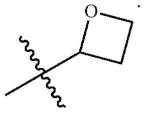.

Exemplary Embodiment No. 13. The compound of any one of the preceding Exemplary Embodiments, wherein Y is —(C($R_Y$)$_2$)$_m$—.

Exemplary Embodiment No. 14. The compound of any one of Exemplary Embodiments 1-12, wherein Y is —O—(C($R_Y$)$_2$)$_6$—, —(C($R_Y$)$_2$)$_m$—O—, —N($R_Y$)—(C($R_Y$)$_2$)$_m$—, or —(C($R_Y$)$_2$)$_m$—N($R_Y$)—.

Exemplary Embodiment No. 15. The compound of any one of the preceding Exemplary Embodiments, wherein Y is —$CH_2$—, —$CH_2$—O—, —O—$CH_2$—, —$CF_2$—, —$CH_2$—NH—, —NH—$CH_2$—, —$CH_2$—N($CH_2CF_3$)—, or —N($CH_2$—$CF_3$)—$CH_2$—.

Exemplary Embodiment No. 16. The compound of Exemplary Embodiment 15, wherein Y is —$CH_2$—.

Exemplary Embodiment No. 17. The compound of any one of the preceding Exemplary Embodiments, wherein each $R_{X1}$ independently is H.

Exemplary Embodiment No. 18. The compound of any one of the preceding Exemplary Embodiments, wherein each $R_{X1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

Exemplary Embodiment No. 19. The compound of any one of the preceding Exemplary Embodiments, wherein two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

Exemplary Embodiment No. 20. The compound of any one of the preceding Exemplary Embodiments, wherein each $R_{X2}$ independently is H.

Exemplary Embodiment No. 21. The compound of any one of the preceding Exemplary Embodiments, wherein each $R_{X2}$ independently is $C_1$-$C_6$ alkyl, $C_2$-$C_6$ alkenyl, $C_2$-$C_6$ alkynyl, or $C_1$-$C_6$ haloalkyl.

Exemplary Embodiment No. 22. The compound of any one of the preceding Exemplary Embodiments, wherein two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

Exemplary Embodiment No. 23. The compound of any one of the preceding Exemplary Embodiments, wherein each $R_Y$ independently is H.

Exemplary Embodiment No. 24. The compound of any one of the preceding Exemplary Embodiments, wherein each $R_Y$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

Exemplary Embodiment No. 25. The compound of any one of the preceding Exemplary Embodiments, wherein $R_Z$ is H.

Exemplary Embodiment No. 26. The compound of any one of the preceding Exemplary Embodiments, wherein $R_Z$ is $C_1$-$C_6$ alkyl, $C_2$-$C_6$ alkenyl, $C_2$-$C_6$ alkynyl, or $C_1$-$C_6$ haloalkyl.

Exemplary Embodiment No. 27. The compound of any one of the preceding Exemplary Embodiments, wherein $Ar_1$ is $C_h$-aryl or 5- or 6-membered heteroaryl, wherein the aryl or heteroaryl is optionally substituted with one or more $R_3$.

Exemplary Embodiment No. 28. The compound of Exemplary Embodiment 27, wherein $Ar_1$ is $C_6$-aryl optionally substituted with one or more $R_3$.

Exemplary Embodiment No. 29. The compound of Exemplary Embodiment 27, wherein $Ar_1$ is 5-membered heteroaryl optionally substituted with one or more $R_3$.

Exemplary Embodiment No. 30. The compound of Exemplary Embodiment 27, wherein $Ar_1$ is 6-membered heteroaryl optionally substituted with one or more $R_3$.

Exemplary Embodiment No. 31. The compound of Exemplary Embodiment 27, wherein $Ar_1$ is $C_6$-aryl.

Exemplary Embodiment No. 32. The compound of Exemplary Embodiment 27, wherein $Ar_1$ is 5-membered heteroaryl.

Exemplary Embodiment No. 33. The compound of Exemplary Embodiment 27, wherein $Ar_1$ is 6-membered heteroaryl.

Exemplary Embodiment No. 34. The compound of any one of the preceding Exemplary Embodiments, wherein $R_1$ is —$NH_2$, —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl).

Exemplary Embodiment No. 35. The compound of any one of the preceding Exemplary Embodiments, wherein $R_1$ is $C_1$-$C_6$ alkyl, $C_2$-$C_6$ alkenyl, $C_2$-$C_6$ alkynyl, or $C_1$-$C_6$ haloalkyl.

Exemplary Embodiment No. 36. The compound of any one of the preceding Exemplary Embodiments, wherein $R_1$ is methyl, isopropyl, ethyl, —$CF_3$, —$CHF_2$, $CH_2F$, —$CF_2CH_3$, —$CF(CH_3)_2$, cyclopropyl, or fluorocyclopropyl.

Exemplary Embodiment No. 37. The compound of any one of the preceding Exemplary Embodiments, wherein each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy.

Exemplary Embodiment No. 38. The compound of any one of the preceding Exemplary Embodiments, wherein $R_{1S}$ is halogen.

Exemplary Embodiment No. 39. The compound of any one of the preceding Exemplary Embodiments, wherein each $R_{1S}$ independently is $C_3$-$C_7$ cycloalkyl or 3- to 7-membered heterocycloalkyl.

Exemplary Embodiment No. 40. The compound of any one of the preceding Exemplary Embodiments, wherein $R_2$ is —CN, $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the alkyl, alkenyl, aryl, heteroaryl, cycloalkyl, and heterocycloalkyl are optionally substituted with one or more $R_{2S}$.

Exemplary Embodiment No. 41. The compound of any one of the preceding Exemplary Embodiments, wherein $R_2$ is phenyl optionally substituted with one or more $R_{2S}$.

Exemplary Embodiment No. 42. The compound of any one of the preceding Exemplary Embodiments, wherein $R_2$ is

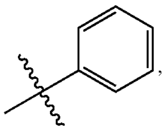, 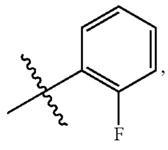, 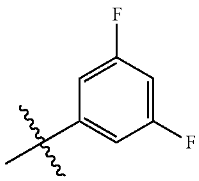,

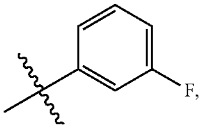 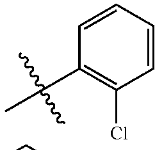,

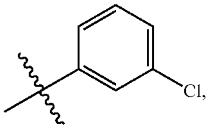 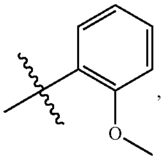, 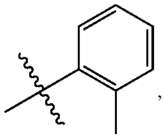,

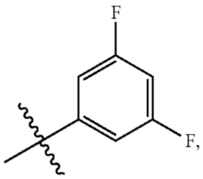 —CN, 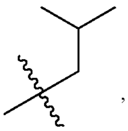,

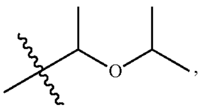, 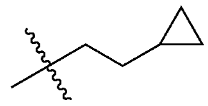,

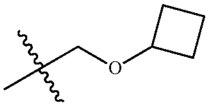, 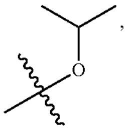, 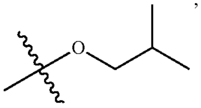,

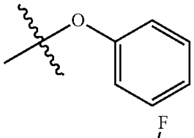, 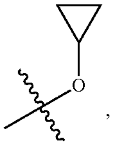, 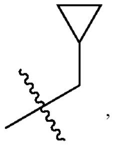,

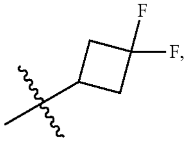 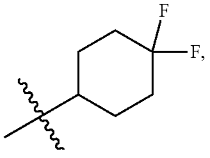

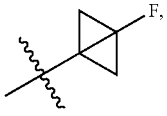 or 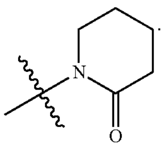.

Exemplary Embodiment No. 43. The compound of any one of the preceding Exemplary Embodiments, wherein each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy.

Exemplary Embodiment No. 44. The compound of any one of the preceding Exemplary Embodiments, wherein each $R_{2S}$ independently is $C_3$-$C_7$ cycloalkyl or 3- to 7-membered heterocycloalkyl.

Exemplary Embodiment No. 45. The compound of any one of the preceding Exemplary Embodiments, wherein each $R_3$ independently is halogen, —CN, —OH, —$NH_2$, —NH($C_1$-$C_6$ alkyl), or —N($C_1$-$C_6$ alkyl)$_2$.

Exemplary Embodiment No. 46. The compound of any one of the preceding Exemplary Embodiments, wherein each $R_3$ independently is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

Exemplary Embodiment No. 47. The compound of any one of the preceding Exemplary Embodiments, wherein $R_{4a}$ is H.

Exemplary Embodiment No. 48. The compound of any one of the preceding Exemplary Embodiments, wherein $R_{4a}$ is $C_1$-$C_6$ alkyl, $C_2$-$C_6$ alkenyl, $C_2$-$C_6$ alkynyl, or $C_1$-$C_6$ haloalkyl.

Exemplary Embodiment No. 49. The compound of any one of the preceding Exemplary Embodiments, wherein $R_{4b}$ is H.

Exemplary Embodiment No. 50. The compound of any one of the preceding Exemplary Embodiments, wherein $R_{4b}$ is $C_1$-$C_6$ alkyl, $C_2$-$C_6$ alkenyl, $C_2$-$C_6$ alkynyl, or $C_1$-$C_6$ haloalkyl.

Exemplary Embodiment No. 51. The compound of any one of the preceding Exemplary Embodiments, wherein n is 1 or 2.

Exemplary Embodiment No. 52. The compound of any one of the preceding Exemplary Embodiments, wherein m is 0, 1, or 2.

Exemplary Embodiment No. 53. The compound of any one of the preceding Exemplary Embodiments, wherein p is 0, 1, or 2.

Exemplary Embodiment No. 54. The compound of any one of the preceding Exemplary Embodiments, wherein the compound is of Formula (I-1)

(I-1)

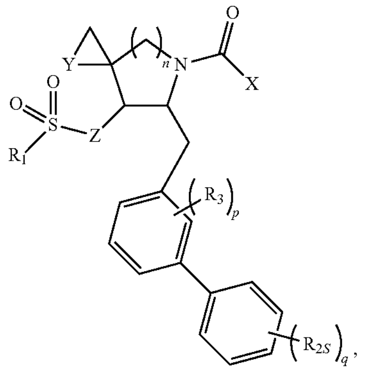

or a prodrug, solvate, or pharmaceutically acceptable salt thereof, wherein q is 0, 1, 2, 3, 4, or 5.

Exemplary Embodiment No. 55. The compound of any one of the preceding Exemplary Embodiments, wherein the compound is of Formula (I-1a), (I-1b), or (I-1c):

(I-1a)

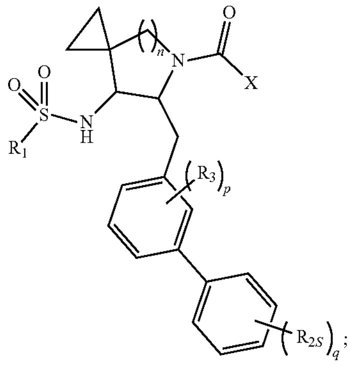

(I-1b)

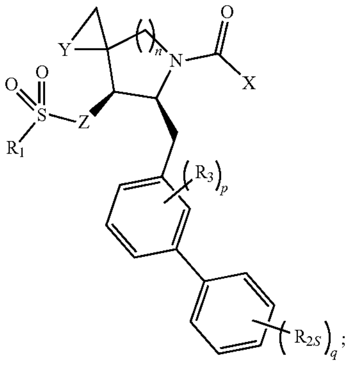

or (I-1c)

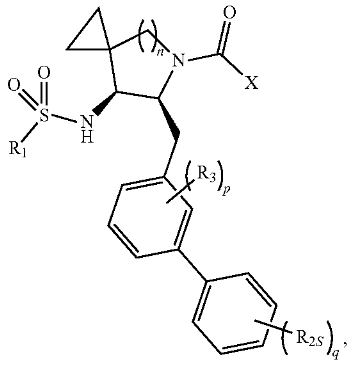

or a prodrug, solvate, or pharmaceutically acceptable salt thereof, wherein q is 0, 1, 2, 3, 4, or 5.

Exemplary Embodiment No. 56. The compound of any one of the preceding Exemplary Embodiments, wherein the compound is of Formula (I-2)

(I-2)

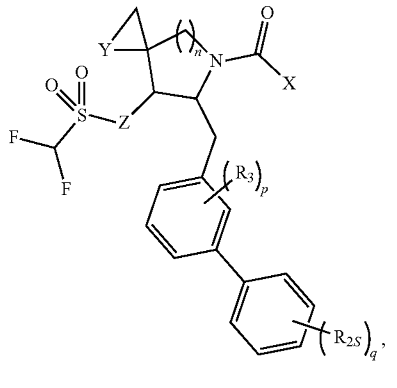

or a prodrug, solvate, or pharmaceutically acceptable salt thereof, wherein q is 0, 1, 2, 3, 4, or 5.

Exemplary Embodiment No. 57. The compound of any one of the preceding Exemplary Embodiments, wherein the compound is of Formula (I-2a), (I-2b), or (I-2c):

(I-2a)

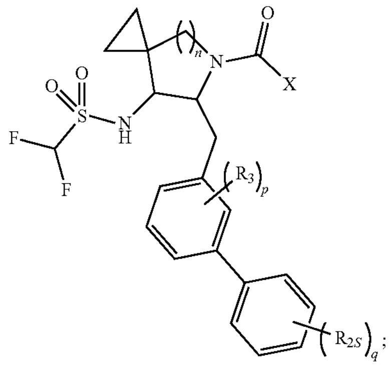

(I-2b)

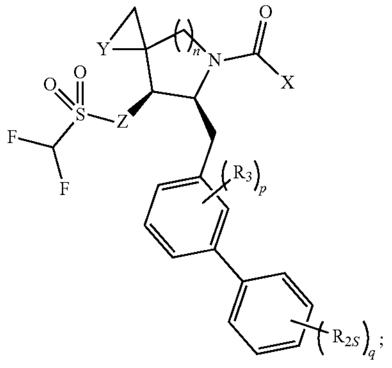

or

-continued (I-2c)

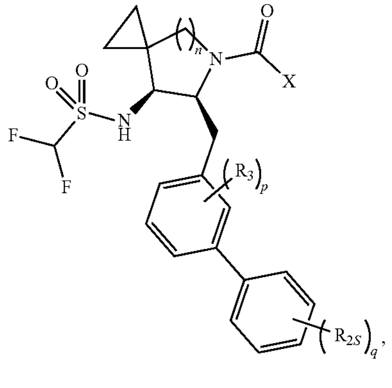

or a prodrug, solvate, or pharmaceutically acceptable salt thereof, wherein q is 0, 1, 2, 3, 4, or 5.

Exemplary Embodiment No. 58. The compound of any one of the preceding Exemplary Embodiments, wherein the compound is of Formula (I-3)

(I-3)

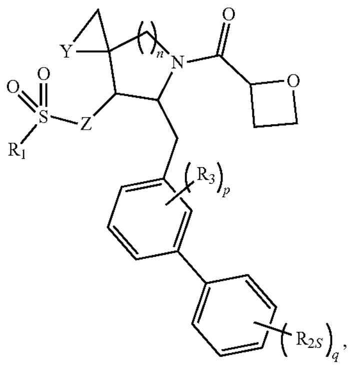

or a prodrug, solvate, or pharmaceutically acceptable salt thereof, wherein q is 0, 1, 2, 3, 4, or 5.

Exemplary Embodiment No. 59. The compound of any one of the preceding Exemplary Embodiments, wherein the compound is of Formula (I-3a), (I-3b), or (I-3c):

(I-3a)

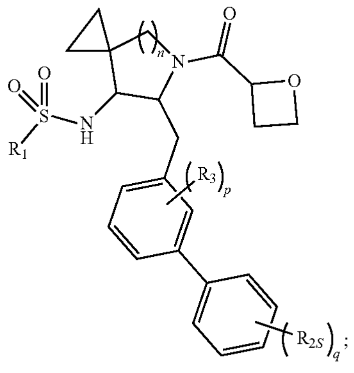

-continued (I-3b)

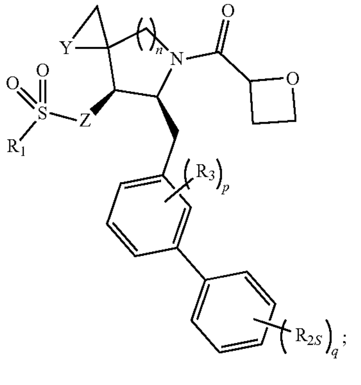

or (I-3c)

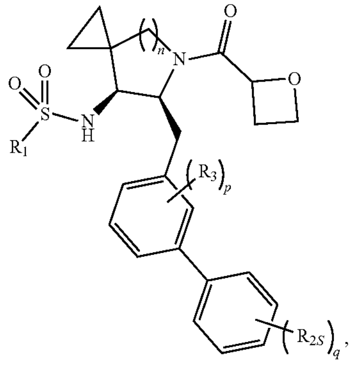

or a prodrug, solvate, or pharmaceutically acceptable salt thereof, wherein q is 0, 1, 2, 3, 4, or 5.

Exemplary Embodiment No. 60. The compound of any one of the preceding Exemplary Embodiments, wherein the compound is of Formula (II-1);

(II-1)

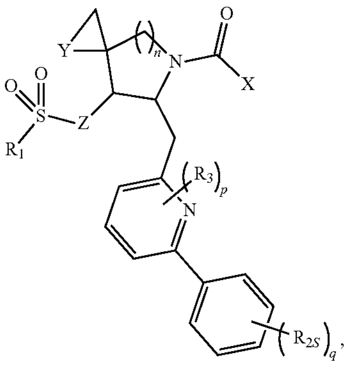

or a prodrug, solvate, or pharmaceutically acceptable salt thereof, wherein q is 0, 1, 2, 3, 4, or 5.

Exemplary Embodiment No. 61. The compound of any one of the preceding Exemplary Embodiments, wherein the compound is of Formula (II-1a), (II-1b), or (II-1c):

(II-1a)

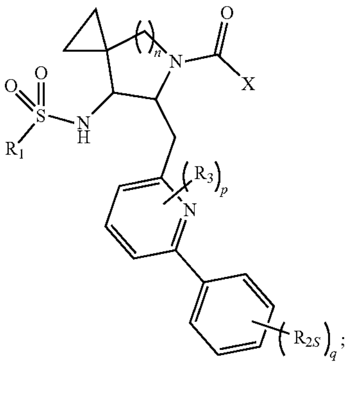

(II-1b)

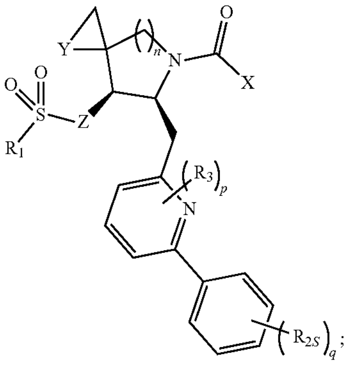

or (II-1c)

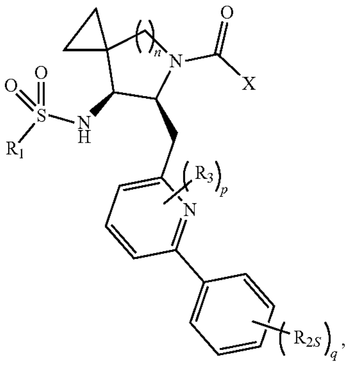

or a prodrug, solvate, or pharmaceutically acceptable salt thereof, wherein q is 0, 1, 2, 3, 4, or 5.

Exemplary Embodiment No. 62. The compound of any one of the preceding Exemplary Embodiments, wherein the compound is of Formula (III-1):

(III-1)

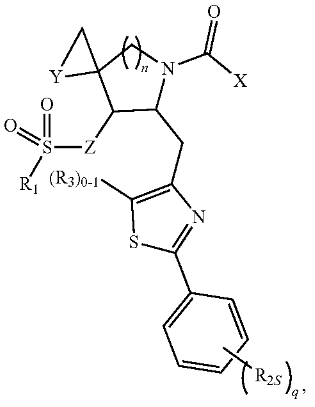

or a prodrug, solvate, or pharmaceutically acceptable salt thereof, wherein q is 0, 1, 2, 3, 4, or 5.

Exemplary Embodiment No. 63. The compound of any one of the preceding Exemplary Embodiments, wherein the compound is of Formula (III-1a), (III-1b), or (III-1c):

(III-1a)

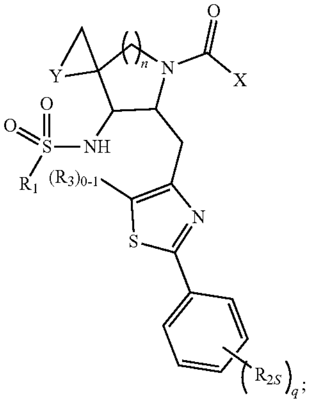

(III-1b)

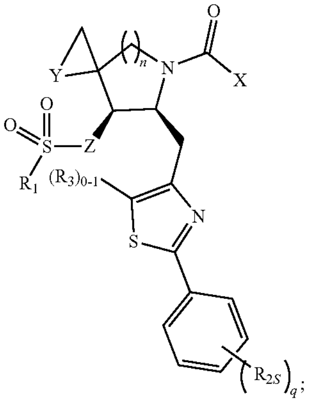

or

-continued (III-1c)

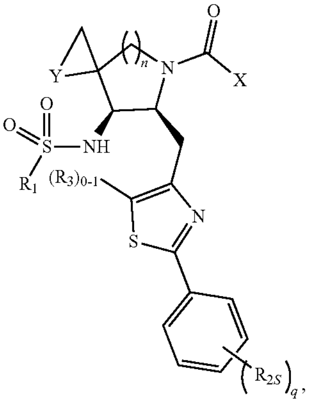

or a prodrug, solvate, or pharmaceutically acceptable salt thereof, wherein q is 0, 1, 2, 3, 4, or 5.

Exemplary Embodiment No. 64. The compound of any one of the preceding Exemplary Embodiments, being selected from the compounds described in Table 1 or Table 4 and prodrugs and pharmaceutically acceptable salts thereof.

Exemplary Embodiment No. 65. The compound of any one of the preceding Exemplary Embodiments, being selected from the compounds described in Table 1 or Table 4 and pharmaceutically acceptable salts thereof.

Exemplary Embodiment No. 66. The compound of any one of the preceding Exemplary Embodiments, being selected from the compounds described in Table 1.

Exemplary Embodiment No. 67. The compound of any one of the preceding Exemplary Embodiments, being selected from Compound Nos. 21, 59, 129, 144, 145, 154, and 175, and pharmaceutically acceptable salts thereof.

Exemplary Embodiment No. 68. A compound obtainable by, or obtained by, a method described herein;

optionally, the method comprises one or more steps described in Scheme 1.

Exemplary Embodiment No. 69. A pharmaceutical composition comprising the compound of any one of Exemplary Embodiments 1-68 or a pharmaceutically acceptable salt thereof, and a pharmaceutically acceptable diluent or carrier.

Exemplary Embodiment No. 70. The pharmaceutical composition of Exemplary Embodiment 69, wherein the compound is selected from the compounds described in Table 1.

Exemplary Embodiment No. 71. A method of modulating orexin-2 receptor activity, comprising contacting a cell with an effective amount of the compound of any one of Exemplary Embodiments 1-68 or a pharmaceutically acceptable salt thereof; optionally the activity is in vitro or in vivo.

Exemplary Embodiment No. 72. A method of treating or preventing a disease or disorder in a subject in need thereof, comprising administering to the subject a therapeutically effective amount of the compound of any one of Exemplary Embodiments 1-68 or a pharmaceutically acceptable salt thereof, or the pharmaceutical composition of Exemplary Embodiment 69 or Exemplary Embodiment 70.

Exemplary Embodiment No. 73. The compound of any one of Exemplary Embodiments 1-68 or a pharmaceutically acceptable salt thereof, or the pharmaceutical composition of Exemplary Embodiment 69 or Exemplary Embodiment 70, for use in modulating orexin-2 receptor activity; optionally, the activity is in vitro or in vivo.

Exemplary Embodiment No. 74. The compound of any one of Exemplary Embodiments 1-68, or the pharmaceutical composition of Exemplary Embodiment 69 or Exemplary Embodiment 70, for use in treating or preventing a disease or disorder.

Exemplary Embodiment No. 75. Use of the compound of any one of Exemplary Embodiments 1-68 or a pharmaceutically acceptable salt thereof in the manufacture of a medicament for modulating orexin-2 receptor activity; optionally, the activity is in vitro or in vivo.

Exemplary Embodiment No. 76. Use of the compound of any one of Exemplary Embodiments 1-68 or a pharmaceutically acceptable salt thereof in the manufacture of a medicament for treating or preventing a disease or disorder.

Exemplary Embodiment No. 77. The method, compound, pharmaceutical composition, or use of any one of Exemplary Embodiments 71-76, wherein the disease or disorder is associated with an implicated orexin receptor.

Exemplary Embodiment No. 78. The method, compound, pharmaceutical composition, or use of any one of Exemplary Embodiments 71-77, wherein the disease or disorder is associated with an implicated orexin-2 receptor.

Exemplary Embodiment No. 79. The method, compound, pharmaceutical composition, or use of any one of Exemplary Embodiments 71-78, wherein the disease or disorder is narcolepsy, a hypersomnia disorder, a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or facilitating emergence from anesthesia.

Exemplary Embodiment No. 80. The method, compound, pharmaceutical composition, or use of any one of Exemplary Embodiments 71-78, wherein the disease or disorder is narcolepsy, idiopathic hypersomnia, or sleep apnea.

EXAMPLES

For exemplary purpose, neutral compounds of Formula (I'), Formula (I), Formula (II), or Formula (III) are synthesized and tested in the examples. It is understood that the neutral compounds of Formula (I'), Formula (I), Formula (II), or Formula (III) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

NMR spectra were recorded on Bruker Avance III HD UltraShield 400 MHz with a 5 mm PABBO probe, Bruker AVANCE NEO 400 MHz equipped with a 5 mm Iprobe, Bruker AVANCE II HD 400 MHz with a 5 mm BBO probe, Varian 400MR equipped with a 5 mm 4NUC PFG. The samples were recorded at 25° C. using DMSO-$d_6$, MeOH-$d_4$ or MeCN-$d_3$ as a solvent.

LC-MS chromatograms and spectra were as follows:

A: LC/MS(The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% $CF_3CO_2H$ in water, mobile phase B was 0.018% $CF_3CO_2H$ in $CH_3CN$. The column used for the chromatography is a Chromolith Flash RP-18e 25-2 mm column. Detection methods are diode array (DAD) and evaporative light scattering (ELSD) detection as well as positive electrospray ionization (MS).

B: LC/MS(The column used for chromatography was a Luna-C18 2.0*30 mm, (3 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min).

C: LC/MS(The column used for chromatography was a HALO AQ-C18 2.1*30 mm 2.7 μm. Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min. 5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min).

D: LC/MS(The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.037% trifluoroacetic acid in water, mobile phase B was 0.018% trifluoroacetic acid in acetonitrile. The column used for chromatography was a Kinetex $C_{18\ 50\times2.1}$ mm column (5 μm particles). Detection methods are diode array (DAD) and evaporative light scattering (ELSD) detection as well as positive electrospray ionization. MS range was 100-1000.

E: LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 μm, C18, 30×2 mm. Column oven temp of 40° C. Diode Array Detector with UV detection from 190 to 400 nm and Agilent Mass Spectrometer 6120 Single Quadrupole with API-ES source. Gradients written in the following format: [Time (min)/% A2: % B2], Short Run: [0.00/95:5], [2.0/5:95], [2.5/5:95], [2.6/95:5], [3.0/95:5].

F: LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 μm, C18, 30×2 mm. Column oven temp of 40° C. Diode Array Detector with UV detection from 190 to 400 nm and Agilent Mass Spectrometer 6120 Single Quadrupole with API-ES source. Gradients written in the following format: [Time (min)/% A2: % B2], Long Run: [0.00/98:2], [0.1/98:2], [8.4/5:95], [10.0/5:95], [10.1/98:2], [12.0/98:2].

G: Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 μm, C18, 30×2 mm. Column oven temp of 45° C. Hewlett Packard G1315A Diode Array Detector with UV detection from 230 to 400 nm and Waters micromass ZQ mass spectrometer. Gradients written in the following format: [Time (min)/% C: % D], Long Run: [0.00/98:2], [0.1/98:2], [8.4/5:95], [10.0/5:95].

H: Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 μm, C18, 30×2 mm. Column oven temp of 45° C. Hewlett Packard G1315A Diode Array Detector with UV detection from 230 to 400 nm and Waters micromass ZQ mass spectrometer. Gradients written in the following format: [Time (min)/% C: % D], Short Run: [0.00/98:2], [0.1/98:2], [2.5/5:95], [3.5/5:95].

1: LC/MS(The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was H2O+10 mM NH4HCO3, mobile phase B was Acetonitrile. The column used for chromatography was a Xbridge Shield RP18 2.1*50 mm column (5 μm particles). Detection methods are diode array (DAD) and evaporative light scattering (ELSD) detection as well as negative electrospray ionization. MS range was 100-1000.

J: LC/MS(The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% Trifluoroacetic Acid in water, mobile phase B was 0.02% Trifluoroacetic Acid in acetonitrile. The column used for chromatography was a Luna C18 50*2.0 mm column (5 μm particles). Detection methods are diode array (DAD) and evaporative light scattering (ELSD) detection as well as positive electrospray ionization. MS range was 100-1000.

K: LC/MS(The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was H2O+10 mM NH4HCO3, mobile phase B was Acetonitrile. The column used for chromatography was a Xbridge-C18 2.1*50 mm column (5 μm particles). Detection methods are diode array (DAD) and evaporative light scattering (ELSD) detection as well as positive electrospray ionization. MS range was 100-1000.

L: LC/MS(The column used for chromatography was Xbridge Shield RP18 2.1*50 mm, (5 μm particles). Detection methods are diode array (DAD). MS mode was negative electrospray ionization. MS range was 100-1000. Mobile phase A was 10 mM Ammonium bicarbonate in water, and mobile phase B was HPLC grade acetonitrile. The gradient was 5-95% B in 4.5 min 0.5% B in 0.01 min, 5-95% B (0.01-3.00 min), 95% B (3.00-3.50 min), 95-5% B (3.50-4.00 min) and hold at 5% B for 0.3 min. The flow rate was 1.0 mL/min.

M: LC/MS(The column used for chromatography was a Kinetex 5 μm EVO C18 100A. Detection methods are diode array (DAD). MS mode was positive electrospray ionization. MS range was 100-1000. Mobile phase A was 0.04% Trifluoroacetic acid in water, and mobile phase B was 0.02% Trifluoroacetic acid in HPLC grade acetonitrile. The gradient was 5-95% B in 1.50 min 0.5% B in 0.01 min, 5-95% B (0.01-0.70 min), 95% B for 0.46 min. 95-5% B (1.61-1.50 min) with a hold at 5% B for 0.11 min. The flow rate was 1.5 mL/min.

N: LC/MS(The column used for chromatography was Xbridge-C18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min) and hold at 95% B within 0.5 min, 95-5% B (3.50-3.51 min), with a hold at 5% B for 0.79 min. The flow rate was 1.0 mL/min (0.01-4.30 min).

O: LC/MS(The column used for chromatography was a Kinetex 5 μm EVO C18 100A 2.1*30 mm. Detection methods are diode array (DAD). MS mode was positive electrospray ionization. MS range was 100-1000. Mobile phase A was 0.04% TFA in water, and mobile phase B was 0.02% TFA in HPLC grade acetonitrile. The gradient was 5-95% B in 4.30 min 0.5% B in 0.01 min, 5-95% B (0.01-3.00 min), with a hold at 95% B for 0.5 mins, 95-5% B (3.50-3.51 min), with a hold at 5% B for 0.79 min. The flow rate was 1.0 mL/min.

Abbreviations

ACN acetonitrile
AIBN azobisisobutyronitrile
BOC tert-butyl carbamate
BOP (benzotriazol-1-yloxy)tris(dimethylamino)phosphonium hexafluorophosphate
BTC bis(trichloromethyl) carbonate
CDI carbonyl diimidazole
DAD diode array detector
DCM dichloromethane
DIEA/DIPEA N,N-diisopropylethylamine
DMF N,N-dimethylformamide
DMSO dimethylsulfoxide
EA ethyl acetate
EDCI 1-ethyl-3-(3-dimethylaminopropyl) carbodiimide
ELSD evaporative light scattering detector
ES/ESI electrospray ionisation
HATU 1-[Bis(dimethylamino)methylene]-1H-1,2,3-triazolo[4,5-b]pyridinium 3-oxid hexafluorophosphate
HOAT 1-hydroxy-7-azabenzotriazole
HOBT hydroxy benzotriazole
HPLC high-performance liquid chromatography
IPA isopropylalcohol
LC liquid chromatography
LiHMDS lithium hexamethyl disilazide
MS mass spectrometry
NMR nuclear magnetic resonance
Py pyridine
RT retention time
SFC supercritical fluid chromatography
TBAI tetrabutyl ammonium iodide
TEA triethylamine
TFA trifluoroacetic acid
TFAA trifluoroacetic anhydride
THF tetrahydrofuran
TLC thin layer chromatography
TMS tetramethyl silane
UV ultraviolet Synthesis of Intermediate 1

Step-1: tert-butyl 6-(3-bromobenzyl)-7-oxo-5-azaspiro[2.4]heptane-5-carboxylate

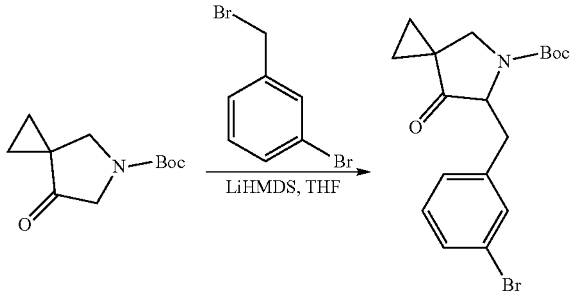 [SMILES: CC(C)(C)OC(=O)N1CC(=O)C2(CC2)C1 ; BrCc1cccc(Br)c1 ; CC(C)(C)OC(=O)N1CC2(CC2)C(=O)C1Cc1cccc(Br)c1]

To a solution of tert-butyl 7-oxo-5-azaspiro[2.4]heptane-5-carboxylate (0.9 g, 4.26 mmol, 1 eq) in tetrahydrofuran (1.0 mL) was added a solution of bis(trimethylsily)amine lithium in tetrahydrofuran (1 M, 4.26 mL, 1 eq) drop-wise at −70° C. over a period of 5 mins under nitrogen, during which the temperature was maintained below −70° C. The reaction mixture was warmed to 25° C. over a period of 5 min and stirred at 25° C. for 0.5 hour. Then 1-bromo-3-(bromomethyl)benzene (1.12 g, 4.47 mmol, 1.05 eq) in tetrahydrofuran (1 mL) was added at −70° C. for 5 min. The reaction mixture was stirred at 25° C. for another 2 h. The reaction mixture was quenched by MeOH and concentrated under reduced pressure to give a residue. The residue was purified by column chromatography ($SiO_2$, Petroleum ether/Ethyl acetate=100/0 to 95/5) to afford the title compound (0.42 g, 23% yield) as colorless oil. LCMS(method A)(ESI+): m/z 324 $(M+H-55)^+$, RT: 0.876 min.

Step-2: tert-butyl 7-amino-6-(3-bromobenzyl)spiro[2.4]heptane-5-carboxylate_cis racemic

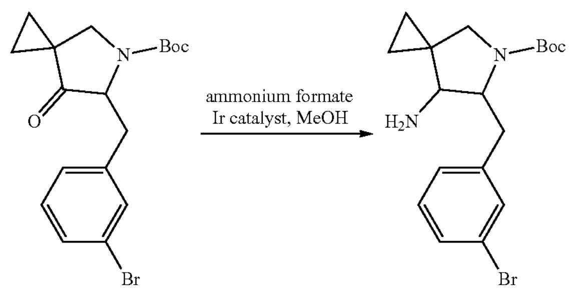 [SMILES: CC(C)(C)OC(=O)N1CC2(CC2)C(=O)C1Cc1cccc(Br)c1 ; CC(C)(C)OC(=O)N1CC2(CC2)C(N)C1Cc1cccc(Br)c1]

A mixture of tert-butyl 6-(3-bromobenzyl)-7-oxo-5-azaspiro[2.4]heptane-5-carboxylate (0.42 g, 1.10 mmol, 1 eq), ammonia formate (244 mg, 3.87 mmol, 3.5 eq) in methanol (1.0 mL) was degassed and purged with nitrogen 3 times, then bis[2-(2-pyridyl)phenyl]iridium(1+); 2-(2-pyridyl)pyridine; hexafluorophosphate (18 mg, 22.1 μmol, 0.02 eq) was added. The mixture was stirred at 80° C. for 3 h under nitrogen atmosphere. The reaction mixture was quenched by water (5.0 mL), and then extracted with ethyl acetate (5.0 mL×3). The combined organic layers were washed with brine, dried over anhydrous sodium sulfate, filtered and concentrated under reduced pressure to afford the title compound (420 mg, crude) which was used for next step directly. LCMS (method A)(ESI+): m/z 325 $(M+H-55)^+$, RT: 0.670 min.

Step-3: tert-butyl 6-(3-bromobenzyl)-7-(methylsulfonamido)-5-azaspiro[2.4]heptane-5-carboxylate_cis racemic (Intermediate 1)

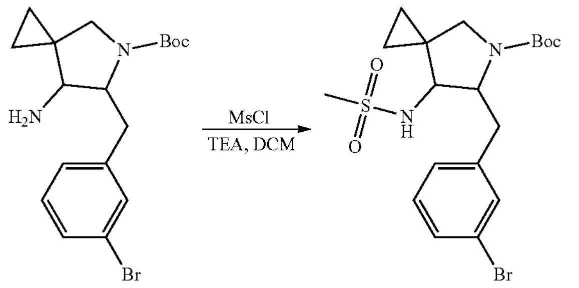 [SMILES: "MsCl" ; CC(C)(C)OC(=O)N1CC2(CC2)C(N)C1Cc1cccc(Br)c1 ; CC(C)(C)OC(=O)N1CC2(CC2)C(NS(C)(=O)=O)C1Cc1cccc(Br)c1]

To a solution of tert-butyl 7-amino-6-(3-bromobenzyl)spiro[2.4]heptane-5-carboxylate_cis racemic (0.15 g, 393 μmol, 1 eq) in dichloromethane (4.0 mL) was added mesyl chloride (37 μL, 472 μmol, 1.2 eq) and triethylamine (110 μL, 787 μmol, 2 eq). The mixture was stirred at 20° C. for 3 h. The reaction mixture was concentrated under reduced pressure to afford the title compound (0.13 g, 65% yield) as brown oil, which was used for next step directly.

LCMS(method A)(ESI+): m/z 361 $(M+H-55)^+$, RT: 0.809 min.

Synthesis of Intermediate 2

Step-1: tert-butyl 6-(3-bromo-2-fluorobenzyl)-7-oxo-5-azaspiro[2.4]heptane-5-carboxylate

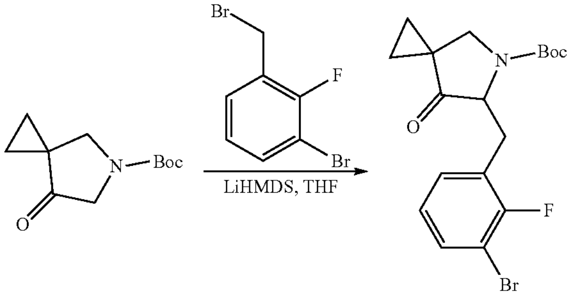

To a solution of tert-butyl 7-oxo-5-azaspiro[2.4]heptane-5-carboxylate (2.0 g, 9.47 mmol) in tetrahydrofuran (4.0 mL) at −78° C. was added a solution of bis(trimethylsily)amine lithium in tetrahydrofuran (14.2 mL, 1 M, 14.2 mmol). The reaction mixture was stirred at −78° C. for 5 min, then warmed up to 0° C. and stirred at this temperature for 30 min, then stirred at room temperature for another 30 min. Then 1-bromo-3-(bromomethyl)-2-fluoro-benzene (2.66 g, 9.94 mmol) was added at room temperature. The reaction mixture was then allowed to warm up to room temperature and stirred for another 90 min. The reaction mixture was quenched with water, diluted with EtOAc and washed with 1 M aq. HCl and brine, filtered over hydrophobic frit and evaporated in vacuo. The residue was purified by flash column chromatography [gradient 0% to 20% Ethyl Acetate in Iso-hexane] to afford the title compound (1.25 g, 33% yield) as a yellow oil. LCMS(method E)(ESI+): m/z 342 $(M+H-56)^+$, RT: 1.71 min.

Step-2: tert-butyl 7-amino-6-(3-bromo-2-fluorobenzyl)-5-azaspiro[2.4]heptane-5-carboxylate_cis racemic

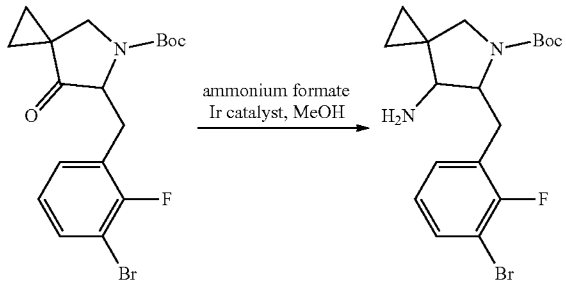 [SMILES: CC(C)(C)OC(=O)N1CC2(CC2)C(=O)C1Cc1cccc(Br)c1F ; CC(C)(C)OC(=O)N1CC2(CC2)C(N)C1Cc1cccc(Br)c1F]

A solution of tert-butyl 6-(3-bromo-2-fluorobenzyl)-7-oxo-5-azaspiro[2.4]heptane-5-carboxylate (1.25 g, 3.14 mmol) in Methanol (10 mL) was degassed before addition of ammonium formate (2.97 g, 47.1 mmol) and chloro[N-[4-(dimethylamino)phenyl]-2-pyridinecarboxamidato] (pentamethylcyclopentadienyl)iridium(I)(189 mg, 0.31 mmol). The reaction was heated at 70° C. for 7 h. The reaction mixture was diluted with 1 M NaOH, brine and EtOAc, and the layers were separated. The aqueous layer was extracted twice with EtOAc. The combined organic layer was dried over MgSO4, filtered over hydrophobic frit and evaporated in vacuo. The residue was purified by flash column chromatography [gradient 10% to 100% Ethyl Acetate in Iso-hexane, then gradient 0% A to 100% MeOH in dichloromethane] to afford the title compound (964 mg, 77% yield) as a yellow/orange oil. LCMS(method E) (ESI+): m/z 343 $(M+H-56)^+$, RT: 1.52 min.

Step-3: tert-butyl 6-(3-bromo-2-fluorobenzyl)-7-(methylsulfonamido)-5-azaspiro[2.4]heptane-5-carboxylate_cis racemic (Intermediate 2)

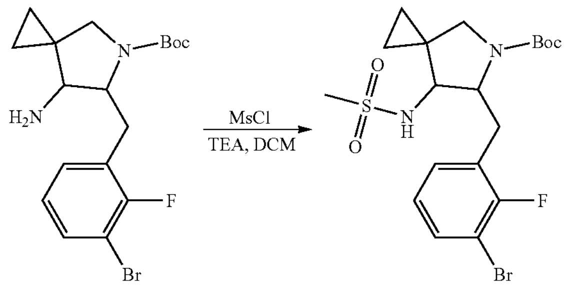 [SMILES: "MsCl" ; CC(C)(C)OC(=O)N1CC2(CC2)C(N)C1Cc1cccc(Br)c1F ; CC(C)(C)OC(=O)N1CC2(CC2)C(NS(C)(=O)=O)C1Cc1cccc(Br)c1F]

To a solution of tert-butyl 7-amino-6-(3-bromo-2-fluorobenzyl)-5-azaspiro[2.4]heptane-5-carboxylate_cis racemic (964 mg, 2.41 mmol) and triethylamine (0.47 mL, 3.38 mmol) in dichloromethane (12 mL) was added methanesulfonyl chloride (0.22 mL, 2.9 mmol). The reaction mixture was stirred at room temperature for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] to afford the title compound (1.05 g, 91% yield) as a white solid. LCMS(method E)(ESI+): m/z 421 $(M+H-56)^+$, RT: 1.52 min.

Synthesis of Intermediate 3

Step-1: tert-butyl 6-([1,1'-biphenyl]-3-ylmethyl)-7-oxo-5-azaspiro[2.4]heptane-5-carboxylate

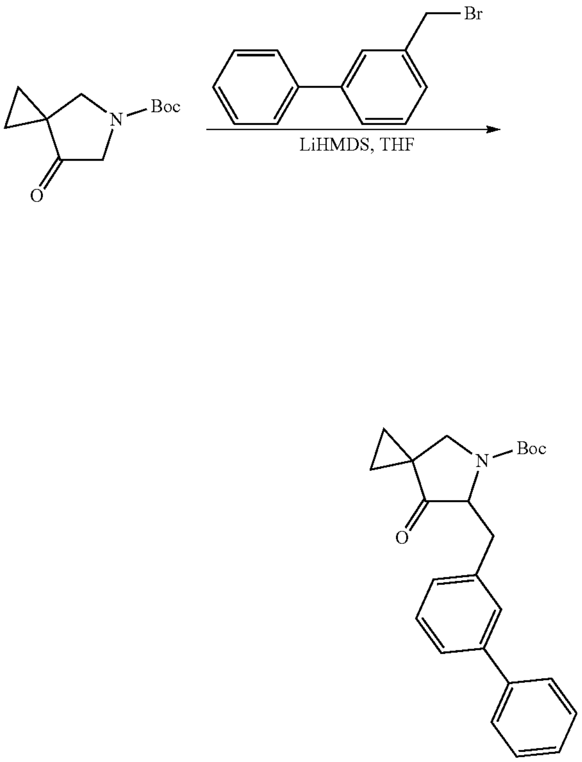

To a solution of tert-butyl 7-oxo-5-azaspiro[2.4]heptane-5-carboxylate (4.0 g, 18.9 mmol, 1 eq) in tetrahydrofuran (40 mL) was added a solution of bis(trimethylsily)amine lithium (1 M in tetrahydrofuran, 19 mL, 1 eq) drop-wise at −70° C. over a period of 5 min under nitrogen. During the addition the temperature was maintained below −70° C. The reaction mixture was warmed to 25° C. over a period of 5 min and stirred at 25° C. for 0.5 h. Then 3-(bromomethyl)-1,1'-biphenyl (4.45 g, 18 mmol, 0.95 eq) in tetrahydrofuran (40 mL) was added at −70° C. over 5 min. The reaction mixture was stirred at 25° C. for another 6 h. The reaction mixture was quenched by addition water (10 mL), and then diluted with ethyl acetate and extracted with ethyl acetate (10 mL) three times. The combined organic layers were washed with brine, dried over anhydrous sodium sulfate, filtered and concentrated under reduced pressure, The crude product was purified by column chromatography ($SiO_2$, Petroleum ether/Ethyl acetate=100/0 to 95/5) to afford the title compound (5.0 g, 33% yield) as brown oil. LCMS (method A)(ESI+): m/z 322 $(M+H-55)^+$, RT: 0.910 min.

Step-2: tert-butyl 6-([1,1'-biphenyl]-3-ylmethyl)-7-amino-5-azaspiro[2.4]heptane-5-carboxylate_cis racemic

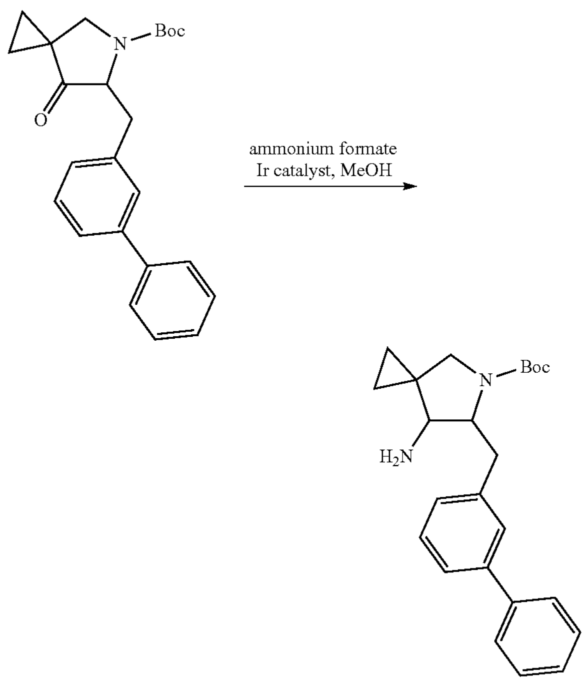

A mixture of tert-butyl 6-([1,1'-biphenyl]-3-ylmethyl)-7-oxo-5-azaspiro[2.4]heptane-5-carboxylate (4.40 g, 12 mmol, 1 eq), ammonium formate (2.28 g, 36 mmol, 3.1 eq), bis[2-(2-pyridyl)phenyl]iridium(1+); 2-(2-pyridyl)pyridine; hexafluorophosphate (94 mg, 117 μmol, 0.02 eq) in methanol (40 mL) was degassed and purged with nitrogen for 3 times, and then the mixture was stirred at 80° C. for 16 h under nitrogen atmosphere. The reaction mixture was concentrated under reduced pressure. The residue was purified by column chromatography ($SiO_2$, Petroleum ether/Ethyl acetate=100/0 to 50/50) to afford the title compound (0.65 g, 28% yield) as yellow solid. LCMS(method A)(ESI+): m/z 323 $(M+H-55)^+$, RT: 0.689 min.

Step-3: tert-butyl 6-([1,1'-biphenyl]-3-ylmethyl)-7-(methylsulfonamido)-5-azaspiro[2.4]heptane-5-carboxylate_cis racemic

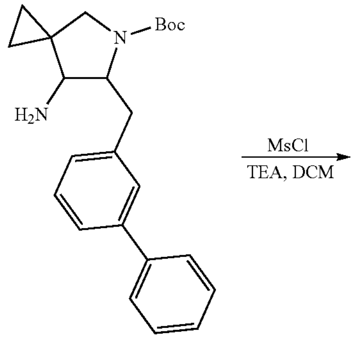

-continued

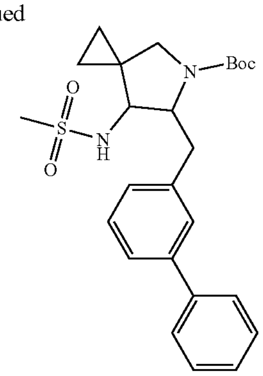

To a solution of tert-butyl 6-([1,1'-biphenyl]-3-ylmethyl)-7-amino-5-azaspiro[2.4]heptane-5-carboxylate_cis racemic (0.8 g, 2.11 mmol, 1 eq) in dichloromethane (5.0 mL) was added mesyl chloride (196 μL, 2.54 mmol, 1.2 eq) and triethylamine (735 μL, 5.28 mmol, 2.5 eq). The mixture was stirred at 20° C. for 2 h. The reaction mixture was quenched by water (10 mL), and then diluted with ethyl acetate and extracted with ethyl acetate (10 mL) three times. The combined organic layers were washed with brine, dried over anhydrous sodium sulfate, filtered and concentrated under reduced pressure to afford the title compound (0.8 g, 78% yield) as brown oil, which was used for next step directly. LCMS(method B)(ESI+): m/z 401 $(M+H-55)^+$, RT: 0.816 min.

Step-4: N-(6-([1,1'-biphenyl]-3-ylmethyl)-5-azaspiro[2.4]heptan-7-yl)methanesulfonamide hydrochloride_cis racemic (Intermediate 3)

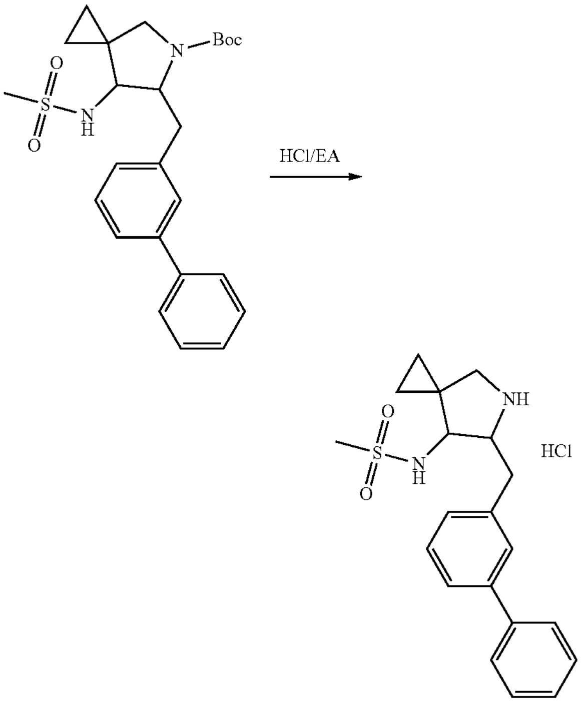

A solution of tert-butyl 6-([1,1'-biphenyl]-3-ylmethyl)-7-(methylsulfonamido)-5-azaspiro[2.4]heptane-5-carboxylate_cis racemic (0.8 g, 1.75 mmol, 1 eq) in HC/ethyl acetate (4 M, 18 mL, 40 eq). The mixture was stirred at 20° C. for 2 h. The mixture was concentrated under reduced pressure to afford the title compound (0.55 g, 82% yield) as a white solid, which was used for next step directly. LCMS(method C)(ESI+): m/z 357 $(M+H)^+$, RT: 0.635 min.

Synthesis of Intermediate 4

Step-1: tert-butyl 6-([1,1'-biphenyl]-3-ylmethyl)-7-(ethylsulfonamido)-5-azaspiro[2.4]heptane-5-carboxylate_cis racemic

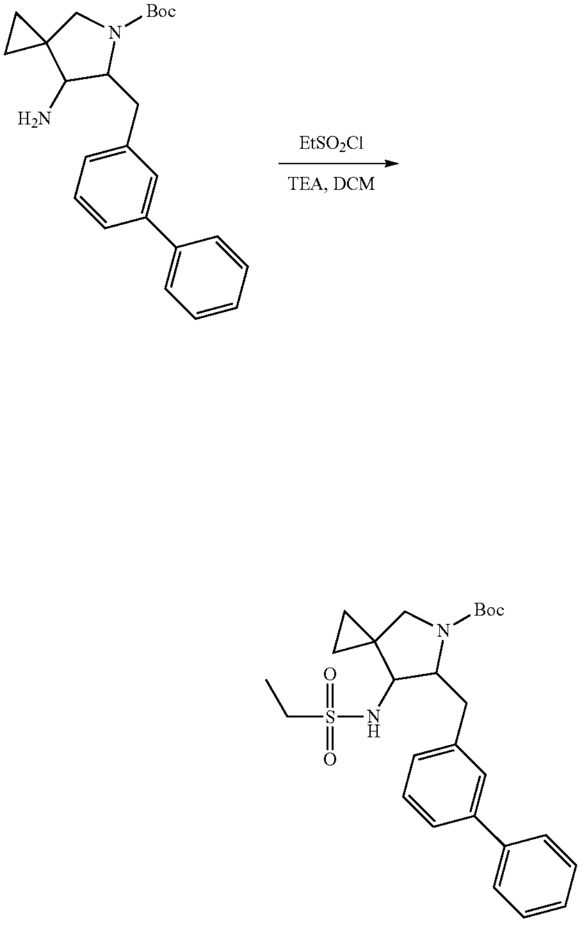

To a solution of tert-butyl 6-([1,1'-biphenyl]-3-ylmethyl)-7-amino-5-azaspiro[2.4]heptane-5-carboxylate_cis racemic (0.5 g, 1.32 mmol, 1 eq) and ethanesulfonyl chloride (150 µL, 1.59 mmol, 1.2 eq) in dichloromethane (5.0 mL) was added pyridine (266 µL, 3.30 mmol, 2.5 eq). The mixture was stirred at 20° C. for 2 h. The reaction mixture was concentrated under reduced pressure to afford the title compound (0.42 g, 66% yield) as yellow oil, which was used for next step directly. LCMS(method B)(ESI+): m/z 415 $(M+H-55)^+$, RT: 0.835 min.

Step-2: N-(6-([1,1'-biphenyl]-3-ylmethyl)-5-azaspiro[2.4]heptan-7-yl)ethanesulfonamide hydrochloride_cis racemic (Intermediate 4)

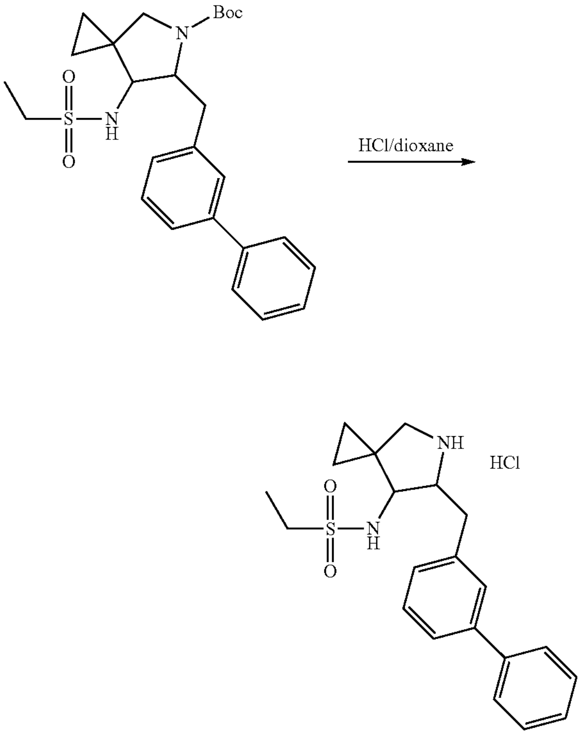

A solution of tert-butyl 6-([1,1'-biphenyl]-3-ylmethyl)-7-(ethylsulfonamido)-5-azaspiro[2.4]heptane-5-carboxylate_cis racemic (0.42 g, 892 µmol, 1 eq) in HCl/dioxane (4 M, 8.92 mL, 40 eq) was stirred at 20° C. for 2 h. The reaction mixture was concentrated under reduced pressure to afford the title compound (250 mg, 74% yield) as yellow solid, which was used for next step directly. LCMS(method C)(ESI+): m/z 371 $(M+H)^+$, RT: 0.672 min.

Synthesis of Intermediate 5

Step 1: tert-butyl 6-((2-fluoro-[1,1'-biphenyl-3-yl)methyl)-7-(methylsulfonamido)-5-azaspiro[2.4]heptane-5-carboxylate_cis racemic

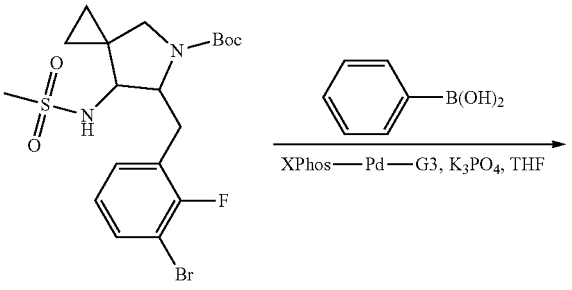

-continued

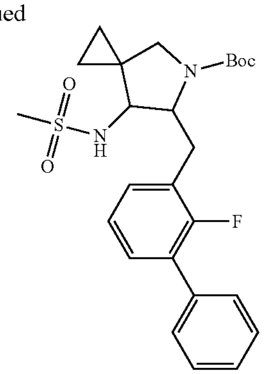

To a solution of phenylboronic acid (128 mg, 1.05 mmol), XPhos-G3-Palladacycle (25 mg, 0.03 mmol) and tert-butyl 6-(3-bromo-2-fluorobenzyl)-7-(methylsulfonamido)-5-azaspiro[2.4]heptane-5-carboxylate_cis racemic (intermediate 2)(250 mg, 0.52 mmol) in tetrahydrofuran (2.5 mL) was added 1 M aq. tripotassium phosphate solution (1.6 mL, 1.6 mmol) and the mixture was heated to 70° C. for 2 h. The reaction was partitioned between EtOAc and sat aq $NaHCO_3$, washed with sat. brine, the organic layer separated and concentrated in vacuo. The residue was purified by flash column chromatography (gradient 0% to 100% Ethyl Acetate in Iso-hexane] to afford the title compound (285 mg, quantitative). LCMS(method E) (ESI+): m/z 497 $(M+Na)^+$, RT: 1.66 min.

Step 2: N-(6-((2-fluoro-[1,1'-biphenyl]-3-yl)methyl)-5-azaspiro[2.4]heptan-7-yl)methanesulfonamide hydrochloride_cis racemic (Intermediate 5)

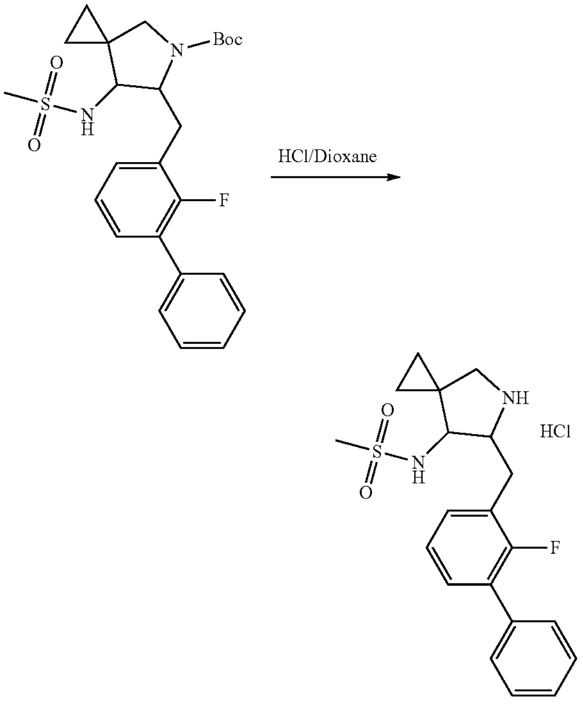

To a solution of tert-butyl 6-((2-fluoro-[1,1'-biphenyl]-3-yl)methyl)-7-(methylsulfonamido)-5-azaspiro[2.4]heptane-5-carboxylate_cis racemic (285 mg, 0.60 mmol) in 1,4-Dioxane (1.0 mL) was added 4 M HCl in dioxane (5.0 mL, 0.60 mmol). The reaction mixture was stirred for 18 h, then evaporated in vacuo to afford the title compound (246 mg, 99% yield) as a white solid. LCMS(method E)(ESI+): m/z 375 $(M+H)^+$, RT: 1.37 min.

Synthesis of Intermediate 6

Step 1: tert-butyl 6-((2,3'-difluoro-[1,1'-biphenyl]-3-yl)methyl)-7-(methylsulfonamido)-5-azaspiro[2.4]heptane-5-carboxylate_cis racemic

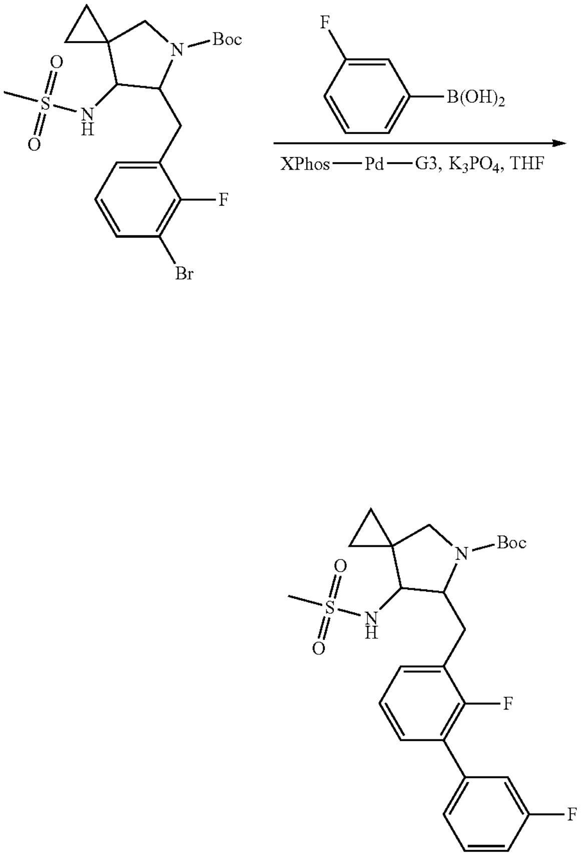

To a solution of 3-Fluorophenylboronic acid (234 mg, 1.68 mmol), XPhos-G3-Palladacycle (39 mg, 0.04 mmol) and tert-butyl 6-(3-bromo-2-fluorobenzyl)-7-(methylsulfonamido)-5-azaspiro[2.4]heptane-5-carboxylate_cis racemic (intermediate 2)(400 mg, 0.84 mmol) in tetrahydrofuran (4.0 mL) was added 1 M aq. tripotassium phosphate solution (2.5 mL, 2.5 mmol) and the mixture was heated to 70° C. for 2 h. The reaction was partitioned between EtOAc and sat aq $NaHCO_3$, washed with sat. brine, the organic layer separated and concentrated in vacuo. The residue was purified by flash column chromatography (gradient 0% to 100% Ethyl Acetate in Iso-hexane] to afford the title compound (439 mg, quantitative).

LCMS(method E)(ESI+): m/z 515 $(M+Na)^+$, RT: 1.67 min.

Step 2: N-(6-((2,3'-difluoro-[1,1'-biphenyl]-3-yl) methyl)-5-azaspiro[2.4]heptan-7-yl)methanesulfonamide hydrochloride_cis racemic (Intermediate 6)

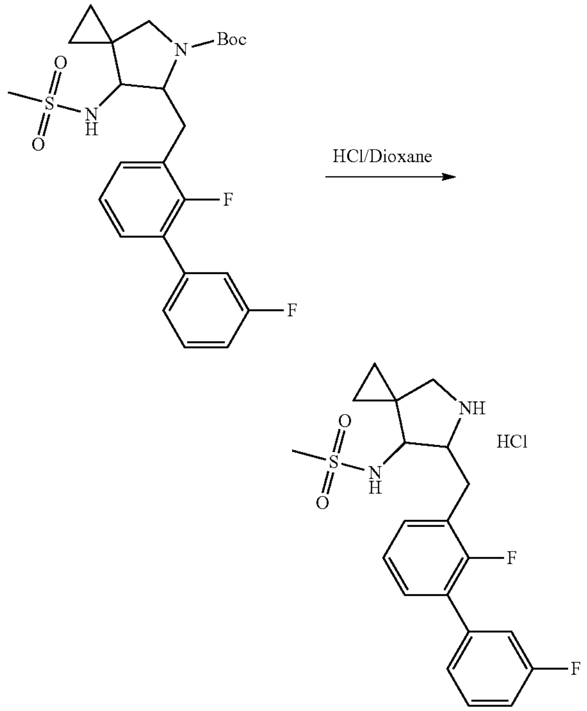

To a solution of tert-butyl 6-((2,3'-difluoro-[1,1'-biphenyl]-3-yl)methyl)-7-(methylsulfonamido)-5-azaspiro[2.4] heptane-5-carboxylate_cis racemic (439 mg, 0.89 mmol) in 1,4-Dioxane (1.0 mL) was added 4 M HCl in dioxane (5.0 mL, 0.89 mmol). The reaction mixture was stirred for 18 h, then evaporated in vacuo to afford the title compound (382 mg, 99% yield) as a yellow oil. LCMS(method E)(ESI+): m/z 393 $(M+H)^+$, RT: 1.39 min.

Synthesis of Intermediate 7

Step 1: tert-butyl 7-(methylsulfonamido)-6-((2,3',5'-trifluoro-[1,1'-biphenyl]-3-yl)methyl)-5-azaspiro [2.4]heptane-5-carboxylate_cis racemic

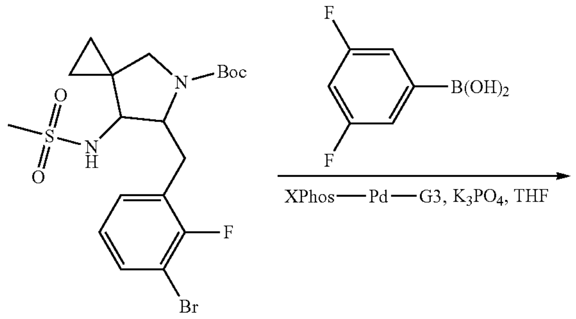

-continued

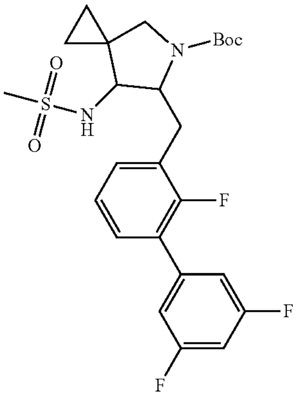

To a solution or tert-butyl 6-(3-bromo-2-fluorobenzyl)-7-(methylsulfonamido)-5-azaspiro[2.4]heptane-5-carboxylate_cis racemic (intermediate 2)(400 mg, 0.84 mmol), XPhos-G3-Palladacycle (39 mg, 0.04 mmol) and (3,5-difluorophenyl)boronic acid (265 mg, 1.68 mmol) in tetrahydrofuran (4.0 mL) was added 1 M aq. tripotassium phosphate solution (2.5 mL, 2.5 mmol) and the mixture was heated to 70° C. for 1 h. The reaction was partitioned between EtOAc and sat aq $NaHCO_3$, washed with sat. brine, the organic layer separated and concentrated in vacuo. The residue was purified by flash column chromatography (gradient 0% to 100% Ethyl Acetate in Iso-hexane] to afford the title compound (440 mg, quantitative). LCMS(method E) (ESI+): m/z 533 $(M+Na)^+$, RT: 1.71 min.

Step 2: N-(6-((2,3',5'-trifluoro-[1,1'-biphenyl]-3-yl) methyl)-5-azaspiro[2.4]heptan-7-yl)methanesulfonamide hydrochloride_cis racemic (Intermediate 7)

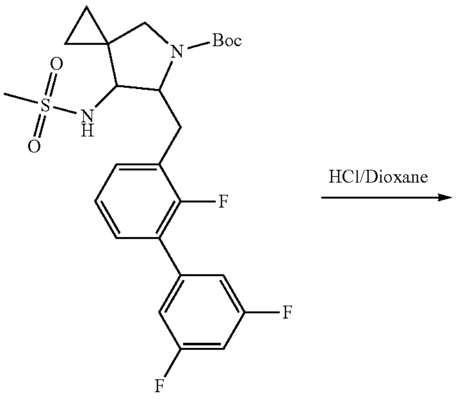

-continued

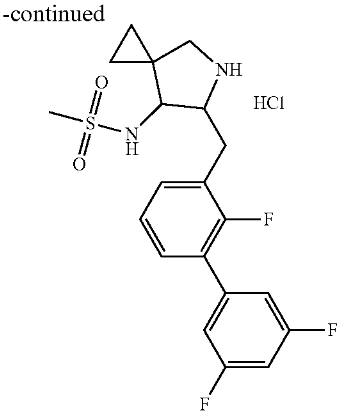

To a solution tert-butyl 7-(methylsulfonamido)-6-((2,3',5'-trifluoro-[1,1'-biphenyl]-3-yl)methyl)-5-azaspiro[2.4]heptane-5-carboxylate_cis racemic (440 mg, 0.86 mmol) in 1,4-Dioxane (1.0 mL) was added 4 M HCl in dioxane (5.0 mL, 0.86 mmol). The reaction mixture was stirred for 18 h, then evaporated in vacuo to afford the title compound (385 mg, 99% yield) as a white solid. LCMS(method E)(ESI+): m/z 411 $(M+H)^+$, RT: 1.43 min.

Synthesis of Intermediate 8

Step-1: tert-butyl 6-(3-bromo-2-fluorobenzyl)-7-oxo-5-azaspiro[2.4]heptane-5-carboxylate

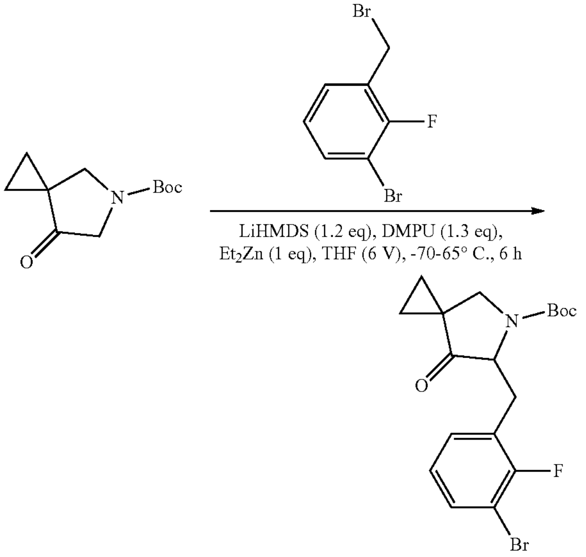

Charge tetrahydrofuran (1.4 L) to a reactor under nitrogen and add LiHMDS(4.0 L, 1 M in THF, 1.2 eq). Cool the reaction mixture to −70° C. to −65° C. A solution of tert-butyl 7-oxo-5-azaspiro[2.4]heptane-5-carboxylate (700 g, 1.0 eq) in THF (1.4 L) was added dropwise to the reactor at −70° C. to −65° C. and stirred for 3 hrs. Then, $Et_2Zn$ (3.3 L, 1 M in toluene, 1.0 eq) was added dropwise to the reactor at −70° C. to −65° C., following by DMPU (552 g, 1.3 eq) dropwise to the reactor at −70° C. to −65° C. Then, a solution of 1-bromo-3-(bromomethyl)-2-fluorobenzene (977 g, 1.1 eq) in THF (1.4 L) was added dropwise to the reactor and stirred at −70° C. to −65° C. for at least 3 h. Then the reaction mixture was poured into the ice-water (1.5 kg) at 0° C. and was extracted with ethyl acetate (14 L) twice. Separate and combine the organic phase and wash the organic phase with brine (3.5 L) twice and then dry the organic phases with $Na_2SO_4$ (500 g) and filter. Concentrate the organic phase under vacuum to give crude product which was purified by column chromatography ($SiO_2$, eluted with petroleum ether:ethyl acetate=1:0 to 13:1) to afford the title compound (969 g, yield 91.7%) as white solid. LCMS (method O)(ESI+): m/z 341.9 $(M+H-55)^+$, RT: 1.97 min Step-2: tert-butyl (E/Z)-6-(3-bromo-2-fluorobenzyl)-7-(((R)-tert-butylsulfinyl)imino)-5-azaspiro[2.4]heptane-5-carboxylate

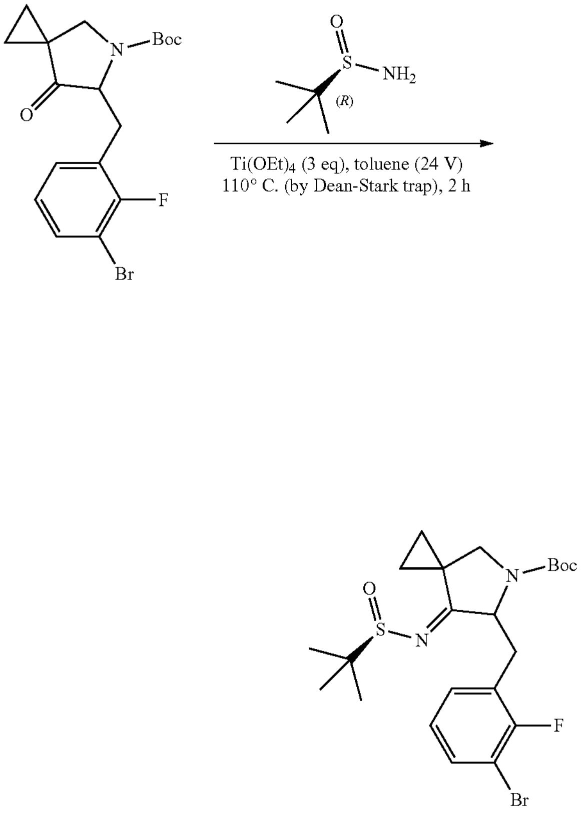

To a solution of tert-butyl 6-(3-bromo-2-fluorobenzyl)-7-oxo-5-azaspiro[2.4]heptane-5-carboxylate (100 g, 1.0 eq) in toluene (2.4 L) was added $Ti(OEt)_4$ (171.8 g, 3 eq) and (R)-2-methylpropane-2-sulfinamide (70 g, 2.3 eq). The mixture was heated to 110° C. and refluxed for 3-4 hrs. Totally 10 batches were set up, combined, cooled to 15-25° C. and poured into ice-water (1.5 kg) at 0° C. and the resulting white solid precipitate was filtered. The filtrate was extracted with ethyl acetate (3 L) and washed with brine (1 L) twice. The organic phases were dried over $Na_2SO_4$ (500 g) and concentrated to afford crude product which was purified by column chromatography ($SiO_2$, eluted with petroleum ether: ethyl acetate=100:1 to 5:1) to afford the title compound (954 g, 75.8% yield) as yellow oil. LCMS(method O)(ESI+): m/z 445.1 $(M+H-56)^+$, R.T=2.18 and 2.24.

Step-3: tert-butyl (6S,7S)-6-(3-bromo-2-fluorobenzyl)-7-(((R)-tert-butylsulfinyl)amino)-5-azaspiro[2.4]heptane-5-carboxylate

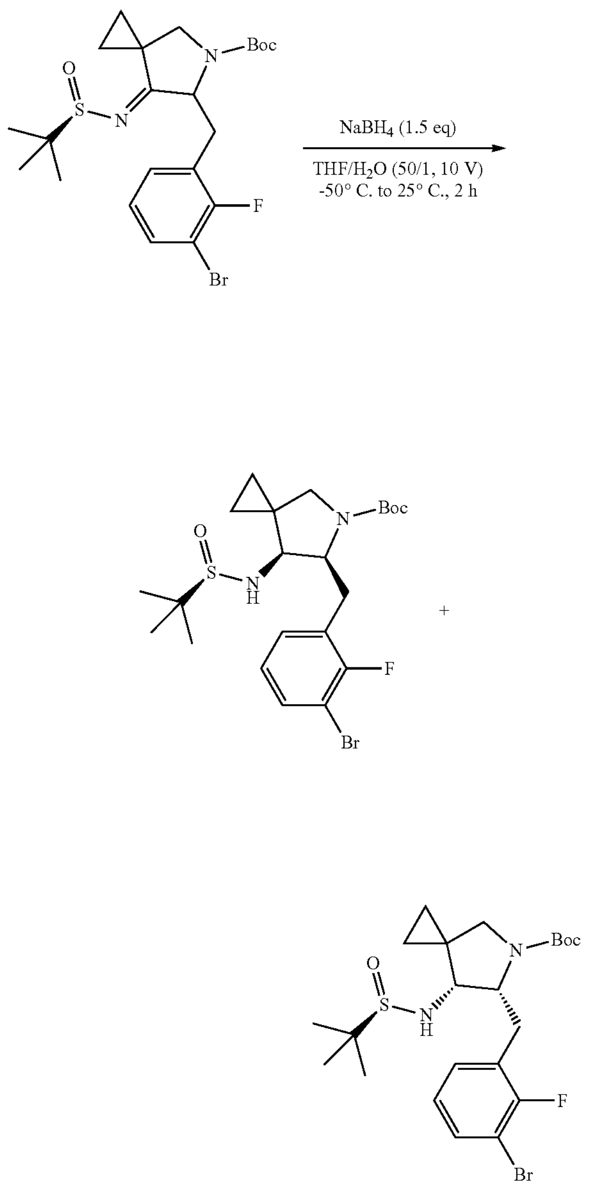

A solution of tert-butyl (E/Z)-6-(3-bromo-2-fluorobenzyl)-7-(((R)-tert-butylsulfinyl)imino)-5-azaspiro[2.4]heptane-5-carboxylate (150 g, 1.0 eq) in THF (1.5 L, 10 V) and $H_2O$ (30 mL, 0.2 V) was cooled to −50° C. $NaBH_4$ (17 g, 1.5 eq) was added to the reactor under nitrogen at −50° C. The mixture was stirred for at least 2 h at 25±5° C. MeOH (0.9 L) was added to the reactor at 25-40° C. and stirred for at least 3 h at 25±5° C. Another seven reactions were set up as above, combined and concentrated under vacuum at 45° C. The residue was purified by column chromatography ($SiO_2$, eluted with petroleum ether:ethyl acetate=10:1 to 1:1) to obtained crude product which was triturated with petroleum ether/ethyl acetate=8/1 (6 V) for 8 h to afford the desired compound (318 g, 30.1% yield) as white solid. LCMS (method 0)(ESI+): m/z 447.1 $(M+H-56)^+$, R.T=2.03.

Step-4: tert-butyl (6S,7S)-7-amino-6-(3-bromo-2-fluorobenzyl)-5-azaspiro[2.4]heptane-5-carboxylate (Intermediate 8)

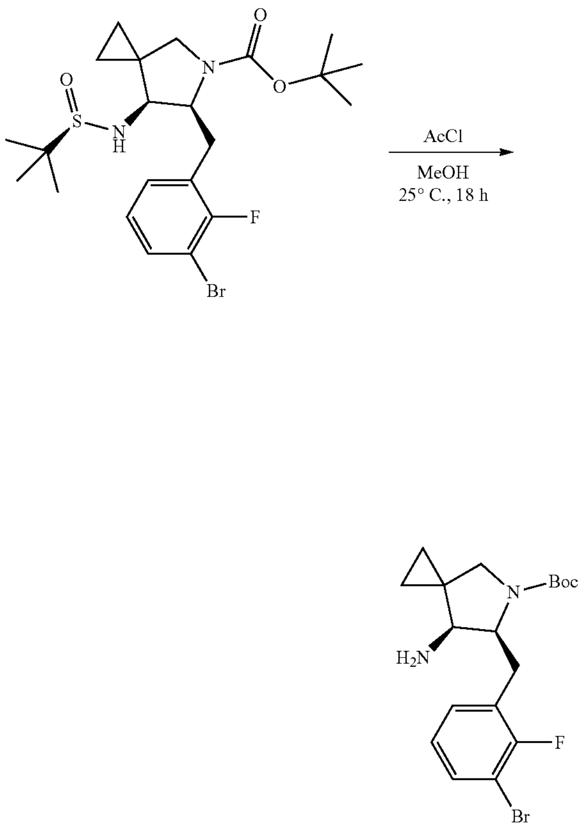

A solution of tert-butyl (6S,7S)-6-(3-bromo-2-fluorobenzyl)-7-(((R)-tert-butylsulfinyl)amino)-5-azaspiro[2.4]heptane-5-carboxylate (110 g, 1.0 eq) in MeOH (2.2 L) was cooled to 0° C. Then Acetyl chloride (18.9 g, 1.1 eq) was added dropwise and stirred for at least 18 h at 25+5° C. under nitrogen. Totally 3 batches were set up, combined and transferred to a saturated $NaHCO_3$ solution (2.2 L) at 0-5° C. The pH was maintained between 7 to 8, brine (1.1 L) added and the product extracted with ethyl acetate (2.2 L) twice. The organic phases were separated, combined and dried over $Na_2SO_4$ (300 g). The organic phase was concentrated under vacuum below 45° C. to give a residue, which was triturated with petroleum ether:ethyl acetate=10:1, 1 L for 8 h. The precipitated was collected and dried under vacuum <40° C. for 8 h to afford the title compound (178 g, 68.2% yield) as a yellow solid. $^1H$ NMR (400 MHz, methanol-$d_4$) δ 0.39-0.68 (m, 3H), 0.88-1.02 (m, 1H), 1.07-1.33 (m, 9H), 2.96-3.09 (m, 1H), 3.13 (m, 2H), 3.44-3.72 (m, 2H), 4.26 (ddd, 1H), 6.94-7.06 (m, 1H), 7.17 (br t, 1H), 7.48 (br t, 1H).

Synthesis of Intermediate 9 tert-butyl (6S,7S)-6-(3-bromo-2-fluorobenzyl)-7-(methylsulfonamido)-5-azaspiro[2.4]heptane-5-carboxylate (Intermediate 9)

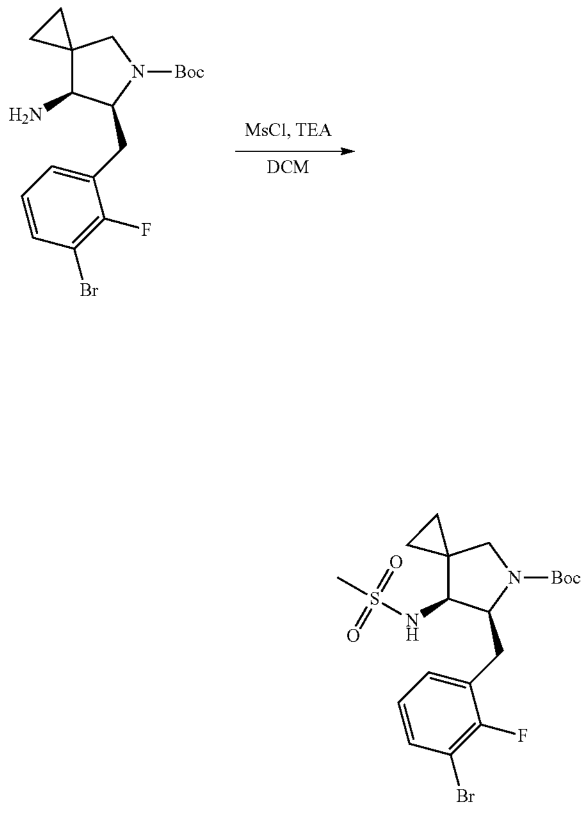

To a solution of tert-butyl (6S,7S)-7-amino-6-(3-bromo-2-fluorobenzyl)-5-azaspiro[2.4]heptane-5-carboxylate, intermediate 8 (1 g, 2.50 mmol, 1 eq) in dichloromethane (20 mL) was added triethylamine (1.05 mL, 7.51 mmol, 3 eq) and MsCl (250 μL, 3.23 mmol, 1.29 eq) at 0° C. The mixture was stirred at 20° C. for 3 hrs. Further MsCl (331 μL, 4.28 mmol, 1.71 eq) was added at 0° C. The resulting reaction mixture was stirred at 20° C. for an additional 5 hrs. After quenching by addition of 20 mL of water, the organic layer was separated, dried over $Na_2SO_4$, filtered and concentrated under reduced pressure. The residue was purified by column chromatography on silica gel (eluted with petroleum ether/ethyl acetate=50/1 to 2/1) to afford the title compound (0.98 g, 73.8% yield) as a white solid. $^1H$ NMR (400 MHz, chloroform-d) δ 0.44 (br s, 1H), 0.60-0.76 (m, 3H), 1.20-1.45 (m, 9H), 2.66-2.97 (m, 3H), 3.01-3.12 (m, 2H), 3.50-3.78 (m, 1H), 4.20 (br d, 1H), 4.36-4.54 (m, 2H), 6.94-7.02 (m, 1H), 7.11 (br s, 1H), 7.44 (br t, 1H).

Procedure for the Preparation of Intermediate 10 tert-butyl (6S,7S)-6-(3-bromo-2-fluorobenzyl)-7-(ethylsulfonamido)-5-azaspiro[2.4]heptane-5-carboxylate (Intermediate 10)

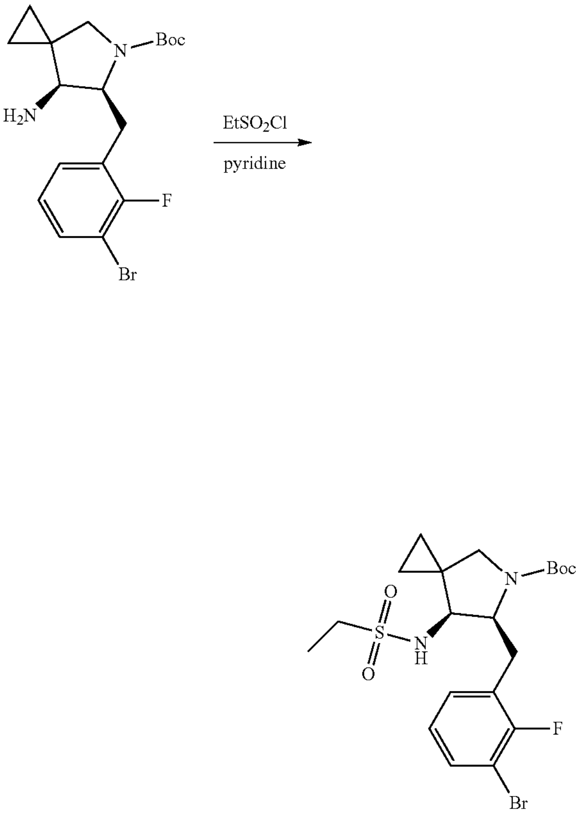

To a solution of tert-butyl (6S,7S)-7-amino-6-(3-bromo-2-fluorobenzyl)-5-azaspiro[2.4]heptane-5-carboxylate, intermediate 8 (6 g, 15 mmol, 1 eq) in pyridine (66 mL) was added ethanesulfonyl chloride (2.90 g, 22.54 mmol, 2.13 mL, 1.5 eq) dropwise at 25° C. The mixture was stirred at 90° C. for 12 hrs. The mixture was concentrated in vacuum. The residue was dissolved in ethyl acetate (100 mL). The organic phase was washed with 0.5 N HCl (2×30 mL), saturated $NaHCO_3$ solution (2×20 mL), brine (20 mL), dried over $Na_2SO_4$ and concentrated under reduced pressure to afford a residue. The residue was purified by column chromatography on silica gel (petroleum ether/ethyl acetate=100/1 to 1/1) to afford the title compound (3 g, 5.72 mmol, 38.1% yield) as a yellow solid. $^1H$ NMR (400 MHz, chloroform-d) δ 0.34-0.46 (m, 1H), 0.63-0.72 (m, 3H), 1.26-1.47 (m, 11H), 2.67-3.10 (m, 6H), 3.64-3.73 (m, 1H), 4.12-4.19 (m, 2H), 4.34-4.44 (m, 1H), 6.93-7.02 (m, 1H), 7.06-7.15 (m, 1H), 7.39-7.47 (m, 1H).

Synthesis of Intermediate 11 tert-butyl (6S,7S)-6-(3-bromo-2-fluorobenzyl)-7-((fluoromethyl)sulfonamido)-5-azaspiro[2.4]heptane-5-carboxylate (Intermediate 11)

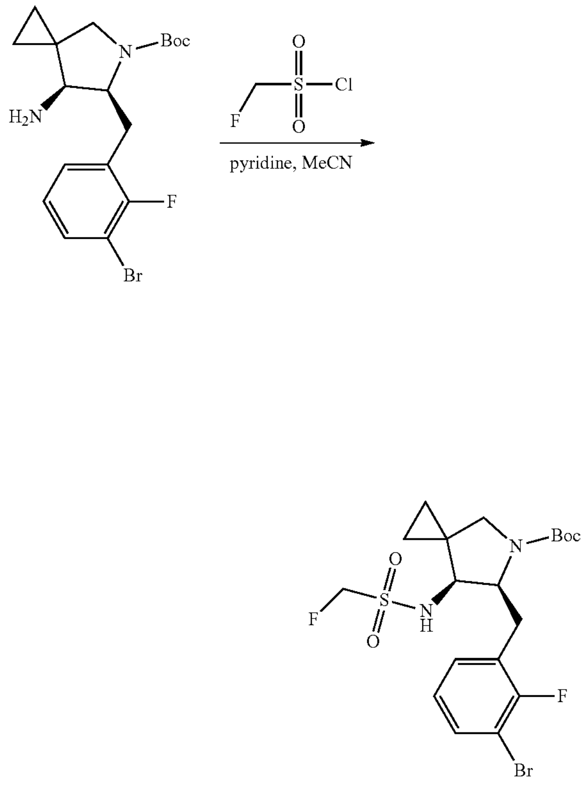

To a solution of tert-butyl (6S,7S)-7-amino-6-(3-bromo-2-fluorobenzyl)-5-azaspiro[2.4]heptane-5-carboxylate, intermediate 8 (0.75 g, 1.88 mmol, 1 eq) in acetonitrile (35 mL) were added pyridine (758 μL, 9.39 mmol, 5 eq) and fluoromethanesulfonyl chloride (1.37 M in acetonitrile, 1.65 mL, 1.2 eq) at 0° C. The reaction mixture was warmed to 20° C. and stirred at 20° C. for 3 hrs. Another reaction was set up as described above and the two batches were combined. The reaction mixture was concentrated under reduced pressure, the residue was poured into water (20 mL) and extracted with ethyl acetate (3×10 mL). The combined organic layers were dried over $Na_2SO_4$, filtered and concentrated under reduced pressure. The crude product was purified by chromatography on silica (eluted with petroleum ether/ethyl acetate=100/1 to 7/1) to afford the title compound (1.5 g, 2.73 mmol, 67.8% yield) as a white solid. $^1$H NMR (400 MHz, chloroform-d) δ ppm 0.38-0.76 (m, 4H) 1.25-1.50 (m, 9H) 2.72-3.12 (m, 3H) 3.68 (br s, 1H) 4.21 (br dd, 1H) 4.39 (br s, 1H) 4.76 (br d, J=10.26 Hz, 1H) 4.83-5.16 (m, 2H) 6.94-7.02 (m, 1H) 7.12 (br s, 1H) 7.44 (br t, 1H).

Synthesis of Intermediate 12 tert-butyl (6S,7S)-6-(3-bromo-2-fluorobenzyl)-7-((difluoromethyl)sulfonamido)-5-azaspiro[2.4]heptane-5-carboxylate (Intermediate 12)

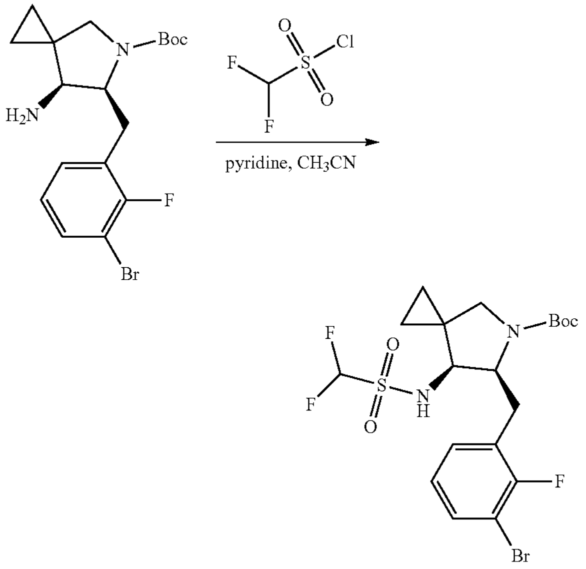

To a solution of tert-butyl (6S,7S)-7-amino-6-(3-bromo-2-fluorobenzyl)-5-azaspiro[2.4]heptane-5-carboxylate, intermediate 8 (0.5 g, 1.25 mmol, 1 eq) in acetonitrile (12 mL) were added pyridine (505 μL, 6.26 mmol, 5 eq) and difluoromethanesulfonyl chloride (226 mg, 1.50 mmol, 1.2 eq) dropwise at 0° C. The reaction mixture was stirred at 25° C. for 12 hrs. Another four reactions were set up as above, the five reaction mixtures were combined and quenched by addition of 60 mL of water and extracted with ethyl acetate (2-60 mL). The combined organic layers were dried over $Na_2SO_4$, filtered and concentrated under reduced pressure. The residue was purified by column chromatography silica gel (eluted with petroleum ether/ethyl acetate=100/0 to 10/1) to afford the title compound (1.9 g, 56.2% yield) as a white solid. $^1$H NMR (400 MHz, methanol-$d_4$) δ 0.58-0.76 (m, 3H), 1.00-1.29 (m, 10H), 2.65-2.92 (m, 1H), 3.08 (br d, 1H), 3.20 (br d, 1H), 3.68 (br d, 1H), 4.20 (br d, 1H), 4.34 (br d, 1H), 6.49-6.82 (m, 1H), 7.03 (br t, 1H), 7.16 (br t, 1H), 7.36-7.55 (m, 1H).

Synthesis of Intermediate 13

Step 1: 3-bromo-2,5-difluorobenzaldehyde

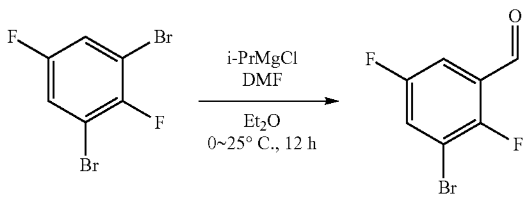 [SMILES: Fc1cc(Br)c(F)c(Br)c1 ; O=Cc1cc(F)cc(Br)c1F]

To a solution of 1,3-dibromo-2,5-difluorobenzene (2.4 kg, 8.83 mol, 1 eq) in ethyl ether (24 L) was added dropwise i-PrMgCl (2 M in THF, 4.41 L, 1 eq) at 0° C., the mixture was stirred at 0° C. for 2 h, and then N,N-dimethylformamide (645 g, 8.83 mol, 1 eq) was added dropwise at 0° C. The resulting mixture was stirred at 25° C. for 10 h. The mixture was poured into saturated aqueous $NH_4Cl$ solution (15 L), and extracted with petroleum ether (3×10 L). The organic layer was washed with brine (10 L), and dried over $Na_2SO_4$, concentrated under reduced pressure to give crude product. The residue was purified by column chromatography ($SiO_2$, Petroleum ether/Ethyl acetate=1/0 to 20/1) to afford the title compound (1.3 kg, 62% yield) as a colourless oil. $^1H$ NMR (400 MHz, DMSO-d6) δ ppm 7.63 (ddd, 1H) 8.09 (ddd, 1H) 10.12 (d, 1H).

Step 2: (3-bromo-2,5-difluorophenyl)methanol

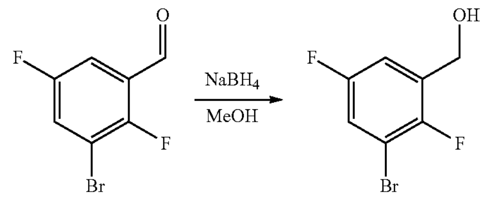 [SMILES: "MeOH" ; O=Cc1cc(F)cc(Br)c1F ; "NaBH4" ; OCc1cc(F)cc(Br)c1F]

To a solution of 3-bromo-2,5-difluorobenzaldehyde (1.3 kg, 5.88 mol, 1 eq) in methanol (13 L) was added $NaBH_4$ (289 g, 7.65 mol, 1.3 eq) at 0° C. Then the reaction mixture was warmed to 25° C. and stirred for 12 h. The mixture was poured into saturated aqueous $NH_4Cl$ solution (10 L) and extracted with ethyl acetate (3×5 L). The organic layer was washed with brine (5 L), dried over $Na_2SO_4$ and concentrated under reduced pressure to afford the title compound (1.4 Kg, 77.8% yield) as a white solid which was used in the next step without further purification. $^1H$ NMR (400 MHz, $CDCl_3$) δ 1.98 (br s, 1H), 4.78 (s, 2H), 7.19 (dddd, 2H).

Step 3: 1-bromo-3-(bromomethyl)-2,5-difluorobenzene

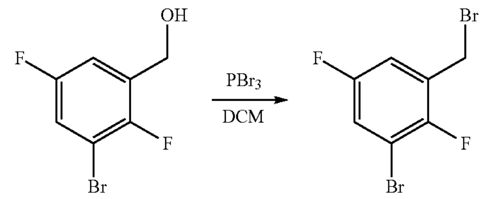

To a solution of (3-bromo-2,5-difluorophenyl)methanol (1.2 kg, 5.38 mol, 1 eq) in methylene chloride (12 L) was added tribromophosphane (728 g, 2.69 mol, 0.5 eq) at 0° C. The mixture was stirred at 25° C. for 12 h. The organic layer was poured into the saturated aqueous $NaHCO_3$ solution (10 L) and extracted with petroleum ether (3×5 L). The organic layer was washed with brine (5 L), dried over $Na_2SO_4$ and concentrated under reduced pressure to afford the title compound (1.2 kg, 74.1% yield) as a white solid which was used in the next step without further purification. $^1H$ NMR (400 MHz, DMSO-d&) S 4.67 (d, 2H), 7.49 (ddd, 1H), 7.66 (ddd, 1H).

Step 4: tert-butyl 6-(3-bromo-2,5-difluorobenzyl)-7-oxo-5-azaspiro[2.4]heptane-5-carboxylate

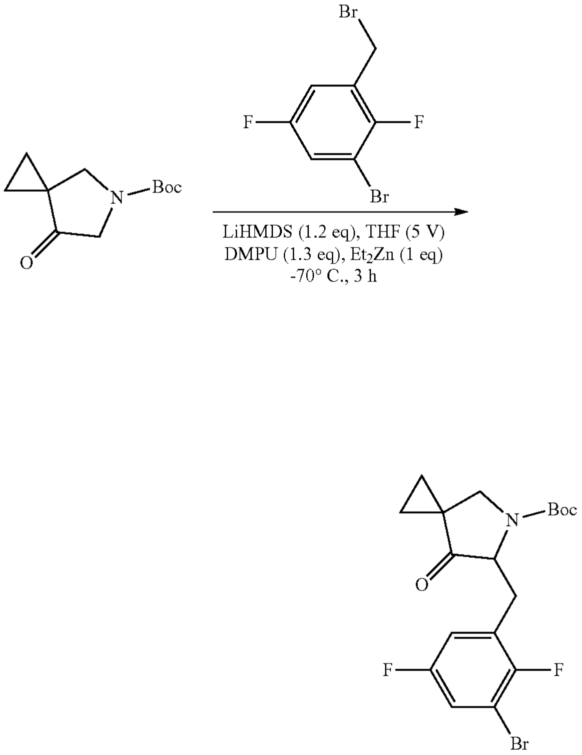

A mixture of tetrahydrofuran (200 mL) and [bis(trimethylsilyl)amino]lithium (1 M in tetrahydrofuran, 1.14 L, 1.2 eq) was cooled to −70° C. and then a solution of tert-butyl 7-oxo-5-azaspiro[2.4]heptane-5-carboxylate (200 g, 947 mmol, 1 eq) in tetrahydrofuran (400 mL) was added dropwise at −70° C. The resulting mixture was stirred at −70° C. After 2 h, diethylzinc (1 M in toluene, 947 mL, 1 eq), 1,3-dimethylhexahydropyrimidin-2-one (149 mL, 1.23 mol, 1.3 eq) and a solution of 1-bromo-3-(bromomethyl)-2,5-difluoro-benzene (325 g, 1.14 mol, 1.2 eq) in tetrahydrofuran (400 mL) was added dropwise at −70° C. The mixture was stirred at −70° C. for 2 h. Three additional batches were set up as described above. All four reaction mixtures were combined. The reaction mixture was quenched by ice water (10 L) at 0° C. The precipitate was filtered, the filter cake was washed with ethyl acetate (5 L) and the filtrate extracted with ethyl acetate (5 L) three times. The combined organic layers were washed with aqueous NaCl (sat. 2 L), dried over $Na_2SO_4$, filtered and concentrated under reduced pressure to afford a residue. The residue was purified by flash silica gel chromatography (eluent of 0-100% ethyl acetate/petroleum ether gradient) to afford the title compound (1.2 Kg, 65% yield) as a white solid. $^1H$ NMR (400 MHz, DMSO-$d_6$) δ ppm 0.84-1.21 (m, 4H) 1.27-1.47 (m, 9H) 2.89-3.19 (m, 2H) 3.21-3.31 (m, 1H) 3.60-3.87 (m, 1H) 4.36 (br 1H) 6.85-7.23 (m, 1H), 7.63 (br s, 1H).

Step 5: tert-butyl (E/Z)-6-(3-bromo-2,5-difluorobenzyl)-7-(((R)-tert-butylsulfinyl)imino)-5-azaspiro[2.4]heptane-5-carboxylate

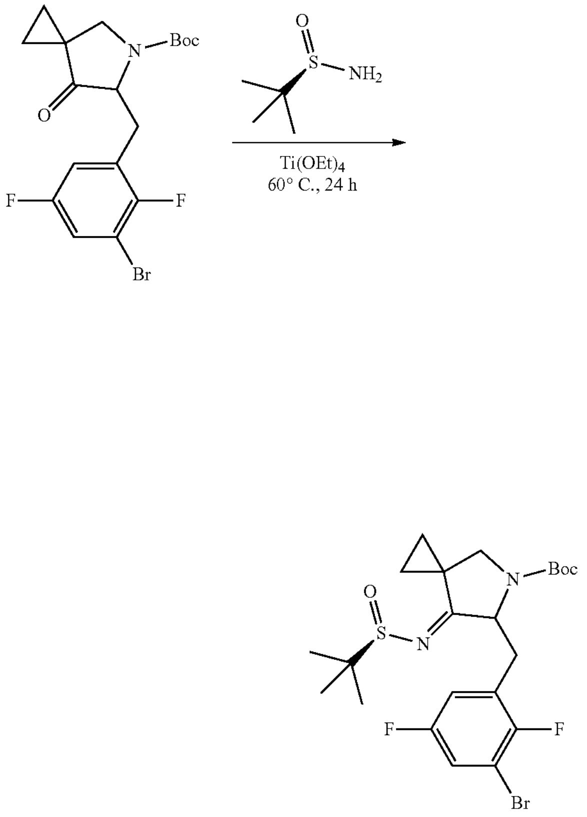

To a mixture of tert-butyl 6-(3-bromo-2,5-difluorobenzyl)-7-oxo-5-azaspiro[2.4]heptane-5-carboxylate (200 g, 480 mmol, 1 eq), (R)-2-methylpropane-2-sulfinamide (116.5 g, 961 mmol, 2 eq), tetraethoxytitanium (548 g, 2.40 mol, 498 mL, 5 eq) was degassed, purged with $N_2$ three times and then the mixture was stirred at 60° C. for 24 h under $N_2$ atmosphere. Five additional batches were set up as described above. All six reaction mixtures were combined. The combined reaction was diluted with tetrahydrofuran (1.1 L) and poured into ice water (2.2 L). The collected reaction mixture was filtered through celite and washed by tetrahydrofuran (5 L) and the filtrate was extracted with ethyl acetate (2 L) three times. The combined organic layers were washed with aqueous NaCl (sat, 3 L), dried over $Na_2SO_4$, filtered and concentrated under reduced pressure to afford a residue. The residue was purified by flash silica gel chromatography (eluent of 0-100% ethyl acetate/petroleum ether gradient) to afford the title compound (1.1 Kg, 70% yield) as yellow oil. $^1$H NMR (400 MHz, DMSO-$d_6$) δ ppm 0.81-1.07 (m, 2H) 1.10-1.25 (m, 16H) 1.27-1.41 (m, 4H) 2.87-3.24 (m, 2H) 3.35-3.78 (m, 2H) 5.10-5.59 (m, 1H) 6.84-7.28 (m, 1H) 7.52-7.74 (m, 1H).

Step 6: tert-butyl (6S,7S)-6-(3-bromo-2,5-difluorobenzyl)-7-(((R)-tert-butylsulfinyl)amino)-5-azaspiro[2.4]heptane-5-carboxylate

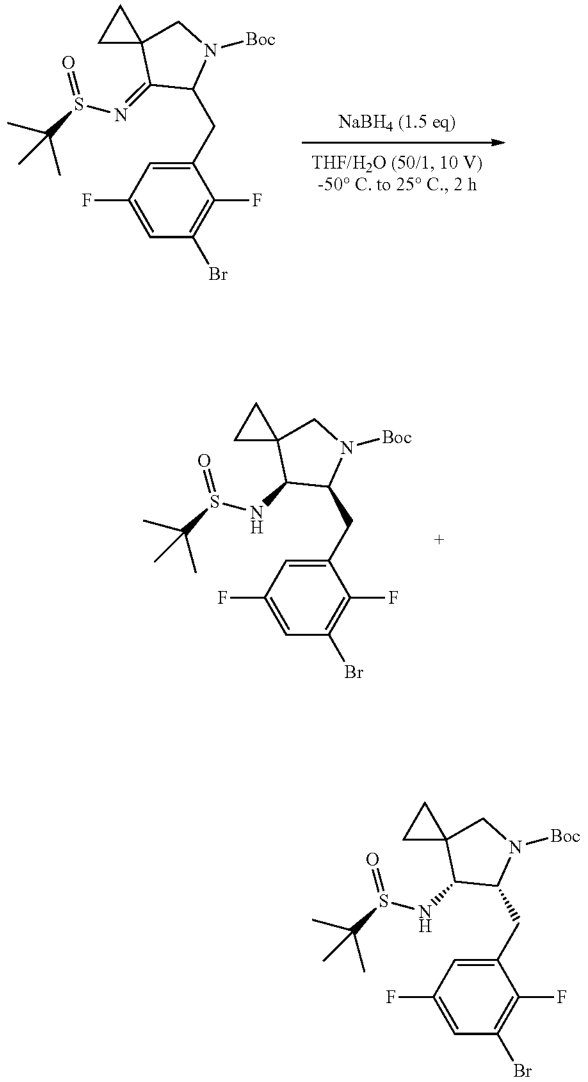

To a solution of tert-butyl (E/Z)-6-(3-bromo-2,5-difluorobenzyl)-7-(((R)-tert-butylsulfinyl)imino)-5-azaspiro[2.4]heptane-5-carboxylate (220 g, 424 mmol, 1 eq) in tetrahydrofuran (2 L) and $H_2O$ (40 mL) was added slowly sodium borohydride (24 g, 635 mmol, 1.5 eq) at −50° C. The mixture was stirred at 20° C. for 2 h. Four additional batches were set up as described above. All five reaction mixtures were combined. The combined reaction mixture was quenched by addition ice water (1 L) at 0° C., and then diluted with ethyl acetate (500 mL) and extracted with ethyl acetate (2 L) three times. The combined organic layers were washed with aqueous NaCl (sat. 2 L), dried over $Na_2SO_4$, filtered and concentrated under reduced pressure to afford crude product which was purified by flash silica gel chromatography (eluent of 0-100% ethyl acetate/petroleum ether gradient) to afford the title compound (380 g, 34.5% yield) as a white solid. $^1$H NMR (400 MHz, DMSO-d6) δ ppm 0.46-0.80 (m, 3H) 0.96-1.18 (m, 16H) 1.24 (br d, 3H) 2.55-2.75 (m, 1H) 2.84-3.25 (m, 2H) 3.56 (br d, 1H) 3.97 (br s, 2H) 4.87 (br d, 1H) 7.11-7.70 (m, 2H).

Step 7: tert-butyl (6S,7S)-7-amino-6-(3-bromo-2,5-difluorobenzyl)-5-azaspiro[2.4]heptane-5-carboxylate (Intermediate 13)

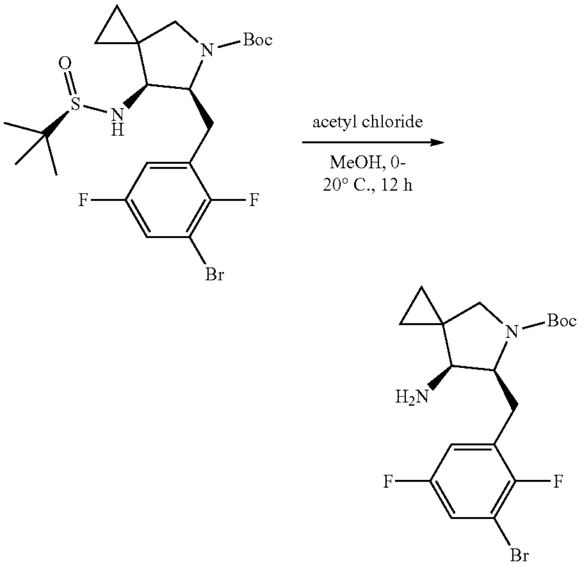

A mixture of methanol (7.6 L) and tert-butyl (6S,7S)-6-(3-bromo-2,5-difluorobenzyl)-7-(((R)-tert-butylsulfinyl)amino)-5-azaspiro[2.4]heptane-5-carboxylate (380 g, 729 mmol, 1 eq) was cooled to 0° C. and then acetyl chloride (60.06 g, 765 mmol, 1.05 eq) was added dropwise and purged with $N_2$ for three times at 0° C. The mixture was stirred at 20° C. for 12 h under $N_2$ atmosphere. The reaction mixture was poured into ethyl acetate/saturated sodium bicarbonate solution (1/1, 10 L) at 0° C. and extracted with ethyl acetate (2 L) three times. The combined organic layers were washed with aqueous NaCl (1 L), dried over $Na_2SO_4$, filtered and concentrated under reduced pressure to afford a residue. The residue was purified by flash silica gel chromatography (eluent of 0~100% ethyl acetate/petroleum ether gradient) to afford the title compound (185 g, 60% yield) as a white solid. LCMS(method J)(ESI+): m/z=361 $(M-56)^+$, RT: 2.130 min.

Synthesis of Intermediate 14

Step 1: tert-butyl (6S,7S)-6-(3-bromo-2,5-difluorobenzyl)-7-(methylsulfonamido)-5-azaspiro[2.4]heptane-5-carboxylate (Intermediate 14)

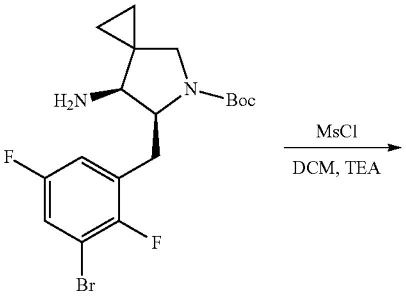

-continued

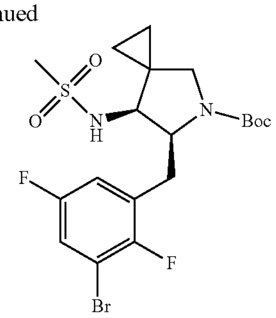

To a mixture of tert-butyl (6S,7S)-7-amino-6-(3-bromo-2,5-difluorobenzyl)-5-azaspiro[2.4]heptane-5-carboxylate, intermediate 13 (2.5 g, 5.99 mmol, 1 eq) and triethylamine (2.50 mL, 17.97 mmol, 3 eq) in dichloromethane (25 mL) was added methanesulfonyl chloride (1.64 mL, 21.21 mmol, 3.54 eq) in one portion at 0° C. under nitrogen. The mixture was stirred at 25° C. for 12 h. The mixture was poured into saturated sodium bicarbonate (50 mL) and stirred for 3 mins. The aqueous phase was extracted with triethylamine (3×25 mL). The combined organic phase was dried with anhydrous sodium sulfate, filtered and concentrated under reduced pressure to afford crude product. The mixture was purified by column chromatography (silica, Petroleum ether/Ethyl acetate=I/O to 1/1) to afford the title compound (2.8 g, yield 90.5%) as a white solid. LCMS(method M)(ESI+): m/z 439.1 $(M-56)^+$, RT: 0.802 min.

Synthesis of Intermediate 15 tert-butyl (6S,7S)-7-amino-6-((2,5-difluoro-[1,1'-biphenyl]-3-yl)methyl)-5-azaspiro[2.4]heptane-5-carboxylate (Intermediate 15)

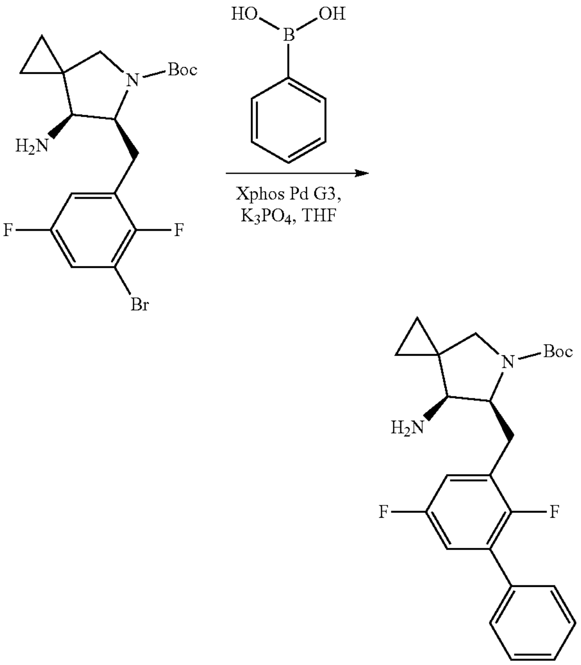

To a solution of tert-butyl (6S,7S)-7-amino-6-(3-bromo-2,5-difluorobenzyl)-5-azaspiro[2.4]heptane-5-carboxylate, intermediate 13 (1.93 g, 4.63 mmol, 1 eq) in tetrahydrofuran (20 mL) was added XPhos-Pd-G3 (391 mg, 462 umol, 0.1 eq), potassium phosphate (2.95 g, 13.9 mmol, 3 eq) and phenylboronic acid (1.13 g, 9.25 mmol, 2 eq). The mixture was stirred at 80° C. for 12 hours. The mixture was poured into water (50 mL) and extracted with dichloromethane (3×40 mL). The organic layer was washed with brine (30 mL), and dried over magnesium sulfate, concentrated under reduced pressure to afford crude product. The residue was purified by column chromatography ($SiO_2$, Petroleum ether/Ethyl acetate=3:1 to 2:1) to afford the title compound (1.87 g, 97.6% yield) as yellow oil. LCMS(method M) (ESI+): m/z 359.0 ($M-56^+$), RT: 0.670 min.

Synthesis of Intermediate 16

Step 1: N-((6S,7S)-6-((2,5-difluoro-[1,1'-biphenyl]-3-yl)methyl)-5-azaspiro[2.4]heptan-7-yl)-1-fluoromethanesulfonamide

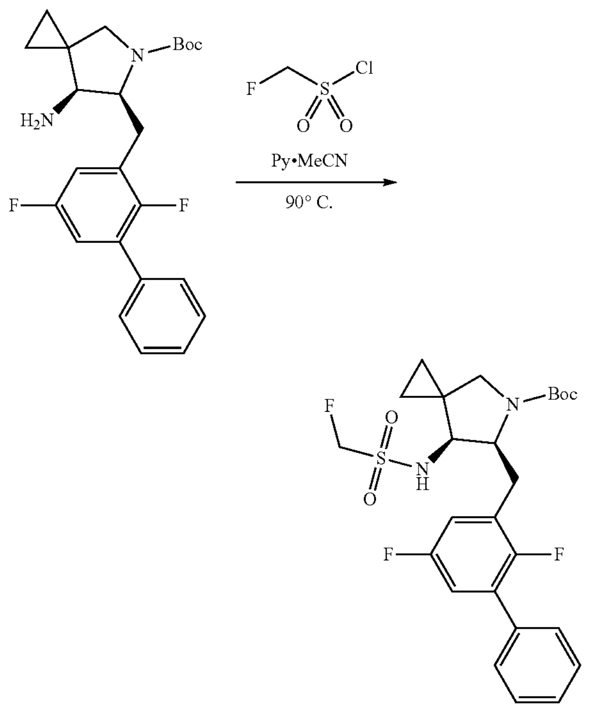

To a solution of tert-butyl (6S,7S)-7-amino-6-((2,5-difluoro-[1,1'-biphenyl]-3-yl)methyl)-5-azaspiro[2.4]heptane-5-carboxylate (1.87 g, 4.51 mmol, 1 eq) in acetonitrile (20 mL) was added pyridine (1.82 mL, 22.56 mmol, 5 eq) and fluoromethanesulfonyl chloride (777 mg, 5.87 mmol, 1.2 eq). The mixture was stirred at 90° C. for 12 hours. The mixture was poured into the saturated aqueous ammonium chloride solution (80 mL) and extracted with dichloromethane (3×50 mL). The organic layer was washed with brine (100 mL), and dried over magnesium sulfate, concentrated under reduced pressure to afford crude product. The residue was purified by column chromatography ($SiO_2$, Petroleum ether/Ethyl acetate=4:1 to 3:1) to afford the title compound (1.75 g, 76% yield) as yellow oil. LCMS(method M)(ESI+): m/z 411.1 $(M+H-100)^+$, RT: 1.145 min.

Step 2: N-((6S,7S)-6-((2,5-difluoro-[1,1'-biphenyl]-3-yl)methyl)-5-azaspiro[2.4]heptan-7-yl)-1-fluoromethanesulfonamide hydrochloride (Intermediate 16)

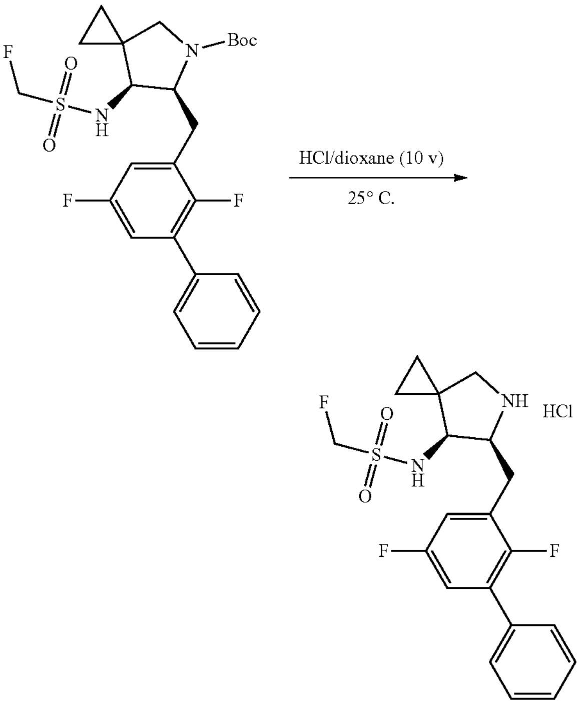

To a solution of N-((6S,7S)-6-((2,5-difluoro-[1,1'-biphenyl]-3-yl)methyl)-5-azaspiro[2.4]heptan-7-yl)-1-fluoromethanesulfonamide (1.75 g, 3.52 mmol, 1 eq) in HCl/dioxane (20 mL) was stirred at 25° C. for 2 hours. The reaction mixture was concentrated under reduced pressure to afford the title compound (1.3 g, 93.1% yield) as yellow oil which was used in the next step without further purification. LCMS(method M)(ESI+): m/z 411.1 $(M+H)^+$, RT: 0.810 min

Synthesis of Intermediate 17 tert-butyl (6S,7S)-6-(3-bromo-2,5-difluorobenzyl)-7-((difluoromethyl)sulfonamido)-5-azaspiro[2.4]heptane-5-carboxylate (Intermediate 17

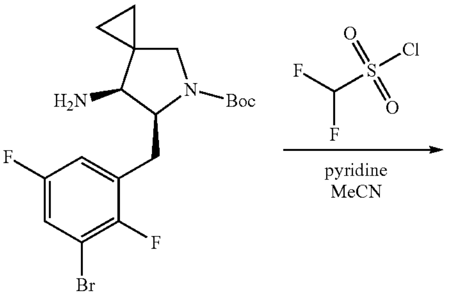

-continued

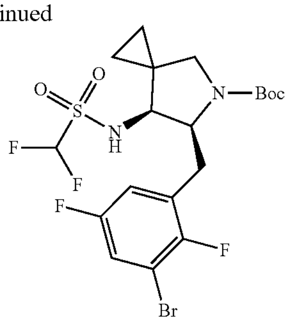

To a solution of tert-butyl (6S,7S)-7-amino-6-(3-bromo-2,5-difluorobenzyl)-5-azaspiro[2.4]heptane-5-carboxylate, intermediate 13 (1.25 g, 3.00 mmol, 1 eq) in acetonitrile (50 mL) were added difluoromethanesulfonyl chloride (902 mg, 5.99 mmol, 2 eq) and pyridine (1.21 mL, 14.98 mmol, 5 eq) at 0° C. The reaction mixture was stirred at 20° C. for 12 hrs. The mixture was poured into water (100 mL) and extracted with ethyl acetate (3-50 mL). The combined organic layers were dried over $Na_2SO_4$, filtered and the filtrate was concentrated under reduced pressure. The crude product was purified by prep-TLC (petroleum ether/ethyl acetate=3/1) to afford the title compound (0.98 g, 55.4% yield) as white solid. $^1H$ NMR (400 MHz, chloroform-d) δ 0.29-0.77 (m, 4H), 1.25-1.46 (m, 9H), 2.71-3.20 (m, 3H), 3.70 (br s, 1H), 4.26-4.34 (m, 1H), 4.40 (br s, 1H), 4.63 (br s, 1H), 5.95-6.32 (m, 1H), 6.90 (br s, 1H), 7.20 (br s, 1H).

Example 1 & 2. N-(6-([1,1'-biphenyl]-3-ylmethyl)-5-(2-fluoropropanoyl)-5-azaspiro[2.4]heptan-7-yl) methanesulfonamide_isomer 1 & N-(6-([1,1'-biphenyl]-3-ylmethyl)-5-(2-fluoropropanoyl)-5-azaspiro [2.4]heptan-7-yl)methanesulfonamide_isomer 2

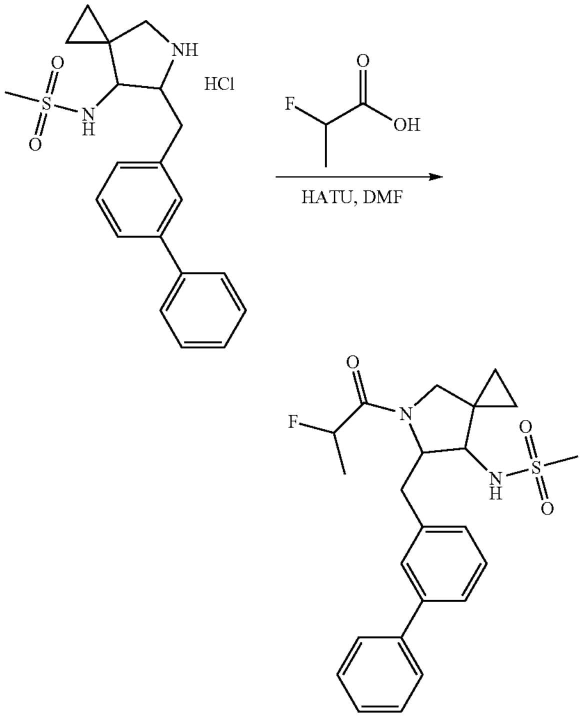

To a mixture of N-(6-([1,1'-biphenyl]-3-ylmethyl)-5-azaspiro[2.4]heptan-7-yl)methanesulfonamide hydrochloride_cis racemic, intermediate 3 (80 mg, 224 μmol) and 2-fluoropropanoic acid (23 mg, 245 μmol) in DMF (0.5 mL) was added DIPEA (87 mg, 673 μmol) and HATU (111 mg, 292 μmol) in one portion at 25° C. under $N_2$. The mixture was stirred at 25° C. for 2 hours. The mixture was purified by prep-HPLC: column: Waters Xbridge Prep OBD C18 150*40 mm*10 μm; mobile phase: [water (0.05% $NH_3H_2O$+10 mM $NH_4HCO_3$)-ACN]; B %: 40%-60%, 8 min to afford the title compound, isomer 1 (12 mg, 12% yield) as a white solid and isomer 2 (8.0 mg, 8% yield) as a white solid.

Example 3. N-(6-([1,1'-biphenyl]-3-ylmethyl)-5-(azetidine-1-carbonyl)-5-azaspiro[2.4]heptan-7-yl) ethanesulfonamide_cis racemic

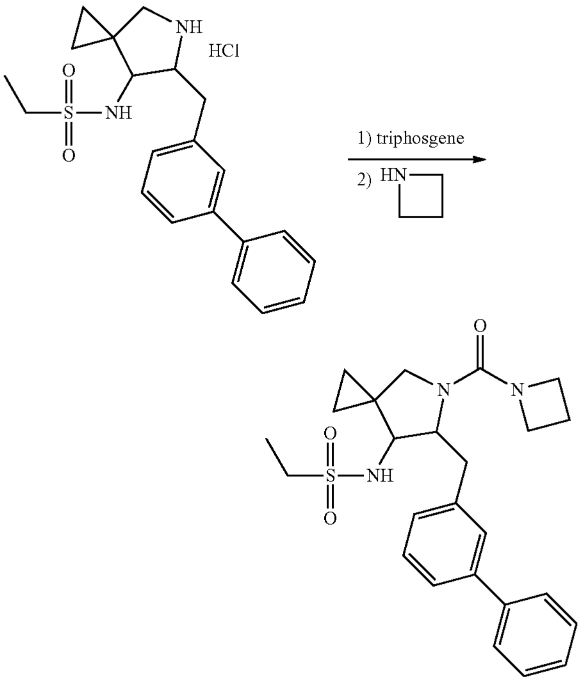

A mixture of N-(6-([1,1'-biphenyl]-3-ylmethyl)-5-azaspiro[2.4]heptan-7-yl)ethanesulfonamide hydrochloride_cis racemic, intermediate 4 (50 mg, 135 μmol, 1 eq), bis(trichloromethyl) carbonate (60 mg, 202 μmol, 1.5 eq), diisopropylethylamine (71 μL, 405 μmol, 3 eq) in dichloromethane (1.0 mL) was degassed and purged with nitrogen for 3 times, and then the mixture was stirred at 20° C. for 2 h under nitrogen atmosphere. The reaction mixture was concentrated under reduced pressure to give crude product as brown oil, which was used for next step directly. To a solution of crude product in tetrahydrofuran (1.0 mL) was added diisopropylethylamine (101 μL, 577 μmol, 5 eq). Then azetidine (23 μL, 346 μmol, 3 eq) was added at 20° C. The mixture was stirred at 20° C. for 2 h. The reaction mixture was concentrated under reduced pressure to give a residue which was purified by prep-HPLC (TFA condition) to afford the title compound (40 mg, 72% yield) as white solid.

Example 4. N-(6-([1,1'-biphenyl]-3-ylmethyl)-5-(2,2,2-trifluoroacetyl)-5-azaspiro[2.4]heptan-7-yl)methanesulfonamide_cis racemic

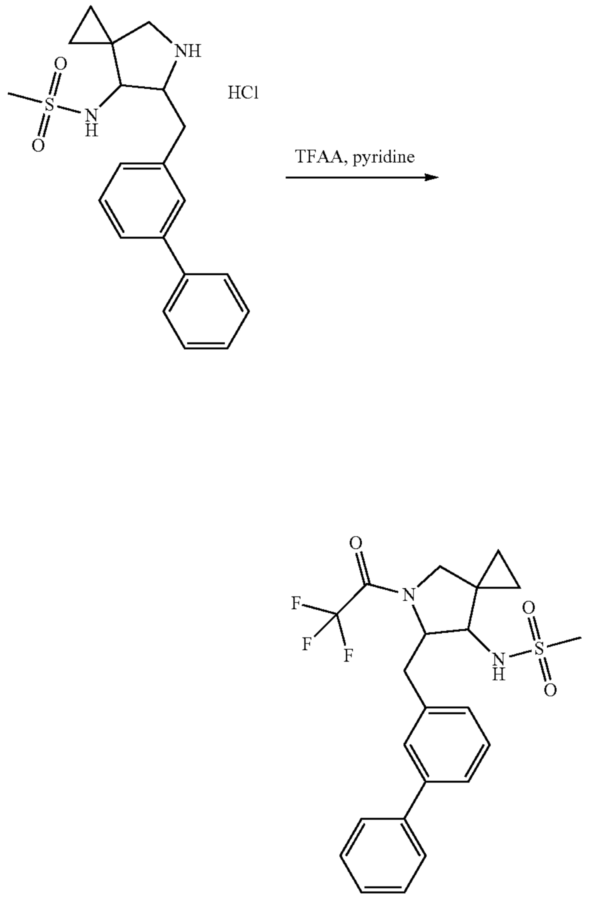

To a mixture of N-(6-([1,1'-biphenyl]-3-ylmethyl)-5-azaspiro[2.4]heptan-7-yl)methanesulfonamide hydrochloride_cis racemic, intermediate 3 (50 mg, 140 μmol, 1 eq) in Pyridine (1.0 mL) was added TFAA (29 μL, 210 μmol, 1.5 eq) in one portion at 0° C. under $N_2$. The mixture was stirred at 20° C. for 1 hour. The reaction mixture was poured into $H_2O$ (10 mL). The mixture was extracted with ethyl acetate (2×10 mL). The organic phase was washed with brine (10 mL), dried over anhydrous $Na_2SO_4$, concentrated in vacuum to give a residue. The residue was purified by prep-HPLC (column. Waters Xbridge BEH C18 100*30 mm*10 μm; mobile phase: [water (10 mM $NH_4HCO_3$)-MeCN]; B %: 45%-75%, 6 min) to afford the title compound (10 mg) as a white solid.

Example 5. N-(6-([1,1'-biphenyl]-3-ylmethyl)-5-(2,2-difluoroacetyl)-5-azaspiro[2.4]heptan-7-yl)methanesulfonamide_cis racemic

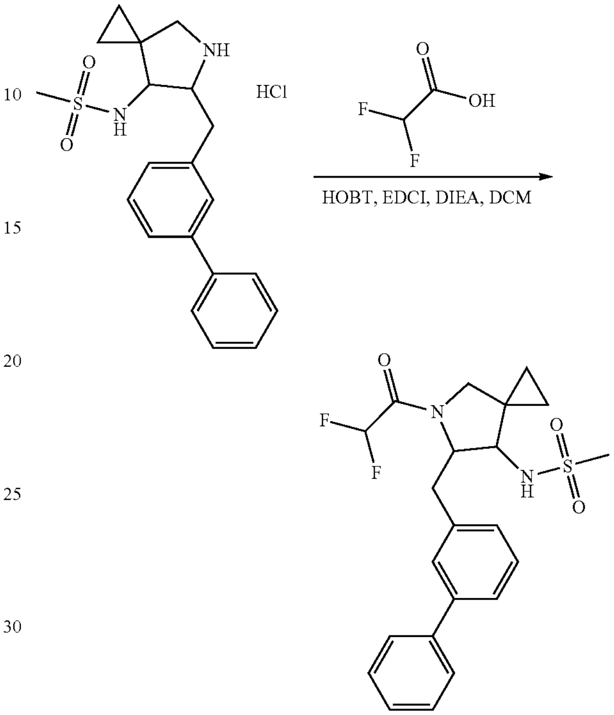

To a solution of N-(6-([1,1'-biphenyl]-3-ylmethyl)-5-azaspiro[2.4]heptan-7-yl)methanesulfonamide hydrochloride_cis racemic, intermediate 3 (40 mg, 112 μmol, 1 eq) in dichloromethane (2.0 mL) was added 2,2-difluoroacetic acid (14 μL, 224 μmol, 2 eq), HOBT (30 mg, 224 μmol, 2 eq), EDCI (43 mg, 224 μmol, 2 eq) and DIEA (78 μL, 449 μmol, 4 eq), the reaction solution was stirred at 25° C. for 12 hours. The reaction solution was concentrated under reduced pressure to give the crude product, which was purified by pre-HPLC (column: Phenomenex Luna C18 150*30 mm*5 μm; mobile phase: [water (0.1% TFA)-MeCN]; B %: 45%-75%, 8 min) to afford the title compound (17 mg, 34% yield) as off-white solid.

Example 6. methyl 6-([1,1'-biphenyl]-3-ylmethyl)-7-(ethylsulfonamido)-5-azaspiro[2.4]heptane-5-carboxylate_cis racemic

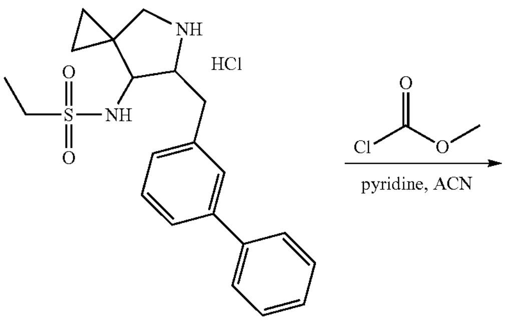

-continued

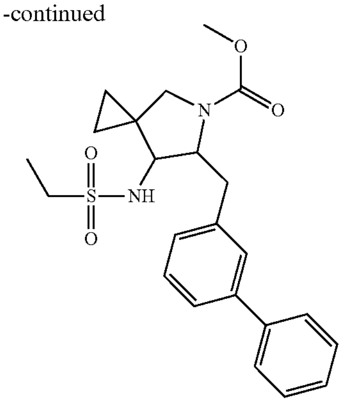

To a solution of N-(6-([1,1'-biphenyl]-3-ylmethyl)-5-azaspiro[2.4]heptan-7-yl)ethanesulfonamide hydrochloride_cis racemic, intermediate 3 (50 mg, 135 μmol, 1 eq) in acetonitrile (1.0 mL) was added pyridine (33 μL, 405 μmol, 3 eq) and methyl carbonochloridate (21 μL, 270 μmol, 2 eq) at 0° C. The mixture was stirred at 25° C. for 12 hrs. The mixture was poured into the water (5.0 mL) and extracted with ethyl acetate (5.0 mL×3). The organic layer was washed with brine (5.0 mL), and dried over $MgSO_4$, and concentrated by the reduced pressure to give crude product. The residue was purified by prep-HPL, column: Waters Xbridge BEH C18 100*30 mm*110 μm; mobile phase: [water (10 mM $NH_4HCO_3$)-MeCN]; B %: 30%/-50%. 6 min to afford the title compound (32 mg, 55% yield) as a white solid.

Example 7. N-(6-([1,1'-biphenyl]-3-ylmethyl)-5-isobutyryl-5-azaspiro[2.4]heptan-7-yl)ethanesulfonamide_cis racemic

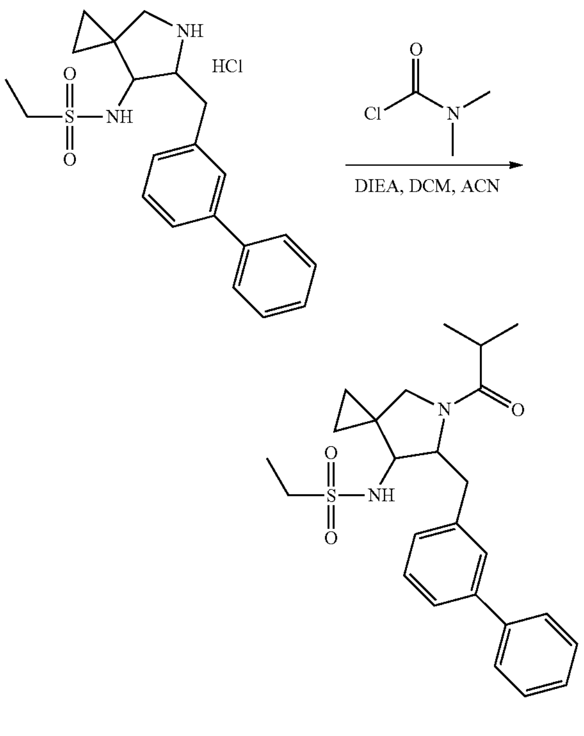

To a solution of N-(6-([1,1'-biphenyl]-3-ylmethyl)-5-azaspiro[2.4]heptan-7-yl)ethanesulfonamide hydrochloride_cis racemic, intermediate 4 (50 mg, 135 μmol) and N,N-diisopropylethylamine (26 mg, 202 μmol) in dichloromethane (1.0 mL) and acetonitrile (0.25 mL) was added a solution of 2-methylpropanoyl chloride (17 mg, 162 μmol) drop-wise at 0° C. over a period of 2 mins under nitrogen. The reaction mixture was warmed to 15° C. over a period of 2 mins and stirred at 15° C. for 3 hours. The reaction mixture concentrated under reduced pressure to give a residue. The residue was purified by prep-HPLC to afford the title compound (24 mg, 41% yield) was obtained as a white solid.

Example 8. N-(6-((3'-fluoro-[1,1'-biphenyl]-3-yl)methyl)-5-isobutyryl-5-azaspiro[2.4]heptan-7-yl)methanesulfonamide_cis racemic Step 1: tert-butyl 6-((3'-fluoro-[1,1'-biphenyl]-3-yl)methyl)-7-(methylsulfonamido)-5-azaspiro[2.4]heptane-5-carboxylate_cis racemic

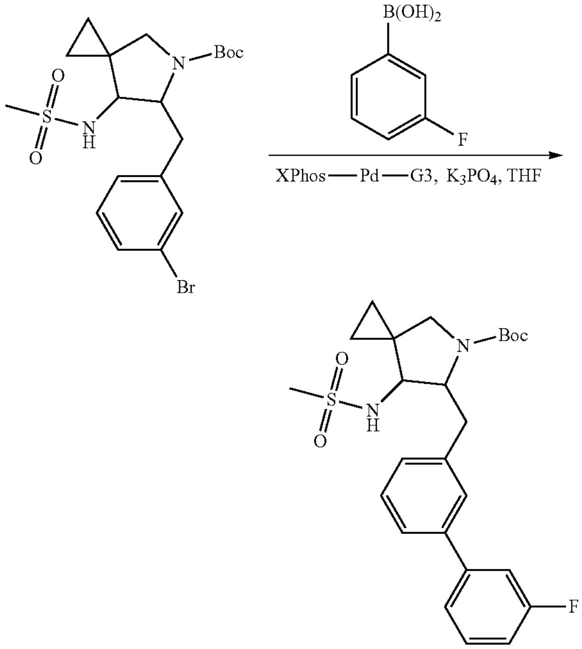

A mixture of tert-butyl 6-(3-bromobenzyl)-7-(methylsulfonamido)-5-azaspiro[2.4]heptane-5-carboxylate_cis racemic, intermediate 1 (130 mg, 283 μmol, 1 eq), (3-fluorophenyl) boronic acid (59 mg, 424 μmol, 1.50 eq), XPhos Pd G3 (7 mg, 8.49 μmol, 0.03 eq), potassium phosphate (1 M, 849 μL, 3 eq) in tetrahydrofuran (2.0 mL) was degassed and purged with nitrogen for 3 times, and then the mixture was stirred at 70° C. for 2 h under nitrogen atmosphere. The reaction mixture was quenched by water (10 mL), and then diluted with ethyl acetate and extracted with ethyl acetate (10 mL) three times. The combined organic layers were washed with brine, dried over anhydrous sodium sulfate, filtered and concentrated under reduced pressure to give crude product, which was purified by prep-TLC (petroleum ether:ethyl acetate=3:1) to afford the title compound (0.1 g, 71% yield) as a white solid. LCMS(method C) (ESI+): m/z 419 $(M+H-55)^+$, RT: 1.068 min Step 2: N-(6-((3'-fluoro-[1,1'-biphenyl]-3-yl)methyl)-5-azaspiro[2.4]heptan-7-yl)methanesulfonamide hydrochloride_cis racemic

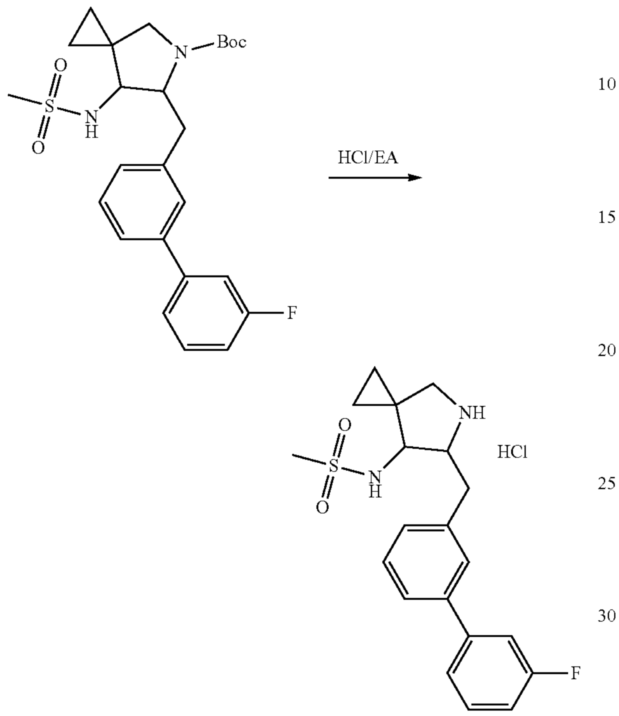

To a solution of tert-butyl 6-((3'-fluoro-[1,1'-biphenyl]-3-yl)methyl)-7-(methylsulfonamido)-5-azaspiro[2.4]heptane-5-carboxylate_cis racemic (0.1 g, 211 μmol, 1 eq) in HCl/dioxane (4 M, 2.11 mL, 40 eq). The mixture was stirred at 20° C. for 2 h. The reaction mixture was concentrated under reduced pressure to afford the title compound (80 mg) as white solid, which was used for next step directly. LCMS (method C)(ESI+): m/z 375 $(M+H)^+$, RT: 0.720 min Step 3: N-(6-((3'-fluoro-[1,1'-biphenyl]-3-yl)methyl)-5-isobutyryl-5-azaspiro[2.4]heptan-7-yl)methanesulfonamide_cis racemic

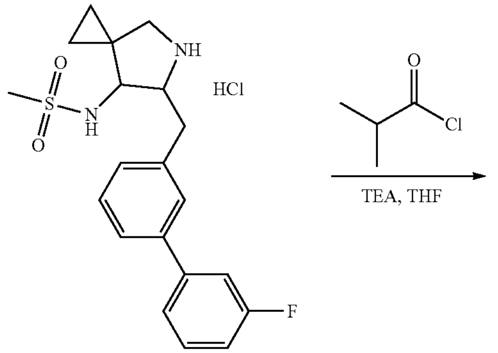

-continued

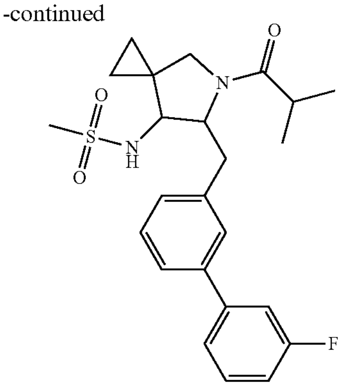

A mixture of N-(6-((3'-fluoro-[1,1'-biphenyl]-3-yl)methyl)-5-azaspiro[2.4]heptan-7-yl)methanesulfonamide hydrochloride_cis racemic (0.08 g, 214 μmol, 1 eq), 2-methylpropanoyl chloride (31 μL, 299 μmol, 1.4 eq), triethylamine (89 μL, 641 μmol, 3 eq) in tetrahydrofuran (1.0 mL) was degassed and purged with nitrogen for 3 times, and then the mixture was stirred at 20° C. for 10 h. The reaction mixture was concentrated under reduced pressure to give a residue. The residue was purified by prep-HPLC (TFA condition) to afford the title compound (70 mg, 72% yield) as a white solid.

Example 9. N-(6-([1,1'-biphenyl]-3-ylmethyl)-5-(2,2-difluoropropanoyl)-5-azaspiro[2.4]heptan-7-yl)methanesulfonamide_cis racemic

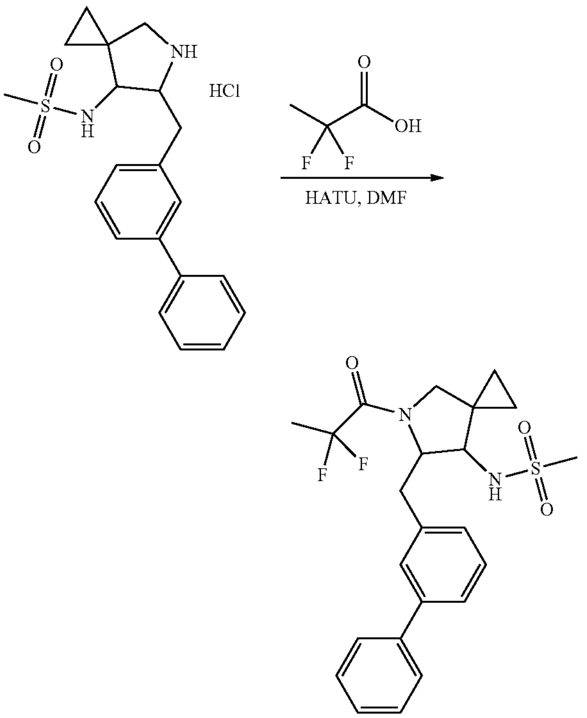

To a mixture of N-(6-([1,1'-biphenyl]-3-ylmethyl)-5-azaspiro[2.4]heptan-7-yl)methanesulfonamide hydrochloride_cis racemic, intermediate 3 (50 mg, 140 μmol) and 2,2-difluoropropanoic acid (17 mg, 154 μmol) in DMF (0.5 mL) was added HATU (69 mg, 182 μmol) and DIPEA (54 mg, 421 μmol) in one portion at 25° C. under $N_2$. The mixture was stirred at 25° C. for 12 hours and purified by prep-HPLC:column: Waters Xbridge Prep OBD C18 150*40 mm*10 μm; mobile phase: [water (0.04% $NH_3H_2O$+10 mM $NH_4HCO_3$)-MeCN]; B %: 35%-65%, 8 min to afford the title compound (22 mg, 35% yield) as a white solid.

Example 10. N-(6-([1,1'-biphenyl]-3-ylmethyl)-5-(3,3-difluoroazetidine-1-carbonyl)-5-azaspiro[2.4]heptan-7-yl)methanesulfonamide_cis racemic

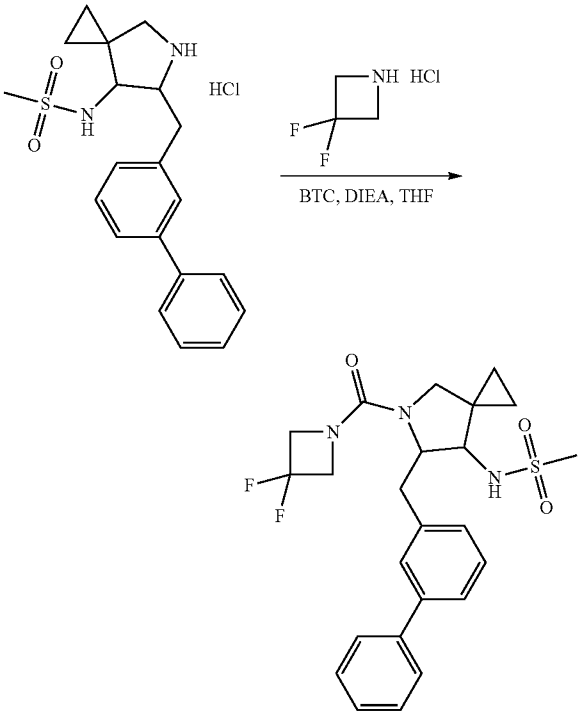

To a solution of N-(6-([1,1'-biphenyl]-3-ylmethyl)-5-azaspiro[2.4]heptan-7-yl)methanesulfonamide hydrochloride_cis racemic, intermediate 3 (50 mg, 140 μmol, 1 eq) in tetrahydrofuran (2.0 mL) was added (trichloromethyl) carbonate (42 mg, 140 μmol, 1 eq) and DIPEA (49 μL, 280 μmol, 2 eq) at 0° C. The reaction solution was stirred at 25° C. for 1 hour. Then the mixture was concentrated under reduced pressure to give a residue to which was added tetrahydrofuran (2.0 mL) and 3,3-difluoroazetidine hydrochloride (65 mg, 701 μmol, 5 eq), the mixture was stirred at 25° C. for 11 hours. The reaction solution was diluted with ethyl acetate (5.0 mL) and 0.5 M HCl aqueous solution (5.0 mL), separated out the organic layer and the aqueous solution was extracted with ethyl acetate (2×5.0 mL), the combined organic layer was washed with saturated aqueous $NaHCO_3$ solution (3×5.0 mL), brine (2×5.0 mL), dried over $MgSO_4$, filtered and the filtrate was concentrated under reduced pressure to give the crude product, which was purified by pre-HPLC (column: Phenomenex Gemini-NX C18 75*30 mm*3 μm; mobile phase: [water (10 mM $NH_4HCO_3$)-MeCN]; B %: 30%-60%, 8 min) to afford the title compound (36 mg, 54% yield) as white solid.

Example 11. N-(6-([1,1'-biphenyl]-3-ylmethyl)-5-(3-fluoroazetidine-1-carbonyl)-5-azaspiro[2.4]heptan-7-yl)methanesulfonamide_cis racemic

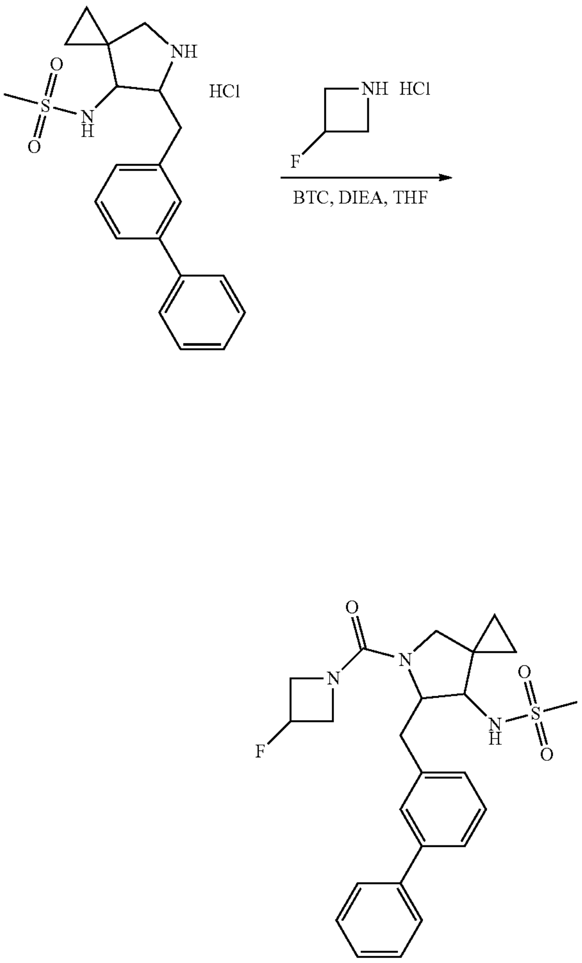

To a solution of N-(6-([1,1'-biphenyl]-3-ylmethyl)-5-azaspiro[2.4]heptan-7-yl)methanesulfonamide hydrochloride_cis racemic, intermediate 3 (50 mg, 140 μmol, 1 eq) in tetrahydrofuran (2.0 mL) was added bis (trichloromethyl) carbonate (42 mg, 140 μmol, 1 eq) and DIPEA (49 μL, 281 μmol, 2 eq) at 0° C., the reaction solution was stirred at 25° C. for 1 hour. The mixture was concentrated under reduced pressure to give a residue to which was added tetrahydrofuran (2.0 mL) and 3-fluoroazetidine hydrochloride (78 mg, 701 μmol, 5 eq), the mixture was stirred at 25° C. for 11 hours. The reaction solution was diluted with ethyl acetate (5.0 mL) and 0.5 M HCl aqueous solution (5.0 mL), separated out the organic layer and the aqueous solution was extracted with ethyl acetate (2×5.0 mL), the combined organic layer was washed with saturated aqueous $NaHCO_3$ solution (3×5.0 mL), brine (2×5.0 mL), dried over $MgSO_4$, filtered and the filtrate was concentrated under reduced pressure to give the crude product. The crude product was purified by pre-HPLC (column: Phenomenex Gemini-NX C18 75*30 mm*3 μm; mobile phase: [water (10 mM $NH_4HCO_3$)-MeCN]; B %: 25%-50%, 8 min) to afford the title compound (56 mg, 88% yield) as white solid.

Example 12. N-(6-([1,1'-biphenyl]-3-ylmethyl)-5-(3,3-difluorocyclobutane-1-carbonyl)-5-azaspiro[2.4]heptan-7-yl)methanesulfonamide_cis racemic

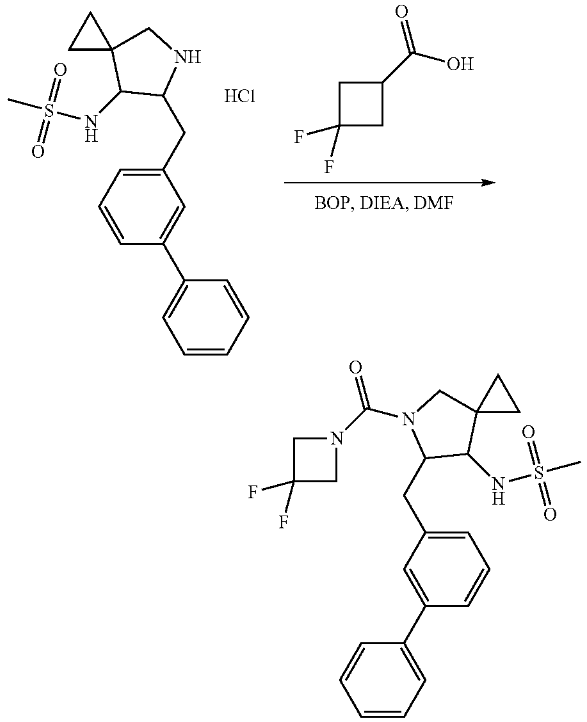

To a mixture of N-(6-([1,1'-biphenyl]-3-ylmethyl)-5-azaspiro[2.4]heptan-7-yl)methanesulfonamide hydrochloride_cis racemic, intermediate 3 (50 mg, 140 μmol) and 3,3-difluorocyclobutanecarboxylic acid (23 mg, 168 μmol) in DMF (1.0 mL) was added BOP (74 mg, 168 μmol) and DIPEA (54 mg, 421 μmol) in one portion at 25° C. under $N_2$. The mixture was stirred at 25° C. for 12 hours. The mixture was purified by prep-HPLC:column: Phenomenex luna C18 100*40 mm*5 μm; mobile phase: [water (0.1% TFA)-MeCN]; B %: 25%-63%, 8 min to afford the title compound (31 mg, 46% yield) as a white solid.

Example 13. N-(6-([1,1'-biphenyl]-3-ylmethyl)-5-(2-fluoro-2-methylpropanoyl)-5-azaspiro[2.4]heptan-7-yl)methanesulfonamide_cis racemic

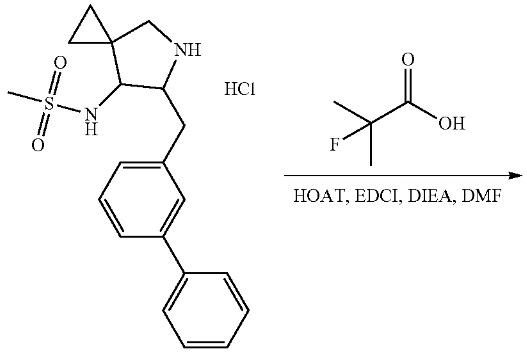

-continued

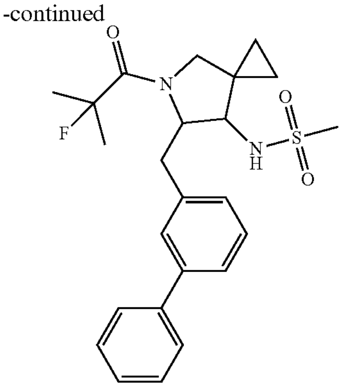

To a mixture of N-(6-([1,1'-biphenyl]-3-ylmethyl)-5-azaspiro[2.4]heptan-7-yl)methanesulfonamide hydrochloride_cis racemic, intermediate 3 (40 mg, 112 μmol) and 2-fluoro-2-methyl-propanoic acid (13 mg, 123 μmol) in DMF (1.0 mL) was added DIPEA (98 μL, 561 μmol), EDCI (28 mg, 146 μmol) and HOAt (20 mg, 146 μmol) in one portion at 25° C. under $N_2$. The mixture was stirred at 25° C. for 12 hours. The mixture was purified by prep-HPLC: column: Phenomenex luna C18 100*40 mm*5 μm; mobile phase: [water (0.1% TFA)-MeCN]; B %: 25%-65%, 8 min to afford the title compound (21 mg, 42%) as a white solid.

Example 14. methyl 5-([1,1'-biphenyl]-3-ylmethyl)-4-(methylsulfonamido)-6-azaspiro[2.5]octane-6-carboxylate_cis racemic Step 1: tert-butyl 5-([1,1'-biphenyl]-3-ylmethyl)-4-oxo-6-azaspiro[2.5]octane-6-carboxylate

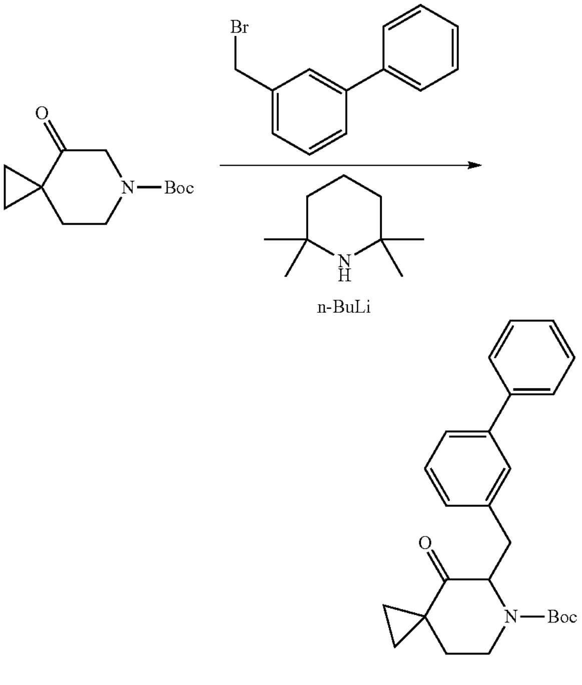

n-BuLi (2.66 mL, 6.66 mmol) was added to a solution of 2,2,6,6-tetramethylpiperidine (1.5 g, 7.99 mmol) in tetrahydrofuran (20 mL) at −70° C. and the solution was stirred at −70° C. for 30 min. A solution of tert-butyl 4-oxo-6-azaspiro[2.5]octane-6-carboxylate (1.0 g, 4.44 mmol) in tetrahydrofuran (5.0 mL) was added at −70° C. After stirring at −70° C. for 30 min, a solution of 3-(bromomethyl)-1,1'-biphenyl (1.1 g, 4.44 mmol) in tetrahydrofuran (5.0 mL) was added at −70° C. The reaction mixture was stirred at −70-25° C. for 12 h. Saturated $NH_4Cl$ solution (50 mL) was added at 0° C. The mixture was extracted with ethyl acetate (3-30 mL). The organic were combined, dried over $Na_2SO_4$, filtered and concentrated. The residue was chromatographed on silica gel (petroleum ether:acetate=50:1 to 10:1) to afford the title compound (1.33 g, 51% yield) as a yellow oil. LCMS (method B)(ESI+): m/z 336 $(M+H-55)^+$, RT: 1.35 min Step 2: 5-([1,1'-biphenyl]-3-ylmethyl)-6-azaspiro[2.5]octan-4-one 2,2,2-trifluoroacetate

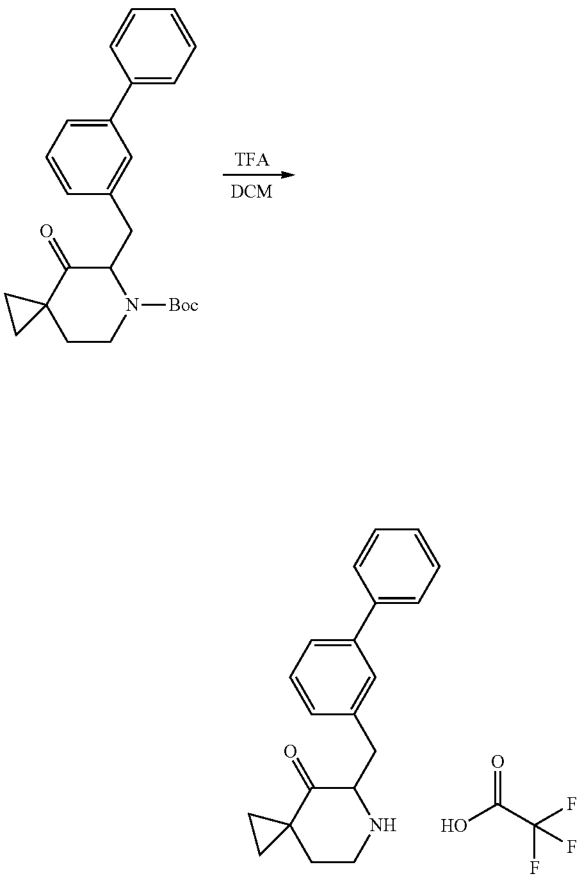

Tert-butyl 5-([1,1'-biphenyl]-3-ylmethyl)-4-oxo-6-azaspiro[2.5]octane-6-carboxylate (1.33 g) was taken up in dichloromethane (20 mL) and TFA (4.0 mL) added. The mixture was stirred at 20° C. for 2 h. The reaction mixture was concentrated under reduced pressure and purified by prep-HPLC (column: Phenomenex Luna C18 200*40 mm*10 µm; mobile phase: [water (0.1% TFA)-MeCN]; B %: 30%-65%, 8 min) to afford the title compound (1.0 g, 75% yield) as white solid. LCMS(method B)(ESI+): m/z 292 $(M+H-100)^+$, RT: 0.68 min Step 3: methyl 5-([1,1'-biphenyl]-3-ylmethyl)-4-oxo-6-azaspiro[2.5]octane-6-carboxylate

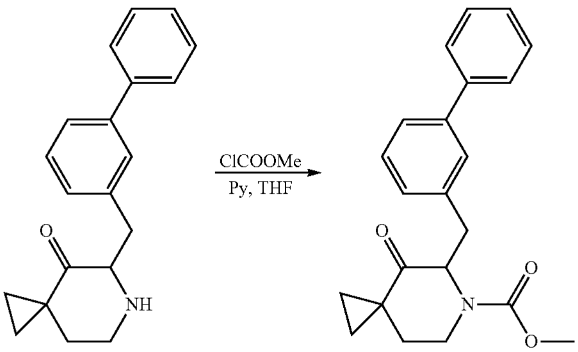

To a solution of 5-([1,1'-biphenyl]-3-ylmethyl)-6-azaspiro[2.5]octan-4-one 2,2,2-trifluoroacetate (1.0 g, 3.43 mmol) in tetrahydrofuran (10 mL) at 25° C. was added methyl carbonochloridate (500 mg, 5.29 mmol) and pyridine (543 mg, 6.86 mmol). The mixture was stirred at 25° C. for 12 h under $N_2$. $H_2O$ (30 mL) was added at 25° C. The mixture was extracted with ethyl acetate (3x30 mL). The organic were combined, dried over $Na_2SO_4$, filtered and concentrated under vacuum to afford the title compound (700 mg, 58% yield) as a colorless oil, which was used to next step without further purification. LCMS(method B)(ESI+): m/z 292 (M+H−100)+, RT: 0.68 min Step 4: methyl 5-([1,1'-biphenyl]-3-ylmethyl)-4-amino-6-azaspiro[2.5]octane-6-carboxylate_cis racemic

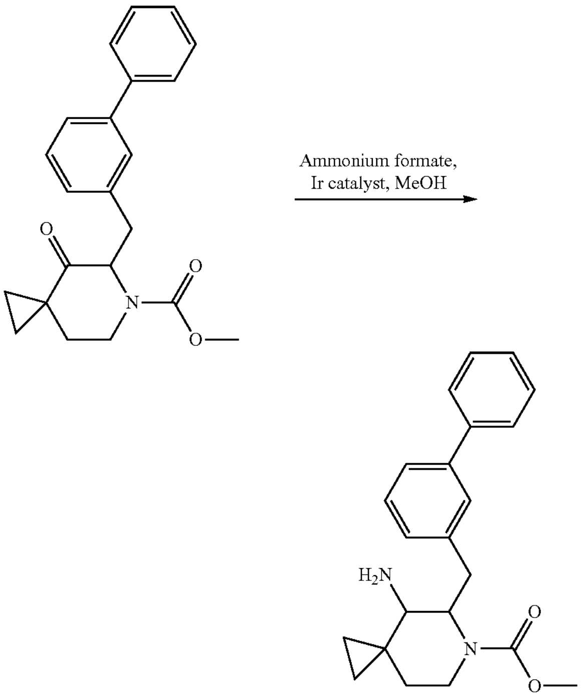

To a solution of methyl 5-([1,1'-biphenyl]-3-ylmethyl)-4-oxo-6-azaspiro[2.5]octane-6-carboxylate (140 mg, 401 μmol) in MeOH (5.0 mL) at 25° C. were added, ammonium formate (126 mg, 2.00 mmol) and bis[2-(2-pyridyl)phenyl] iridium(1+); 2-(2-pyridyl)pyridine; hexafluorophosphate (6.42 mg, 0.02 eq). The mixture was stirred at 25° C. for 2 h under $N_2$. $H_2O$ (10 mL) was added at 25° C. The mixture was extracted with ethyl acetate (3×10 mL). The organic extracts were combined, dried over $Na_2SO_4$, filtered and concentrated to afford the title compound (140 mg, 97% yield) as colourless oil. The crude product was used to next step without further purification. LCMS(method B)(ESI+): m/z 351 $(M+H)^+$, RT: 0.75 min Step 5: methyl 5-([1,1'-biphenyl]-3-ylmethyl)-4-(methylsulfonamido)-6-azaspiro[2.5]octane-6-carboxylate_cis racemic

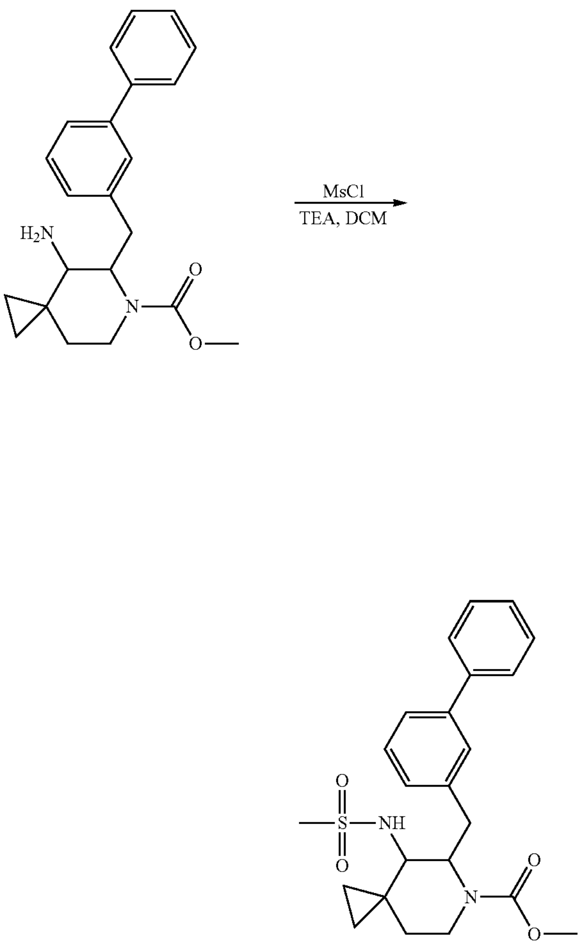

A solution of methyl 5-([1,1'-biphenyl]-3-ylmethyl)-4-amino-6-azaspiro[2.5]octane-6-carboxylate_cis racemic (140 mg, 399 μmol) and MsCl (55 mg, 479 μmol) in dichloromethane (1.0 mL) was added TEA (81 mg, 799 μmol) at 25° C. The mixture was stirred at 25° C. for 2 h under $N_2$. The mixture was purified by pre-HPLC:column: Phenomenex Luna C18 200*40 mm*10 μm; mobile phase: [water (0.1% TFA)-MeCN]; B %: 30%-65%, 8 min to afford the title compound (21 mg, 12% yield) as white solid.

Example 15. N-(6-([1,1'-biphenyl]-3-ylmethyl)-5-isobutyryl-5-azaspiro[2.4]heptan-7-yl)methanesulfonamide_cis racemic Step 1: tert-butyl 6-([1,1'-biphenyl]-3-ylmethyl)-7-(methylsulfonamido)-5-azaspiro[2.4]heptane-5-carboxylate

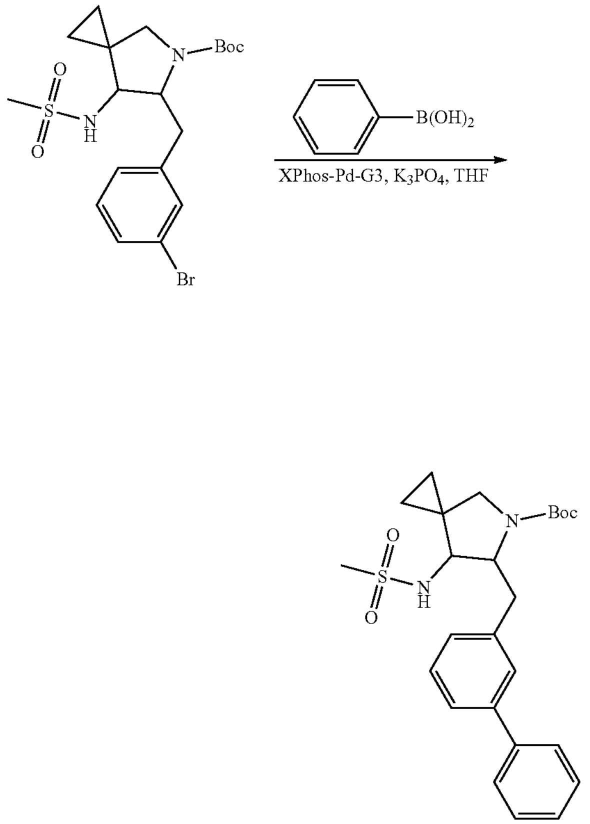

To a solution of tert-butyl 6-(3-bromobenzyl)-7-(methylsulfonamido)-5-azaspiro[2.4]heptane-5-carboxylate_cis racemic (intermediate 1)(160 mg, 0.35 mmol), phenylboronic acid (85 mg, 0.70 mmol) and XPhos-G3-Palladacycle (16 mg, 0.02 mmol) in tetrahydrofuran (4.0 mL) was added 1 M aq. tripotassium phosphate solution (1.0 mL, 1.0 mmol) and the mixture was heated to 70° C. for 1 h. The reaction was partitioned between EtOAc and sat aq $NaHCO_3$, washed with sat. brine, the organic layer separated and concentrated in vacuo. The residue was purified by flash column chromatography (gradient 0% to 100% Ethyl Acetate in Iso-hexane] followed by reverse phase HPLC (Biotage SNAP KP-C18-HS cartridge 30 g, 25 mL/min, gradient of 10% methanol in aqueous to 100%, solvents: Aqueous=Water with 0.1% of 28% Ammonia solution, Organic=Methanol) to afford the title compound (100 mg, 63% yield) as a yellow oil. LCMS(method H)(ESI+): m/z 457 $(M+H)^+$, RT: 2.43 min Step 2: N-(6-(1,1'-biphenyl-3-ylmethyl)-5-azaspiro[2.4]heptan-7-yl)methanesulfonamide hydrochloride_cis racemic

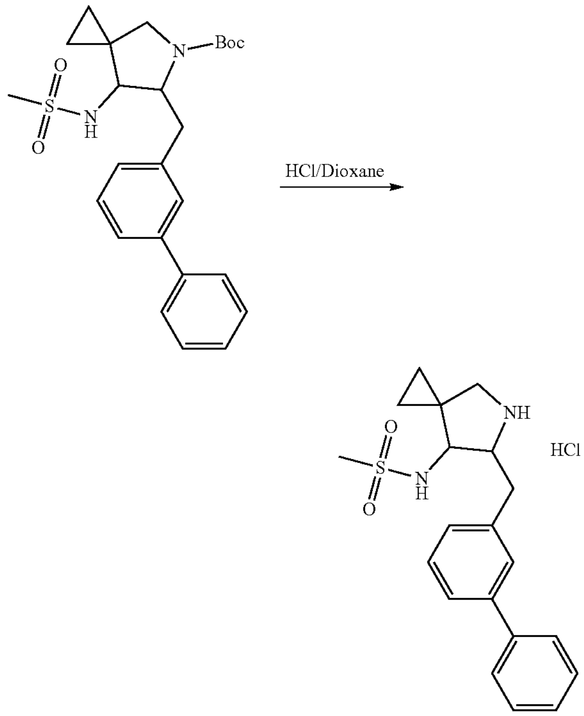

To a solution of tert-butyl 6-([1, 1'-biphenyl]-3-ylmethyl)-7-(methylsulfonamido)-5-azaspiro[2.4]heptane-5-carboxylate_cis racemic (110 mg, 0.24 mmol) in 1,4-Dioxane (3.0 mL) was added 4 M HCl in dioxane (2.2 mL, 8.8 mmol). The reaction mixture was stirred at room temperature for 24 h. The reaction mixture was evaporated in vacuo to afford the title compound (116 mg, quantitative) as a pink oil. LCMS (method H)(ESI+): m/z 357 $(M+H)^+$, RT: 2.10 min Step 3: N-(6-([1,1'-biphenyl]-3-ylmethyl)-5-isobutyryl-5-azaspiro[2.4]heptan-7-yl)methanesulfonamide_cis racemic

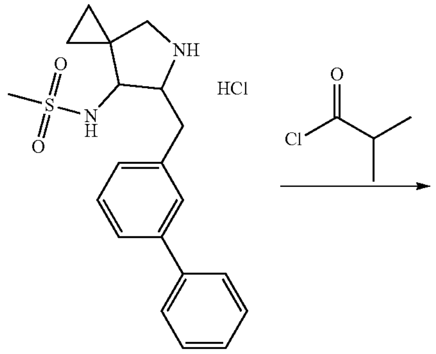

-continued

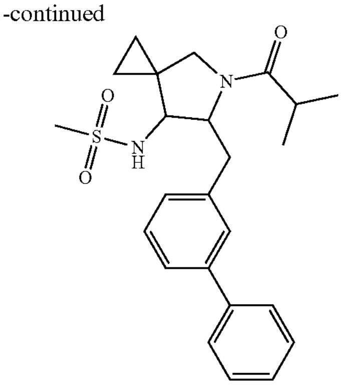

To a solution of N-(6-([1,1'-biphenyl]-3-ylmethyl)-5-azaspiro[2.4]heptan-7-yl)methanesulfonamide hydrochloride_cis racemic (116 mg, 0.30 mmol) and $Et_3N$(0.09 mL, 0.65 mmol) in dichloromethane (3.0 mL) was added isobutyryl chloride (38 mg, 0.35 mmol). The reaction mixture was stirred at room temperature for 3 h. The reaction mixture was diluted with EtOAc, washed with 1M aq. HCl, saturated aq. sol. of $NaHCO_3$ and brine. The organic extract was dried over $MgSO_4$, passed over hydrophobic frit and evaporated in vacuo. The residue was purified by flash column chromatography [gradient 0% to 100% Ethyl Acetate in Isohexane] and further purified by reverse phase HPLC (Phenomenex Gemini column, 100x30 mm, 5 μm, 30 mL/min, gradient of 40% to 100% (over 8.7 min) then 100% hold (1 min), solvents: Aqueous=Water with 0.2% of 28% Ammonia solution, Organic=Acetonitrile) to afford the title compound (39 mg, 31% yield).

Example 16 & 17. N-((6R,7R)-6-([1,1'-biphenyl]-3-ylmethyl)-5-isobutyryl-5-azaspiro[2.4]heptan-7-yl)methanesulfonamide & N-((6S,7S)-6-([1,1'-biphenyl]-3-ylmethyl)-5-isobutyryl-5-azaspiro[2.4]heptan-7-yl)methanesulfonamide N-(6-([1,1'-biphenyl]-3-ylmethyl)-5-isobutyryl-5-azaspiro[2.4]heptan-7-yl)methanesulfonamide_cis racemic (Example 15) resolved on the Sepiatec SFC Prep100 system using a Lux A1 column and isocratic conditions of $CO_2$: IPA+0.2% $NH_3$ 80:20.

N-((6R,7R)-6-([1,1'-biphenyl]-3-ylmethyl)-5-isobutyryl-5-azaspiro[2.4]heptan-7-yl)methanesulfonamide: Isomer 1: 99% e.e. retention time=1.84 mins N-((6S,7S)-6-([1,1'-biphenyl]-3-ylmethyl)-5-isobutyryl-5-azaspiro[2.4]heptan-7-yl)methanesulfonamide: Isomer 2: 99% e.e. retention time=1.95 mins Example 18. N-(5-(azetidine-1-carbonyl)-6-((2-fluoro-[1,1'-biphenyl]-3-yl)methyl)-5-azaspiro[2.4]heptan-7-yl)methanesulfonamide_cis racemic

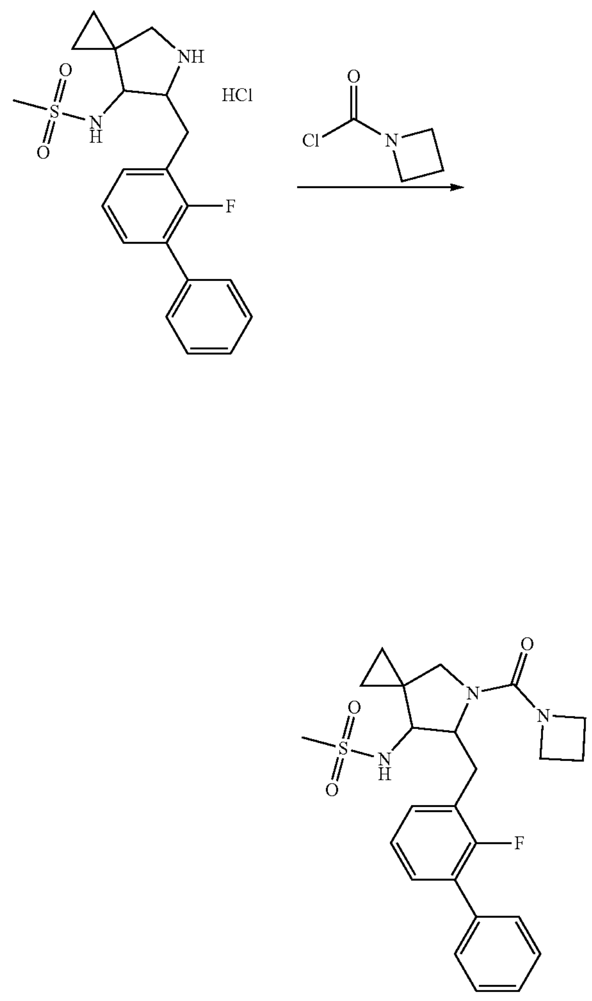

To a solution of N-(6-((2-fluoro-[1,1'-biphenyl]-3-yl)methyl)-5-azaspiro[2.4]heptan-7-yl)methanesulfonamide hydrochloride_cis racemic (intermediate 5)(122 mg, 0.30 mmol) and $Et_3N$(0.09 mL, 0.65 mmol) in MeCN(3.0 mL) was added Azetidine-1-carbonyl chloride (42 mg, 0.36 mmol). The reaction mixture was stirred for 18 h. The reaction mixture was diluted with EtOAc and washed with 1M aq. HCl solution, sat. aq. $NaHCO_3$ solution, brine, dried over MgSO4, passed over hydrophobic frit and evaporated in vacuo. The residue was purified by flash column chromatography [gradient 0% to 100% Ethyl Acetate in Iso-hexane] to afford the title compound (84 mg, 62% yield) as a white solid.

Example 19 & 20. N-((6R,7R)-6-((2-fluoro-[1,1'-biphenyl]-3-yl)methyl)-5-((S)-oxetane-2-carbonyl)-5-azaspiro[2.4]heptan-7-yl)methanesulfonamide (isomer 1) & N-((6S,7S)-6-((2-fluoro-[1,1'-biphenyl]-3-yl)methyl)-5-((S)-oxetane-2-carbonyl)-5-azaspiro[2.4]heptan-7-yl)methanesulfonamide (isomer 2)

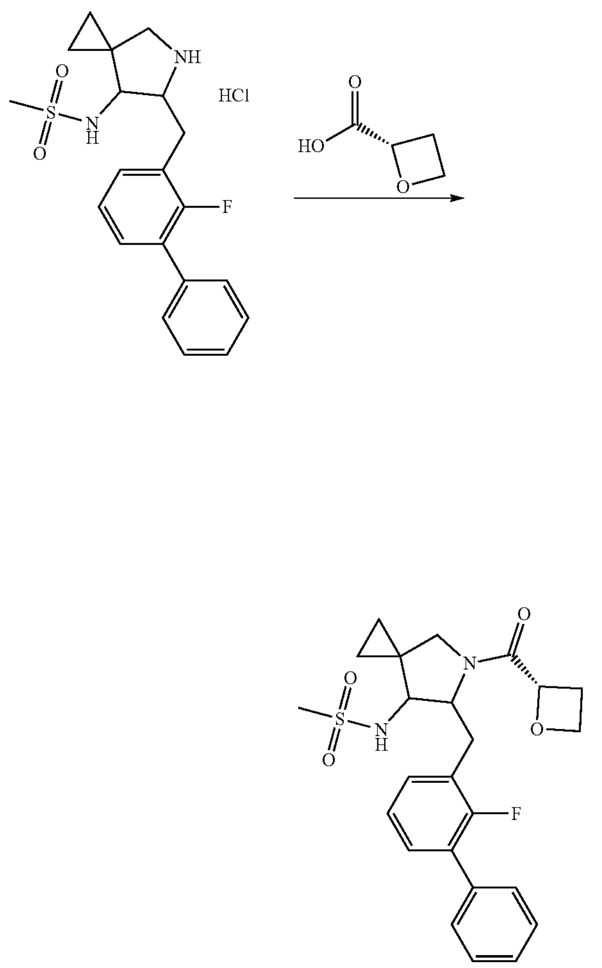

N-(6-((2-fluoro-[1,1'-biphenyl]-3-yl)methyl)-5-azaspiro[2.4]heptan-7-yl)methanesulfonamide hydrochloride_cis racemic (intermediate 5)(62 mg, 0.15 mmol), (2S)-oxetane-2-carboxylic acid (31 mg, 0.30 mmol), HOBt monohydrate (41 mg, 0.30 mmol) and DIPEA (0.08 mL, 0.45 mmol) were stirred in tetrahydrofuran (5.0 mL) to which 1-(3-dimethylaminopropyl)-3-ethylcarbodiimide hydrochloride (58 mg, 0.30 mmol) was added. The mixture was stirred at room temperature for 24 h and concentrated in vacuo. The residue was purified by flash column chromatography [gradient 0% to 100% Ethyl Acetate in Iso-hexane, then gradient 0% to 10% MeOH in dichloromethane]. The mixture of diastereoisomers were separated by reverse phase HPLC (Phenomenex Kinetex column, 100×30 mm, 5 μm, 30 mL/min, gradient of 30% to 60% (over 8.7 min) then a 100% hold (1 min), solvents: Aqueous=Water with 0.1% Ammonia, Organic=Acetonitrile) to afford the title compounds, isomer 1 (7.4 mg, 11% yield) and isomer 2 (6.9 mg, 10% yield).

Example 21 & 22. N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide_isomer 1 & N-((6R,7R)-6-((2-fluoro-[1,1'-biphenyl]-3-yl)methyl)-5-((R)-oxetane-2-carbonyl)-5-azaspiro[2.4]heptan-7-yl)methanesulfonamide_isomer 2

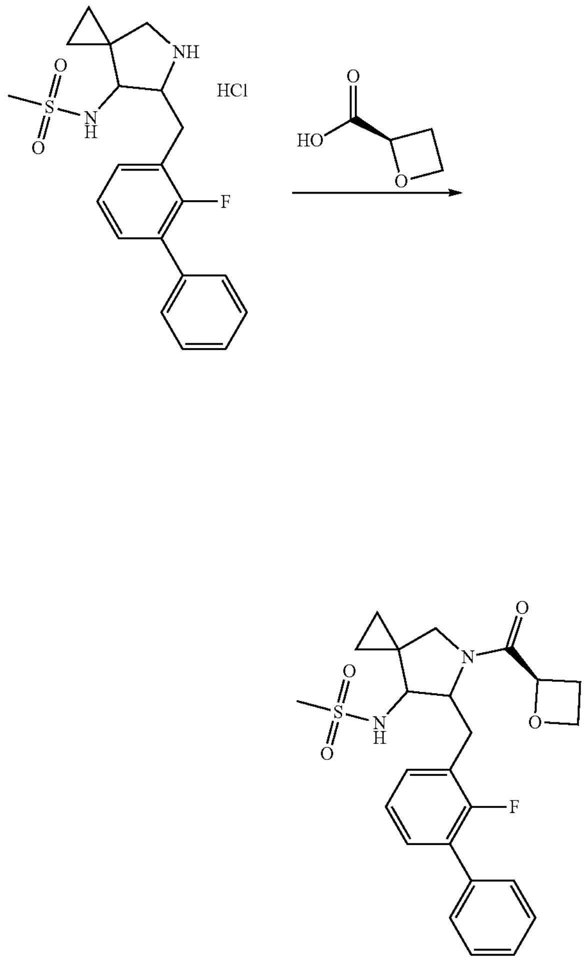

N-(6-((2-fluoro-[1,1'-biphenyl]-3-yl)methyl)-5-azaspiro[2.4]heptan-7-yl)methanesulfonamide hydrochloride_cis racemic (intermediate 5)(62 mg, 0.15 mmol), (2R)-oxetane-2-carboxylic acid (31 mg, 0.30 mmol), DIPEA (0.08 mL, 0.45 mmol) and HOBt monohydrate (41 mg, 0.30 mmol) were stirred in tetrahydrofuran (5.0 mL) to which was added 1-(3-dimethylaminopropyl)-3-ethylcarbodiimide hydrochloride (58 mg, 0.30 mmol). The mixture stirred for 24 h at room temperature and concentrated in vacuo. The residue was purified by flash column chromatography [gradient 0% to 10% MeOH in dichloromethane]. The mixtures of diastereoisomers were separated by reverse phase HPLC (Phenomenex Kinetex column, 100x30 mm, 5 μm, 30 mL/min, gradient of 30% to 60% (over 8.7 min) then a 100% hold (1 min), solvents: Aqueous=Water with 0.1% Ammonia, Organic=Acetonitrile) to afford the title compounds, isomer 1 (13.1 mg, 19% yield) and isomer 2 (7 mg, 10% yield).

Example 23. N-(6-((2,3'-difluoro-[1,1'-biphenyl]-3-yl)methyl)-5-pivaloyl-5-azaspiro[2.4]heptan-7-yl) methanesulfonamide_cis racemic

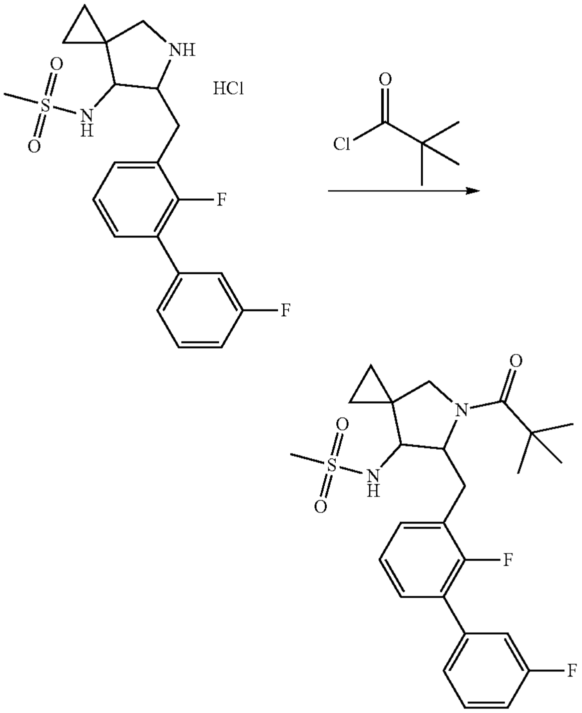

To a solution of N-(6-((2,3'-difluoro-[1,1'-biphenyl]-3-yl) methyl)-5-azaspiro[2.4]heptan-7-yl)methanesulfonamide hydrochloride_cis racemic (intermediate 6)(127 mg, 0.30 mmol) in dichloromethane (4.0 mL) was added DIPEA (154 μL, 0.89 mmol) followed by pivaloyl chloride (40 μL, 0.36 mmol) and the reaction stirred at room temperature for 18 h. The reaction mixture was diluted with EtOAc, washed with 1M aq. HCl solution, sat. brine, the organic layer separated, dried over $MgSO_4$, filtered over hydrophobic frit and concentrated in vacuo. The residue was purified by flash column chromatography eluting with 0%-100% Ethyl acetate/iso-hexane to afford the title compound (84.7 mg, 60% yield) as a colourless gum.

Example 24. N-(6-((2,3'-difluoro-[1,1'-biphenyl]-3-yl)methyl)-5-(2,2-difluoropropanoyl)-5-azaspiro[2.4]heptan-7-yl)methanesulfonamide_cis racemic

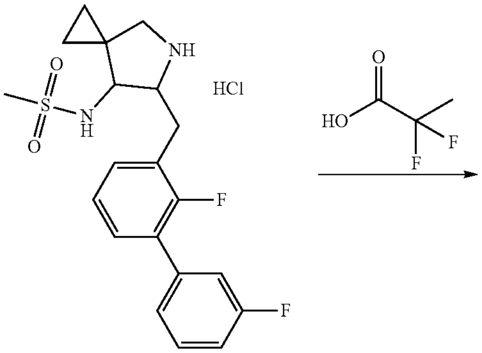

-continued

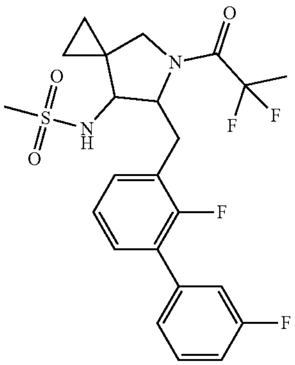

N-(6-((2,3'-difluoro-[1,1'-biphenyl]-3-yl)methyl)-5-azaspiro[2.4]heptan-7-yl)methanesulfonamide hydrochloride_cis racemic (intermediate 6)(127 mg, 0.30 mmol) and 2,2-difluoropropanoic acid (65 mg, 0.59 mmol) were stirred in tetrahydrofuran (4.0 mL) to which HOBt monohydrate (80 mg, 0.59 mmol) and 1-(3-dimethylaminopropyl)-3-ethylcarbodiimide hydrochloride (113 mg, 0.59 mmol) were added. DIPEA (0.15 mL, 0.89 mmol) was added and the mixture stirred for 24 h at room temperature. The reaction mixture was diluted with EtOAc and washed with 1M aq. HCl solution, sat. aq. $NaHCO_3$ solution, brine, dried over MgSO4, passed over hydrophobic frit and evaporated in vacuo. The residue was purified by flash column chromatography [gradient 0% to 100% Ethyl Acetate in Iso-hexane] and further purified by flash column chromatography (reverse phase, gradient 10% to 100% MeOH in $H_2O$ to afford the title compound (43.4 mg, 30% yield).

Example 25. N-(5-(azetidine-1-carbonyl)-6-((2,3'-difluoro-[1,1'-biphenyl]-3-yl)methyl)-5-azaspiro[2.4]heptan-7-yl)methanesulfonamide_cis racemic

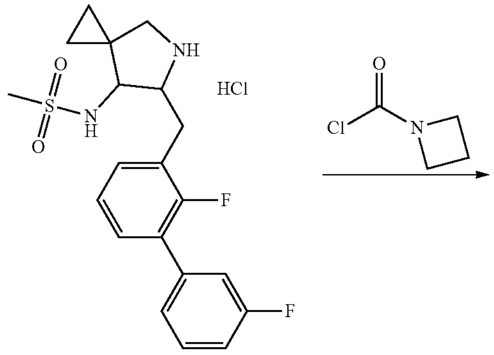

-continued

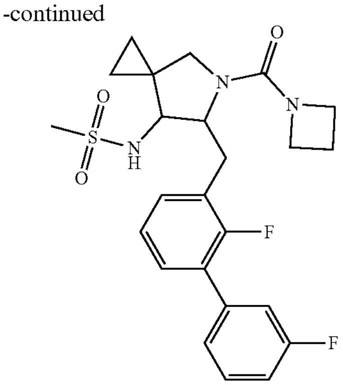

To a solution of N-(6-((2,3'-difluoro-[1,1'-biphenyl]-3-yl)methyl)-5-azaspiro[2.4]heptan-7-yl)methanesulfonamide hydrochloride_cis racemic (intermediate 6)(127 mg, 0.30 mmol) and $Et_3N$(0.09 mL, 0.65 mmol) in MeCN(3.0 mL) was added azetidine-1-carbonyl chloride (42 mg, 0.36 mmol). The reaction mixture was stirred for 18 h. The reaction mixture was diluted with EtOAc and washed with 1 M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] to afford the title compound (81.2 mg, 58% yield) as a white solid.

Example 26 & 27. N-((6R,7R)-5-(azetidine-1-carbonyl)-6-((2,3'-difluoro-[1,1'-biphenyl]-3-yl)methyl)-5-azaspiro[2.4]heptan-7-yl)methanesulfonamide & N-((6S,7S)-5-(azetidine-1-carbonyl)-6-((2,3'-difluoro-[1,1'-biphenyl]-3-yl)methyl)-5-azaspiro[2.4]heptan-7-yl)methanesulfonamide N-(5-(azetidine-1-carbonyl)-6-((2,3'-difluoro-[1,1'-biphenyl]-3-yl)methyl)-5-azaspiro[2.4]heptan-7-yl)methanesulfonamide_cis racemic (Example 25) resolved on the Sepiatec SFC Prep100 system using a Lux A1 column and isocratic conditions of $CO_2$:(IPA+0.2% $NH_3$) 60:40.

N-((6R,7R)-5-(azetidine-1-carbonyl)-6-((2,3'-difluoro-[1,1'-biphenyl]-3-yl)methyl)-5-azaspiro[2.4]heptan-7-yl)methanesulfonamide: Isomer 1: 99% e.e. retention time=2.13 mins N-((6S,7S)-5-(azetidine-1-carbonyl)-6-((2,3'-difluoro-[1,1'-biphenyl]-3-yl)methyl)-5-azaspiro[2.4]heptan-7-yl)methanesulfonamide: Isomer 2: 99% e.e. retention time=2.38 mins Example 28. N-(5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide_cis racemic

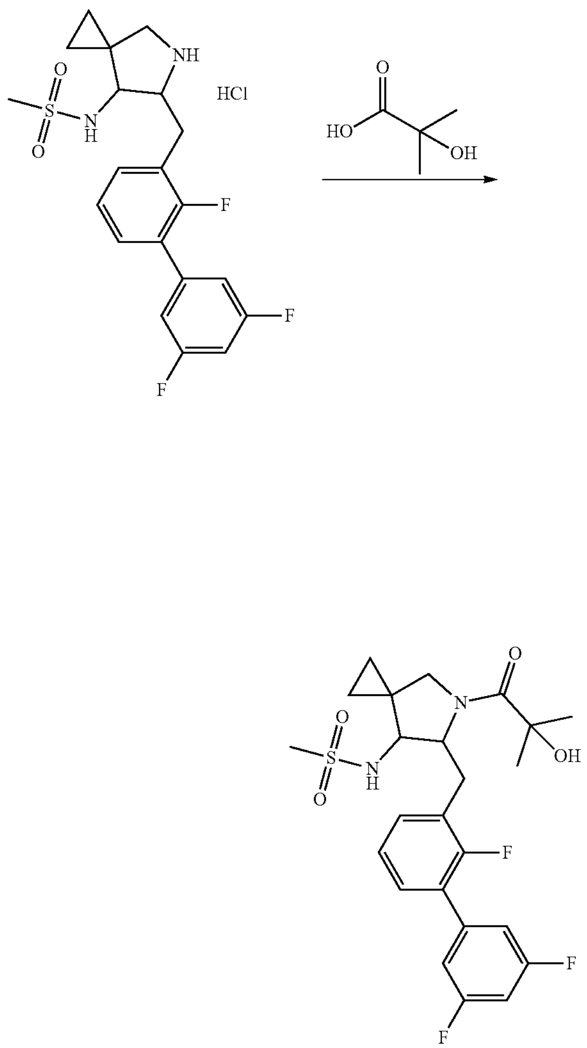

To a suspension of N-(6-((2,3',5'-trifluoro-[1,1'-biphenyl]-3-yl)methyl)-5-azaspiro[2.4]heptan-7-yl)methanesulfonamide hydrochloride_cis racemic (intermediate 7)(128 mg, 0.29 mmol) in THF (3.0 mL) were added 2-hydroxy-2-methyl-propanoic acid (36 mg, 0.34 mmol), HOBt monohydrate (46 mg, 0.34 mmol), $Et_3N$(0.12 mL, 0.86 mmol) and 1-(3-dimethylaminopropyl)-3-ethylcarbodiimide hydrochloride (66 mg, 0.34 mmol), and the mixture was stirred at room temperature for 18 h. The mixture was diluted with EtOAc and washed sequentially with water, sat aq $NaHCO_3$, 1 M HCl aq then brine, dried through a hydrophobic frit and concentrated. The residue was purified by flash column chromatography [gradient 0% to 100% Ethyl Acetate in Iso-hexane] and then by reverse phase column chromatography (gradient of 100% methanol in aqueous to 100%, solvents: Aqueous=Water with 0.1% of 28% Ammonia solution, Organic=Methanol) to afford the title compound (25.4 mg, 18% yield).

Example 29. N-(5-(cyclobutanecarbonyl)-6-((2,3',5'-trifluoro-[1,1'-biphenyl]-3-yl)methyl)-5-azaspiro[2.4]heptan-7-yl)methanesulfonamide_cis racemic

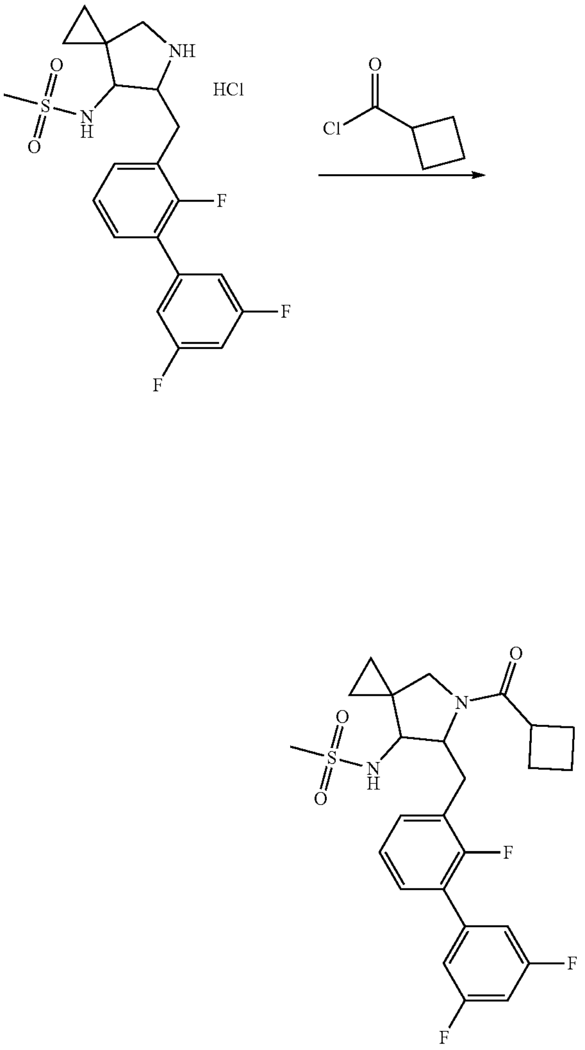

To a solution of N-(6-((2,3',5'-trifluoro-[1,1'-biphenyl]-3-yl)methyl)-5-azaspiro[2.4]heptan-7-yl)methanesulfonamide hydrochloride_cis racemic (intermediate 7)(128 mg, 0.29 mmol) and $Et_3N$(0.09 mL, 0.63 mmol) in dichloromethane (3.0 mL) was added cyclobutane carbonyl chloride (41 mg, 0.34 mmol). The reaction mixture was stirred for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] to afford the title compound (101 mg, 72% yield) as a white solid.

Example 30. N-(5-(azetidine-1-carbonyl)-6-((2,3',5'-trifluoro-[1,1'-biphenyl]-3-yl)methyl)-5-azaspiro[2.4]heptan-7-yl)methanesulfonamide_cis racemic

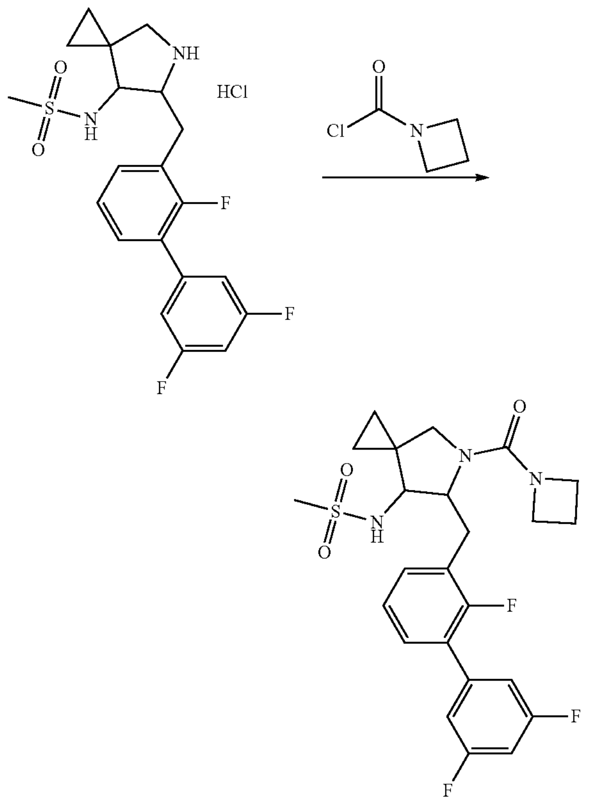

To a solution of N-(6-((2,3',5'-trifluoro-[1,1'-biphenyl]-3-yl)methyl)-5-azaspiro[2.4]heptan-7-yl)methanesulfonamide hydrochloride_cis racemic (intermediate 7)(128 mg, 0.29 mmol) and $Et_3N$(0.09 mL, 0.63 mmol) in MeCN(3.0 mL) was added Azetidine-1-carbonyl chloride (41 mg, 0.34 mmol). The reaction mixture was stirred for 18 h. The reaction mixture was diluted with EtOAc and washed with 1M aq. HCl solution, sat. aq. $NaHCO_3$ solution, brine, dried over $MgSO_4$, passed over hydrophobic frit and evaporated in vacuo. The residue was purified by flash column chromatography [gradient 0% to 100% Ethyl Acetate in Iso-hexane] to afford the title compound (74 mg, 52% yield) as a white solid.

Example 31 & 32. N-((6R,7R)-5-(azetidine-1-carbonyl)-6-((2,3',5'-trifluoro-[1,1'-biphenyl]-3-yl)methyl)-5-azaspiro[2.4]heptan-7-yl)methanesulfonamide & N-((6S,7S)-5-(azetidine-1-carbonyl)-6-((2,3',5'-trifluoro-[1,1'-biphenyl]-3-yl)methyl)-5-azaspiro[2.4]heptan-7-yl)methanesulfonamide N-(5-(azetidine-1-carbonyl)-6-((2,3',5'-trifluoro-[1,1'-biphenyl]-3-yl)methyl)-5-azaspiro[2.4]heptan-7-yl)methanesulfonamide_cis racemic (Example 30) resolved on the Sepiatec SFC Prep100 system using a Lux A1 column and isocratic conditions of $CO_2$:(IPA+0.2% $NH_3$) 70:30.

N-((6R,7R)-5-(azetidine-1-carbonyl)-6-((2,3',5'-trifluoro-[1,1'-biphenyl]-3-yl)methyl)-5-azaspiro[2.4]heptan-7-yl)methanesulfonamide: Isomer 1: 99% e.e. retention time=2.05 mins N-((6S,7S)-5-(azetidine-1-carbonyl)-6-((2,3',5'-trifluoro-[1,1'-biphenyl]-3-yl)methyl)-5-azaspiro[2.4]heptan-7-yl)methanesulfonamide: Isomer 2: 99% e.e. retention time=2.21 mins Example 33 (Compound 39). N-((6S,7S)-5-((R)-oxetane-2-carbonyl)-6-((2,3',5'-trifluoro-[1,1'-biphenyl]-3-yl)methyl)-5-azaspiro[2.4]heptan-7-yl)methanesulfonamide

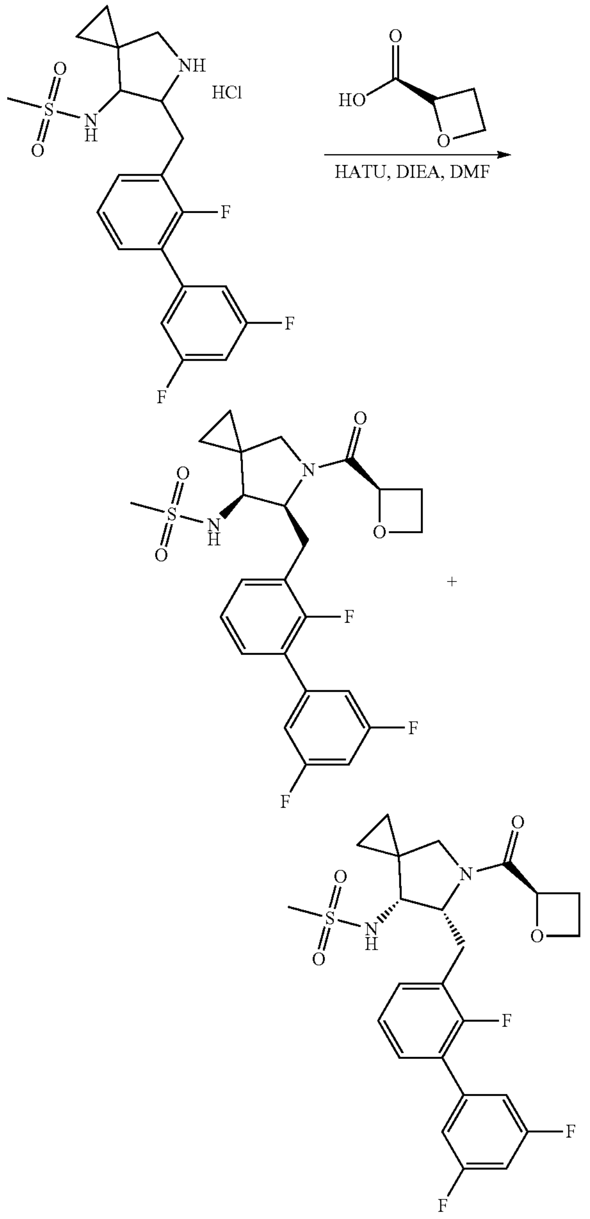

To a solution of N-(6-((2,3',5'-trifluoro-[1,1'-biphenyl]-3-yl)methyl)-5-azaspiro[2.4]heptan-7-yl)methanesulfonamide hydrochloride_cis racemic, intermediate 7 (150 mg, 365 μmol, 1 eq) in dimethyl formamide (2 mL) was added N,N-diisopropylethylamine (191 μL, 1.10 mmol, 3 eq), (2R)-oxetane-2-carboxylic acid (56 mg, 548 μmol, 1.5 eq) and HATU (208 mg, 548 μmol, 1.5 eq). The mixture was stirred at 25° C. for 12 hours, poured into the water (10 mL)

and extracted with ethyl acetate (10 mL×3). The organic layer was washed with brine (10 mL), and dried over $Mg_2SO_4$, concentrated under reduced pressure to afford crude product. The residue was purified by prep-HPLC (column: Phenomenex Gemini-NX 150*30 mm*5 μm; mobile phase: [water (0.1% TFA)-ACN]; B %: 35%-65%, 9 min) to afford the title compound (25 mg, 13.4% yield) and as an off white solid.

Example 34 (Compound 54)

Step 1: tert-butyl 6-(3-bromo-2-methoxybenzyl)-7-oxo-5-azaspiro[2.4]heptane-5-carboxylate

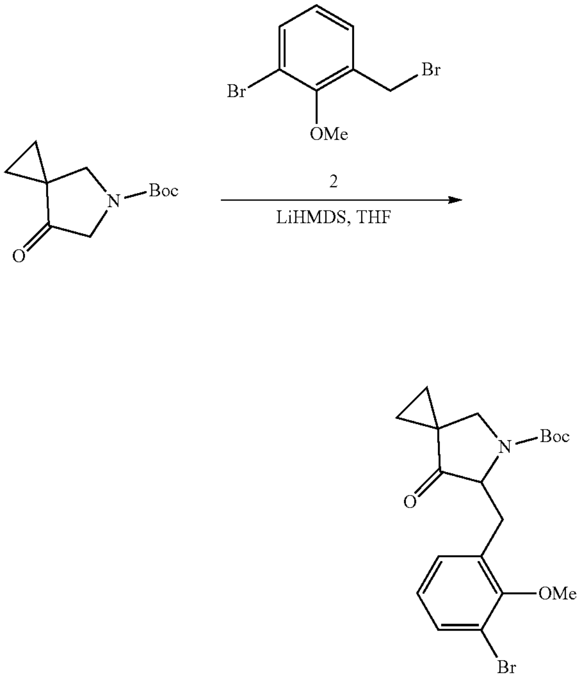

To a solution of tert-butyl 7-oxo-5-azaspiro[2.4]heptane-5-carboxylate (0.8 g, 3.79 mmol, 1 eq) in tetrahydrofuran (10 mL) was added dropwise bis(trimethylsily)amine lithium (1 M, 4.54 mL, 1.2 eq) at −70° C. over 15 min. After addition, the mixture was stirred at this temperature for 30 min, and then a solution of 1-bromo-3-(bromomethyl)-2-methoxybenzene (1.27 g, 4.54 mmol, 1.2 eq) in tetrahydrofuran (15 mL) was added dropwise at −70° C. The resulting mixture was stirred at 20° C. for 2 h under nitrogen atmosphere. The reaction mixture was quenched by addition water (10 mL), and then diluted with ethyl acetate (10 mL) and extracted with ethyl acetate (10 mL×3). The combined organic layers were washed with brine, dried over anhydrous magnesium sulfate, filtered and concentrated under reduced pressure to afford an oil. The residue was purified by column chromatography ($SiO_2$, Petroleum ether/Ethyl acetate=I/O to 3/1) to afford the title compound (1 g, yield 64.4%) as yellow oil. $^1$H NMR (400 MHz, chloroform-d) δ ppm 0.83-1.07 (m, 1H), 1.12 (br s, 1H), 1.23-1.37 (m, 2H), 1.43 (br s, 9H), 1.61 (br s, 1H), 2.00-2.96 (m, 3H), 3.53 (br s, 1H), 3.71-3.76 (m, 1H), 3.95 (br s, 1H), 4.42 (br s, 1H), 6.89 (br s, 1H), 7.06 (br d, 1H), 7.39-7.47 (m, 1H).

Step 2: tert-butyl 7-amino-6-(3-bromo-2-methoxybenzyl)-5-azaspiro[2.4]heptane-5-carboxylate_cis racemic

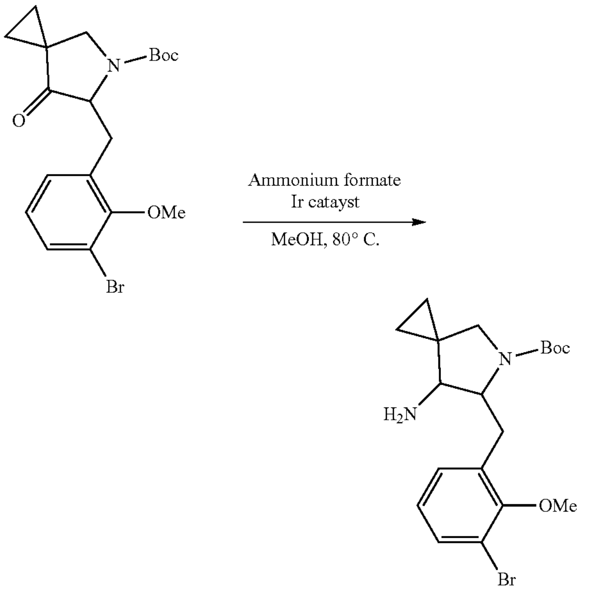

A mixture of tert-butyl 6-(3-bromo-2-methoxybenzyl)-7-oxo-5-azaspiro[2.4]heptane-5-carboxylate (564 mg, 1.37 mmol, 1 eq), ammonium formate (286 mg, 4.53 mmol, 3.3 eq), bis[2-(2-pyridyl)phenyl]iridium(1+); 2-(2-pyridyl)pyridine; hexafluorophosphate (11 mg, 13.74 μmol, 0.01 eq) in methanol (6 mL) was degassed and purged with nitrogen for 3 times, and then the mixture was stirred at 80° C. for 12 h under nitrogen atmosphere. The reaction mixture was quenched by addition water (10 mL), and then diluted with ethyl acetate and extracted with ethyl acetate (10 mL×3). The combined organic layers were washed with brine, dried over anhydrous magnesium sulfate, filtered and concentrated under reduced pressure to afford an oil. The residue was purified by prep-TLC ($SiO_2$, ethyl acetate:methanol=10:1) to afford the title compound (100 mg, 18% yield) as a yellow oil. LCMS(method M)(ESI+): m/z 411.0 $(M+H)^+$, RT: 0.702 min Step 3: tert-butyl 6-(3-bromo-2-methoxybenzyl)-7-(methylsulfonamido)-5-azaspiro[2.4]heptane-5-carboxylate_cis racemic

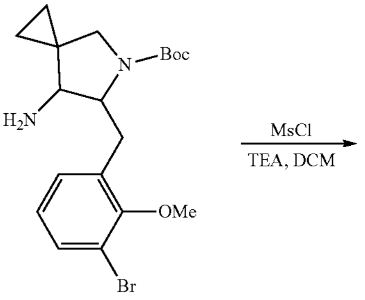

-continued

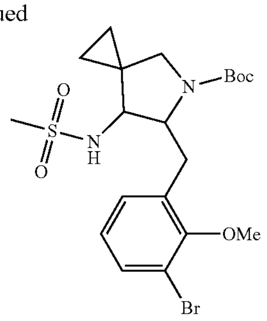

To a solution of tert-butyl 7-amino-6-(3-bromo-2-methoxybenzyl)-5-azaspiro[2.4]heptane-5-carboxylate_cis racemic (0.11 g, 267 µmol, 1 eq) in dichloromethane (2 mL) was added methanesulfonyl chloride (31 uL, 401 µmol, 1.5 eq) and triethylamine (112 µL, 802 µmol, 3 eq). The mixture was stirred at 20° C. for 2 h. The reaction mixture was quenched by addition water (10 mL), and then diluted with dichloromethane and extracted with dichloromethane (10 mL×3). The combined organic layers were washed with brine, dried over anhydrous magnesium sulfate, filtered and concentrated under reduced pressure to afford the title compound (120 mg, 91.7% yield) as a yellow oil. The product was used for next step directly.

LCMS(method M)(ESI+): m/z 389.0 (M+H)~, RT: 0.854 min.

Step 4: tert-butyl 6-((2-methoxy-[1,1'-biphenyl]-3-yl)methyl)-7-(methylsulfonamido)-5-azaspiro[2.4]heptane-5-carboxylate_cis racemic

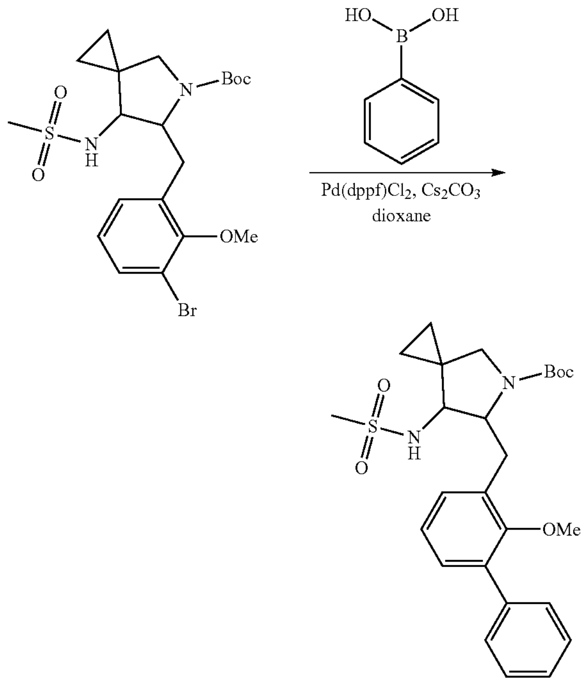

A mixture of tert-butyl 6-(3-bromo-2-methoxybenzyl)-7-(methylsulfonamido)-5-azaspiro[2.4]heptane-5-carboxylate_cis racemic (120 mg, 245 µmol, 1 eq), phenylboronic acid (39 mg, 318 µmol, 1.3 eq), caesium carbonate (240 mg, 735 µmol, 3 eq), Pd(dppf)$Cl_2$ (21 mg, 25 µmol, 0.1 eq) in dioxane (2 mL) was degassed and purged with nitrogen for 3 times, and then the mixture was stirred at 80° C. for 12 hours under nitrogen atmosphere. The reaction mixture was filtered with celite and the filtrate was concentrated under reduced pressure to afford crude product. The residue was purified by prep-TLC ($SiO_2$, petroleum ether:ethyl acetate=5:1) to afford the title compound (110 mg, 92.2% yield) as colorless oil. LCMS(method M)(ESI+): m/z 387.3 $(M+H-100)^+$, RT: 0.904 min.

Step 5 N-(6-((2-methoxy-[1,1'-biphenyl]-3-yl)methyl)-5-azaspiro[2.4]heptan-7-yl)methanesulfonamide hydrochloride_cis racemic

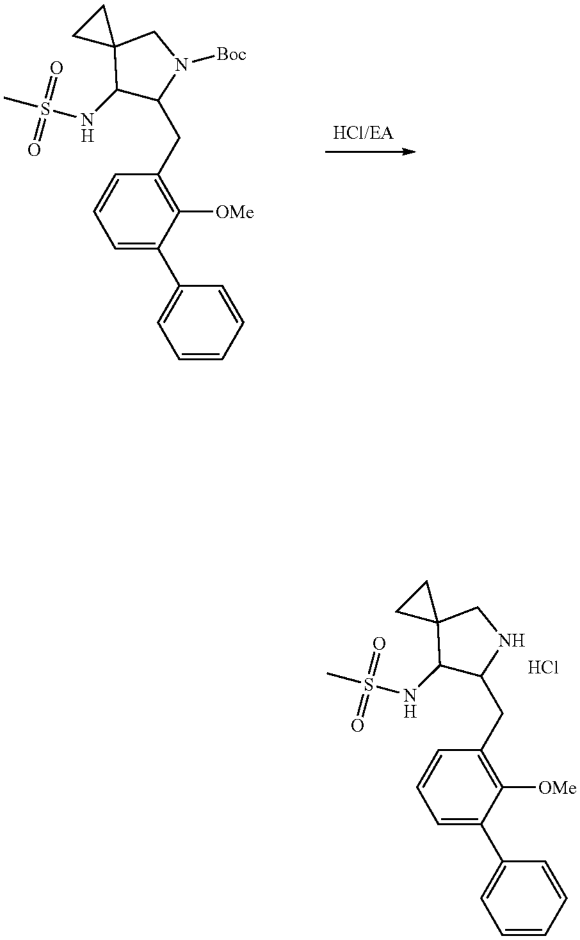

A solution of tert-butyl 6-((2-methoxy-[1,1'-biphenyl]-3-yl)methyl)-7-(methylsulfonamido)-5-azaspiro[2.4]heptane-5-carboxylate_cis racemic (100 mg, 205 µmol, 1 eq) in HCl/dioxane (4 M, 2 mL) was stirred at 20° C. for 2 h. The reaction mixture was concentrated under reduced pressure to afford the title compound (0.07 g, 88.1% yield) as a yellow solid. The product was used for next step directly. LCMS (method M)(ESI+): m/z 387.1 $(M+H)^+$, RT: 0.818 min.

Step 6: (6S,7S)—N-ethyl-6-((2-methoxy-[1,1'-biphenyl]-3-yl)methyl)-7-(methylsulfonamido)-5-azaspiro[2.4]heptane-5-carboxamide

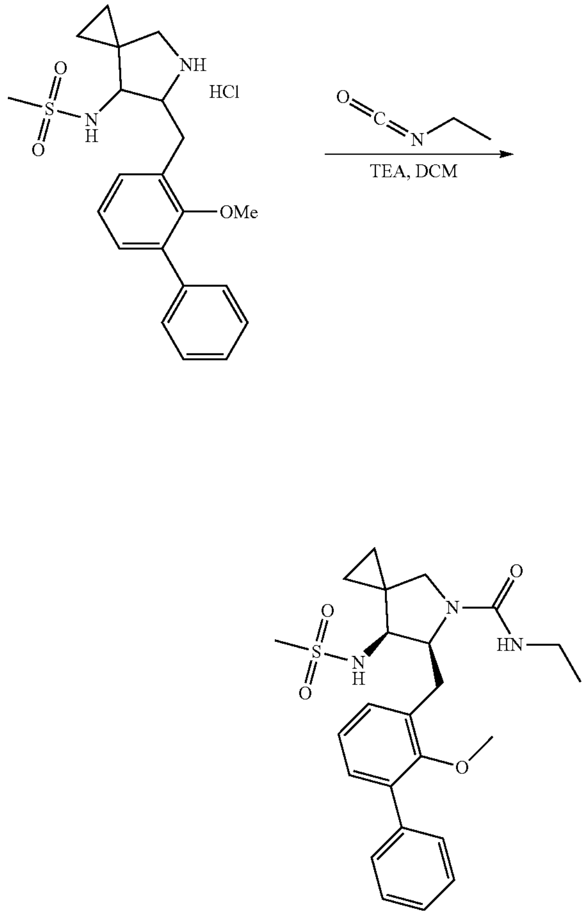

To a solution of N-(6-((2-methoxy-[1,1'-biphenyl]-3-yl) methyl)-5-azaspiro[2.4]heptan-7-yl)methanesulfonamide hydrochloride_cis racemic (120 mg, 310 μmol, 1 eq), triethylamine (94 mg, 931 μmol, 3 eq) in dichloromethane (8 mL) was added isocyanatoethane (29 μL, 372 μmol, 1.2 eq). The mixture was stirred at 20° C. for 2 h. The reaction mixture was partitioned between water (20 mL) and ethyl acetate (20 mL). The aqueous phase was separated, washed with ethyl acetate (20 mL-3), dried over anhydrous sodium sulfate, and filtered. The organic layers were concentrated under reduced pressure. The residue was purified by prep-HPLC (Phenomenex Gemini-NX C18 75*30 mm*3 μm; mobile phase: [water (0.05% $NH_3H_2O$+10 mM $NH_4HCO_3$)-ACN]; B %: 30%-60%, 8 min to afford the racemic product which was further separated by SFC (condition: column: DAICEL CHIRALPAK IG (250 mm*30 mm, 10 μm); mobile phase: [Neu-ETOH]; B %: 50%-50%, min) to afford the title compound (18 mg, 12% yield) with the longer retention time as a white solid.

Example 35 (Compound 56)

Step 1: tert-butyl (6S,7S)-7-amino-6-((2-fluoro-[1,1'-biphenyl]-3-yl)methyl)-5-azaspiro[2.4]heptane-5-carboxylate (Intermediate 18)

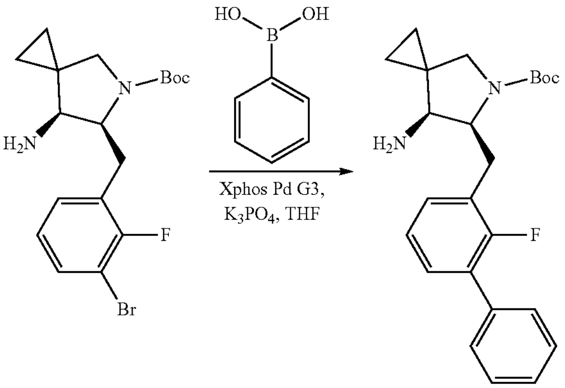 [SMILES: CC(C)(C)OC(=O)N1CC2(CC2)[C@H](N)[C@@H]1Cc1cccc(Br)c1F ; OB(O)c1ccccc1 ; CC(C)(C)OC(=O)N1CC2(CC2)[C@H](N)[C@@H]1Cc1cccc(-c2ccccc2)c1F]

To a solution of tert-butyl (6S,7S)-7-amino-6-(3-bromo-2-fluorobenzyl)-5-azaspiro[2.4]heptane-5-carboxylate, intermediate 8 (3 g, 7.51 mmol, 1 eq) in tetrahydrofuran (30 mL) were added phenylboronic acid (1.83 g, 15.03 mmol, 2 eq), $K_3PO_4$ (4.79 g, 22.54 mmol, 3 eq) and XPhos Pd G3 (318 mg, 376 μmol, 0.05 eq) under $N_2$ atmosphere at 25° C. The resulting mixture was stirred at 80° C. for 8 hrs. The resulting mixture was treated with $H_2O$ (10 mL) and extracted with ethyl acetate (3-10 mL). The organic layer was combined and dried over $Na_2SO_4$, concentrated under reduced pressure to afford crude product. The crude product was purified by column chromatography on silica gel (eluted with petroleum ether/ethyl acetate=100/1 to 0/1) to afford the title compound (2.2 g, 73.9% yield) as white solid. $^1H$ NMR (400 MHz, dimethyl sulfoxide-$d_6$) δ 0.24-0.55 (m, 3H), 0.77-0.92 (m, 1H), 0.96-1.22 (m, 9H), 1.38-1.77 (m, 2H), 2.56-2.89 (m, 2H), 2.94-3.14 (m, 2H), 3.54 (br d, 1H), 4.06-4.22 (m, 1H), 7.19 (br d, 2H), 7.28-7.42 (m, 2H), 7.42-7.62 (m, 4H).

Step 2: tert-butyl (6S,7S)-6-((2-fluoro-[1,1'-biphenyl]-3-yl)methyl)-7-(methylsulfonamido)-5-azaspiro[2.4]heptane-5-carboxylate

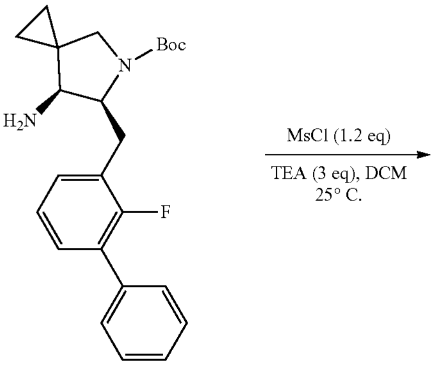

-continued

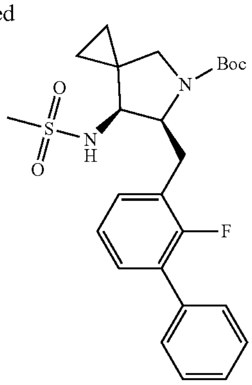

To a solution of tert-butyl (6S,7S)-7-amino-6-((2-fluoro-[1,1'-biphenyl]-3-yl)methyl)-5-azaspiro[2.4]heptane-5-carboxylate (intermediate 18)(250 mg, 630 μmol, 1 eq) in dichloromethane (1 mL) was added methanesulfonyl chloride (58 μL, 756 μmol, 1.2 eq) and triethylamine (263 μL, 1.89 mmol, 3 eq). The mixture was stirred at 20° C. for 2 hr. The reaction mixture was partitioned between aqueous solution of sodium bicarbonate (5 mL) and dichloromethane (5 mL). The aqueous phase was separated, washed with dichloromethane (5 mL×3), dried over sodium sulfate, filtered and concentrated under reduced pressure to afford a residue. The residue was purified by prep-TLC ($SiO_2$, petroleum ether: Ethyl acetate=1:1) to afford the title compound (200 mg, 66.8% yield) as a yellow oil. LCMS(method M)(ESI+): m/z 520.4 $(M+H)^+$, RT: 1.012 min.

Step 3: N-((6S,7S)-6-((2-fluoro-[1,1'-biphenyl]-3-yl)methyl)-5-azaspiro[2.4]heptan-7-yl)methanesulfonamide hydrochloride (Intermediate 19)

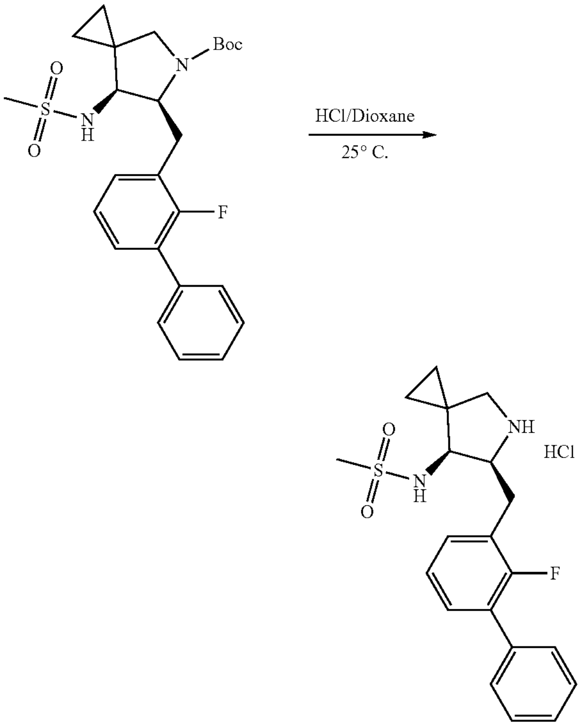

To a solution of tert-butyl (6S,7S)-6-((2-fluoro-[1,1'-biphenyl]-3-yl)methyl)-7-(methylsulfonamido)-5-azaspiro[2.4]heptane-5-carboxylate (200 mg, 421 μmol, 1 eq) in HCl/dioxane (2 mL) was stirred at 25° C. for 2 hours. The mixture was concentrated under reduced pressure to afford the title compound (140 mg, 88.7% yield) which was used without further purification. LCMS(method M)(ESI+): m/z 375.2 $(M+H)^+$, RT: 0.625 min.

Step 4: N-((6S,7S)-6-((2-fluoro-[1,1'-biphenyl]-3-yl)methyl)-5-((S)-3,3,3-trifluoro-2-hydroxypropanoyl)-5-azaspiro[2.4]heptan-7-yl)methanesulfonamide

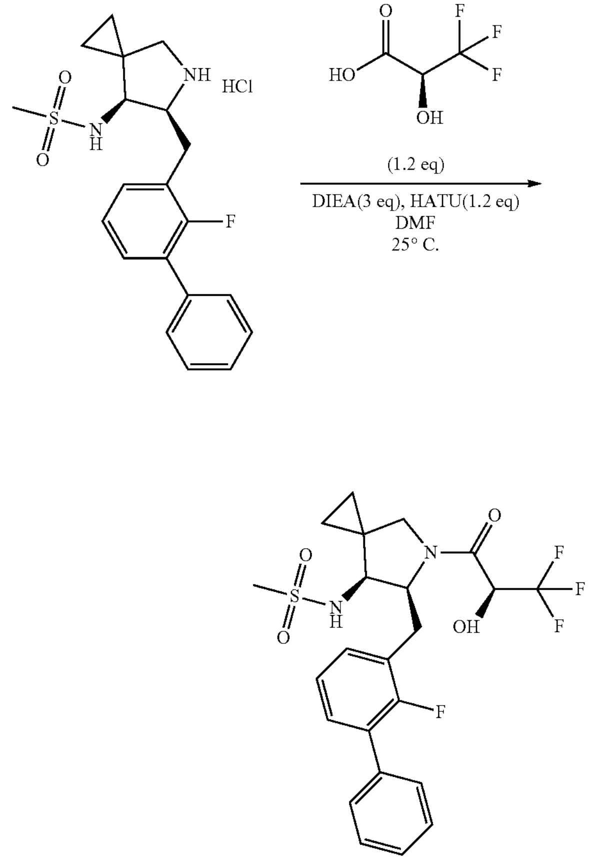

To a solution of N-((6S,7S)-6-((2-fluoro-[1,1'-biphenyl]-3-yl)methyl)-5-azaspiro[2.4]heptan-7-yl)methanesulfonamide hydrochloride (120 mg, 320 μmol, 1 eq) in N,N-dimethylformamide (1 mL) was added (2S)-3,3,3-trifluoro-2-hydroxy-propanoic acid (55 mg, 384 μmol, 1.2 eq), N,N-Diisopropylethylamine (167 μL, 961.36 μmol, 3 eq) and HATU (146 mg, 384 μmol, 1.2 eq). The mixture was stirred at 25° C. for 12 hours. The reaction mixture was partitioned between $H_2O$ (10 mL) and ethyl acetate (10 mL). The aqueous phase was separated, washed with ethyl acetate (5 mL×3), dried over anhydrous sodium sulfate, filtered and concentrated under reduced pressure to afford a residue. The residue was purified by prep-HPLC (basic condition. column: Phenomenex Gemini-NX C18 75*30 mm*3 μm; mobile phase: [water (0.05% $NH_3H_2O$+10 mM $NH_4HCO_3$)-ACN]; B %: 35%-55%, 8 min) to afford the title compound (20 mg, 12.5% yield) as a white solid.

Example 36 (Compound 58). N-((6S,7S)-6-([1,1'-biphenyl]-3-ylmethyl)-5-((S)-3,3,3-trifluoro-2-hydroxypropanoyl)-5-azaspiro[2.4]heptan-7-yl)ethanesulfonamide

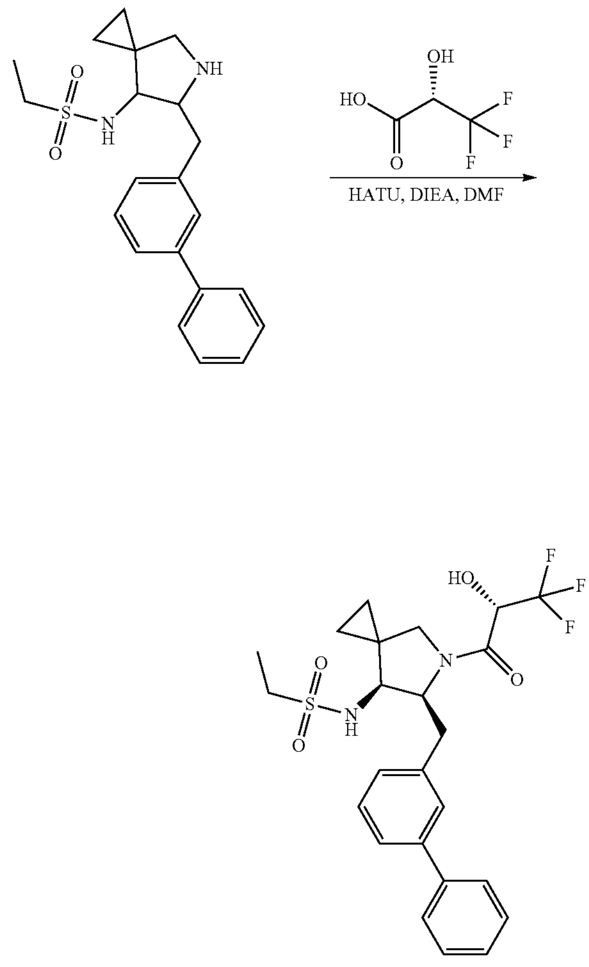

To a solution of N-(6-([1,1'-biphenyl]-3-ylmethyl)-5-azaspiro[2.4]heptan-7-yl)ethanesulfonamide hydrochloride_cis racemic, intermediate 4 (0.2 g, 540 μmol, 1 eq) and (2S)-3,3,3-trifluoro-2-hydroxy-propanoic acid (93.3 mg, 648 μmol, 1.2 eq) and N,N-diisopropylethylamine (470 μL, 2.70 mmol, 5 eq) in dimethyl formamide (2 mL) was added HATU (246 mg, 648 μmol, 1.2 eq). The mixture was stirred at 20° C. for 12 h. The reaction mixture was partitioned between dichloromethane (20 mL) and water (20 mL). The organic phase was separated, washed with dichloromethane (20 mL×3), dried over anhydrous magnesium sulfate, filtered and concentrated under reduced pressure to afford a residue. The residue was purified by prep-HPLC (column: Phenomenex luna C18 80*40 mm*3 μm; mobile phase: [water (0.1% TFA)-ACN]; B %: 55%-65%, 7 min) to afford the title compound (0.027 g, yield 10.1%) as a white solid.

Example 37 (Compound 59)

Step 1: tert-butyl (6S,7S)-6-((2,5-difluoro-[1,1'-biphenyl]-3-yl)methyl)-7-(methylsulfonamido)-5-azaspiro[2.4]heptane-5-carboxylate

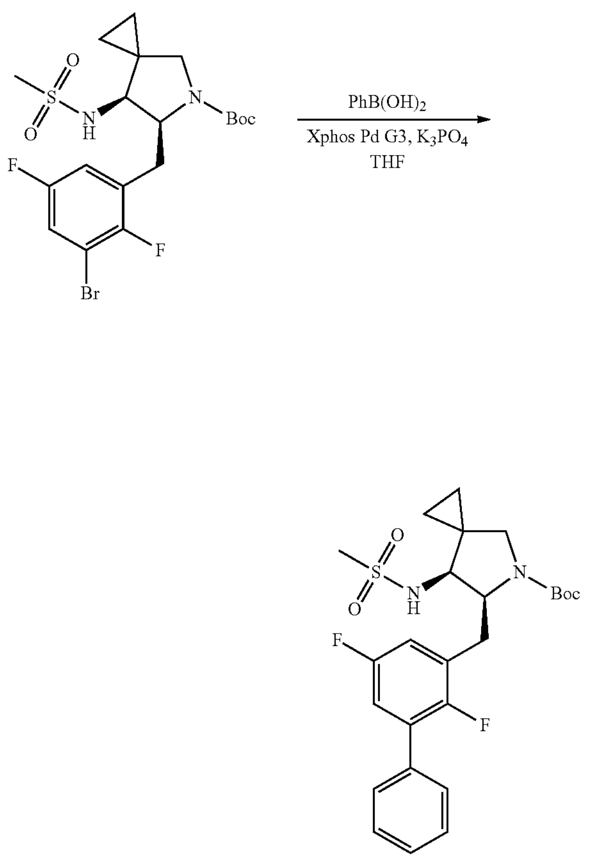

To a mixture of tert-butyl (6S,7S)-6-(3-bromo-2,5-difluorobenzyl)-7-(methylsulfonamido)-5-azaspiro[2.4]heptane-5-carboxylate (2.3 g, 4.64 mmol, 1 eq) and phenylboronic acid (679 mg, 5.57 mmol, 1.2 eq) in tetrahydrofuran (30 mL) was added potassium phosphate (2.96 g, 13.9 mmol, 3 eq), then was added XPhos-Pd-G3 (393 mg, 464 μmol, 0.1 eq) in one portion at 25° C. under nitrogen. The mixture was stirred at 25° C. for 3 min, then heated to 80° C. and stirred for 2 h. The mixture was poured into ice-water (w/w=1/1)(50 mL) and stirred for 3 min. The aqueous phase was extracted with ethyl acetate (3×50 mL). The combined organic phase was dried with anhydrous sodium sulfate, filtered and concentrated under reduced pressure to afford crude product. The mixture was purified by column chromatography (silica, Petroleum ether/Ethyl acetate=I/O to 5/1) to afford the title compound (2 g, yield 76.1%) as a white solid. LCMS (method M)(ESI+): m/z 437.1 $(M-55)^+$, RT: 0.703 min Step 2: N-((6S,7S)-6-((2,5-<difluoro-[1,1'-biphenyl]-3-yl)methyl)-5-azaspiro[2.4]heptan-7-yl)methanesulfonamide hydrochloride

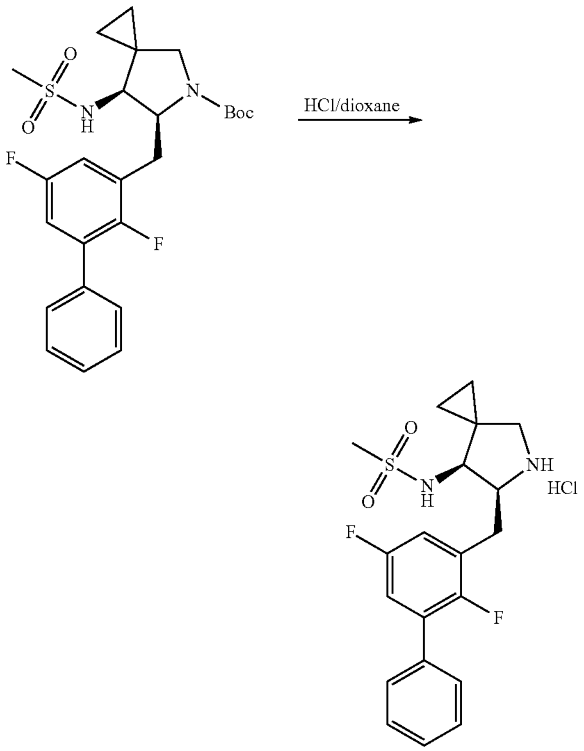

To a solution of tert-butyl (6S,7S)-6-((2,5-difluoro-[1,1'-biphenyl]-3-yl)methyl)-7-(methylsulfonamido)-5-azaspiro[2.4]heptane-5-carboxylate (2 g, 4.06 mmol, 1 eq) was added HCl/dioxane (30 mL) in one portion at 25° C. under nitrogen. The mixture was stirred at 25° C. for 3 min and stirred for 12 h. The mixture was concentrated under reduced pressure to afford the title compound (1.6 g, yield 88.4%) as a white solid.

Step 3: N-((6S,7S)-6-((2,5-difluoro-[1,1'-biphenyl]-3-yl)methyl)-5-((R)-oxetane-2-carbonyl)-5-azaspiro[2.4]heptan-7-yl)methanesulfonamide

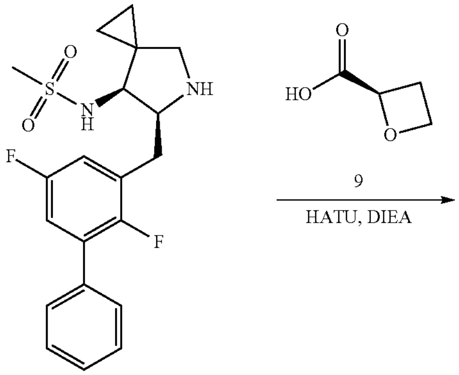

-continued

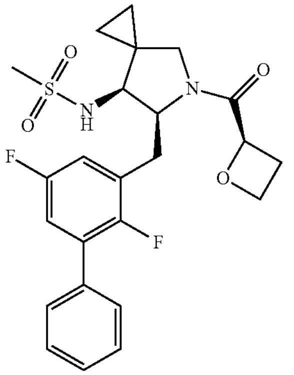

To a mixture of (2R)-oxetane-2-carboxylic acid (371.98 mg, 3.64 mmol, 1.1 eq) and N-((6S,7S)-6-((2,5-difluoro-[1,1'-biphenyl]-3-yl)methyl)-5-azaspiro[2.4]heptan-7-yl)methanesulfonamide hydrochloride (1.3 g, 3.31 mmol, 1 eq) in N,N-dimethylformamide (15 mL) was added N,N-Diisopropylethylamine (1.73 mL, 9.94 mmol, 3 eq) and HATU (1.64 g, 4.31 mmol, 1.3 eq) in one portion at 25° C. Then nitrogen was bubbled into the reaction mixture for 2 mins. The mixture was stirred at 25° C. for 12 h. The mixture was poured into water (w/w=1/1)(50 mL) and stirred for 3 min. The aqueous phase was extracted with ethyl acetate (3×50 mL). The combined organic phase was washed with brine (3×50 mL), dried with anhydrous sodium sulfate, filtered and concentrated under reduced pressure to afford crude product. The mixture was purified by normal phase HPLC (column: NP-1; mobile phase: [Heptane-EtOH]; B %: 5%-30%, 10 min) to afford the title compound (510 mg, yield 31.7%) as a white solid.

Example 38 (Compound 64)

Step 1: tert-butyl (6S,7S)-7-amino-6-((2-fluoro-[1,1'-biphenyl]-3-yl)methyl)-5-azaspiro[2.4]heptane-5-carboxylate

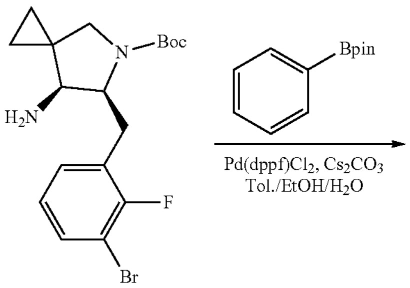

-continued

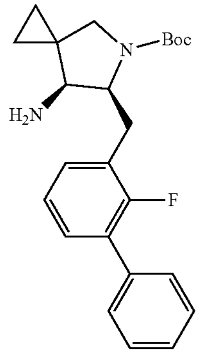

To a mixture of phenylboronic acid (687 mg, 5.63 mmol, 1.5 eq) and tert-butyl (6S,7S)-7-amino-6-(3-bromo-2-fluorobenzyl)-5-azaspiro[2.4]heptane-5-carboxylate, intermediate 8 (1.5 g, 3.76 mmol, 1 eq) in toluene (12 mL), water (2.4 mL) and ethanol (12 mL) was added cesium carbonate (2.45 g, 7.51 mmol, 2 eq) and Pd(dppf)$Cl_2$ (275 mg, 376 μmol, 0.1 eq) in one portion at 25° C. under nitrogen. The mixture was stirred 70° C. for 12 h. The mixture was cooled to 25° C. and poured into water (50 mL) and extracted with ethyl acetate (30 mL). The aqueous phase was extracted with ethyl acetate (3×10 mL). The combined organic phase was dried with anhydrous sodium sulfate, filtered and concentrated to afford a residue. The residue was purified by column chromatography (Silica, Petroleum ether/Ethyl acetate=I/O to 2/1) to afford the title compound (1.2 g, 68.5% yield) as yellow solid. LCMS(method M)(ESI+): m/z 397.2 $(M+H)^+$, RT: 0.789 min.

Step 2: tert-butyl (6S,7S)-7-((N,N-dimethylsulfamoyl)amino)-6-((2-fluoro-[1,1'-biphenyl]-3-yl)methyl)-5-azaspiro[2.4]heptane-5-carboxylate

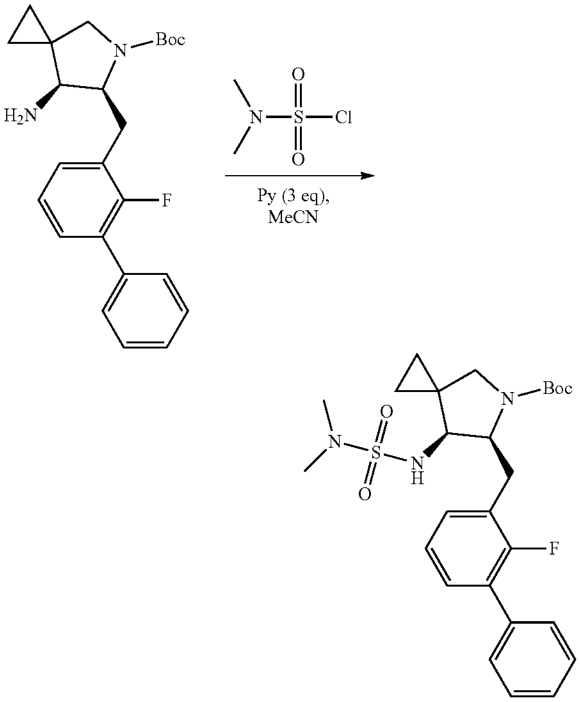

To a mixture of tert-butyl (6S,7S)-7-amino-6-((2-fluoro-[1,1'-biphenyl]-3-yl)methyl)-5-azaspiro[2.4]heptane-5-carboxylate (300 mg, 757 μmol, 1 eq) in acetonitrile (5 mL) was added pyridine (299 mg, 3.78 mmol, 5 eq) and N,N-dimethylsulfamoyl chloride (243 μL, 2.27 mmol, 3 eq) in one portion at 0° C. under nitrogen. The mixture was stirred at 60° C. for 12 h. The mixture was poured into saturated sodium bicarbonate (50 mL) and extracted with ethyl acetate (15 mL). The aqueous phase was extracted with dichloromethane (3×10 mL). The combined organic phase was dried with anhydrous sodium sulfate, filtered and concentrated under reduced pressure to afford a residue. The residue was purified by prep-TLC (petroleum ether:ethyl acetate=1:1) to afford the title compound (238 mg, 41.9% yield) as a yellow solid. LCMS (method M)(ESI+): m/z 448.1 $(M-56)^+$, RT: 1.063 min.

Step 3: N-((6S,7S)-6-((2-fluoro-[1,1'-biphenyl]-3-yl)methyl)-5-azaspiro[2.4]heptan-7-yl)-N,N-dimethylsulfuric diamide hydrochloride

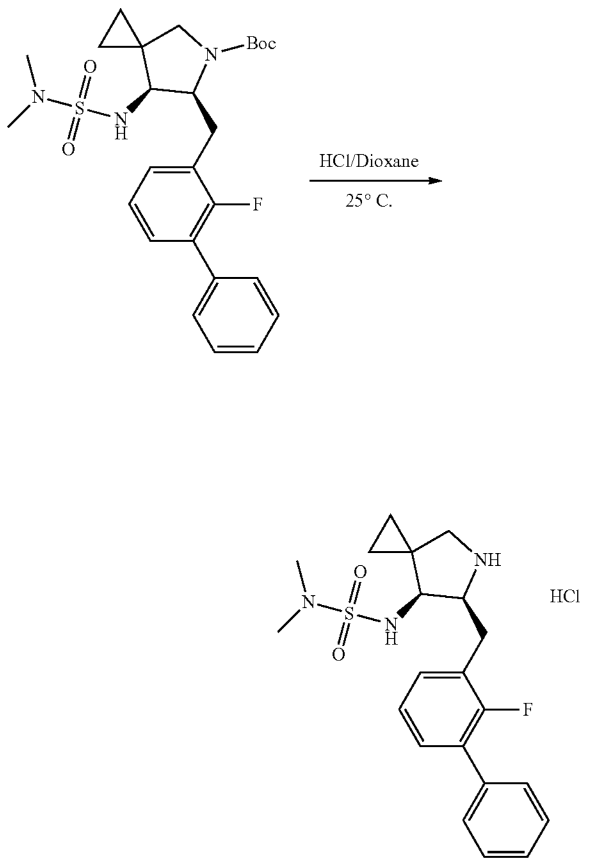

A mixture of tert-butyl (6S,7S)-7-((N,N-dimethylsulfamoyl)amino)-6-((2-fluoro-[1,1'-biphenyl]-3-yl)methyl)-5-azaspiro[2.4]heptane-5-carboxylate (273 mg, 542 μmol, 1 eq) in HCl/dioxane (3 mL) was stirred at 25° C. for 3 h. The organic phase was concentrated under reduced pressure to afford the title compound (210 mg, quant.) as a white solid which was used directly without purification. LCMS (method M)(ESI+): m/z 404.3 $(M+H)^+$, RT: 0.654 min.

Step 4: N-((6S,7S)-6-((2-fluoro-[1,1'-biphenyl]-3-yl)methyl)-5-((R)-oxetane-2-carbonyl)-5-azaspiro[2.4]heptan-7-yl)-N,N-dimethylsulfuric diamide

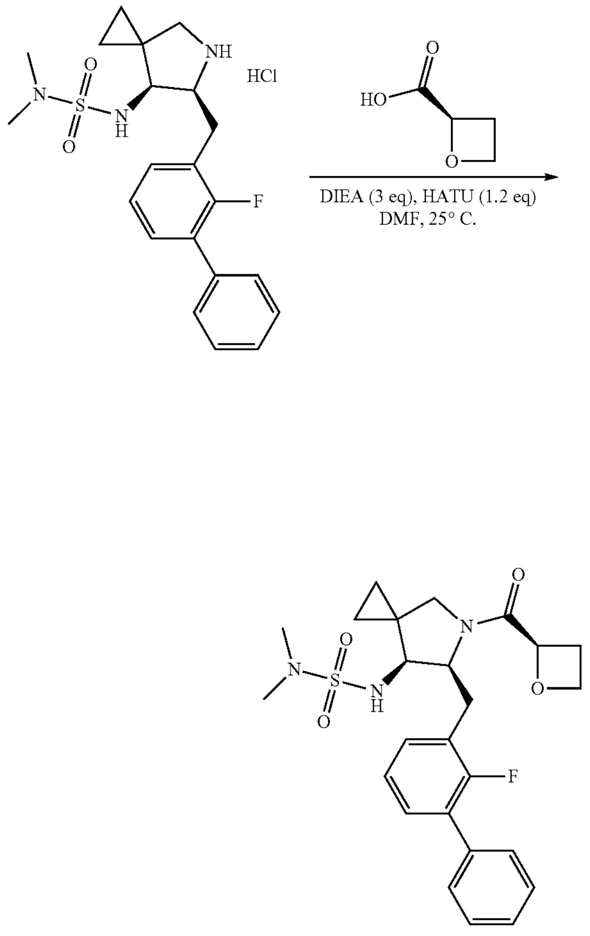

To a mixture of N-((6S,7S)-6-((2-fluoro-[1,1'-biphenyl]-3-yl)methyl)-5-azaspiro[2.4]heptan-7-yl)-N,N-dimethylsulfuric diamide hydrochloride (100 mg, 248 μmol, 1 eq) and (2R)-oxetane-2-carboxylic acid (28 mg, 273 μmol, 1.1 eq) in dimethyl formamide (1 mL) was added N,N-diisopropylethylamine (130 μL, 743 μmol, 3 eq) and HATU (123 mg, 322 μmol, 1.3 eq) in one portion at 25° C. under nitrogen atmosphere. The mixture was stirred at 25° C. for 12 h. The mixture was concentrated under reduced pressure. The residue was purified by prep-HPLC (neutral condition, column: Waters Xbridge BEH C18 100x30 mmx10 μm; mobile phase: [water (10 mM ammonium bicarbonate)-acetonitrile]; B %: 35%-65%, 8 min) to afford the title compound (12 mg, 9.9% yield over two steps) as a white solid.

Example 39 (Compound 67)

Step 1: tert-butyl 6-(2-fluoro-3-(4,4,5,5-tetramethyl-1,3,2-dioxaborolan-2-yl)benzyl)-7-(methylsulfonamido)-5-azaspiro[2.4]heptane-5-carboxylate

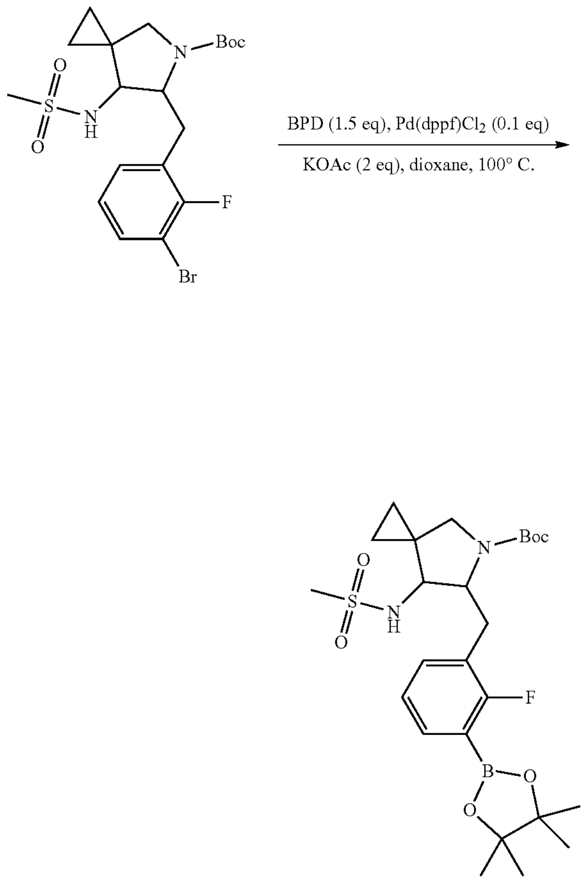

To a mixture of BPD (798 mg, 3.14 mmol, 1.5 eq) and tert-butyl 6-(3-bromo-2-fluorobenzyl)-7-(methylsulfonamido)-5-azaspiro[2.4]heptane-5-carboxylate_cis racemic, intermediate 2 (1 g, 2.09 mmol, 1 eq) in dioxane (20 mL) was added Pd(dppf)$Cl_2$ (77 mg, 105 μmol, 0.05 eq) and potassium acetate (514 mg, 5.24 mmol, 2.5 eq) in one portion at 25° C. under $N_2$ atmosphere. The mixture was stirred at 25° C. for 3 min, then heated to 100° C. and stirred for 12 hours. The mixture was poured into ice-water (w/w=1/1, 100 mL) and stirred for 3 min. The aqueous phase was extracted with ethyl acetate (50 mLx3). The combined organic phase was dried with anhydrous sodium sulfate, filtered and concentrated by reduced pressure vacuum. The residue was purified by silica gel chromatography (Petroleum ether/Ethyl acetate=1/0-1/1) to afford the title compound (700 mg, 63.7% yield) as a white solid. $^1$H NMR (400 MHz, chloroform-d) δ 0.40 (br s, 1H), 0.55-0.79 (m, 3H), 1.10-1.64 (m, 21H), 2.40-2.95 (m, 2H), 2.98-3.13 (m, 2H), 3.64 (br s, 1H), 4.08-4.25 (m, 2H), 4.38 (q, 1H), 4.47-4.67 (m, 1H), 6.94-7.63 (m, 3H).

Step 2: tert-butyl 6-((2,3'-difluoro-[1,1'-biphenyl]-3-yl)methyl)-7-(methylsultonamido)-5-azaspiro[2.4]heptane-5-carboxylate_cis racemic

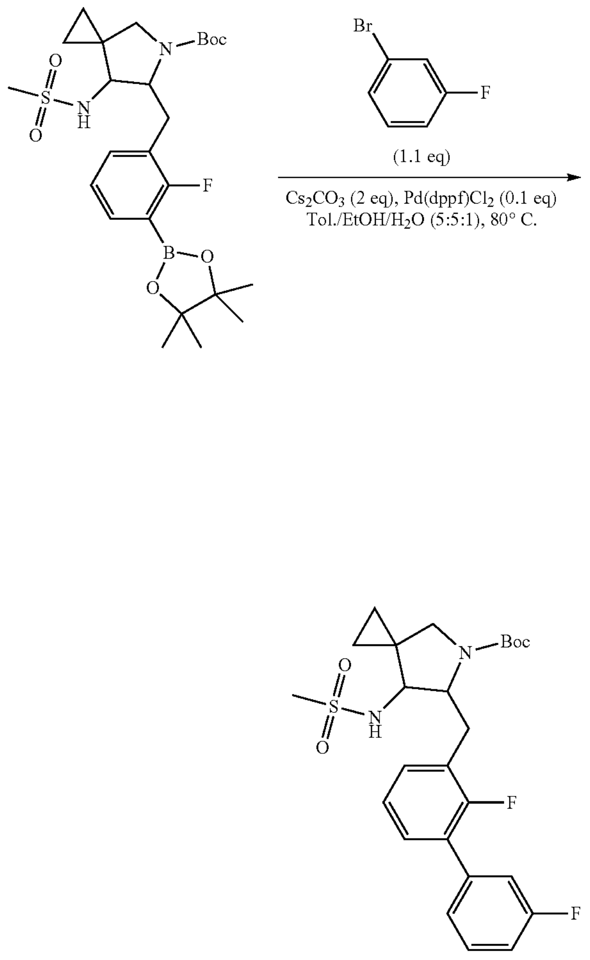

To a solution of tert-butyl 6-{[2-fluoro-3-(4,4,5,5-tetramethyl-1,3,2-dioxaborolan-2-yl)phenyl]methyl}-7-methanesulfonamido-5-azaspiro[2.4]heptane-5-carboxylate_cis racemic (100 mg, 191 μmol, 1 eq) in ethanol (0.5 mL), toluene (0.5 mL) and water (0.1 mL) was added 1-bromo-3-fluoro-benzene (40 mg, 229 μmol, 1.2 eq) and cesium carbonate (124 mg, 381 μmol, 2 eq) at 20° C. Then Pd(dppf)$Cl_2$ (7 mg, 9.5 μmol, 0.05 eq) was added to the reaction at 20° C. The mixture was stirred at 80° C. for 12 h under $N_2$ atmosphere. The reaction was poured into water (10 mL) and extracted with ethyl acetate (5 mL×2). The organic phases were combined and washed with brine (5 mL). The organic phase was dried over magnesium sulfate and concentrated to afford a residue. The residue was purified by prep-HPLC (column: Phenomenex Gemini-NX C18 75*30 mm*3 μm; mobile phase: [water (0.05% $NH_3 \cdot H_2O$+10 mM $NH_4HCO_3$)-ACN]; B %: 45%-75%, 8 min) to afford the title compound (50 mg, 66.5% yield) as a white solid. $^1$H NMR (400 MHz, CD30D) S 0.50-0.77 (m, 3H), 1.01-1.30 (m, 10H), 2.75-2.90 (m, 1H), 3.03 (s, 3H), 3.09 (br d, 1H), 3.20 (d, 1H), 3.69 (br d, 1H), 4.19 (br d, 1H), 4.37-4.54 (m, 1H), 7.03-7.15 (m, 1H), 7.17-7.32 (m, 3H), 7.33-7.59 (m, 3H).

Step 3: N-(6-((2,3'-difluoro-[1,1'-biphenyl]-3-yl)methyl)-5-azaspiro[2.4]heptan-7-yl)methanesulfonamide_cis racemic hydrochloride

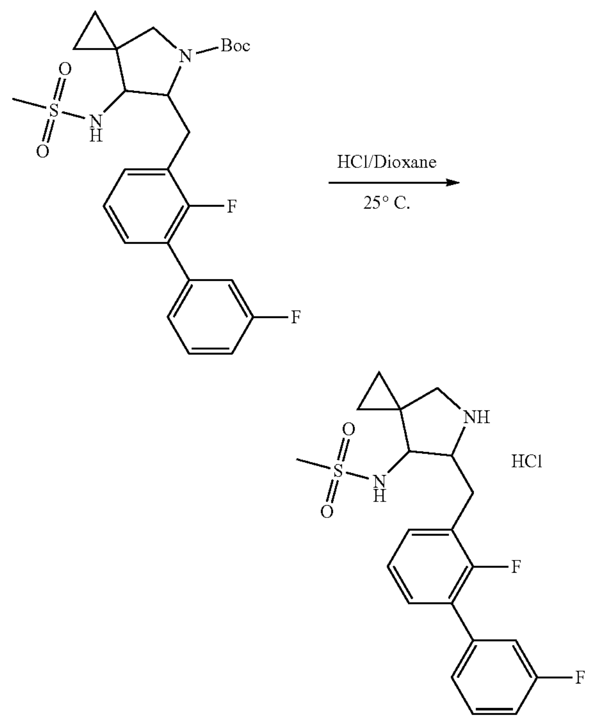

A solution of tert-butyl 6-((2,3'-difluoro-[1,1'-biphenyl]-3-yl)methyl)-7-(methylsulfonamido)-5-azaspiro[2.4]heptane-5-carboxylate_cis racemic (35 mg, 71 μmol, 1 eq) in HCl/dioxane (3 mL) was added stirred at 25° C. for 1 hour. The reaction mixture was concentrated under reduced pressure to afford the title compound (30 mg, 72.2%, yield) as a white solid.

LCMS(method M)(ESI+): m/z 393.2 $(M+H)^+$, RT: 0.630 min.

Step 4: N-((6S,7S)-6-((2,3'-difluoro-[1,1'-biphenyl]-3-yl)methyl)-5-((R)-oxetane-2-carbonyl)-5-azaspiro[2.4]heptan-7-yl)methanesulfonamide

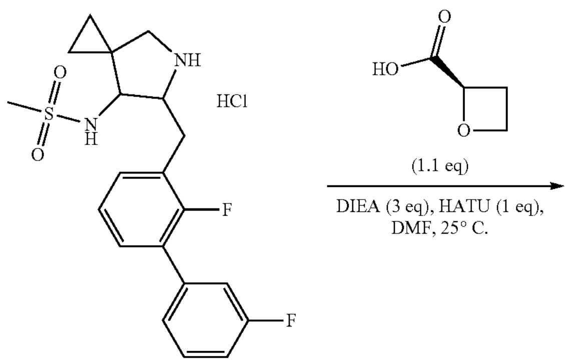

-continued

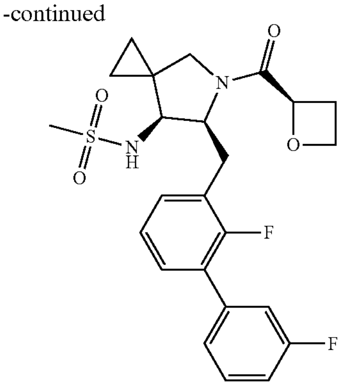

To a mixture of N-(6-((2,3'-difluoro-[1,1'-biphenyl]-3-yl)methyl)-5-azaspiro[2.4]heptan-7-yl)methanesulfonamide_cis racemic hydrochloride (30 mg, 76 μmol, 1 eq) and (2R)-oxetane-2-carboxylic acid (9 mg, 84 μmol, 1.1 eq) in dimethyl formamide (0.5 mL) were added N,N-diisopropylethylamine (40 μL, 229 μmol, 3 eq) and HATU (29 mg, 76 μmol, 1 eq) at 20° C. The mixture was stirred at 20° C. for 12 h. The reaction mixture was purified by prep-HPLC (column: Phenomenex Gemini-NX C18 75*30 mm*3 μm; mobile phase: [water (0.05% $NH_3 \cdot H_2O$+10 mM $NH_4HCO_3$)-ACN]; B %: 25%-55%, 8 min) to afford the title compound (6 mg, 16.5% yield) as a white solid.

Example 40 (Compound 69)

Step 1: tert-butyl (6S,7S)-6-(3-bromo-2-fluorobenzyl)-7-(cyclopropanesulfonamido)-5-azaspiro[2.4]heptane-5-carboxylate

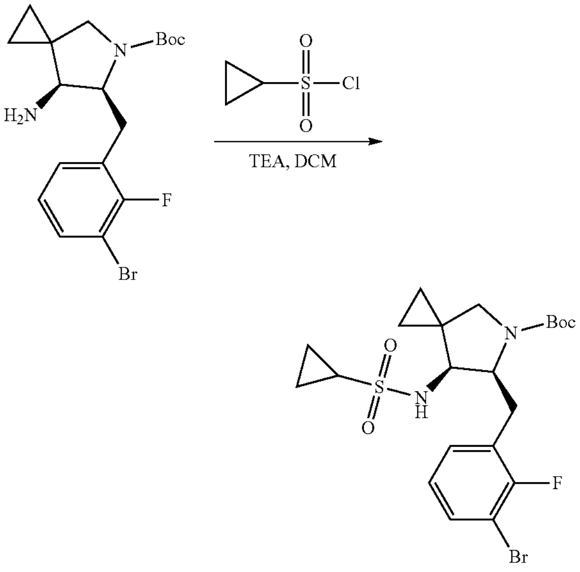

To a mixture of tert-butyl (6S,7S)-7-amino-6-(3-bromo-2-fluorobenzyl)-5-azaspiro[2.4]heptane-5-carboxylate, intermediate 8 (1.0 g, 2.5 mmol, 1 eq) and triethylamine (760 mg, 751 μmol, 3 eq) in dichloromethane (10 mL) was added cyclopropanesulfonyl chloride (528 mg, 3.76 mmol, 1.5 eq) in one portion at 0° C. under nitrogen atmosphere. The mixture was stirred at 25° C. for 12 hours, poured into ice-water (w/w=1/1, 20 mL) and stirred for 3 min. The aqueous phase was extracted with dichloromethane (10 mL×3). The combined organic phase was dried with anhydrous sodium sulfate, filtered and concentrated in vacuum. The residue was purified by column chromatography (silica, petroleum ether:ethyl acetate=3:1 to 1:1) to afford the title compound (600 mg, 47.6% yield) as a white solid. LCMS (method M)(ESI+): m/z 402.9 $(M+H-100)^+$, RT: 0.830 min.

Step 2: tert-butyl (6S,7S)-7-(cyclopropanesulfonamido)-6-((2-fluoro-[1,1'-biphenyl]-3-yl)methyl)-5-azaspiro[2.4]heptane-5-carboxylate

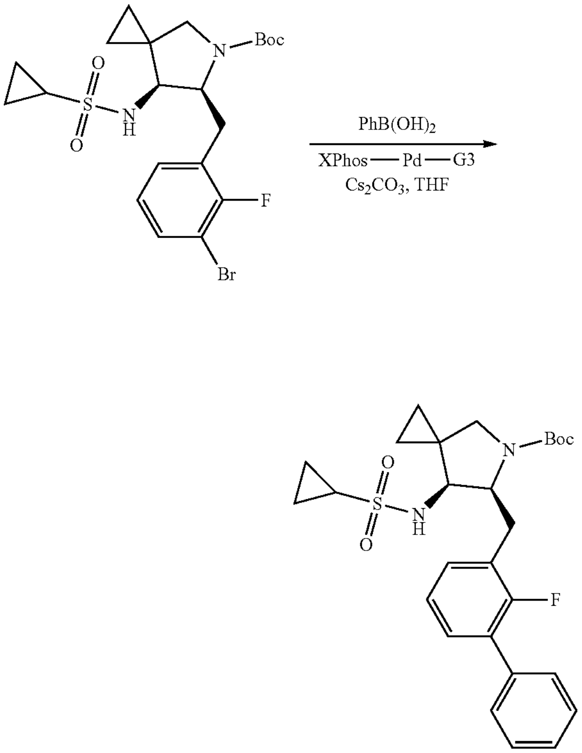

To a mixture of phenylboronic acid (127 mg, 1.04 mmol, 1.5 eq) and tert-butyl (6S,7S)-6-(3-bromo-2-fluorobenzyl)-7-(cyclopropanesulfonamido)-5-azaspiro[2.4]heptane-5-carboxylate (350 mg, 695 μmol, 1 eq) in tetrahydrofuran (10 mL) was added XPhos-Pd-G3 (8 mg, 10 μmol, 0.02 eq) and cesium carbonate (665 mg, 2.09 mmol, 3 eq) in one portion at 25° C. under nitrogen atmosphere. The mixture was stirred at 25° C. for 3 min, then heated to 70° C. and stirred for 12 hours. The mixture was cooled to 25° C., poured into ice-water (w/w=1/1, 20 mL) and stirred for 3 min. The aqueous phase was extracted with ethyl acetate (10 mL×3). The combined organic phase was dried with anhydrous sodium sulfate, filtered and concentrated in vacuum. The residue was purified by prep-TLC (silica, petroleum ether: ethyl acetate=1:1) to afford the title compound (220 mg, 63.2% yield) as a white solid. $^1$H NMR (400 MHz, DMSO-$d_6$) δ ppm 0.44-0.59 (m, 3H) 0.62 (br d, 1H), 0.93-0.99 (m, 11H), 1.14 (br s, 2H), 2.67 (br d, 2H), 3.02-3.14 (m, 2H), 3.51-3.63 (m, 1H), 3.99-4.05 (m, 1H), 4.23-4.42 (m, 1H), 7.18-7.23 (m, 2H), 7.29 (br s, 1H), 7.38 (br t, 2H), 7.45-7.51 (m, 4H).

Step 3: N-((6S,7S)-6-((2-fluoro-[1,1'-biphenyl]-3-yl) methyl)-5-azaspiro[2.4]heptan-7-yl)cyclopropane-sulfonamide hydrochloride

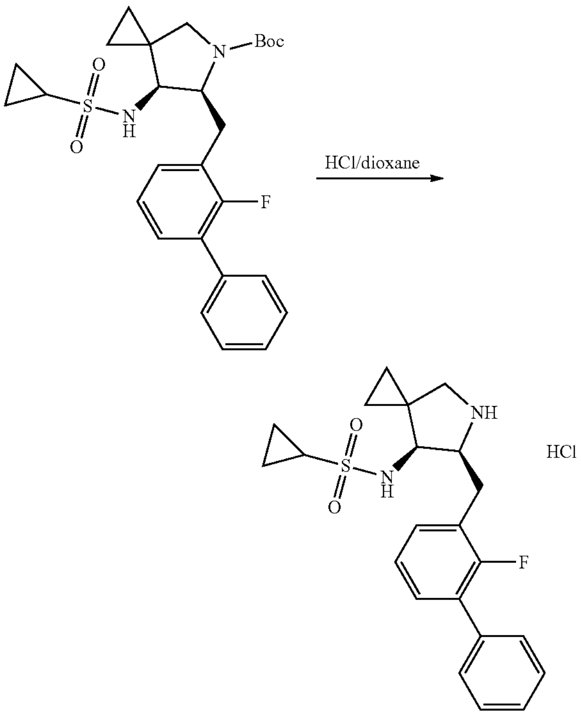

A mixture of tert-butyl (6S,7S)-7-(cyclopropanesulfonamido)-6-((2-fluoro-[1,1'-biphenyl]-3-yl)methyl)-5-azaspiro [2.4]heptane-5-carboxylate (200 mg, 399 μmol, 1 eq) in hydrochloric acid/dioxane (2 mL) was stirred at 20° C. for 2 hour. The mixture was concentrated to afford the title compound (160 mg, 89% yield) as a white solid, which was used to next step without further purification. LCMS (method M)(ESI+): m/z 401.1 $(M+H)^+$, RT: 0.733 min.

Step 4: N-((6S 7S)-6-((2-fluoro-[1,1'-biphenyl]-3-yl)methyl)-5-((R)-oxetane-2-carbonyl)-5-azaspiro [2.4]heptan-7-yl)cyclopropanesulfonamide

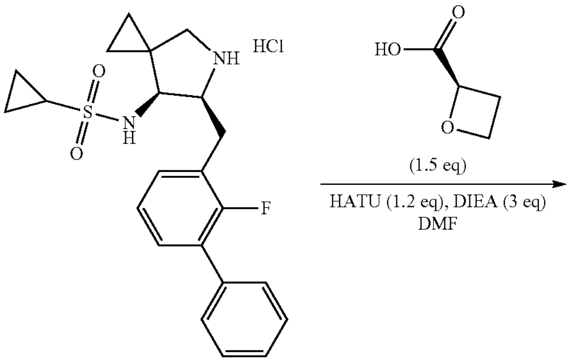

-continued

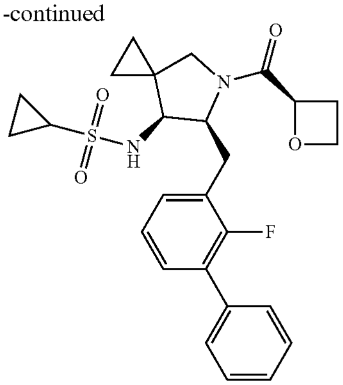

To a mixture of (2R)-oxetane-2-carboxylic acid (42 mg, 412 μmol, 1.1 eq) and N-((6S,7S)-6-((2-fluoro-[1,1'-biphenyl]-3-yl)methyl)-5-azaspiro[2.4]heptan-7-yl)cyclopropanesulfonamide hydrochloride (150 mg, 374 μmol, 1 eq) in N,N-dimethylformamide (15 mL) was added HATU (185 mg, 487 μmol, 1.3 eq) and N,N-diisopropylethylamine (196 μL, 1.12 mmol, 3 eq) in one portion at 25° C. under nitrogen. The mixture was stirred at 25° C. for 12 hours. The mixture was concentrated in vacuum and the residue purified by prep-HPLC (neutral condition: column: Phenomenex Gemini-NX C18 75*30 mm*3 μm; mobile phase: [water (10 mM ammonium bicarbonate)-acetonitrile]; B %: 35%-55%, 8 min) to afford the title compound (43 mg, yield 23.7%) as a white solid.

Example 41 (Compound 93)

Step 1: tert-butyl (6S,7S)-6-((2-fluoro-[1,1'-biphenyl]-3-yl)methyl)-7-((fluoromethyl)sulfonamido)-5-azaspiro[2.4]heptane-5-carboxylate

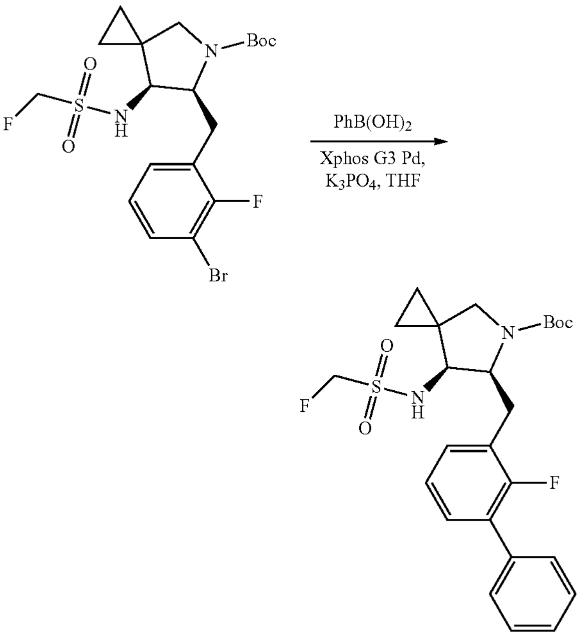

To a solution of tert-butyl (6S,7S)-6-(3-bromo-2-fluorobenzyl)-7-((fluoromethyl)sulfonamido)-5-azaspiro[2.4]

heptane-5-carboxylate, intermediate 11 (0.5 g, 1.01 mmol, 1 eq) in tetrahydrofuran (10 mL) were added phenylboronic acid (148 mg, 1.21 mmol, 1.2 eq), $K_3PO_4$ (428 mg, 2.02 mmol, 2 eq) and Xphos G3 Pd (43 mg, 50.5 μmol, 0.05 eq) at 25° C. The resulting reaction mixture was stirred at 80° C. for 12 hrs under $N_2$, during which the mixture maintained as a yellow solution. Another reaction was set up as described above and the two reactions were combined. The reaction mixture was poured into water (20 mL) and extracted with ethyl acetate (3×10 mL). The combined organic layers were dried over $Na_2SO_4$, filtered and the filtrate was concentrated under reduced pressure. The crude product was purified by chromatography on silica (eluted with petroleum ether/ethyl acetate=100/1 to 5/1) to afford the title compound (0.8 g, 80.5% yield) as a white solid. $^1$H NMR (400 MHz, chloroform-d) δ 0.40 (br s, 1H) 0.57-0.75 (m, 3H), 1.37 (br s, 9H), 2.86-3.22 (m, 3H), 3.67 (br s, 1H), 4.24 (br dd, 1H), 4.38-5.05 (m, 3H), 7.29-7.38 (m, 1H), 7.40 (m, 1H), 7.43-7.46 (m, 4H), 7.47-7.57 (m, 2H).

Step 2: 1-fluoro-N-((6S,7S)-6-((2-fluoro-[1,1'-biphenyl]-3-yl)methyl)-5-azaspiro[2.4]heptan-7-yl)methanesulfonamide hydrochloride (Intermediate 20)

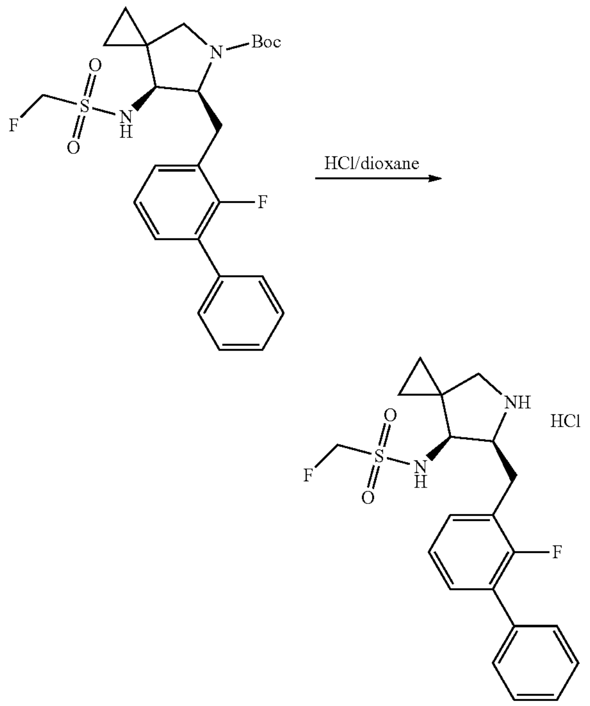

To a solution of tert-butyl (6S,7S)-6-((2-fluoro-[1,1'-biphenyl]-3-yl)methyl)-7-((fluoromethyl)sulfonamido)-5-azaspiro[2.4]heptane-5-carboxylate (390 mg, 792 μmol, 1 eq) in dioxane (7.5 mL) was added HCl/dioxane (5.8 M, 19.50 mL, 143 eq) at 0° C. The reaction mixture was stirred at 25° C. for 12 hrs. Another reaction was set up as described above and the two reactions were combined. The mixture was concentrated under reduced pressure to afford the title compound (630 mg, 1.32 mmol, 83.5% yield) as a white solid. $^1$H NMR (400 MHz, methanol-d$_4$) δ 0.81-0.94 (m, 2H) 1.00-1.07 (m, 1H) 1.11-1.18 (m, 1H) 3.07 (d, 1H) 3.17 (br dd, 1H) 3.45 (br d, 1H) 3.60 (br d, 1H) 3.90 (d, 1H) 4.23 (dt, 1H) 5.21-5.32 (m, 1H) 5.33-5.44 (m, 1H) 7.26-7.33 (m, 1H) 7.36-7.42 (m, 1H) 7.42-7.51 (m, 4H) 7.56 (br d, 2H).

Step 3: 1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide

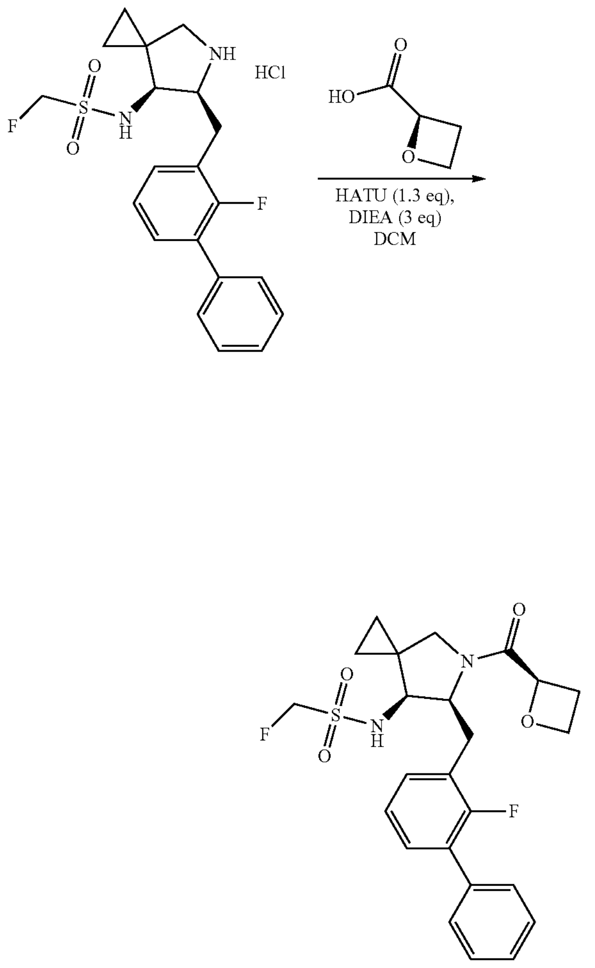

To a solution of 1-fluoro-N-((6S,7S)-6-((2-fluoro-[1,1'-biphenyl]-3-yl)methyl)-5-azaspiro[2.4]heptan-7-yl)methanesulfonamide hydrochloride, intermediate 20 (300 mg, 764 μmol, 1 eq) and (R)-oxetane-2-carboxylic acid (94 mg, 917 μmol, 1.2 eq) in N,N-dimethylformamide (4 mL) was added N,N-diisopropylethylamine (399 μL, 2.29 mmol, 3 eq) and HATU (349 mg, 917 μmol, 1.2 eq). The reaction mixture was partitioned between $H_2O$ (10 mL) and ethyl acetate (10 mL). The aqueous phase was separated, washed with ethyl acetate (3 mL×3), dried over anhydrous sodium sulfate, filtered and concentrated under reduced pressure. The residue was purified by normal phase HPLC (NP-2; mobile phase: [Heptane-EtOH]; B %: 5%-95%, 12 min) to afford the title compound (250 mg, 68.6% yield) as a white solid.

Example 42 (Compound 95)

Step 1: tert-butyl 6-([1,1'-biphenyl]-3-ylmethyl)-7-oxo-5-azaspiro[2.4]heptane-5-carboxylate

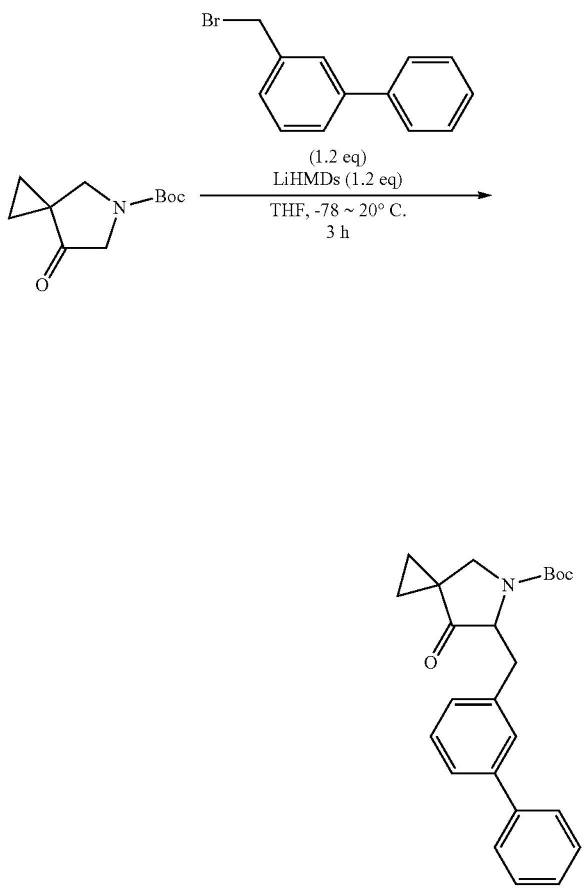

To a solution of tert-butyl 7-oxo-5-azaspiro[2.4]heptane-5-carboxylate (10 g, 47.34 mmol, 1 eq) in tetrahydrofuran (50 mL) was added dropwise bis(trimethylsily)amine lithium (1 M, 56.80 mL, 1.2 eq) at −78° C. over 15 mins. After addition, the mixture was stirred at this temperature for 30 min, and then 1-(bromomethyl)-3-phenyl-benzene (14 g, 56.8 mmol, 1.2 eq) in tetrahydrofuran (50 mL) was added dropwise at −78° C. The resulting mixture was stirred at 20° C. for 3 h. The reaction mixture was quenched by addition of water (100 mL), and then diluted with ethyl acetate and extracted with ethyl acetate (100 mL) three times. The combined organic layers were washed with brine, dried over anhydrous magnesium sulfate, filtered and concentrated under reduced pressure to afford an oil. The reaction mixture was concentrated under reduced pressure and the crude product was purified by column chromatography ($SiO_2$, Petroleum ether/Ethyl acetate=I/O to 8/1) to afford the title compound (8 g, 44.3% yield) as light yellow oil. H NMR (400 MHz, methanol-$d_4$) δ ppm 0.51-0.69 (m, 1H), 0.84-0.98 (m, 1H), 1.04 (br s, 1H), 1.20-1.28 (m, 1H), 1.46-1.59 (m, 9H), 2.80-2.93 (m, 1H), 3.09 (br d, 1H), 3.34-3.67 (m, 2H), 4.40 (br d, 1H), 6.97-7.05 (m, 1H), 7.26-7.38 (m, 3H), 7.42 (t, 2H), 7.49 (br d, 1H), 7.54-7.59 (m, 2H).

Step 2: tert-butyl 6-([1,1'-biphenyl]-3-ylmethyl)-7-amino-5-azaspiro[2.4]heptane-5-carboxylate_cis racemic

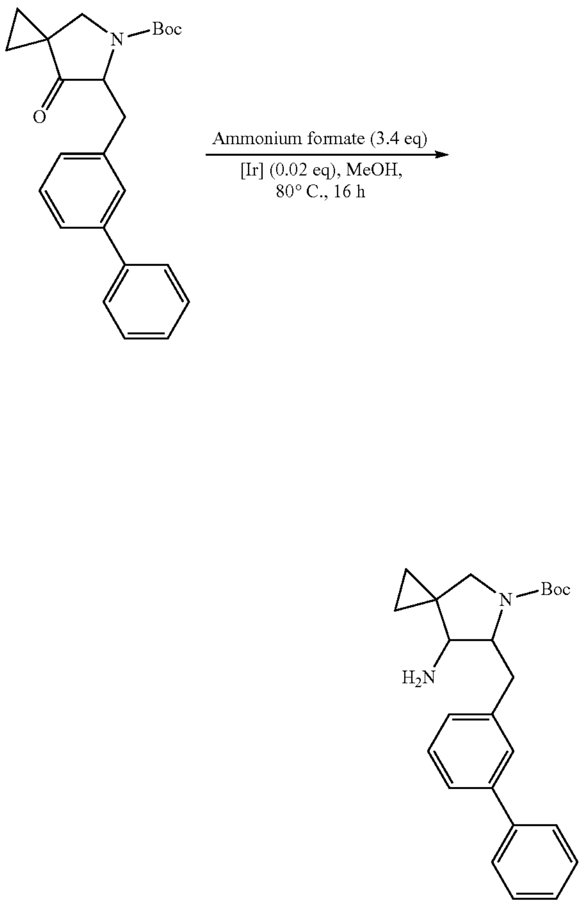

A mixture of tert-butyl 6-([1,1'-biphenyl]-3-ylmethyl)-7-oxo-5-azaspiro[2.4]heptane-5-carboxylate (12.5 g, 33.11 mmol, 1 eq), ammonium formate (7.10 g, 113 mmol, 3.4 eq), bis[2-(2-pyridyl)phenyl]iridium(1+); 2-(2-pyridyl)pyridine; hexafluorophosphate (531 mg, 662 µmol, 0.02 eq) in methanol (125 mL) was degassed and purged with nitrogen for 3 times, and then the mixture was stirred at 80° C. for 16 h under nitrogen atmosphere. The reaction mixture was concentrated under reduced pressure to afford a residue. The residue was purified by column chromatography ($SiO_2$, Petroleum ether/Ethyl acetate=I/O to 1/1) to afford the title compound (6 g, 45% yield) as yellow solid. 1H NMR (400 MHz, methanol-$d_4$) δ ppm 0.48 (br s, 1H), 0.53-0.68 (m, 2H), 0.94 (br s, 1H), 1.06 (br s, 7H), 1.34 (br s, 2H), 2.69-2.83 (m, 1H), 3.01 (br d, 1H), 3.21 (d, 1H), 3.48-3.67 (m, 2H), 4.26 (br d, 1H), 7.19 (br d, 1H), 7.28-7.38 (m, 2H), 7.38-7.49 (m, 4H), 7.55-7.63 (m, 2H).

Step 3: ten-butyl 6-([1,1'-biphenyl]-3-ylmethyl)-7-(2,2,2-trifluoroacetamido)-5-azaspiro[2.4]heptane-5-carboxylate_cis racemic

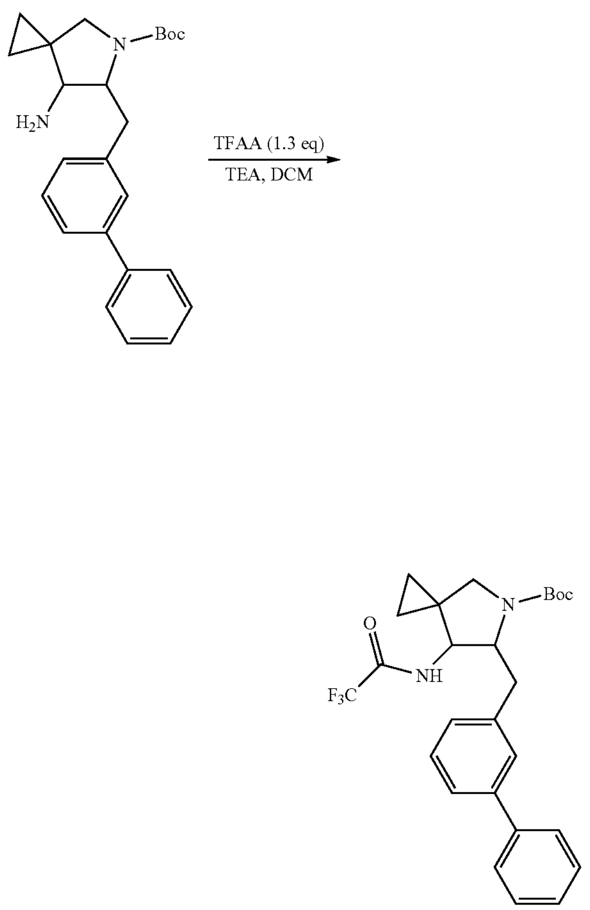

To a solution of tert-butyl 6-([1,1'-biphenyl]-3-ylmethyl)-7-amino-5-azaspiro[2.4]heptane-5-carboxylate_cis racemic (15 g, 39.6 mmol, 1 eq) in dichloromethane (150 mL) was added trifluoroacetic anhydride (7.17 mL, 51.5 mmol, 1.3 eq) and triethylamine (11 mL, 79 mmol, 2 eq). The mixture was stirred at 20° C. for 2 h. The reaction mixture was quenched by addition sodium bicarbonate aqueous (100 mL), and then diluted with dichloromethane and extracted with dichloromethane (60 mL) three times. The combined organic layers were washed with brine, dried over anhydrous magnesium sulfate, filtered and concentrated under reduced pressure to afford the title compound (12 g, 63.8% yield) as colorless oil which was used directly in the next step. $^1$H NMR (400 MHz, chloroform-d) δ ppm 0.45-0.73 (m, 1H), 0.45-0.71 (m, 3H), 1.48 (s, 9H), 2.90-3.10 (m, 2H), 3.29 (d, 2H), 3.64 (br d, 1H), 4.52-4.68 (m, 2H), 6.06 (br d, 1H), 7.18 (d, 1H), 7.35-7.50 (m, 6H), 7.53-7.57 (m, 2H).

Step 4: N-(6-([1,1'-biphenyl]-3-ylmethyl)-5-azaspiro[2.4]heptan-7-yl)-2,2,2-trifluoroacetamide_cis racemic hydrochloride

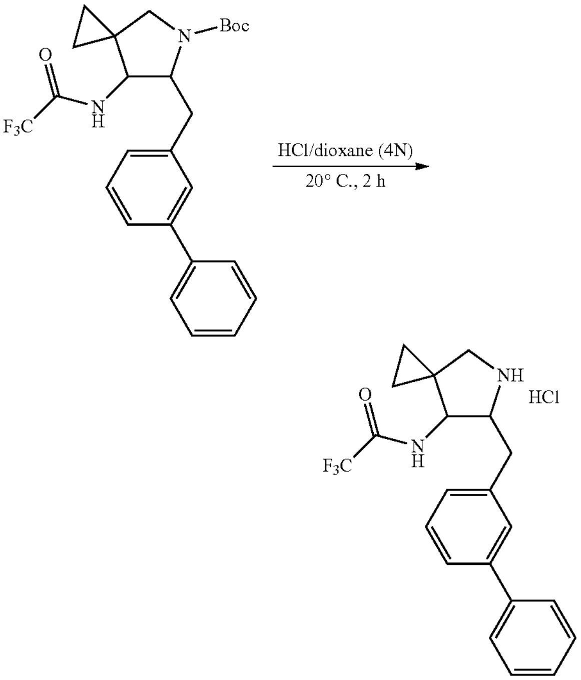

A solution of tert-butyl 6-([1,1'-biphenyl]-3-ylmethyl)-7-(2,2,2-trifluoroacetamido)-5-azaspiro[2.4]heptane-5-carboxylate_cis racemic (1.2 g, 2.53 mmol, 1 eq) in HCl/dioxane (15 mL) was stirred at 20° C. for 2 h. The reaction mixture was concentrated under reduced pressure to afford the title compound (1 g, 96.2% yield) as colourless oil which was used directly in the next step. $^1$H NMR (400 MHz, chloroform-d) δ ppm 0.71 (s, 2H), 0.88-1.04 (m, 2H), 3.11 (br s, 1H), 3.27 (s, 1H), 3.39 (br s, 1H), 3.54 (br s, 1H), 4.17 (br d, 2H), 7.17 (br d, 1H), 7.30-7.43 (m, 5H), 7.47 (br d, 1H), 7.54 (d, 2H), 8.82 (br d, 1H), 9.78 (s, 1H), 10.11-10.30 (m, 1H).

Step 5: N-((6S,7S)-6-([1,1'-biphenyl]-3-ylmethyl)-5-((R)-oxetane-2-carbonyl)-5-azaspiro[2.4]heptan-7-yl)-2,2,2-trifluoroacetamide

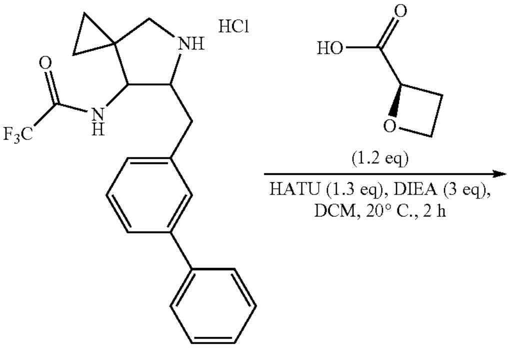

-continued

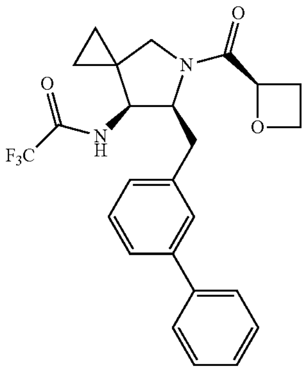

To a solution of N-(6-([1,1'-biphenyl]-3-ylmethyl)-5-azaspiro[2.4]heptan-7-yl)-2,2,2-trifluoroacetamide_cis racemic hydrochloride (1 g, 2.67 mmol, 1 eq) and (2R)-oxetane-2-carboxylic acid (327 mg, 3.21 mmol, 1.2 eq) in dichloromethane (10 mL) was added HATU (1.32 g, 3.47 mmol, 1.3 eq) and N,N-diisopropylethylamine (1.40 mL, 8.01 mmol, 3 eq). The mixture was stirred at 20° C. for 2 h. The reaction mixture was quenched by addition water (10 mL), and then diluted with dichloromethane and extracted with dichloromethane (10 mL) three times. The combined organic layers were washed with brine, dried over anhydrous magnesium sulfate, filtered and concentrated under reduced pressure to afford an oil. The oil was purified by column chromatography ($SiO_2$, Petroleum ether/Ethyl acetate=10/1 to 1/1) to afford the title compound (0.36 g, 29.4% yield) as yellow solid. $^1H$ NMR (400 MHz, methanol-$d_4$) δ ppm 0.52-1.07 (m, 4H), 2.47-3.01 (m, 3H), 3.26-3.50 (m, 1H), 3.68-3.96 (m, 2H), 4.16-4.28 (m, 1H), 4.35-4.83 (m, 3H), 5.37 (t, 1H), 7.17-7.25 (m, 1H), 7.26-7.37 (m, 2H), 7.41 (br t, 3H), 7.47 (s, 1H), 7.55-7.61 (m, 2H).

Step 6. ((6S,7S)-6-([1,1'-biphenyl]-3-ylmethyl)-7-amino-5-azaspiro[2.4]heptan-5-yl)((R)-oxetan-2-yl) methanone

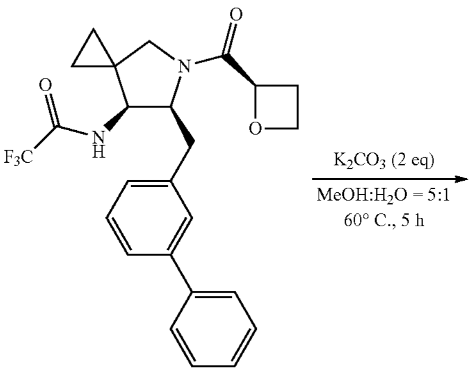

-continued

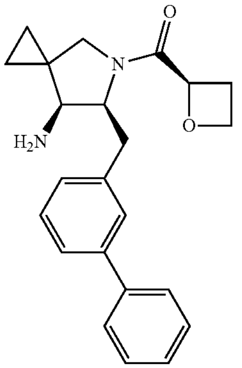

To a solution of N-((6S,7S)-6-([1,1'-biphenyl]-3-ylmethyl)-5-((R)-oxetane-2-carbonyl)-5-azaspiro[2.4]heptan-7-yl)-2,2,2-trifluoroacetamide (2.7 g, 5.89 mmol, 1 eq) in methanol (27 mL) and water (5.4 mL) was added potassium carbonate (1.63 g, 11.78 mmol, 2 eq). The mixture was stirred at 60° C. for 5 h. The reaction mixture was quenched by addition water (5 mL), and then diluted with acetate ethyl and extracted with acetate ethyl (5 mL) three times. The combined organic layers were washed with brine, dried over anhydrous magnesium sulfate, filtered and concentrated under reduced pressure to give an oil. The oil was purified by column chromatography ($SiO_2$, Ethyl acetate/methanol=100/1 to 1/1) to afford the title compound (0.46 g, 21.6% yield) as white solid. LCMS(method J)(ESI+): m/z 363.2 $(M+H)^+$, RT: 2.595 min Step 7: N-((6S,7S)-6-([1,1'-biphenyl]-3-ylmethyl)-5-((R)-oxetane-2-carbonyl)-5-azaspiro[2.4]heptan-7-yl)-N,N-dimethylsulfuric diamide

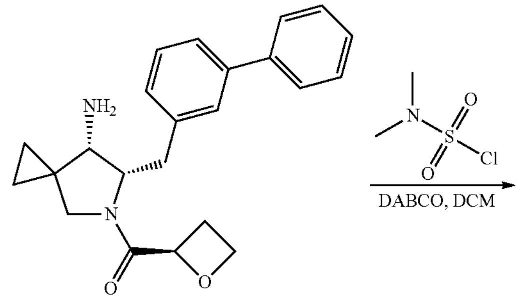

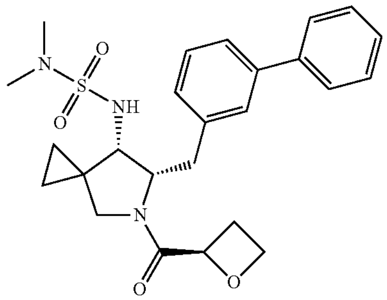

To a solution of ((6S,7S)-6-([1,1'-biphenyl]-3-ylmethyl)-7-amino-5-azaspiro[2.4]heptan-5-yl)((R)-oxetan-2-yl) methanone (15 mg, 41 μmol, 1 eq) and N,N-dimethylsulfamoyl chloride (13 μL, 124 μmol, 3 eq) in dichloromethane (0.5 mL) was added 1,4-diazabicyclo[2.2.2]octane (23 μL, 207 μmol, 5 eq) at 25° C. The mixture was stirred at 25° C. for 12 hrs. The reaction mixture was filtered and the filtrate was concentrated under reduced pressure to afford a residue, which was purified by prep-HPLC (column: Phenomenex Gemini-NX C18 75*30 mm*3 μm; mobile phase: [water (10 mM $NH_4HCO_3$)-ACN]; B %: 30%-50%, 8 min) to afford the title compound (4 mg, 20.1% yield) as a white solid.

Example 43 (Compound 98). 1-fluoro-N-((6S,7S)-6-((2-fluoro-[1,1'-biphenyl]-3-yl)methyl)-5-((S)-3,3,3-trifluoro-2-hydroxypropanoyl)-5-azaspiro[2.4]heptan-7-yl)methanesulfonamide

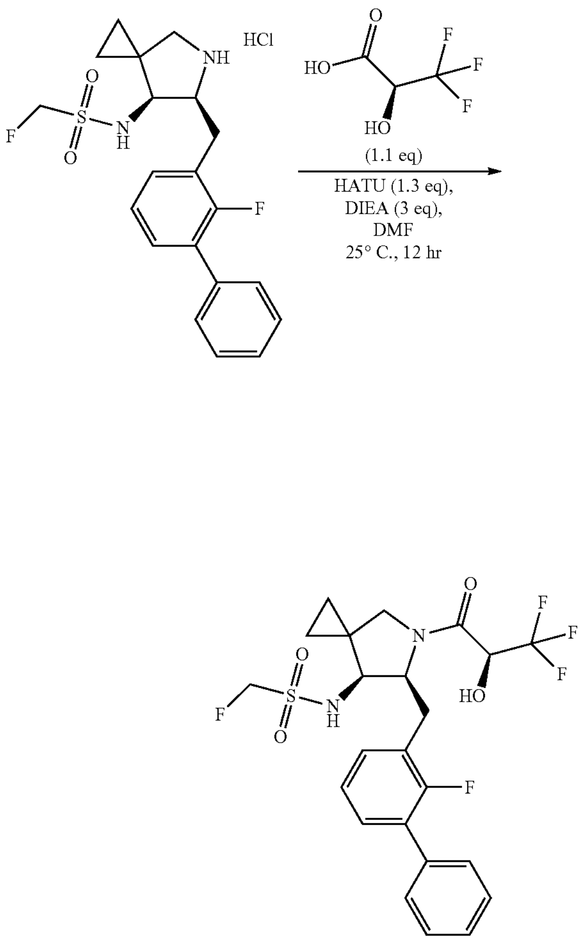

To a mixture of 1-fluoro-N-((6S,7S)-6-((2-fluoro-[1,1'-biphenyl]-3-yl)methyl)-5-azaspiro[2.4]heptan-7-yl)methanesulfonamide hydrochloride, intermediate 20 (100 mg, 255 μmol, 1 eq) and (2S)-3,3,3-trifluoro-2-hydroxy-propanoic acid (40 mg, 280 μmol, 1.1 eq) in N,N-dimethylformamide (1 mL) was added N,N-Diisopropylethylamine (133 μL, 764 μmol, 3 eq), then was added HATU (126 mg, 331 μmol, 1.3 eq) in one portion at 25° C. under nitrogen atmosphere. The mixture was stirred at 25° C. for 12 h. The mixture was filtered and then purified by prep-HPLC (column: Phenomenex luna C18 100*40 mm*5 μm; mobile phase: [water (0.1% trifluoroacetic acid)-acetonitrile]; B %: 40%-60%, 8 min) to afford the title compound (13 mg, 9.8% yield) as a yellow solid.

Example 44 (Compound 99). (6S,7S)-6-((2-fluoro-[1,1'-biphenyl]-3-yl)methyl)-7-(methylsulfonamido)-N-(2,2,2-trifluoroethyl)-5-azaspiro[2.4]heptane-5-carboxamide

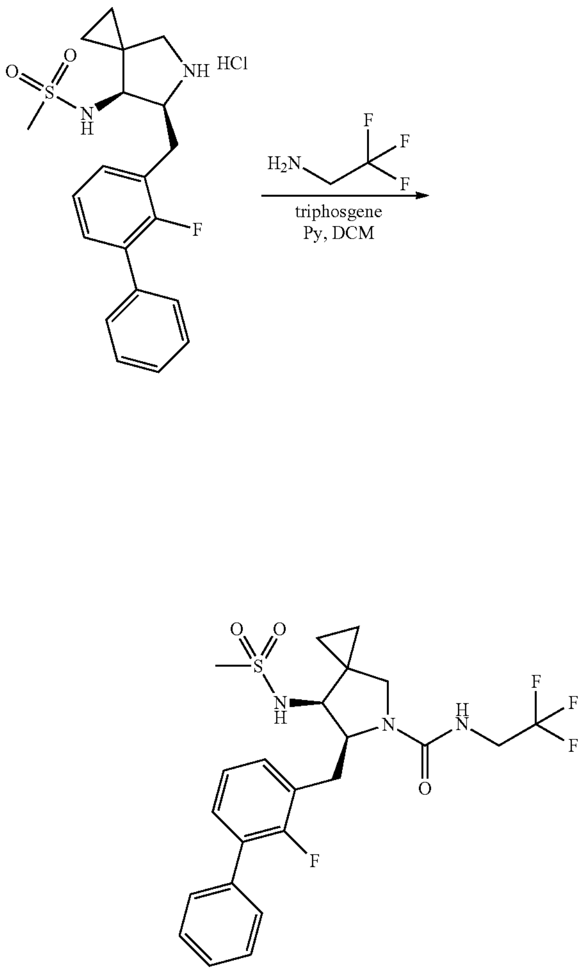

To a solution of 2,2,2-trifluoroethanamine (8 μL, 73 μmol, 1.5 eq) and pyridine (34 μL, 243 μmol, 5 eq) in dichloromethane (1.5 mL) was added triphosgene (8 mg, 27 μmol, 0.55 eq) at 0° C. The mixture was stirred at 20° C. for 1 hr. This was then added to a solution of N-((6S,7S)-6-((2-fluoro-[1,1'-biphenyl]-3-yl)methyl)-5-azaspiro[2.4]heptan-7-yl)methanesulfonamide hydrochloride, intermediate 19 (18 mg, 49 μmol, 1 eq) in dichloromethane (1.5 mL) and TEA (20 μL, 146 μmol, 3 eq) at 0° C. The reaction was stirred at 20° C. for 12 hrs. The mixture was concentrated under reduced pressure to afford a residue. The residue was purified by Prep-HPLC (neutral condition: column: Waters Xbridge BEH C18 100*30 mm*10 μm; mobile phase: [water (10 mM $NH_4HCO_3$)-ACN]; B %: 30%-60%, 10 min) and lyophilized to afford the title compound (8 mg, 32.9% yield) as off-white solid.

Example 45 (Compound 104). (6S,7S)-6-((2-fluoro-[1,1'-biphenyl]-3-yl)methyl)-N-((1-fluorocyclopropyl)methyl)-7-(methylsulfonamido)-5-azaspiro[2.4]heptane-5-carboxamide

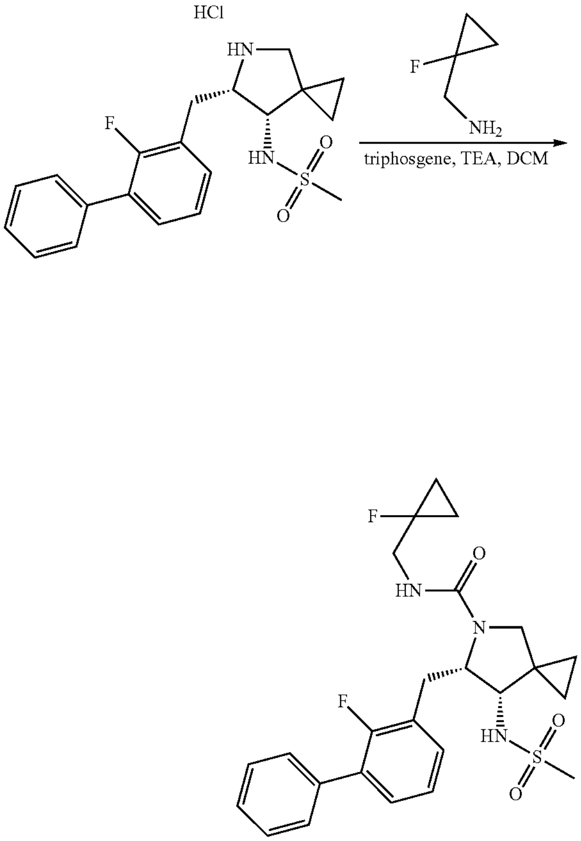

To a mixture of N-((6S,7S)-6-((2-fluoro-[1,1'-biphenyl]-3-yl)methyl)-5-azaspiro[2.4]heptan-7-yl)methanesulfonamide hydrochloride, intermediate 19 (25 mg, 67 μmol, 1 eq) in dichloromethane (2 mL) was added triethylamine (28 μL, 200 μmol, 3 eq). Then triphosgene (6 mg, 20.0 μmol, 0.3 eq) in dichloromethane (0.5 mL) was added dropwise into the reaction mixture. The reaction mixture was stirred at 25° C. for 2 h and concentrated to afford a residue. (1-fluorocyclopropyl)methanamine (30 mg, 334 μmol, 5 eq) and triethylamine (28 μL, 200 μmol, 3 eq) in dichloromethane (2.5 mL) was added into the residue. The mixture was stirred at 25° C. for 12 h and concentrated under reduced pressure. The resulting residue was purified by prep-HPLC (base condition, column: Phenomenex Gemini-NX C18 75 30 mm×3 μm; mobile phase: [water (0.05% $NH_3 \cdot H_2O$+10 mM ammonium bicarbonate)-acetonitrile]; B %: 35%-55%, 8 min) to afford the title compound (15 mg, 45.9% yield) as white solid.

Example 46 (Compound 110). (6S,7S)-6-((2-fluoro-[1,1'-biphenyl]-3-yl)methyl)-N,N-dimethyl-7-(methylsulfonamido)-5-azaspiro[2.4]heptane-5-carboxamide

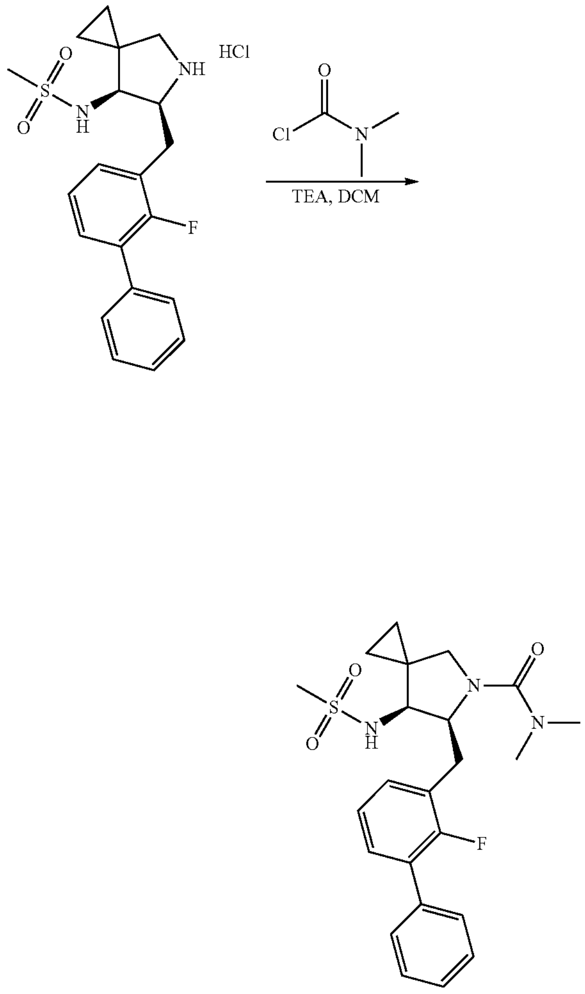

To a solution of N-((6S,7S)-6-((2-fluoro-[1,1'-biphenyl]-3-yl)methyl)-5-azaspiro[2.4]heptan-7-yl)methanesulfonamide hydrochloride, intermediate 19 (140 mg, 374 μmol, 1 eq) in dichloromethane (3 mL) was added triethylamine (156 μL, 1.12 mmol, 3 eq) and N,N-dimethylcarbamoyl chloride (41 μL, 449 μmol, 1.2 eq). The mixture was stirred at 20° C. for 2 hours. The mixture was filtered and the filtrate was concentrated under reduced pressure. The residue was purified by prep-HPLC (basic condition: Waters Xbridge BEH C18 100 30 mm×10 μm; mobile phase: [water (0.05% $NH_3H_2O$+10 mM $NH_4HCO$)-ACN]; B %: 35%-65%, 8 min to afford the title compound (48 mg, 28.8% yield) as a white solid.

Example 47 (Compound 114)

Step 1: tert-butyl 6-([1,1'-biphenyl]-3-ylmethyl)-7-((1-methylethyl)sulfonamido)-5-azaspiro[2.4]heptane-5-carboxylate_cis racemic

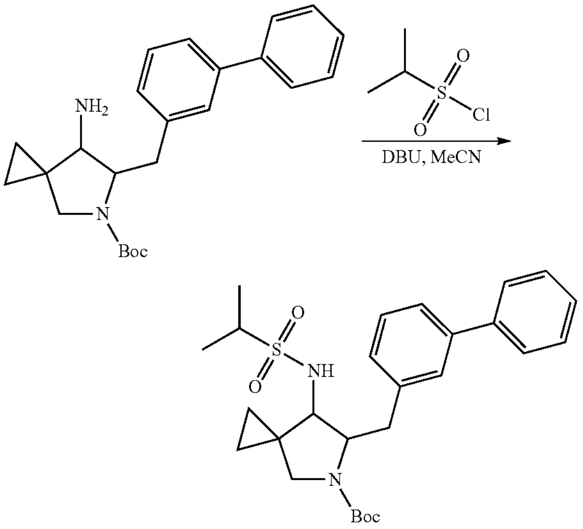

To a solution of tert-butyl 6-([1,1'-biphenyl]-3-ylmethyl)-7-amino-5-azaspiro[2.4]heptane-5-carboxylate_cis racemic (200 mg, 528 μmol, 1 eq) and propane-2-sulfonyl chloride (294 μL, 2.64 mmol, 5 eq) in MeCN(3 mL) was added DBU (80 μL, 528 μmol, 1 eq) at 25° C. The mixture was stirred at 25° C. for 12 hrs. The reaction mixture was poured into water (10 mL), and then extracted with ethyl acetate (2×5 mL). The organic layer was washed with brine (10 mL), dried over anhydrous magnesium sulfate, filtered and concentrated under reduced pressure to afford a residue, which was purified by prep-TLC (Petroleum ether/Ethyl acetate=3/1) to afford the title compound (80 mg, 28.1% yield) as a white solid. $^1$H NMR (400 MHz, MeOH-d4) δ 0.50-0.74 (m, 4H), 0.93-1.13 (m, 8H), 1.02-1.37 (m, 15H), 2.68-2.83 (m, 1H), 3.06 (dd, 1H), 3.16-3.27 (m, 2H), 3.58-3.75 (m, 1H), 4.13 (br s, 1H), 4.26-4.41 (m, 1H), 7.19 (br d, 1H), 7.28-7.51 (m, 6H), 7.59 (br d, 2H).

Step 2: N-(6-([1,1'-biphenyl]-3-ylmethyl)-5-azaspiro[2.4]heptan-7-yl)propane-2-sulfonamide hydrochloride_cis racemic

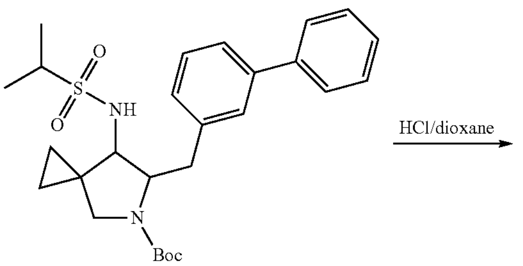

-continued

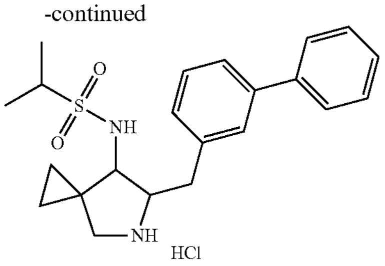

A solution of tert-butyl 6-([1,1'-biphenyl]-3-ylmethyl)-7-((1-methylethyl)sulfonamido)-5-azaspiro[2.4]heptane-5-carboxylate_cis racemic (80.0 mg, 165 μmol, 1 eq) in HC/dioxane (42 mL) was stirred at 25° C. for 12 hrs. The solution was concentrated under reduced pressure to afford the title compound (50 mg, 70.9% yield) as a white solid. $^1$H NMR (400 MHz, MeOH-d4) 0.78-0.91 (m, 2H) 0.97-1.04 (m, 1H) 1.15 (dt, 1H) 1.39 (dd, 6H) 2.98-3.10 (m, 2H) 3.20-3.26 (m, 1H) 3.45 (br dd, 1H) 3.54-3.60 (m, 1H) 3.89 (d, 1H) 4.19-4.32 (m, 1H) 7.30-7.41 (m, 2H) 7.48 (dt, 3H) 7.59 (d, 1H) 7.63-7.70 (m, 3H).

Step 3: N-((6S,7S)-6-([1,1'-biphenyl]-3-ylmethyl)-5-((R)-oxetane-2-carbonyl)-5-azaspiro[2.4]heptan-7-yl)propane-2-sulfonamide

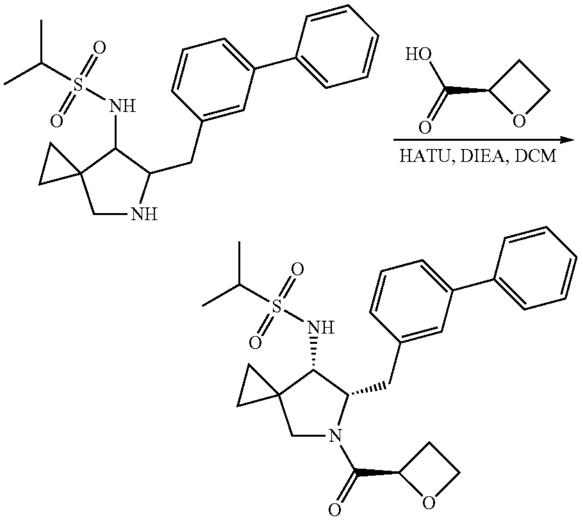

To a solution of N-(6-([1,1'-biphenyl]-3-ylmethyl)-5-azaspiro[2.4]heptan-7-yl)propane-2-sulfonamide hydrochloride_cis racemic (45 mg, 117 μmol, 1 eq) and (2R)-oxetane-2-carboxylic acid (12 mg, 117 μmol, 1 eq) in dichloromethane (0.5 mL) were added DIEA (61 μL, 351 μmol, 3 eq) and HATU (53 mg, 140 μmol, 1.2 eq). The mixture was stirred at 20° C. for 2 hrs. The reaction mixture was treated with water (10 mL) and then extracted with dichloromethane (10 mL) three times. The organic layer was washed with brine (10 mL), dried over anhydrous magnesium sulfate, filtered and concentrated under reduced pressure to afford a residue, which was purified by Prep-HPLC: (column: Waters Xbridge BEH C18 100*30 mm*10 μm; mobile phase: [water (10 mM $NH_4HCO_3$)-ACN]; B %: 25%-50%, 8 min) to afford the title compound (10 mg, 18.2% yield) as a white solid.

Example 48 (Compound 115)

Step 1: tert-butyl (6S,7S)-7-amino-6-(3-bromobenzyl)-5-azaspiro[2.4]heptane-5-carboxylate

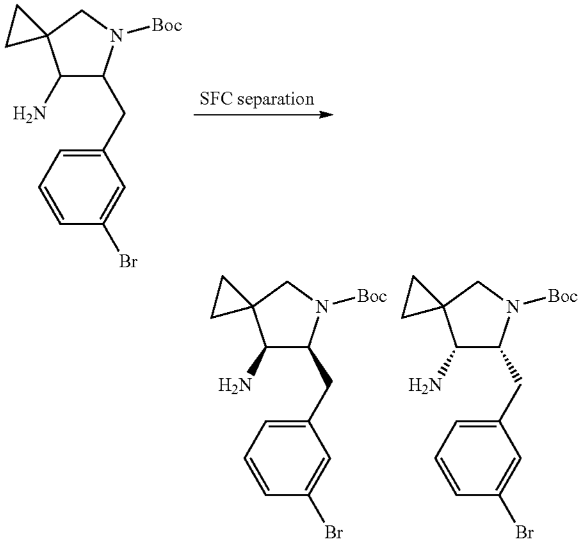

Tert-butyl 7-amino-6-(3-bromobenzyl)-5-azaspiro[2.4]heptane-5-carboxylate_cis racemic (20 g, 40.2 mmol, 1 eq) was separated by SFC (Column: Chiralcel OJ-3, 50-4.6 mm I.D., 3 μm; Mobile phase: A: $CO_2$ B: EtOH (0.1% IPAm, v/v); Gradient: B %: 5%-50%, 3 min) to afford the title compound (6.95 g, 31.9% yield) as colourless oil with the shorter retention time.

Step 2: tert-butyl (6S,7S)-6-(3-bromobenzyl)-7-((difluoromethyl)sulfonamido)-5-azaspiro[2.4]heptane-5-carboxylate

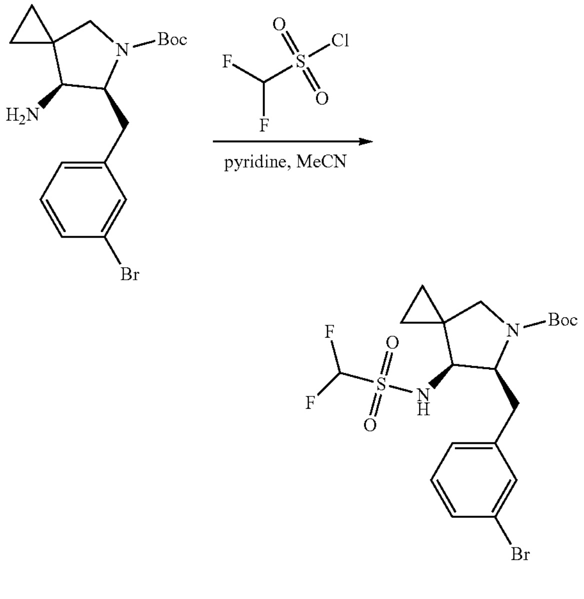

To the solution of tert-butyl (6S,7S)-7-amino-6-(3-bromobenzyl)-5-azaspiro[2.4]heptane-5-carboxylate (0.8 g, 2.10 mmol, 1 eq), pyridine (846 μL, 10.5 mmol, 5 eq) in MeCN(6 mL) was added difluoromethanesulfonyl chloride (411 mg, 2.73 mmol, 1.3 eq) at 0° C. Then the reaction mixture was stirred at 60° C. for 12 hrs. The reaction mixture was quenched by addition of water (20 mL), and then extracted with ethyl acetate (3×10 mL). The organic layer was washed with brine (10 mL), dried over anhydrous magnesium sulfate, filtered and concentrated under reduced pressure to afford a residue, which was purified by Prep-TLC (petroleum ether/ethyl acetate=1/1) to afford the title compound (600 mg, 52% yield) as a white solid. $^1H$ NMR (400 MHz, methanol-$d_4$) 0.46-0.78 (m, 3H), 0.99-1.34 (m, 10H), 2.56-2.80 (m, 1H), 2.93 (dd, 1H), 3.21 (d, 1H), 3.59-3.74 (m, 1H), 4.14-4.30 (m, 2H), 6.50-6.82 (m, 1H), 7.08-7.27 (m, 2H), 7.30-7.45 (m, 2H).

Step 3: tert-butyl (6S,7S)-6-([1,1'-biphenyl]-3-ylmethyl)-7-((difluoromethyl)sulfonamido)-5-azaspiro[2.4]heptane-5-carboxylate

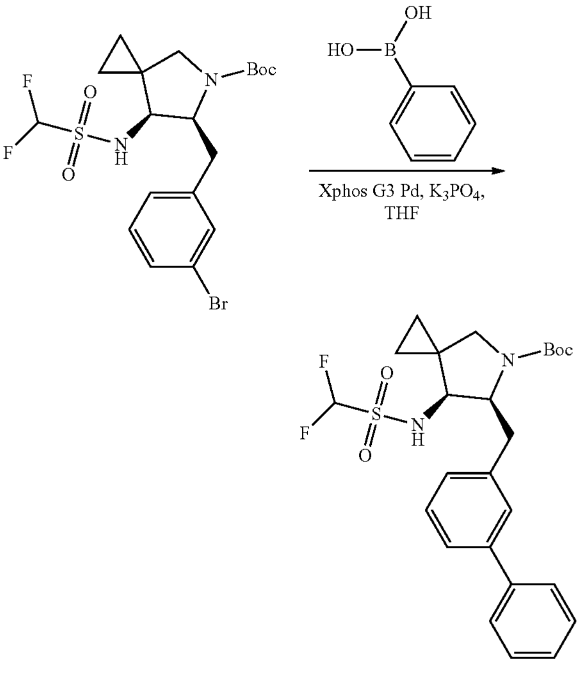

To a solution of tert-butyl (6S,7S)-6-(3-bromobenzyl)-7-((difluoromethyl)sulfonamido)-5-azaspiro[2.4]heptane-5-carboxylate (600 mg, 1.21 mmol, 1 eq) in THF (5 mL) was added XPhos Pd G3 (51 mg, 61 μmol, 0.05 eq), phenylboronic acid (222 mg, 1.82 mmol, 1.5 eq) and $K_3PO_4$ (771 mg, 3.63 mmol, 3 eq) at 25° C., the reaction mixture was stirred at 80° C. for 8 hrs under $N_2$ atmosphere. The reaction mixture was quenched by addition of water (20 mL), and then extracted with ethyl acetate (3×10 mL). The organic layer was washed with brine (10 mL), dried over anhydrous magnesium sulfate, filtered and concentrated under reduced pressure to afford a residue, which was purified by Prep-TLC (Petroleum ether: Ethyl acetate=0/1) to afford the title compound (560 mg, 84.5% yield) as a white solid. $^1H$ NMR (400 MHz, methanol-$d_4$) 0.56-0.78 (m, 3H) 0.91-1.32 (m, 10H) 2.75 (br s, 1H) 3.01 (dd, 1H) 3.27 (d, 1H) 3.70 (br d, 1H) 4.19 (br d, 1H) 4.27-4.40 (m, 1H) 6.46-6.83 (m, 1H) 7.13-7.24 (m, 1H) 7.27-7.52 (m, 6H) 7.59 (br d, 2H).

Step 4: N-((6S 7S)-6-([1,1'-biphenyl]-3-ylmethyl)-5-azaspiro[2.4]heptan-7-yl)-1,1-difluoromethanesulfonamide hydrochloride

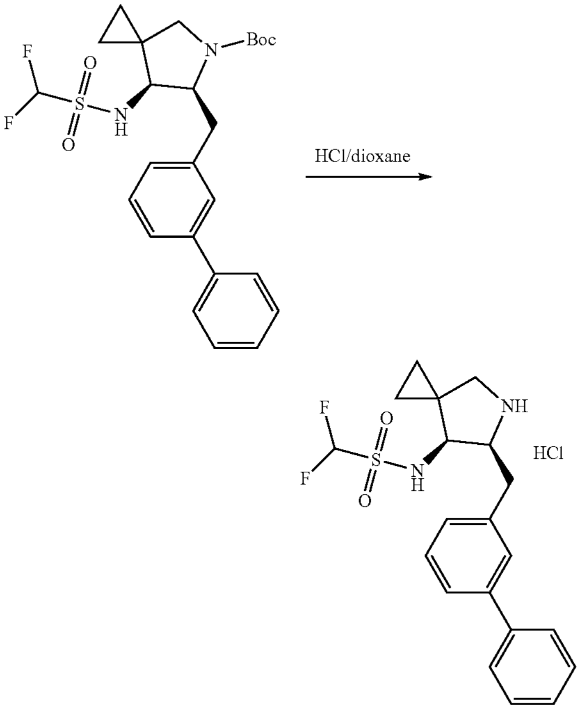

A solution of tert-butyl (6S,7S)-6-([1,1'-biphenyl]-3-ylmethyl)-7-((difluoromethyl)sulfonamido)-5-azaspiro[2.4]heptane-5-carboxylate (0.56 g, 1.14 mmol, 1 eq) in HCl/dioxane (5 mL) was stirred at 25° C. for 12 hrs. The reaction mixture was concentrated under reduced pressure to afford the title compound (500 mg, 92.3% yield) as a white solid. $^1H$ NMR (400 MHz, methanol-$d_4$) 0.83-0.93 (m, 2H) 0.97-1.05 (m, 1H) 1.11-1.19 (m, 1H) 3.01-3.09 (m, 2H) 3.42 (dd, 1H) 3.57-3.62 (m, 1H) 3.95 (d, 1H) 4.23-4.38 (m, 1H) 6.70 (t, 1H) 7.33-7.53 (m, 5H) 7.60 (d, 1H) 7.64-7.73 (m, 3H).

Step 5: N-((6S,7S)-6-([1,1'-biphenyl]-3-ylmethyl)-5-((R)-oxetane-2-carbonyl)-5-azaspiro[2.4]heptan-7-yl)-1,1-difluoromethanesulfonamide

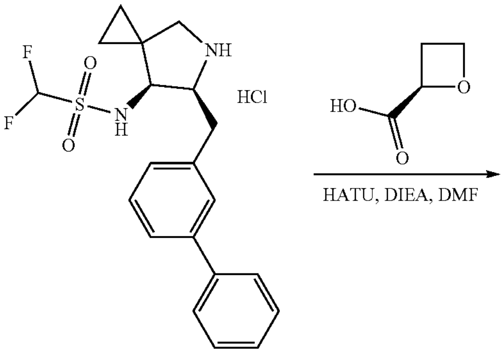

-continued

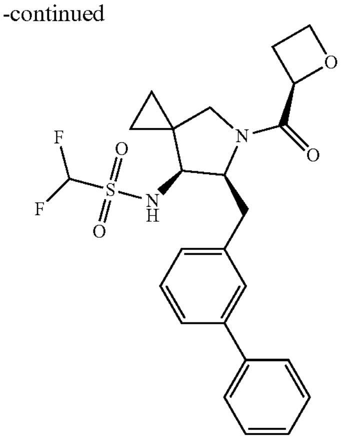

To a solution of N-((6S,7S)-6-([1,1'-biphenyl]-3-ylmethyl)-5-azaspiro[2.4]heptan-7-yl)-1,1-difluoromethanesulfonamide hydrochloride (500 mg, 1.27 mmol, 1 eq) in DMF (3 mL) was added (2R)-oxetane-2-carboxylic acid (156 mg, 1.53 mmol, 1.2 eq), DIEA (666 μL, 3.82 mmol, 3 eq), and HATU (581 mg, 1.53 mmol, 1.2 eq). The mixture was stirred at 25° C. for 12 hrs. The reaction mixture was poured into ice-water (10 mL), and then extracted with ethyl acetate (3×5 mL). The organic layer was washed with brine (10 mL), dried over anhydrous magnesium sulfate, filtered and concentrated under reduced pressure to afford a residue, which was purified by Prep-HPLC: (column: Waters Xbridge BEH C18 100*30 mm*10 μm; mobile phase: [water ($NH_4HCO_3$)-ACN]; B %: 30%-60%, 8 min) to afford the title compound (265 mg, 43.7% yield) as a white solid.

Example 49 (Compound 116)

Step 1: tert-butyl (6S,7S)-6-(3-bromo-2-fluorobenzyl)-7-((N,N-dimethylsulfamoyl)amino)-5-azaspiro[2.4]heptane-5-carboxylate (Intermediate 21)

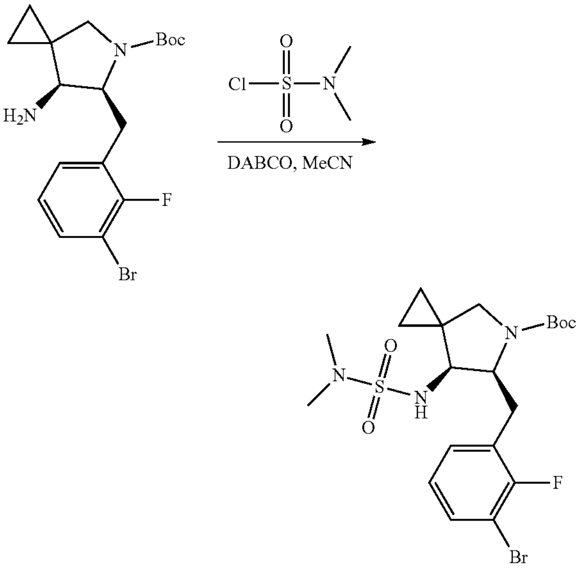

To a solution of tert-butyl (6S,7S)-7-amino-6-(3-bromo-2-fluorobenzyl)-5-azaspiro[2.4]heptane-5-carboxylate, intermediate 8 (0.2 g, 501 μmol, 1 eq) and DABCO (281 mg, 2.50 mmol, 275 μL, 5 eq) in dichloromethane (4 mL) was added N,N-dimethylsulfamoyl chloride (161 μL, 1.50 mmol, 3 eq) at 20° C. The mixture was stirred at 20° C. for 12 hrs, 5 mL of water was added and the organic layer was separated, dried over $Na_2SO_4$, filtered and concentrated under reduced pressure. The residue was purified by column chromatography on silica gel (eluted with petroleum ether/ethyl acetate=50/1 to 1/1) to afford the title compound (0.2 g, 71% yield) as a white solid. $^1H$ NMR (400 MHz, chloroform-d) δ 0.38 (br s, 1H), 0.58-0.78 (m, 3H), 1.27 (br s, 9H), 2.77 (br s, 6H), 3.01 (br s, 1H), 3.09 (br dd, 1H), 3.67 (br s, 1H), 4.01-4.19 (m, 2H), 4.42 (br s, 1H), 6.93-7.03 (m, 1H), 7.12 (br s, 1H), 7.43 (br s, 1H).

Step 2: tert-butyl (6S,7S)-7-((N,N-dimethylsulfamoyl)amino)-6-((2-fluoro-[1,1'-biphenyl]-3-yl)methyl)-5-azaspiro[2.4]heptane-5-carboxylate

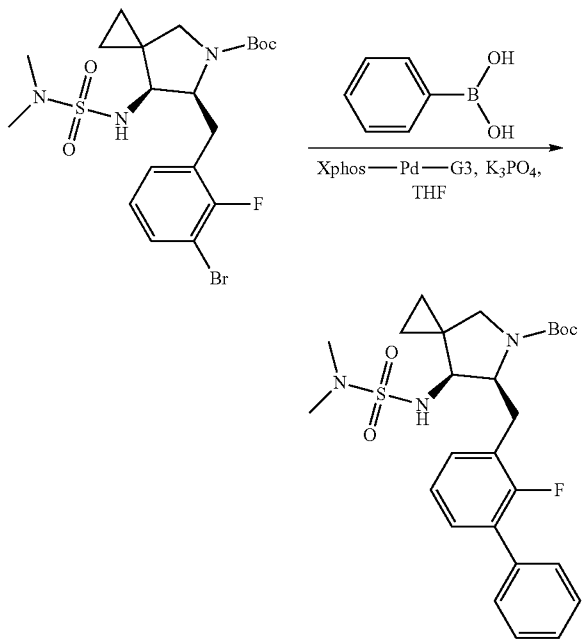

To a mixture of tert-butyl (6S,7S)-6-(3-bromo-2-fluorobenzyl)-7-((N,N-dimethylsulfamoyl)amino)-5-azaspiro[2.4]heptane-5-carboxylate, intermediate 21 (600 mg, 1.18 mmol, 1 eq) in tetrahydrofuran (8 mL) were added phenylboronic acid (173 mg, 1.42 mmol, 1.2 eq), $K_3PO_4$ (503 mg, 2.37 mmol, 2 eq) and XPhos-Pd-G3 (50 mg, 59 μmol, 0.05 eq) at 25° C. under $N_2$ atmosphere. The mixture was stirred at 80° C. for 4 hrs. The mixture was diluted with water (30 mL) and extracted with ethyl acetate (3×10 mL). The combined organic layers were dried over $Na_2SO_4$, filtered and concentrated under reduced pressure. The residue was purified by prep-TLC (petroleum ether/ethyl acetate=2/1) to afford the title compound (500 mg, 75.4% yield) as a white solid. $^1H$ NMR (400 MHz, methanol-$d_4$) δ 0.58-0.75 (m, 3H), 0.98-1.13 (m, 9H), 1.22-1.30 (m, 2H), 2.82 (s, 6H), 3.14 (br d, 1H), 3.22 (d, 1H), 3.70 (br d, 1H), 4.04-4.12 (m, 1H), 4.40 (br d, 1H), 7.20 (br d, 2H), 7.38 (br d, 2H), 7.45 (br t, 2H), 7.55 (br d, 2H).

Step 3: N-((6S,7S)-6-((2-fluoro[1,1'-biphenyl]-3-yl)methyl)-5-azaspiro[2.4]heptan-7-yl)-N,N-dimethylsulfuric diamide hydrochloride

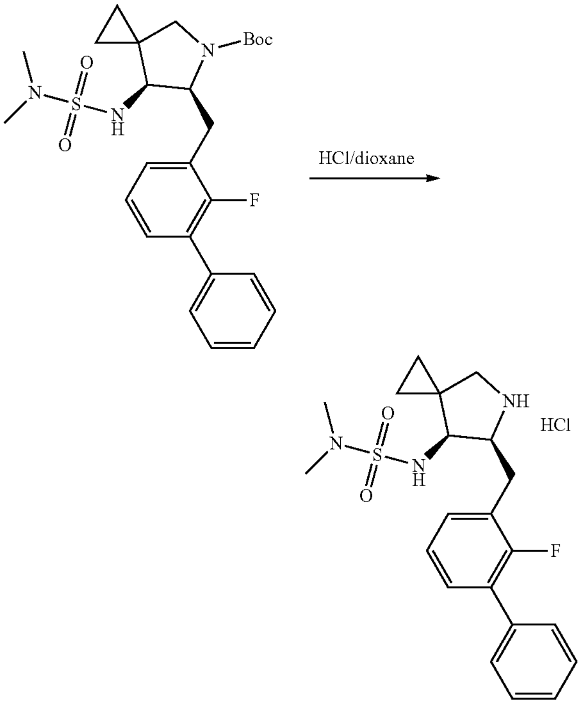

A solution of tert-butyl (6S,7S)-7-((N,N-dimethylsulfamoyl)amino)-6-((2-fluoro-[1,1'-biphenyl]-3-yl)methyl)-5-azaspiro[2.4]heptane-5-carboxylate (400 mg, 794 μmol, 1 eq) in HCl/dioxane (4 M, 8 mL, 40 eq) was stirred at 20° C. for 6 hrs. The reaction mixture was concentrated under reduced pressure to afford the title compound (380 mg, 97.9% yield, 90%) as a white solid. $^1H$ NMR (400 MHz, methanol-$d_4$) δ 0.77-0.92 (m, 2H), 0.94-1.02 (m, 1H), 1.15-1.23 (m, 1H), 2.80-2.84 (m, 6H), 3.05 (d, 1H), 3.13-3.24 (m, 1H), 3.47 (br d, 1H), 3.57 (d, 1H), 3.78-3.84 (m, 1H), 4.22 (ddd, 1H), 7.27-7.33 (m, 1H), 7.36-7.41 (m, 1H), 7.46 (t, 4H), 7.53-7.60 (m, 2H).

Step 4: N-((6S,7S)-5-(azetidine-1-carbonyl)-6-((2-fluoro-[1,1'-biphenyl]-3-yl)methyl)-5-azaspiro[2.4]heptan-7-yl)-N,N-dimethylsulfuric diamide

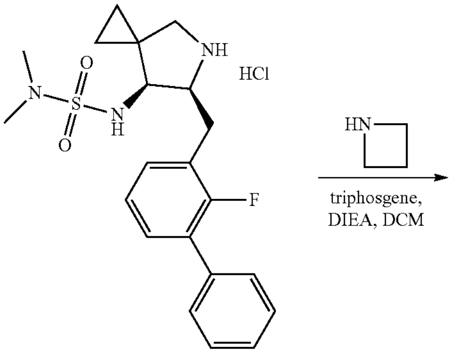

-continued

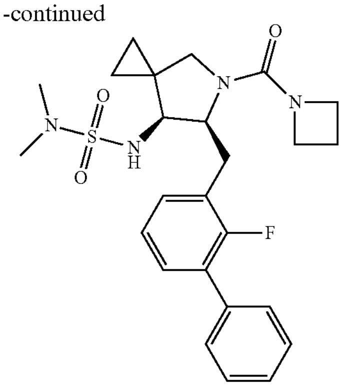

A solution of N-((6S,7S)-6-((2-fluoro[1,1'-biphenyl]-3-yl)methyl)-5-azaspiro[2.4]heptan-7-yl)-N,N-dimethylsulfuric diamide hydrochloride (40 mg, 90 μmol, 1 eq) and N,N-diisopropylethylamine (79 μL, 454 μmol, 5 eq) in dichloromethane (1.5 mL) was stirred at 20° C. for 10 min. The solution was added to a solution of triphosgene (13 mg, 45 μmol, 0.5 eq) in dichloromethane (1 mL) dropwise at 0° C. under $N_2$ atmosphere. After stirring at 20° C. for 1 hr, a solution of azetidine (50 μL, 454 μmol, 5 eq, HCl salt) and N,N-diisopropylethylamine (79 μL, 454.57 μmol, 5 eq) in dichloromethane (0.5 mL) was added at 0° C. The resulting reaction mixture was stirred at 20° C. for 12 hrs. The mixture was concentrated under reduced pressure. The residue was purified by prep-HPLC (Column: Waters Xbridge Prep OBD C18 150*40 mm*10 μm; mobile phase: [water (10 mM $NH_4HCO_3$)-ACN]; B %: 35%-65%, 8 min) to afford the title compound (31 mg, 69.4% yield) as a white solid.

Example 50 (Compound 126)

Step 1: tert-butyl (6S,7S)-6-((2,3'-difluoro-[1,1'-biphenyl]-3-yl)methyl)-7-((N,N-dimethylsulfamoyl)amino)-5-azaspiro[2.4]heptane-5-carboxylate

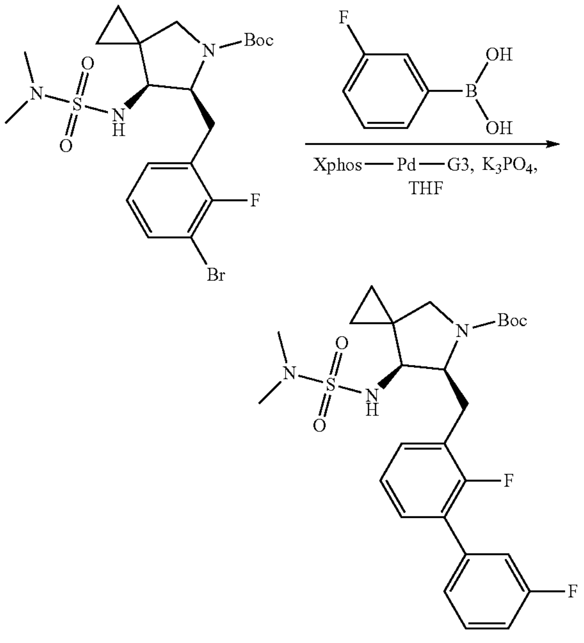

To a solution of tert-butyl (6S,75)-6-(3-bromo-2-fluorobenzyl)-7-((N,N-dimethylsulfamoyl)amino)-5-azaspiro[2.4]heptane-5-carboxylate, intermediate 21 (195 mg, 385 μmol, 1 eq) in tetrahydrofuran (4 mL) was added (3-fluorophenyl)boronic acid (65 mg, 462 μmol, 1.2 eq), $K_3PO_4$ (163 mg, 770 μmol, 2 eq) and Xphos-Pd-G3 (16 mg, 19 μmol, 0.05 eq) at 20° C. The resulting reaction mixture was stirred at 80° C. for 5 hrs under $N_2$ atmosphere. The reaction mixture was diluted with 20 mL of ethyl acetate and 10 mL of water, the organic layer separated and dried over $Na_2SO_4$, filtered and concentrated under reduced pressure. The residue was purified by column chromatography on silica gel (eluted with petroleum ether/ethyl acetate=50/1 to 1/1) to afford the title compound (120 mg, 53.8% yield) as a white solid. $^1$H NMR (400 MHz, methanol-$d_4$) δ 0.56-0.74 (m, 3H), 1.04 (s, 9H), 1.20-1.26 (m, 2H), 2.81 (s, 6H), 3.12 (br d, 1H), 3.20 (d, 1H), 3.58-3.73 (m, 1H), 4.01-4.09 (m, 1H), 4.35-4.51 (m, 1H), 7.06-7.15 (m, 1H), 7.18-7.31 (m, 3H), 7.33-7.49 (m, 3H).

Step 2: N-((6S,7S)-6-((2,3'-difluoro-[1,1'-biphenyl]-3-yl)methyl)-5-azaspiro[2.4]heptan-7-yl)-N,N-dimethylsulfuric diamide hydrochloride

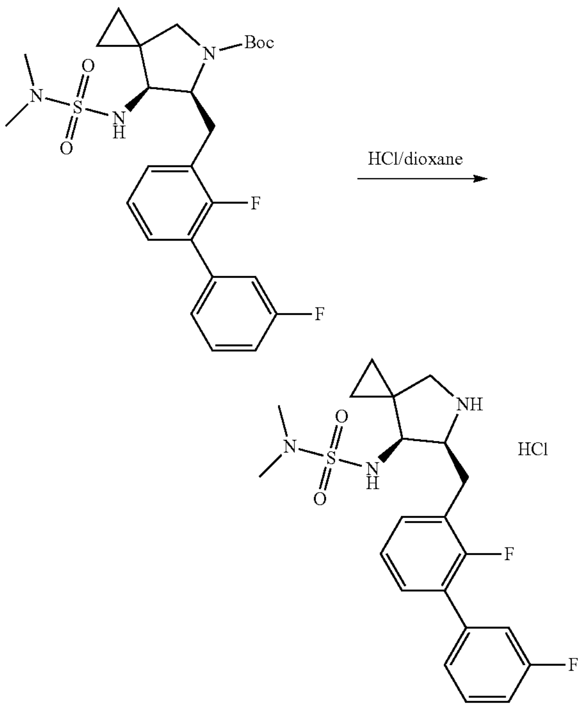

A solution of tert-butyl (6S,7S)-6-((2,3'-difluoro-[1,1'-biphenyl]-3-yl)methyl)-7-((N,N-dimethylsulfamoyl)amino)-5-azaspiro[2.4]heptane-5-carboxylate (120 mg, 230 μmol, 1 eq) in HCl/dioxane (4 M, 3 mL) was stirred at 20° C. for 12 hrs. The reaction mixture was concentrated under reduced pressure to afford the title compound (80 mg, 68.3% yield) as a white solid.

$^1$H NMR (400 MHz, methanol-$d_4$) δ 0.77-0.92 (m, 2H), 0.99 (ddd, 1H), 1.15-1.23 (m, 1H), 2.82 (s, 6H), 3.06 (d, 1H), 3.19 (dd, 1H), 3.47 (br d, 1H), 3.58 (d, 1H), 3.81 (d, 1H), 4.18-4.26 (m, 1H), 7.11-7.18 (m, 1H), 7.29-7.41 (m, 3H), 7.45-7.53 (m, 3H).

Step 3: N-((6S,7S)-6-((2,3'-difluoro-[1,1'-biphenyl]-3-yl)methyl)-5-((R)-oxetane-2-carbonyl)-5-azaspiro[2.4]heptan-7-yl)-N,N-dimethylsulfuric diamide

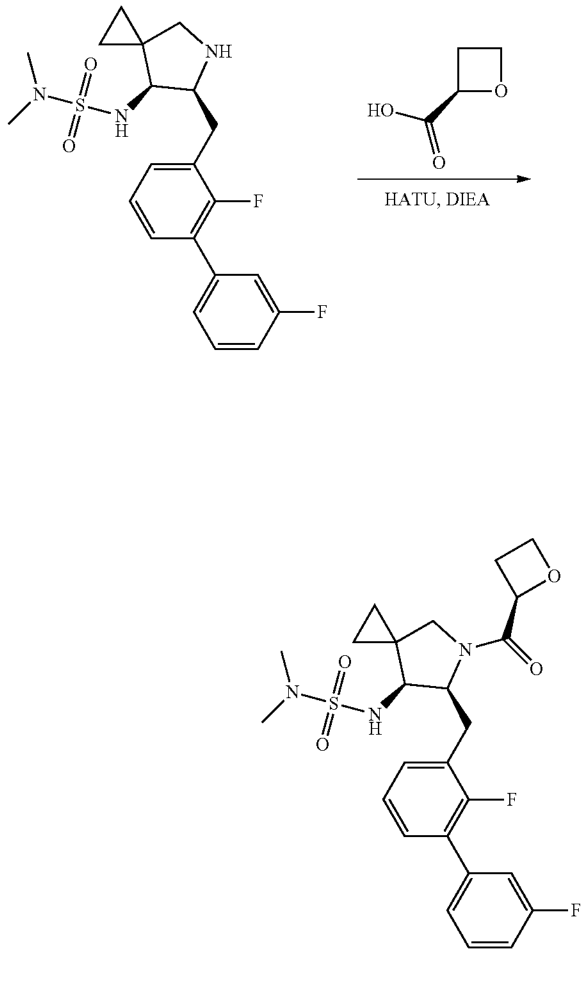

To a solution of N-((6S,7S)-6-((2,3'-difluoro-[1,1'-biphenyl]-3-yl)methyl)-5-azaspiro[2.4]heptan-7-yl)-N,N-dimethylsulfuric diamide hydrochloride (70 mg, 153 μmol, 1 eq) in DMF (4 mL) was added (2R)-oxetane-2-carboxylic acid (23 mg, 229 μmol, 1.5 eq), N,N-diisopropylethylamine (133 μL, 764.25 μmol, 5 eq) and HATU (70 mg, 183 μmol, 1.2 eq) at 0° C. The resulting reaction mixture was stirred at 20° C. for 5 hrs. The reaction mixture was purified by prep-HPLC (Column: Waters Xbridge Prep OBD C18 150*40 mm*10 μm; mobile phase: [water (10 mM $NH_4HCO_3$)-ACN]; B %: 30%-60%, 8 min)) directly to afford the title compound (63.4 mg, 82% yield) as a white solid.

Example 51 (Compound 128)

Step 1: tert-butyl (6S,7S)-7-((fluoromethyl)sulfonamido)-6-((2,3',5'-trifluoro-[1,1'-biphenyl]-3-yl)methyl)-5-azaspiro[2.4]heptane-5-carboxylate

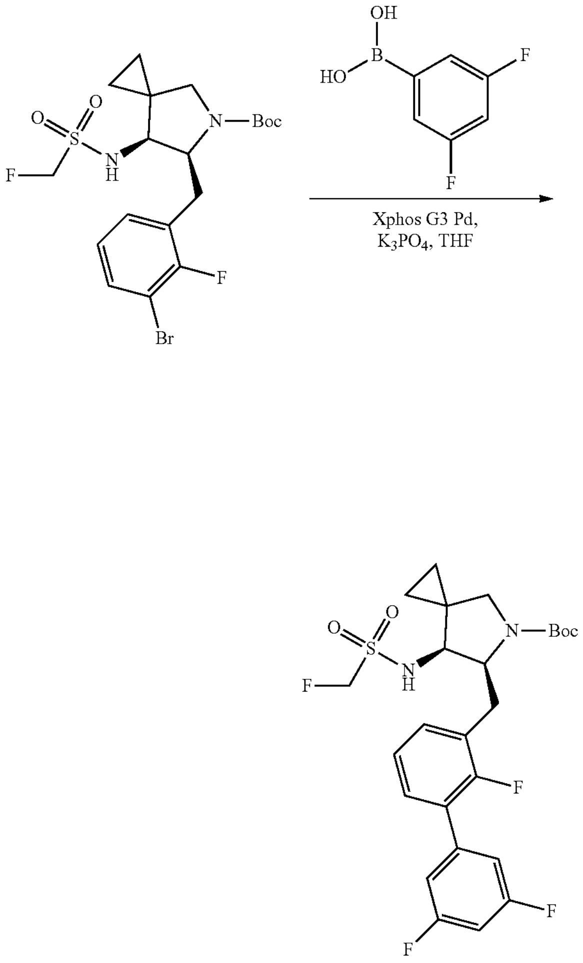

To a solution of tert-butyl (6S,7S)-6-(3-bromo-2-fluorobenzyl)-7-((fluoromethyl)sulfonamido)-5-azaspiro[2.4]heptane-5-carboxylate, intermediate 11 (720 mg, 1.45 mmol, 1 eq) in tetrahydrofuran (10 mL) were added (3,5-difluorophenyl)boronic acid (574 mg, 3.63 mmol, 2.5 eq), Xphos G3 Pd (62 mg, 72.7 μmol, 0.05 eq) and $K_3PO_4$ (617 mg, 2.91 mmol, 2 eq) at 20° C. The reaction mixture was stirred at 80° C. for 12 hrs under $N_2$ atmosphere. The reaction mixture was filtered and concentrated under reduced pressure. The residue was purified by prep-TLC (petroleum ether/ethyl acetate=3/1) to afford the title compound (750 mg, 87.9% yield) as white solid. $^1H$ NMR (400 MHz, methanol-$d_4$) δ 0.56-0.74 (m, 3H), 0.99-1.23 (m, 10H), 2.79-2.92 (m, 1H), 3.03-3.13 (m, 1H), 3.22 (d, 1H), 3.69 (br d, 1H), 4.20 (br d, 1H), 4.32-4.51 (m, 1H), 5.22 (s, 1H), 5.33 (s, 1H), 6.91-7.01 (m, 1H), 7.14-7.43 (m, 5H).

Step 2: 1-fluoro-N-((6S,7S)-6-((2,3',5'-trifluoro-[1,1'-biphenyl]-3-yl)methyl)-5-azaspiro[2.4]heptan-7-yl)methanesulfonamide hydrochloride (Intermediate 22)

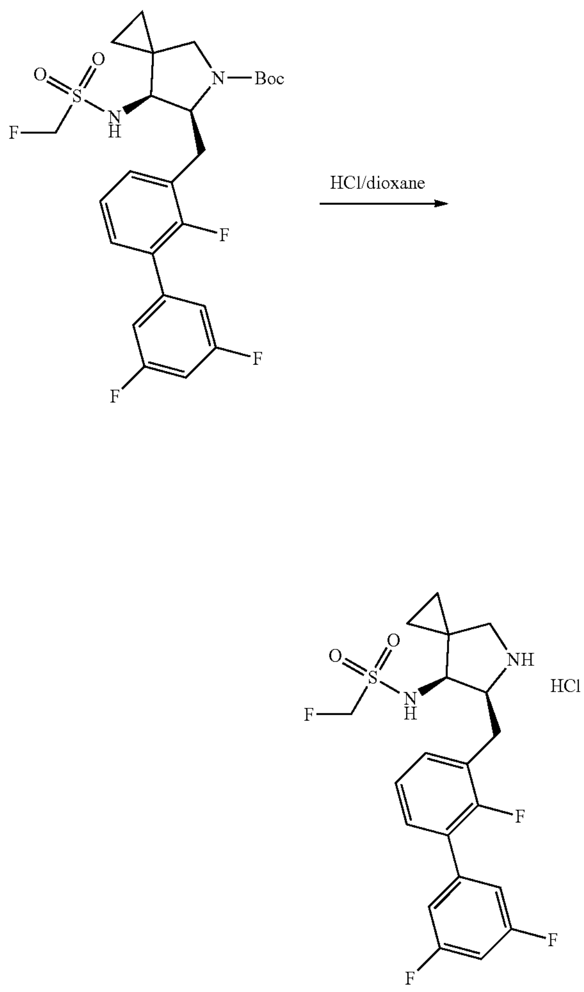

A solution of tert-butyl (6S,7S)-7-((fluoromethyl)sulfonamido)-6-((2,3',5'-trifluoro-[1,1'-biphenyl]-3-yl)methyl)-5-azaspiro[2.4]heptane-5-carboxylate (750 mg, 1.42 mmol, 1 eq) in HCl/dioxane (6 M, 76 mL, 323 eq) was stirred at 20° C. for 12 hrs. The reaction mixture was concentrated under reduced pressure to afford the title compound (700 mg, 97.9% yield) as a white solid. $^1$H NMR (400 MHz, methanol-$d_4$) δ 0.81-0.93 (m, 2H), 1.01-1.08 (m, 1H), 1.11-1.19 (m, 1H), 3.04-3.21 (m, 2H), 3.46 (br d, 1H), 3.57-3.62 (m, 1H), 3.90 (d, 1H), 4.20-4.29 (m, 1H), 5.20-5.44 (m, 2H), 6.91-7.05 (m, 1H), 7.20-7.36 (m, 3H), 7.48-7.55 (m, 2H).

Step 3: 1-fluoro-N-((6S,7S)-5-((R)-oxetane-2-carbonyl)-6-((2.3',5'-trifluoro-[1,1'-biphenyl]-3-yl)methyl)-5-azaspiro[2.4]heptan-7-yl)methanesulfonamide

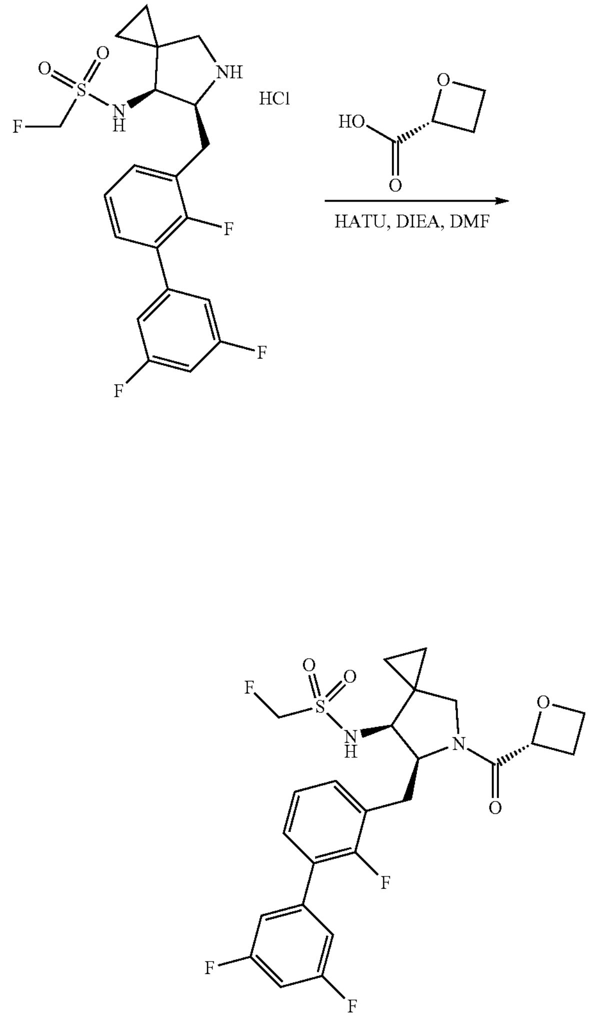

To a solution of 1-fluoro-N-((6S,7S)-6-((2,3',5'-trifluoro-[1,1'-biphenyl]-3-yl)methyl)-5-azaspiro[2.4]heptan-7-yl)methanesulfonamide hydrochloride, intermediate 22 (70 mg, 163 μmol, 1 eq) in DMF (1 mL) were added (2R)-oxetane-2-carboxylic acid (25 mg, 245 μmol, 1.5 eq), N,N-diisopropylethylamine (85 μL, 490 μmol, 3 eq) and HATU (75 mg, 196 μmol, 1.2 eq) at 0° C. The reaction mixture was stirred at 25° C. for 3 hrs. The mixture was purified by prep-HPLC (neutral condition: column: Waters Xbridge Prep OBD C18 150*40 mm*10 μm; mobile phase: [water ($NH_4HCO_3$)-ACN]; B %: 35%-65%, 8 min) to afford the title compound (41.0 mg, 49% yield) as a white solid.

Example 52 (Compound 129)

Step 1: tert-butyl (6S,7S)-6-((2,3'-difluoro-[1,1'-biphenyl]-3-yl)methyl)-7-(ethylsulfonamido)-5-azaspiro[2.4]heptane-5-carboxylate

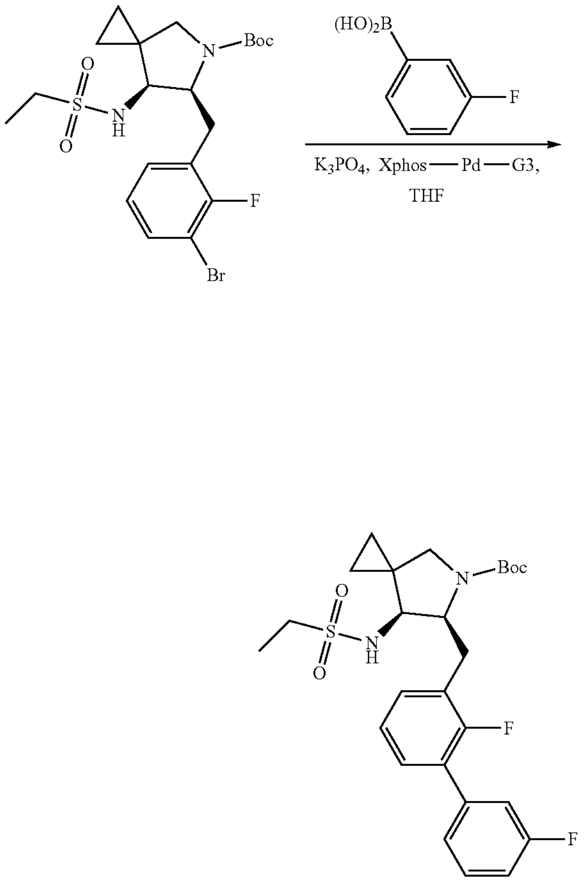

To a solution of tert-butyl (6S,7S)-6-(3-bromo-2-fluorobenzyl)-7-(ethylsulfonamido)-5-azaspiro[2.4]heptane-5-carboxylate, intermediate 10 (3 g, 6.10 mmol, 1 eq) and (3-fluorophenyl)boronic acid (1.28 g, 9.16 mmol, 1.5 eq) in tetrahydrofuran (30 mL) was added $K_3PO_4$ (3.89 g, 18.3 mmol, 3 eq) and Xphos-Pd-G3 (258 mg, 305 μmol, 0.05 eq) at 25° C. The mixture was stirred at 80° C. for 12 hrs. The reaction mixture was poured into water (50 mL) and the solution was extracted with ethyl acetate (3x30 mL). The combined organic layers were washed with brine (30 mL), dried over $Na_2SO_4$ and concentrated in reduced pressure to afford a residue. The residue was purified by column chromatography ($SiO_2$, petroleum ether/ethyl acetate=I/O to 0/1) to afford the title compound (2 g, 64.7% yield) as a yellow solid. LCMS (method M)(ESI+): m/z 451.1 $(M-55+H)^+$, RT: 0.715 min Step 2: N-((6S,7S)-6-((2,3'-difluoro-[1,1'-biphenyl]-3-yl)methyl)-5-azaspiro[2.4]heptan-7-yl)ethanesulfonamide hydrochloride

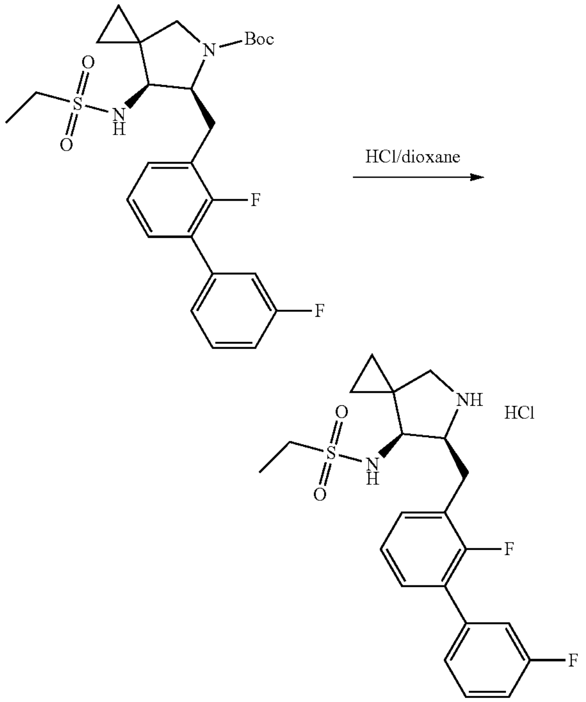

To a solution of tert-butyl (6S,7S)-6-((2,3'-difluoro-[1,1'-biphenyl]-3-yl)methyl)-7-(ethylsulfonamido)-5-azaspiro[2.4]heptane-5-carboxylate (2 g, 3.95 mmol, 1 eq) in dioxane (10 mL) was added HCl/dioxane (4 mol/L, 40 mL) at 0° C. The mixture was stirred at 25° C. for 0.5 hrs. The reaction mixture was concentrated under reduced pressure to afford the title compound (1.5 g, 82% yield) which was used in the next step without further purification.

$^1H$ NMR (400 MHz, chloroform-d) δ 0.65-0.90 (m, 3H), 1.11-1.19 (m, 1H), 1.36 (t, 3H), 2.98 (q, 3H), 3.28-3.47 (m, 2H), 3.54-3.68 (m, 2H), 4.19 (br s, 1H), 6.95-7.16 (m, 3H), 7.26-7.45 (m, 4H), 9.23 (br s, 1H), 9.86 (br s, 1H).

Step 3: N-((6S,7S)-6-((2,3'-difluoro-[1,1'-biphenyl]-3-yl)methyl)-5-((R)-oxetane-2-carbonyl)-5-azaspiro[2.4]heptan-7-yl)ethanesulfonamide

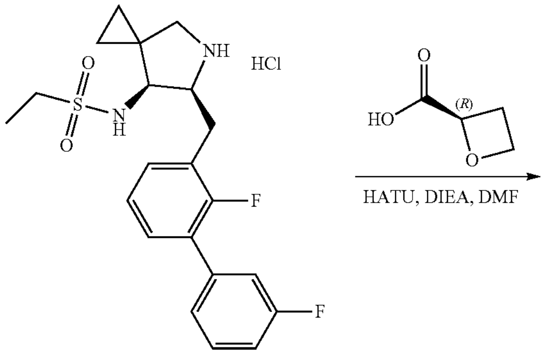

-continued

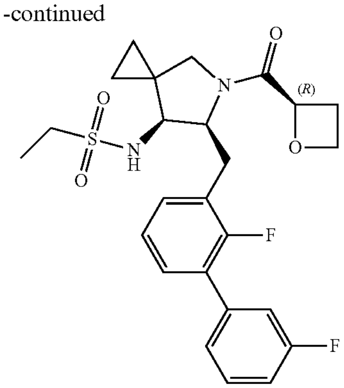

To a solution of N-((6S,7S)-6-((2,3'-difluoro-[1,1'-biphenyl]-3-yl)methyl)-5-azaspiro[2.4]heptan-7-yl)ethanesulfonamide hydrochloride (1.5 g, 3.69 mmol, 1 eq) and (2R)-oxetane-2-carboxylic acid (452 mg, 4.42 mmol, 1.2 eq) in dimethyl formamide (20 mL) was added o-(7-azabenzotriazol-1-yl)-N,N,N',N'-tetramethyluronium hexafluorophosphate (1.68 g, 4.42 mmol, 1.2 eq) and N,N-diisopropylethylamine (3.21 mL, 18.45 mmol, 5 eq). The resulting mixture was stirred at 25° C. for 2 hrs. The reaction mixture was poured into water (50 mL) and extracted with ethyl acetate (3-20 mL). The combined organic layers were washed with brine (20 mL), dried over $Na_2SO_4$ and concentrated in reduced pressure to afford a residue. The residue was purified by prep-HPLC (neutral condition column: Waters Xbridge BEH C18 250*50 mm*10 μm; mobile phase: [water ($NH_4HCO_3$)-ACN]; B %: 30%-70%, 10 min) to afford the title compound (1 g, 55.2% yield) as a white solid.

Example 53 (Compound 131)

Step 1: tert-butyl (6S,7S)-6-((2,3'-difluoro-[1,1'-biphenyl]-3-yl)methyl)-7-(methylsulfonamido)-5-azaspiro[2.4]heptane-5-carboxylate

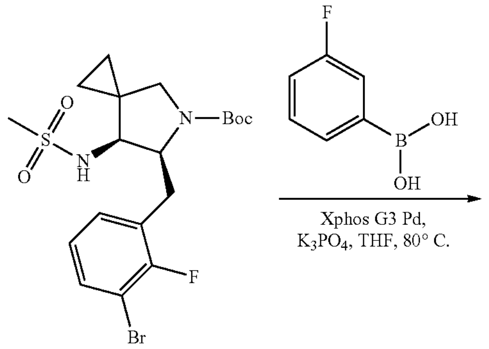

-continued

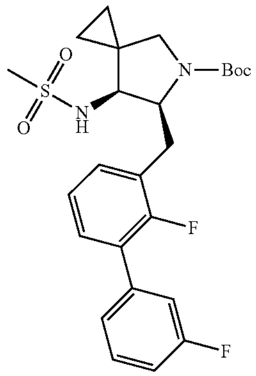

To a solution of tert-butyl (6S,7S)-6-(3-bromo-2-fluorobenzyl)-7-(methylsulfonamido)-5-azaspiro[2.4]heptane-5-carboxylate (intermediate 9)(100 mg, 209 μmol, 1 eq) in tetrahydrofuran (1 mL) was added (3-fluorophenyl)boronic acid (35 mg, 251 μmol, 1.2 eq), $K_1P04$ (89 mg, 419 μmol, 2 eq) and Xphos-Pd-G3 (9 mg, 10 μmol, 0.05 eq) at 20° C. The resulting reaction mixture was stirred at 80° C. for 4 hrs under $N_2$ atmosphere, diluted with 20 mL of ethyl acetate and 10 mL of water, the organic layer separated, dried over $Na_2SO_4$, filtered and concentrated under reduced pressure. The residue was purified by column chromatography silica gel (eluted with petroleum ether/ethyl acetate=50/1 to 1/1) to afford the title compound (80 mg, 69.8% yield) as a light yellow solid. $^1H$ NMR (400 MHz, methanol-$d_4$) δ 0.58-0.73 (m, 3H), 0.90-1.12 (m, 10H), 2.76-2.89 (m, 1H), 2.99-3.05 (m, 3H), 3.09 (br d, 1H), 3.16-3.25 (m, 1H), 3.60-3.74 (m, 1H), 4.15-4.24 (m, 1H), 4.37-4.54 (m, 1H), 7.07-7.15 (m, 1H), 7.18-7.32 (m, 3H), 7.33-7.49 (m, 3H).

Step 2: N-((6S,7S)-6-((2,3'-difluoro-[1,1'-biphenyl]-3-yl)methyl)-5-azaspiro[2.4]heptan-7-yl)methanesulfonamide hydrochloride

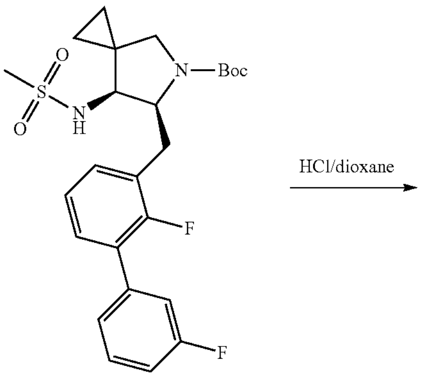

-continued

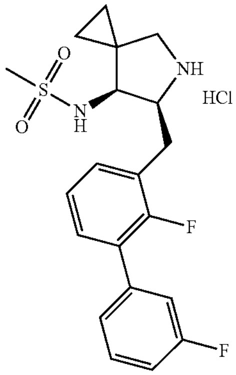

To a solution of tert-butyl (6S,7S)-6-((2,3'-difluoro-[1,1'-biphenyl]-3-yl)methyl)-7-(methylsulfonamido)-5-azaspiro[2.4]heptane-5-carboxylate (80 mg, 168 μmol, 1 eq) in dioxane (1 mL) was added HCl/dioxane (4 M, 4 mL, 95 eq) at 20° C. The reaction mixture was stirred at 20° C. for 12 hrs, concentrated under reduced pressure to afford the title compound (70 mg, 81.8% yield) as a white solid. LCMS (method M)(ESI+): m/z 393.1 $(M+H)^+$, RT: 0.607 min.

Step 3: N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)methanesulfonamide

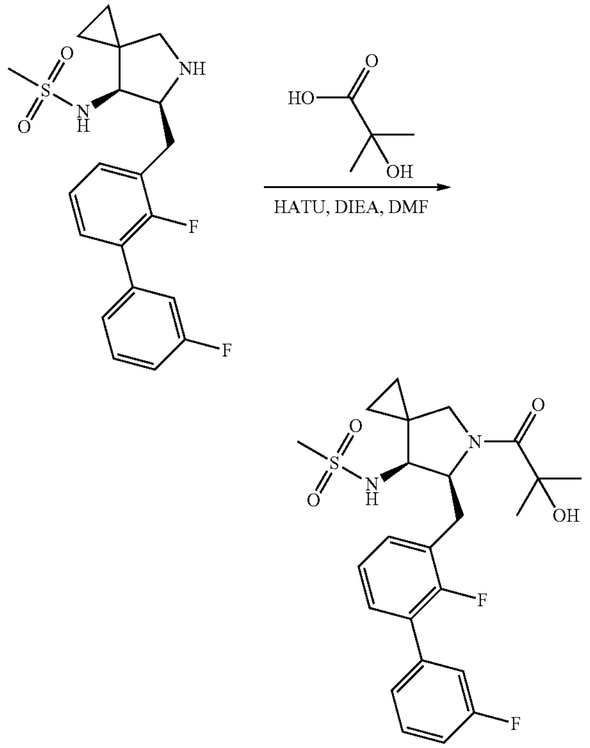

To a solution of N-((6S,7S)-6-((2,3'-difluoro-[1,1'-biphenyl]-3-yl)methyl)-5-azaspiro[2.4]heptan-7-yl)methanesulfonamide hydrochloride (65 mg, 151 μmol, 1 eq) in DMF (3 mL) was added 2-hydroxy-2-methyl-propanoic acid (24 mg, 227 μmol, 1.5 eq), HATU (69 mg, 182 μmol, 1.2 eq) and N,N-diisopropylethylamine (132 μL, 758 μmol, 5 eq) at 0° C. The resulting reaction mixture was stirred at 20° C. for 12 hrs and purified directly by prep-HPLC (Column: Waters Xbridge Prep OBD C18 150*40 mm*10 μm; mobile phase: [water (10 mM $NH_4HCO_3$)-ACN]; B %: 35%-55%, 8 min) to afford the title compound (32.6 mg, 41.6% yield) as a white solid.

Example 54 (Compound 132)

Step 1: tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate

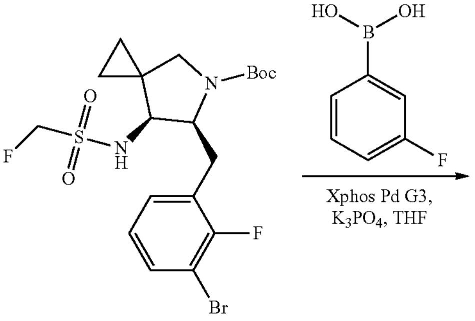

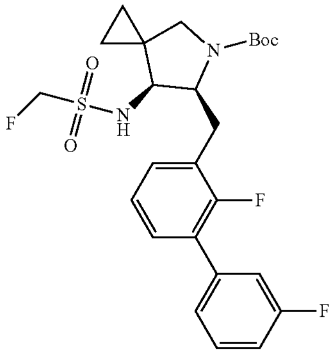

To a solution of tert-butyl (6S,7S)-6-(3-bromo-2-fluorobenzyl)-7-((fluoromethyl)sulfonamido)-5-azaspiro[2.4]heptane-5-carboxylate, intermediate 11 (150 mg, 303 μmol, 1 eq) in tetrahydrofuran (3 mL) were added (3-fluorophenyl) boronic acid (47 mg, 333 μmol, 1.1 eq), Xphos Pd G3 (13 mg, 15 μmol, 0.05 eq) and $K_3PO_4$ (129 mg, 606 μmol, 2 eq) at 25° C. under $N_2$ atmosphere. The mixture was stirred at 80° C. for 8 hrs, during which time the mixture maintained as a brown solution. The reaction mixture was filtered and the filtrate was concentrated under reduced pressure. The crude product was purified by prep-TLC (petroleum ether/ethyl acetate=2/1) to afford the title compound (120 mg, 69.9% yield) as a white solid. $^1H$ NMR (400 MHz, methanol-$d_4$) δ 0.59-0.73 (m, 3H), 1.04 (s, 9H), 1.22 (br d, 1H), 2.78-2.92 (m, 1H), 3.08 (br d, 1H), 3.22 (d, 1H), 3.69 (br d, 1H), 4.20 (br d, 1H), 4.33-4.50 (m, 1H), 5.18-5.38 (m, 2H), 7.07-7.31 (m, 4H), 7.31-7.50 (m, 3H).

Step 2: N-((6S,7S)-6-((2,3'-difluoro-[1,1'-biphenyl]-3-yl)methyl)-5-azaspiro[2.4]heptan-7-yl)-1-fluoromethanesulfonamide hydrochloride

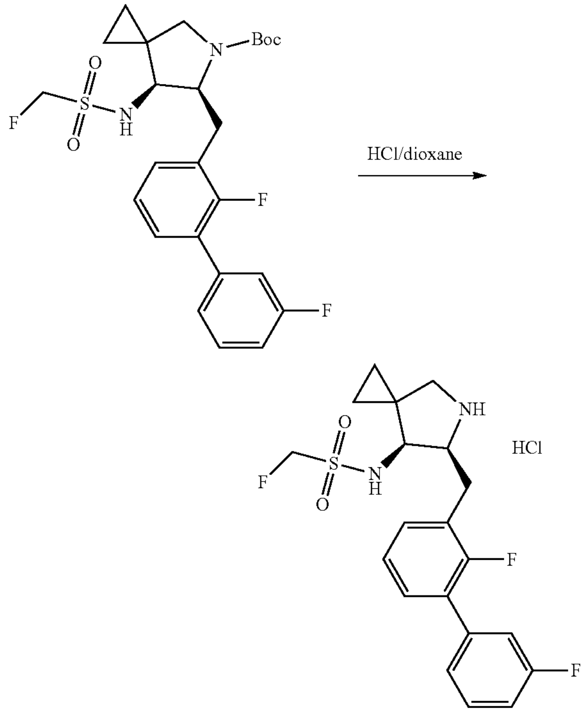

To a solution of tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate (100 mg, 196 μmol, 1 eq) in dioxane (1 mL) was added HCl/dioxane (4 M, 247 μL, 5.04 eq) and the mixture was stirred at 20° C. for 6 hrs. The reaction mixture was concentrated under reduced pressure to afford the title compound (70 mg, 78.4% yield) as a white solid which was used directly in the next step without further purification.

Step 3: N-((6S,7S)-6-((2,3'-d fluoro-1,1'-biphenyl-3-yl)methyl)-5-((R)-oxetane-2-carbonyl)-5-azaspiro[2.4]heptan-7-yl)-1-fluoromethanesulfonamide

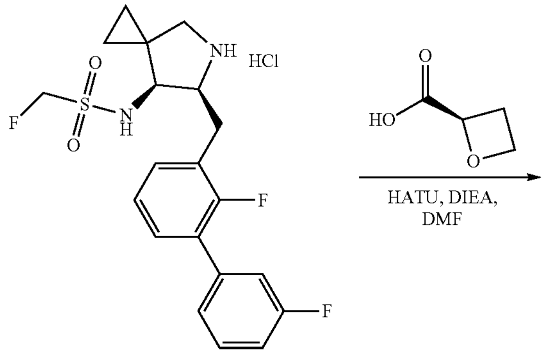

-continued

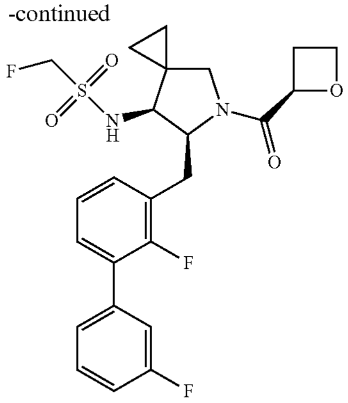

To a solution of N-((6S,7S)-6-((2,3'-difluoro-[1,1'-biphenyl]-3-yl)methyl)-5-azaspiro[2.4]heptan-7-yl)-1-fluoromethanesulfonamide hydrochloride (50 mg, 122 μmol, 1 eq) in N, N-dimethylformamide (2 mL) were added (2R)-oxetane-2-carboxylic acid (19 mg, 183 μmol, 1.5 eq), N,N-diisopropylethylamine (106 μL, 609 μmol, 5 eq) and HATU (56 mg, 146 μmol, 1.2 eq) at 0° C. The mixture was stirred at 25° C. for 12 hrs and purified directly by prep-HPLC (Column: Waters Xbridge Prep OBD C18 150*40 mm*10 um; mobile phase: [water (10 mM $NH_4HCO_3$)-ACN]; B %: 35%-65%, 8 min.) to afford the title compound (35.6 mg, 59.1% yield) as a white solid.

Example 55 (Compound 133). N-((6S,7S)-5-((R)-2-cyclopropyl-2-hydroxyacetyl)-6-((2-fluoro-[1,1'-biphenyl]-3-yl)methyl)-5-azaspiro[2.4]heptan-7-yl)-1-fluoromethanesulfonamide

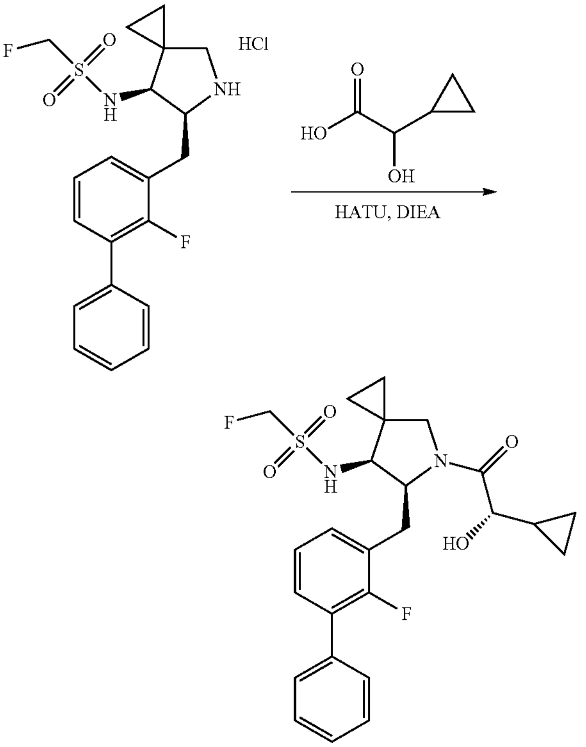

To a solution of I-fluoro-N-((6S,7S)-6-((2-fluoro-[1,1'-biphenyl]-3-yl)methyl)-5-azaspiro[2.4]heptan-7-yl)methanesulfonamide hydrochloride, intermediate 20 (0.1 g, 233 umol, 1 eq) and 2-cyclopropyl-2-hydroxy-acetic acid (41 mg, 350 μmol, 1.5 eq) in N, N-dimethylformamide (1 mL) were added HATU (106 mg, 280 μmol, 1.2 eq) and dipropylethylamine (122 μL, 700 μmol, 3 eq) at 0° C. The mixture was stirred at 25° C. for 12 hrs, LCMS showed the starting material was consumed, two main products with desired MS were detected. The reaction mixture was purified by prep-HPLC (Column: Waters Xbridge BEH C18 100*30 mm*10 μm; mobile phase: [water (10 mM $NH_4HCO_3$)-ACN]; B %: 25%-50%, 8 min) to afford the title compound (36.9 mg, 32.3% yield) as white solid.

Example 56 (Compound 134). 1-fluoro-N-((6S,7S)-6-((2-fluoro-[1,1'-biphenyl]-3-yl)methyl)-5-(2-hydroxy-2-methylpropanoyl)-5-azaspiro[2.4]heptan-7-yl)methanesulfonamide

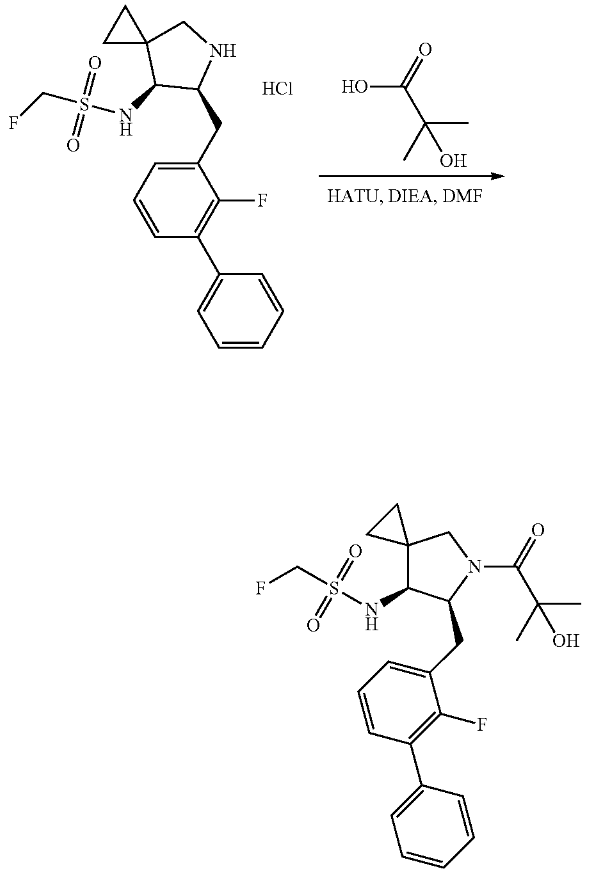

To a solution of 1-fluoro-N-((6S,7S)-6-((2-fluoro-[1,1'-biphenyl]-3-yl)methyl)-5-azaspiro[2.4]heptan-7-yl)methanesulfonamide hydrochloride, intermediate 20 (0.05 g, 117 umol, 1 eq) and 2-hydroxy-2-methyl-propanoic acid (18 mg, 175 μmol, 1.5 eq) in N, N-dimethylformamide (1 mL) were added HATU (53 mg, 140 μmol, 1.2 eq) and dipropylethylamine (61 μL, 349.71 μmol, 3 eq) at 0° C. The mixture was stirred at 25° C. for 12 hrs and purified by prep-HPLC (Column: Waters Xbridge BEH C18 100*30 mm*10 μm; mobile phase: [water (10 mM $NH_4HCO_3$)-ACN]; B %: 30%-60%, 8 min) to afford the title compound (35.7 mg, 32% yield) as a white solid.

Example 57 (Compound 137)

Step 1: tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate

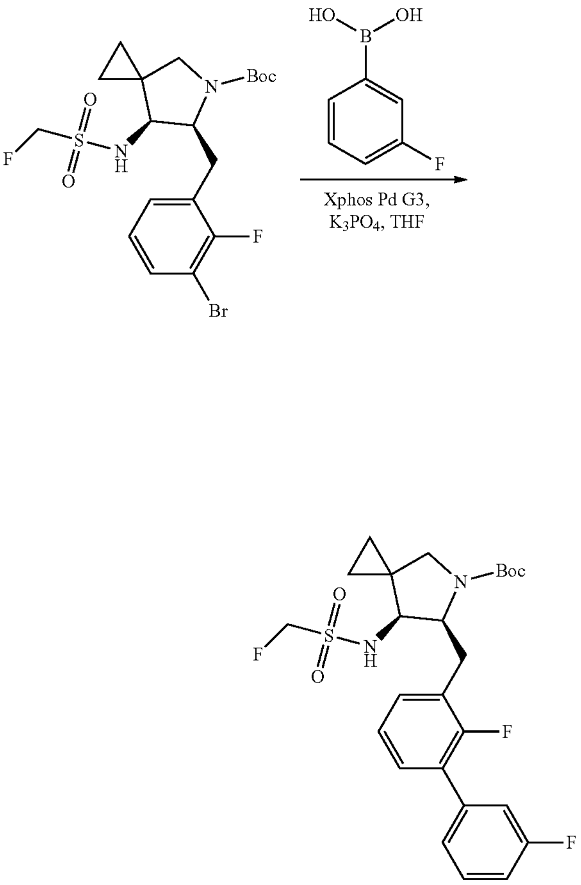

To a solution of tert-butyl (6S,7S)-6-(3-bromo-2-fluorobenzyl)-7-((fluoromethyl)sulfonamido)-5-azaspiro[2.4]heptane-5-carboxylate, intermediate 11 (150 mg, 303 μmol, 1 eq) in tetrahydrofuran (3 mL) were added (3-fluorophenyl) boronic acid (47 mg, 333 μmol, 1.1 eq), Xphos Pd G3 (13 mg, 15 μmol, 0.05 eq) and $K_3PO_4$ (129 mg, 606 μmol, 2 eq) at 25° C. under $N_2$ atmosphere. The mixture was stirred at 80° C. for 8 hrs, filtered and the filtrate concentrated under reduced pressure. The crude product was purified by prep-TLC (petroleum ether/ethyl acetate=2/1) to afford the title compound (120 mg, 69.9% yield) as a white solid. $^1H$ NMR (400 MHz, methanol-$d_4$) δ 0.59-0.73 (m, 3H), 1.04 (s, 9H), 1.22 (br d, 1H), 2.78-2.92 (m, 1H), 3.08 (br d, 1H), 3.22 (d, 1H), 3.69 (br d, 1H), 4.20 (br d, 1H), 4.33-4.50 (m, 1H), 5.18-5.38 (m, 2H), 7.07-7.31 (m, 4H), 7.31-7.50 (m, 3H).

Step 2: N-((6S,7S)-6-((2,3'-difluoro-[1,1'-biphenyl]-3-yl)methyl)-5-azaspiro[2.4]heptan-7-yl)-1-fluoromethanesulfonamide hydrochloride

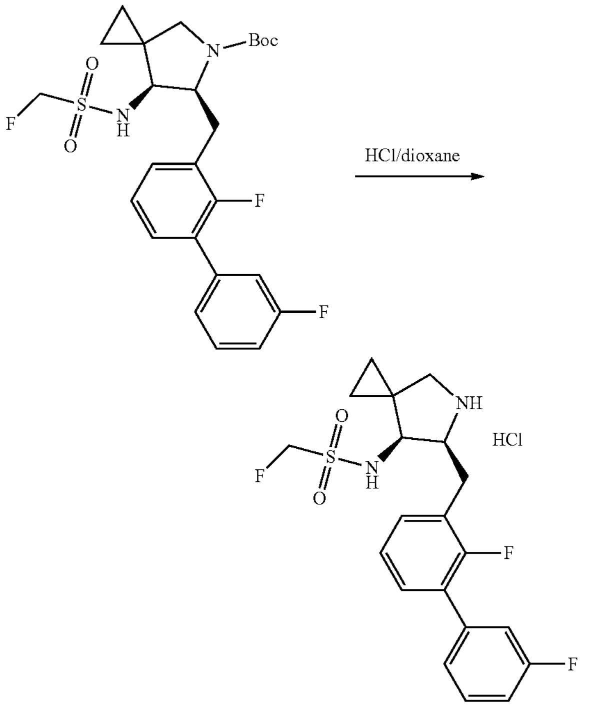

To a solution of tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate (100 mg, 196 μmol, 1 eq) in dioxane (1 mL) was added HCl/dioxane (4 M, 247 μL, 5.04 eq) and the mixture was stirred at 20° C. for 6 hrs. The reaction mixture was concentrated under reduced pressure to afford the title compound (70 mg, 153 μmol, 78.4% yield) as a white solid. $^1$H NMR (400 MHz, methanol-$d_4$) δ 0.79-0.92 (m, 2H), 0.99-1.08 (m, 1H), 1.10-1.20 (m, 1H), 3.07 (d, 1H), 3.16 (dd, 1H), 3.46 (br d, 1H), 3.55-3.63 (m, 1H), 3.90 (d, 1H), 4.24 (dt, 1H), 5.20-5.45 (m, 2H), 7.14 (td, 1H), 7.27-7.42 (m, 3H), 7.42-7.55 (m, 3H).

Step 3: N-(6S,7S)-6-((2,2'-difluoro-[1,1'-biphenyl]-3-yl)methyl)-5-((R)-oxetane-2-carbonyl)-5-azaspiro[2.4]heptan-7-yl)-1-fluoromethanesulfonamide

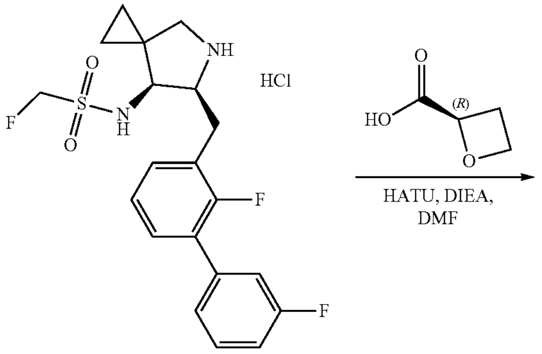

-continued

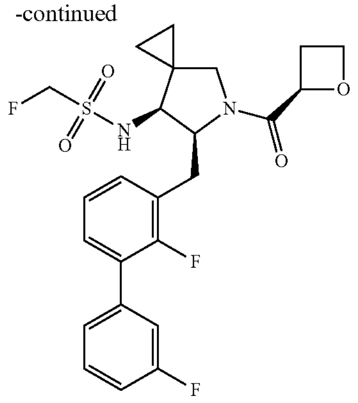

To a solution of N-((6S,7S)-6-((2,3'-difluoro-[1,1'-biphenyl]-3-yl)methyl)-5-azaspiro[2.4]heptan-7-yl)-1-fluoromethanesulfonamide hydrochloride (50 mg, 122 μmol, 1 eq) in N, N-dimethylformamide (2 mL) were added (2R)-oxetane-2-carboxylic acid (19 mg, 183 μmol, 1.5 eq), N,N-diisopropylethylamine (106 μL, 609.08 μmol, 5 eq) and HATU (56 mg, 146 μmol, 1.2 eq) at 0° C. The mixture was stirred at 25° C. for 12 hrs and purified by prep-HPLC (Column: Waters Xbridge Prep OBD C18 150*40 mm*10 um; mobile phase: [water (10 mM $NH_4HCO_3$)-ACN]; B %: 35%-65%, 8 min.) to afford the title compound (35.6 mg, 59.1% yield) as a white solid.

Example 58 (Compound 144)

Step 1: tert-butyl (6S,7S)-7-((difluoromethyl)sulfonamido)-6-((2-fluoro-[1,1'-biphenyl]-3-yl)methyl)-5-azaspiro[2.4]heptane-5-carboxylate

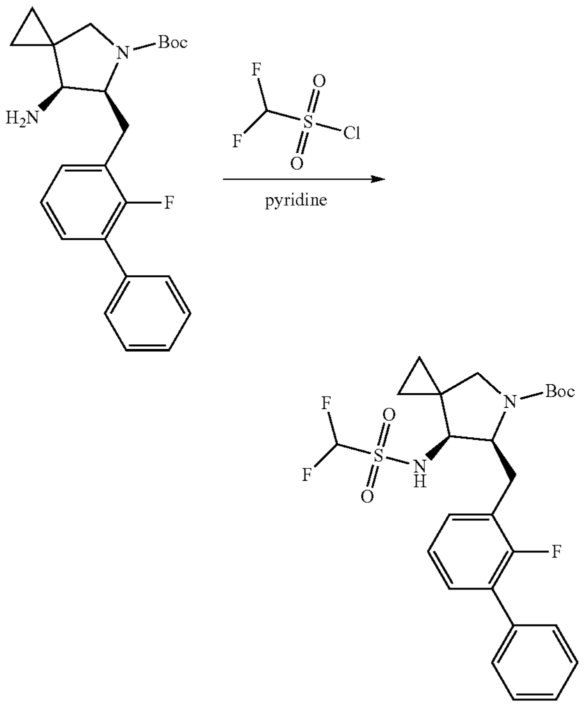

To a solution of tert-butyl (6S,7S)-7-amino-6-((2-fluoro-[1,1'-biphenyl]-3-yl)methyl)-5-azaspiro[2.4]heptane-5-carboxylate (2.20 g, 5.55 mmol, 1 eq) in pyridine (20 mL) was added difluoromethanesulfonyl chloride (1.25 g, 8.32 mmol, 1.5 eq) at 0° C. The resulting mixture was stirred at 25° C. for 2 hrs, treated with $H_2O$ (100 mL) and extracted with ethyl acetate (3×50 mL). The organic layer was combined and dried over $Na_2SO_4$, concentrated under reduced pressure to afford the crude product. The crude product was purified by column chromatography on silica gel (eluted with petroleum ether/ethyl acetate=100/1 to 0/1) to afford the title compound (1 g, 1.96 mmol, 35.30% yield) as a white solid. $^1H$ NMR (400 MHz, dimethyl sulfoxide-d6) S 0.52-0.71 (m, 3H), 0.93 (br s, 9H), 1.03-1.12 (m, 2H), 2.59-2.73 (m, 1H), 3.01 (br d, 1H), 3.06-3.22 (m, 1H), 3.52-3.64 (m, 1H), 4.04-4.12 (m, 1H), 4.21 (br d, 1H), 7.16-7.24 (m, 2H), 7.31-7.43 (m, 2H), 7.43-7.55 (m, 4H), 8.60 (br d, 1H).

Step 2: 1,1-difluoro-N-((6S,7S)-6-((2-fluoro-[1,1'-biphenyl]-3-yl)methyl)-5-azaspiro[2.4]heptan-7-yl) methanesulfonamide hydrochcloride

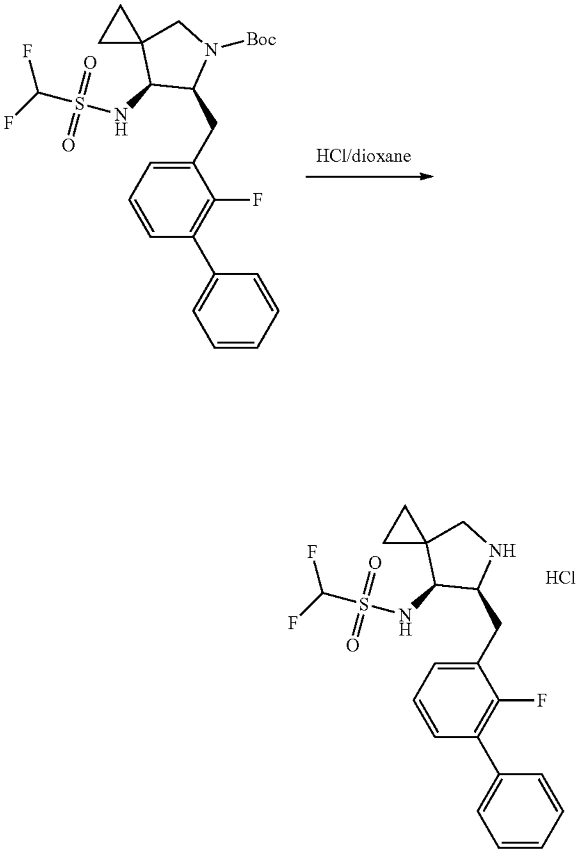 [SMILES: CC(C)(C)OC(=O)N1CC2(CC2)[C@H](NS(=O)(=O)C(F)F)[C@@H]1Cc1cccc(-c2ccccc2)c1F ; O=S(=O)(N[C@@H]1[C@H](Cc2cccc(-c3ccccc3)c2F)NCC12CC2)C(F)F ; Cl]

A solution of tert-butyl (6S,7S)-7-((difluoromethyl)sulfonamido)-6-((2-fluoro-[1,1'-biphenyl]-3-yl)methyl)-5-azaspiro[2.4]heptane-5-carboxylate (1 g, 1.96 mmol, 1 eq) in HCl/dioxane (4 M, 15 mL) was stirred at 20° C. for 3 hrs. The resulting mixture was concentrated under reduced pressure to afford the title compound (0.8 g, 99.5% yield) as white solid, which was used in next step without purification. LCMS(method 0)(ESI+): m/z 411.1 $(M+H)^+$, RT: 1.296 min.

Step 3: 1,1-difluoro-N-((6S,7S)-6-((2-fluoro-[1,1'-biphenyl]-3-yl)methyl)-5-((R)-oxetane-2-carbonyl)-5-azaspiro[2.4]heptan-7-yl)methanesulfonamide

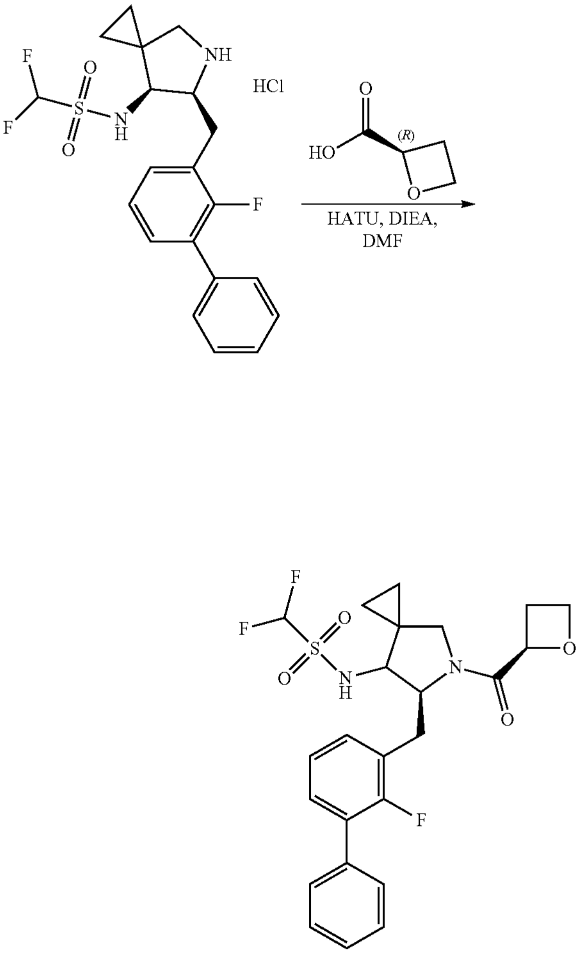

To a solution of 1,1-difluoro-N-((6S,7S)-6-((2-fluoro-[1,1'-biphenyl]-3-yl)methyl)-5-azaspiro[2.4]heptan-7-yl)methanesulfonamide hydrochloride (0.7 g, 1.95 mmol, 1 eq) in N,N-dimethylformamide (5 mL) were added (2R)-oxetane-2-carboxylic acid (298 mg, 2.92 mmol, 1.5 eq), N,N-diisopropylethylamine (1.70 mL, 9.72 mmol, 5 eq) and o-(7-azabenzotriazol-1-yl)-N,N,N',N'-tetramethyluronium hexafluorophosphate (887 mg, 2.33 mmol, 1.2 eq). The resulting mixture was stirred at 25° C. for 8 hrs. The mixture was poured into water (10 mL) and extracted with ethyl acetate (3×10 mL). The organic layer was washed with brine (10 mL), and dried over $Na_2SO_4$, concentrated under reduced pressure to afford a residue. The residue was purified by prep-HPLC (column: Waters Xbridge BEH C18 100*30 mm*10 um; mobile phase: [water($NH_4HCO_3$)-ACN]; B %: 30%-60%, 8 min) to afford the title compound (200 mg, 23.7% yield) as white solid.

Example 59 (Compound 145). N-((6S,7S)-6-((2,5-difluoro-[1,1'-biphenyl]-3-yl)methyl)-5-((R)-oxetane-2-carbonyl)-5-azaspiro[2.4]heptan-7-yl)-1-fluoromethanesulfonamide

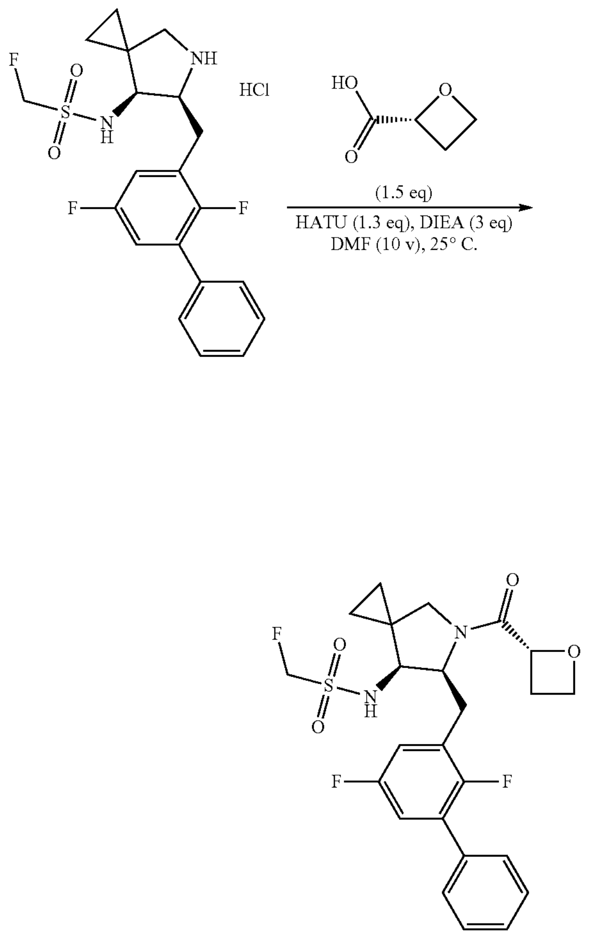

To a solution of N-((6S,7S)-6-((2,5-difluoro-[1,1'-biphenyl]-3-yl)methyl)-5-azaspiro[2.4]heptan-7-yl)-1-fluoromethanesulfonamide hydrochloride, intermediate 16 (1.4 g, 3.41 mmol, 1 eq) in dimethyl formamide (15 mL) was added N,N-diisopropylethylamine (1.78 mL, 10.2 mmol, 3 eq), (2R)-oxetane-2-carboxylic acid (522 mg, 5.12 mmol, 1.5 eq) and HATU (1.69 g, 4.43 mmol, 1.3 eq). The resulting mixture was stirred at 25° C. for 2 hours. The residue was purified by prep-HPLC (neutral condition: column: Waters Xbridge BEH C18 100*25 mm*5 um; mobile phase: [water (10 mM $NH_4HCO_3$)-ACN]; B %: 40%-60%, 10 min) to afford the title compound (1.16 g, 68.9% yield) was obtained as a white solid.

Example 60 (Compound 146)

Step 1: tert-butyl (6S,7S)-6-((2,5-difluoro-[1,1'-biphenyl]-3-yl)methyl)-7-(ethylsulfonamido)-5-azaspiro[2.4]heptane-5-carboxylate

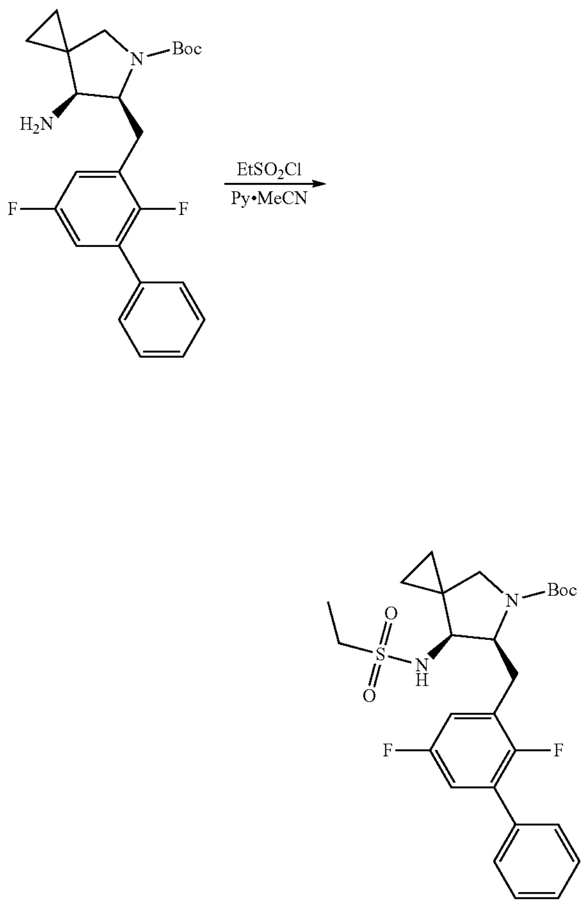

To a solution of tert-butyl (6S,7S)-7-amino-6-((2,5-difluoro-[1,1'-biphenyl]-3-yl)methyl)-5-azaspiro[2.4]heptane-5-carboxylate (Intermediate 15)(600 mg, 1.45 mmol, 1 eq) in acetonitrile (6 mL) was added pyridine (343 mg, 4.34 mmol, 3 eq) and ethanesulfonyl chloride (279 mg, 2.17 mmol, 1.5 eq). The mixture was stirred at 25° C. for 12 h. The reaction mixture was diluted with water (50 mL), extracted with ethyl acetate (3x30 mL), the combined organic phase was washed with brine (100 mL), dried over anhydrous sodium sulfate, filtered and the filtrate was concentrated under reduce pressure. The residue was purified by column chromatography on silica gel ($SiO_2$, petroleum ether:ethyl acetate=20:1 to 1:1) to afford the title compound (500 mg, 68% yield) as a white solid. $^1$H NMR (400 MHz, chloroform-d): δ 0.17-0.54 (m, 1H), 0.17-0.54 (m, 1H), 0.69 (br s, 3H), 1.19-1.50 (m, 12H), 2.71-3.24 (m, 5H), 3.51-3.80 (m, 1H), 4.15-4.21 (m, 1H), 4.41 (br s, 1H), 6.86-7.10 (m, 2H), 7.38-7.53 (m, 5H).

Step 2: N-((6S,7S)-6-((2,5-difluoro-[1,1'-biphenyl]-3-yl)methyl)-5-azaspiro[2.4]heptan-7-yl)ethanesulfonamide hydrochloride

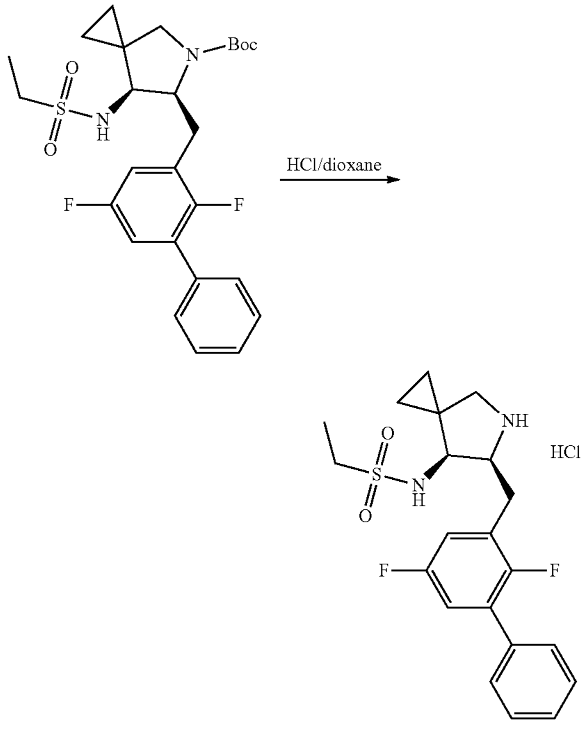

A solution of tert-butyl (6S,7S)-6-((2,5-difluoro-[1,1'-biphenyl]-3-yl)methyl)-7-(ethylsulfonamido)-5-azaspiro[2.4]heptane-5-carboxylate (500 mg, 986 μmol, 1 eq) in HCl/dioxane (10 mL) was stirred at 25° C. for 0.5 h. The reaction mixture was concentrated under reduced pressure to afford the title compound (350 mg, 87% yield) as a white solid. The crude product was used in next steps directly without purification.

Step 3: N-((6S,7S)-6-((2,5-difluoro-[1,1'-biphenyl]-3-yl)methyl)-5-((R)-oxetane-2-carbonyl)-5-azaspiro[2.4]heptan-7-yl)ethanesulfonamide

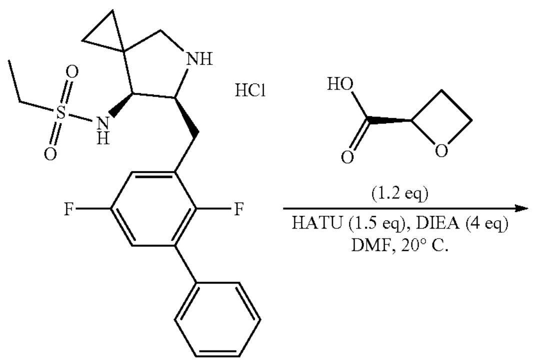

-continued

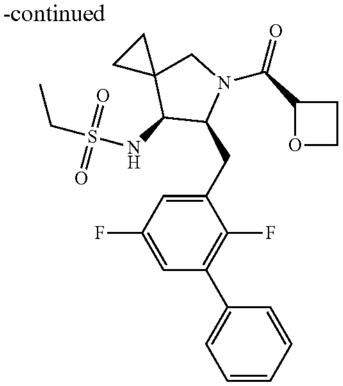

To a solution of N-((6S,7S)-6-((2,5-difluoro-[1,1'-biphenyl]-3-yl)methyl)-5-azaspiro[2.4]heptan-7-yl)ethanesulfonamide hydrochloride (100 mg, 246 μmol, 1 eq) in N,N-dimethylformamide (1 mL) was added (2R)-oxetane-2-carboxylic acid (30 mg, 295 μmol, 1.2 eq), HATU (140 mg, 369 μmol, 1.5 eq) and N, N-diisopropylethylamine (127 mg, 984 μmol, 4 eq). The mixture was stirred at 25° C. for 12 h. The reaction mixture was concentrated under reduced pressure. The residue was purified by prep-HPLC (neutral condition, column: Waters Xbridge BEH C18 100*30 mm*10 um; mobile phase: [water($NH_4HCO_3$)-ACN]; B %: 35%-55%, 8 min) to afford the title compound (24.2 mg, 20% yield) as a white solid.

Example 61 (Compound 147)

Step 1: tert-butyl (6S,7S)-7-amino-6-((2,3',5-trifluoro-[1,1'-biphenyl]-3-yl)methyl)-5-azaspiro[2.4]heptane-5-carboxylate

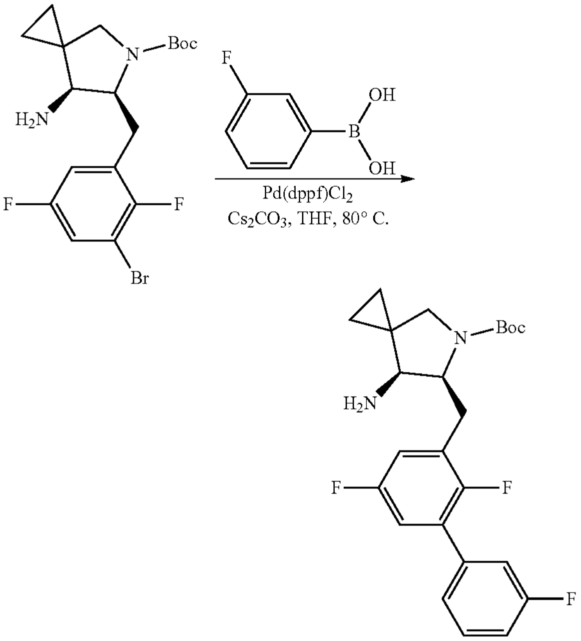

To a solution of tert-butyl (6S,7S)-7-amino-6-(3-bromo-2,5-difluorobenzyl)-5-azaspiro[2.4]heptane-5-carboxylate, intermediate 13 (900 mg, 2.16 mmol, 1 eq) in dioxane (8 mL) and water (2 mL) was added cesium carbonate (2.11 g, 6.47 mmol, 3 eq), 3-fluorophenyl)boronic acid (362 mg, 2.59 mmol, 1.2 eq) and Pd(dppf)$Cl_2$ (158 mg, 216 umol, 0.1 eq) in one portion at 25° C. under nitrogen atmosphere. The mixture was stirred at 25° C. for 3 min, then heated to 80° C. and stirred for 12 h. The mixture was poured into water (w/w=1/1, 50 mL) and stirred for 3 min. The aqueous phase was extracted with ethyl acetate (3x25 mL). The combined organic phase was dried with anhydrous sodium sulfate, filtered and concentrated under reduced pressure to afford crude product. The residue was purified by column chromatography (Silica, Petroleum ether/Ethyl acetate=3/1 to 1/1) to afford the title compound (600 mg, 59.2% yield) as a black oil. LCMS(method M)(ESI+): m/z 377.0 $(M-56+H)^+$, RT: 0.704 min.

Step 2: tert-butyl (6S,7S)-7-(ethylsulfonamido)-6-((2,3',5-trifluoro-[1,1'-biphenyl]-3-yl)methyl)-5-azaspiro[2.4]heptane-5-carboxylate

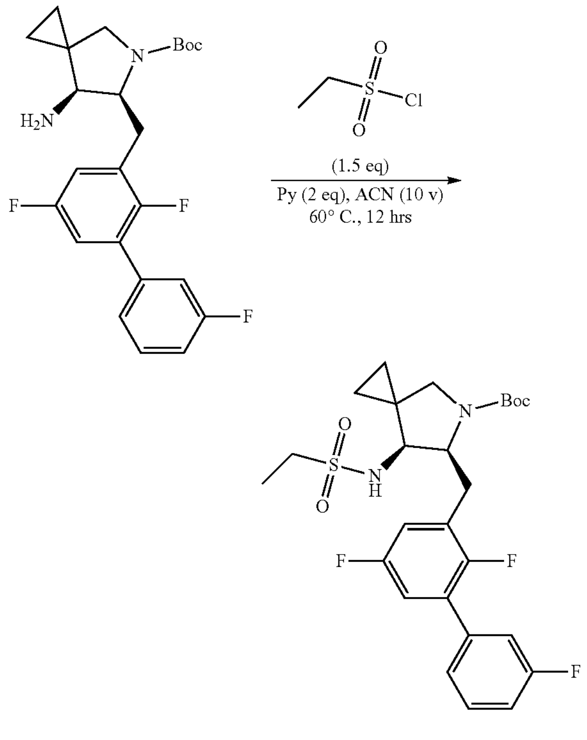

A solution of tert-butyl (6S,7S)-7-amino-6-((2,3',5-trifluoro-[1,1'-biphenyl]-3-yl)methyl)-5-azaspiro[2.4]heptane-5-carboxylate (230 mg, 532 μmol, 1 eq) in acetonitrile (3 mL) was added ethanesulfonyl chloride (75 μL, 798 μmol, 1.5 eq) and pyridine (86 μL, 1.06 mmol, 2 eq) in one portion at 60° C. under nitrogen atmosphere. The mixture was stirred at 60° C. for 12 h. The mixture was poured into water (50 mL) and stirred for 3 min. The aqueous phase was extracted with ethyl acetate (25 mL×3). The combined organic phase was dried with anhydrous sodium sulfate, filtered and concentrated under reduced pressure to afford crude product. The mixture was purified by prep-TLC (Silica, petroleum ether:ethyl acetate=1:1) to afford the title compound (200 mg, 69.5% yield) as yellow oil. LCMS (method M)(ESI+): m/z 425.0 $(M-100+H)^+$, RT: 0.880 min.

Step 3: N-((6S,7S)-6-((2,3',5-trifluoro-[1,1'-biphenyl]-3-yl)methyl)-5-azaspiro[2.4]heptan-7-yl)ethanesulfonamide hydrochloride

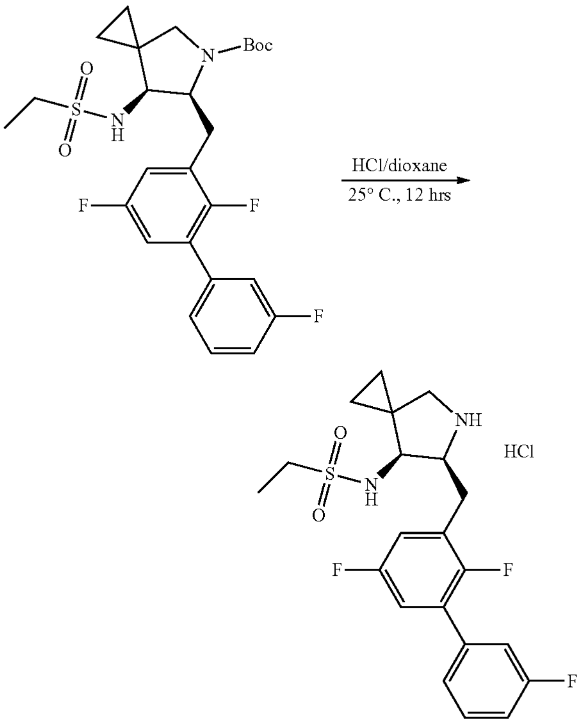

A solution of tert-butyl (6S,7S)-7-(ethylsulfonamido)-6-((2,3',5-trifluoro-[1,1'-biphenyl]-3-yl)methyl)-5-azaspiro[2.4]heptane-5-carboxylate (200 mg, 381 μmol, 1 eq) was added HCl/dioxane (4M, 2 mL) in one portion at 25° C. under nitrogen. The mixture was stirred at 25° C. for 3 min and stirred for 12 h. The mixture was concentrated under reduced pressure to afford the title compound (150 mg, 87.1% yield) as a white solid. LCMS(method M)(ESI+): m/z 425.0 (M+H)~, RT: 0.673 min.

Step 4: N-((6S,7S)-5-((R)-oxetane-2-carbonyl)-6-((2,3',5-trifluoro-[1,1'-biphenyl]-3-yl)methyl)-5-azaspiro[2.4]heptan-7-yl)ethanesulfonamide

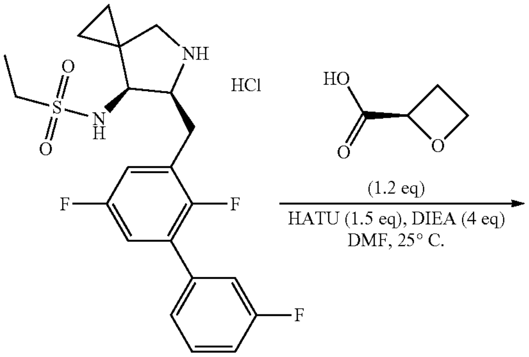

-continued

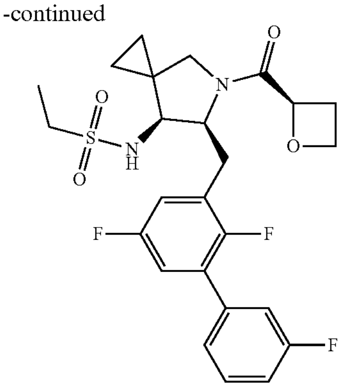

To a mixture of N-((6S,7S)-6-((2,3',5-trifluoro-[1,1'-biphenyl]-3-yl)methyl)-5-azaspiro[2.4]heptan-7-yl)ethanesulfonamide (150 mg, 353 umol, 1 eq) and (2R)-oxetane-2-carboxylic acid (40 mg, 389 umol, 1.1 eq) in N,N-dimethylformamide (1.5 mL) was added N,N-diisopropylethylamine (185 uL, 1.06 mmol, 3 eq), then was added HATU (175 mg, 459 umol, 1.3 eq) in one portion at 25° C. under nitrogen. The mixture was stirred at 25° C. for 12 h. The mixture was filtered and purified by prep-HPLC (column: Waters Xbridge BEH C18 100*30 mm*10 um; mobile phase: [water (10 mM ammonium bicarbonate)-acetonitrile]; B %: 35%-65%, 8 min) to afford the title compound (34.7 mg, 19.1% yield) as a white solid.

Example 62 (Compound 154)

Step 1: tert-butyl (6S,7S)-6-2,3'-difluoro-[1,1'-biphenyl]-3-yl)methyl)-7-((difluoromethyl)sulfonamido)-5-azaspiro[2.4]heptane-5-carboxylate

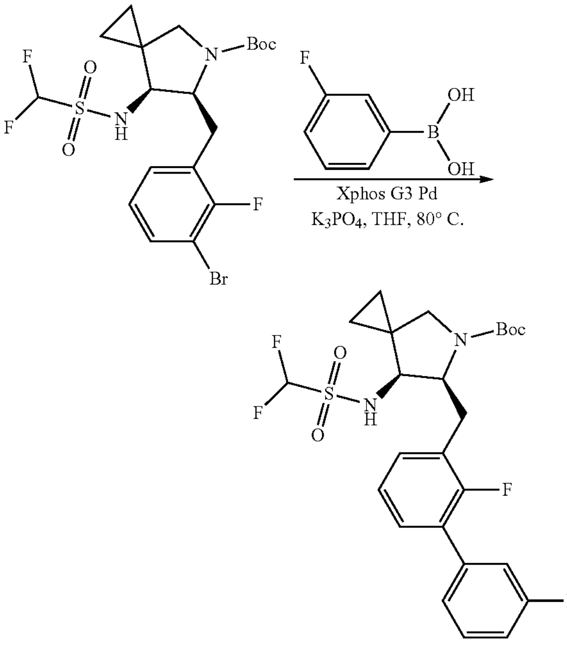

To a solution of tert-butyl (6S,7S)-6-(3-bromo-2-fluorobenzyl)-7-((difluoromethyl)sulfonamido)-5-azaspiro[2.4]heptane-5-carboxylate, intermediate 12 (0.38 g, 740 umol, 1 eq) in tetrahydrofuran (10 mL) were added (3-fluorophenyl) boronic acid (259 mg, 1.85 mmol, 2.5 eq), Xphos G3 Pd (31 mg, 37 μmol, 0.05 eq) and $K_3PO_4$ (314 mg, 1.48 mmol, 2 eq) at 20° C. The mixture was stirred at 80° C. for 12 hrs under $N_2$ atmosphere. Another four reactions were set up as above and the five reaction mixtures were combined and treated with water (30 mL), then extracted with ethyl acetate (3-10 mL). The organic layer was dried over $Na_2SO_4$, filtered and concentrated under reduced pressure. The residue was purified by column chromatography on silica gel (eluted with petroleum ether/ethyl acetate=100/0 to 10/1) to afford the title compound (1.4 g, 68% yield) as a white solid. $^1$H NMR (400 MHz, methanol-$d_4$) δ 0.58-0.78 (m, 3H), 0.98-1.26 (m, 10H), 2.76-2.95 (m, 1H), 3.07 (br d, 1H), 3.24 (d, 1H), 3.69 (br d, 1H), 4.21 (br d, 1H), 4.38 (br s, 1H), 6.47-6.81 (m, 1H), 7.10 (br t, 1H), 7.17-7.32 (m, 3H), 7.33-7.50 (m, 3H).

Step 2: N-((6S,7S)-6-((2,3'-difluoro-[1,1'-biphenyl]-3-yl)methyl)-5-azaspiro[2.4]heptan-7-yl)-1,1-difluoromethanesulfonamide hydrochloride

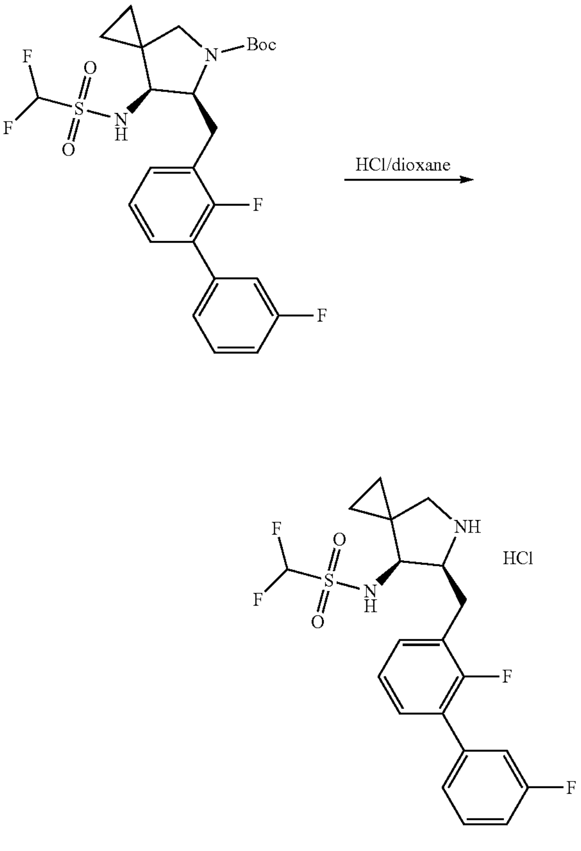 [SMILES: CC(C)(C)OC(=O)N1CC2(CC2)[C@H](NS(=O)(=O)C(F)F)[C@@H]1Cc1cccc(-c2cccc(F)c2)c1F ; O=S(=O)(N[C@@H]1[C@H](Cc2cccc(-c3cccc(F)c3)c2F)NCC12CC2)C(F)F ; Cl]

To a solution of tert-butyl (6S,7S)-6-((2,3'-difluoro-[1,1'-biphenyl]-3-yl)methyl)-7-((difluoromethyl)sulfonamido)-5-azaspiro[2.4]heptane-5-carboxylate (0.28 g, 530 mol, 1 eq) in dioxane (4 mL) was added HCl/dioxane (4 M, 11.67 mL, 88 eq) at 25° C. The reaction mixture was stirred at 25° C. for 12 hrs. Another four reactions were set up as above and the five reaction mixtures were combined and concentrated under reduced pressure to afford the title compound (1.2 g, 95.8% yield) as a white solid. LCMS(method M)(ESI+): m/z 429.1 $(M+H)^+$, RT: 0.864 min.

Step 3: N-((6S,7S)-6-((2,3'-difluoro-[1,1'-biphenyl]-3-yl)methyl)-5-((R)-oxetane-2-carbonyl)-5-azaspiro[2.4]heptan-7-yl)-1,1-difluoromethanesulfonamide

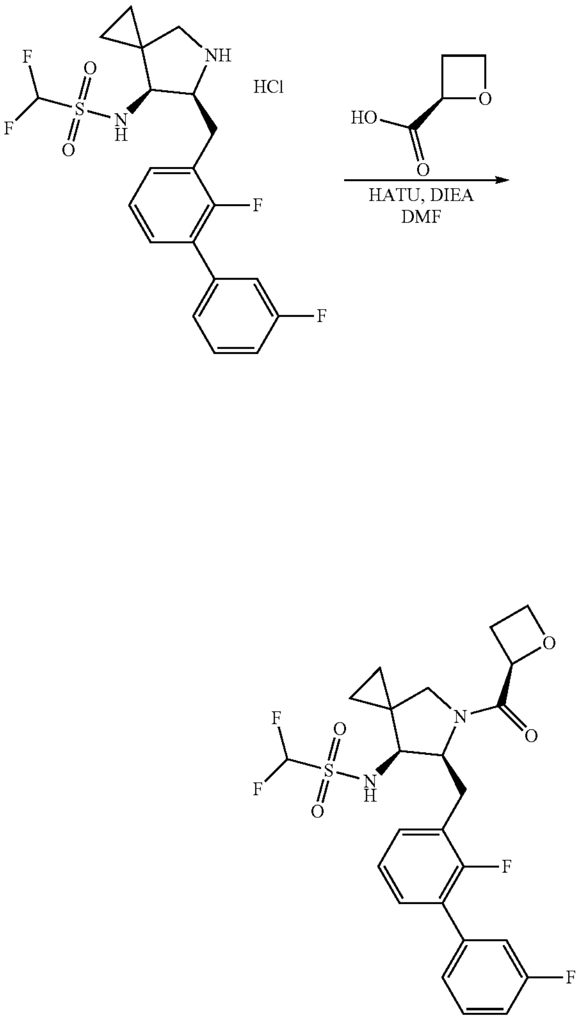 [SMILES: O=S(=O)(N[C@@H]1[C@H](Cc2cccc(-c3cccc(F)c3)c2F)NCC12CC2)C(F)F ; Cl ; O=C(O)[C@H]1CCO1 ; O=C([C@H]1CCO1)N1CC2(CC2)[C@H](NS(=O)(=O)C(F)F)[C@@H]1Cc1cccc(-c2cccc(F)c2)c1F]

To a solution of N-((6S,7S)-6-((2,3'-difluoro-[1,1'-biphenyl]-3-yl)methyl)-5-azaspiro[2.4]heptan-7-yl)-1,1-difluoromethanesulfonamide hydrochloride (0.6 g, 1.29 mmol, 1 eq) in DMF (25 mL) were added (2R)-oxetane-2-carboxylic acid (198 mg, 1.94 mmol, 1.5 eq), N,N-diisopropylethylamine (1.12 mL, 6.45 mmol, 5 eq) and HATU (589 mg, 1.55 mmol, 1.2 eq) at 0° C. The resulting reaction mixture was stirred at 25° C. for 12 hrs. Another one reaction was set up as above. The two reaction mixtures were combined and purified by prep-HPLC (neutral condition: Column: Phenomenex Gemini-NX 0*40 mm*3 um; mobile phase: [water (10 mM $NH_4HCO_3$)-ACN]; B %: 25%-55%, 8 min) to afford the title compound (650 mg, 49.2% yield) as a white solid.

Example 63 (Compound 162)

Step 1: tert-butyl (6S,7S)-6-((2-fluoro-[1,1'-biphenyl]-3-yl)methyl)-7-((1-methylethyl)sulfonamido)-5-azaspiro[2.4]heptane-5-carboxylate

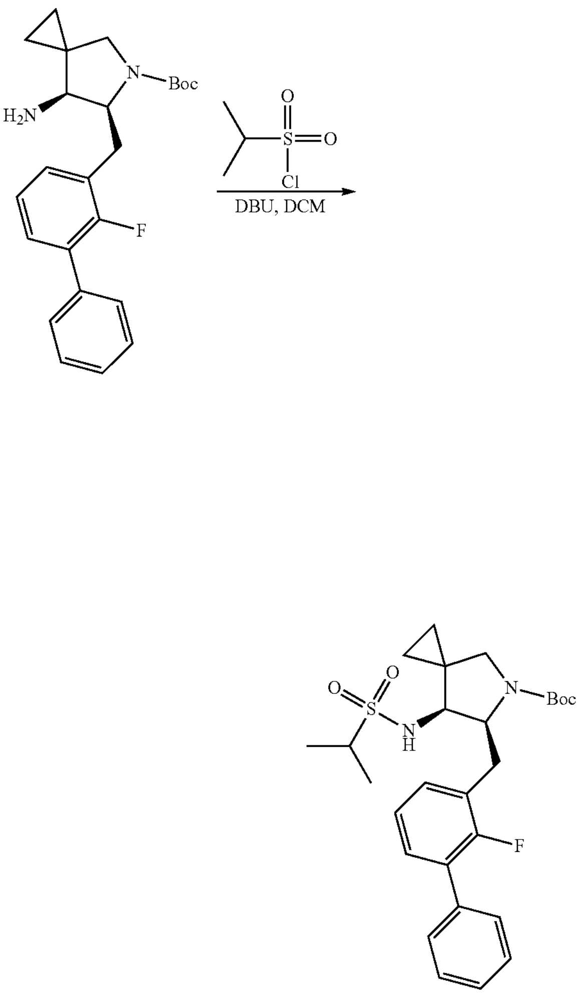

To a solution of tert-butyl (6S,7S)-7-amino-6-((2-fluoro-[1,1'-biphenyl]-3-yl)methyl)-5-azaspiro[2.4]heptane-5-carboxylate, intermediate 18 (116 mg, 292 mol, 1 eq) and 1,8-diazabicyclo[5.4.0]undec-7-ene (134 mg, 878 μmol, 132 uL, 3 eq) in dichloromethane (5 mL) and added propane-2-sulfonyl chloride (55 uL, 497 μmol, 1.7 eq) at 0° C. Stirring was continued at 0° C. for 1 h. The mixture was stirred at 25° C. for 12 hours, quenched by addition dichloromethane (5 mL), and then diluted with 1N hydrochloric acid (4 mL) and extracted with dichloromethane (5 mL×3). The crude product was purified by prep-TLC (petroleum ether/ethyl acetate=2/1) to afford the title compound (100 mg, 68.0% yield) as a white solid. LCMS(method M)(ESI+): m/z 525.2 $(M+Na)^+$, RT: 0.870 min.

Step 2: N-((6S,7S)-6-((2-fluoro-[1,1'-biphenyl]-3-yl)methyl)-5-azaspiro[2.4]heptan-7-yl)propane-2-sulfonamide hydrochloride

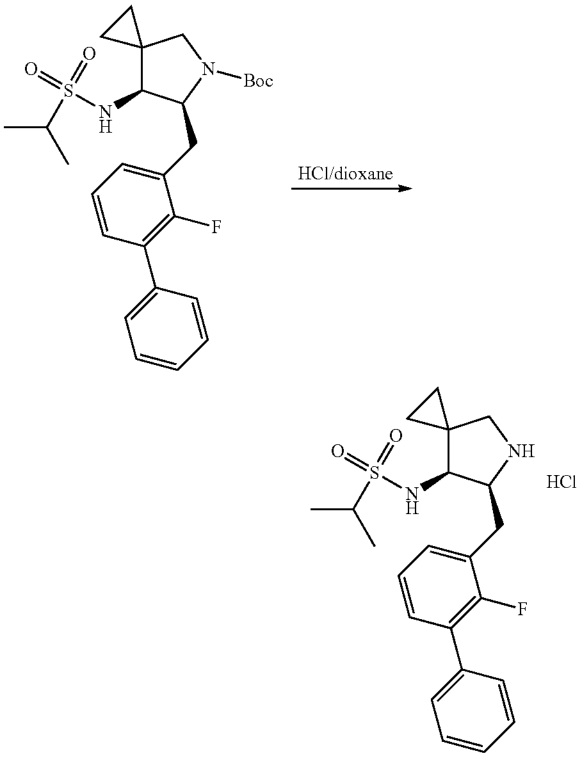

To a solution of tert-butyl (6S,7S)-6-((2-fluoro-[1,1'-biphenyl]-3-yl)methyl)-7-((1-methylethyl)sulfonamido)-5-azaspiro[2.4]heptane-5-carboxylate (50.0 mg, 100 μmol, 1 eq) in HCl/dioxane (1 mL) was stirred at 20° C. for 2 hours. The mixture was concentrated under reduced pressure to afford the title compound (40.0 mg, 99.9% yield), which was used directly without further purification.

Step 3: N-((6S,7S)-6-((2-fluoro-[1,1'-biphenyl]-3-yl)methyl)-5-((R)-oxetane-2-carbonyl)-5-azaspiro[2.4]heptan-7-yl)propane-2-sulfonamide

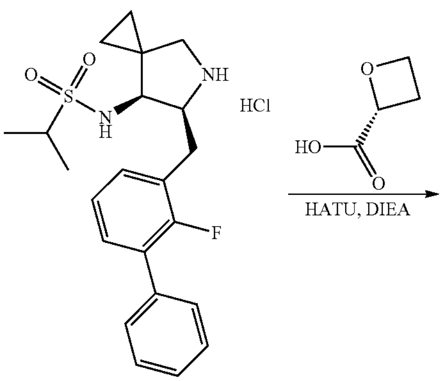

-continued

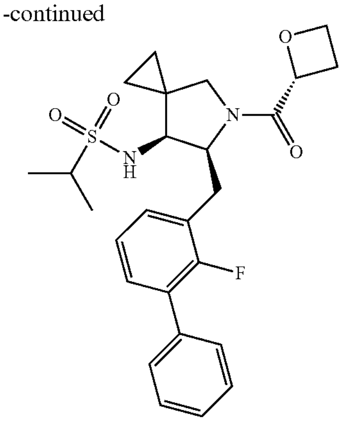

To a solution of N-((6S,7S)-6-((2-fluoro-[1,1'-biphenyl]-3-yl)methyl)-5-azaspiro[2.4]heptan-7-yl)propane-2-sulfonamide hydrochloride (40 mg, 99 μmol, 1 eq) and (2R)-oxetane-2-carboxylic acid (11 mg, 109 μmol, 1.1 eq) in dimethyl formamide (0.5 mL) were added HATU (49 mg, 129 μmol, 1.3 eq) and DIEA (52 μL, 298 μmol, 3 eq) at 20° C. The mixture was stirred at 20° C. for 4 hours. The residue was purified by prep-HPLC (column: Waters Xbridge BEH C18 100*30 mm*10 um; mobile phase: [water (0.05% NH3H2O+10 mM NH4HCO3)-ACN]; B %: 35%-65%, 8 min) to afford the title compound (26 mg, 53.7% yield) as a white solid.

Example 64 (Compound 170)

Step 1: tert-butyl (6S,7S)-7-((difluoromethyl)sulfonamido)-6-((2-fluoro-[1,1'-biphenyl]-3-yl)methyl)-5-<azaspiro[2.4]heptane-5-carboxylate

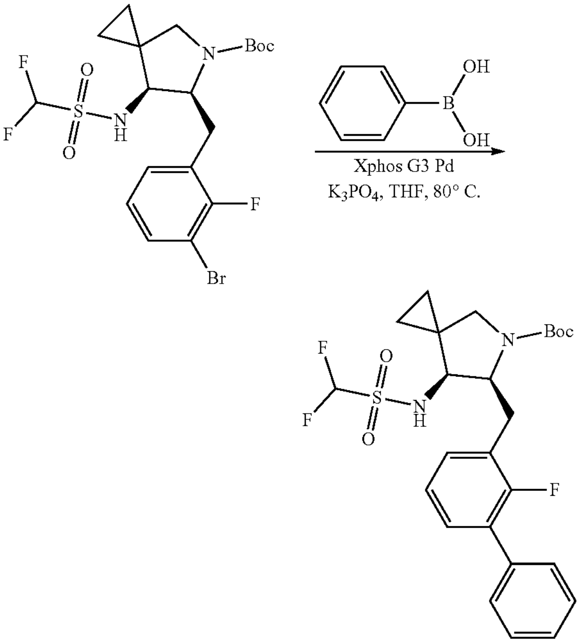 [SMILES: CC(C)(C)OC(=O)N1CC2(CC2)[C@H](NS(=O)(=O)C(F)F)[C@@H]1Cc1cccc(Br)c1F ; OB(O)c1ccccc1 ; CC(C)(C)OC(=O)N1CC2(CC2)[C@H](NS(=O)(=O)C(F)F)[C@@H]1Cc1cccc(-c2ccccc2)c1F]

To a solution of tert-butyl (6S,7S)-6-(3-bromo-2-fluorobenzyl)-7-((difluoromethyl)sulfonamido)-5-azaspiro[2.4]heptane-5-carboxylate, intermediate 12 (1 g, 1.95 mmol, 1 eq) in tetrahydrofuran (10 mL) was added potassium phosphate (1.24 g, 5.84 mmol, 3 eq) and XPhos-Pd-G3 (165 mg, 195 μmol, 0.1 eq), phenylboronic acid (285 mg, 2.34 mmol, 1.2 eq). The mixture was stirred at 80° C. for 8 hours. The reaction mixture was partitioned between $H_2O$ (20 mL) and ethyl acetate (20 mL). The aqueous phase was separated, washed with ethyl acetate (20 mL×3), dried over anhydrous sodium sulfate, filtered and concentrated under reduced pressure. The residue was purified by column chromatography ($SiO_2$, Petroleum ether/Ethyl acetate=100:1 to 3:1) to afford the title compound (840 mg, 84.5% yield) as a white solid. LCMS (method M)(ESI+): m/z 455.0 $(M+H-56)^+$, RT: 1.114 min.

Step 2: 1,1-difluoro-N-((6S. 7S)-6-((2-fluoro-[1,1'-biphenyl]-3-yl)methyl)-5-azaspiro[2.4]heptan-7-yl) methanesulfonamide hydrochloride

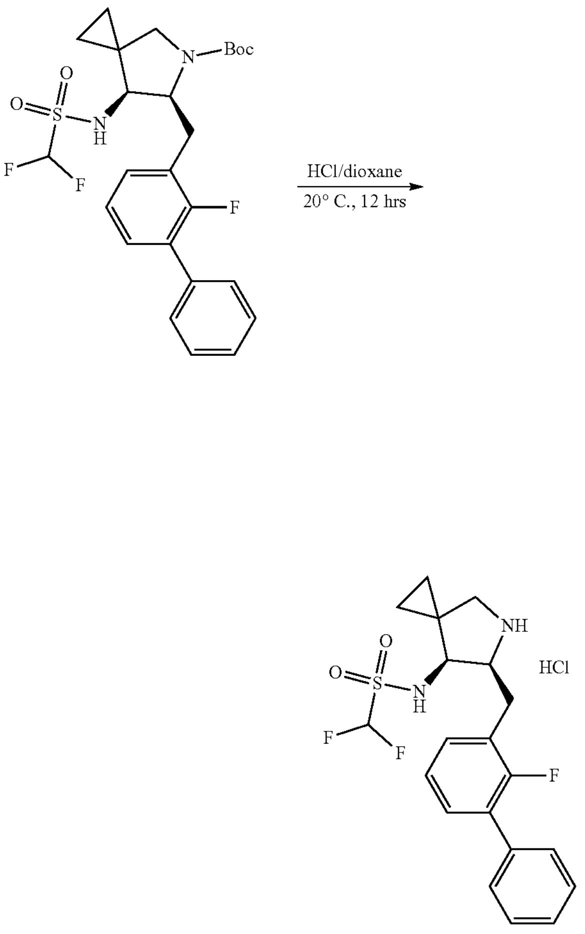

To a solution of tert-butyl (6S,7S)-7-((difluoromethyl) sulfonamido)-6-((2-fluoro-[1,1'-biphenyl]-3-yl)methyl)-5-azaspiro[2.4]heptane-5-carboxylate (840 mg, 1.65 mmol, 1 eq) in HCl/dioxane (10 mL). The mixture was stirred at 20° C. for 12 hours. The mixture was concentrated under reduced pressure to afford the title compound (740 mg, 98.6% yield) as a white solid, which was used into the next step without further purification. LCMS(method M) (ESI+): m/z 411.1 $(M+H)^+$, RT: 0.826 min.

Step 3: N-((6S 7S)-5-((S)-2-cyclopropyl-2-hydroxy-acetyl)-6-((2-fluoro-[1,1'-biphenyl]-3-yl)methyl)-5-azaspiro[2.4]heptan-7-yl)-1,1-difluoromethanesulfonamide

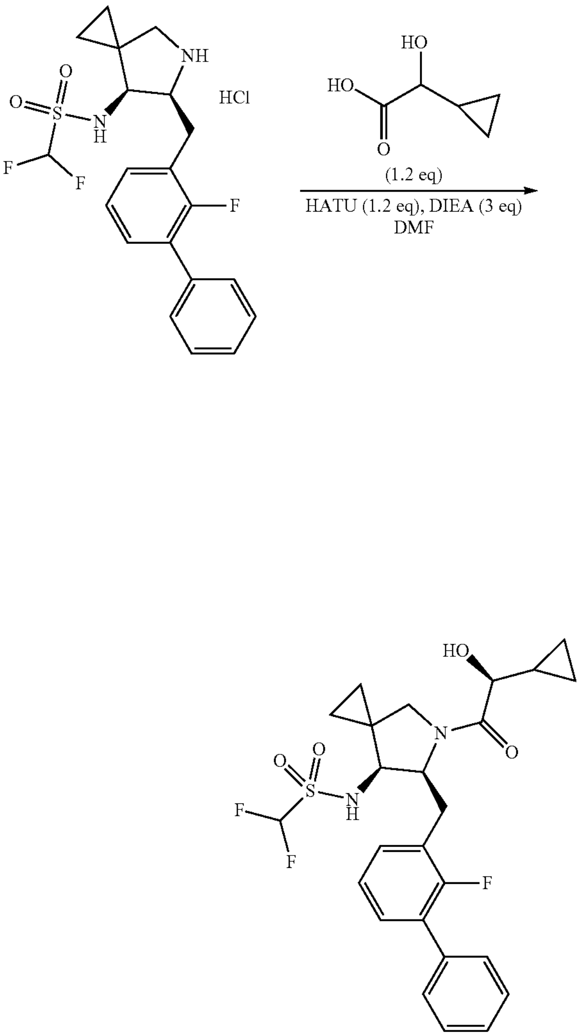

To a solution of 1,1-difluoro-N-((6S,7S)-6-((2-fluoro-[1,1'-biphenyl]-3-yl)methyl)-5-azaspiro[2.4]heptan-7-yl)methanesulfonamide hydrochloride (200 mg, 487 μmol, 1 eq) in N,N-dimethylformamide (3 mL) was added (2R)-2-cyclopropyl-2-hydroxy-acetic acid (68 mg, 585 μmol, 1.2 eq), N,N-diisopropylethylamine (255 μL, 1.46 mmol, 3 eq) and HATU (222 mg, 585 μmol, 1.2 eq). The mixture was stirred at 20° C. for 2 hours. The reaction mixture was partitioned between $H_2O$ (5 mL) and ethyl acetate (5 mL). The aqueous phase was separated, washed with ethyl acetate (5 mL×3), dried over anhydrous sodium sulfate, filtered and concentrated under reduced pressure. The residue was purified by prep-HPLC (TFA condition: column: Phenomenex Luna 80*30 mm*3 um; mobile phase: [water(TFA)-ACN]; B %: 30%-50%, 8 min) to afford the title compound (56 mg, 22.6% yield) as a white solid.

Example 65 (Compound 171)

Step 1: tert-butyl (6S,7S)-7-((difluoromethyl)sulfonamido)-6-((2.2',5'-trifluoro-[1,1'-biphenyl]-3-yl)methyl)-5-azaspiro[2.4]heptane-5-carboxylate

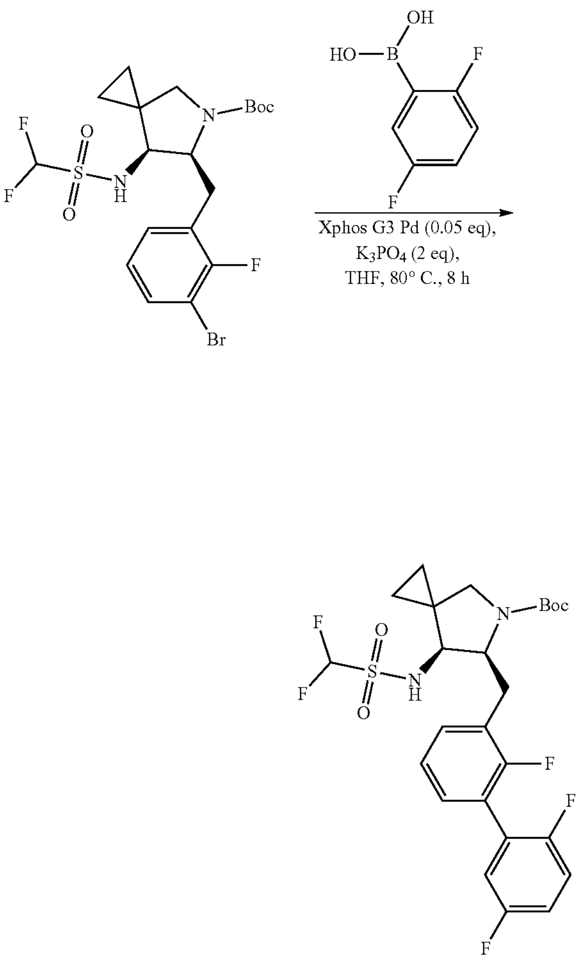

To a solution of tert-butyl (6S,7S)-6-(3-bromo-2-fluorobenzyl)-7-((difluoromethyl)sulfonamido)-5-azaspiro[2.4]heptane-5-carboxylate, intermediate 12 (250 mg, 487 μmol, 1 eq) in THF (20 mL) was added dropwise XPhos-Pd-G3 (18 mg, 24 μmol, 0.05 eq), (2,5-difluorophenyl)boronic acid (100 mg, 633 μmol, 1.3 eq) and potassium phosphate (206 mg, 0.97 mmol, 2 eq). The resulting mixture was stirred at 80° C. for 8 hours. The mixture was poured into the saturated aqueous ammonium chloride solution (80 mL) and extracted with dichloromethane (3×50 mL). The organic layer was washed with brine (100 mL), dried over anhydrous sodium sulfate and concentrated under reduced pressure. The residue was purified by column chromatography ($SiO_2$, petroleum ether/ethyl acetate=3:1) to afford the title compound (200 mg, 75.1% yield) as a yellow oil. LCMS(method M)(ESI+): m/z 491.0 $(M+H-56)^+$, RT: 0.873 min.

Step 2: 1,1-difluoro-N-((6S,7S)-6-((2,2',5'-trifluoro-[1,1'-biphenyl]-3-yl)methyl)-5-azaspiro[2.4]heptan-7-yl)methanesulfonamide hydrochloride

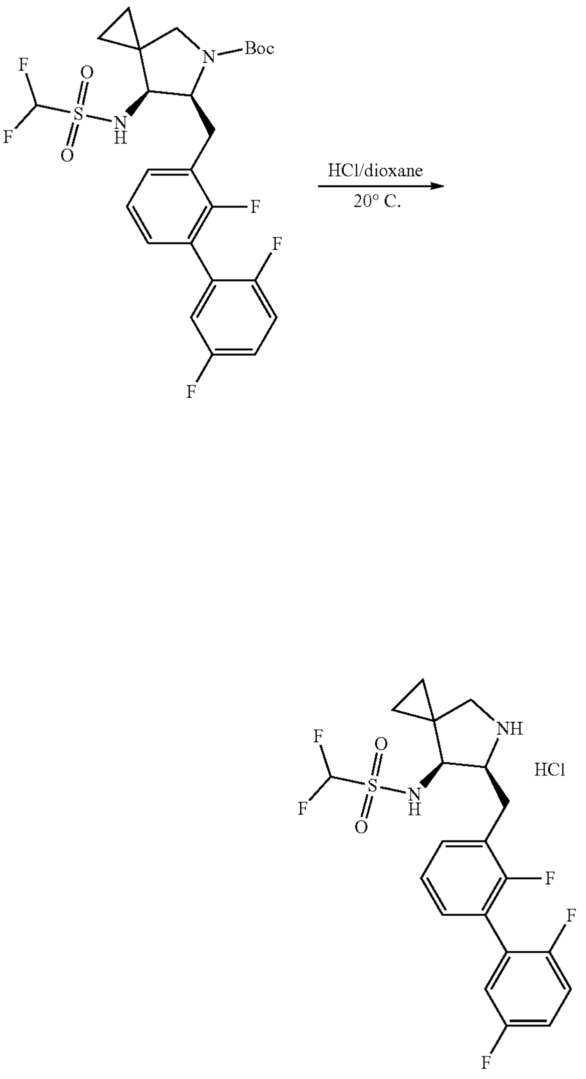

A solution of tert-butyl (6S,7S)-7-((difluoromethyl)sulfonamido)-6-((2,2',5'-trifluoro-[1,1'-biphenyl]-3-yl)methyl)-5-azaspiro[2.4]heptane-5-carboxylate (200 mg, 366 μmol, 1 eq) in HCl/dioxane (2 mL) was stirred at 20° C. for 2 hour. The reaction mixture was concentrated under reduced pressure to afford the title compound (160 mg, 97.9% yield) as yellow oil, which was used into the next step without further purification. LCMS(method M)(ESI+): m/z 447.0 $(M+H-100)^+$, RT: 0.672 min.

Step 3: 1,1-difluoro-N-((6S,7S)-5-((R)-oxetane-2-carbonyl)-6-((2,2',5'-trifluoro-[1,1'-biphenyl]-3-yl)methyl)-5-azaspiro[2A]heptan-7-yl)methanesulfonamide

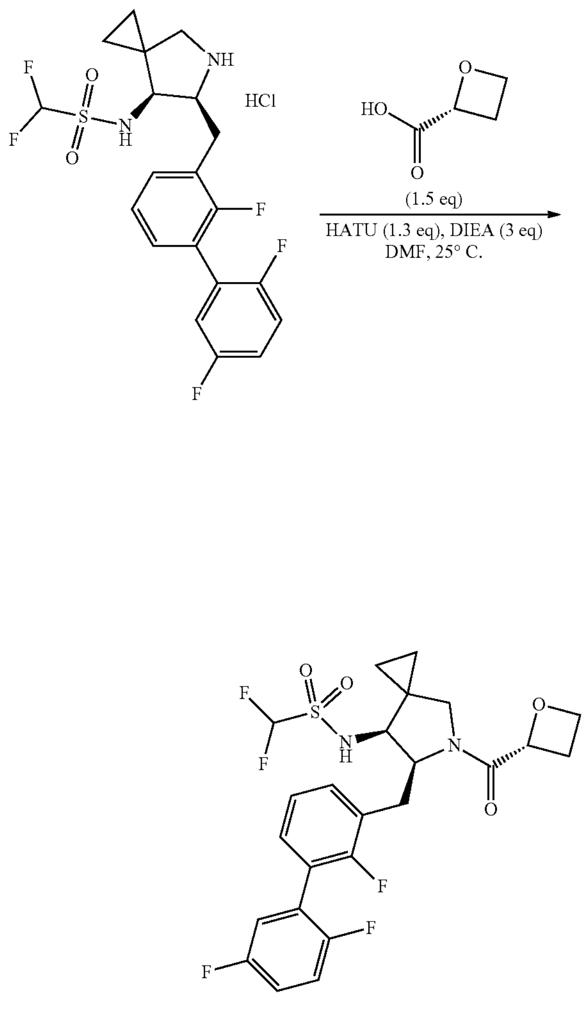

To a solution of 1,1-difluoro-N-((6S,7S)-6-((2,2',5'-trifluoro-[1,1'-biphenyl]-3-yl)methyl)-5-azaspiro[2.4]heptan-7-yl)methanesulfonamide hydrochloride (160 mg, 358 μmol, 1 eq) in dimethyl formamide (2 mL) was added dropwise N,N-diisopropylethylamine (187 μL, 1.08 mmol, 3 eq), (2R)-oxetane-2-carboxylic acid (55 mg, 537 μmol, 1.5 eq) and HATU (177 mg, 466 μmol, 1.3 eq). The resulting mixture was stirred at 25° C. for 2 hours. The residue was purified by prep-HPLC (neutral condition: column: Waters Xbridge BEH C18 100*25 mm*5 μm; mobile phase: [water (10 mM $NH_4HCO_3$)-ACN]; B %: 25%-55%, 10 min) to afford the title compound (32 mg, 16.8% yield) as a white solid.

Example 66 (Compound 175)

Step 1: tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate

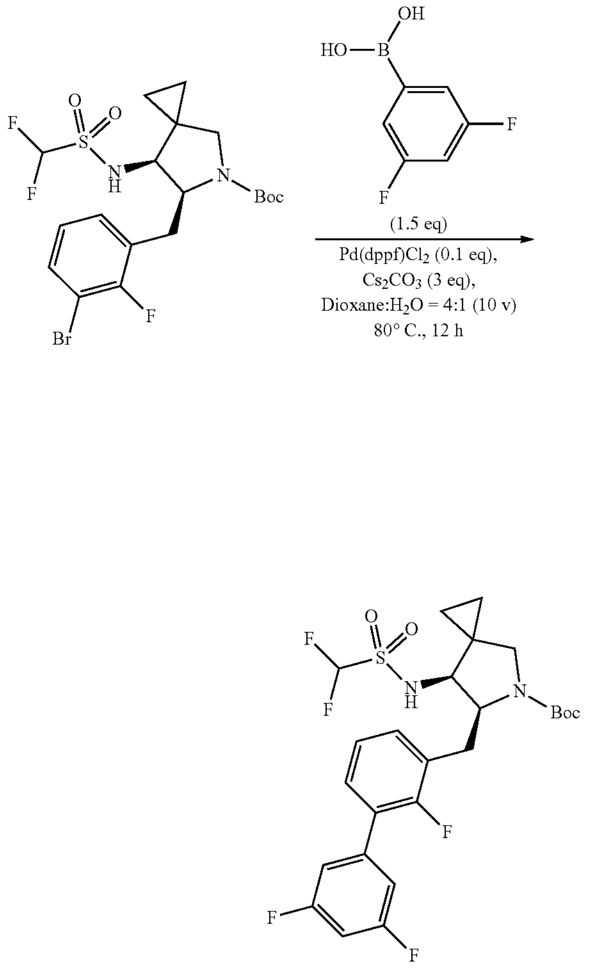

To a mixture of tert-butyl (6S,7S)-6-(3-bromo-2-fluorobenzyl)-7-((difluoromethyl)sulfonamido)-5-azaspiro[2.4]heptane-5-carboxylate, intermediate 12 (161 mg, 314 μmol, 1 eq) and (3,5-difluorophenyl)boronic acid (74 mg, 470 mol, 1.5 eq) in dioxane (1.6 mL) and water (0.4 mL) was added cesium carbonate (307 mg, 941 μmol, 3 eq) and Pd(dppf)$Cl_2$ (23 mg, 31 μmol, 0.1 eq) in one portion at 80° C. under nitrogen atmosphere. The mixture was stirred for 12 hours. The mixture was poured into water (w/w=1/1, 100 mL) and stirred for 3 min. The aqueous phase was extracted with ethyl acetate (3-50 mL). The combined organic phase was dried with anhydrous sodium sulfate, filtered and concentrated in vacuum. The mixture was purified by prep-TLC (Silica, petroleum ether:ethyl acetate=3:1) to afford the title compound (166 mg, 77.5% yield) as colourless oil. LCMS (method M)(ESI+): m/z 491.0 $(M-56+H)^+$, RT: 0.886 min.

Step 2: 1,1-difluoro-N-((6S,7S)-6-((2,3',5'-trifluoro-[1,1'-biphenyl]-3-yl)methyl)-5-azaspiro[2.4]heptan-7-yl)methanesulfonamide hydrochloride

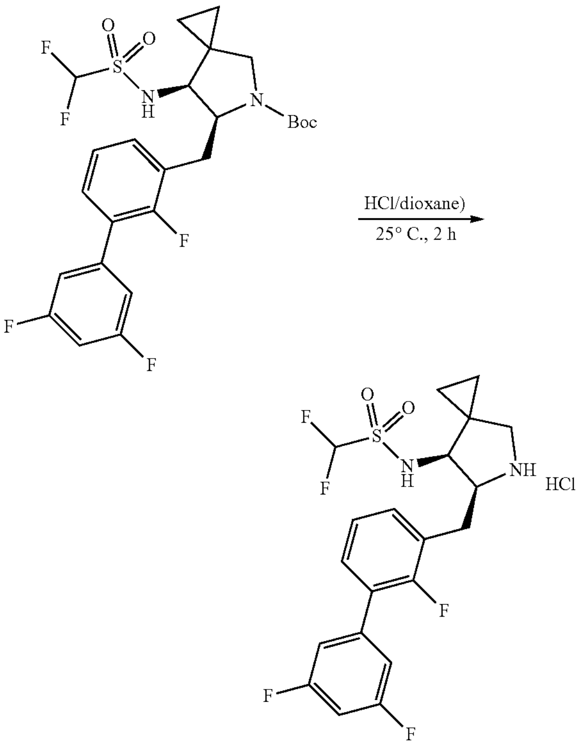

A solution of tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate (166 mg, 304 μmol, 1 eq) in HCl/dioxane (2 mL) was degassed and purged with nitrogen for 3 times, and then the mixture was stirred at 25° C. for 2 hours under nitrogen atmosphere. The mixture was concentrated under reduced pressure to afford the title compound (150 mg, 92.9% yield) as a white solid. LCMS (method M)(ESI+): m/z 447.1 $(M+H)^+$, RT: 0.880 min.

Step 3: 1,1-difluoro-N-((6S,7S)-5-((R)-oxetane-2-carbonyl)-6-((2,3,5'-trifluoro-[1,1'-biphenyl]-3-yl)methyl)-5-azaspiro[2.4]heptan-7-yl)methanesulfonamide

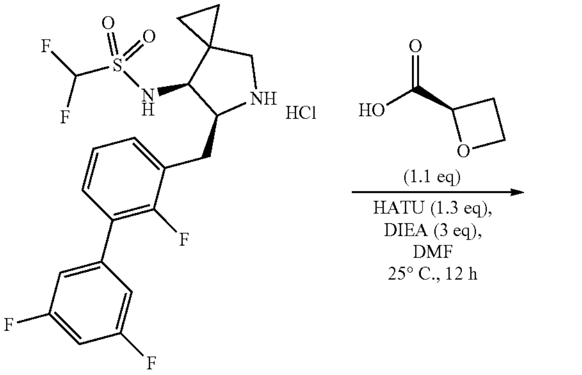

-continued

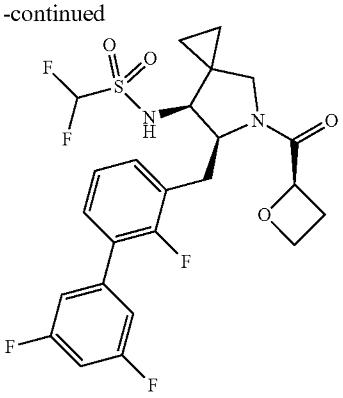

To a mixture of 1,1-difluoro-N-((6S,7S)-6-((2,3',5'-trifluoro-[1,1'-biphenyl]-3-yl)methyl)-5-azaspiro[2.4]heptan-7-yl)methanesulfonamide hydrochloride (150 mg, 336 μmol, 1 eq) and (2R)-oxetane-2-carboxylic acid (38 mg, 370 μmol, 1.1 eq) in N,N-dimethylformamide (1.5 mL) was added N,N-Diisopropylethylamine (176 μL mg, 1.01 mmol, 3 eq), then was added HATU (166 mg, 437 μmol, 1.3 eq) in one portion at 25° C. under nitrogen atmosphere. The mixture was stirred at 25° C. for 12 hours. The reaction mixture was filtered and purified by prep-HPLC (column: Waters Xbridge BEH C18 100*30 mm*10 um; mobile phase: [water(ammonium bicarbonate)-acetonitrile]; B %: 35%-55%, 8 min) to afford the title compound (54 mg, 29.7% yield) as a white solid.

Example 67 (Compound 176)

Step 1: tert-butyl (6S,7S)-7-((difluoromethyl)sulfonamido)-6-((2,3'5-trifluoro-[1,1'-biphenyl]-3-yl)methyl)-5-azaspiro[2.4]heptane-5-carboxylate

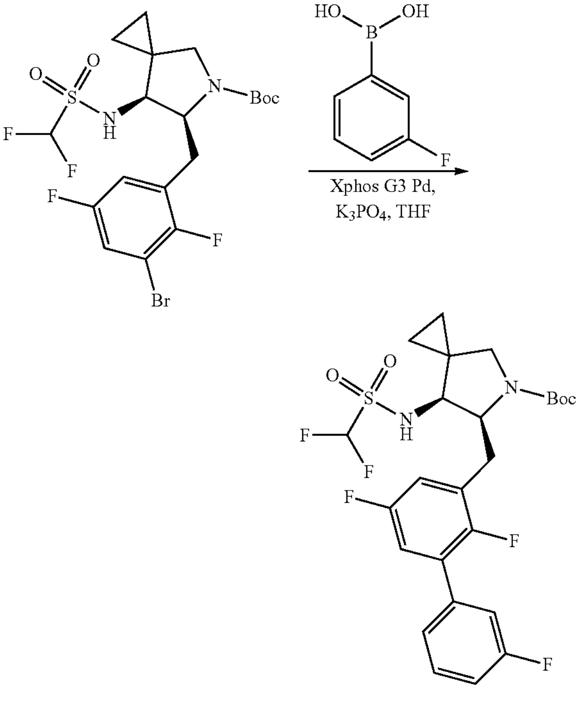 [SMILES: CC(C)(C)OC(=O)N1CC2(CC2)[C@H](NS(=O)(=O)C(F)F)[C@@H]1Cc1cc(F)cc(Br)c1F ; OB(O)c1cccc(F)c1 ; CC(C)(C)OC(=O)N1CC2(CC2)[C@H](NS(=O)(=O)C(F)F)[C@@H]1Cc1cc(F)cc(-c2cccc(F)c2)c1F]

To a solution of tert-butyl (6$,7S)-6-(3-bromo-2,5-difluorobenzyl)-7-((difluoromethyl)sulfonamido)-5-azaspiro[2.4]heptane-5-carboxylate, intermediate 17 (220 mg, 414 μmol, 1 eq) in tetrahydrofuran (3 mL) was added (3-fluorophenyl) boronic acid (104 mg, 745 mol, 1.8 eq) and potassium phosphate (219 mg, 1.04 mmol, 2.5 eq) and XPhos-Pd-G3 (35 mg, 41 μmol, 0.1 eq). The mixture was stirred at 80° C. for 8 hours. The reaction mixture was diluted with water (10 mL), extracted with ethyl acetate (3×10 mL), the combined organic phase was washed with brine (10 mL), dried over anhydrous sodium sulfate, filtered and the filtrate was concentrated under reduce pressure. The residue was purified by column chromatography (SiO2, petroleum ether:ethyl acetate=50:1 to 1:1) to afford the title compound (200 mg, 88% yield) as a white solid. LCMS(method M)(ESI+): m/z 491.0 $(M+H-56)^+$, RT: 0.880 min Step 2: 1,1-difluoro-N-((6S,7S)-6-((2,3',5-trifluoro-[1,1'-biphenyl]-3-yl)methyl)-5-azaspiro[2.4]heptan-7-yl)methanesulfonamide hydrochloride

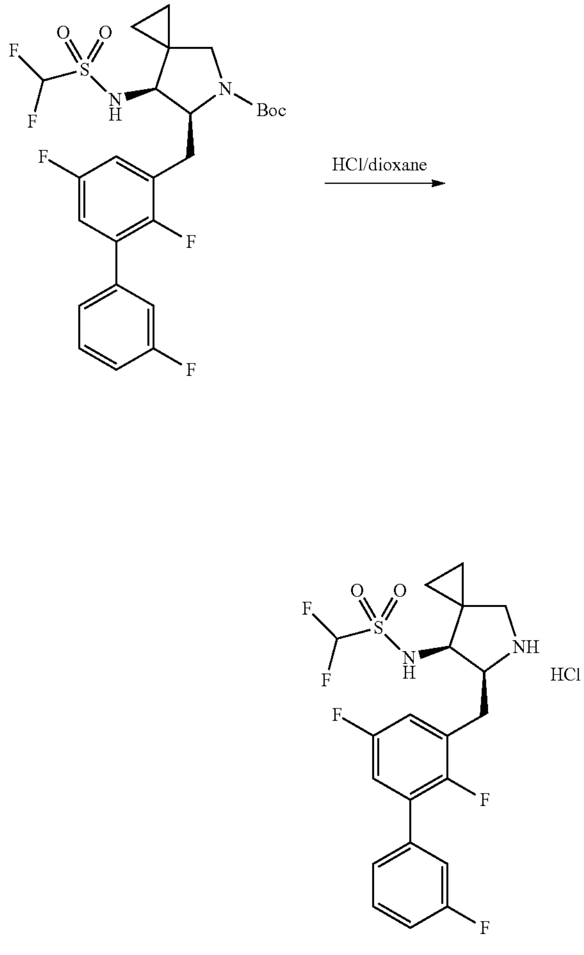

A solution of tert-butyl (6S,7S)-7-((difluoromethyl)sulfonamido)-6-((2,3',5-trifluoro-[1,1'-biphenyl]-3-yl)methyl)-5-azaspiro[2.4]heptane-5-carboxylate (200 mg, 365 μmol, 1 eq) in HCl/dioxane (2 mL) was stirred at 25° C. for 12 h. The reaction mixture was concentrated under reduce pressure to afford the title compound (150 mg, 91% yield) as a white solid. The crude product was used in the next step without further purification.

Step 3: 1,1-difluoro-N-((6S,7S)-5-((R)-oxetane-2-carbonyl)-6-((2,3',5-trifluoro-[1,1'-biphenyl]-3-yl)methyl)-5-azaspiro[2.4]heptan-7-yl)methanesulfonamide

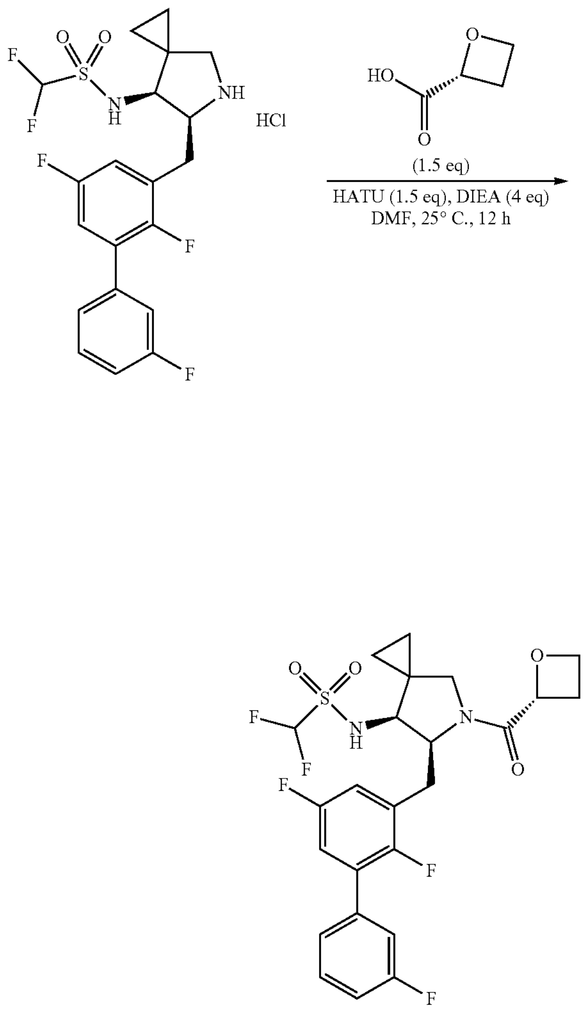

To a solution of 1,1-difluoro-N-((6S,7S)-6-((2,3',5-trifluoro-[1,1'-biphenyl]-3-yl)methyl)-5-azaspiro[2.4]heptan-7-yl)methanesulfonamide hydrochloride (150 mg, 336 μmol, 1 eq) in N,N-dimethylformamide (1.5 mL) was added N,N-diisopropylethylamine (173 mg, 1.34 mmol, 4 eq) and HATU (191 mg, 503 μmol, 1.5 eq) and (2R)-oxetane-2-carboxylic acid (51 mg, 503 μmol, 1.5 eq). The mixture was stirred at 25° C. for 12 hours. The reaction mixture was concentrated under reduce pressure. The residue was purified by prep-HPLC (neutral condition, column: Phenomenex Cis 80*40 mm*3 um; mobile phase: [water($NH_4HCO_3$)-ACN]; B %: 30%-60%, 8 min) to afford the title compound (80 mg, 44% yield) as a white solid.

Example 68 (Compound 177)

Step 1: tert-butyl (6S,7S)-7-amino-6-((2,3'-difluoro-[1,1'-biphenyl]-3-yl)methyl)-5-azaspiro[2.4]heptane-5-carboxylate

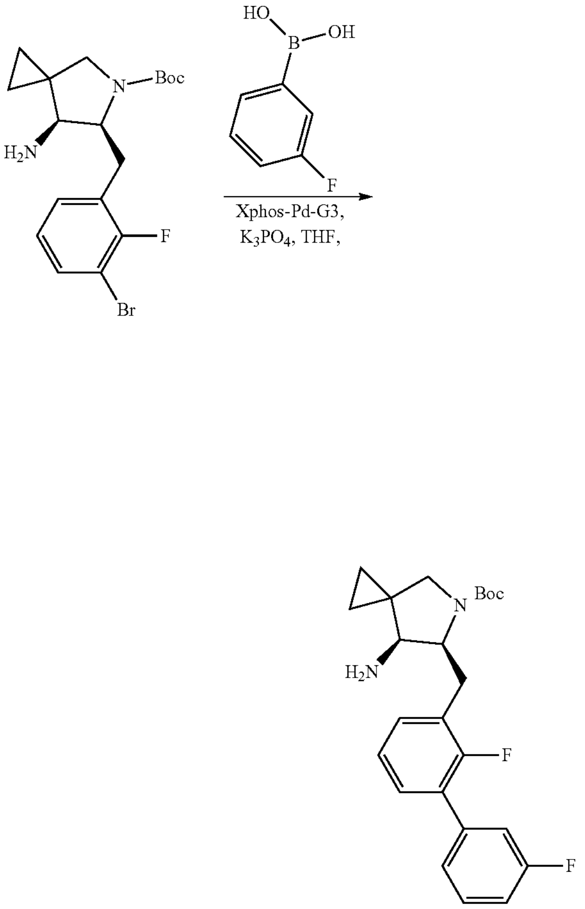

To a solution of tert-butyl (6S,7S)-7-amino-6-(3-bromo-2-fluorobenzyl)-5-azaspiro[2.4]heptane-5-carboxylate, intermediate 8 (0.4 g, 1.00 mmol, 1 eq) in tetrahydrofuran (10 mL) was added (3-fluorophenyl) boronic acid (421 mg, 3.01 mmol, 3 eq), XPhos-Pd-G3 (42 mg, 50 μmol, 0.05 eq) and potassium phosphate (638 mg, 3.01 mmol, 3 eq) at 25° C. The mixture was stirred at 80° C. for 2 hrs. After cooling down to 25° C., the reaction was concentrated under reduced pressure to afford a residue. The residue was purified by prep-TLC ($SiO_2$, petroleum ether/ethyl acetate=1/1) to afford the title compound (0.1 g, 24.1% yield) as yellow solid. 1H NMR (400 MHz, chloroform-d) δ 0.09-0.91 (m, 4H), 0.94-1.48 (m, 9H), 1.82-2.79 (m, 2H), 3.00 (br s, 2H), 3.41-3.68 (m, 2H), 4.23-4.72 (m, 1H), 5.44-5.90 (m, 1H), 6.40-6.65 (m, 2H), 6.93-7.13 (m, 3H), 7.20-7.47 (m, 2H).

Step 2: tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate

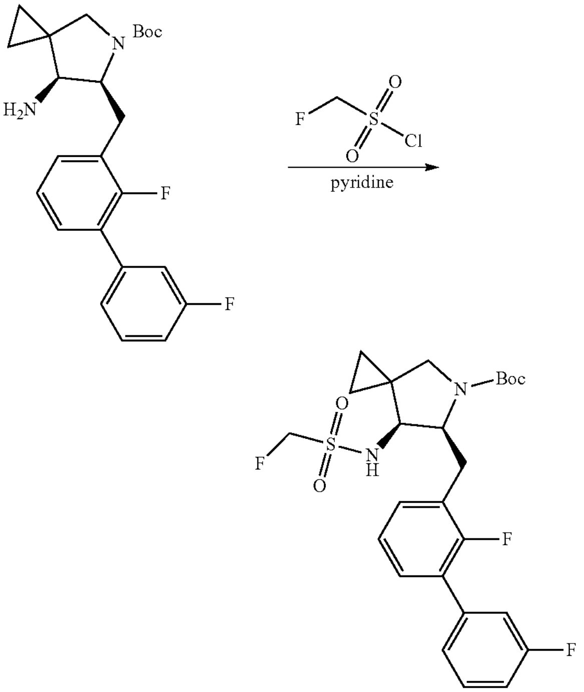

To a solution of tert-butyl (6S,7S)-7-amino-6-((2,3'-difluoro-[1,1'-biphenyl]-3-yl)methyl)-5-azaspiro[2.4]heptane-5-carboxylate (250 mg, 603 μmol, 1 eq) in acetonitrile (5 mL) was added fluoromethanesulfonyl chloride (160 mg, 1.21 mmol, 2 eq) and pyridine (243 μL, 3.02 mmol, 5 eq) at 25° C. The mixture was stirred at 90° C. for 0.5 hr. The reaction was filtered and the filtrate was concentrated under reduced pressure to afford a residue. The residue was purified by prep-TLC ($SiO_2$, petroleum ether/ethyl acetate=2/1) to afford the title compound (0.1 g, 32.5% yield) as white solid.

Step 3: N-((6S,7S)-6-((2,3'-difluoro-[1,1'-biphenyl]-3-yl)methyl)-5-azaspiro[2.4]heptan-7-yl)-1-fluoromethanesulfonamide hydrochloride

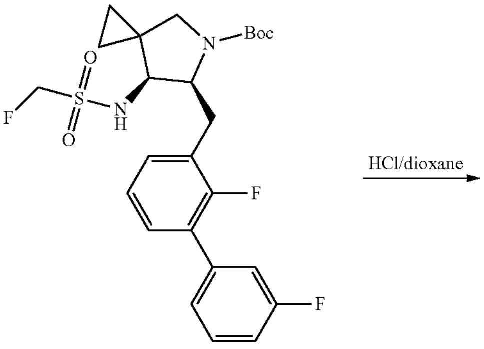

-continued

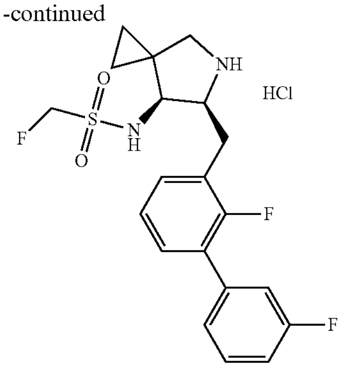

A solution of tert-butyl (6S,7S)-6-((2,3'-difluoro-[1,1'-biphenyl]-3-yl)methyl)-7-((fluoromethyl)sulfonamido)-5-azaspiro[2.4]heptane-5-carboxylate (100 mg, 39.17 μmol, 1 eq) in HCl/dioxane (4 M, 5 mL) was stirred at 20° C. for 0.5 hr. The reaction was concentrated under reduced pressure to afford the title compound (60 mg, 62.2% yield) as a yellow solid.

LCMS-(method M)(ESI+): m/z 411.1 (M+H)~, RT: 0.650 min.

Step 4: N-((6S,7S)-6-((2,3'-difluoro-[1,1'-biphenyl]-3-yl)methyl)-5-(2-hydroxy-2-methylpropanoyl)-5-azaspiro[2.4]heptan-7-yl)-1-fluoromethanesulfonamide

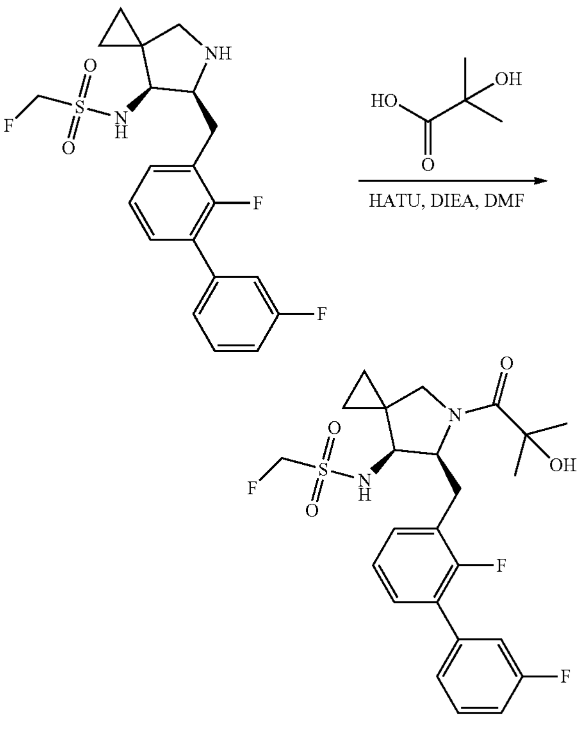

To a solution of N-((6S,7S)-6-((2,3'-difluoro-[1,1'-biphenyl]-3-yl)methyl)-5-azaspiro[2.4]heptan-7-yl)-1-fluoromethanesulfonamide hydrochloride (60 mg, 292 mol, 1 eq) in N, N-dimethylformamide (2 mL) were added 2-hydroxy-2-methyl-propanoic acid (61 mg, 585 μmol, 2 eq), o-(7-azabenzotriazol-1-yl)-N,N,N'N'-tetramethyluronium hexafluorophosphate (167 mg, 439 μmol, 1.5 eq) and N,N-diisopropylethylamine (255 μL, 1.46 mmol, 5 eq) at 20° C. The mixture was stirred at 25° C. for 2 hrs. The reaction mixture was concentrated under reduced pressure to afford a residue. The residue was purified by prep-TLC ($SiO_2$, petroleum ether/ethyl acetate=1/2) to afford the title compound (17.5 mg, 12.1% yield) as white solid.

Example 69 (Compound 180). 1-fluoro-N-((6S,7S)-6-((2-fluoro-[1,1'-biphenyl]-3-yl)methyl)-5-(1-methoxycyclopropane-1-carbonyl)-5-azaspiro[2.4]heptan-7-yl)methanesulfonamide

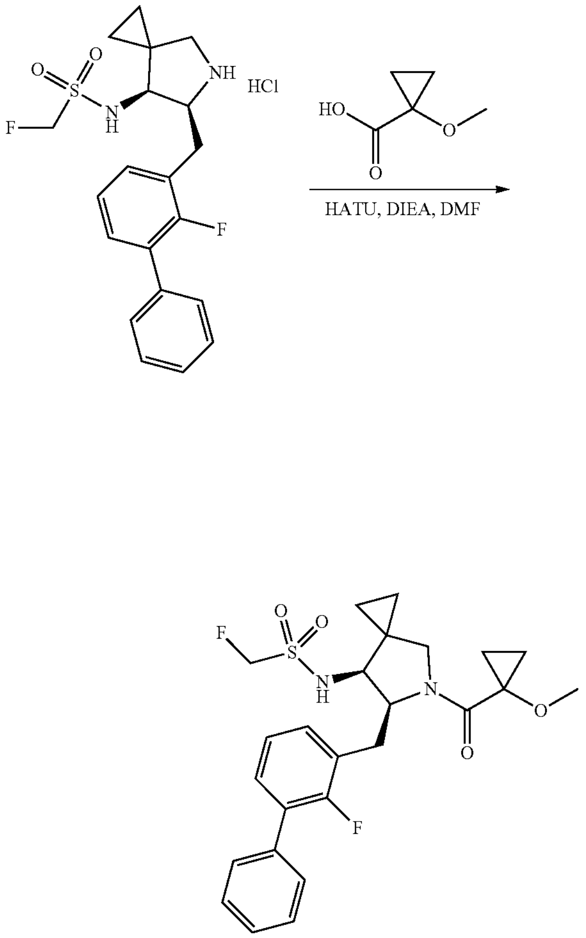

To a mixture of 1-fluoro-N-((6S,7S)-6-((2-fluoro-[1,1'-biphenyl]-3-yl)methyl)-5-azaspiro[2.4]heptan-7-yl)methanesulfonamide, intermediate 20 (100 mg, 229 μmol, 1 eq) in DMF (1 mL) were added 1-methoxycyclopropanecarboxylic acid (36 mg, 306 μmol, 1.2 eq), HATU (97 mg, 255 μmol, 1 eq) and DIEA (133 μL, 764 μmol, 3 eq). The mixture was stirred at 25° C. for 12 hrs. The reaction mixture was poured into water (10 mL) and extracted with ethyl acetate (3×5 mL). The organic layer was washed with brine (10 mL), dried over anhydrous $Na_2SO_4$, filtered and concentrated under reduced pressure. The residue was purified by Prep-HPLC (column: Waters Xbridge BEH C18 100*30 mm*10 um; mobile phase: [water ($NH_4HCO_3$)-ACN]; B %: 35%-65%, 8 min.) to afford the title compound (20 mg, 16% yield) as white solid.

Example 70 (Compound 181). N-((6S,7S)-5-(1-cyanocyclobutane-1-carbonyl)-6-((2-fluoro-[1,1'-biphenyl]-3-yl)methyl)-5-azaspiro[2.4]heptan-7-yl)-1-fluoromethanesulfonamide

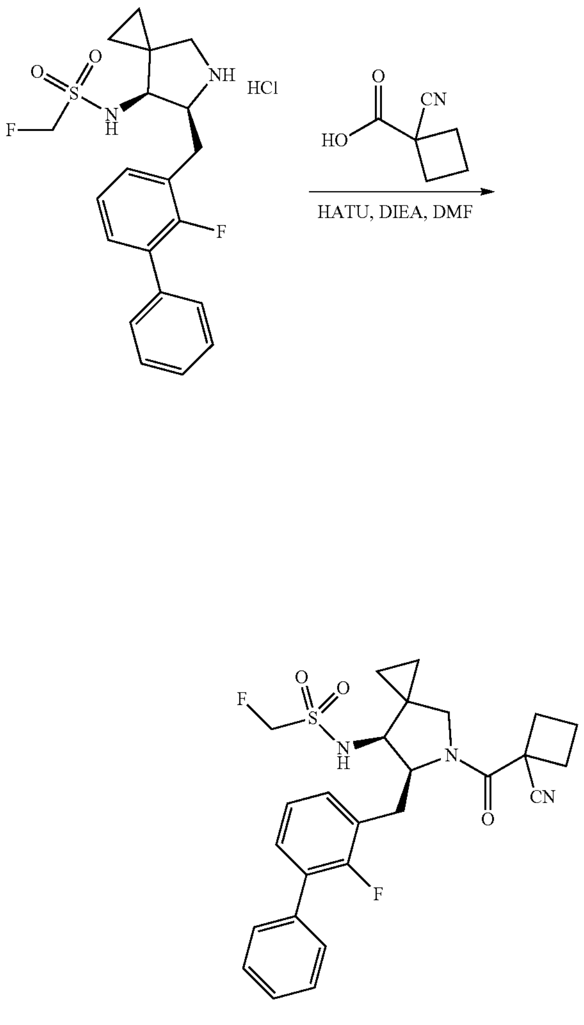

To a mixture of 1-fluoro-N-((6S,7S)-6-((2-fluoro-[1,1'-biphenyl]-3-yl)methyl)-5-azaspiro[2.4]heptan-7-yl)methanesulfonamide, intermediate 20 (100 mg, 229 μmol, 1 eq) in DMF (1 mL) were added 1-cyanocyclobutane-1-carboxylic acid (35 mg, 29 μmol, 1.2 eq), HATU (139 mg, 365 μmol, 1.5 eq) and DIEA (127 μL, 731 μmol, 3 eq). The mixture was stirred at 25° C. for 12 hrs. The reaction mixture was poured into water (10 mL), then extracted with ethyl acetate (3×5 mL). The combined organic layers were washed with brine (10 mL), dried over anhydrous sodium sulfate, filtered and concentrated under reduced pressure. The residue was purified by Prep-HPLC (column: Waters Xbridge Prep OBD C18 150*40 mm*10 um; mobile phase: [water (NH4HCO3)-ACN]; B %: 40%-70%, 8 min.) to afford the title compound (20 mg, 16.1% yield) as a white solid.

Example 71 (Compound 185)

Step 1: tert-butyl (6S,7S)-7-(ethylsulfonamido)-6-((2,3',5'-trifluoro-[1,1'-biphenyl]-3-yl)methyl)-5-azaspiro[2.4]heptane-5-carboxylate

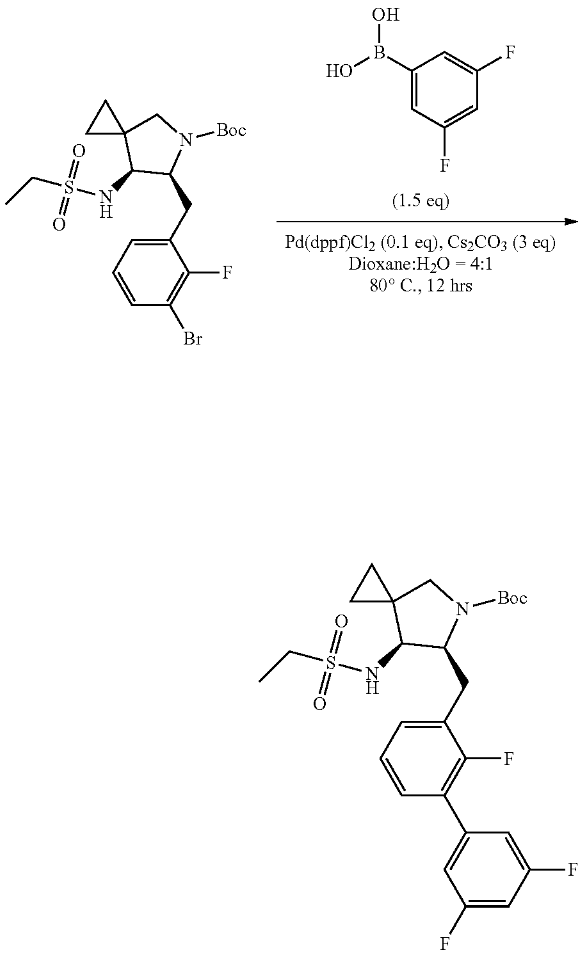

To a mixture of tert-butyl (6S,7S)-6-(3-bromo-2-fluorobenzyl)-7-(ethylsulfonamido)-5-azaspiro[2.4]heptane-5-carboxylate, intermediate 10 (197 mg, 401 μmol, 1 eq) and (3,5-difluorophenyl)boronic acid (95 mg, 601 μmol, 1.5 eq) in dioxane (1.6 mL) and water (0.4 mL) was added cesium carbonate (392 mg, 1.20 mmol, 3 eq) and $Pd(dppf)Cl_2$ (29 mg, 40 μmol, 0.1 eq) in one portion at 80° C. under nitrogen. The mixture was stirred for 12 hours. The mixture was poured into ice-water (w/w=1/1, 50 mL) and stirred for 3 min. The aqueous phase was extracted with ethyl acetate (3×25 mL). The combined organic phase was dried with anhydrous sodium sulfate, filtered and concentrated under reduced pressure to afford crude product. The mixture was purified by prep-TLC (Silica, petroleum ether:ethyl acetate=3:1) to afford the title compound (160 mg, 75.3% yield) as colourless oil. LCMS(method M)(ESI+): m/z 425.0 $(M-100+H)^+$, RT: 0.870 min.

Step 2: N-((6S,7S)-6-((2,3',5-trifluoro-[1,1'-biphenyl]-3-yl)methyl)-5-azaspiro[2.4]heptan-7-yl)ethanesulfonamide hydrochloride

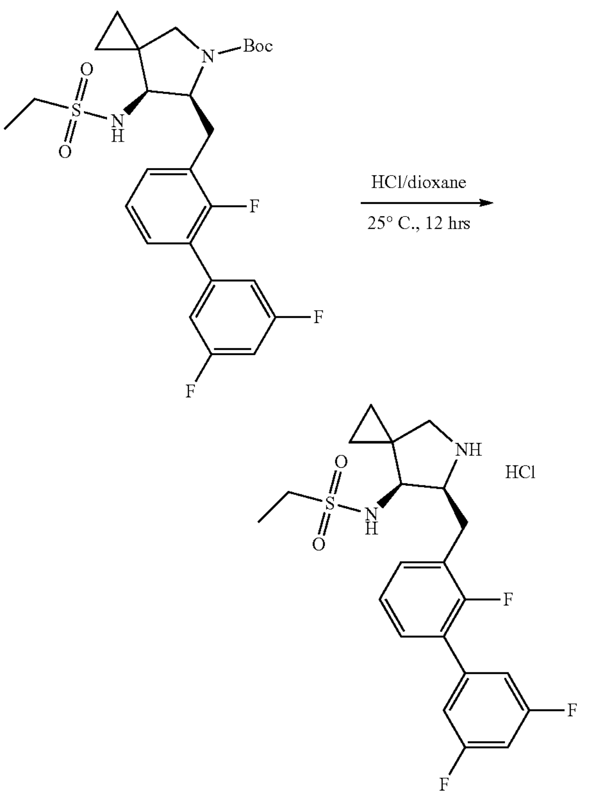

A solution of tert-butyl (6S,7S)-7-(ethylsulfonamido)-6-((2,3',5'-trifluoro-[1,1'-biphenyl]-3-yl)methyl)-5-azaspiro[2.4]heptane-5-carboxylate (160 mg, 305 μmol, 1 eq) in HCl/dioxane (2 mL) was degassed and purged with nitrogen for 3 times, and then the mixture was stirred at 25° C. for 12 hours under nitrogen atmosphere. The mixture was concentrated under reduced pressure to afford the title compound (129 mg, 97.7% yield) as a white solid. LCMS(method M)(ESI+): m/z 425.0 $(M+H)^+$, RT: 0.666 min.

Step 3: N-((6S,7S)-5-((R)-oxetane-2-carbonyl)-6-((2,3',5'-trifluoro-[, 1'-biphenyl]-3-yl)methyl)-5-azaspiro[2.4]heptan-7-yl)ethanesulfonamide

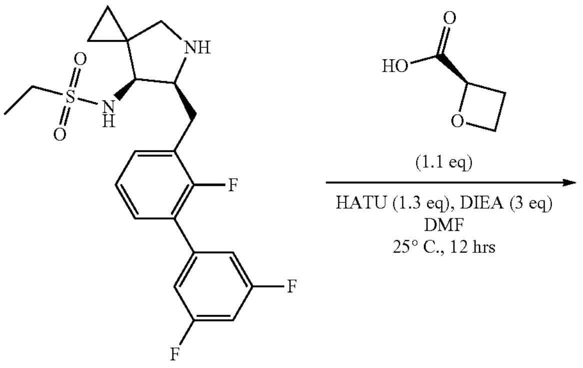

-continued

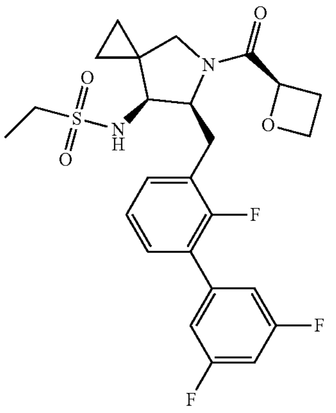

To a mixture of N-((6S,7S)-6-((2,3',5'-trifluoro-[1,1'-biphenyl]-3-yl)methyl)-5-azaspiro[2.4]heptan-7-yl)ethanesulfonamide hydrochloride (70 mg, 165 μmol, 1 eq) and (2R)-oxetane-2-carboxylic acid (19 mg, 181 μmol, 1.1 eq) in N,N-dimethylformamide (0.7 mL) was added N,N-Diisopropylethylamine (86 uL, 495 μmol, 3 eq) and HATU (82 mg, 214 μmol, 1.3 eq) in one portion at 25° C. under nitrogen. The mixture was stirred at 25° C. for 12 hours. The reaction mixture was filtered and purified by prep-HPLC (column: Waters Xbridge BEH C18 100*30 mm*10 um; mobile phase: [water(ammonium bicarbonate)-acetonitrile]; B %: 35%-65%, 8 min) to afford the title compound (22.5 mg, 26.8% yield) as a white solid.

Example 192

Step 1: tert-butyl (6S,7S)-7-amino-6-((2,3',5'-trifluoro-[1,1'-biphenyl]-3-yl)methyl)-5-azaspiro[2.4]heptane-5-carboxylate

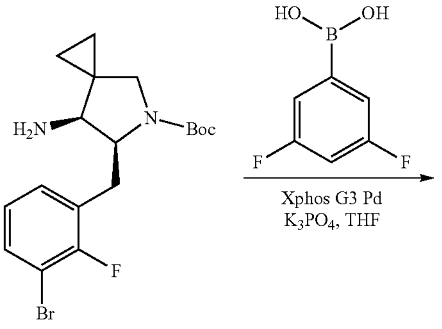

-continued

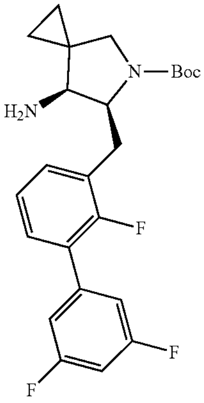

To a solution of tert-butyl (6S,7S)-7-amino-6-(3-bromo-2-fluorobenzyl)-5-azaspiro[2.4]heptane-5-carboxylate, intermediate 8 (0.1 g, 250 μmol, 1 eq) in THF (2 mL) were added (3,5-difluorophenyl)boronic acid (99 mg, 626 μmol, 2.5 eq), Xphos G3 Pd (11 mg, 12 μmol, 0.05 eq) and $K_3PO_4$ (106 mg, 501 μmol, 2 eq) at 20° C. The resulting reaction mixture was stirred at 80° C. under $N_2$ atmosphere for 8 hrs. Another four batches were set up as above and all of five reaction mixtures were combined and diluted with 30 mL of ethyl acetate, then washed with 10 mL of water. The organic layer was dried over $Na_2SO_4$, filtered and concentrated under reduced pressure. The residue was purified by prep-HPLC (column: Waters Xbridge BEH C18 100*30 mm*10 um; mobile phase: [water ($NH_4HCO_3$)-ACN]; B %: 40%-70%, 8 min) to afford the title compound (190 mg, 33.3% yield) as a light yellow solid. $^1$H NMR (400 MHz, methanol-$d_4$) δ 0.40-0.70 (m, 3H), 0.88-1.02 (m, 1H), 1.03-1.31 (m, 9H), 2.80-2.97 (m, 1H), 3.04 (br d, 1H), 3.17 (d, 1H), 3.52 (br d, 1H), 3.56-3.71 (m, 1H), 4.23-4.42 (m, 1H), 6.97 (br t, 1H), 7.09-7.25 (m, 3H), 7.26-7.31 (m, 1H), 7.40 (br t, 1H).

-continued

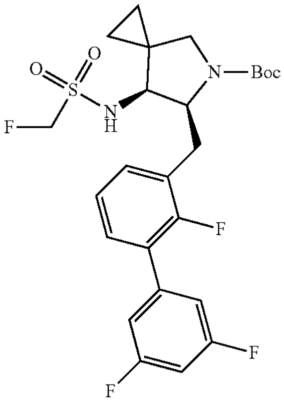

To a solution of tert-butyl (6S,7S)-7-amino-6-((2,3',5'-trifluoro-[1,1'-biphenyl]-3-yl)methyl)-5-azaspiro[2.4]heptane-5-carboxylate (90 mg, 208 μmol, 1 eq) in acetonitrile (1 mL) were added pyridine (84 μL, 1.04 mmol, 5 eq) and fluoromethanesulfonyl chloride (55 mg, 416 μmol, 2 eq) dropwise at 0° C. The reaction mixture was stirred at 20° C. for 12 hrs. The mixture was filtered over celite and the filtrate was concentrated under reduced pressure. The residue was purified by prep-TLC (petroleum ether/ethyl acetate=2/1) to afford the title compound (90 mg, 73.6% yield) as a white solid. $^1$H NMR (400 MHz, methanol-$d_4$) δ 0.59-0.73 (m, 3H), 1.00-1.24 (m, 10H), 2.78-2.92 (m, 1H), 3.08 (br d, 1H), 3.22 (d, 1H), 3.60-3.74 (m, 1H), 4.20 (br d, 1H), 4.32-4.50 (m, 1H), 5.22 (s, 1H), 5.34 (s, 1H), 6.98 (br t, 1H), 7.16 (br d, 2H), 7.20-7.33 (m, 2H), 7.42 (br t, 1H).

Step 2: tert-butyl (6S,7S)-7-((fluoromethyl)sulfonamide)-6-((2,3',5'-trifluoro-[1,1'-biphenyl]-3-yl)methyl)-5-azaspiro[2.4]heptane-5-carboxylate

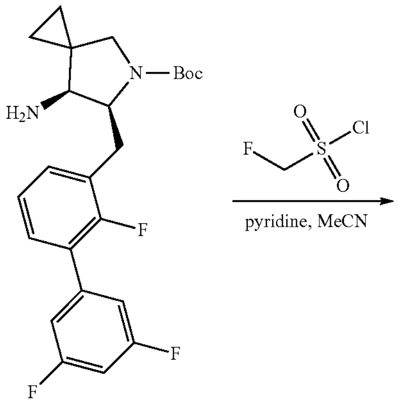

Step 3: 1-fluoro-N-((6S,7S)-6-((2,3',5'-trifluoro-[1,1'-biphenyl]-3-yl)methyl)-5-azaspiro[2.4]heptan-7-yl)methanesulfonamide hydrochloride

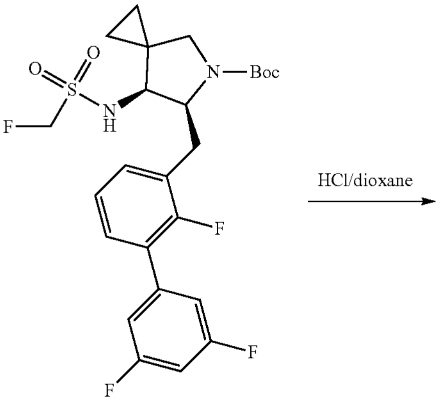

-continued

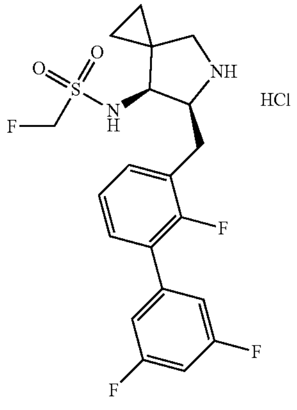

A solution of tert-butyl (6S,7S)-7-((fluoromethyl)sulfonamido)-6-((2,3',5'-trifluoro-[1,1'-biphenyl]-3-yl)methyl)-5-azaspiro[2.4]heptane-5-carboxylate (110 mg, 208 μmol, 1 eq) in HCl, dioxane (4 M, 5 mL) was stirred at 20° C. for 12 hrs. The reaction mixture was concentrated under reduced pressure to afford the title compound (80 mg, 80.8% yield) as a white solid. $^1H$ NMR (400 MHz, methanol-$d_4$) δ 0.82-0.93 (m, 2H), 1.02-1.08 (m, 1H), 1.11-1.19 (m, 1H), 3.05-3.22 (m, 2H), 3.46 (br d, 1H), 3.59 (d, 1H), 3.90 (d, 1H), 4.18-4.28 (m, 1H), 5.21-5.45 (m, 2H), 7.02 (tt, 1H), 7.22 (dd, 2H), 7.29-7.36 (m, 1H), 7.51 (t, 2H).

Step 4: 1-fluoro-N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide

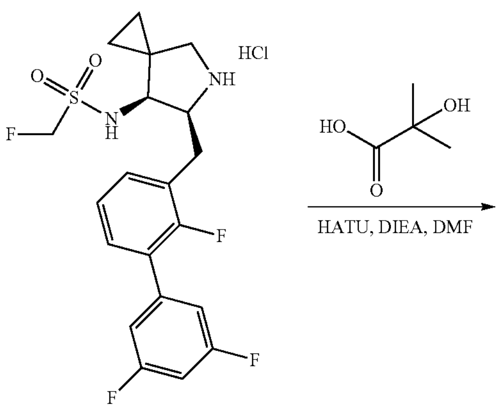

-continued

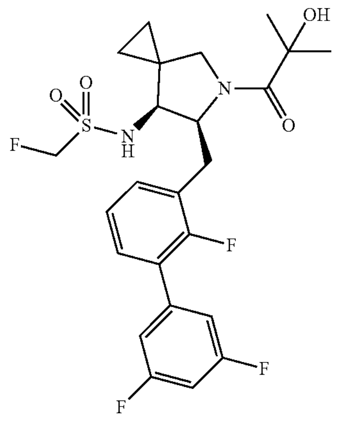

To a solution of 1-fluoro-N-((6S,7S)-6-((2,3',5'-trifluoro-[1,1'-biphenyl]-3-yl)methyl)-5-azaspiro[2.4]heptan-7-yl)methanesulfonamide hydrochloride (80 mg, 186 μmol, 1 eq) in N, N-dimethylformamide (1 mL) was added 2-hydroxy-2-methyl-propanoic acid (29 mg, 280 μmol, 1.5 eq), HATU (85 mg, 224 μmol, 1.2 eq) and N,N-diisopropylethylamine (98 μL, 560 μmol, 3 eq) at 0° C. The reaction mixture was stirred at 20° C. for 3 hrs. The crude product was purified by prep-HPLC (neutral condition: Column: Waters Xbridge Prep OBD C18 150*40 mm*10 um; mobile phase: [water (10 mM $NH_4HCO_3$)-ACN]; B %: 35%-65%, 8 min) to afford the title compound (54 mg, 56.2% yield) as a white solid.

Example 72 (Compounds 193 and 194)

Step 1: N,N-bis[(2,4-dimethoxyphenyl)methyl]-ethanesulfonamide

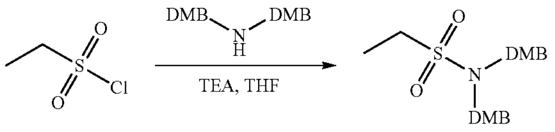

To a solution of 1-(2,4-dimethoxyphenyl)-N-[(2,4-dimethoxyphenyl)methyl]methanamine (4.33 g, 13.7 mmol, 1 eq) in tetrahydrofuran (20 mL) was added TEA (5.70 mL, 41 mmol, 3 eq) at 0° C. The mixture was stirred for 30 mins, then ethanesulfonyl chloride (2.00 g, 13.7 mmol, 1 eq) was added dropwise to the mixture at 0° C. The reaction mixture was stirred at 20° C. for 3 hrs. Four additional batches were set up as detailed above and all five reaction mixtures were combined. The mixture was treated with water (500 mL) and extracted with ethyl acetate (3×500 mL). The combined organic layers were dried over $Na_2SO_4$, filtered and the filtrate was concentrated under reduced pressure. The residue was purified by column chromatography on silica gel (eluted with petroleum ether/ethyl acetate=50/1 to 5/1) to afford the title compound (24 g, 78.2% yield) as a yellow solid. $^1H$ NMR (400 MHz, chloroform-d) δ 1.24 (t, 3H), 2.87 (q, 2H), 3.79 (d, 12H), 4.39 (s, 4H), 6.42-6.48 (m, 4H), 7.23 (d, 2H).

Step 2: N,N-bis[(2,4-dimethoxyphenyl)methyl]-1-fluoro-ethanesulfonamide

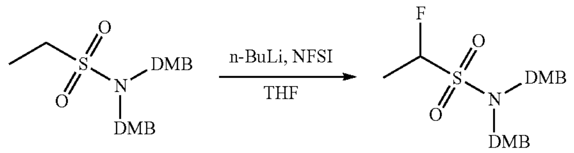

To a solution of N,N-bis[(2,4-dimethoxyphenyl)methyl]-ethanesulfonamide (3 g, 7.33 mmol, 1 eq) in tetrahydrofuran (187 mL) was added n-BuLi (2.5 M in hexane, 8.32 mL, 2.84 eq) at −65° C. under $N_2$. The reaction mixture was stirred at −65° C. for 1 hr and a solution of NFSI (5.78 g, 18.3 mmol, 2.5 eq) in tetrahydrofuran (39 mL) was added dropwise. The mixture was stirred at −65° C. for an additional 2 hrs. Three additional batches were set up as detailed above and all four reaction mixtures were combined. The reaction was quenched with saturated $NH_4Cl$ solution (800 mL) and extracted with ethyl acetate (3-500 mL). The combined organic layers were dried over $Na_2SO_4$, filtered and concentrated under reduced pressure. The residue was purified by column chromatography on silica gel (eluted with petroleum ether/ethyl acetate=50/1 to 511) to afford the title compound (4.7 g, 33.8% yield) as a yellow oil. $^1$H NMR (400 MHz, chloroform-d) δ 1.61-1.72 (m, 3H), 3.75-3.87 (m, 12H), 4.32-4.41 (m, 2H), 4.52 (br d, 2H), 4.87-5.05 (m, 1H), 6.41-6.51 (m, 4H), 7.22 (d, 2H).

Step 3: 1-fluoroethanesulfonamide

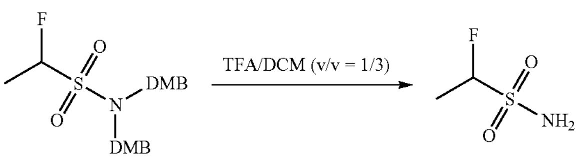

To a solution of N,N-bis[(2,4-dimethoxyphenyl)methyl]-1-fluoro-ethanesulfonamide (0.9 g, 2.11 mmol, 1 eq) in dichloromethane (45 mL) was added TFA (18 mL, 243 mmol, 115 eq) at 0° C. The reaction mixture was stirred at 25° C. for 2 hrs under $N_2$. Four additional batches were set up as detailed above and all five reaction mixtures were combined, and concentrated to afford the crude product as a pink solid. The residue was triturated with isopropyl ether (20 mL) and filtered. The filtrate was concentrated to afford the title compound (1.4 g, 94.2% yield) as a pink oil. $^1$H NMR (400 MHz, methanol-$d_4$) δ 1.61-1.71 (m, 3H), 4.85 (s, 2H), 5.22-5.41 (m, 1H).

Step 4: tert-butyl 6-(3-bromo-2-fluorobenzyl)-7-((1-fluoroethyl)sulfonamido)-5-azaspiro[2.4]heptane-5-carboxylate_cis racemic

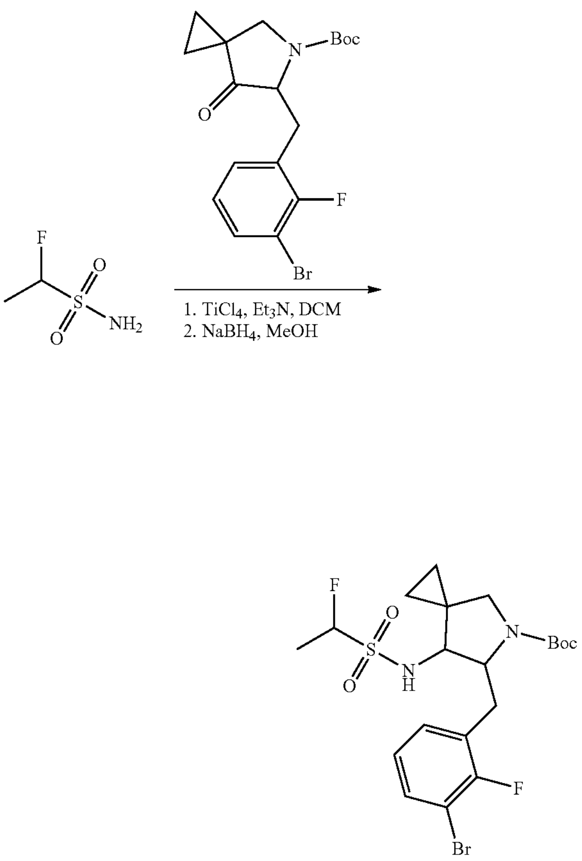

A solution of tert-butyl 6-(3-bromo-2-fluorobenzyl)-7-oxo-5-azaspiro[2.4]heptane-5-carboxylate (0.4 g, 1.00 mmol, 1 eq), 1-fluoroethanesulfonamide (192 mg, 1.51 mmol, 1.5 eq) and TEA (419 μL, 3.01 mmol, 3 eq) in dichloromethane (4 mL) was cooled to 0° C. $TiCl_4$ (190 mg, 1.00 mmol, 1 eq) was diluted with 2 mL of dichloromethane and added to the above mixture dropwise at 0° C. The mixture was stirred at 25° C. for 12 hrs, then concentrated under reduced pressure. The residue was dissolved in methanol (4 mL) and cooled to 0° C., then $NaBH_4$ (38 mg, 1.00 mmol, 1 eq) was added to the mixture. The resulting reaction mixture was stirred at 25° C. for 1 hr. The mixture was quenched with water (10 mL) and extracted with ethyl acetate (3×20 mL). The combined organic layers were concentrated under reduced pressure. The residue was purified by prep-TLC (petroleum ether/ethyl acetate=2/1) to afford the title compound (0.26 g, 25% yield) as a yellow oil. $^1$H NMR (400 MHz, methanol-$d_4$) δ 0.58-0.73 (m, 3H), 0.98-1.05 (m, 1H), 1.07 (s, 9H), 1.65-1.78 (m, 3H), 2.65-2.91 (m, 1H), 2.96-3.21 (m, 2H), 3.59-3.73 (m, 1H), 4.17 (br d, 1H), 4.30-4.39 (m, 1H), 5.34-5.62 (m, 1H), 6.92-7.08 (m, 1H), 7.16 (q, 1H), 7.37-7.55 (m, 1H).

Step 5: tert-butyl 6-((2-fluoro-[1,1'-biphenyl]-3-yl) methyl)-7-((1J-fluoroethyl)sulfonamido)-5-azaspiro [2.4]heptane-5-carboxylate_cis racemic

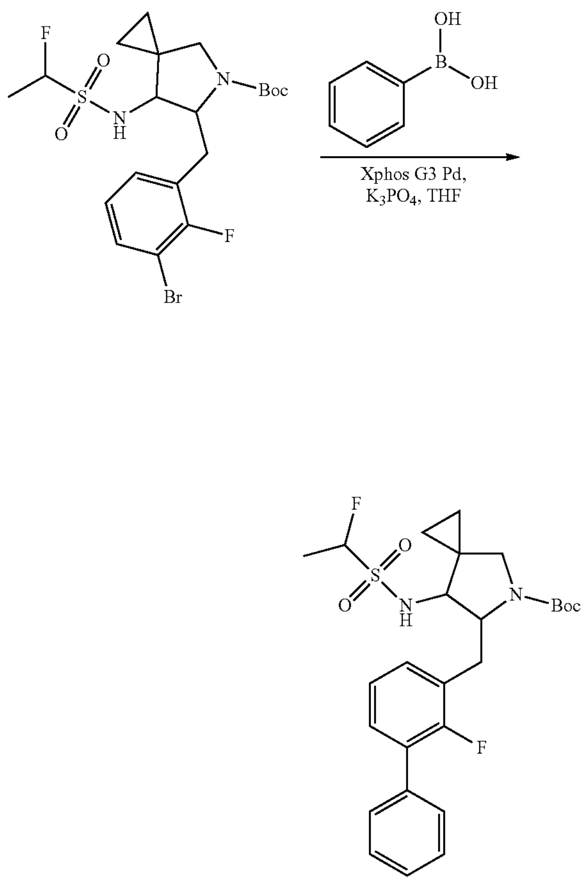

To a solution of tert-butyl 6-(3-bromo-2-fluorobenzyl)-7-((1-fluoroethyl)sulfonamido)-5-azaspiro[2.4]heptane-5-carboxylate_cis racemic (0.2 g, 393 μmol, 1 eq) in tetrahydrofuran (2 mL) were added phenylboronic acid (57 mg, 471 μmol, 1.2 eq), Xphos G3 Pd (17 mg, 20 μmol, 0.05 eq) and $K_3PO_4$ (167 mg, 785 μmol, 2 eq) at 20° C. The mixture was stirred at 80° C. for 12 hrs under $N_2$. The mixture was cooled to 20° C. and poured into water (5 mL), then extracted with ethyl acetate (3×10 mL). The combined organic layers were dried over $Na_2SO_4$, filtered and the filtrate was concentrated under reduced pressure. The residue was purified by prep-TLC (petroleum ether/ethyl acetate=4/1) to afford the title compound (190 mg, 86% yield) as a yellow solid. $^1H$ NMR (400 MHz, chloroform-d) δ 0.10-0.46 (m, 1H), 0.53-0.79 (m, 3H), 1.28-1.49 (m, 9H), 1.66 (br d, 3H), 2.81-3.26 (m, 3H), 3.50-3.75 (m, 1H), 4.24 (br dd, 1H), 4.34-4.59 (m, 2H), 4.62-5.35 (m, 1H), 7.11-7.26 (m, 2H), 7.32 (br s, 1H), 7.36-7.42 (m, 1H), 7.45 (t, 2H), 7.49-7.55 (m, 2H).

Step 6: 1-fluoro-N-(6-((2-fluoro-[1,1'-biphenyl]-3-yl)methyl)-5-azaspiro[2.4]heptan-7-yl)ethane-1-sulfonamide_cis racemic hydrochloride

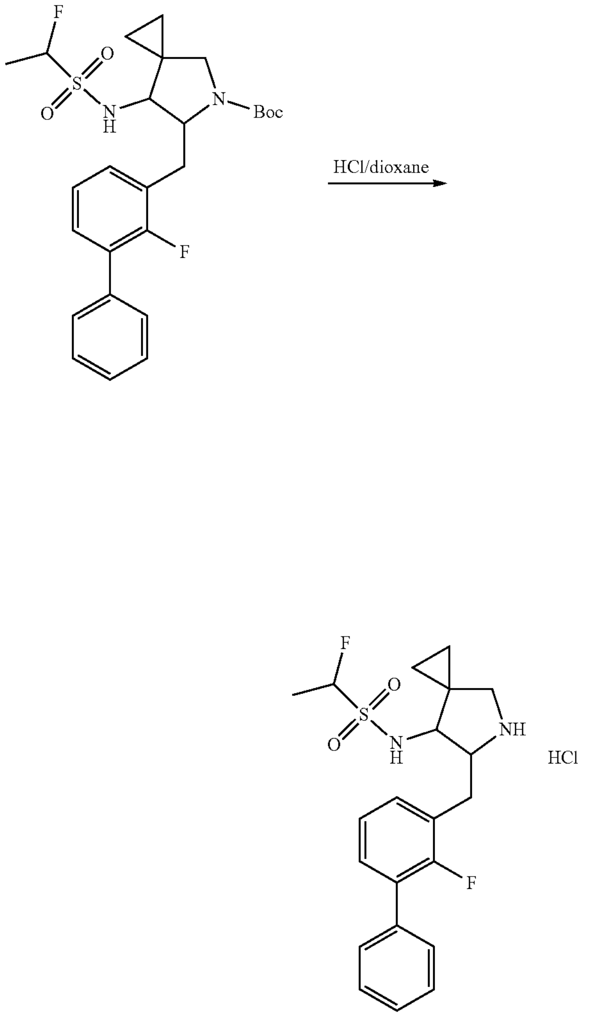

To a solution of tert-butyl 6-((2-fluoro-[1,1'-biphenyl]-3-yl)methyl)-7-((1-fluoroethyl)sulfonamido)-5-azaspiro[2.4] heptane-5-carboxylate_cis racemic (0.1 g, 197 μmol, 1 eq) in dioxane (0.5 mL) was added HCl/dioxane (4 M, 1.67 mL, 34 eq) at 0° C. The mixture was stirred at 25° C. for 12 hrs. The reaction mixture was concentrated under reduced pressure to afford the title compound (0.18 g, 92.6% yield) as a white solid. $^1H$ NMR (400 MHz, methanol-$d_4$) δ 0.79-0.92 (m, 2H), 0.98-1.06 (m, 1H), 1.13-1.23 (m, 1H), 1.65-1.77 (m, 3H), 3.07 (dd, 1H), 3.15 (ddd, 1H), 3.42-3.52 (m, 1H), 3.59 (t, 1H), 3.88-3.96 (m, 1H), 4.18-4.27 (m, 1H), 5.42-5.63 (m, 1H), 7.27-7.33 (m, 1H), 7.36-7.42 (m, 1H), 7.46 (t, 4H), 7.56 (br d, 2H).

Step 7: (S)-1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethane-1-sulfonamide (Isomer 1) (R)-1-fluoro-N-((6S,7S)-6-((2-fluoro-[1,1'-biphenyl]-3-yl)methyl)-5-((R)-oxetane-2-carbonyl)-5-azaspiro[2.4]heptan-7-yl)ethane-)-sulfonamide (Isomer 2)

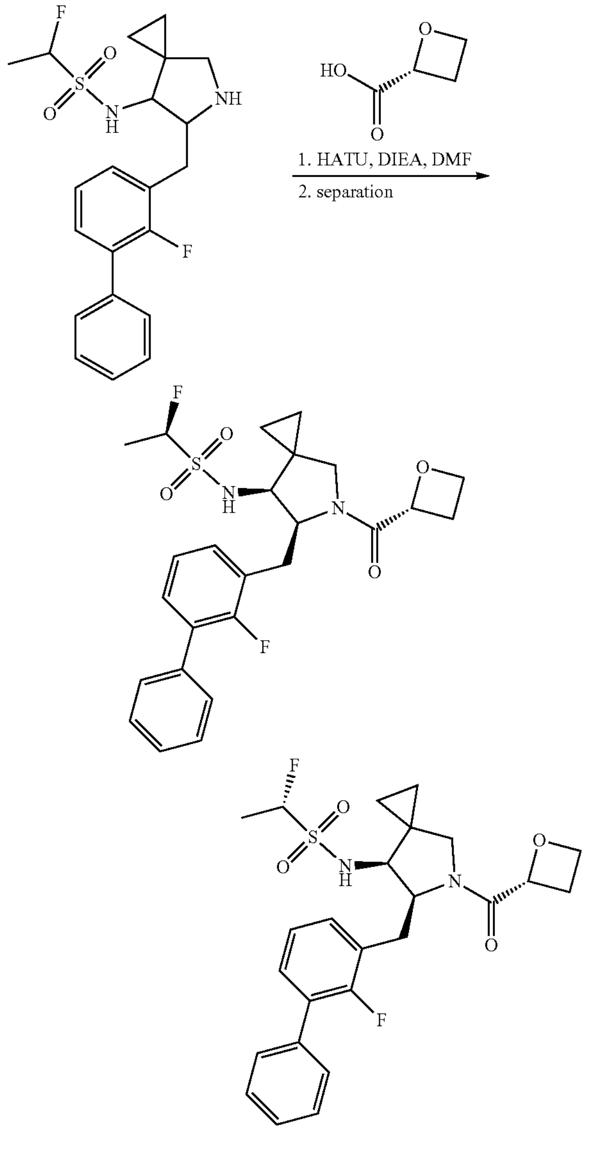

To a solution of 1-fluoro-N-(6-((2-fluoro-[1,1'-biphenyl]-3-yl)methyl)-5-azaspiro[2.4]heptan-7-yl)ethane-1-sulfonamide_cis racemic hydrochloride (90 mg, 203 μmol, 1 eq) and (2R)-oxetane-2-carboxylic acid (31 mg, 305 μmol, 1.5 eq) in N, N-dimethylformamide (1 mL) were added N,N-diisopropylethylamine (106 μL, 610 μmol, 3 eq) and HATU (93 mg, 244 μmol, 1.2 eq) at 0° C. The mixture was stirred at 25° C. for 12 hrs, during which time the mixture maintained as a yellow solution. Another batch was set up as described above and combined for purification. The reaction was poured into water (10 mL) and extracted with ethyl acetate (3-10 mL). The combined organic layers were washed with brine (3-10 mL), dried over $Na_2SO_4$, filtered and the filtrate was concentrated under reduced pressure. The crude product was purified by prep-TLC (ethyl acetate/methanol=5/1) first, and then separated by SFC separation (Column: DAICEL CHIRALPAK AD (250 mm*30 mm, 10 um); mobile phase: [Neu-ETOH]; B %: 33%-33%, 7 min) to afford isomer 1 (23.4 mg, 33.4% yield) with the shorter retention time and isomer 2 (30.1 mg, 43% yield) with the longer retention time both as white solids.

Example 73 (Compound 195)

Step 1: tert-butyl (6S 7S)-7-amino-6-((2,3',5'-trifluoro-[1,1'-biphenyl]-3-yl)methyl)-5-azaspiro[2.4]heptane-5-carboxylate

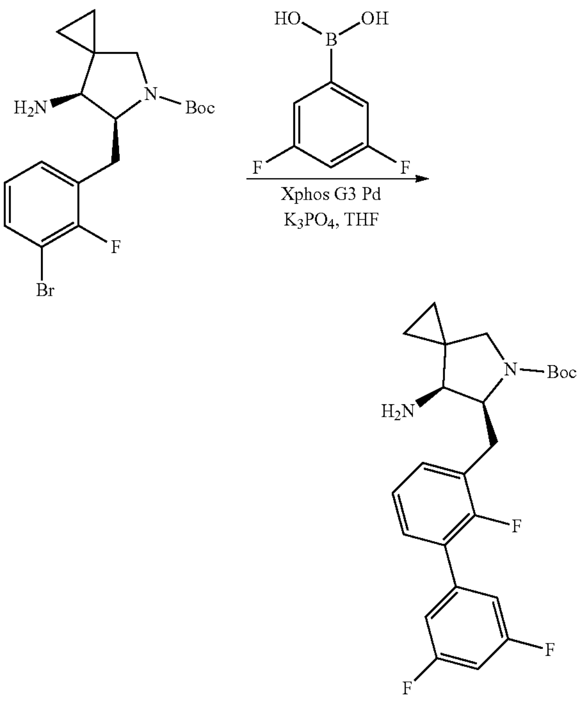

To a solution of tert-butyl (6S,7S)-7-amino-6-(3-bromo-2-fluorobenzyl)-5-azaspiro[2.4]heptane-5-carboxylate, intermediate 8 (0.1 g, 250 μmol, 1 eq) in THF (2 mL) were added (3,5-difluorophenyl)boronic acid (99 mg, 626 μmol, 2.5 eq), Xphos G3 Pd (11 mg, 12.5 μmol, 0.05 eq) and $K_3PO_4$ (106. mg, 501 μmol, 2 eq) at 20° C. The resulting reaction mixture was stirred at 80° C. for 8 hrs under $N_2$ atmosphere, during which time the mixture maintained as a yellow solution. Another four batches were set up as detailed above. All five reaction mixtures were combined and treated with water (10 mL), then extracted with ethyl acetate (3×5 mL). The organic layer was dried over $Na_2SO_4$, filtered and concentrated under reduced pressure. The residue was purified by prep-HPLC (neutral condition: column: Waters Xbridge BEH C18 100*30 mm*10 um; mobile phase: [water($NH_4HCO_3$)-ACN]; B %: 40%-70%, 8 min) to afford the title compound (190 mg, 33.3% yield) as a light yellow solid. $^1H$ NMR (400 MHz, methanol-$d_4$) δ 0.40-0.70 (m, 3H), 0.88-1.02 (m, 1H), 1.03-1.31 (m, 9H), 2.80-2.97 (m, 1H), 3.04 (br d, 1H), 3.17 (d, 1H), 3.52 (br d, 1H), 3.56-3.71 (m, 1H), 4.23-4.42 (m, 1H), 6.97 (br t, 1H), 7.09-7.25 (m, 3H), 7.26-7.31 (m, 1H), 7.40 (br t, 1H).

Step 2: tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate

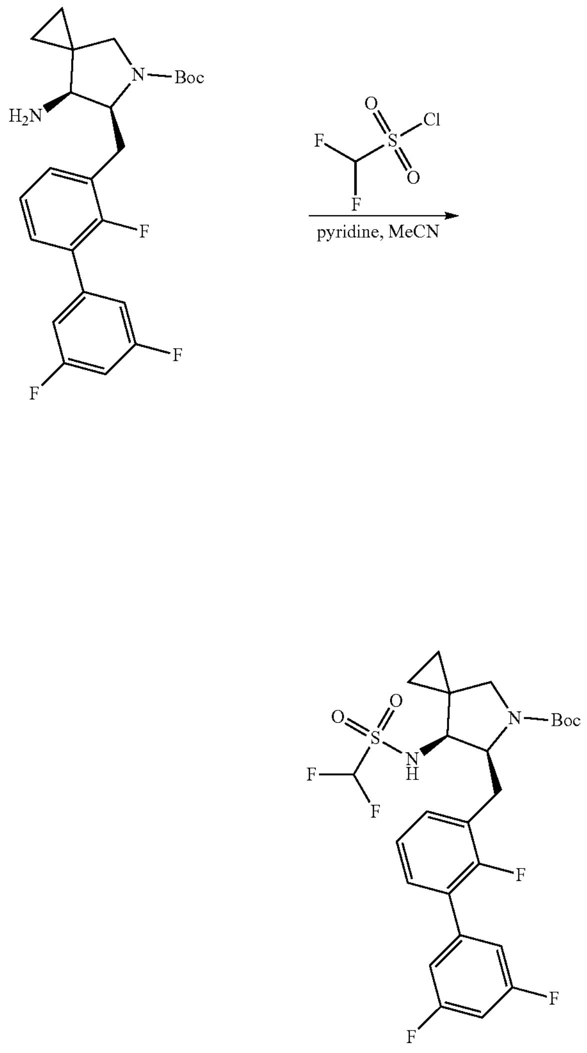

To a solution of tert-butyl (6S,7S)-7-amino-6-((2,3',5'-trifluoro-[1,1'-biphenyl]-3-yl)methyl)-5-azaspiro[2.4]heptane-5-carboxylate (95 mg, 220 μmol, 1 eq) in $CH_3CN$(3 mL) were added pyridine (89 μL, 1.10 mmol, 5 eq) and difluoromethanesulfonyl chloride (66 mg, 439 μmol, 2 eq) dropwise at 0° C. The reaction mixture was warmed to 20° C. and stirred at 20° C. for 12 hrs. The reaction was quenched by addition of 10 mL of water and extracted with ethyl acetate (2×20 mL). The organic layer was dried over $Na_2SO_4$, filtered and concentrated under reduced pressure. The residue was purified by prep-TLC (petroleum ether/ethyl acetate=1/1) to afford the title compound (90 mg, 56.5% yield) as a yellow solid. LCMS(method N)(ESI+): m/z 545.1 (M−H), RT: 0.964 min.

Step 3: 1,1-di fluoro-N-((6S,7S)-6-((2,3',5'-trifluoro-[1,1'-biphenyl]-3-yl)methyl)-5-azaspiro[2.4]heptan-7-yl)methanesulfonamide hydrochloride

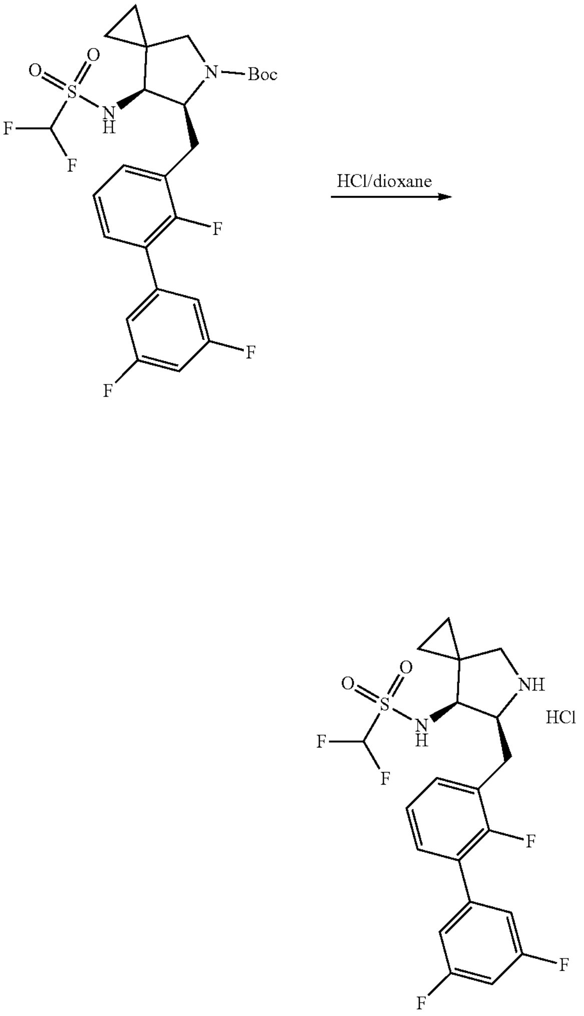

To a solution of tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate (90 mg, 124 μmol, 1 eq) in dioxane (1 mL) was added HCl/dioxane (4 M, 1.80 mL, 58 eq) at 20° C. The reaction mixture was stirred at 20° C. for 12 hrs and concentrated under reduced pressure to afford the title compound (70 mg, 66.8% yield) as a yellow solid. LCMS(method N)(ESI+): m/z 447.1 $(M+H)^+$, RT: 0.873 min.

Step 4: 1,1-difluoro-N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)methanesulfonamide

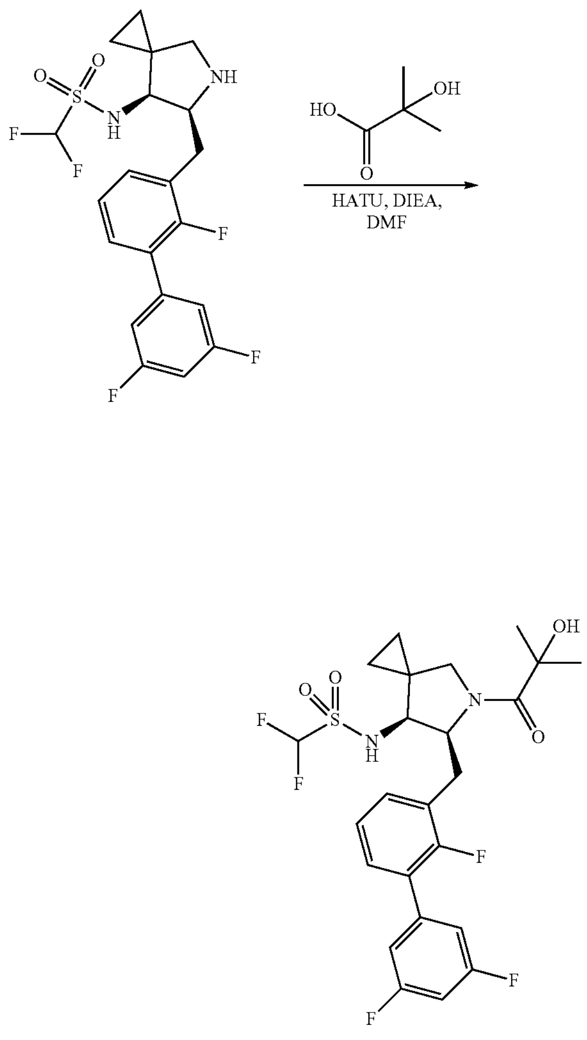

To a solution of 1,1-difluoro-N-((6S,7S)-6-((2,3',5'-trifluoro-[1,1'-biphenyl]-3-yl)methyl)-5-azaspiro[2.4]heptan-7-yl)methanesulfonamide hydrochloride (70 mg, 83 μmol) in DMF (2 mL) were added 2-hydroxy-2-methyl-propanoic acid (32 mg, 307 μmol, 4 eq), DIEA (67 L, 383 μmol, 5 eq) and HATU (73 mg, 192 μmol, 2.5 eq) at 0° C. The resulting reaction mixture was stirred at 25° C. for 12 hrs. The reaction mixture was purified by prep-HPLC (neutral condition: Column: Waters Xbridge Prep OBD C18 150*40 mm*10 μm; mobile phase: [water (10 mM $NH_4HCO_3$)-ACN]; B %: 35%-65%, 8 min) to afford the title compound (15.5 mg, 37.5% yield) as a white solid.

Example 74 (Compound 206). (6S,7S)-6-((2-fluoro-[1,1'-biphenyl]-3-yl)methyl)-7-((fluoromethyl)sulfonamido)-N—((R)-2-fluoropropyl)-5-azaspiro[2.4]heptane-5-carboxamide

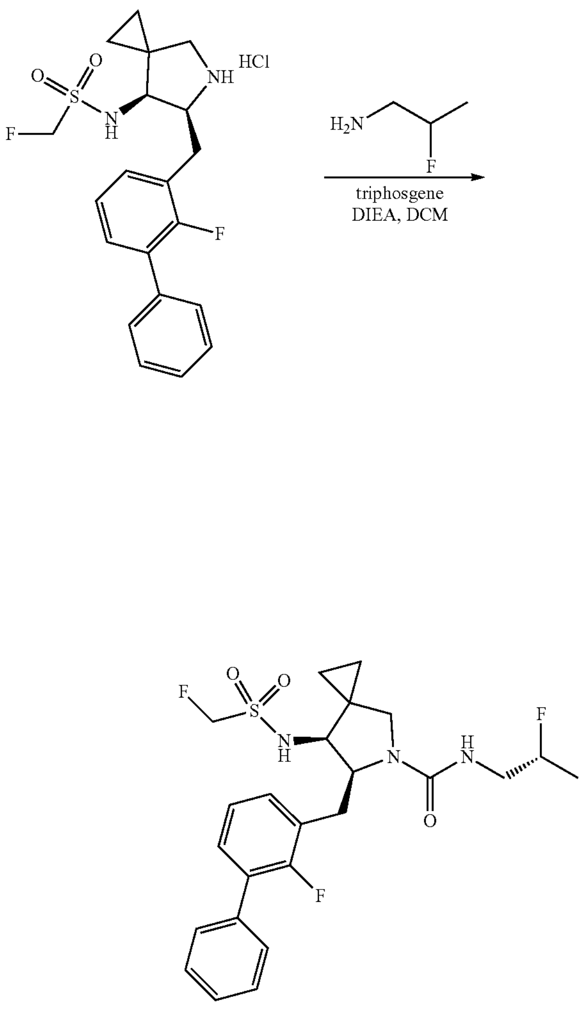

To a solution of 1-fluoro-N-((6S,7S)-6-((2-fluoro-[1,1'-biphenyl]-3-yl)methyl)-5-azaspiro[2.4]heptan-7-yl)methanesulfonamide, intermediate 20 (90 mg, 229 μmol, 1 eq) in dichloromethane (6 mL) was added triethylamine (96 μL, 688 μmol, 3 eq) and a solution of triphosgene (34 mg, 115 μmol, 0.5 eq) in dichloromethane (3 mL) was added dropwise into the reaction mixture. The mixture was stirred at 25° C. for 2 hours. 2-fluoropropan-1-amine (104 mg, 917 μmol, 4 eq, HCl salt) in dichloromethane (9 mL) and triethylamine (96 μL, 688 μmol, 3 eq) was added into the residue above. The reaction mixture was stirred at 25° C. for 12 hours and concentrated to afford a residue. The residue was purified by prep-HPLC (base conditions: column: waters Xbridge BEH C18 100×30 mm×10 μm; mobile phase: [water ($NH_3 \cdot H_2O$+ammonium bicarbonate)-acetonitrile]; B %: 25%-60%, 8 min). The filtration was lyophilized and purified again by SFC separation (column: DAICEL CHIRALPAK AD (250 mm×30 mm, 10 μm); mobile phase: [0.1% $NH_3 \cdot H_2O$ ethanol]; B %: 38%-38%, 7 min) to afford the title compound (13 mg, 11.4% yield) as a white solid.

Example 75 (Compound 220)

Step 1: tert-butyl (6S,7S)-7-((difluoromethyl)sulfonamido)-6-((2,3',5,5'-tetrafluoro-[1,1'-biphenyl]-3-yl)methyl)-5-azaspiro[2.4]heptane-5-carboxylate

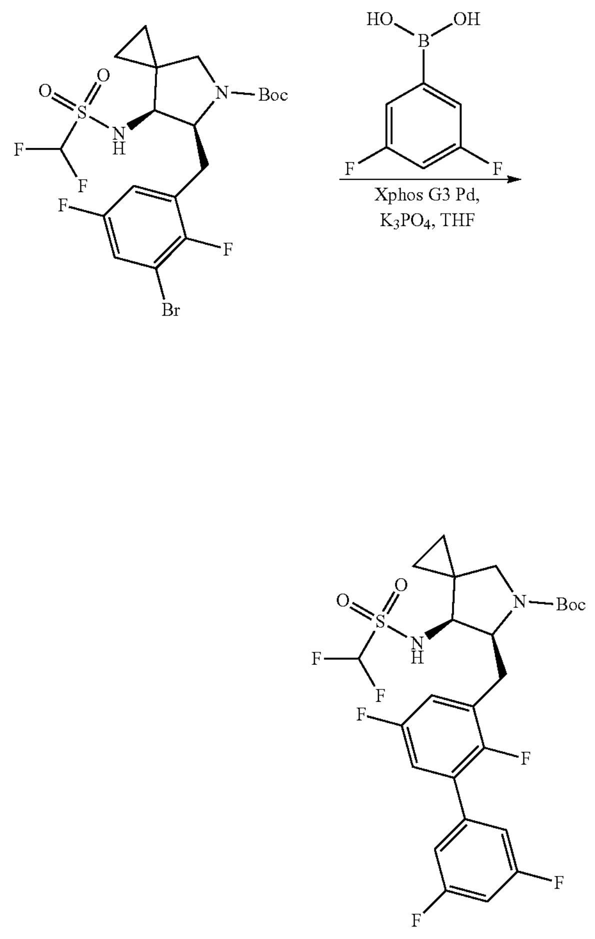

To a solution of tert-butyl (6S,7S)-6-(3-bromo-2,5-difluorobenzyl)-7-((difluoromethyl)sulfonamido)-5-azaspiro[2.4]heptane-5-carboxylate, intermediate 17 (240 mg, 452 μmol, 1 eq) in tetrahydrofuran (4 mL) were added (3,5-difluorophenyl)boronic acid (143 mg, 903 μmol, 2 eq), Xphos G3 Pd (19 mg, 23 μmol, 0.05 eq) and $K_3PO_4$ (192 mg, 903 μmol, 2 eq) at 20° C. The reaction mixture was stirred at 80° C. for 12 hrs under $N_2$ atmosphere. The mixture was filtered over celite and the filtrate was concentrated under reduced pressure. The residue was purified by prep-TLC (petroleum ether/ethyl acetate=3/1) to afford the title compound (200 mg, 70.6% yield) as a white solid. $^1H$ NMR (400 MHz, methanol-$d_4$) δ 0.67 (br s, 3H), 1.02-1.18 (m, 7H), 1.22-1.29 (m, 3H), 2.83 (br t, 1H), 3.06 (br d, 1H), 3.23 (br d, 1H), 3.58-3.76 (m, 1H), 4.22 (br d, 1H), 4.29-4.48 (m, 1H), 6.48-6.84 (m, 1H), 6.92-7.27 (m, 5H).

Step 2: 1,1-difluoro-N-((6S,7S)-6-((2,3',5,5'-tetrafluoro-[1,1'-biphenyl]-3-yl)methyl)-5-azaspiro[2.4]heptan-7-yl)methanesulfonamide hydrochloride (Intermediate 23)

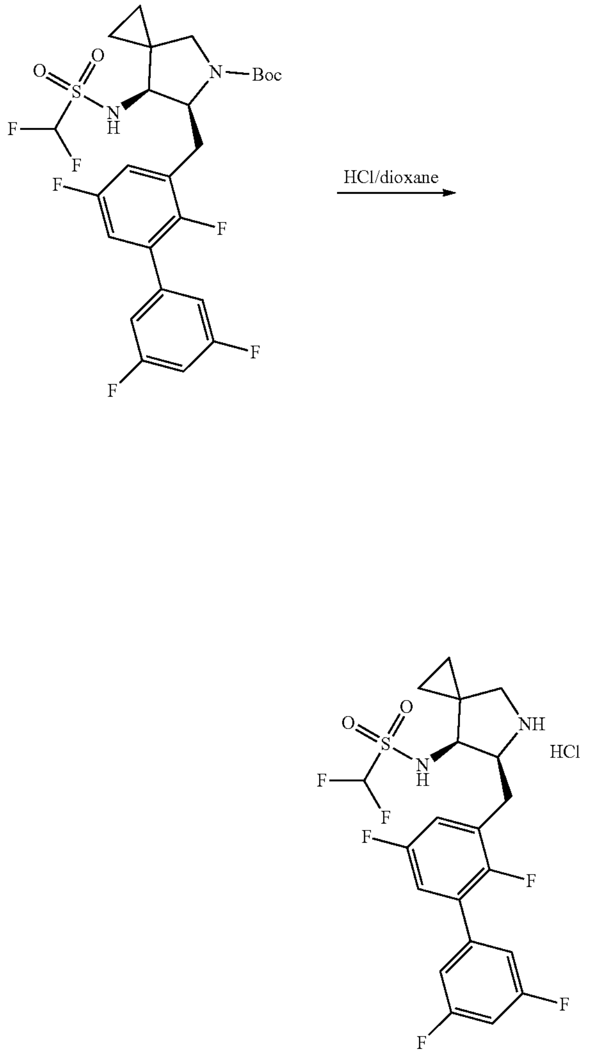

A solution of tert-butyl (6S,7S)-7-((difluoromethyl)sulfonamido)-6-((2,3',5,5'-tetrafluoro-[1,1'-biphenyl]-3-yl)methyl)-5-azaspiro[2.4]heptane-5-carboxylate (180 mg, 319 μmol, 1 eq) in HCl/dioxane (4 M, 10.5 mL, 132 eq) was stirred at 20° C. for 12 hrs. The mixture was concentrated under reduced pressure to afford the title compound (150 mg, 91.2% yield) as a white solid.

Step 3: 1,1-difluoro-N-((6S,7S)-5-((R)-oxetane-2-carbonyl)-6-((2,3',5,5'-tetrafluoro-[1,1'-biphenyl]-3-yl)methyl)-5-azaspiro[2.4]heptan-7-yl)methanesulfonamide

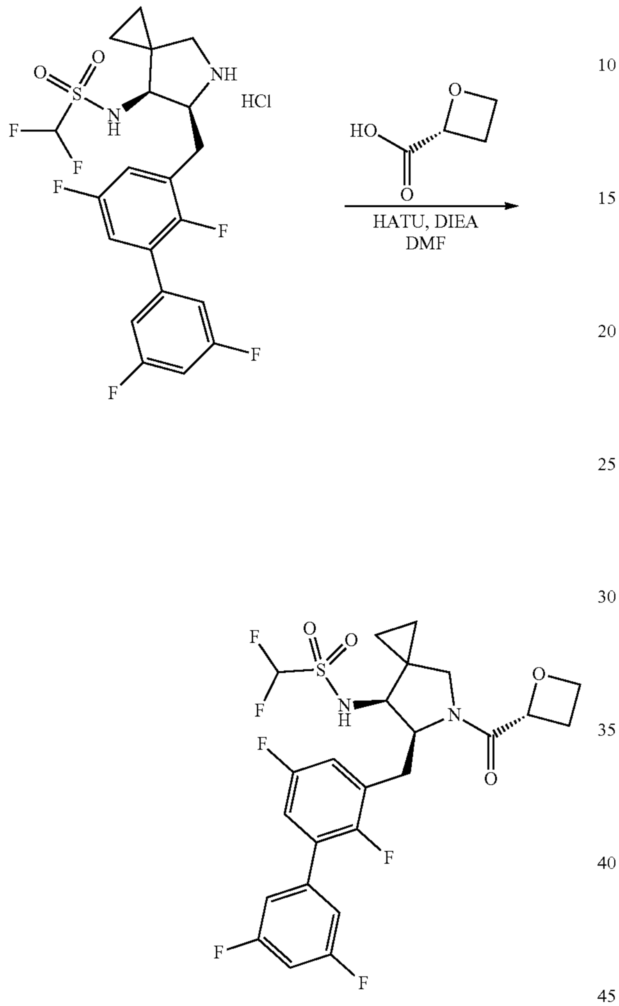

To a solution of 1,1-difluoro-N-((6S,7S)-6-((2,3',5,5'-tetrafluoro-[1,1'-biphenyl]-3-yl)methyl)-5-azaspiro[2.4]heptan-7-yl)methanesulfonamide hydrochloride, intermediate 23 (50 mg, 108 μmol, 1 eq) in DMF (0.5 mL) were added (2R)-oxetane-2-carboxylic acid (17 mg, 161 μmol, 1.5 eq), N,N-diisopropylethylamine (56 μL, 322.98 μmol, 3 eq) and HATU (49 mg, 129 μmol, 1.2 eq) at 0° C. The reaction mixture was stirred at 20° C. for 3 hrs. The crude product was purified by prep-HPLC (neutral condition: column: Waters Xbridge Prep OBD C18 150*40 mm*10 μm; mobile phase: [water ($NH_4HCO_3$)-ACN]; B %: 30%-60%, 8 min) to afford the title compound (44.2 mg, 74.9% yield) as a white solid.

Example 76 (Compound 221). 1,1-difluoro-N-((6S,7S)-5-((S)-3-fluoro-2-hydroxypropanoyl)-6-((2,3',5,5'-tetrafluoro-[1,1'-biphenyl]-3-yl)methyl)-5-azaspiro[2.4]heptan-7-yl)methanesulfonamide

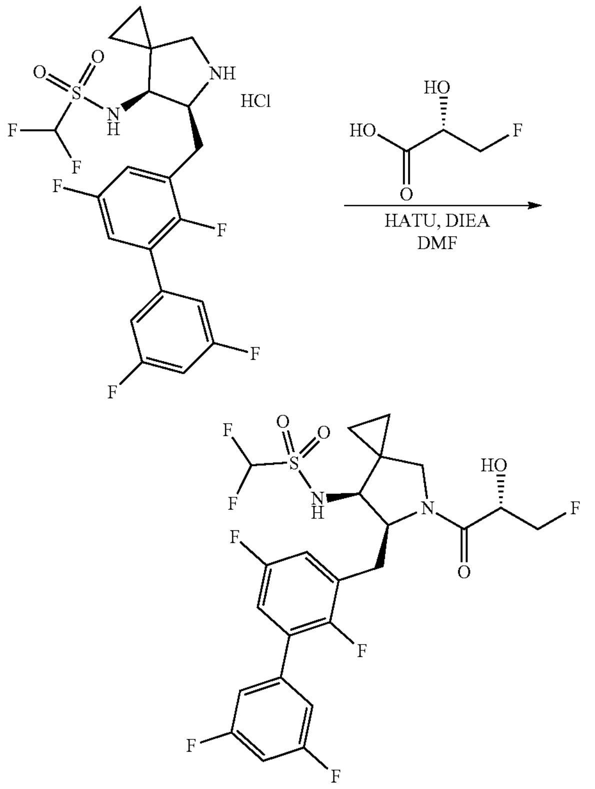

To a solution of 1,1-difluoro-N-((6S,7S)-6-((2,3',5,5'-tetrafluoro-[1,1'-biphenyl]-3-yl)methyl)-5-azaspiro[2.4]heptan-7-yl)methanesulfonamide hydrochloride, intermediate 23 (55 mg, 118 μmol, 1 eq) in DMF (1 mL) were added (2S)-3-fluoro-2-hydroxy-propanoic acid (19 mg, 178 μmol, 1.5 eq), N,N-diisopropylethylamine (62 μL, 355 μmol, 3 eq) and HATU (54 mg, 142 μmol, 1.2 eq) at 0° C. The reaction mixture was stirred at 20° C. for 3 hrs. The mixture was purified by prep-HPLC (neutral condition: column: Waters Xbridge Prep OBD C18 150*40 mm*10 μm; mobile phase: [water($NH_4HCO_3$)-ACN]; B %: 35%-65%, 8 min) to afford the title compound (20.5 mg, 31.2% yield) as a white solid.

Example 77 (Compounds 225 and 226)

Step 1: benzyl 2-cyano-2-diazo-acetate

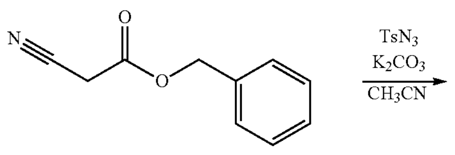

-continued

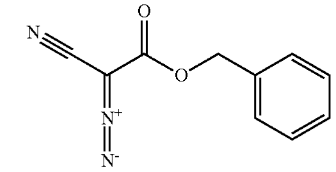

To a solution of benzyl 2-cyanoacetate (25 g, 143 mmol, 1 eq) in $CH_3CN$(400 mL) was added 4-methylbenzenesulfonyl azide (56.3 g, 214 mmol, 75% purity, 1.5 eq) and $K_2C_{03}$ (39.5 g, 285 mmol, 2 eq) at 25° C. The mixture was stirred at 25° C. for 12 hr. To the mixture was added saturated aqueous $NH_4Cl$ solution (500 mL) slowly at 0° C. The mixture was stirred at 0° C. for 10 min. The aqueous phase was extracted with ethyl acetate (5×100 mL). The combined organic phase was washed with brine (2×100 mL), dried over anhydrous $Na_2SO_4$, filtered and the filtrate was concentrated in vacuum to afford a residue. The residue was purified by column chromatography on silica gel (eluted with petroleum ether/ethyl acetate=50/1 to 5/1) to afford the title compound (2 g, 7.0% yield) as white solid. H NMR (400 MHz, chloroform-d) δ 5.30 (s, 2H), 7.36-7.40 (m, 5H).

Step 2: benzyl 2-(2-bromoethoxy)-2-cyanoacetate

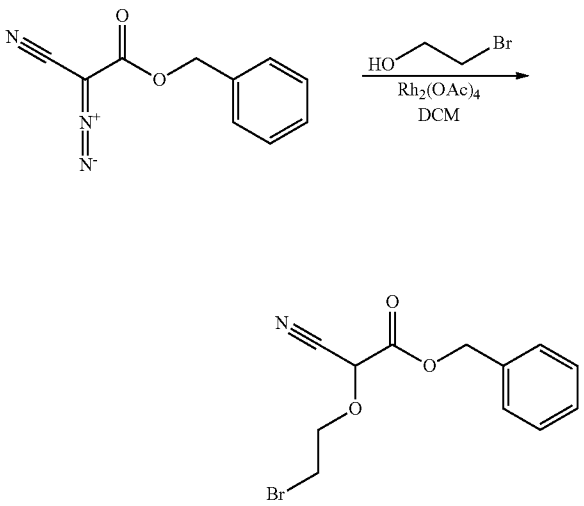

To a solution of benzyl 2-cyano-2-diazo-acetate (2 g, 9.94 mmol, 1 eq) in $CH_2Cl_2$ (20 mL) was added 2-bromoethanol (1.37 g, 10.94 mmol, 776 μL, 1.1 eq) and diacetoxyrhodium (220 mg, 497 μmol, 0.05 eq) at 25° C. The mixture was stirred at 25° C. for 12 hr. The mixture was poured into water (20 mL) and the two phases were separated. The aqueous phase was extracted with ethyl acetate (2×20 mL). The combined organic layers were dried over anhydrous $Na_2SO_4$, filtered and the filtrate was concentrated under reduced pressure to afford a residue. The residue was purified by column chromatography on silica gel (eluted with petroleum ether/ethyl acetate=100/1 to 1/1) to afford the title compound (2 g, 67.5% yield) as a white solid. 1H NMR (400 MHz, chloroform-d) δ 3.53 (t, 2H), 3.97-4.05 (m, 1H), 4.06-4.14 (m, 1H), 4.99 (s, 1H), 5.20-5.38 (m, 2H), 7.40 (s, 5H).

Step 3: benzyl 2-cyanooxetane-2-carboxylate

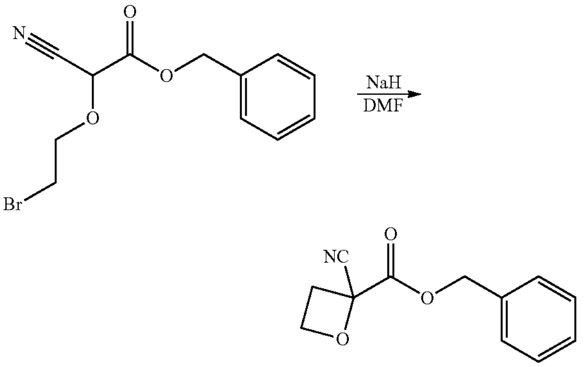

N,N-dimethylformamide (140 mL) was added to NaH (322 mg, 8.05 mmol, 60% purity, 1.2 eq) at 0° C. Then a solution of benzyl 2-(2-bromoethoxy)-2-cyanoacetate (2 g, 6.71 mmol, 1 eq) in N,N-dimethylformamide (60 mL) was added dropwise at 0° C. over 8 min. The reaction mixture was stirred at 0° C. for 1 h. The mixture was added to a saturated aqueous $NH_4Cl$ solution (200 mL) slowly at 0° C. The mixture was stirred at 0° C. for 10 min. The aqueous phase was extracted with ethyl acetate (3×100 mL). The combined organic phase was washed with brine (2×50 mL), dried over anhydrous $Na_2SO_4$, filtered and the filtrate was concentrated under vacuum to afford a residue. The residue was purified by prep-HPLC (neutral condition: column: waters X-bridge BEH C18 100*30 mm*10 μm. mobile phase: [water($NH_4HCO_3$)—$CH_3CN$]; B %: 40%-60%, 8 min) to afford the title compound (0.2 g, 13.7% yield) as a white solid. $^1H$ NMR (400 MHz, chloroform-d) δ ppm 3.04-3.14 (m, 1H), 3.15-3.26 (m, 1H), 4.70 (dt, 1H), 4.75-4.84 (m, 1H), 5.26 (s, 2H), 7.26-7.36 (m, 5H).

Step 4: lithium 2-cyanooxetane-2-carboxylate

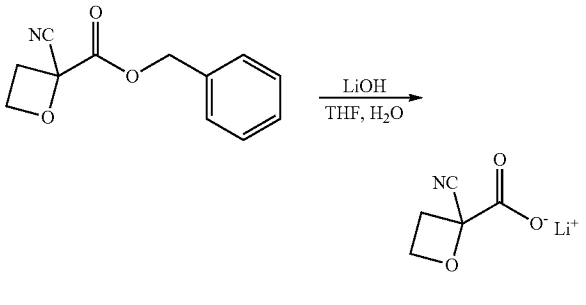

To a solution of benzyl 2-cyanooxetane-2-carboxylate (0.230 g, 1.06 mmol, 1 eq) in tetrahydrofuran (18 mL) and $H_2O$ (6 mL) was added $LiOH·H_2O$ (44 mg, 1.06 mmol, 1 eq) at 25° C. The mixture was stirred at 25° C. for 0.5 hr. The mixture was lyophilized to afford the title compound (0.230 g, crude) as a white solid, which was used directly to next step without further purification. $^1H$ NMR (400 MHz, dimethyl sulfoxide-$d_6$) S 2.84 (dd, 1H), 2.90 (dd, 1H), 4.33-4.42 (m, 1H), 4.49-4.58 (m, 1H).

Step 5: tert-butyl (6S,7S)-7-amino-6-((2-fluoro-[1,1'-biphenyl]-3-yl)methyl)-5-azaspiro[2.4]heptane-5-carboxylate

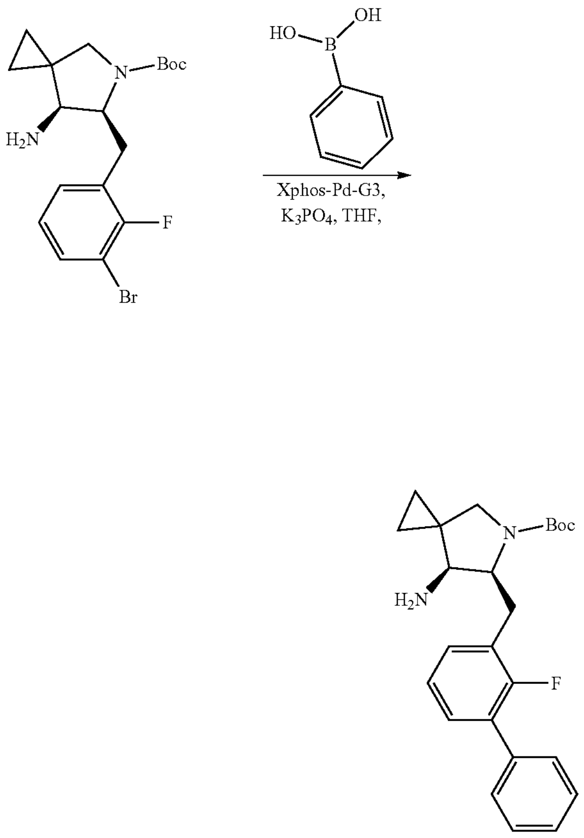

Step 6: tert-butyl (6S,7S)-6-((2-fluoro-[1,1'-biphenyl]-3-yl)methyl)-7-((fluoromethyl)sulfonamido)-5-azaspiro[2.4]heptane-5-carboxylate

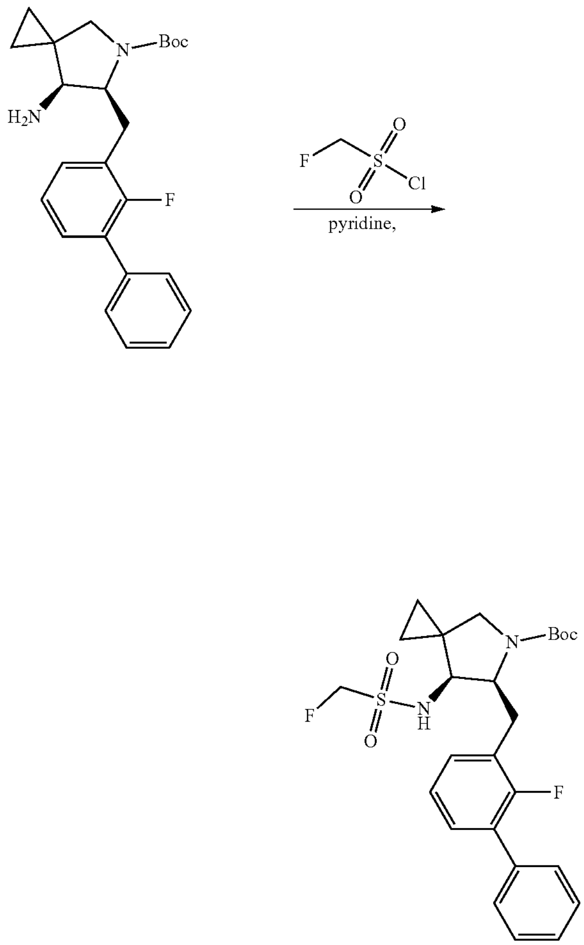

To a solution of tert-butyl (6S,7S)-7-amino-6-(3-bromo-2-fluorobenzyl)-5-azaspiro[2.4]heptane-5-carboxylate, intermediate 8 (5 g, 12.52 mmol, 1 eq) and phenylboronic acid (3.05 g, 25.04 mmol, 2 eq) in tetrahydrofuran (50 mL) was added Xphos-Pd-G3 (530 mg, 626 μmol, 0.05 eq) and $K_3PO_4$ (7.97 g, 37.6 mmol, 3 eq) under $N_2$ atmosphere at 25° C. The mixture was stirred at 80° C. for 12 hr. The mixture was poured into water (50 mL) and the two phases were separated. The aqueous phase was extracted with ethyl acetate (3-30 mL). The combined organic layers were dried over anhydrous $Na_2SO_4$, filtered and the filtrate was concentrated under reduced pressure to afford a residue. The residue was purified by column chromatography on silica gel (eluted with petroleum ether/ethyl acetate=100/1 to 0/1) to afford the title compound (4 g, 10.1 mmol, 80.6% yield) as a white solid. $^1$H NMR (400 MHz, chloroform-d) δ ppm 0.18-0.86 (m, 4H) 1.21 (br s, 5H) 1.40 (br s, 4H) 2.85 (br s, 1H) 3.01-3.26 (m, 2H) 3.35-3.75 (m, 2H) 4.29 (br s, 1H) 7.09-7.22 (m, 2H) 7.29 (br s, 1H) 7.33-7.39 (m, 1H) 7.40-7.48 (m, 2H) 7.48-7.56 (m, 2H).

To a solution of tert-butyl (6S,7S)-7-amino-6-((2-fluoro-[1,1'-biphenyl]-3-yl)methyl)-5-azaspiro[2.4]heptane-5-carboxylate (0.8 g, 2.02 mmol, 1 eq) in pyridine (10 mL) was added fluoromethanesulfonyl chloride (535 mg, 4.04 mmol, 2 eq) at 25° C. The mixture was stirred at 90° C. for 12 hrs. The reaction mixture was concentrated under reduced pressure to afford a residue. The residue was purified by column chromatography on silica gel (eluted with petroleum ether/ethyl acetate=100/1 to 1/1) to afford the title compound (0.8 g, 80.5% yield) as a white solid. $^1$H NMR (400 MHz, chloroform-d) δ ppm 0.21-0.77 (m, 4H), 1.38 (br s, 9H), 2.82-3.28 (m, 3H), 3.47-3.74 (m, 1H), 4.24 (br dd, 1H), 4.33-4.67 (m, 2H), 4.79-5.12 (m, 1H), 7.11-7.27 (m, 2H), 7.33 (br t, 1H), 7.36-7.41 (m, 1H), 7.42-7.48 (m, 2H), 7.49-7.54 (m, 2H).

Step 7: 1-fluoro-N-((6S,7S)-6-((2-fluoro-[1,1'-biphenyl]-3-yl)methyl)-5-azaspiro[2.4]heptan-7-yl)methanesulfonamide hydrochloride

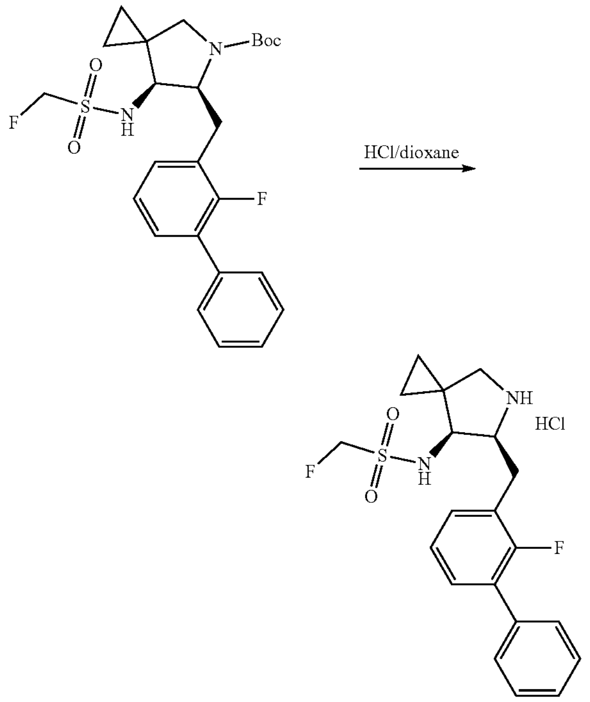

To a solution of tert-butyl (6S,7S)-6-((2-fluoro-[1,1'-biphenyl]-3-yl)methyl)-7-((fluoromethyl)sulfonamido)-5-azaspiro[2.4]heptane-5-carboxylate (0.7 g, 1.42 mmol, 1 eq) in dioxane (5 mL) was added HCl/dioxane (4 M, 5 mL) at 25° C. The mixture was stirred at 25° C. for 1 hr. The reaction mixture was concentrated under reduced pressure to afford the title compound (0.7 g, crude) as white solid, which was used in next step without purification.

Step 8: N-((6S,7S)-5-((R)-2-cyanooxetane-2-carbonyl)-6-((2-fluoro-[1,1'-biphenyl]-3-yl)methyl)-5-azaspiro[2.4]heptan-7-yl)-1-fluoromethanesulfonamide (Isomer 1) N-((6S,7S)-5-((S)-2-cyanooxetane-2-carbonyl)-6-((2-fluoro-[1,1'-biphenyl]-3-yl)methyl)-5-azaspiro[2.4]heptan-7-yl)-1-fluoromethanesulfonamide (Isomer 2)

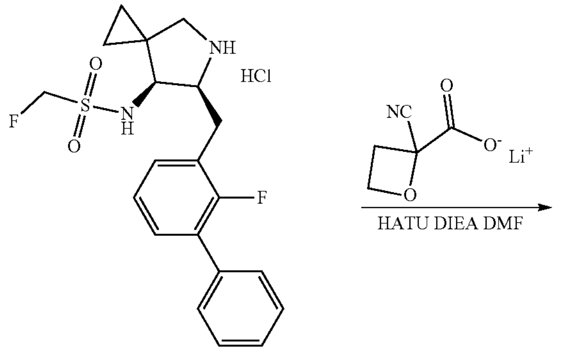

-continued

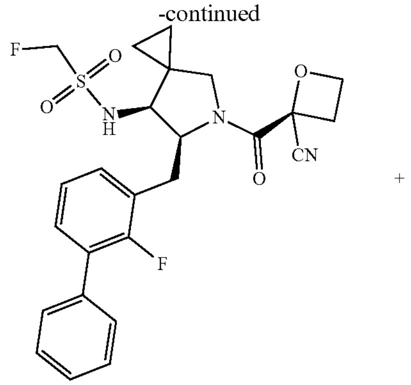

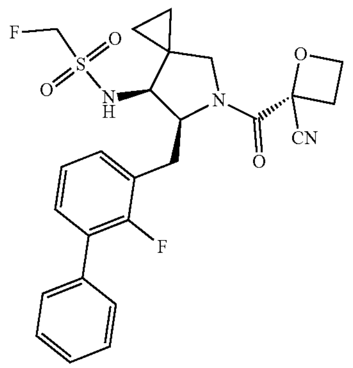

To a solution of 1-fluoro-N-((6S,7S)-6-((2-fluoro-[1,1'-biphenyl]-3-yl)methyl)-5-azaspiro[2.4]heptan-7-yl)methanesulfonamide hydrochloride (0.2 g, 466 μmol, 1 eq) and lithium 2-cyanooxetane-2-carboxylate (154 mg, 606 μmol, 50% purity, 1.3 eq) in N,N-dimethylformamide (2 mL) was added dropwise N,N-diisopropylethylamine (406 μL, 2.33 mmol, 5 eq) and o-(7-azabenzotriazol-1-yl)-N,N,N',N'-tetramethyluronium hexafluorophosphate (230 mg, 606 μmol, 1.3 eq) at 0° C. The resulting mixture was stirred at 25° C. for 12 hr. The reaction mixture was filtered and concentrated under reduced pressure to give a residue. The residue was purified by prep-HPLC (neutral condition: column: Waters Xbridge BEH C18 100*30 mm*10 μm; mobile phase: [water($NH_4HCO_3$)—$CH_3CN$]; B %: 45%-75%, 8 min) to afford a racemic white solid, which was further separated by SFC separation (condition: 1.173 column: DAICEL CHIRALPAK IG (250 mm*30 mm, 10 μm); mobile phase: [Neu-EtOH]; B %: 45%-45%, 15 min) to afford the title compounds isomer 1 (0.03 g, 12.8% yield) as a white solid and isomer 2 (0.030 g, 12.7% yield) as a white solid.

Example 78 (Compound 228). (6S,7S)-6-((2,5-difluoro-[1,1'-biphenyl]-3-yl)methyl)-N-((1-fluorocyclopropyl)methyl)-7-((fluoromethyl)sulfonamido)-5-azaspiro[2.4]heptane-5-carboxamide

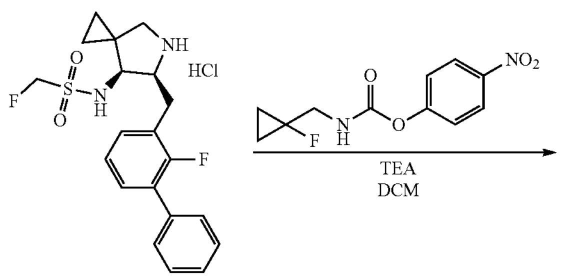

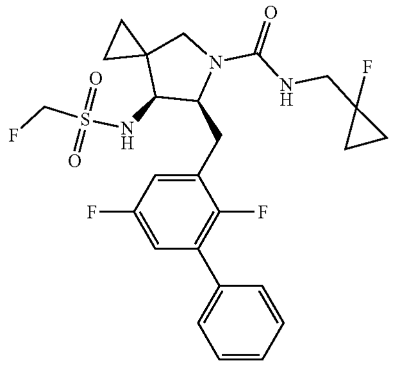

To a solution of 4-nitrophenyl carbonochloridate (271 mg, 1.35 mmol, 1.2 eq) in $CH_2Cl_2$ (2 mL) was added (1-fluorocyclopropyl)methanamine (0.1 g, 1.12 mmol, 1 eq) and DIEA (391 μL, 2.24 mmol, 2 eq) at 25° C. The mixture was stirred at 25° C. for 12 hrs. The reaction mixture was concentrated under reduced pressure to afford (4-nitrophenyl) N-[(1-fluorocyclopropyl) methyl]carbamate (0.3 g, crude) as a white solid.

To a solution of (4-nitrophenyl)N-[(1-fluorocyclopropyl) methyl]carbamate (248 mg, 975 μmol, 2 eq) in $CH_2Cl_2$ (2 mL) was added (6S,7S)-6-((2,5-difluoro-[1,1'-biphenyl]-3-yl)methyl)-N-((1-fluorocyclopropyl)methyl)-7-(fluoromethylsulfonamido)-5-azaspiro[2.4]heptane-5-carboxamide hydrochloride, intermediate 16 (0.2 g, 487 μmol, 1 eq) and triethylamine (339 μL, 2.44 mmol, 5 eq) at 25° C. The mixture was stirred at 25° C. for 2 hrs. The reaction mixture was concentrated under reduced pressure to afford a residue. The residue was purified by prep-HPLC (neutral condition: column: Waters Xbridge BEH C18 100*30 mm*10 μm; mobile phase: [water($NH_4HCO_3$)-ACN]; B %: 45%-65%, 8 min) to afford the title compound (0.080 g, 31.2% yield) as a white solid.

Example 79 (Compound 230)

Step 1: tert-butyl (6S,7S)-6-(3-bromo-2-fluorobenzyl)-7-(cyclopropanesulfonamido)-5-azaspiro[2.4]heptane-5-carboxylate

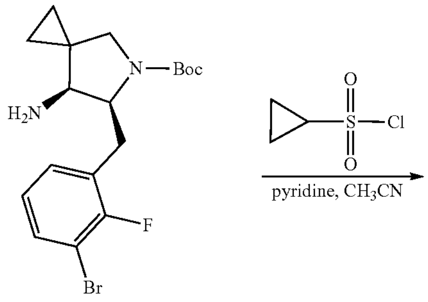

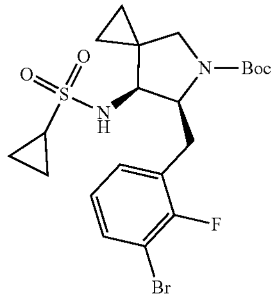

To a solution of tert-butyl (6S,7S)-6-(3-bromo-2-fluorobenzyl)-7-(methylsulfonamido)-5-azaspiro[2.4]heptane-5-carboxylate, intermediate 9 (450 mg, 1.13 mmol, 1 eq) in $CH_3CN$(4.5 mL) was added pyridine (446 mg, 5.63 mmol, 455 μL, 5 eq) and cyclopropanesulfonyl chloride (317 mg, 2.25 mmol, 2 eq) at 25° C. The mixture was stirred at 25° C. for 12 hrs. The residue was diluted with ethyl acetate (10 mL). The organic phase was washed with 0.5 N HCl (2×20 mL), saturated $NaHCO_3$ solution (2×20 mL), dried over $Na_2SO_4$ and concentrated in reduced pressure to afford the title compound (550 mg, 96.9% yield), which was used in next step without further purification. $^1H$ NMR (400 MHz, chloroform-d) δ 0.42-0.79 (m, 4H), 1.11-1.32 (m, 9H), 1.35-1.43 (m, 4H), 2.64-3.16 (m, 3H), 3.25-3.32 (m, 1H), 3.51-3.77 (m, 1H), 4.15-4.24 (m, 1H), 4.37 (br s, 2H), 6.94-7.02 (m, 1H), 7.04-7.17 (m, 1H), 7.37-7.51 (m, 1H).

Step 2: tert-butyl (6S,7S)-7-(cyclopropanesulfonamido)-6-((2,3',5'-trifluoro-[1,1'-biphenyl]-3-yl)methyl)-5-azaspiro[2.4]heptane-5-carboxylate

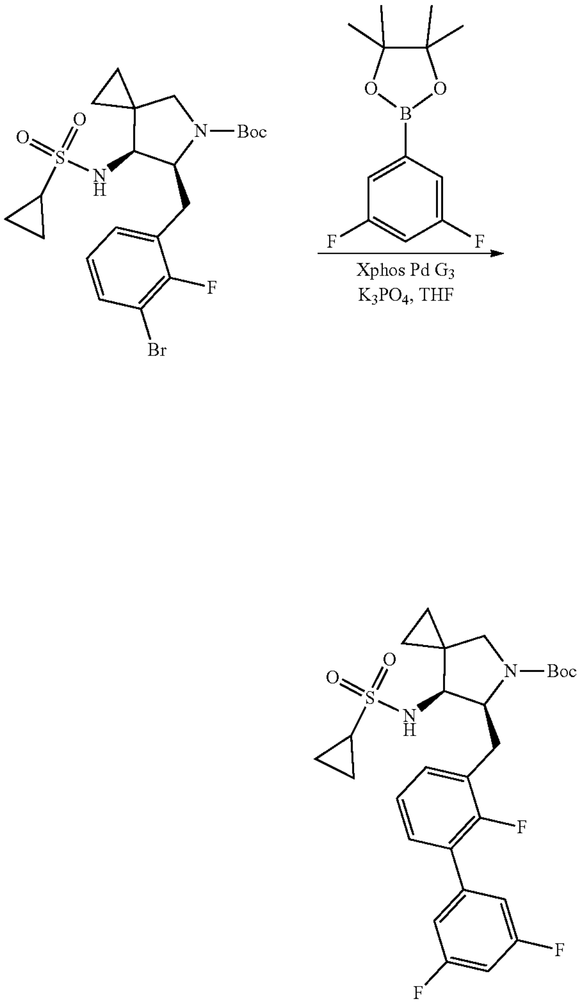

To a solution of tert-butyl (6S,7S)-6-(3-bromo-2-fluorobenzyl)-7-(cyclopropanesulfonamido)-5-azaspiro[2.4]heptane-5-carboxylate (500 mg, 1.12 mmol, 1 eq) and 2-(3,5-difluorophenyl)-4,4,5,5-tetramethyl-1,3,2-dioxaborolane (322 mg, 1.34 mmol, 1.2 eq) in THF (5 mL) was added $K_3PO_4$ (712 mg, 3.35 mmol, 3 eq) and XPhos Pd G3 (95 mg, 112 μmol, 0.1 eq) under $N_2$ atmosphere at 25° C. The mixture was stirred at 80° C. for 12 hrs. The reaction mixture was poured into water (50 mL) and extracted with ethyl acetate (3×20 mL). The combined organic layers were washed with brine (20 mL), dried over $Na_2SO_4$ and concentrated under reduced pressure to afford a residue. The residue was purified by column chromatography on silica gel (petroleum ether/ethyl acetate=100/1 to 2/1) to afford the title compound (580 mg, 96.7% yield) as yellow solid. LCMS(method 0)(ESI+): m/z 481.1 $(M-56)^+$, RT: 2.220 min Step 3: N-((6S,7S)-6-((2,3',5-trifluoro-[1,1'-biphenyl]-3-yl)methyl)-5-azaspiro[2.4]heptan-7-yl)cyclopropanesulfonamide hydrochloride

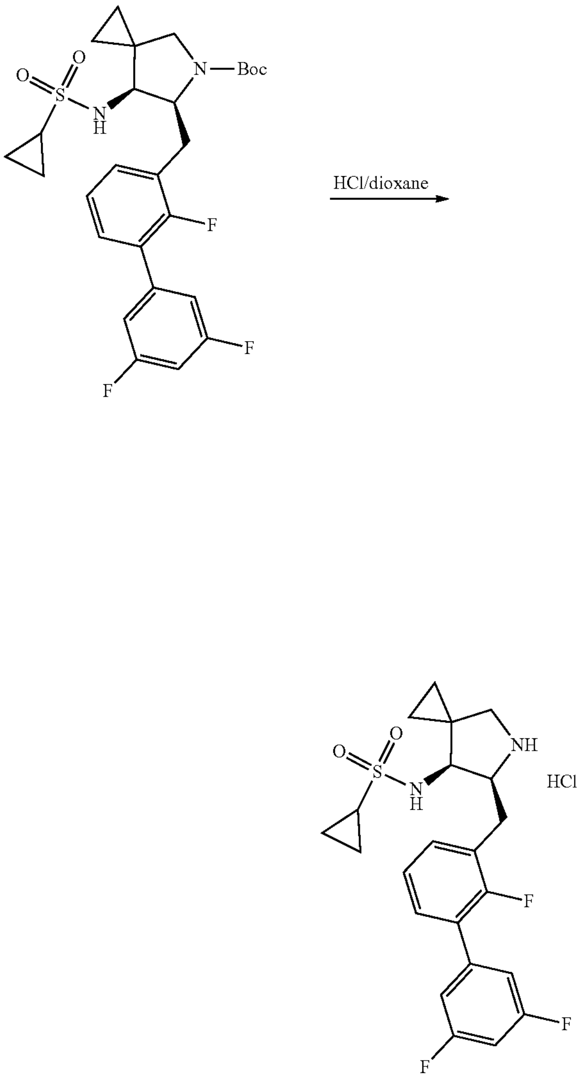

To a solution of tert-butyl (6S,7S)-7-(cyclopropanesulfonamido)-6-((2,3',5'-trifluoro-[1,1'-biphenyl]-3-yl)methyl)-5-azaspiro[2.4]heptane-5-carboxylate (500 mg, 932 μmol, 1 eq) in dioxane (1 mL) was added HCl/dioxane (4 mol/L, 5 mL) at 0° C. The mixture was stirred at 25° C. for 0.5 hr. The mixture was concentrated under reduced pressure to afford the title compound (400 mg, 98.4% yield), which was used in next step without further purification. LCMS(method 0)(ESI+): m/z 437.1 $(M+H)^+$, RT: 1.340 min Step 4: N-((6S,7S)-5-(2-hydroxy-2-methylpropanoyl)-6-((2,3',5'-trifluoro-[1,1'-biphenyl]-3-yl)methyl)-5-azaspiro[2.4]heptan-7-yl)cyclopropanesulfonamide

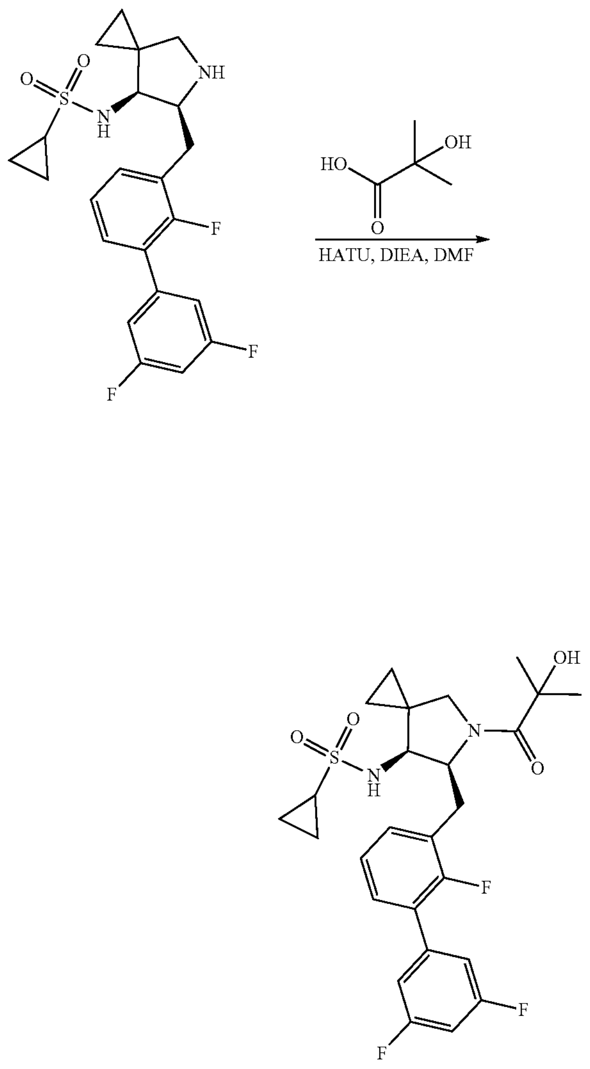

To a solution of N-((6S,7S)-6-((2,3',5'-trifluoro-[1,1'-biphenyl]-3-yl)methyl)-5-azaspiro[2.4]heptan-7-yl)cyclopropanesulfonamide hydrochloride (400 mg, 916 μmol, 1 eq) and 2-hydroxy-2-methyl-propanoic acid (114 mg, 1.10 mmol, 1.2 eq) in N,N-dimethylformamide (4 mL) was added o-(7-azabenzotriazol-1-yl)-N,N,N',N'-tetramethyluronium hexafluorophosphate (418 mg, 1.10 mmol, 1.2 eq) and N,N-diisopropylethylamine (798 μL, 4.58 mmol, 5 eq) at 25° C. The mixture was stirred at 25° C. for 2 hrs. The reaction mixture was poured into water (30 mL) and extracted with ethyl acetate (3×10 mL). The combined organic layers were washed with brine (5 mL), dried over $Na_2SO_4$ and concentrated in reduced pressure to afford a residue. The residue was purified by prep-HPLC (neutral condition column: Phenomenex C18 80*40 mm*3 μm; mobile phase: [water($NH_4HCO_3$)-ACN]; B %: 35%-65%, 8 min) to afford the title compound (95 mg, 19.8% yield) as a white solid.

Example 80 (Compound 231). N-((6S,7S)-5-(1-cyanocyclobutane-1-carbonyl)-6-((2,3',5'-trifluoro-[1,1'-biphenyl]-3-yl)methyl)-5-azaspiro[2.4]heptan-7-yl)-1-fluoromethanesulfonamide

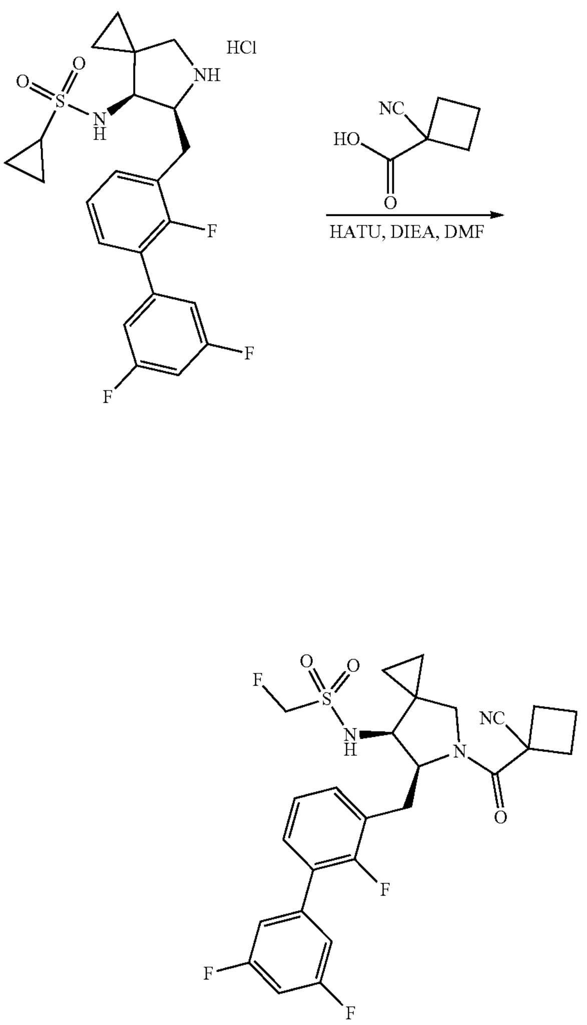

To a solution of 1-fluoro-N-((6S,7S)-6-((2,3',5'-trifluoro-[1,1'-biphenyl]-3-yl)methyl)-5-azaspiro[2.4]heptan-7-yl)methanesulfonamide hydrochloride, intermediate 22 (70 mg, 163 μmol, 1 eq) in DMF (1 mL) were added 1-cyano-cyclobutanecarboxylic acid (31 mg, 245 μmol, 1.5 eq), N,N-diisopropylethylamine (85 μL, 490.15 μmol, 3 eq) and HATU (75 mg, 196 μmol, 1.2 eq) at 0° C. The reaction mixture was stirred at 25° C. for 3 hrs. The mixture was purified by prep-HPLC (neutral condition: column: Waters Xbridge Prep OBD C18 150*40 mm*10 μm; mobile phase: [water ($NH_4HCO_3$)-ACN]; B %: 45%-80%, 8 min) to afford the title compound (39.3 mg, 44.9% yield) as a white solid.

Example 81 (Compound 234). N-((6S,7S)-5-((S)-3,3-difluoro-2-hydroxy-2-methylpropanoyl)-6-((2-fluoro-[1,1'-biphenyl]-3-yl)methyl)-5-azaspiro[2.4]heptan-7-yl)-1-fluoromethanesulfonamide

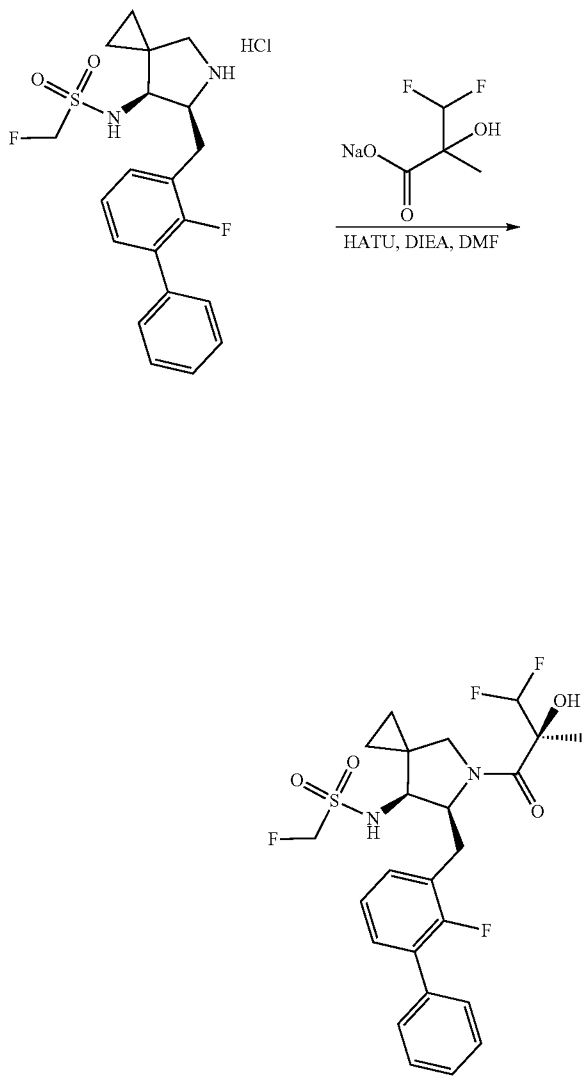

To a solution of 1-fluoro-N-((6S,7S)-6-((2-fluoro-[1,1'-biphenyl]-3-yl)methyl)-5-azaspiro[2.4]heptan-7-yl)methanesulfonamide hydrochloride, intermediate 20 (120 mg, 280 μmol, 1 eq) in DMF (2 mL) were added (3,3-difluoro-2-hydroxy-2-methyl-propanoyl)oxysodium (68 mg, 420 μmol, 1.5 eq), dipropylethylamine (244 μL, 1.40 mmol, 5 eq) and HATU (128 mg, 336 μmol, 1.2 eq) at 0° C. The resulting reaction mixture was stirred at 25° C. for 12 hrs and purified directly by prep-HPLC (neutral condition: column: Waters Xbridge Prep OBD C18 150*40 mm*10 μm; mobile phase: [water($NH_4HCO_3$)-ACN]; B %: 35%-65%, 8 min) and then chiral purification (Column: DAICEL CHIRALPAK IC (250 mm*30 mm, 10 μm); mobile phase: [0.1% $NH_3H_2O$ MeOH]; B %: 33%-33%, 4 min) to afford the title compound (34 mg, 31.2% yield) with the longer retention time as white solid.

Example 82 (Compound 235)

Step 1: tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate

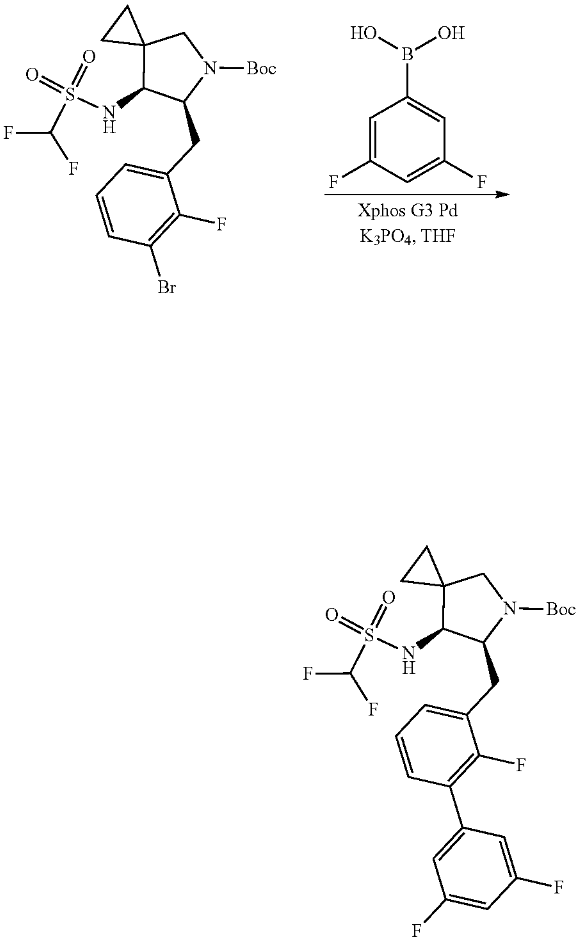

To a solution of tert-butyl (6S,7S)-6-(3-bromo-2-fluorobenzyl)-7-((difluoromethyl)sulfonamido)-5-azaspiro[2.4]heptane-5-carboxylate, intermediate 12 (0.2 g, 390 μmol, 1 eq) in THF (8 mL) were added (3,5-difluorophenyl)boronic acid (154 mg, 974 μmol, 2.5 eq), Xphos G3 Pd (16 mg, 19 μmol, 0.05 eq) and $K_3PO_4$ (165 mg, 779 μmol, 2 eq) at 20° C. The mixture was stirred at 80° C. for 8 hrs under $N_2$ atmosphere. Another reaction was set up as above. The two reaction mixtures were combined, diluted with 30 mL of ethyl acetate and 10 mL of water, the organic layer dried over $Na_2SO_4$, filtered and concentrated under reduced pressure. The residue was purified by prep-TLC (petroleum ether/ethyl acetate=3/1) to afford the title compound (0.3 g, 63.4% yield) as a white solid. 1H NMR (400 MHz, methanol-$d_4$) δ 0.59-0.92 (m, 3H), 0.97-1.24 (m, 10H), 2.78-2.92 (m, 1H), 3.03-3.14 (m, 1H), 3.24 (d, 1H), 3.69 (br d, 1H), 4.21 (br d, 1H), 4.32-4.52 (m, 1H), 6.48-6.83 (m, 1H), 6.98 (br t, 1H), 7.06-7.47 (m, 5H).

Step 2: 1,1-difluoro-N-((6S,7S)-6-((2,3',5'-trifluoro-[1,1'-biphenyl]-3-yl)methyl)-5-azaspiro[2.4]heptan-7-yl)methanesulfonamide hydrochloride

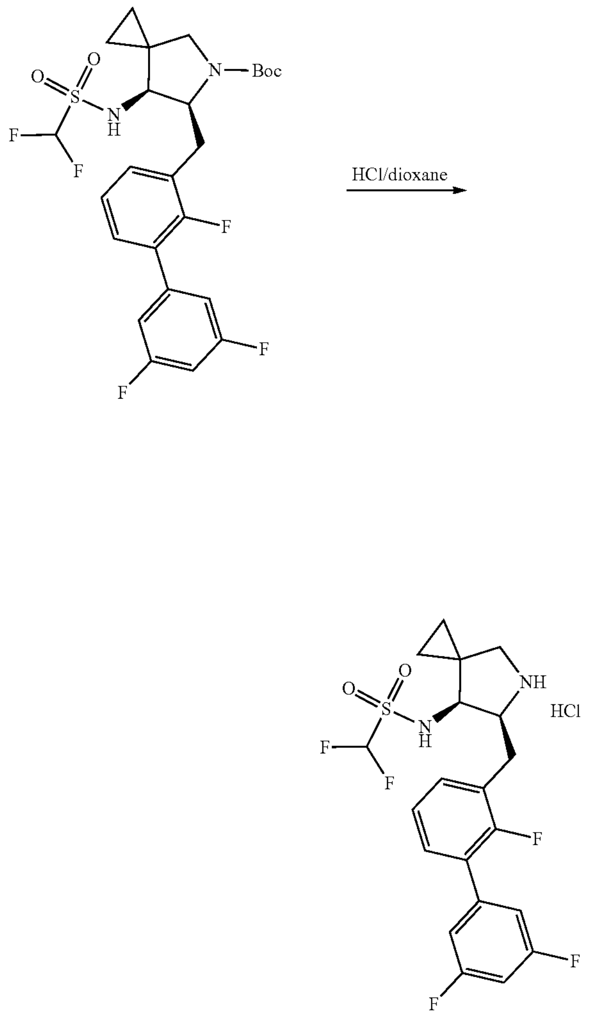

To a solution of tert-butyl (6S,7S)-7-((difluoromethyl)sulfonamido)-6-((2,3',5'-trifluoro-[1,1'-biphenyl]-3-yl)methyl)-5-azaspiro[2.4]heptane-5-carboxylate (0.15 g, 274 µmol, 1 eq) in dioxane (1 mL) was added HCl/dioxane (4 M, 3.00 mL, 44 eq) at 25° C. The reaction mixture was stirred at 25° C. for 12 hrs. Another reaction was set up as above. The two reaction mixtures were combined and concentrated under reduced pressure to afford the title compound (0.2 g, 67.9% yield) as a white solid. $^1$H NMR (400 MHz, methanol-$d_4$) δ 0.84-0.94 (m, 2H), 0.99-1.07 (m, 1H), 1.11-1.20 (m, 1H), 3.05-3.22 (m, 2H), 3.44 (br d, 1H), 3.56-3.64 (m, 1H), 3.98 (d, 1H), 4.29 (ddd, 1H), 6.56-6.86 (m, 1H), 7.01 (tt, 1H), 7.17-7.26 (m, 2H), 7.29-7.37 (m, 1H), 7.47-7.57 (m, 2H).

Step 3: (6S,7S)-7-((difluoromethyl)sulfonamido)-N-((1-fluorocyclopropyl)methyl)-6-((2,3',5'-trifluoro-[1,1'-biphenyl]-3-yl)methyl)-5-azaspiro[2.4]heptane-5-carboxamide

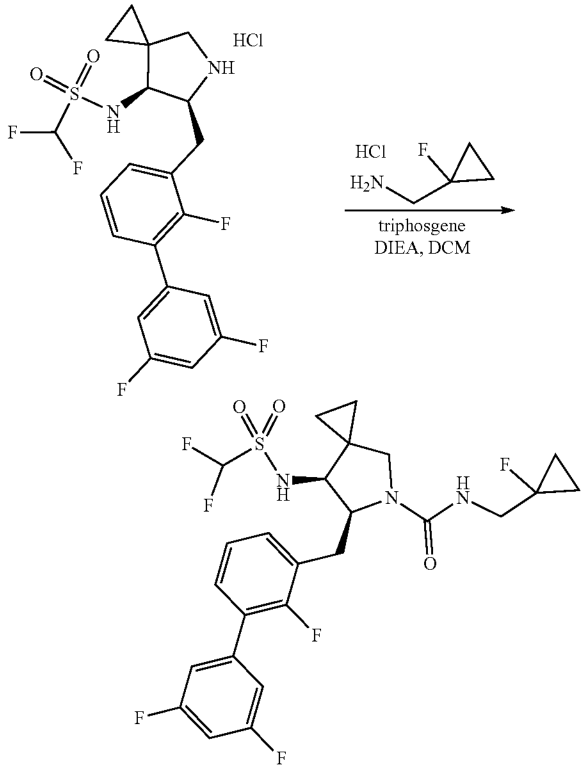

A solution of 1,1-difluoro-N-((6S,7S)-6-((2,3',5'-trifluoro-[1,1'-biphenyl]-3-yl)methyl)-5-azaspiro[2.4]heptan-7-yl)methanesulfonamide hydrochloride (100 mg, 207 µmol, 1 eq) and N,N-diisopropylethylamine (180 µL, 1.04 mmol, 5 eq) in dichloromethane (1 mL) was stirred at 25° C. for 10 min. The solution was added to a solution of triphosgene (49 mg, 166 µmol, 0.8 eq) in dichloromethane (1 mL) dropwise at 0° C. under $N_2$ atmosphere. After stirring at 25° C. for 1 hour, a solution of (1-fluorocyclopropyl)methanamine hydrochloride (130 mg, 1.04 mmol, 5 eq) and N,N-diisopropylethylamine (180 µL, 1.04 mmol, 5 eq) in dichloromethane (1 mL) was added to the above mixture at 0° C. The resulting reaction mixture was stirred at 25° C. for 12 hrs. The reaction mixture was concentrated under reduced pressure. The residue was purified by prep-HPLC (neutral condition: Column: Waters Xbridge Prep OBD C18 150*40 mm*10 µm; mobile phase: [water (10 mM $NH_4HCO_3$)-ACN]; B %: 40%-70%, 8 min) to afford the title compound (50.3 mg, 43.3% yield) as a white solid.

TABLE A

| Examples 1-32 Experimental Details | |
|---|---|
| Ex. | Structural Analysis |
| 1 | $^1$H NMR (400 MHZ, Methanol-$d_4$) δ 7.73-7.17 (m, 9H), 5.27-4.82 (m, 1H), 4.34-4.23 (m, 1H), 4.23-4.01 (m, 1H), 3.93- |

TABLE A-continued

| Examples 1-32 Experimental Details | |
|---|---|
| Ex. | Structural Analysis |
| | 3.74 (m, 1H), 3.50-3.38 (m, 1H), 3.22-2.94 (m, 3H), 2.73 (s, 2H), 1.39-1.01 (m, 3H), 0.82-0.57 (m, 4H). Exchangeable NH signal not observed. Mixture of rotamers in 1:1 ratio LCMS (method D): m/z 431 $(M + H)^+$ (ES+), at 2.49 min |
| 2 | $^1$H NMR (400 MHz, Methanol-$d_4$) δ 7.67-7.18 (m, 9H), 5.31-4.26 (m, 2H), 4.17-3.36 (m, 3H), 3.22-2.60 (m, 5H), 1.40 (dd, 1H), 1.20-1.02 (m, 1H), 0.87-0.52 (m, 5H). Exchangeable NH signal not observed. Mixture of rotamers in 2:1 ratio. LCMS (method D): m/z 431 $(M + H)^+$ (ES+), at 2.50 min |
| 3 | $^1$H NMR (400 MHz, Methanol-$d_4$) δ 7.68-7.63 (m, 2H), 7.54-7.24 (m, 7H), 4.62-4.50 (m, 1H), 3.92-3.81 (m, 3H), 3.66 (q, 2H), 3.41 (d, 1H), 3.37-3.28 (m, 1H), 3.05-2.93 (m, 4H), 1.98 (p, 2H), 1.29 (t, 3H), 1.08-0.98 (m, 1H), 0.69-0.57 (m, 3H). Exchangeable NH signal not observed. LCMS (method D): m/z 454 $(M + H)^+$ (ES+), at 2.55 min |
| 4 | $^1$H NMR (400 MHz, Methanol-$d_4$) δ 7.67-7.58 (m, 3H), 7.51-7.29 (m, 6H), 4.16 (d, 1H), 3.84 (d, 1H), 3.69 (d, 1H), 3.20-2.89 (m, 3H), 2.69 (s, 3H), 1.18-1.06 (m, 1H), 0.81-0.62 (m, 3H). Exchangeable NH signal not observed. LCMS (method D): m/z 453 $(M + H)^+$ (ES+), at 2.68 min |
| 5 | $^1$H NMR (400 MHz, Acetonitrile-$d_3$) δ 7.68-7.19 (m, 9H), 6.29-4.78 (m, 2H), 4.80- 4.02 (m, 2H), 3.91-3.30 (m, 2H), 3.16-2.59 (m, 5H), 1.04-0.90 (m, 1H), 0.79-0.54 (m, 3H). Mixture of rotamers in 1:1 ratio LCMS (method D): m/z 435 $(M + H)^+$ (ES+), at 2.51 min |
| 6 | $^1$H NMR (400 MHZ, DMSO-$d_6$) δ 7.62-7.64 (m, 2H), 7.48-7.44 (m, 4H), 7.37-7.33 (m, 2H), 7.16 (br m, 2H), 4.22 (br 1H), 4.04 (br, 1H), 3.53-3.50 (m, 2H), 3.20-3.18 (m, 1H), 3.01-2.97 (m, 4H), 2.81 (m, 1H), 2.67 (m, 1H), 1.16-1.01 (m, 4H), 0.57-0.48 (m, 3H). LCMS (method D): m/z 429 $(M + H)^+$ (ES+), at 2.56 min |
| 7 | $^1$H NMR (400 MHz, Methanol-$d_4$) δ 7.65-7.26 (m, 8H), 7.20 (d, 1H), 4.80-4.32 (m, 1H), 4.23-4.02 (m, 1H), 3.93-3.72 (m, 1H), 3.50-3.12 (m, 3H), 3.11-2.56 (m, 2H), 1.86 (p, 1H), 1.37 (t, 2H), 1.17 (t, 1H), 1.13-1.06 (m, 1H), 1.01 (d, 1H), 0.88 (d, 1H), 0.85 (d, 2H), 0.77-0.58 (m, 3H), 0.32 (d, 2H). Exchangeable NH signal not observed. Mixture of rotamers in 2:1 ratio LCMS (method D): m/z 441 $(M + H)^+$ (ES+), at 2.55 min |
| 8 | $^1$H NMR (400 MHZ, Methanol-$d_4$) δ 7.65-7.20 (m, 7H), 7.11-7.00 |

TABLE A-continued

| Examples 1-32 Experimental Details | |
|---|---|
| Ex. | Structural Analysis |
| | (m, 1H), 4.81-4.37 (m, 1H), 4.30-4.09 (m, 1H), 3.93-3.73 (m, 1H), 3.52-3.27 (m, 1H), 3.21-2.97 (m, 3H), 2.88-2.59 (m, 2H), 1.88 (p, 1H), 1.25-0.99 (m, 2H), 0.92 (d, 1H), 0.86 (d, 2H), 0.77-0.56 (m, 3H), 0.32 (d, 2H). Exchangeable NH signal not observed. Mixture of rotamers in 2:1 ratio LCMS (method D): m/z 445 $(M + H)^+$ (ES+), at 2.55 min |
| 9 | $^1$H NMR (400 MHZ, Methanol-$d_4$) δ 7.70-7.55 (m, 3H), 7.52-7.28 (m, 6H), 4.83 (q, 1H), 4.10 (d, 1H), 3.98-3.86 (m, 1H), 3.71 (d, 1H), 3.17-2.97 (m, 2H), 2.68 (s, 3H), 1.65 (t, 3H), 1.16-1.05 (m, 1H), 0.78-0.56 (m, 3H). Exchangeable NH signal not observed. Mixture of rotamers in 6:1 ratio LCMS (method D): m/z 449 $(M + H)^+$ (ES+), at 2.68 min |
| 10 | $^1$H NMR (400 MHZ, Methanol-$d_4$) δ 7.65-7.59 (m, 2H), 7.54 (d, 1H), 7.48-7.25 (m, 6H), 4.61 (q, 1H), 4.27-4.13 (m, 2H), 4.03-3.90 (m, 3H), 3.45-3.35 (m, 2H), 3.02 (d, 2H), 2.87 (s, 3H), 1.08-1.00 (m, 1H), 0.70-0.59 (m, 3H). Exchangeable NH signal not observed. LCMS (method D): m/z 476 $(M + H)^+$ (ES+), at 2.56 min |
| 11 | $^1$H NMR (400 MHz, Methanol-$d_4$) δ 7.67-7.59 (m, 2H), 7.54 (s, 1H), 7.47-7.27 (m, 6H), 5.14-4.92 (m, 1H), 4.59 (q, 1H), 4.22-4.08 (m, 1H), 4.01-3.85 (m, 3H), 3.80-3.67 (m, 1H), 3.49-3.25 (m, 2H), 3.01 (d, 2H), 2.86 (s, 3H), 1.09-0.99 (m, 1H), 0.71-0.55 (m, 3H). Exchangeable NH signal not observed. LCMS (method D): m/z 458 $(M + H)^+$ (ES+), at 2.44 min |
| 12 | $^1$H NMR (400 MHZ, Methanol-$d_4$) δ 7.67-7.19 (m, 9H), 4.83-4.39 (m, 1H), 4.31-4.06 (m, 1H), 3.96-3.63 (m, 1H), 3.43-3.33 (m, 1H), 3.19-2.97 (m, 4H), 2.84-2.14 (m, 6H), 1.56-0.99 (m, 1H), 0.80-0.52 (m, 3H). Exchangeable NH signal not observed. Mixture of rotamers in 2:1 ratio. LCMS (method D): m/z 475 $(M + H)^+$ (ES+), at 2.57 min |
| 13 | $^1$H NMR (400 MHz, Methanol-$d_4$) δ 7.66-7.54 (m, 3H), 7.48-7.17 (m, 6H), 5.15-4.83 (m, 1H), 4.33-4.03 (m, 1H), 3.96-3.88 (m, 1H), 3.79-3.35 (m, 1H), 3.12-2.96 (m, 2H), 2.91-2.62 (m, 3H), 1.56-1.41 (m, 3H), 1.36-0.86 (m, 4H), 0.75-0.58 (m, 3H). Exchangeable NH signal not observed. Mixture of rotamers approx. 3.5:1 ratio. LCMS (method D): m/z 445 $(M + H)^+$ (ES+), at 2.62 min |
| 14 | $^1$H NMR (400 MHZ, DMSO-$d_6$) δ 7.62 (br d, 2H), 7.43-7.49 (m, 3H), 7.32-7.42 (m, 3H), 7.16 (br d, 1H), 7.07 (br d, 1H), 4.53 (br s, 1H), 3.83-3.98 (m, 2H), 3.82 (br s, 3H), |

TABLE A-continued

| Ex. | Structural Analysis |
|---|---|
| | Examples 1-32 Experimental Details |
| | 3.15-3.29 (m, 1H), 2.92-3.12 (m, 5H), 1.87-2.03 (m, 1H), 1.01 (br d, 1H), 0.83 (br s, 1H), 0.54-0.63 (m, 1H), 0.42-0.52 (m, 1H), 0.01-0.17 (m, 1H). LCMS (method D): m/z 429 (M + H)$^+$ (ES+), at 2.56 min |
| 15 | $^1$H NMR (400 MHZ, DMSO-d$_6$) δ 7.75-6.99 (m, 10H), 4.64-4.27 (m, 1H), 4.18-3.96 (m, 1H), 3.79-3.66 (m, 1H), 3.40-3.16 (m, 1H), 3.07 (s, 3H), 3.05-2.81 (m, 1H), 2.73-2.53 (m, 1H), 1.79 (p, 1H), 1.22-1.00 (m, 1H), 0.97-0.14 (m, 9H). Rotamers in approx. 3:2 ratio LCMS (method F): m/z 427 (M + H)$^+$ (ES+), at 3.96 min |
| 16 | LCMS (method G): m/z 427 (M + H)$^+$ (ES+), at 4.41 min |
| 17 | LCMS (method G): m/z 427 (M + H)$^+$ (ES+), at 4.41 min |
| 18 | $^1$H NMR (400 MHZ, DMSO-d$_6$) δ 7.56-7.44 (m, 4H), 7.43-7.36 (m, 1H), 7.34-7.23 (m, 3H), 7.17 (t, 1H), 4.55 (dt, 1H), 3.83 (dd, 1H), 3.70 (q, 2H), 3.48 (q, 2H), 3.31-3.22 (m, 2H), 3.00-2.92 (m, 1H), 2.91 (s, 3H), 2.81 (dd, 1H), 2.00-1.85 (m, 2H), 1.05-0.95 (m, 1H), 0.62-0.46 (m, 3H). LCMS (method F): m/z 458 (M + H)$^+$ (ES+), at 3.83 min |
| 19 | $^1$H NMR (400 MHZ, DMSO-d$_6$) δ 7.58-7.06 (m, 9H), 5.20-3.90 (m, 6H), 3.85-3.56 (m, 1H), 3.13-3.00 (m, 1H), 2.91 (s, 3H), 2.84-2.61 (m, 2H), 2.43-2.29 (m, 1H), 1.03 (d, 1H), 0.67-0.43 (m, 3H). Rotamers present in approx. 4:3 ratio LCMS (method F): m/z 459 (M + H)$^+$ (ES+), at 3.46 min |
| 20 | $^1$H NMR (400 MHZ, DMSO-d$_6$) δ 7.58-7.07 (m, 9H), 5.08-3.19 (m, 7H), 3.07-2.60 (m, 5H), 2.46-1.84 (m, 2H), 1.10-0.96 (m, 1H), 0.73-0.43 (m, 3H). Rotamers present in approx. 1:1 ratio LCMS (method F): m/z 459 (M + H)$^+$ (ES+), at 3.63 min |
| 21 | $^1$H NMR (400 MHZ, DMSO-d$_6$) δ 7.58-7.06 (m, 9H), 5.20-3.90 (m, 6H), 3.85-3.56 (m, 1H), 3.13-3.00 (m, 1H), 2.91 (s, 3H), 2.84-2.61 (m, 2H), 2.43-2.29 (m, 1H), 1.03 (d, 1H), 0.67-0.43 (m, 3H). Rotamers present in approx. 4:3 ratio LCMS (method F): m/z 459 (M + H)$^+$ (ES+), at 3.28 min |
| 22 | $^1$H NMR (400 MHZ, DMSO-d$_6$) δ 7.58-7.07 (m, 9H), 5.08-3.19 (m, 7H), 3.07-2.60 (m, 5H), 2.46-1.84 (m, 2H), 1.10-0.96 (m, 1H), 0.73-0.43 (m, 3H). Rotamers present in approx. 1:1 ratio LCMS (method F): m/z 459 (M + H)$^+$ (ES+), at 3.45 min |
| 23 | $^1$H NMR (400 MHZ, DMSO-d$_6$) δ 7.56-7.47 (m, 1H), 7.38-7.18 (m, 6H), 7.13 (t, 1H), 4.91 (dt, 1H), 3.96-3.86 (m, 1H), 3.78 (d, |

TABLE A-continued

| Ex. | Structural Analysis |
|---|---|
| | Examples 1-32 Experimental Details |
| | 1H), 3.55 (d, 1H), 3.02 (dd, 1H), 2.91 (s, 3H), 2.78 (dd, 1H), 1.06-0.99 (m, 1H), 0.96 (s, 9H), 0.69-0.48 (m, 3H). LCMS (method F): m/z 477 (M + H)$^+$ (ES+), at 4.68 min |
| 24 | $^1$H NMR (400 MHZ, DMSO-d$_6$) δ 7.56-7.47 (m, 1H), 7.39-7.28 (m, 5H), 7.27-7.18 (m, 1H), 7.14 (t, 1H), 4.79 (ddd, 1H), 4.08-4.03 (m, 1H), 3.89-3.81 (m, 1H), 3.61 (d, 1H), 3.14-3.04 (m, 1H), 2.96 (s, 3H), 2.89-2.77 (m, 1H), 1.54 (t, 3H), 1.12-1.00 (m, 1H), 0.75-0.50 (m, 3H); Mixture of rotamers in approximately 4:1 ratio LCMS (method F): m/z 485 (M + H)$^+$ (ES+), at 4.46 min |
| 25 | $^1$H NMR (400 MHZ, DMSO-d$_6$) δ 7.61-7.46 (m, 1H), 7.44-7.31 (m, 4H), 7.28-7.13 (m, 3H), 4.55 (dt, 1H), 3.88-3.78 (m, 1H), 3.70 (q, 2H), 3.48 (q, 2H), 3.34-3.20 (m, 2H), 3.00-2.94 (m, 1H), 2.92 (s, 3H), 2.81 (dd, 1H), 1.95 (p, 2H), 1.05-0.89 (m, 1H), 0.60-0.44 (m, 3H). LCMS (method F): m/z 476 (M + H)$^+$ (ES+), at 3.90 min |
| 26 | LCMS (method F): m/z 476 (M + H)$^+$ (ES+), at 4.02 min |
| 27 | LCMS (method F): m/z 476 (M + H)$^+$ (ES+), at 4.02 min |
| 28 | $^1$H NMR (400 MHZ, DMSO-d$_6$) δ 7.35 (t, 2H), 7.28 (dtd, 3H), 7.19-7.10 (m, 2H), 5.00 (s, 1H), 4.81 (s, 1H), 4.20-4.03 (m, 1H), 3.90 (d, 1H), 3.64 (d, 1H), 3.03 (td, 1H), 2.90 (s, 3H), 2.77 (dd, 1H), 1.14 (s, 3H), 1.07-0.92 (m, 4H), 0.71-0.39 (m, 3H); Mixture of rotamers in approximately 4:1 ratio LCMS (method F): m/z 497 (M + H)$^+$ (ES+), at 3.92 min |
| 29 | $^1$H NMR (400 MHZ, DMSO-d$_6$) δ 7.51-7.11 (m, 7H), 4.75-4.24 (m, 1H), 4.13-3.91 (m, 1H), 3.76-3.54 (m, 1H), 3.24-3.12 (m, 1H), 3.08-2.92 (m, 5H), 2.82-2.29 (m, 1H), 2.05-1.46 (m, 6H), 1.05-0.81 (m, 1H), 0.71-0.43 (m, 3H). Rotamers in 1:1 ratio LCMS (method F): m/z 493 (M + H)$^+$ (ES+), at 4.42 min |
| 30 | $^1$H NMR (400 MHZ, DMSO-d$_6$) δ 7.47-7.15 (m, 7H), 4.55 (dt, 1H), 3.84 (dd, 1H), 3.71 (q, 2H), 3.49 (q, 2H), 3.28-3.22 (m, 2H), 2.98 (dd, 1H), 2.93 (s, 3H), 2.82 (dd, 1H), 1.97 (p, 2H), 1.04-0.94 (m, 1H), 0.61-0.49 (m, 3H). LCMS (method F): m/z 494 (M + H)$^+$ (ES+), at 4.08 min |
| 31 | LCMS (method F): m/z 494 (M + H)$^+$ (ES+), at 4.20 min |
| 32 | LCMS (method F): m/z 494 (M + H)$^+$ (ES+), at 4.20 min |
| 33 | LCMS (method F): m/z 493 (M + H) + (ES+), at 4.61 min |
| 34 | LCMS (method F): m/z 497 (M + H) + (ES+), at 3.92 min |

TABLE A-continued

Examples 1-32 Experimental Details

| Ex. | Structural Analysis |
|---|---|
| 35 | LCMS (method F): m/z 458 (M + H) + (ES+), at 3.83 min |
| 36 | LCMS (method )): m/z 445 (M + H) + (ES+), at 2.60 min |
| 37 | LCMS (method K): m/z 443 (M + H) + (ES+), at 2.78 min |
| 38 | LCMS (method J): m/z 446 (M + H) + (ES+), at 2.37 min |
| 39 | 1H NMR (400 MHz, acetonitrile-d3) δ ppm 7.41-7.32 (m, 2H), 7.27-7.15 (m, 3H), 7.03-6.95 (m, 1H), 5.19 (br d, 1H), 5.12 (m, 1H), 4.80 (m, 1H), 4.54-4.45 (m, 1H), 4.40-4.24 (m, 1H), 4.19-4.07 (m, 1H), 3.88-3.57 (m, 1H), 3.25-3.14 (m, 1H), 3.13-3.04 (m, 1H), 2.90-2.86 (m, 3H), 2.78-2.66 (m, 1H), 2.54-2.42 (m, 1H), 0.94-0.86 (m, 1H), 0.75-0.53 (m, 3H). Exchangeable NH signal not observed<br>LCMS (method J): m/z 495 (M + H) + (ES+), at 2.36 min |
| 40 | LCMS (method K): m/z 459 (M + H) + (ES+), at 2.68 min |
| 41 | LCMS (method K): m/z 455 (M + H) + (ES+), at 2.74 min |
| 42 | LCMS (method K): m/z 467 (M + H) + (ES+), at 2.79 min |
| 43 | LCMS (method K): m/z 483 (M + H) + (ES+), at 2.98 min |
| 44 | LCMS (method K): m/z 458 (M + H) + (ES+), at 2.95 min |
| 45 | LCMS (method K): m/z 476 (M + H) + (ES+), at 2.89 min |
| 46 | LCMS (method K): m/z 488 (M + H) + (ES+), at 2.84 min |
| 47 | LCMS (method J): m/z 466 (M + H) + (ES+), at 2.51 min |
| 48 | LCMS (method K): m/z 459 (M + H) + (ES+), at 2.75 min |
| 49 | LCMS (method J): m/z 457 (M + H) + (ES+), at 2.49 min |
| 50 | LCMS (method J): m/z 473 (M + H) + (ES+), at 2.44 min |
| 51 | LCMS (method J): m/z 473 (M + H) + (ES+), at 2.26 min |
| 52 | LCMS (method J): m/z 460 (M + H) + (ES+), at 2.42 min |
| 53 | LCMS (method K): m/z 473 (M + H) + (ES+), at 3.04 min |
| 54 | 1H NMR (400 MHz, methanol-d4) δ ppm 7.65-7.58 (m, 2 H), 7.47-7.40 (m, 2 H), 7.39-7.32 (m, 2 H), 7.27-7.16 (m, 2 H), 4.51 (td, 1 H), 4.16 (d, 1 H), 3.57 (d, 1 H), 3.43 (s, 3 H),3.23-3.11 (m, 3 H), 3.02 (d, 1 H), 2.93 (dd, 1 H), 2.61 (s, 3 H), 1.38-1.26 (m, 1 H), 1.08 (t, 3 H), 0.87-0.77 (m, 1 H), 0.73-0.54 (m, 2 H), 0.39-0.24 (m, 1 H)<br>LCMS (method ): m/z 458 (M + H) + (ES+), at 2.47 min |
| 55 | LCMS (method K): m/z 441 (M + H) + (ES+), at 2.67 min |
| 56 | 1H NMR (400 MHZ, DMSO-d6) δ ppm 7.55-7.43 (m, 4 H), 7.42-7.31 (m, 2 H), 7.29-7.17 (m, 2 H), 7.12-7.05 (m, 1 H), 6.25-5.80 (d, 1 H), 4.88-4.66 (m, 1 H), 4.46 br s, 1 H), 4.13-3.89 (m, 2 H), 3.50-3.40 (m, 1 H), 3.13-2.99 (m, 2 H), 2.95 (s, 2 H), 2.81-2.72 (m, 1 H), 1.05 (br d, 1 H), 0.74-0.49 (m, 3 H)<br>LCMS (method J): m/z 501 (M + H) + (ES+), at 2.49 min |
| 57 | LCMS (method K): m/z 454 (M + H) + (ES+), at 2.96 min |
| 58 | 1H NMR (400 MHZ, DMSO-d6) δ ppm 7.65-7.60 (m, 2 H), 7.51-7.40 (m, 3 H), 7.40-7.25 (m, 3 H), 7.22 (br d, 1 H), 6.53-5.54 (m, 1 H), 4.70-4.38 (m, 2 H), 4.06-3.90 (m, 1 H), 3.90-3.69 (m, 1 H), 3.47 (br d, 1 H), 3.14-2.98 (m, 2 H), 2.90-2.73 (m, 2 H), 1.18-1.02 (m, 4 H), 0.88-0.46 (m, 3 H). Exchangeable NH signal not observed.<br>LCMS (method J): m/z 497 (M + H) + (ES+), at 2.53 min |
| 59 | 1H NMR (400 MHz, acetonitrile-d3) δ ppm 7.59-7.39 (m, 5 H), 7.15-7.04 (m, 2 H), 5.27-5.10 (m, 2 H), 4.79-4.63 (m, 1 H), 4.55-4.38 (m, 1 H), 4.27-4.34 (m, 1 H), 4.08-4.21 (m, 1 H), 3.86-3.61 (m, 1 H), 3.23-3.14 (m, 1 H), 3.13-3.04 (m, 1 H), 2.92-2.88 (m, 3 H), 2.87-2.80 (m, 1 H), 2.80-2.69 (m, 1 H), 2.59-2.42 (m, 1 H), 0.95-0.83 (m, 1 H), 0.74-0.54 (m, 3 H). Exchangeable NH signal not observed.<br>LCMS (method J): m/z 477 (M + H) + (ES+), at 2.43 min |
| 60 | LCMS (method K): m/z 455 (M + H) + (ES+), at 3.05 min |
| 61 | LCMS (method J): m/z 455 (M + H) + (ES+), at 2.36 min |
| 62 | LCMS (method K): m/z 447 (M + H) + (ES+), at 2.75 min |
| 63 | LCMS (method J): m/z 459 (M + H) + (ES+), at 2.28 min |
| 64 | 1H NMR: (400 MHZ, acetonitrile-d3) δ ppm 7.61-7.45 (m, 2 H), 7.50-7.12 (m, 6 H), 5.13-5.00 (m, 1 H), 4.83-4.45 (m, 1 H), 4.48-3.96 (m, 3 H), 3.94-3.61 (m, 1 H), 3.24-3.07 (m, 2 H), 2.88-2.76 (m, 2 H), 2.76-2.66 (s, 6 H), 2.46-2.42 (m, 1 H), 0.98-0.87 (m, 1 H), 0.75-0.50 (m, 3 H). Exchangeable NH signal not observed.<br>LCMS (method J): m/z 488 (M + H) + (ES+), at 2.38 min |
| 65 | LCMS (method J): m/z 474 (M + H) + (ES+), at 2.38 min |
| 66 | LCMS (method K): m/z 437 (M + H) + (ES+), at 2.94 min |
| 67 | 1H NMR (400 MHz, methanol-d4) δ ppm 7.50-7.41 (m, 1H), 7.40-7.29 (m, 3H), 7.29-7.23 (m, 1H), 7.20-7.05 (m, 2H), 5.23-4.95 (m, 1 H), 4.55-4.47 (m, 1H), 4.39-4.31 (m, 1H), 4.30-4.20 (m, 1H), 4.17-4.06 (m, 1H), 3.94-3.67 (d, 1 H), 3.35-3.22 (m, 1 H), 3.17-3.10 (m, 1 H), 3.06-2.98 (m, 3H), 2.97-2.89 (m, 1 H), 2.89-2.74 (m, 1 H), 2.54-2.33 (m, 1 H), 1.09-0.89 (m, 1 H), 0.80-0.58 (m, 3 H). Exchangeable NH signal not observed. |

TABLE A-continued

Examples 1-32 Experimental Details

| Ex. | Structural Analysis |
|---|---|
| | LCMS (method K): m/z 477 (M + H) + (ES+), at 2.75 min |
| 68 | LCMS (method J): m/2 473 (M + H) + (ES+), at 2.44 min |
| 69 | 1H NMR (400 MHz, acetonitrile-d3) δ ppm 7.58-7.50 (m, 2 H), 7.47 (br t, 2 H), 7.42-7.36 (m, 1 H), 7.35-7.25 (m, 2 H), 7.24-7.13 (m, 1 H), 5.30-5.16 (m, 1 H), 5.12-4.86 (m, 1 H), 4.53-4.46 (m, 1 H), 4.31-4.22 (m, 1 H), 4.14-4.05 (m, 1 H), 3.88-3.63 (m, 1 H), 3.23-3.09 (m, 2 H), 2.90-2.80 (m, 1 H), 2.79-2.66 (m, 1 H), 2.55-2.45 (m, 1 H), 2.44-2.33 (m, 1 H),1.03-0.95 (m, 4 H), 0.92-0.87 (m, 1 H), 0.74-0.54 (m, 3 H). Exchangeable NH signal not observed. LCMS (method J): m/z 485 (M + H) + (ES+), at 2.49 min |
| 70 | LCMS (method J): m/z 465 (M + H) + (ES+), at 2.51 min |
| 71 | LCMS (method K): m/z 456 (M + H) + (ES+), at 2.69 min |
| 72 | LCMS (method K): m/z 507 (M + H) + (ES+), at 2.72 min |
| 73 | LCMS (method K): m/z 466 (M + H) + (ES+), at 2.73 min |
| 74 | LCMS (method K): m/z 529 (M + H) + (ES+), at 2.81 min |
| 75 | LCMS (method K): m/z 493 (M + H) + (ES+), at 2.52 min |
| 76 | LCMS (method K): m/z 482 (M + H) + (ES+), at 2.82 min |
| 77 | LCMS (method K): m/z 483 (M + H) + (ES+), at 2.67 min |
| 78 | LCMS (method K): m/z 484 (M + H) + (ES+), at 2.93 min |
| 79 | LCMS (method K): m/z 478 (M + H) + (ES+), at 2.85 min |
| 80 | LCMS (method K): m/z 490 (M + H) + (ES+), at 2.99 min |
| 81 | LCMS (method K): m/z 496 (M + H) + (ES+), at 3.10 min |
| 82 | LCMS (method K): m/z 478 (M + H) + (ES+), at 2.99 min |
| 83 | LCMS (method K): m/z 508 (M + H) + (ES+), at 2.99 min |
| 84 | LCMS (method K): m/z 478 (M + H) + (ES+), at 2.91 min |
| 85 | LCMS (method K): m/z 460 (M + H) + (ES+), at 2.94 min |
| 86 | LCMS (method K): m/z 464 (M + H) + (ES+), at 2.81 min |
| 87 | LCMS (method K): m/z 494 (M + H) + (ES+), at 3.05 min |
| 88 | LCMS (method K): m/z 460 (M + H) + (ES+), at 3.04 min |
| 89 | LCMS (method K): m/z 460 (M + H) + (ES+), at 2.90 min |
| 90 | LCMS (method J): m/z 475 (M + H) + (ES+), at 2.63 min |
| 91 | LCMS (method J): m/z 475 (M + H) + (ES+), at 2.62 min |
| 92 | LCMS (method J): m/z 486 (M + H) + (ES+), at 2.71 min |
| 93 | 1H NMR (400 MHz, acetonitrile-d3) δ ppm 7.62-7.46 (m, 4H), 7.46-7.15 (m, 4H), 5.31-5.18 (m, 1H), 5.19-5.05 (m, 1H), 4.67 (dddd, 1H), 4.44-4.20 (m, 2H), 4.16-4.04 (m, 1H), 3.77 (dd, 1H), 3.23 (dd, 1H), 3,17-3.07 (m, 1H), 2.89 (ddd, 1H), 2.73 (dddd, 1H), 2.56-2.41 (m, 1H), 1.97 (p, 1H), 0.96 (qt, 1H), 0.82-0.54 (m, 3H). Exchangeable NH signal not observed. LCMS (method J): m/z 477 (M + H) + (ES+), at 2.46 min |
| 94 | LCMS (method K): m/z 501 (M + H) + (ES+), at 3.08 min |
| 95 | 1H NMR (400 MHz, methanol-d4) δ ppm 7.67-7.50 (m, 3 H), 7.49-7.27 (m, 5 H), 7.21 (br d, 1 H), 5.24-4.76 (m, 1 H), 4.56-4.25 (m, 2 H), 4.11-3.86 (m, 3 H), 3.65-3.36 (br m, 1 H), 3.22-2.92 (m, 2 H), 2.83-2.66 (m, 7 H), 2.46-2.28 (m, 1 H), 1.19-1.02 (m, 1 H), 0.81-0.52 (m, 3 H). Exchangeable NH signal not observed. LCMS (method K): m/z 470 (M + H) + (ES+), at 2.82 min |
| 96 | LCMS (method K): m/z 496 (M + H) + (ES+), at 2.93 min |
| 97 | LCMS (method K): m/z 496 (M + H) + (ES+), at 2.97 min |
| 98 | 1H NMR (400 MHz, acetonitrile-d3) δ ppm 7.57-7.44 (m, 4 H), 7.35-7.44 (m, 1 H), 7.34-7.20 (m, 2 H), 7.13-7.08 (m, 1 H), 5.89-5.75 (m, 1 H), 5.33-5.08 (m, 2 H), 4.95-4.61 (m, 1 H), 4.41-4.16 (m, 1 H), 3.87-3.81 (m, 1 H), 3.47-3.42 (m, 1 H), 3.13 (dd, 1 H), 3.10-2.92 (m, 1 H), 2.92-2.73 (m, 1 H), 1.03-0.93 (m, 1 H), 0.78-0.63 (m, 3 H). Exchangeable NH signal not observed. LCMS (method K): m/z 519 (M + H) + (ES+), at 3.09 min |
| 99 | 1H NMR (400 MHZ, methanol-d4) δ ppm 7.52 (br d, 2 H), 7.42 (t, 2 H), 7.37-7.21 (m, 3 H), 7.17-7.09 (m, 1 H), 4.69-4.58 (m, 1 H), 4.16 (d, 1 H), 3.68-3.43 (m, 3 H), 3.27 (s, 1 H), 3.11-2.88 (m, 5 H), 1.07-0.96 (m, 1 H), 0.75-0.62 (m, 2 H), 0.60-0.50 (m, 1 H). Two exchangeable NH signals not observed. LCMS (method J): m/z 500 (M + H) + (ES+), at 2.64 min |
| 100 | LCMS (method J): m/z 502 (M + H) + (ES+), at 2.45 min |
| 101 | LCMS (method K): m/z 478 (M + H) + (ES+), at 2.92 min |
| 102 | LCMS (method K): m/z 502 (M + H) + (ES+), at 2.94 min |
| 103 | LCMS (method K): m/z 502 (M + H) + (ES+), at 3.00 min |
| 104 | 1H NMR (400 MHZ, DMSO-d6) δ ppm 7.55-7.49 (m, 2 H), 7.48-7.42 (m, 2 H), 7.41-7.35 (m, 1 H), 7.31-7.23 (m, 2 H), 7.15-7.10 (m, 1 H), 6.04-5.96 (m, 1 H), 4.59-4.52 (m, 1 H), 4.01-3.96 (m, 1 H), 3.54-3.48 (m, 1 H), 3.33-3.26 (m, 1 H), 3.24-3.11 (m, 3 H), 3.00-2.95 (m, 3 H), 2.95-2.85 (m, 1 H), 2.81-2.72 (m, 1 H), 1.05-0.97 (m, 1 H), 0.80-0.66 (m, 2 H), 0.61-0.41 (m, 5 H). LCMS (method J): m/z 490 (M + H) + (ES+), at 2.50 min |

TABLE A-continued

| Ex. | Structural Analysis |
|---|---|
| Examples 1-32 Experimental Details | |
| 105 | LCMS (method J): m/z 494 (M + H) + (ES+), at 2.64 min |
| 106 | LCMS (method J): m/z 475 (M + H) + (ES+), at 2.73 min |
| 107 | LCMS (method K): m/z 477 (M + H) + (ES+), at 2.70 min |
| 108 | LCMS (method J): m/z 491 (M + H) + (ES+), at 2.61 min |
| 109 | LCMS (method J): m/z 464 (M + H) + (ES+), at 2.46 min |
| 110 | 1H NMR (400 MHZ, DMSO-d6)- δ ppm 7.55-7.36 (m, 6 H), 7.35-7.25 (m, 2 H), 7.22-7.10 (m, 1 H), 4.62-4.52 (m, 1 H), 3.74-3.60 (m, 2 H), 3.02 (br d, 1 H), 2.97-2.90 (m, 1 H), 2.89-2.85 (m, 3 H), 2.84-2.76 (m, 1 H), 2.60 (s, 6 H), 1.06-0.48 (m, 4 H) LCMS (method J): m/z 446 (M + H) + (ES+), at 2.55 min |
| 111 | LCMS (method K): m/z 460 (M + H) + (ES+), at 2.94 min |
| 112 | LCMS (method K): m/z 482 (M + H) + (ES+), at 2.91 min |
| 113 | LCMS (method K): m/z 437 (M + H) + (ES+), at 2.95 min |
| 114 | 1H NMR (400 MHz, methanol-d4) δ ppm 7.73-7.17 (m, 9H), 5.36-4.75 (m, 1H), 4.61-3.88 (m, 5H), 3.71-3.34 (m, 1H), 3.29-2.20 (m, 5H), 1.37 (dd, 3H), 1.27 (dd, 3H), 1.19-1.05 (m, 1H), 0.89-0.56 (m, 3H). Exchangeable NH signal not observed. LCMS (method K): m/z 469 (M + H) + (ES+), at 2.85 min |
| 115 | 1H NMR (400 MHz, methanol-d4) δ ppm 7.74-7.14 (m, 9H), 6.59 (dt, 1H), 5.30-3.82 (m, 6H), 3.69-2.69 (m, 4H), 2.51-2.24 (m, 1H), 1.20-1.00 (m, 1H), 0.89-0.57 (m, 3H). Exchangeable NH signal not observed. LCMS (method K): m/z 477 (M + H) + (ES+), at 2.74 min |
| 116 | 1H NMR (400 MHz, methanol-(4) δ ppm 7.58-7.54 (m, 2H), 7.46-7.41 (m, 2H), 7.38-7.30 (m, 2H), 7.28-7.23 (m, 1H), 7.20-7.15 (m, 1H), 4.65 (ddd, 1H), 3.95 (d, 1H), 3.81 (q, 2H), 3.60 (q, 2H), 3.44 (d, 1H), 3.30 (br s, 1H), 3.07 (dd, 1H), 2.92-2.83 (m, 1H), 2.81-2.76 (m, 6H), 2.04-1.94 (m, 2H), 1.07 (dt, 1H), 0.73-0.55 (m, 3H). Exchangeable NH signal not observed. LCMS (method K): m/z 487 (M + H) + (ES+), at 3.04 min |
| 117 | LCMS (method K): m/z 505 (M + H) + (ES+), at 3.03 min |
| 118 | LCMS (method J): m/z 517 (M + H) + (ES+), at 2.62 min |
| 119 | LCMS (method J): m/z 530 (M + H) + (ES+), at 2.75 min |
| 120 | LCMS (method K): m/z 502 (M + H) + (ES+), at 3.00 min. |
| 121 | LCMS (method K): m/z 475 (M + H) + (ES+), at 2.95 min |
| 122 | LCMS (method J): m/z 495 (M + H) + (ES+), at 2.44 min |
| 123 | LCMS (method K): m/z 513 (M + H) + (ES+), at 2.91 min |
| 124 | LCMS (method J): m/z 524 (M + H) + (ES+), at 2.58 min |
| 125 | LCMS (method J): m/z 502 (M + H) + (ES+), at 2.64 min |
| 126 | 1H NMR (400 MHz, methanol-d4) δ ppm 7.56-7.02 (m, 7H), 5.28-4.83 (m, 2H), 4.61-4.27 (m, 2H), 4.24-3.90 (m, 2H), 3.77-3.13 (m, 3H), 3.03-2.85 (m, 1H), 2.82 (s, 3H), 2.81 (s, 3H), 2.56-2.27 (m, 1H), 1.20 0.98 (m, 1H), 0.86-0.52 (m, 3H). Exchangeable NH signal not observed. LCMS (method J): m/z 506 (M + H) + (ES+), at 2.52 min |
| 127 | LCMS (method K): m/z 524 (M + H) + (ES+), at 2.94 min |
| 128 | 1H NMR (400 MHz, methanol-d4) δ ppm 7.46-7.09 (m, 5H), 6.97 (qt, 1H), 5.35-5.19 (m, 2H), 4.57-4.17 (m, 3H), 4.15-4.02 (m, 1H), 3.94-3.67 (m, 1H), 3.37 (br s, 1H), 3.27-3.20 (m, 1H), 3.18-3.09 (m, 1H), 3.02-2.88 (m, 1H), 2.86-2.76 (m, 1H), 2.50-2.31 (m, 1H), 1.08 (br dd, 1H), 0.81-0.60 (m, 3H). Exchangeable NH signal not observed. LCMS (method K): m/z 513 (M + H) + (ES+), at 2.90 min |
| 129 | 1H NMR (400 MHz, chloroform-d) δ ppm 7.51-7.35 (m, 2H), 7.33-7.27 (m, 2H), 7.26-7.17 (m, 2H), 7.14-7.04 (m, 1H), 5.28-5.09 (m, 1H), 4.83-4.49 (m, 2H), 4.45-4.28 (m, 1H), 4.19-4.05 (m, 1H), 4.00-3.80 (m, 1H), 3.33-3.04 (m, 3H), 2.98-2.63 (m, 4H), 1.25-1.17 (m, 1H), 1.15-1.07 (m, 2H), 0.81-0.58 (m, 3H), 0.43-0.34 (m, 1H). Exchangeable NH signal not observed. LCMS (method J): m/z 491 (M + H) + (ES+), at 2.48 min |
| 130 | LCMS (method J): m/z 491 (M + H) + (ES+), at 2.43 min |
| 131 | 1H NMR (400 MHz, methanol-d4) δ ppm 7.47-7.41 (m, 1H), 7.37-7.27 (m, 4H), 7.17-7.06 (m, 2H), 5.04-4.95 (m, 1H), 4.23 (br d, 1H), 4.05 (br d, 1H), 3.78 (br d, 1H), 3.21-3.12 (m, 1H), 2.92 (s, 3H), 2.87 (br s, 1H), 1.27 (s, 3H), 1.17 (s, 3H), 1.06-1.00 (m, 1H), 0.71-0.61 (m, 3H). Exchangeable proton signals not observed. LCMS (method J): m/z 479 (M + H) + (ES+), at 2.55 min |
| 132 | 1H NMR (400 MHz, methanol-d4) δ ppm 7.66-6.91 (m, 7H), 5.39-5.19 (m, 3H), 4.65-3.92 (m, 5H), 3.73-2.71 (m, 4H), 2.56-2.21 (m, 1H), 1.21-0.99 (m, 1H), 0.87-0.56 (m, 4H). LCMS (method K): m/z 495 (M + H) + (ES+), at 2.85 min |
| 133 | 1H NMR (400 MHz, methanol-d4) δ ppm 7.47-6.75 (m, 8H), |

TABLE A-continued

| Examples 1-32 Experimental Details | |
|---|---|
| Ex. | Structural Analysis |
| | 5.22-4.69 (m, 3H), 4.36-3.14 (m, 4H), 2.98-2.60 (m, 3H), 0.93-0.77 (m, 1H), 0.67-0.35 (m, 3H), 0.28-0.06 (m, 1H), 0.06-−0.08 (m, 3H) Exchangeable proton signals not observed. LCMS (method K): m/z 491 (M + H) + (ES+), at 2.96 min |
| 134 | 1H NMR (400 MHz, methanol-d4) δ ppm 7.54 (br d, 2H), 7.45-7.39 (m, 2 H), 7.37-7.31 (m, 1 H), 7.31-7.22 (m, 2 H), 7.19-7.05 (m, 1 H), 5.22 (s, 1 H), 5.11 (s, 1 H), 4.99 (br s, 1 H), 4.25 (br d, 1 H), 4.06 (br d, 1 H), 3.78 (br d, 1 H), 3.16 (br dd, 1 H), 3.00-2.86 (m, 1 H), 1.37-1.10 (m, 6 H), 1.09-1.02 (m, 1 H),0.75-0.60 (m, 3 H). Exchangeable proton signals not observed. LCMS (method K): m/z 479 (M + H) + (ES+), at 2.97 min |
| 135 | LCMS (method K): m/z 476 (M + H) + (ES+), at 3.01 min |
| 136 | LCMS (method K): m/z 506 (M + H) + (ES+), at 2.96 min |
| 137 | 1H NMR (400 MHz, methanol-d4) δ ppm 7.49-7.24 (m, 5H), 7.20-7.05 (m, 2H), 5.35-5.30 (m, 1H), 5.24-5.19 (m, 1H), 4.58-3.67 (m, 6H), 3.38-2.29 (m, 5H), 1.12-1.05 (m, 1H), 0.80-0.62 (m, 3H). Exchangeable NH signal not observed. LCMS (method K): m/z 495 (M + H) + (ES+), at 2.78 min |
| 138 | LCMS (method K): m/z 490 (M + H) + (ES+), at 3.02 min |
| 139 | LCMS (method K): m/z 475 (M + H) + (ES+), at 3.06 min |
| 140 | LCMS (method K): m/z 506 (M + H) + (ES+), at 2.83 min |
| 141 | LCMS (method K): m/z 495 (M + H) +(ES+), at 2.72 min |
| 142 | LCMS (method K): m/z 495 (M + H) + (ES+), at 2.74 min |
| 143 | LCMS (method J): m/z 473 (M + H) + (ES+), at 2.48 min |
| 144 | 1H NMR (400 MHZ, DMSO-d6) δ ppm 8.86-8.36 (m, 1H), 7.57-7.35 (m, 4H), 7.35-7.16 (m, 1H), 7.15-6.85 (m, 2H), 6.97 (m, 1H), 5.09 (dd, 1 H), 4.81-4.59 (m, 1H), 4.47-4.33 (m, 1H), 4.28-3.74 (m, 3H), 3.60 (d, 1H), 3.25-3.13 (m, 1H), 3.11-2.97 (m, 1H), 2.83-2.64 (m, 2H), 2.34-2.27 (m, 1H), 1.26-1.05 (m, 1H), 0.75-0.42 (m, 3H). LCMS (method J): m/z 495 (M + H) + (ES+), at 2.51 min |
| 145 | 1H NMR (400 MHZ, DMSO-d6) δ ppm 7.86 (br s, 1 H), 7.59-7.45 (m, 4 H), 7.45-7.37 (m, 1 H), 7.29-7.13 (m, 2 H), 5.30-5.52 (m, 2 H), 5.11-4.67 (m, 1 H), 4.48-4.37 (m, 1 H), 4.31-4.16 (m, 1 H), 4.13-3.99 (m, 1 H), 3.85-3.54 (m, 1 H), 3.30-3.18 (m, 2 H), 3.10-2.98 (m, 1 H), 2.82-2.63 (m, 2 H), 2.46-2.28 (m, 1 H), 1.07 (br d, 1 H), 0.73-0.43 (m, 3 H). |

TABLE A-continued

| Examples 1-32 Experimental Details | |
|---|---|
| Ex. | Structural Analysis |
| | LCMS (method K): m/z 495 (M + H) + (ES+), at 2.87 min |
| 146 | 1H NMR (400 MHz, DMSO-d6) δ ppm 7.58-7.46 (m, 4 H), 7.45-7.38 (m, 1 H), 7.29-7.15 (m, 3 H), 5.16-5.06 (m, 1 H), 4.71-4.59 (m, 1 H), 4.50-4.35 (m, 1 H), 4.30-3.75 (m, 2 H), 3.95-3.59 (d, 1 H), 3.25-3.16 (m, 1 H), 3.12-2.98 (m, 3 H), 2.80-2.63 (m, 2 H), 2.45-2.27 (m, 1 H), 1.22 (t, 3 H), 1.09-1.00 (m, 1 H), 0.70-0.40 (m, 3 H). LCMS (method J): m/z 491 (M + H) + (ES+), at 2.50 min |
| 147 | 1H NMR (400 MHz, acetonitrile-d3) δ ppm 7.56-7.44 (m, 1 H), 7.43-7.28 (m, 2 H), 7.24-7.03 (m, 3 H), 5.19-5.02 (m, 2 H), 4.80-4.05 (m, 3 H), 3.85-3.63 (m, 1 H), 3.24-3.14 (m, 1 H), 3.13-2.95 (m, 3 H), 2.91-2.67 (m, 2 H), 2.59-2.39 (m, 1 H), 1.33-1.18 (m, 3 H), 0.96-0.84 (m, 1 H), 0.75-0.51 (m, 3 H) Exchangeable NH signal not observed LCMS (method K): m/z 509 (M + H) + (ES+), at 2.89 min |
| 148 | LCMS (method J): m/z 513 (M + H) + (ES+), at 2.50 min |
| 149 | LCMS (method J): m/z 509 (M + H) + (ES+), at 2.49 min |
| 150 | LCMS (method J): m/z 501 (M + H) + (ES+), at 2.55 min |
| 151 | LCMS (method K): m/z 476 (M + H) + (ES+), at 2.98 min |
| 152 | LCMS (method J): m/z 467 (M + H) + (ES+), at 2.62 min |
| 153 | LCMS (method J): m/z 483 (M + H) + (ES+), at 2.52 min |
| 154 | 1H NMR (400 MHz, methanol-d4) δ ppm 7.60-7.04 (m, 7H), 6.67 (td, 1H), 5.30-4.88 (m, 1H), 4.66-3.93 (m, 4H), 3.72-2.73 (m, 5H), 2.54-2.26 (m, 1H), 1.24-1.01 (m, 1H), 0.94-0.53 (m, 3H). Exchangeable NH signal not observed. LCMS (method J): m/z 513 (M + H) + (ES+), at 2.58 min |
| 155 | LCMS (method K): m/z 513 (M + H) + (ES+), at 2.80 min |
| 156 | LCMS (method J): m/z 494 (M + H) + (ES+), at 2.50 min |
| 157 | LCMS (method J): m/z 508 (M + H) + (ES+), at 2.67 min |
| 158 | LCMS (method J): m/z 496 (M + H) + (ES+), at 2.63 min |
| 159 | LCMS (method K): m/z 509 (M + H) + (ES+), at 2.90 min |
| 160 | LCMS (method K): m/z 485 (M + H) + (ES+), at 2.95 min |
| 161 | LCMS (method J): m/z 493 (M + H) + (ES+), at 2.48 min |
| 162 | 1H NMR (400 MHz, chloroform-d) δ ppm 7.56-7.31 (m, 7H), 7.24-7.19 (m, 1H), 5.30-5.15 (m, 1H), 4.83-4.36 (m, 2H), 4.28-4.06 (m, 2H), 4.00-3.82 (m, 1H), 3.36-3.22 (m, 1H), 3.18-3.03 (m, 2H), 3.03-2.78 (m, 3 H), 1.22-1.14 (m, 6 H), 0.90-0.55 (m, 3 H), 0.41-0.29 (m, 1 H). Exchangeable NH signal not observed. |

TABLE A-continued

Examples 1-32 Experimental Details

| Ex. | Structural Analysis |
|---|---|
| | LCMS (method K): m/z 487 (M + H) + (ES+), at 2.87 min |
| 163 | LCMS (method K): m/z 513 (M + H) + (ES+), at 2.75 min |
| 164 | LCMS (method K): m/z 515 (M + H) + (ES+), at 3.03 min |
| 165 | LCMS (method K): m/z 518 (M + H) + (ES+), at 3.01 min |
| 166 | LCMS (method J): m/z 526 (M + H) + (ES+), at 2.72 min |
| 167 | LCMS (method K): m/z 513 (M + H) + (ES+), at 2.49 min |
| 168 | LCMS (method J): m/z 513 (M + H) + (ES+), at 2.47 min |
| 169 | LCMS (method K): m/z 513 (M + H) + (ES+), at 2.81 min |
| 170 | 1H NMR (400 MHZ, DMSO-d6) δ ppm 8.78-8.60 (m, 1 H), 7.55-7.43 (m, 4 H), 7.42-7.32 (m, 1 H), 7.31-7.18 (m, 2 H), 7.15-6.91 (m, 2 H), 4.79 (ddd, 1 H), 4.00 (dd, 1 H), 3.94-3.77 (m, 2 H), 3.53-3.27 (m, 2 H), 3.06 (br dd, 1 H), 2.89-2.72 (m, 1 H), 1.27-1.04 (m, 1 H), 0.90-0.59 (m, 3 H), 0.57-0.46 (m, 1 H), 0.32-0.03 (m, 4 H). LCMS (method K): m/z 509 (M + H) + (ES+), at 2.94 min |
| 171 | 1H NMR (400 MHZ, DMSO-d6) δ ppm 8.63 (br d, 1 H), 7.47-7.24 (m, 5 H), 7.21-7.14 (m, 1 H), 7.06 (br s, 1 H), 5.09-4.02 (m, 4 H), 4.01-3.56 (m, 1 H), 3.33 (br s, 1 H), 3.26-3.16 (m, 1 H), 3.13-2.95 (m, 1 H), 2.84-2.60 (m, 2 H), 2.38-2.26 (m, 1 H), 1.16-1.02 (m, 1 H), 0.76-0.55 (m, 2 H), 0.53-0.39 (m, 1 H). LCMS (method K): m/z 531 (M + H) + (ES+), at 2.77 min |
| 172 | LCMS (method K): m/z 531 (M + H) + (ES+), at 2.77 min |
| 173 | LCMS (method K): m/z 500 (M + H) + (ES+), at 2.75 min |
| 174 | LCMS (method K): m/z 501 (M + H) + (ES+), at 2.82 min |
| 175 | 1H NMR (400 MHz, acetonitrile-d3) δ ppm 7.41-7.32 (m, 2 H), 7.26-7.15 (m, 3 H), 7.04-6.95 (m, 1 H), 6.60-6.27 (m, 1 H), 5.08-4.02 (m, 5 H), 3.88-3.61 (m, 1 H), 3.28-3.19 (m, 1 H), 3.09 (br dd, 1 H), 2.92-2.81 (m, 1 H), 2.74-2.65 (m, 1 H), 2.46-2.37 (m, 1 H), 1.01-0.93 (m, 1 H), 0.70-0.58 (m, 3 H). Exchangeable NH signal not observed. LCMS (method K): m/z 531 (M + H) + (ES+), at 2.85 min |
| 176 | 1H NMR (400 MHZ, DMSO-d6): δ ppm 8.61 (br d, 1H), 7.62-7.49 (m, 1H), 7.46-7.34 (m, 2H), 7.32-7.17 (m, 3H), 7.12-6.83 (m, 1H), 5.11 (dd, 1H), 4.71-4.60 (m, 1H), 4.46-4.36 (m, 1H), 4.31-4.14 (m, 1H), 4.13-3.96 (m, 1H), 3.62-3.55 (m, 1H), 3.24 (d, 1H), 3.03 (br dd, 1H), 2.82-2.63 (m, 2H), 2.43-2.26 (m, 1H), 1.17-1.02 (m, 1H), 0.74-0.56 (m, 2H), 0.55-0.44 (m, 1H). |

TABLE A-continued

Examples 1-32 Experimental Details

| Ex. | Structural Analysis |
|---|---|
| | LCMS (method J): m/z 531 (M + H) + (ES+), at 2.67 min |
| 177 | 1H NMR (400 MHz, chloroform-d) δ ppm 7.53-7.39 (m, 2H), 7.36-7.28 (m, 2H), 7.24 (br t, 2H), 7.09 (td, 1H), 5.01-5.01 (m, 2H), 4.70 (br s, 1H), 4.52-4.36 (m, 1H), 4.23-4.18 (m, 1H), 3.96 (br d, 1H), 3.72 (br s, 1H), 3.43 (br d, 1H), 3.29-3.17 (m, 1H), 3.06 (br d, 1H), 1.45 (d, 6H), 0.86-0.66 (m, 3H), 0.47 (br dd, 1H). LCMS (method K): m/z 497 (M + H) + (ES+), at 2.98 min |
| 178 | LCMS (method K): m/z 479 (M + H) + (ES+), at 2.85 min |
| 179 | LCMS (method K): m/z 503 (M + H) + (ES+), at 3.25 min |
| 180 | 1H NMR (400 MHz, methanol-(4) δ ppm 7.54-7.47 (m, 2H), 7.42 (br t, 2H), 7.38-7.08 (m, 4H), 5.53-5.01 (m, 3H), 4.29-3.50 (m, 3H), 3.21-2.90 (m, 5H), 1.14-0.89 (m, 3H), 0.78-0.18 (m, 5H). Exchangeable NH signal not observed. LCMS (method K): m/z 491 (M + H) + (ES+), at 3.13 min |
| 181 | 1H NMR (400 MHz, methanol-d4) δ ppm 7.54 (br d, 2 H), 7.46-7.21 (m, 5 H), 7.17-7.10 (m, 1 H), 5.36-5.14 (m, 2 H), 4.22-4.09 (m, 1 H), 3.75-3.56 (m, 2 H), 3.15 (br d, 1 H), 2.97 (br d, 1 H), 2.59-2.30 (m, 4 H), 2.18-1.95 (m, 1 H), 1.77-1.56 (m, 1 H), 1.31-1.06 (m, 2 H), 0.84-0.65 (m, 3 H). Exchangeable NH signal not observed. LCMS (method K): m/z 500 (M + H) + (ES+), at 3.20 min |
| 182 | LCMS (method K): m/z 511 (M + H) + (ES+), at 3.08 min |
| 183 | LCMS (method K): m/z 513 (M + H) + (ES+), at 2.74 min |
| 184 | LCMS (method K): m/z 493 (M + H) + (ES+), at 2.97 min |
| 185 | 1H NMR (400 MHz, acetonitrile-d3) δ ppm 7.41-7.30 (m, 2 H), 7.27-7.13 (m, 3 H), 6.99 (dddd, 1 H), 5.14-4.04 (m, 5 H), 3.86-3.62 (m, 1 H), 3.25-3.13 (m, 1 H), 3.10 (br dd, 1 H), 3.04-2.95 (m, 2 H), 2.91-2.79 (m, 1 H), 2.77-2.66 (m, 1 H), 2.52-2.39 (m, 1 H), 1.29-1.21 (m, 3 H), 0.96-0.88 (m, 1 H), 0.74-0.54 (m, 3 H). Exchangeable NH signal not observed. LCMS (method K): m/z 509 (M + H) + (ES+), at 2.88 min |
| 186 | LCMS (method K): m/z 515 (M + H) + (ES+), at 2.94 min |
| 187 | LCMS (method K): m/z 500 (M + H) + (ES+), at 2.99 min |
| 188 | LCMS (method K): m/z 493 (M + H) + (ES+), at 3.09 min |
| 189 | LCMS (method K): m/z 493 (M + H) + (ES+), at 3.07 min |
| 190 | LCMS (method K): m/z 501 (M + H) + (ES+), at 2.75 min |
| 191 | LCMS (method J): m/z 518 (M + H) + (ES+), at 2.74 min |

TABLE A-continued

Examples 1-32 Experimental Details

| Ex. | Structural Analysis |
|---|---|
| 192 | 1H NMR (400 MHz, methanol-d4) δ ppm 7.34-7.27 (m, 2H), 7.21-7.11 (m, 3H), 6.95 (tt,1H), 5.25 (s, 1H), 5.13 (s, 1H), 4.98 (br s, 1H), 4.25 (br d, 1H), 4.07 (br d, 1H), 3.79 (br d, 1H), 3.23-3.09 (m, 1H), 2.96-2.84 (m, 1H), 1.25 (s, 3H), 1.13 (s, 3H), 1.06 (br dd, 1H), 0.73-0.63 (m, 3H). Exchangeable proton signals not observed. LCMS (method K): m/z 515 (M + H) + (ES+), at 3.04 min |
| 193 | 1H NMR (400 MHz, methanol-d4) δ ppm 7.57-7.48 (m, 2H), 7.47-7.12 (m, 6H), 5.55-3.92 (m, 6 H), 3.66-3.23 (d, 2H), 3.17-3.06 (m, 1 H), 3.01-2.90 (m, 1 H), 2.86-2.70 (m, 1 H), 2.50-2.29 (m, 1H), 1.74-1.62 (m, 3 H), 1.12-1.05 (m, 1 H), 0.80-0.61 (m, 3 H). Exchangeable NH signal not observed. LCMS (method K): m/z 491 (M + H) + (ES+), at 2.85 min |
| 194 | 1H NMR (400 MHz, methanol-d4) δ ppm 7.58-7.48 (m, 2 H), 7.47-7.12 (m, 6 H), 5.58-3.67 (m, 7 H), 3.35-3.23 (m, 1 H), 3.19-3.10 (m, 1 H), 2.98-2.88 (m, 1 H), 2.85-2.71 (m, 1 H), 2.49-2.29 (m, 1 H), 1.78-1.65 (m, 3 H), 1.12-1.04 (m, 1 H), 0.78-0.60 (m, 3 H). Exchangeable NH signal not observed. LCMS (method K): m/z 491 (M + H) + (ES+), at 2.86 min |
| 195 | 1H NMR (400 MHZ, methanol-d4) δ ppm 7.29 (br s, 2H), 7.23-7.09 (m, 3H), 6.95 (br t, 1H), 6.74-6.39 (m, 1H), 4.99 (br s, 1H), 4.27 (br d, 1H), 4.09 (br s, 1H), 3.80 (br d, 1H), 3.17 (br d, 1H), 2.96-2.81 (m, 1H), 1.37-1.01 (m, 7H), 0.69 (br s, 3H). Exchangeable proton signals not observed. LCMS (method J): m/z 533 (M + H) + (ES+), at 2.74 min |
| 196 | LCMS (method J): m/z 527 (M + H) + (ES+), at 2.51 min |
| 197 | LCMS (method J): m/z 545 (M + H) + (ES+), at 2.64 min |
| 198 | LCMS (method J): m/z 519 (M + H) + (ES+), at 2.65 min |
| 199 | LCMS (method K): m/z 512 (M + H) + (ES+), at 2.87 min |
| 200 | LCMS (method K): m/z 536 (M + H) + (ES+), at 3.07 min |
| 201 | LCMS (method K): m/z 511 (M + H) + (ES+), at 3.06 min |
| 202 | LCMS (method J): m/z 491 (M + H) + (ES+), at 2.65 min |
| 203 | LCMS (method J): m/z 491 (M + H) + (ES+), at 2.66 min |
| 204 | LCMS (method K): m/z 489 (M + H) + (ES+), at 2.87 min |
| 205 | LCMS (method K): m/z 496 (M + H) + (ES+), at 3.14 min |
| 206 | 1H NMR (400 MHz, acetonitrile-d3) δ ppm 7.57-7.51 (m, 2 H), 7.50-7.43 (m, 2 H), 7.42- 7.36 (m, 1 H), 7.34-7.24 (m, 2 H), 7.19-7.12 (m, 1 H), 5.25-5.15 (m, 1 H), 5.13-5.04 (m, 1 H), 4.74 (br t, 1 H), 4.50-4.29 (m, 1 H), 4.14 (d, 1 H), 3.58 (d, 1 H), 3.20-2.99 (m, 3 H), 2.95-2.81 (m, 2 H), 1.15-1.04 (m, 3 H), 0.96-0.85 (m, 1 H), 0.68-0.52 (m, 3 H). Exchangeable proton signals not observed. LCMS (method K): m/z 496 (M + H) + (ES+), at 3.14 min |
| 207 | LCMS (method K): m/z 500 (M + H) + (ES+), at 3.11 min |
| 208 | LCMS (method K): m/z 536 (M + H) + (ES+), at 3.11 min |
| 209 | LCMS (method J): m/z 532 (M + H) + (ES+), at 2.79 min |
| 210 | LCMS (method K): m/z 515 (M + H) + (ES+), at 3.03 min |
| 211 | LCMS (method J): m/z 518 (M + H) + (ES+), at 2.68 min |
| 212 | LCMS (method K): m/z 514 (M + H) + (ES+), at 3.25 min |
| 213 | LCMS (method J): m/z 495 (M + H) + (ES+), at 2.54 min |
| 214 | LCMS (method J): m/z 513 (M + H) + (ES+), at 2.60 min |
| 215 | LCMS (method J): m/z 538 (M + H) + (ES+), at 2.69 min |
| 216 | LCMS (method K): m/z 503 (M + H) + (ES+), at 3.16 min |
| 217 | LCMS (method K): m/z 531 (M + H) + (ES+), at 3.11 min |
| 218 | LCMS (method J): m/z 531 (M + H) + (ES+), at 2.53 min |
| 219 | LCMS (method J): m/z 514 (M + H) + (ES+), at 2.71 min |
| 220 | 1H NMR (400 MHz, methanol-d4) δ ppm 7.41-6.95 (m, 5H), 6.67 (t, 1H), 5.26 (dd, 1H), 4.66-3.93 (m, 4H), 3.73-2.35 (m, 6H), 1.17-1.06 (m, 1H), 0.72 (q, 3H). Exchangeable NH signal not observed. LCMS (method K): m/z 549 (M + H) + (ES+), at 2.91 min |
| 221 | 1H NMR (400 MHZ, methanol-d4) δ 7.34-6.95 (m, 5H), 6.66 (t, 1H), 4.65-3.83 (m, 5H), 3.63-2.72 (m, 4H), 1.25-1.03 (m, 1H), 0.90-0.59 (m, 3H). Exchangeable signals not observed. LCMS (method K): m/z 555 (M + H) + (ES+), at 2.96 min |
| 222 | LCMS (method K): m/z 523 (M + H) + (ES+), at 2.97 min |
| 223 | LCMS (method )): m/z 521 (M + H) + (ES+), at 2.61 min |
| 224 | LCMS (method K): m/z 497 (M + H) + (ES+), at 2.61 min |
| 225 | 1H NMR (400 MHz, chloroform-d) δ ppm 7.55-7.49 (m, 2H), 7.49-7.42 (m, 2H), 7.42-7.36 (m, 1H), 7.36-7.28 (m, 2H), 7.26-7.19 (m, 1H), 5.03-4.75 (m, 3H), 4.73-4.47 (m, 2H), 4.27-4.18 (m, 1H), 4.06-3.92 (m, 1H), 3.72 (q, 1H), 3.38-3.21 (m, 2H), 3.13-2.99 (m, 2H), 0.81-0.29 (m, 4H). Exchangeable NH signal not observed. |

TABLE A-continued

| Ex. | Structural Analysis |
|---|---|
| | Examples 1-32 Experimental Details |
| | LCMS (method K): m/z 502 (M + H) + (ES+), at 3.27 min |
| 226 | 1H NMR (400 MHz, chloroform-d) δ ppm 7.57-7.48 (m, 2H), 7.44 (t, 2H), 7.40-7.29 (m, 3H), 7.26-7.15 (m, 1H), 5.24-4.85 (m, 2H), 4.83-4.62 (m, 2H), 4.37-4.15 (m, 2H), 3.80-3.66 (m, 2H), 3.28-3.13 (m, 2H), 3.12-2.93 (m, 2H), 0.92-0.60 (m, 3H), 0.54-0.39 (m, 1H). Exchangeable NH signal not observed. LCMS (method K): m/z 502 (M + H) + (ES+), at 3.26 min |
| 227 | LCMS (method K): m/z 531 (M + H) + (ES+), at 2.97 min |
| 228 | 1H NMR (400 MHz, chloroform-d) δ ppm 7.54-7.36 (m, 5H), 7.10-6.99 (m, 2H), 5.07-4.75 (m, 2H), 4.74-4.66 (m, 1H), 4.64-4.48 (m, 1H), 4.26 (dd, 1H), 3.72-3.47 (m, 2H), 3.25-3.11 (m, 1H), 3.08-2.95 (m, 2H), 1.14-0.97 (m, 2H), 0.80-0.60 (m, 5H), 0.38-0.26 (m, 1H). Exchangeable proton signals not observed. LCMS (method K): m/z 526 (M + H) + (ES+), at 3.10 min |
| 229 | LCMS (method K): m/z 494 (M + H) + (ES+), at 2.92 min |
| 230 | 1H NMR (400 MHz, chloroform-d) δ ppm 7.49 (br t, 1H), 7.27 (s, 1H), 7.23-7.17 (m, 1H), 7.08 (br d, 2H), 6.88-6.81 (m, 1H), 4.92-4.82 (m, 1H), 4.61-4.50 (m, 1H), 4.16-4.08 (m, 1H), 4.01-3.93 (m, 1H), 3.75 (s, 1H), 3.45 (br d, 1H), 3.23 (br dd, 1H), 3.03-2.94 (m, 1H), 1.86-1.76 (m, 1H), 1.46-1.43 (m, 3H), 1.42 (s, 3H), 1.13-1.04 (m, 1H), 0.98 (br dd, 1H), 0.92-0.75 (m, 4H), 0.71-0.62 (m, 1H), 0.52-0.45 (m, 1H). LCMS (method K): m/z 523 (M + H) + (ES+), at 3.09 min |
| 231 | 1H NMR (400 MHz, methanol-d4) δ ppm 7.37-7.28 (m, 2H), 7.22-7.12 (m, 3H), 6.96 (tt,1H), 5.31 (s, 1H), 5.20 (s, 1H), 4.17 (d, 1H), 3.70-3.61 (m, 2H), 3.22-3.12 (m, 1H), 2.96-2.88 (m, 1H), 2.59-2.31 (m, 5H), 2.18-2.07 (m, 1H), 1.78-1.68 (m, 1H), 1.14-1.07 (m, 1H), 0.81-0.71 (m, 3H). Exchangeable NH signal not observed. LCMS (method K): m/z 536 (M + H) + (ES+), at 3.29 min |
| 232 | LCMS (method K): m/z 503 (M + H) + (ES+), at 3.08 min |
| 233 | LCMS (method K): m/z 503 (M + H) + (ES+), at 3.16 min |
| 234 | 1H NMR (400 MHz, methanol-d4) δ ppm 7.53 (br d, 2H), 7.42 (t, 2H), 7.37-7.31 (m, 1H), 7.31-7.22 (m, 2H), 7.17-7.08 (m, 1H), 5.77 (br t, 1H), 5.20 (br d, 2H), 5.00 (br d, 1H), 4.39 (br d, 1H), 4.13-4.01 (m, 1H), 3.74 (br d, 1H), 3.17-3.10 (m, 1H), 3.02-2.88 (m, 1H), 1.08 (s, 4H), 0.75-0.58 (m, 3H). Exchangeable proton signals not observed. LCMS (method J): m/z 515 (M + H) + (ES+), at 2.69 min |
| 235 | 1H NMR (400 MHZ, chloroform-d) δ ppm 7.42-7.35 (m, 1H), 7.32-7.29 (m, 1H), 7.25-7.19 (m, 1H), 7.04 (br d, 2H), 6.88-6.80 (m, 1H), 5.99 (t, 1H), 4.85 (br s, 1H), 4.65-4.49 (m, 2H), 4.32 (br t, 1H), 3.70-3.63 (m, 1H), 3.62-3.47 (m, 2H), 3.26-3.16 (m, 1H), 3.11-2.99 (m, 2H), 1.09-0.96 (m, 2H), 0.80-0.64 (m, 5H), 0.41-0.29 (m, 1H). LCMS (method J): m/z 562 (M + H) + (ES+), at 2.87 min |

Example 83. Biological Activity of the Compounds of the Present Disclosure

The biological activity of the compounds of the present disclosure was determined utilizing the assay described herein.

Orexin Type 2 Receptor Agonist Activity of Exemplary Compounds.

Stable cell line generation. Obtainment of cells stably expressing either human orexin type 2 or human orexin type 1 receptor: to obtain a stable cell line the Orexin receptor cDNA was inserted into pcDNA3.1(+) plasmid vector and clones identified by G418 drug resistance selection. Clones demonstrating functional activity Orexin A were selected and taken into continuous culture. A single clone for OX2R—CHO and OX1R—CHO were grown in bulk and frozen to generate a cell bank for routine screening.

Measurement of orexin type 2 receptor agonist activity. Chinese hamster ovary (CHO) cells expressing human orexin type 2 receptor (hOX2R) or human orexin type 2 receptor (hOX1R) were seeded in each well of 384 well black clear bottom plates (BD Flacon) at 10,000 cells per well and cultured for 24 hr in an Ham's F12 (Gibco) medium containing 10% fetal calf serum (Sigma Aldrich) under the conditions of 37° C., 5% $CO_2$. After removal of the medium, 50 μl of assay buffer 1 (0.1% bovine serum albumin (Sigma Aldrich), 20 mM HEPES(Molecular Dimensions), 250 mM probenecid (Sigma Aldrich), IX Calcium 5 dye (Molecular Devices) in Hank's balanced salt solution (Invitrogen)) was added, and the cells were incubated for 60 min under the conditions of 37° C., 5% $CO_2$. A test compound was dissolved in dimethyl sulfoxide (Sigma Aldrich) to 10 mM, and then diluted with assay buffer 2 (20 mM HEPES, Hank's balanced salt solution, 0.1% bovine serum albumin). For the reaction, a test compound solution (10 μl) was added using Fluorescent Imaging Plate Reader TETRA (FLIPR TETRA: manufactured by Molecular Devices), a fluorescence value (excitation wavelength 488 nm, measurement wavelength 570 nm) of each well was measured every one second for 2 min, and the agonist activity was determined using the area of the fluorescence value as an indicator of intracellular $Ca^{2+}$ concentration. The agonist activity of the test compound was calculated assuming that the fluorescence value of the well added with only the dilution buffer was 0% and the fluorescence value of the well added with 10 nM human orexin A (Tocris) buffer was 100%. The agonist activity values $EC_{50}$ and $E_{max}$ of each compound are shown in Table A below. As used herein, E. indicates the value at 10 μM concentration when orexin A is converted to a full agonist (maximum value of agonist activity. 100%).

For hOx2 $pEC_{50}$ values shown in Table A, "*" mean $pEC_{50}$ ranging <6.0; "" means $pEC_{50}$ ranging between 6.0 and 7.0; "*" means $pEC_{50}$ ranging between 7.0 and 8.0; "**" means $pEC_{50}$ ranging between 8.0 and 9.0; "***" means $pEC_{50}$ ranging between 9.0 and 10.1.

For hOx2 $E_{max}$ values (%) shown in Table A. "F" means $E_{max}$ ranging between 40 and 50; "E" means $E_{max}$ ranging between 50 and 60; "D" means $E_{max}$ ranging between 60 and 70; "C" means $E_{max}$ ranging between 70 and 80, "B" means $E_{max}$ ranging between 80 and 90, "A" means $E_{max}$ ranging between 90 and 100.

TABLE A

| Compound No. | $pEC_{50}$ | $E_{max}$ (%) |
|---|---|---|
| 1 | *** | C |
| 2 | ** | C |
| 3 | **** | A |
| 4 | ** | D |
| 5 | ** | A |
| 6 | ** | C |
| 7 | **** | A |
| 8 | **** | A |
| 9 | ** | F |
| 10 | ** | A |
| 11 | *** | A |
| 12 | ** | B |
| 13 | ** | B |
| 14 | * | A |
| 15 | *** | A |
| 16 | ** | E |
| 17 | *** | A |
| 18 | **** | A |
| 19 | * | A |
| 20 | *** | A |
| 21 | **** | A |
| 22 | ** | A |
| 23 | *** | A |
| 24 | *** | B |
| 26 | *** | A |
| 27 | **** | A |
| 27 | ***** | A |
| 28 | *** | A |
| 29 | ***** | A |
| 30 | ***** | A |
| 31 | *** | A |
| 32 | ***** | A |
| 33 | ***** | A |
| 34 | **** | A |
| 35 | **** | A |
| 36 | **** | A |
| 37 | *** | A |
| 38 | **** | A |
| 39 | **** | A |
| 40 | *** | A |
| 41 | **** | A |
| 42 | **** | A |
| 43 | **** | A |
| 44 | **** | B |
| 45 | **** | A |
| 46 | *** | A |
| 47 | *** | A |
| 28 | *** | B |
| 49 | **** | A |
| 50 | ***** | A |
| 51 | **** | A |
| 52 | ***** | A |

TABLE A-continued

| Compound No. | $pEC_{50}$ | $E_{max}$ (%) |
|---|---|---|
| 53 | **** | A |
| 54 | **** | B |
| 55 | *** | A |
| 56 | **** | A |
| 57 | **** | A |
| 58 | **** | A |
| 59 | **** | A |
| 60 | *** | B |
| 61 | **** | A |
| 62 | *** | A |
| 63 | *** | B |
| 64 | ***** | A |
| 65 | **** | A |
| 66 | *** | A |
| 67 | **** | A |
| 68 | ***** | A |
| 69 | ***** | A |
| 70 | **** | A |
| 71 | **** | A |
| 72 | **** | A |
| 73 | *** | A |
| 74 | *** | A |
| 75 | *** | A |
| 76 | *** | A |
| 77 | *** | A |
| 78 | *** | A |
| 79 | **** | A |
| 80 | ***** | A |
| 81 | ***** | A |
| 82 | **** | A |
| 83 | *** | A |
| 84 | ***** | A |
| 85 | ***** | A |
| 86 | **** | A |
| 87 | *** | A |
| 88 | ***** | A |
| 89 | ***** | A |
| 90 | **** | A |
| 91 | *** | A |
| 92 | **** | A |
| 93 | ***** | A |
| 94 | **** | A |
| 95 | **** | A |
| 96 | *** | B |
| 97 | *** | B |
| 98 | **** | A |
| 99 | **** | A |
| 100 | ***** | A |
| 101 | ***** | A |
| 102 | **** | A |
| 103 | *** | A |
| 104 | **** | A |
| 105 | **** | A |
| 106 | ***** | A |
| 107 | **** | A |
| 108 | ***** | A |
| 109 | ***** | A |
| 110 | ***** | A |
| 111 | **** | A |
| 112 | ***** | A |
| 113 | **** | A |
| 114 | **** | B |
| 115 | **** | A |
| 116 | ***** | A |
| 117 | ***** | A |
| 118 | **** | A |
| 119 | ***** | A |
| 120 | ***** | A |
| 121 | ***** | A |
| 122 | ***** | A |
| 123 | ***** | A |
| 124 | ***** | B |
| 129 | ***** | A |
| 132 | ***** | A |
| 134 | **** | A |
| 144 | ***** | A |

TABLE A-continued

| Compound No. | $pEC_{50}$ | $E_{max}$ (%) |
|---|---|---|
| 145 | ***** | A |
| 154 | ***** | A |
| 157 | ***** | A |
| 158 | ***** | A |
| 159 | | |
| 160 | ***** | A |
| 161 | **** | A |
| 162 | **** | A |
| 163 | **** | A |
| 164 | *** | B |
| 165 | **** | A |
| 166 | **** | A |
| 167 | *** | B |
| 168 | **** | A |
| 169 | **** | A |
| 170 | **** | A |
| 171 | **** | A |
| 172 | **** | A |
| 173 | **** | A |
| 174 | **** | A |
| 175 | ***** | A |
| 176 | **** | A |
| 177 | **** | A |
| 178 | **** | A |
| 179 | **** | C |
| 180 | **** | A |
| 181 | **** | A |
| 182 | **** | A |
| 183 | **** | A |
| 184 | **** | A |
| 185 | ***** | A |
| 186 | ***** | A |
| 187 | ***** | A |
| 188 | **** | A |
| 189 | **** | A |
| 190 | **** | A |
| 191 | **** | A |
| 192 | **** | A |
| 193 | **** | A |
| 194 | **** | A |
| 195 | **** | A |
| 196 | ***** | A |
| 197 | *** | B |
| 198 | **** | A |
| 199 | ***** | A |
| 200 | **** | A |
| 201 | **** | A |
| 202 | **** | A |
| 203 | **** | A |
| 204 | *** | A |
| 205 | **** | A |
| 206 | **** | A |
| 207 | **** | A |
| 208 | ***** | A |
| 209 | ***** | A |
| 210 | *** | A |
| 211 | **** | A |
| 212 | **** | A |
| 213 | **** | A |
| 214 | **** | A |
| 215 | ***** | A |
| 216 | **** | A |
| 217 | **** | A |
| 218 | **** | A |
| 219 | **** | A |
| 220 | **** | A |
| 221 | **** | A |
| 222 | ***** | A |
| 223 | ***** | A |
| 224 | **** | A |
| 225 | **** | A |
| 226 | **** | A |
| 227 | **** | A |
| 228 | **** | A |
| 229 | ***** | A |
| 230 | **** | A |

TABLE A-continued

| Compound No. | $pEC_{50}$ | $E_{max}$ (%) |
|---|---|---|
| 231 | **** | A |
| 232 | ***** | A |
| 233 | *** | B |
| 234 | **** | A |
| 235 | **** | A |
| 294 | *** | B |
| 295 | *** | A |
| 296 | *** | A |
| 297 | **** | A |
| 298 | **** | A |
| 299 | *** | A |
| 300 | *** | A |
| 301 | *** | A |
| 302 | **** | A |
| 303 | **** | A |
| 304 | *** | A |
| 305 | *** | A |
| 306 | *** | A |
| 307 | **** | A |
| 308 | *** | A |
| 309 | *** | A |
| 310 | *** | A |
| 311 | **** | A |
| 312 | *** | A |
| 313 | *** | A |
| 314 | **** | A |
| 315 | *** | B |
| 316 | **** | A |
| 317 | **** | A |
| 318 | **** | A |
| 319 | *** | A |
| 320 | *** | A |
| 321 | *** | A |
| 322 | ***** | A |
| 323 | **** | A |
| 324 | *** | A |
| 325 | **** | A |
| 326 | **** | A |
| 327 | **** | A |
| 328 | **** | A |
| 329 | **** | A |
| 330 | **** | A |
| 331 | **** | A |
| 332 | **** | A |
| 333 | **** | A |
| 334 | **** | A |
| 335 | **** | A |
| 336 | **** | A |
| 337 | **** | A |
| 338 | *** | A |
| 339 | *** | C |
| 340 | *** | D |
| 341 | ***** | A |
| 342 | *** | C |
| 343 | *** | C |
| 344 | **** | A |
| 345 | **** | A |
| 346 | **** | A |
| 347 | **** | A |
| 348 | **** | A |
| 349 | **** | A |
| 350 | *** | A |
| 351 | *** | A |
| 352 | **** | A |
| 353 | **** | A |
| 354 | *** | A |
| 355 | *** | A |
| 356 | *** | A |
| 357 | *** | A |
| 358 | **** | A |
| 359 | *** | A |
| 360 | **** | A |
| 361 | *** | B |
| 362 | *** | A |
| 363 | *** | C |
| 364 | ***** | A |

TABLE A-continued

| Compound No. | $pEC_{50}$ | $E_{max}$ (%) |
|---|---|---|
| 365 | **** | A |
| 366 | **** | A |
| 367 | ***** | A |
| 368 | **** | A |
| 369 | **** | A |
| 370 | ***** | A |
| 371 | **** | A |
| 372 | **** | A |
| 373 | **** | A |
| 374 | **** | A |
| 375 | ***** | A |
| 376 | **** | A |
| 377 | ***** | A |
| 378 | ***** | A |
| 379 | **** | A |
| 380 | ***** | A |
| 381 | **** | A |
| 382 | ***** | A |
| 383 | **** | A |
| 384 | **** | A |
| 385 | ***** | A |
| 386 | **** | A |
| 387 | **** | A |
| 388 | **** | A |
| 389 | **** | A |
| 390 | **** | A |
| 391 | ***** | A |
| 392 | ***** | A |
| 393 | **** | A |
| 394 | ***** | A |
| 395 | ***** | A |
| 396 | **** | A |
| 397 | **** | B |
| 398 | **** | A |
| 399 | ***** | A |
| 400 | **** | A |
| 401 | **** | A |
| 402 | **** | A |
| 403 | **** | A |
| 404 | **** | A |
| 405 | **** | A |
| 406 | ***** | A |
| 407 | **** | A |
| 408 | **** | A |
| 409 | **** | A |
| 410 | **** | A |
| 411 | ***** | A |
| 412 | **** | A |
| 413 | **** | A |
| 414 | ***** | A |
| 415 | **** | A |
| 416 | **** | A |
| 417 | **** | A |
| 418 | **** | A |
| 419 | **** | A |
| 420 | ***** | A |

Wake Promoting Efficacy

Wake-promoting efficacy was evaluated in the B6.Cg-Tg (HCRT-MJD)$_1$Stak/J (Atax) mouse model of NT1 and wild type (WT) colony mates. Mice were monitored in home cages using piezoelectric sensors for rapid, non-invasive classification of sleep and wakefulness by unsupervised machine learning on physiologically relevant readouts, such as body movement and breath rate. Piezoelectric detection is highly correlated with conventional time-intensive electroencephalogram/electromyography measures of sleep/wake states in both WT and NT1 mice. In a counterbalanced design, mice were orally dosed at 5 h after light onset with test articles at 0 (vehicle), 3 and 30 mg/kg. The increases in time spent awake over vehicle levels during the first hour post dose are indicated in Table B.

TABLE B

| Example | Oral dose (mg/kg) | Genotype | Wake % time 1 h post dose (increase from vehicle) | P (vs. vehicle) |
|---|---|---|---|---|
| 21 | 3 | Atax | 17.5 | 0.0031 |
| 21 | 30 | Atax | 27.9 | <0.0001 |
| 21 | 30 | WT | 14.4 | 0.0028 |
| 59 | 3 | Atax | 35.5 | <0.0001 |
| 59 | 30 | Atax | 48.6 | <0.0001 |
| 59 | 30 | WT | 21.1 | 0.0041 |
| 129 | 30 | Atax | 25.0 | 0.0002 |
| 129 | 30 | WT | 19.3 | 0.0185 |
| 144 | 3 | Atax | 26.7 | <0.0001 |
| 144 | 30 | Atax | 29.2 | <0.0001 |
| 144 | 30 | WT | 27.2 | 0.0009 |
| 145 | 3 | Atax | 26.9 | <0.0001 |
| 145 | 30 | Atax | 28.3 | <0.0001 |
| 145 | 30 | WT | 25.8 | 0.001 |
| 154 | 3 | Atax | 24.4 | 0.0006 |
| 154 | 30 | Atax | 24.5 | 0.0016 |
| 175 | 3 | Atax | 25.3 | 0.0001 |
| 175 | 30 | Atax A | 29 | <0.0001 |

Atax, B6.Cg-Tg(HCRT-MJD)1Stak/J; WT, wild type;

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I''):

(I''')

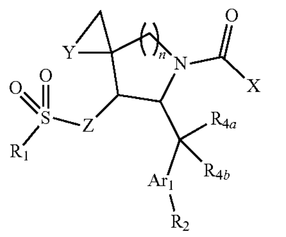

or a pharmaceutically acceptable salt thereof, wherein:

X is —C($R_{X1}$)$_3$, —$OR_{X2}$, or —N($R_{X2}$)$_2$;

Y is —$CH_2$—, —$CH_2$—O—, —O—$CH_2$—, —$CF_2$—, —$CH_2$—NH—, —NH—$CH_2$—, —$CH_2$—N($CH_2CF_3$)—, or —N($CH_2$—$CF_3$)—$CH_2$—;

Z is —O— or —$NR_Z$—;

each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-$C_1$-$C_6$ alkoxy, $C_3$-$C_6$ cycloalkyl, or 3- to 7-membered heterocycloalkyl, or two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with oxo, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy, or three $R_{X1}$ together with the atom to which they are attached form a $C_4$-$C_{10}$ cycloalkyl, wherein the cycloalkyl is optionally substituted with halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_{X2}$ independently is H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, or 3- to 7-membered heterocycloalkyl, wherein the alkyl, alkenyl, alkynyl, haloalkyl, cycloalkyl, or heterocycloalkyl is optionally substituted with one or more halogen, —CN, —OH, $C_1$-$C_6$ alkyl, $C_1$-$C_6$ alkoxy, $C_1$-$C_6$ haloalkyl, $C_3$-$C_6$ cycloalkyl, or 3- to 7-membered heterocycloalkyl, or two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy;

each $R_Z$ is H, $C_1$-$C_6$ alkyl, $C_2$-$C_6$ alkenyl, $C_2$-$C_6$ alkynyl, or $C_1$-$C_6$ haloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_3$;

$R_1$ is —$NH_2$, —NH($C_1$-$C_6$ alkyl), —N($C_1$-$C_6$ alkyl)$_2$, —N($C_1$-$C_6$ alkyl)($C_3$-$C_{10}$ cycloalkyl), —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$;

each $R_{1S}$ independently is oxo, halogen, —CN, —OH, —O—($CH_2$)$_2$—O$C_1$—$C_6$ alkyl, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$R_2$ is halogen, —CN, —OH, —$NH_2$, —NH($C_1$-$C_6$ alkyl), —N($C_1$-$C_6$ alkyl)$_2$, —SH, —S($C_1$-$C_6$ alkyl), —$SO_2$($C_1$-$C_6$ alkyl), —S($C_6$-$C_{10}$ aryl), —$SO_2$($C_6$-$C_{10}$ aryl), $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the alkyl, alkenyl, aryl, heteroaryl, cycloalkyl, and heterocycloalkyl are optionally substituted with one or more $R_{2S}$;

each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_3$-$C_7$ cycloalkyl, or 3- to 7-membered heterocycloalkyl;

each $R_3$ independently is halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4a}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy;

$R_{4b}$ is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_{1-6}$ alkoxy; and n is 0, 1, 2, or 3.

2. The compound of claim 1, wherein Z is —$NR_Z$;

$R_Z$ is H, $C_1$-$C_6$ alkyl, $C_2$-$C_6$ alkenyl, $C_2$-$C_6$ alkynyl, or $C_1$-$C_6$ haloalkyl;

$R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, aryl, heteroaryl, cycloalkyl, and heterocycloalkyl are optionally substituted with one or more $R_{1S}$; and each $R_{1S}$ independently is halogen, —CN, —OH, $C_1$-$C_6$ alkoxy, $C_3$-$C_7$ cycloalkyl or 3- to 7-membered heterocycloalkyl.

3. The compound of claim 1, wherein Z is —NH— and $R_1$ is —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, 5- to 10-membered heteroaryl, $C_3$-$C_7$ cycloalkyl, 3- to 7-membered heterocycloalkyl, —NH—($C_3$-$C_{10}$ cycloalkyl), or —NH-(3- to 7-membered heterocycloalkyl), wherein the alkyl, alkenyl, alkynyl, heteroaryl, cycloalkyl, and heterocycloalkyl are optionally substituted with one or more $R_{1S}$; and each $R_{1S}$ independently is halogen, —CN, —OH, or $C_1$-$C_6$ alkoxy, $C_3$-$C_7$ cycloalkyl or 3- to 7-membered heterocycloalkyl.

4. The compound of claim 1, wherein X is —C($R_{X1}$)$_3$ or —N($R_{X2}$)$_2$, wherein each $R_{X1}$ independently is H, halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; or wherein two $R_{X1}$ together with the atom to which they are attached form a $C_3$-$C_7$ cycloalkyl or 3- to 7-membered heterocycloalkyl, wherein the cycloalkyl or heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy; and each $R_{X2}$ independently is H, $C_1$-$C_6$ alkyl, $C_2$-$C_6$ alkenyl, $C_2$-$C_6$ alkynyl, or $C_1$-$C_6$ haloalkyl; or wherein two $R_{X2}$ together with the atom to which they are attached form a 3- to 7-membered heterocycloalkyl, wherein the heterocycloalkyl is optionally substituted with one or more halogen, —CN, —OH, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ haloalkyl, or $C_1$-$C_6$ alkoxy.

5. The compound of claim 1, wherein X is

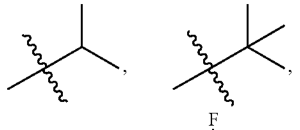

-O(methyl),

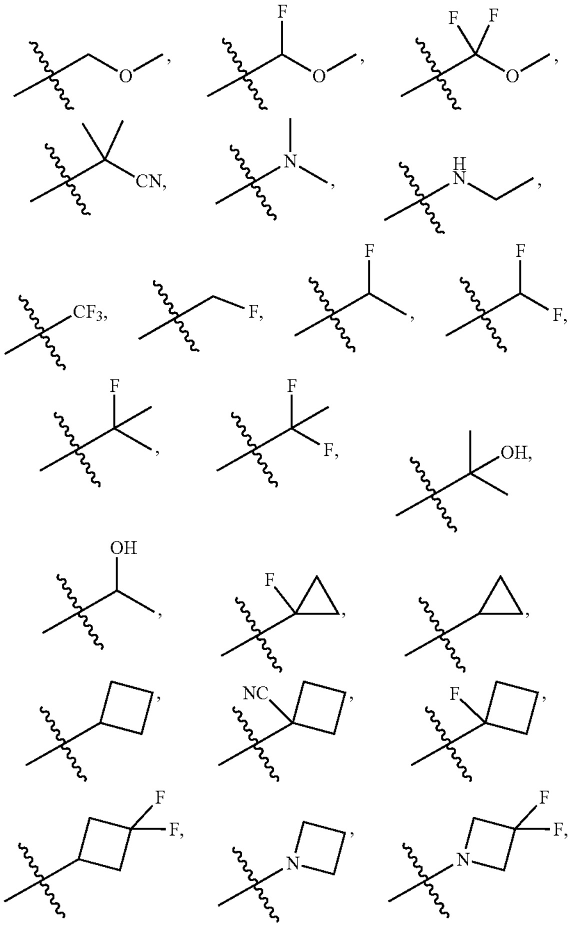

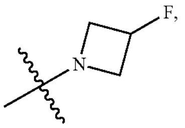

or

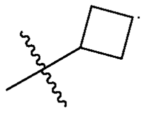

6. The compound of claim 1, wherein $Ar_1$ is $C_6$-aryl or 5- or 6-membered heteroaryl, wherein the aryl or heteroaryl is optionally substituted with one or more $R_3$.

7. The compound of claim 1, wherein $R_1$ is methyl, isopropyl, ethyl, —$CF_3$, —$CHF_2$, $CH_2F$, —$CF_2CH_3$, —CF($CH_3$)$_2$, cyclopropyl, or fluorocyclopropyl.

8. The compound of claim 1, wherein $R_2$ is —CN, $C_1$-$C_6$ alkyl, $C_2$-$C_6$ alkenyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the alkyl, alkenyl, aryl, heteroaryl, cycloalkyl, and heterocycloalkyl are optionally substituted with one or more $R_{2S}$.

9. The compound claim 1, wherein $R_2$ is

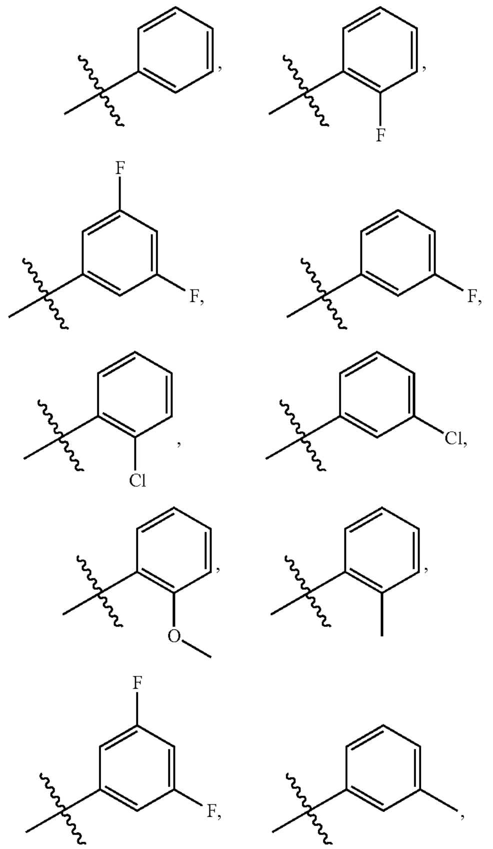

—CN,

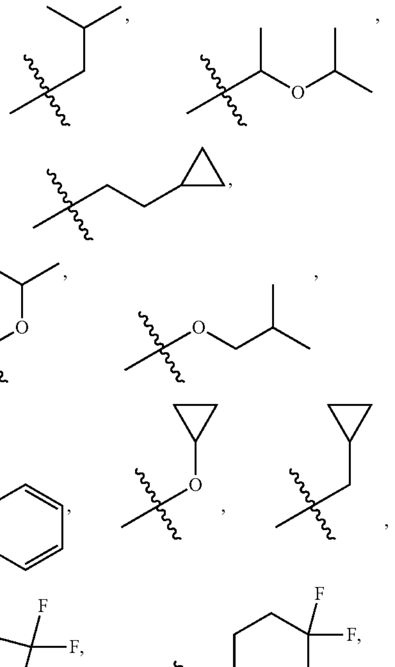

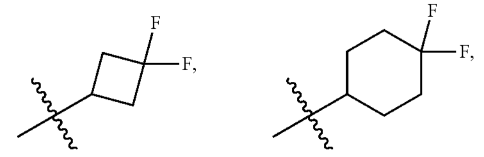

-continued

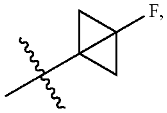

, or

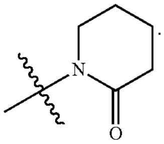

.

10. The compound claim 1, wherein each $R_{2S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, or $C_1$-$C_6$ alkoxy.

11. The compound of claim 1, wherein each $R_3$ independently is halogen, —CN, —OH, —$NH_2$, —NH($C_1$-$C_6$ alkyl), or —N($C_1$-$C_6$ alkyl)$_2$.

12. The compound of claim 1, wherein each $R_3$ independently is $C_1$-$C_6$ alkyl, $C_2$-$C_6$ alkenyl, $C_2$-$C_6$ alkynyl, $C_1$-$C_6$ haloalkyl, or $C_{1-6}$ alkoxy.

13. The compound of claim 1, wherein $R_{4a}$ is H, $C_1$-$C_6$ alkyl, $C_2$-$C_6$ alkenyl, $C_2$-$C_6$ alkynyl, or $C_1$-$C_6$ haloalkyl; and $R_{4b}$ is H, $C_1$-$C_6$ alkyl, $C_2$-$C_6$ alkenyl, $C_2$-$C_6$ alkynyl, or $C_1$-$C_6$ haloalkyl.

14. The compound of claim 1, wherein n is 1 or 2.

15. A compound selected from:

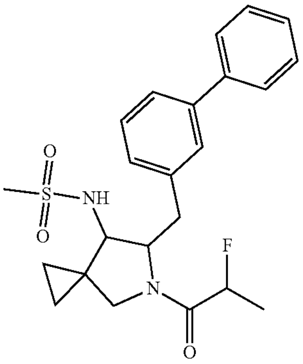

,

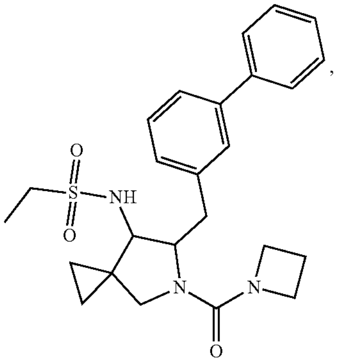

,

-continued

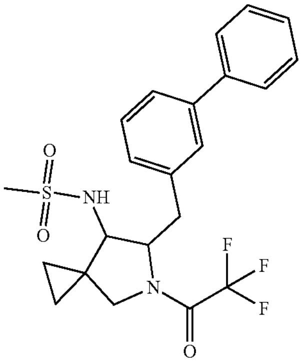

,

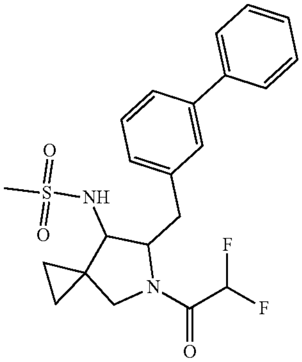

,

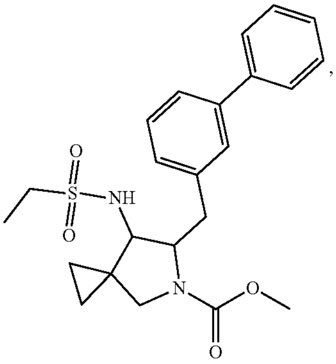

,

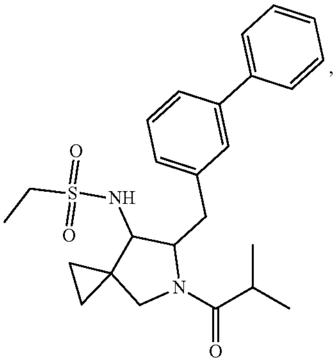

,

-continued
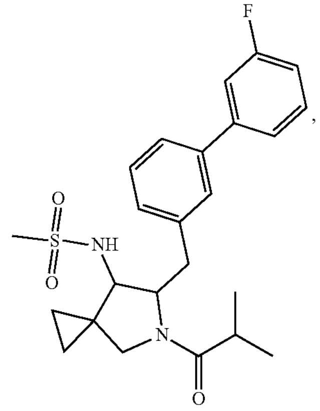
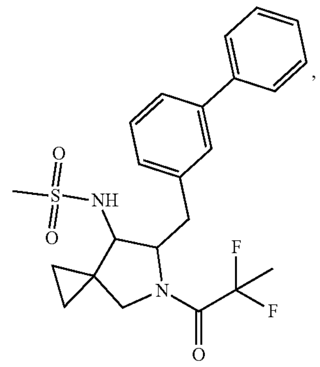
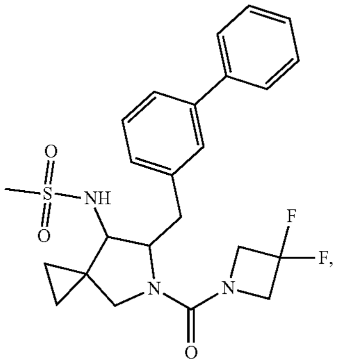
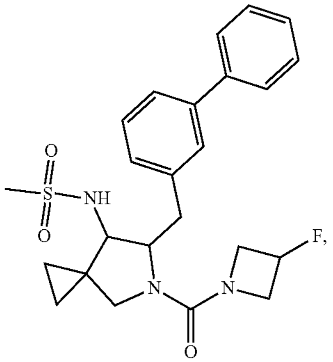
-continued
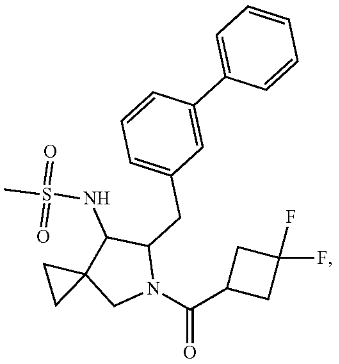
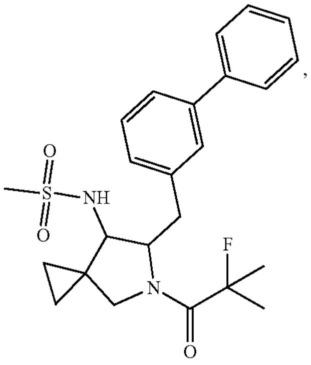
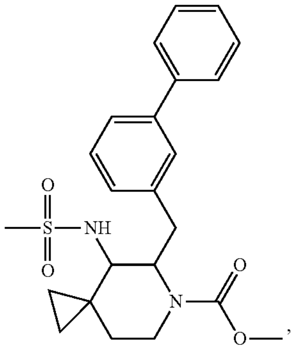
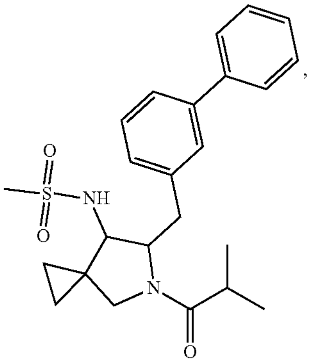

-continued
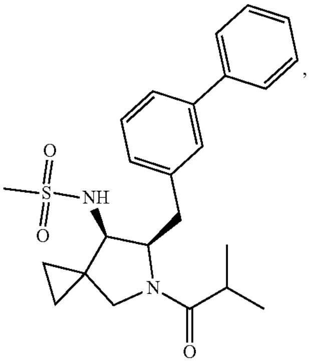
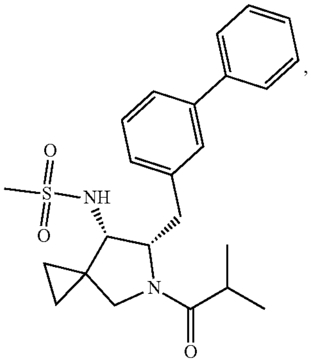
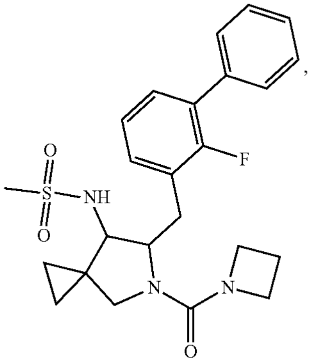
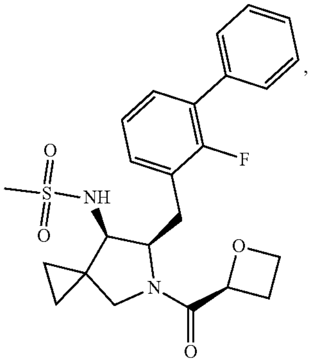
-continued
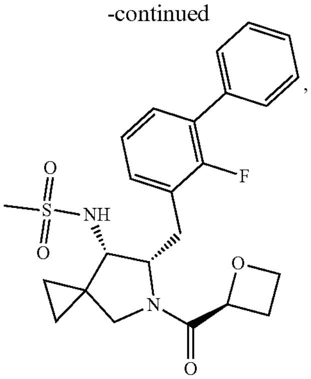
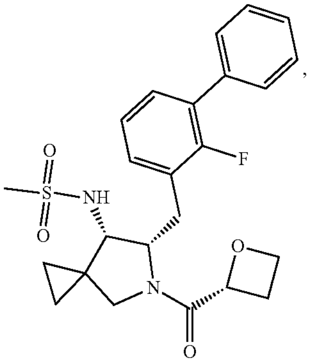
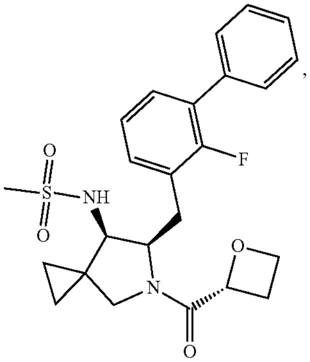
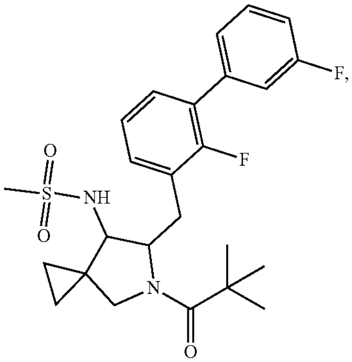

-continued
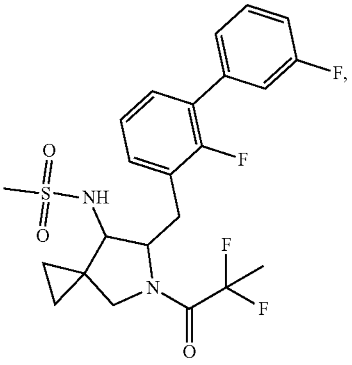
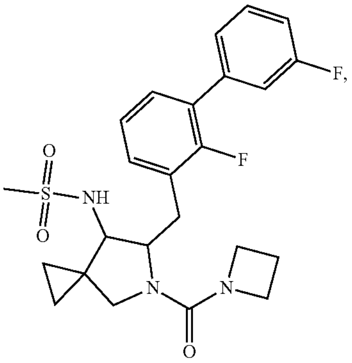
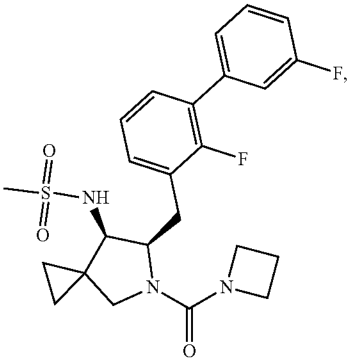
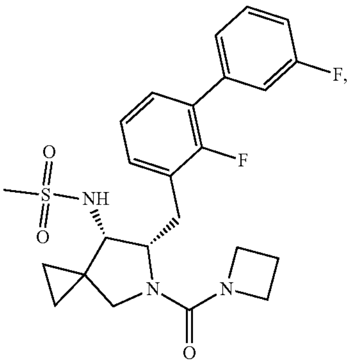
-continued
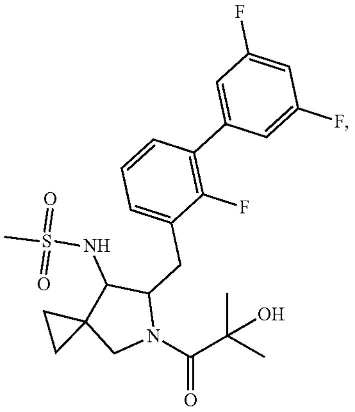
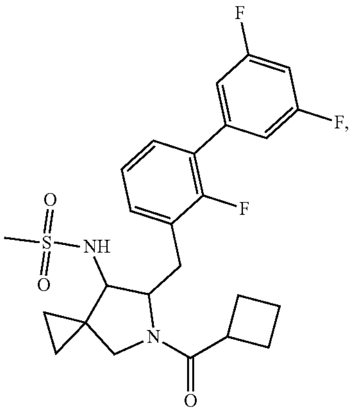
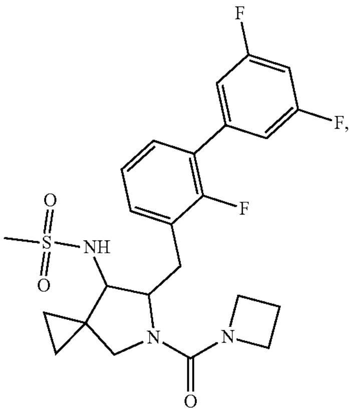
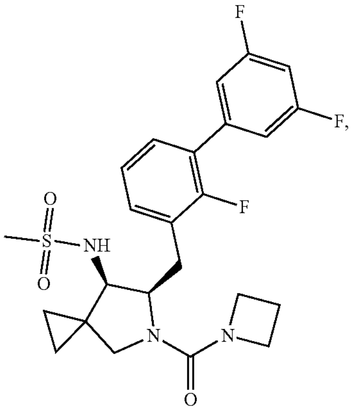

-continued
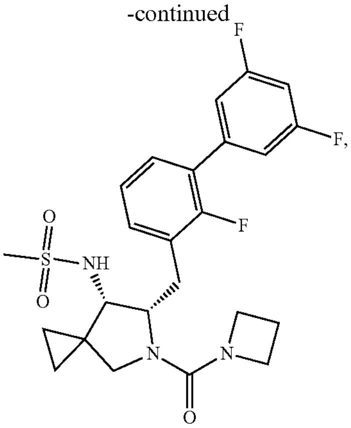
,
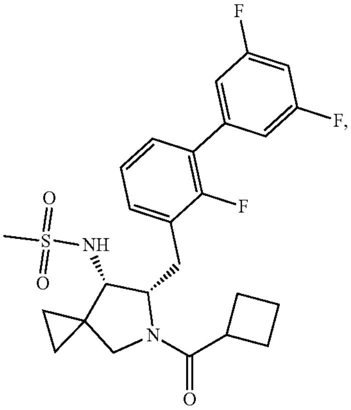
,
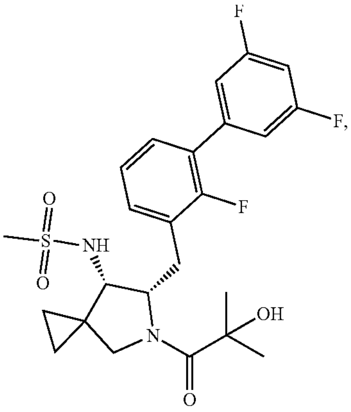
,
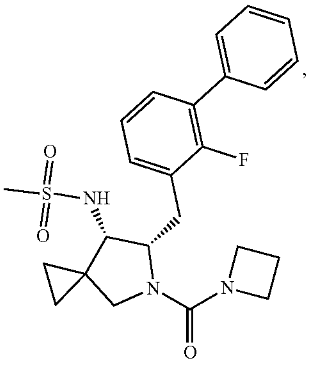
,
-continued
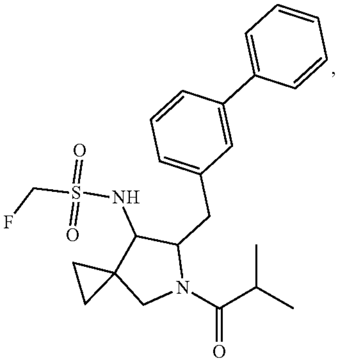
,
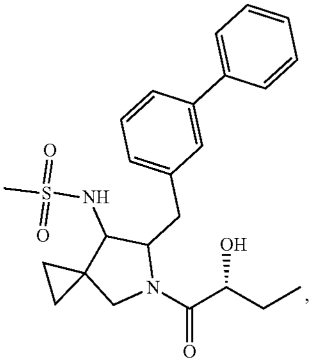
,
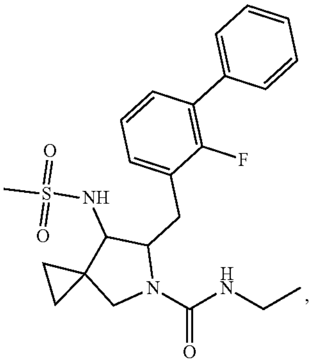
,
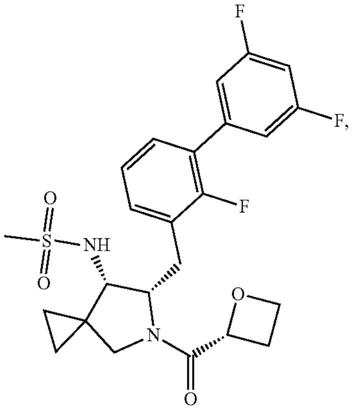
, -continued
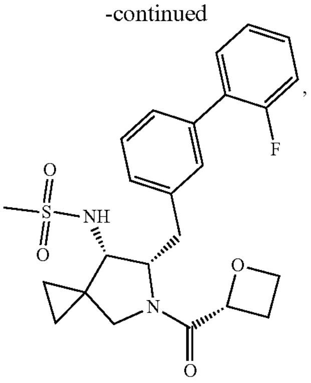
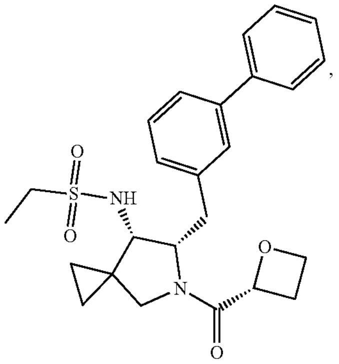
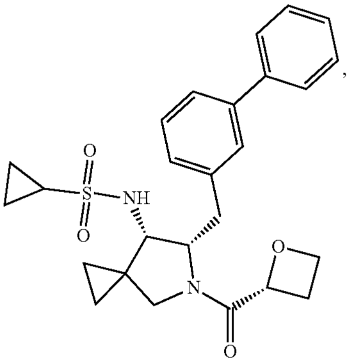
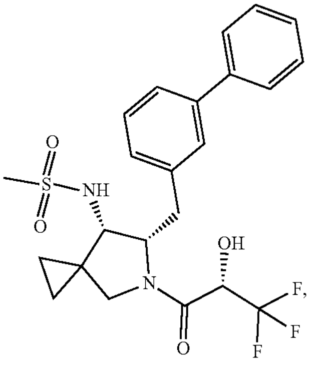
-continued
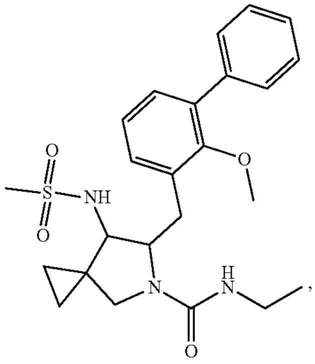
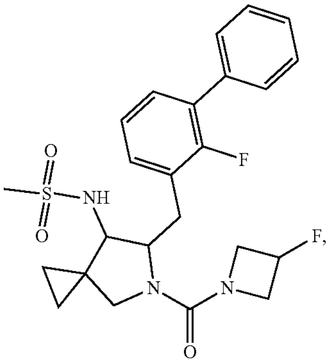
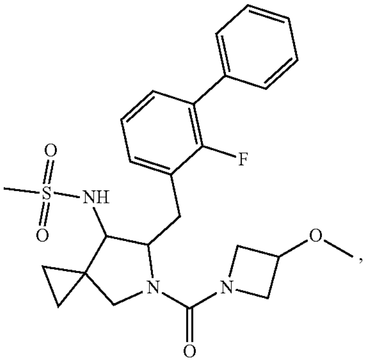
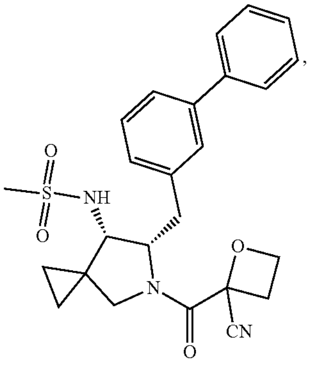

-continued
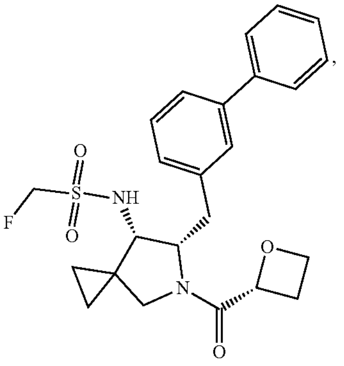
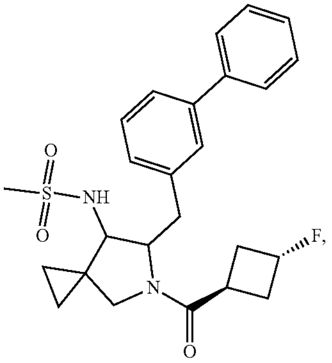
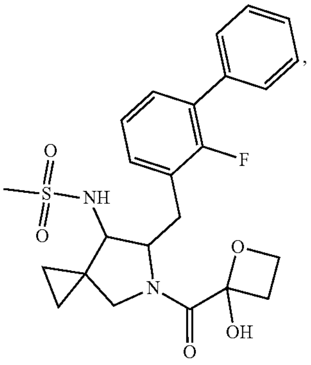
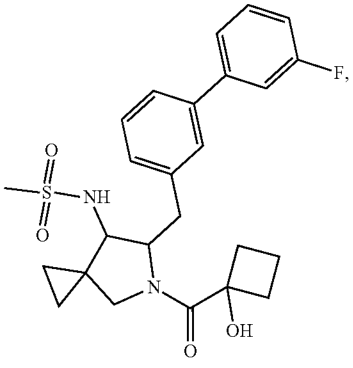
-continued
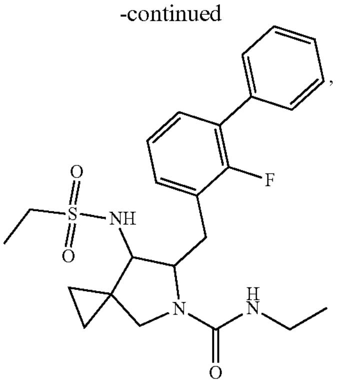
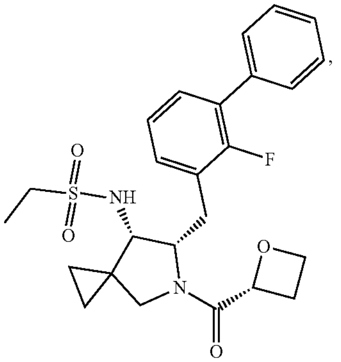
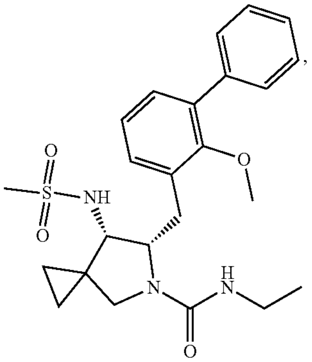
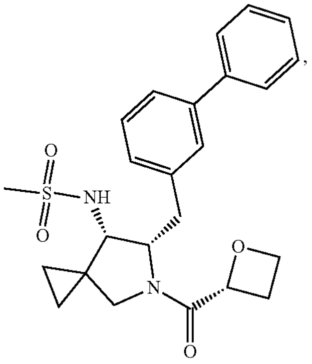

-continued
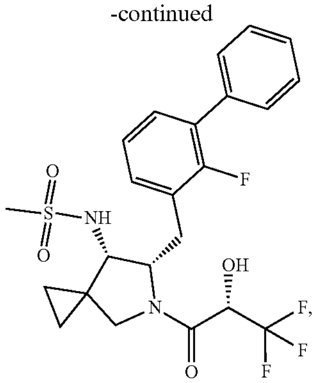
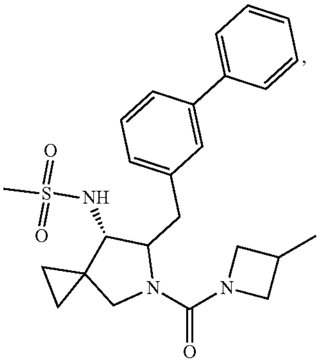
,
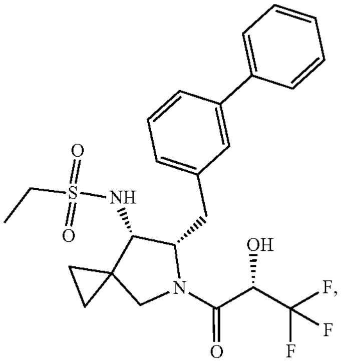
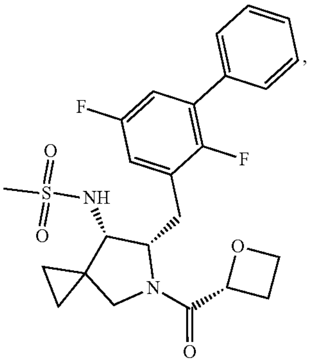
,
-continued
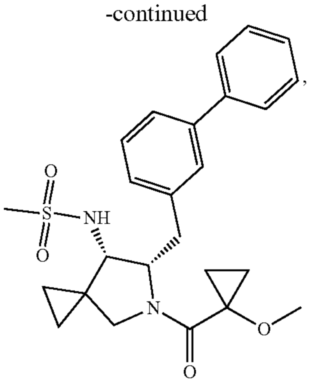
,
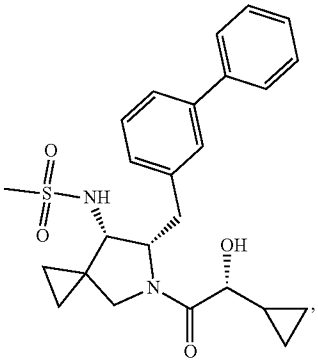
,
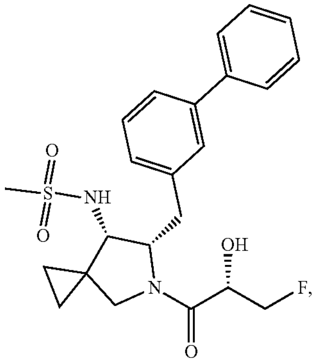
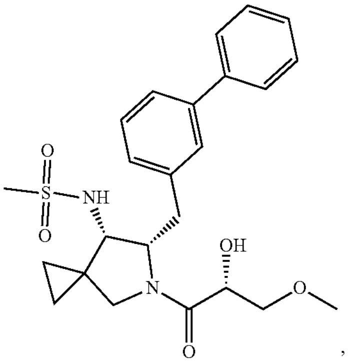
, -continued
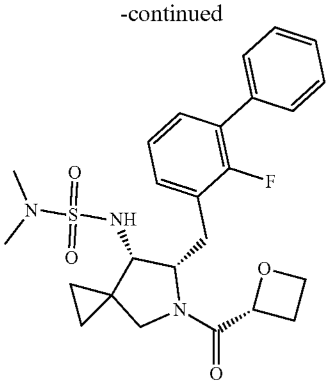
,
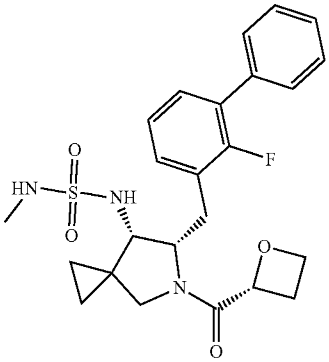
,
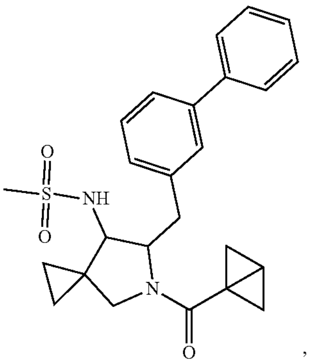
,
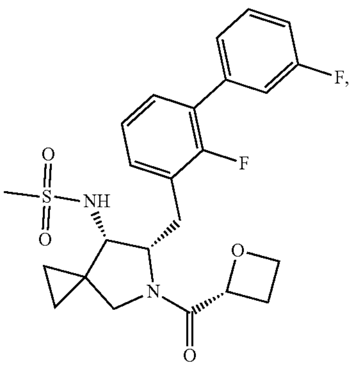
-continued
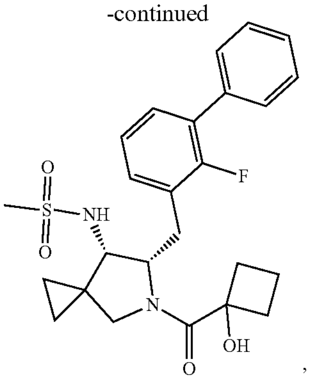
,
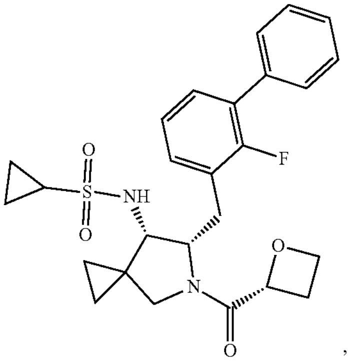
,
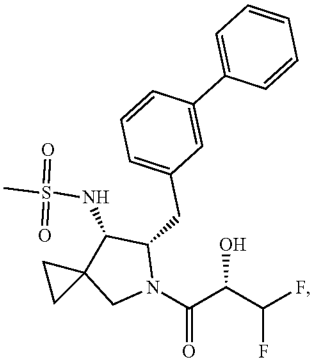
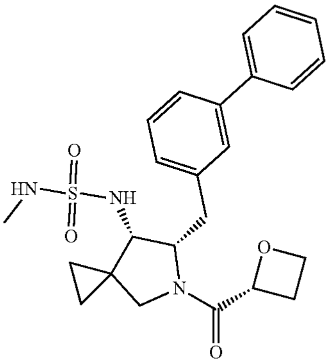
, -continued
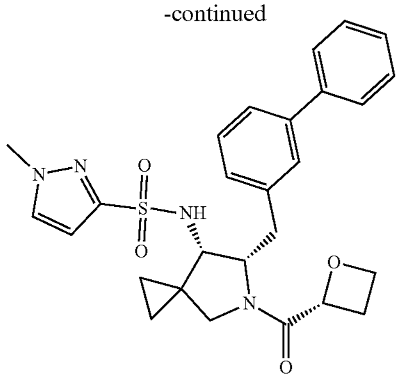
,
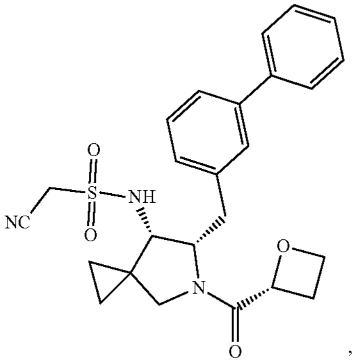
,
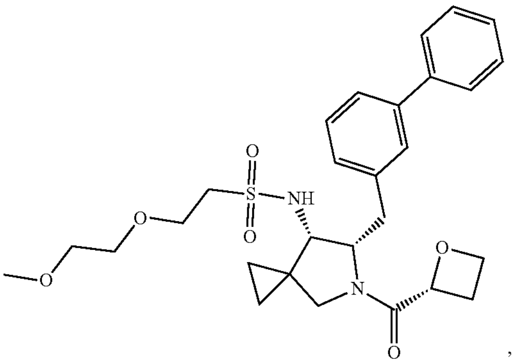
,
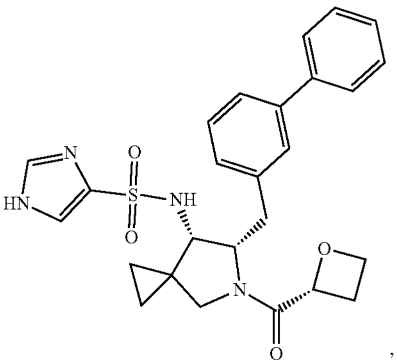
,
-continued
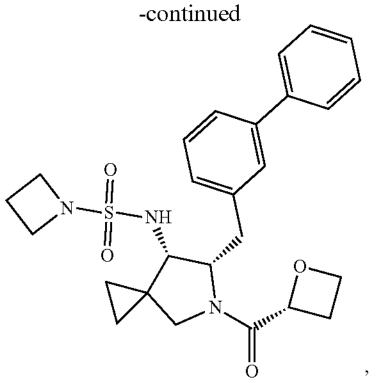
,
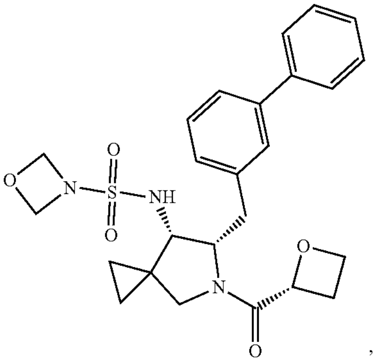
,
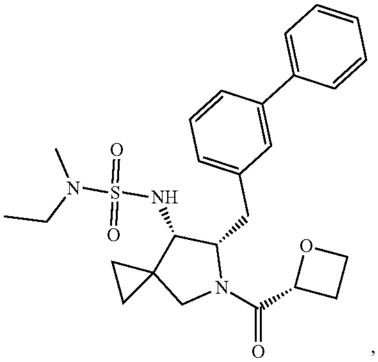
,
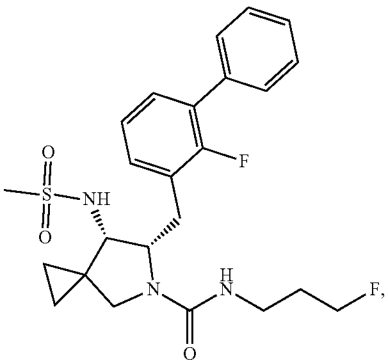

-continued
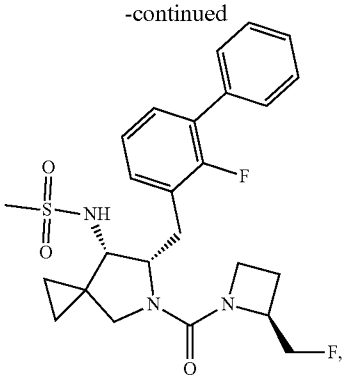
,
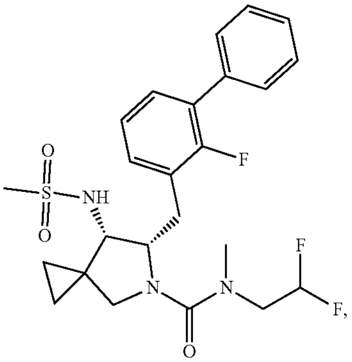
,
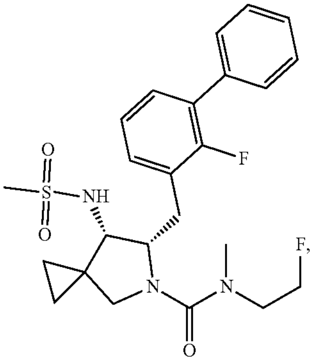
,
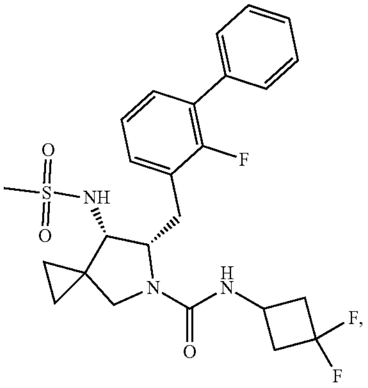
,
-continued
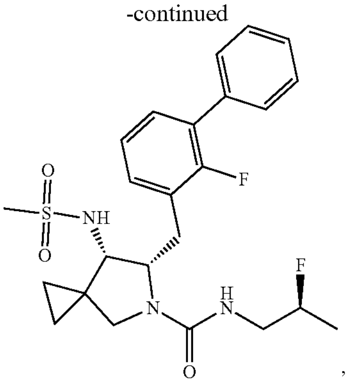
,
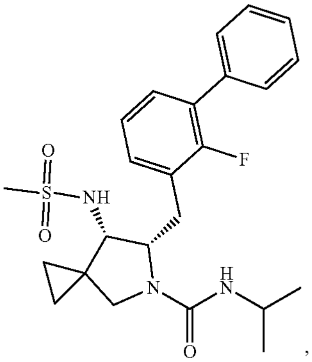
,
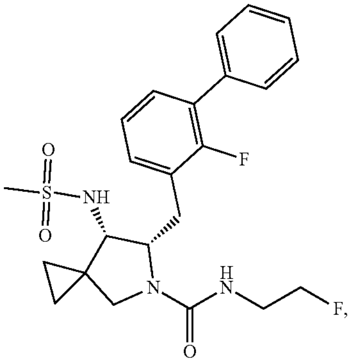
,
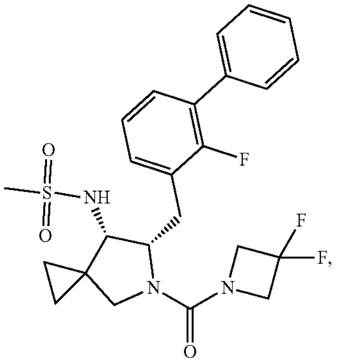
, -continued
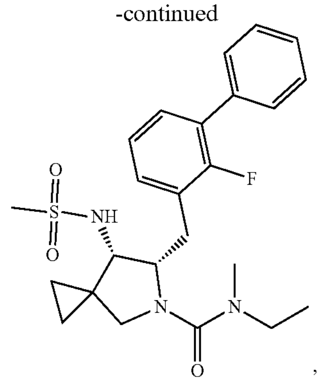
,
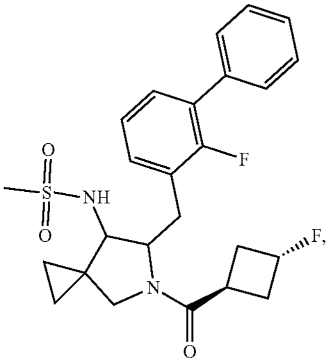
,
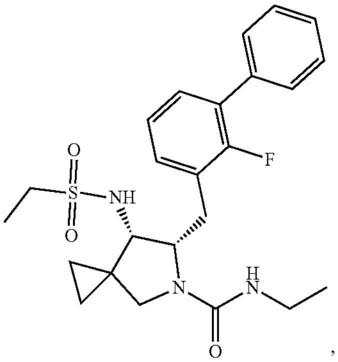
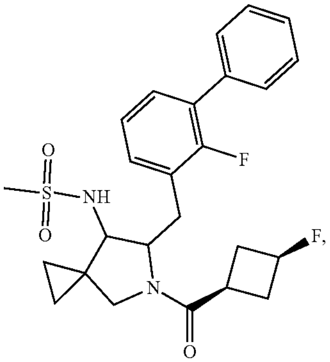
-continued
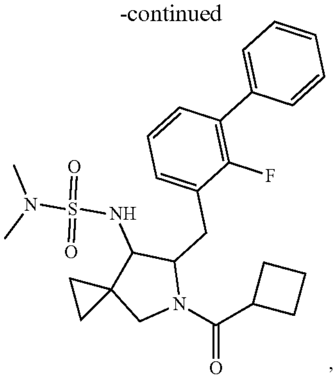
,
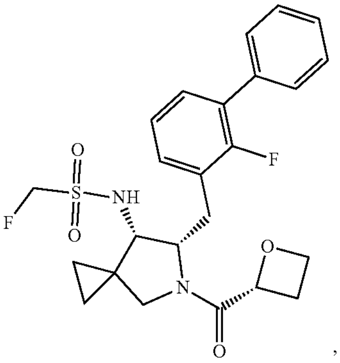
,
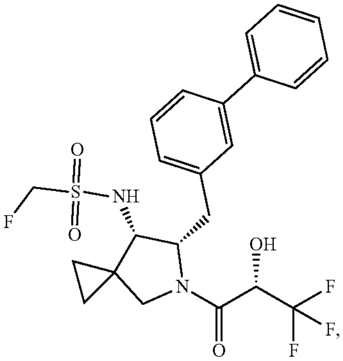
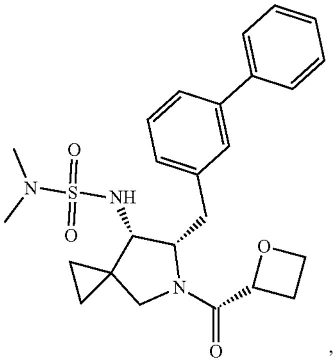
, -continued
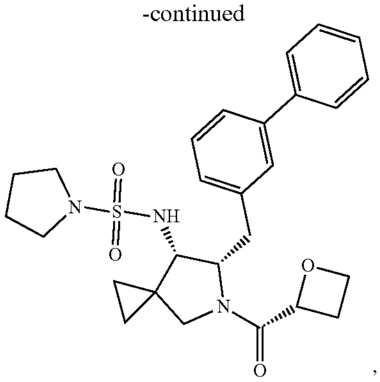
,
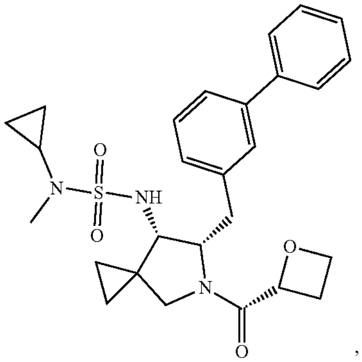
,
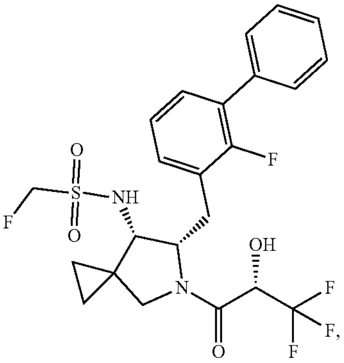
,
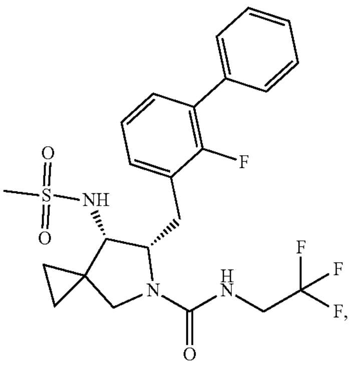
,
-continued
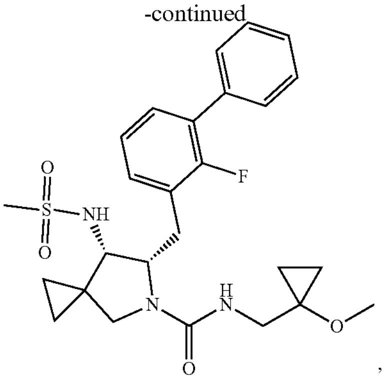
,
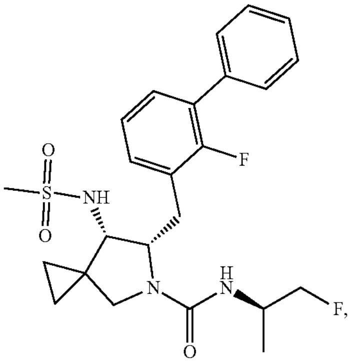
,
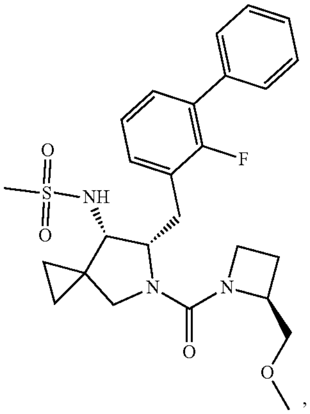
,
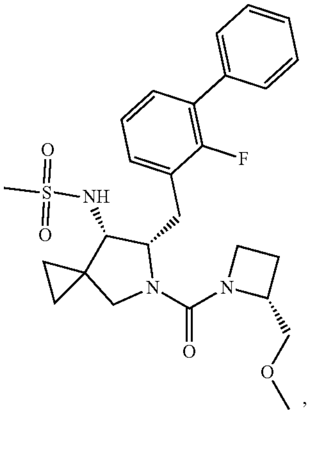
, -continued
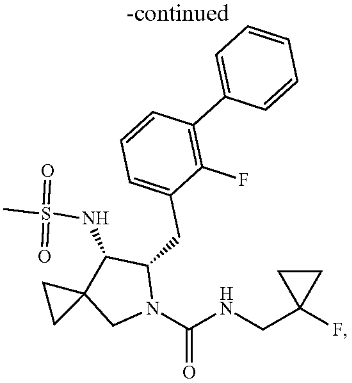
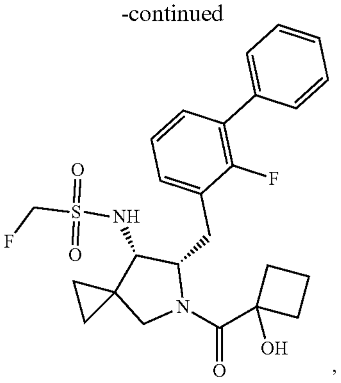
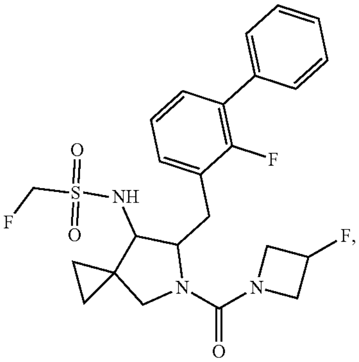
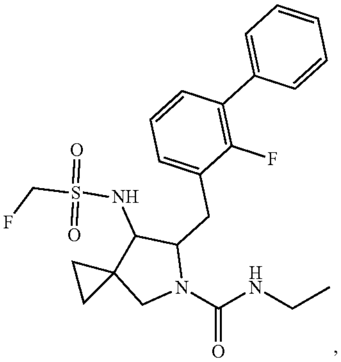
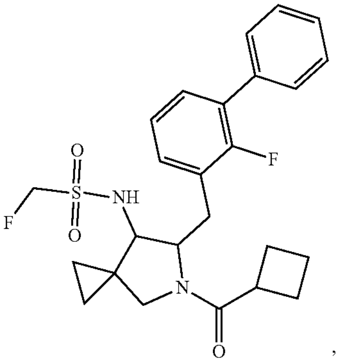
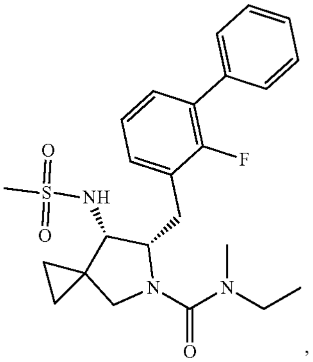
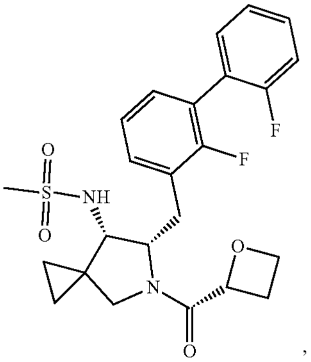
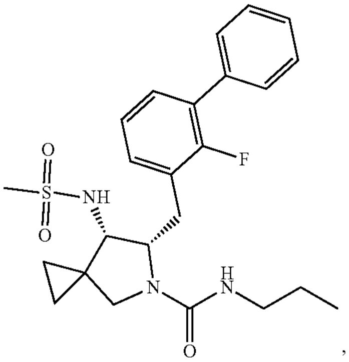
-continued -continued
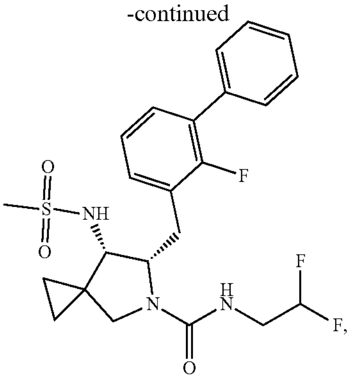
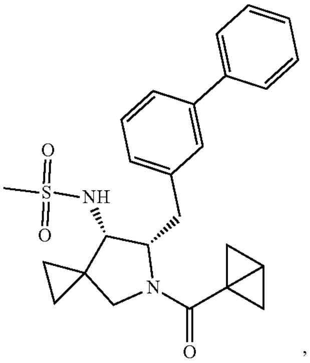
,
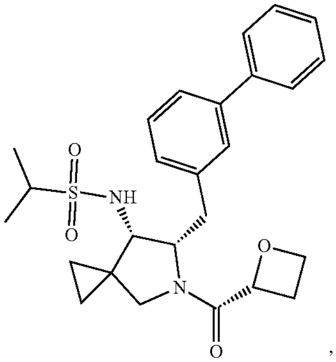
,
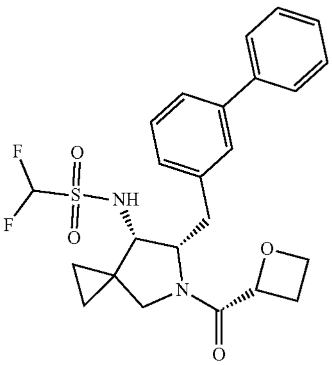
,
-continued
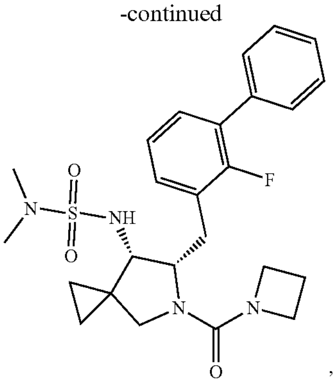
,
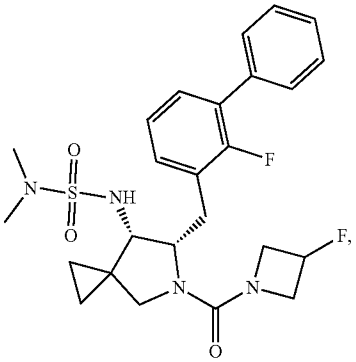
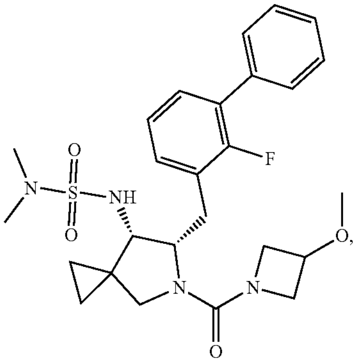
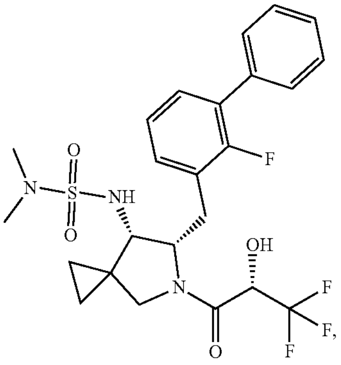

-continued
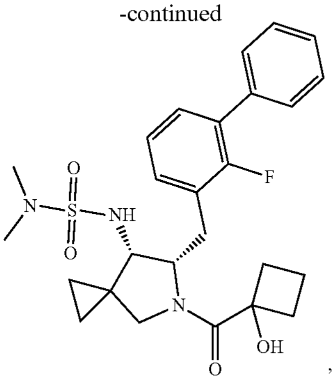
,
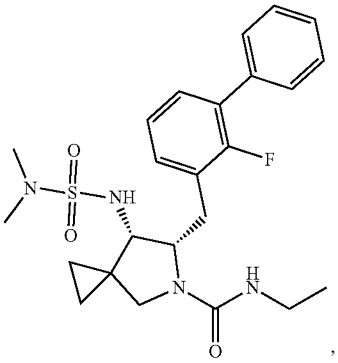
,
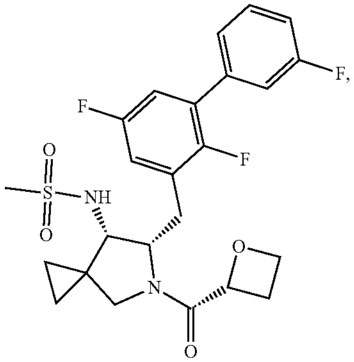
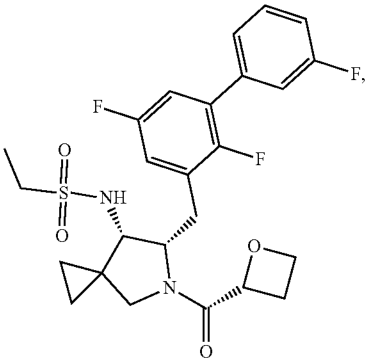
-continued
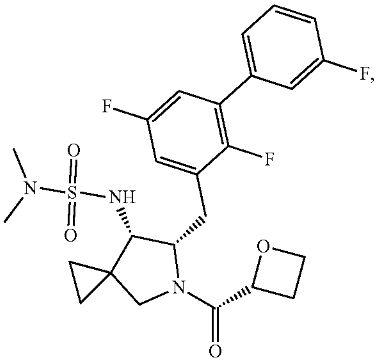
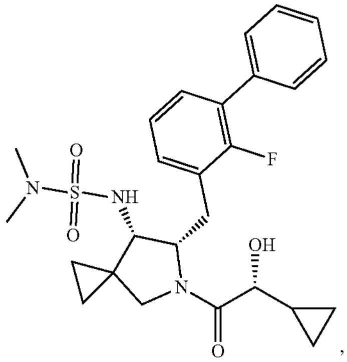
,
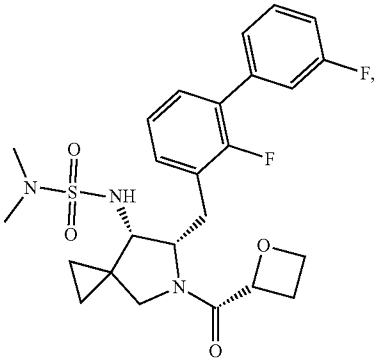
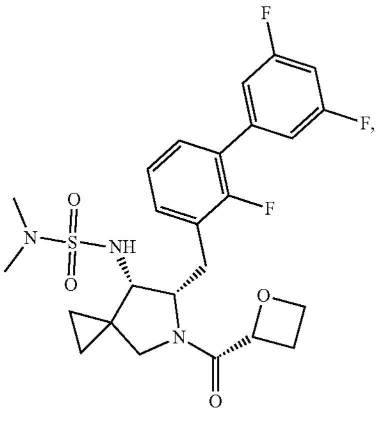

-continued
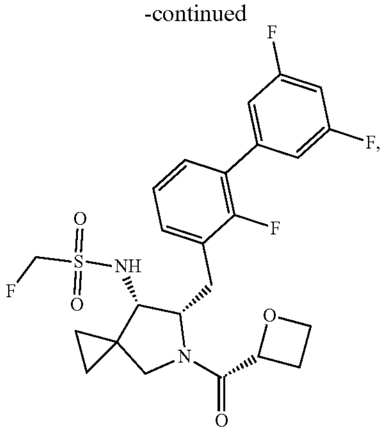
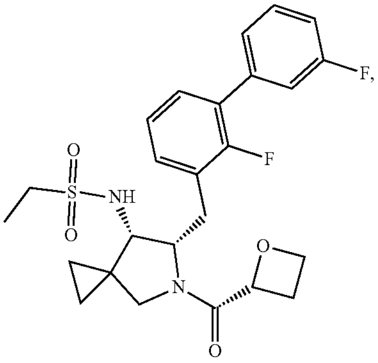
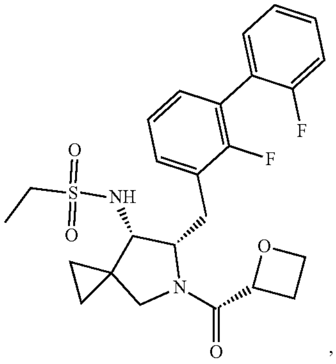
,
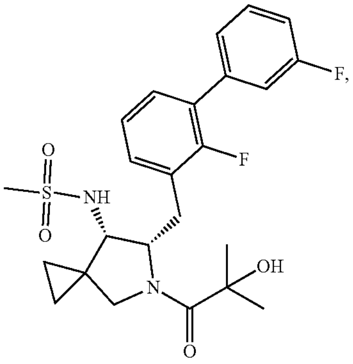
-continued
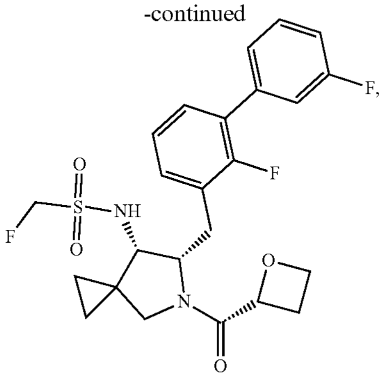
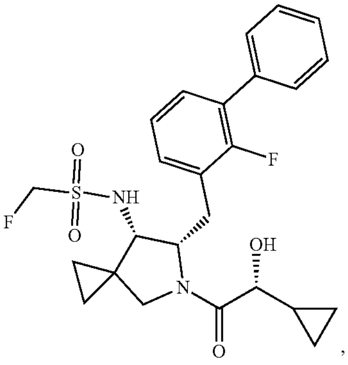
,
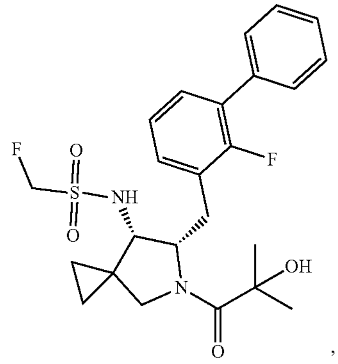
,
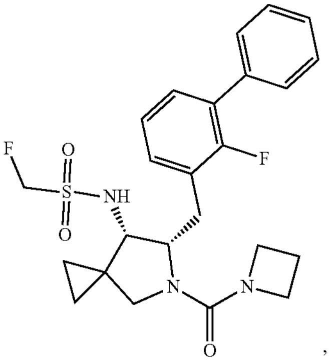
, -continued
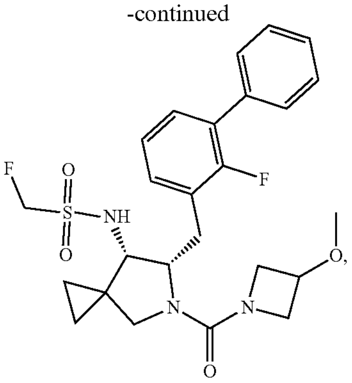
,
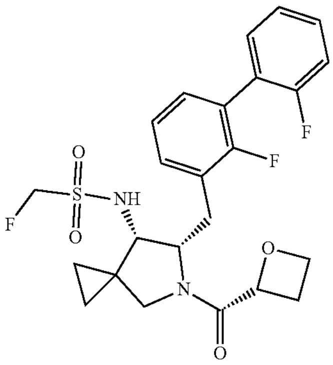
,
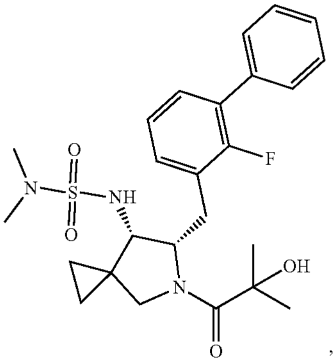
,
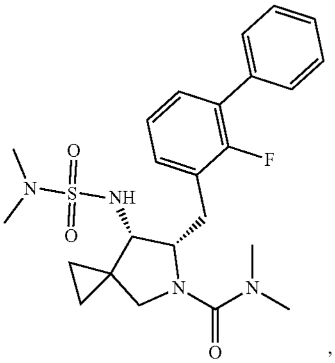
,
-continued
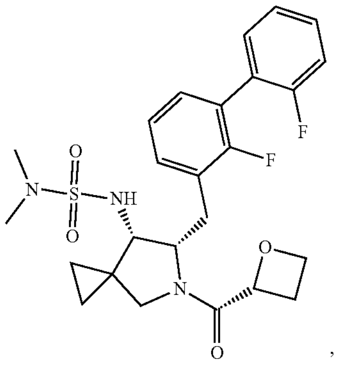
,
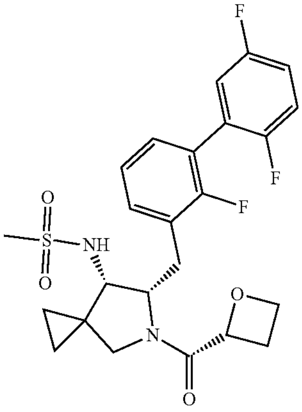
,
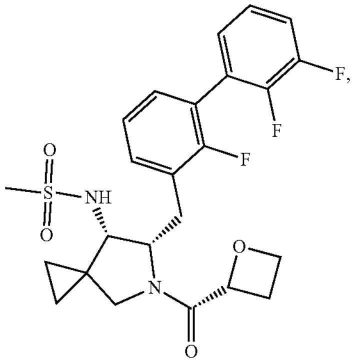
,
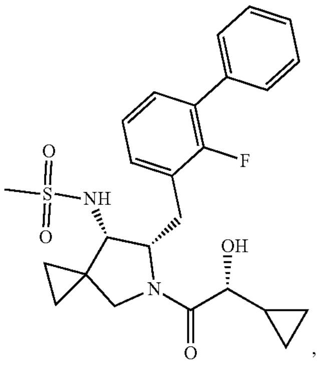
, -continued
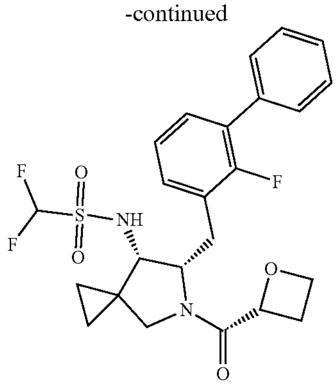
,
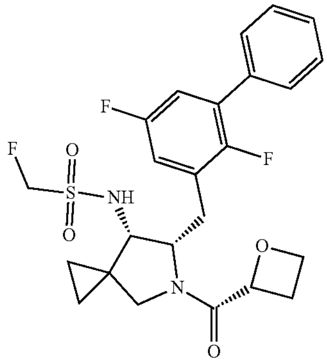
,
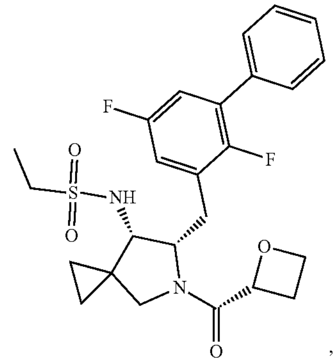
,
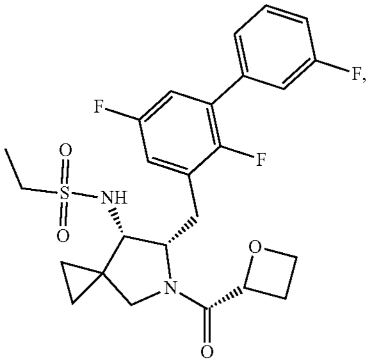
-continued
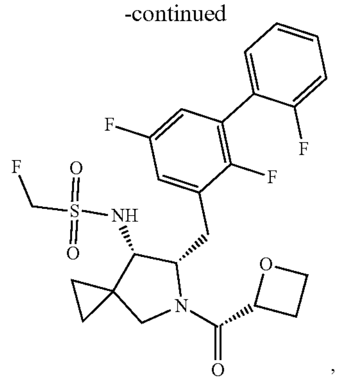
,
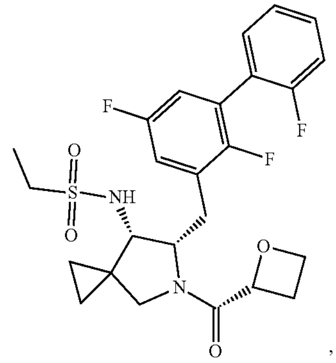
,
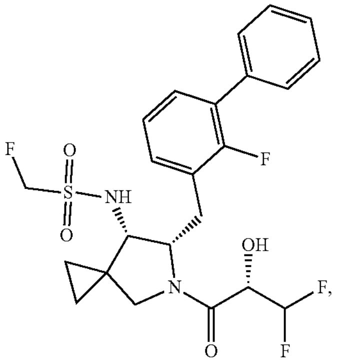 [SMILES: O=C([C@H](O)CF)N1CC2(CC2)[C@H](NS(=O)(=O)CF)[C@@H]1Cc1cccc(-c2ccccc2)c1F]
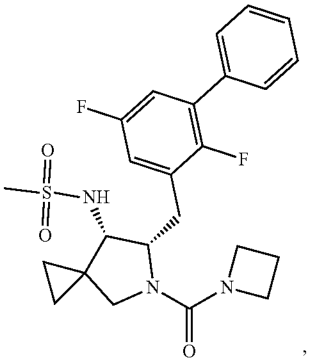
, -continued
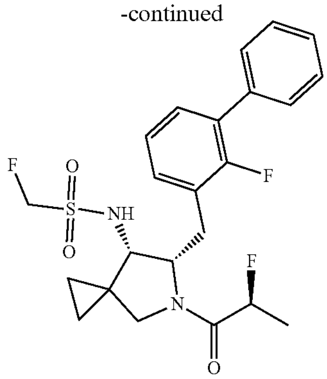
,
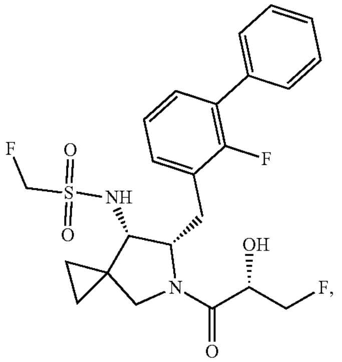
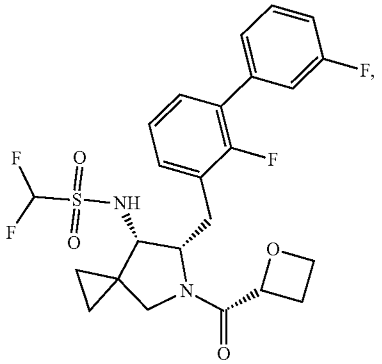
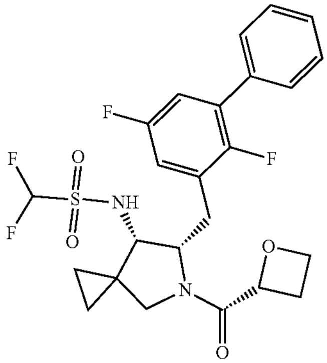
,
-continued
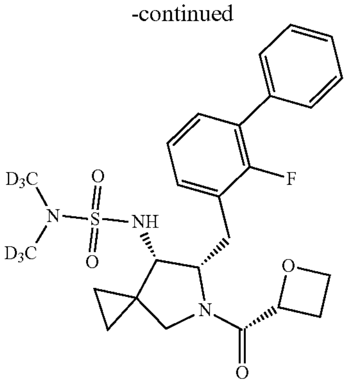
,
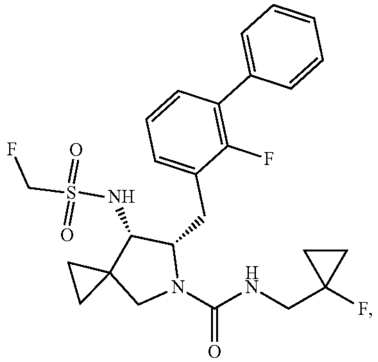
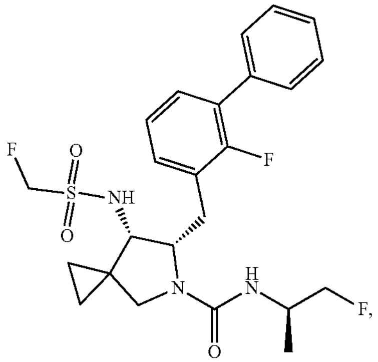
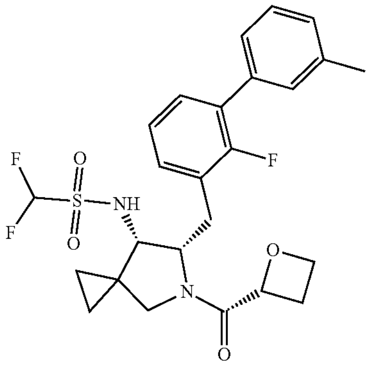
, -continued
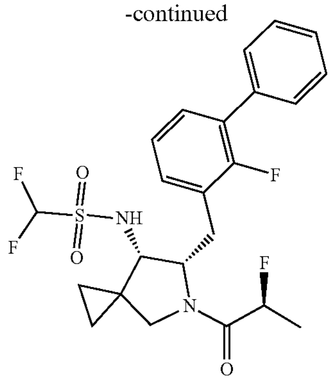
,
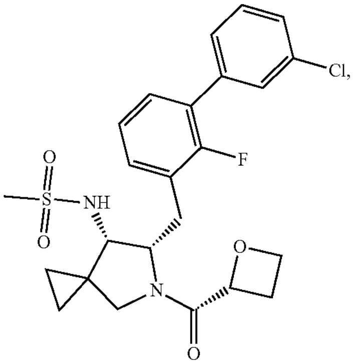
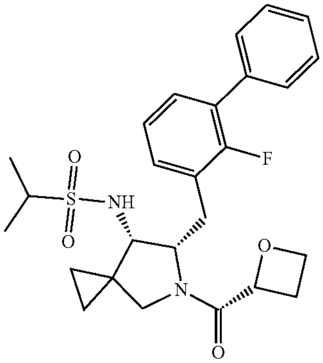
,
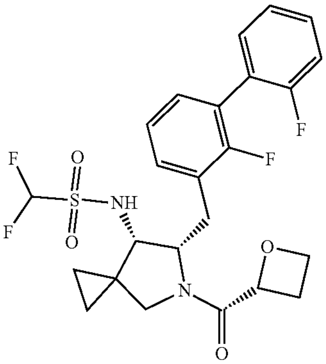
,
-continued
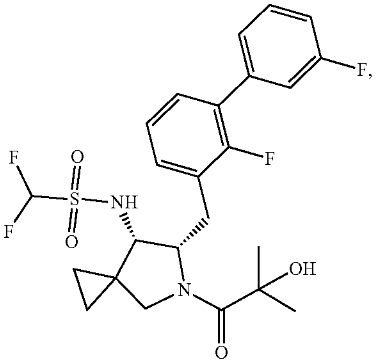
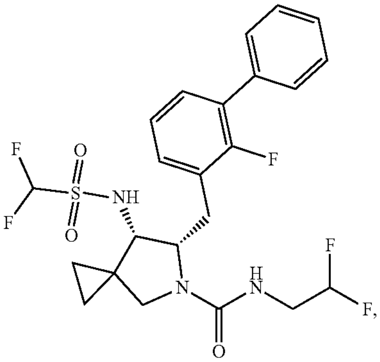
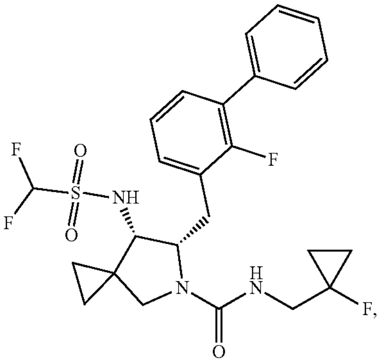
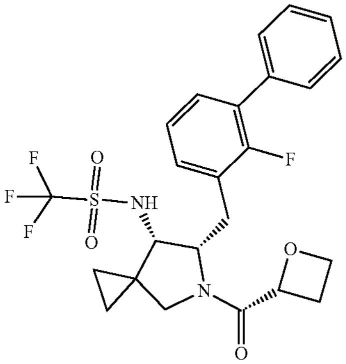
, -continued
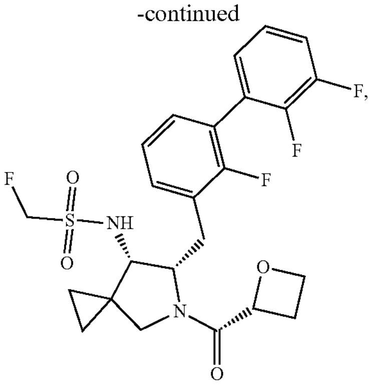
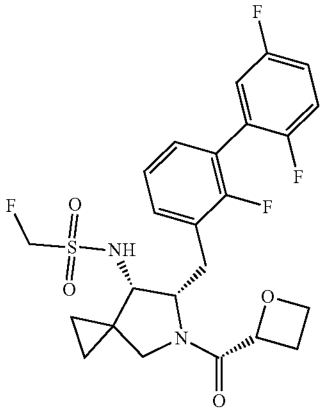
,
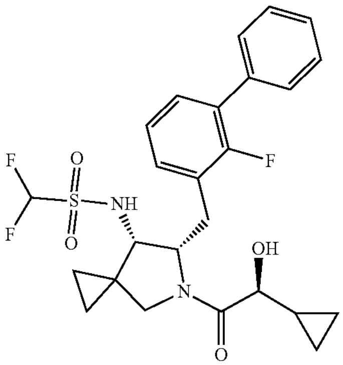
,
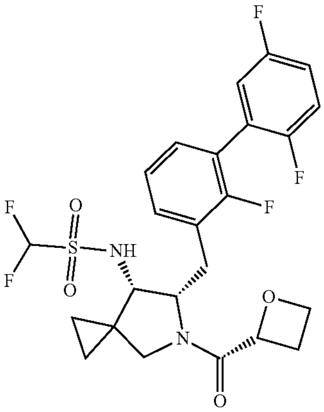
,
-continued
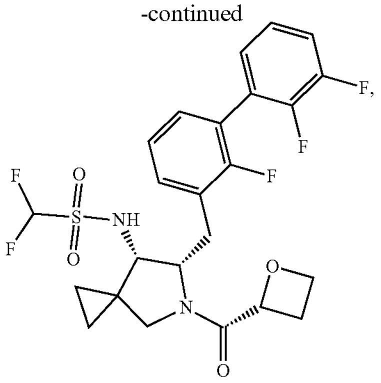
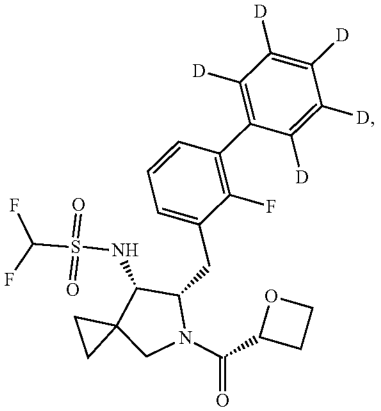
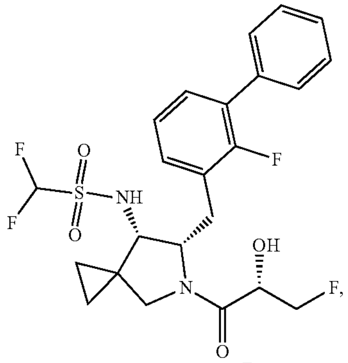
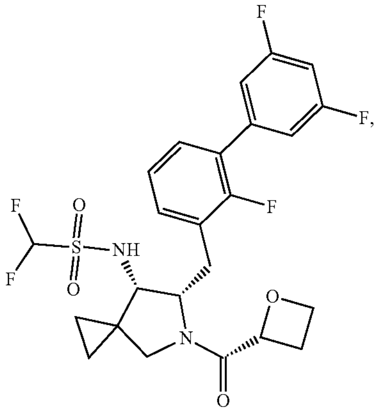

-continued
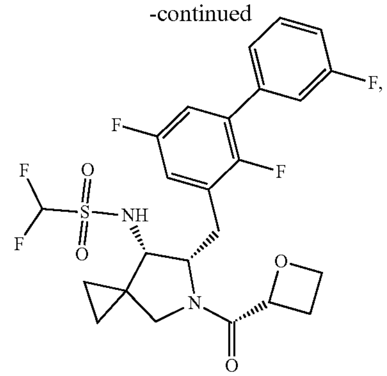
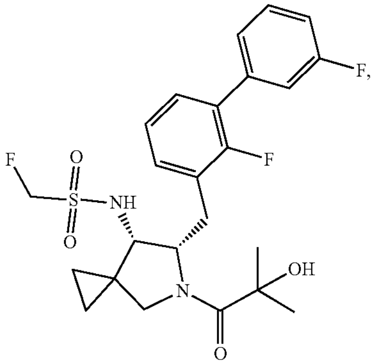
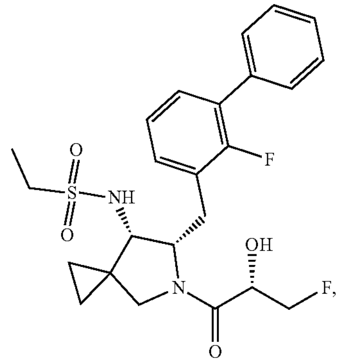
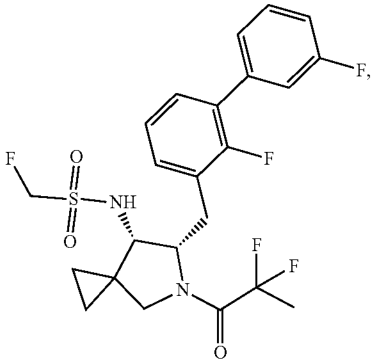
-continued
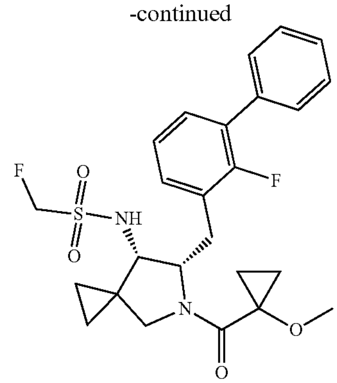
,
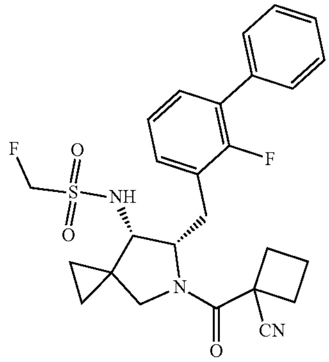
,
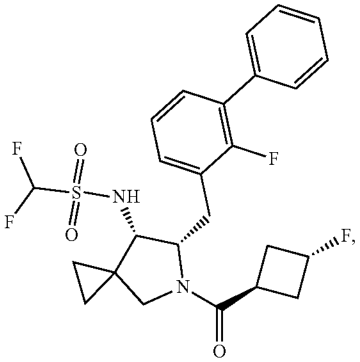
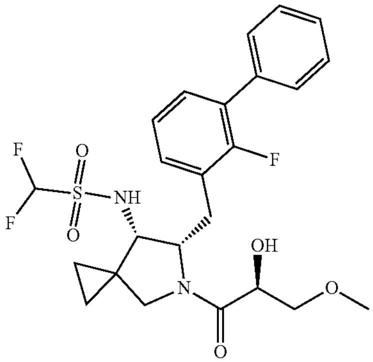
, -continued
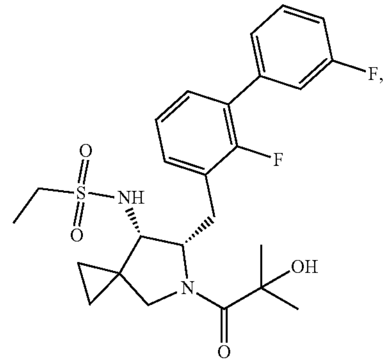
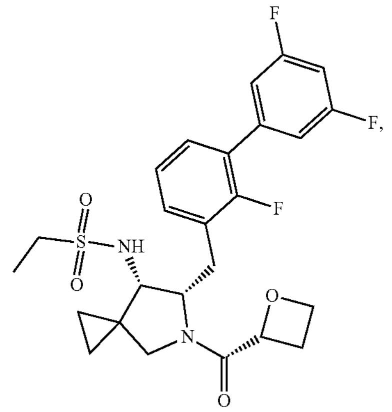
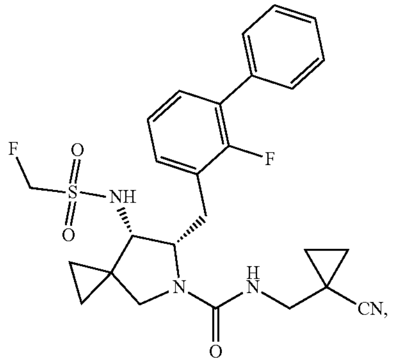
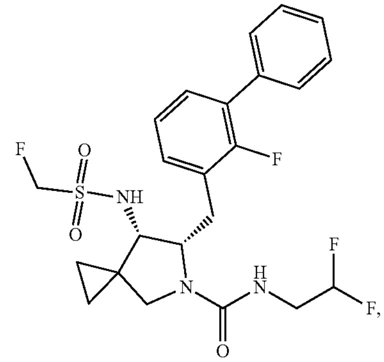
-continued
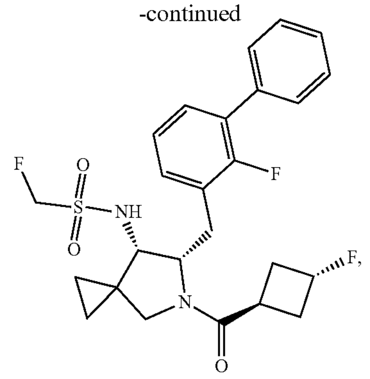
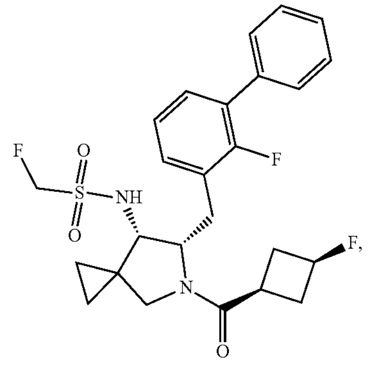
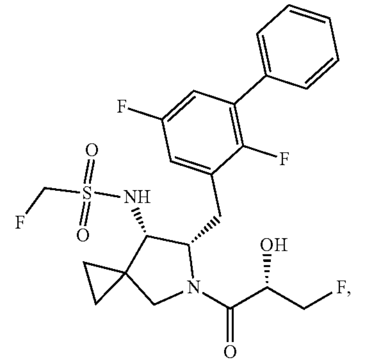
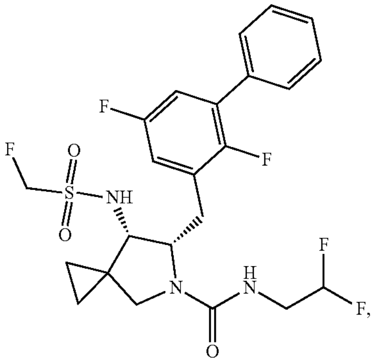

-continued
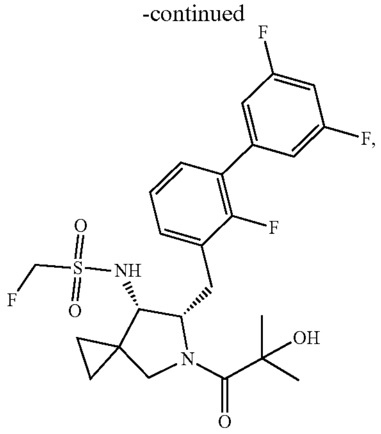
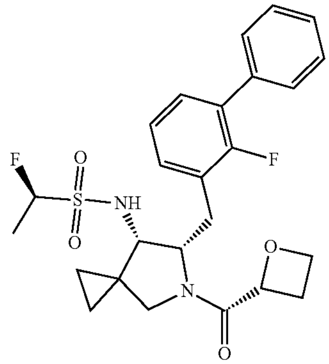
,
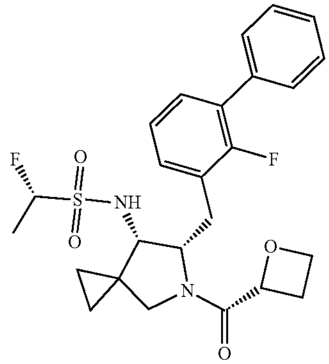
,
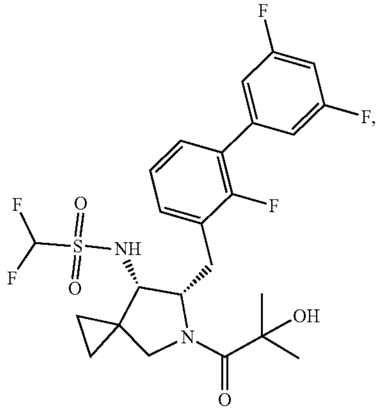
-continued
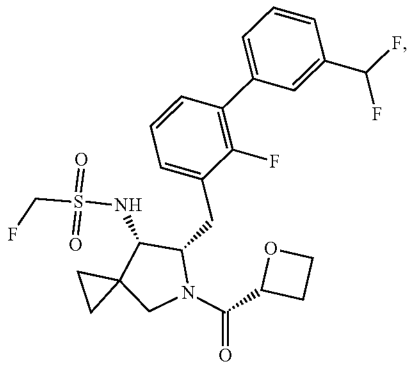
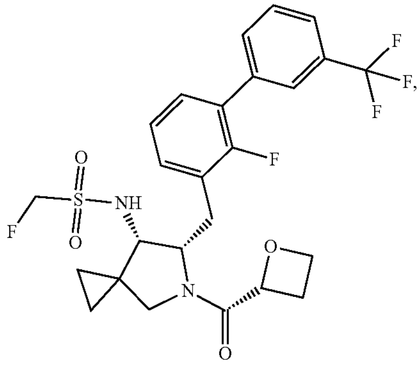
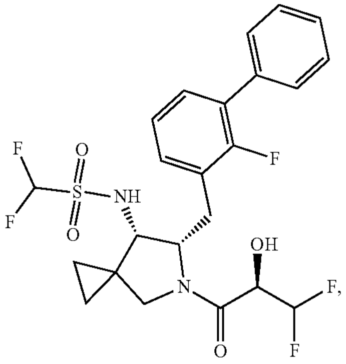
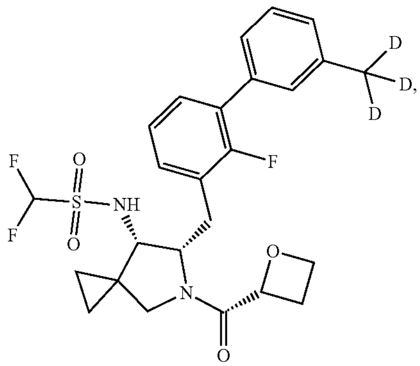

-continued
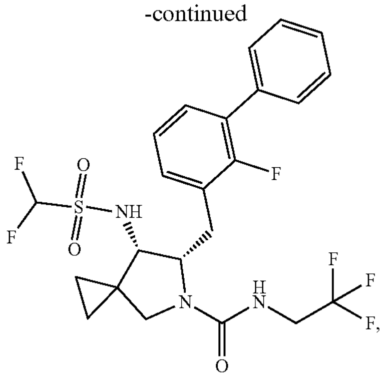
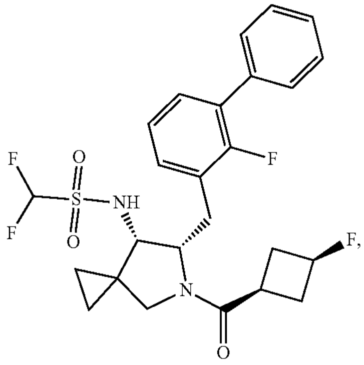
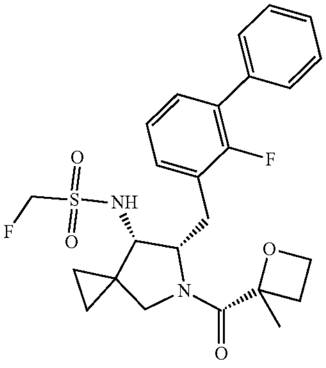
,
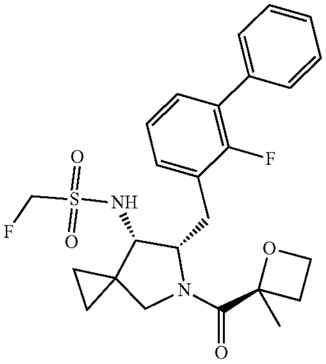
,
-continued
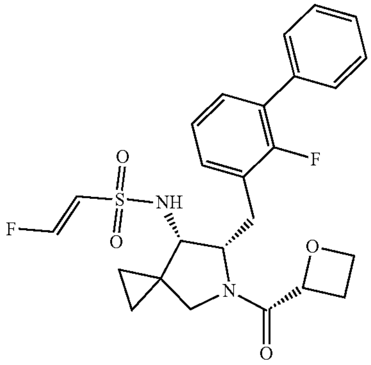
,
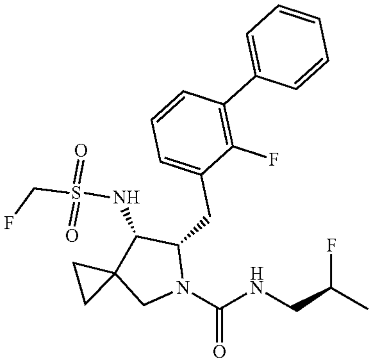
,
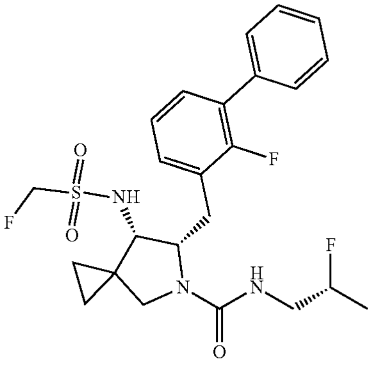
,
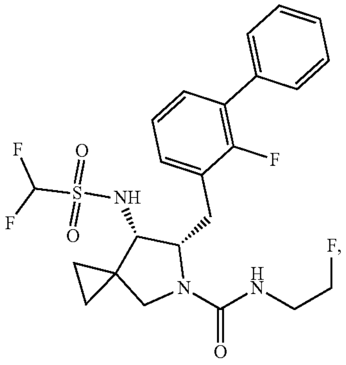

-continued
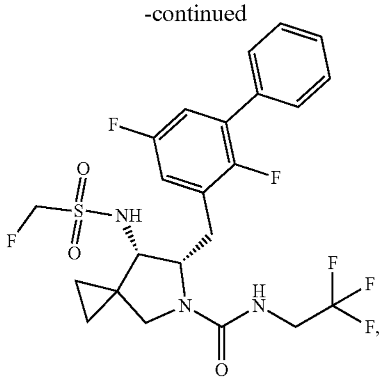
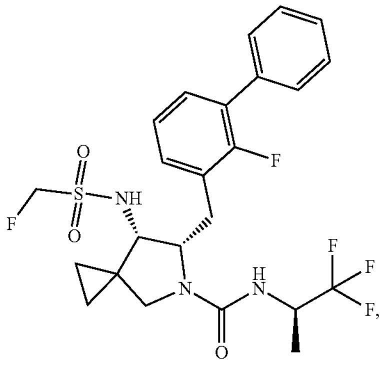
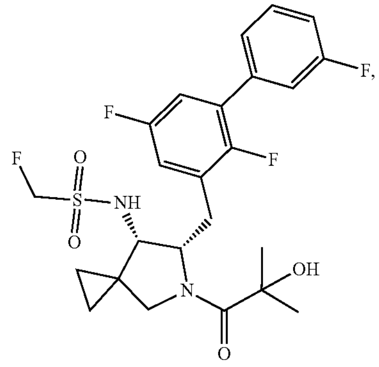
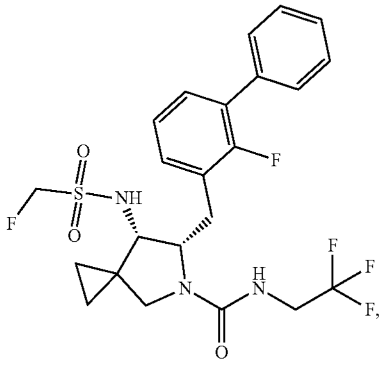
-continued
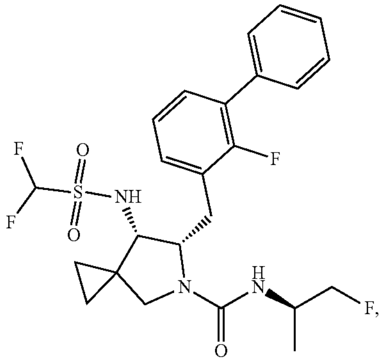
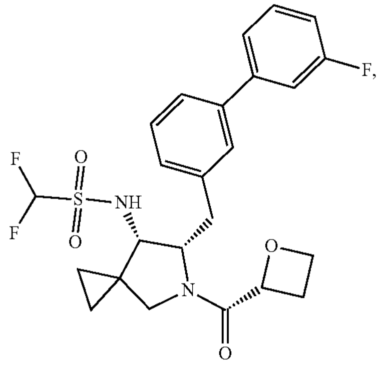
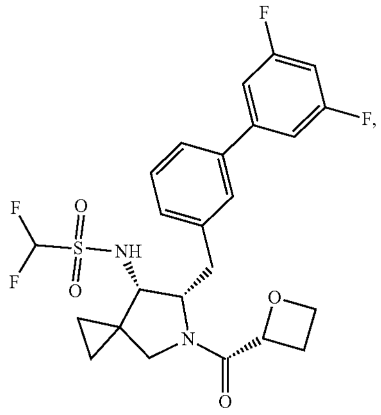
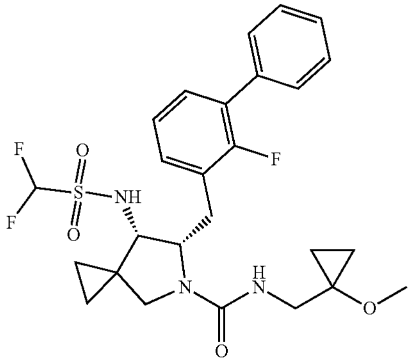
, -continued
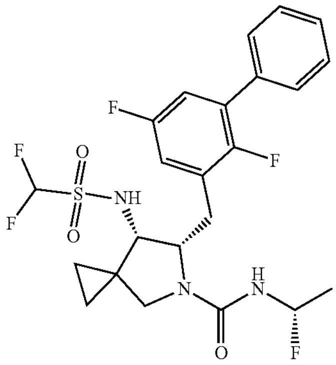
,
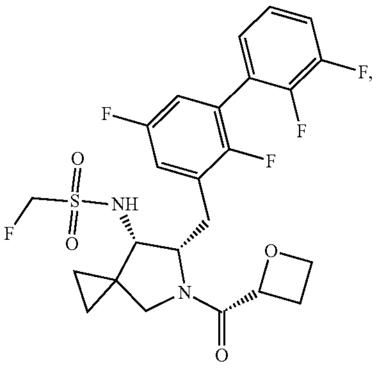
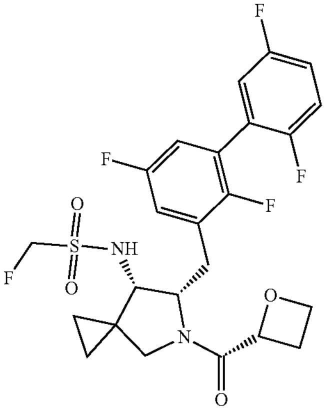
,
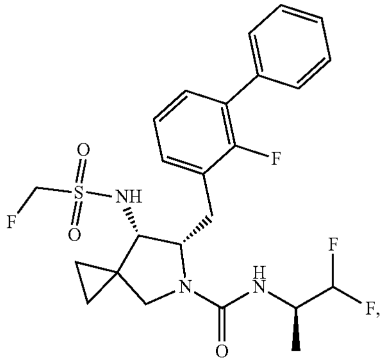
-continued
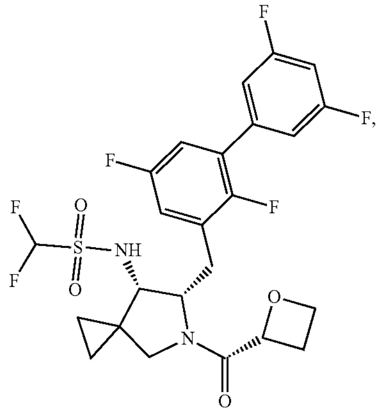
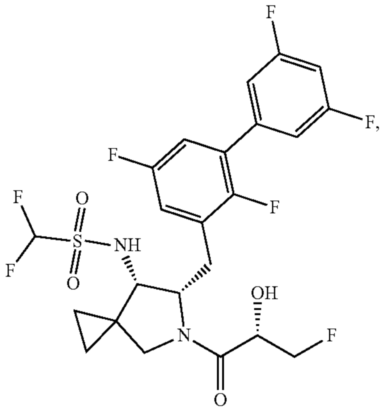
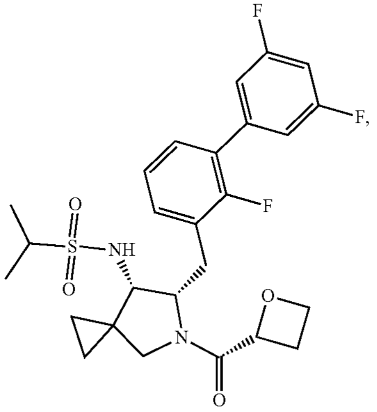
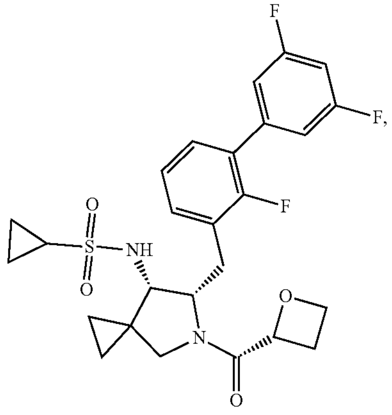

-continued
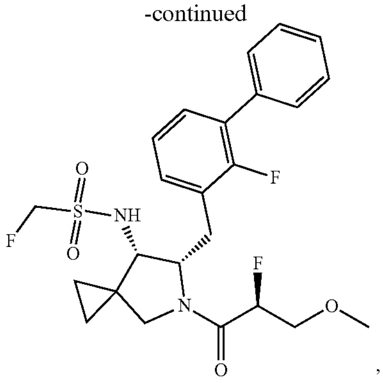
,
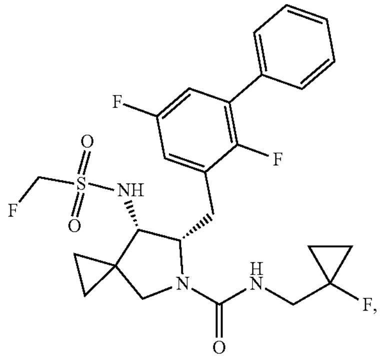
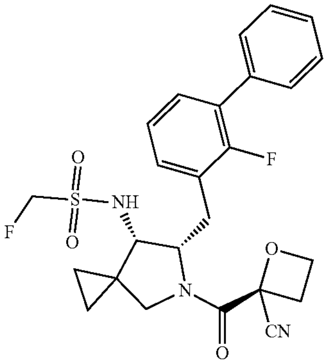
,
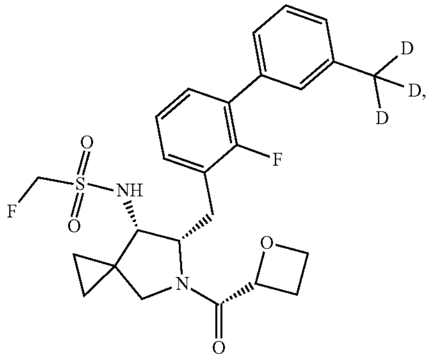
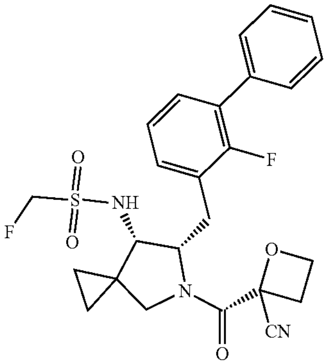
,
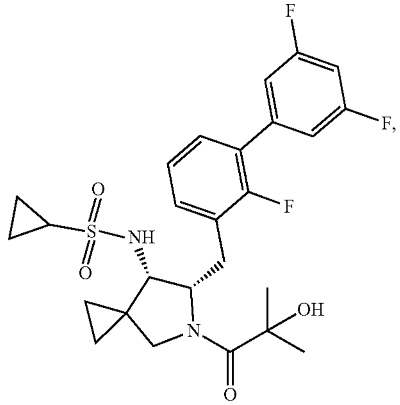
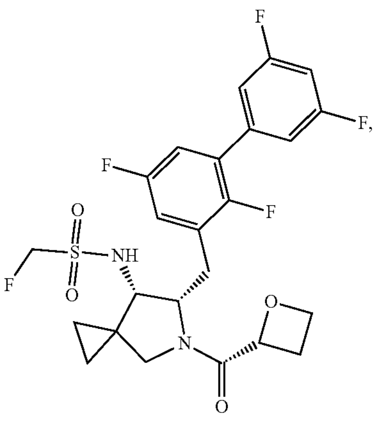
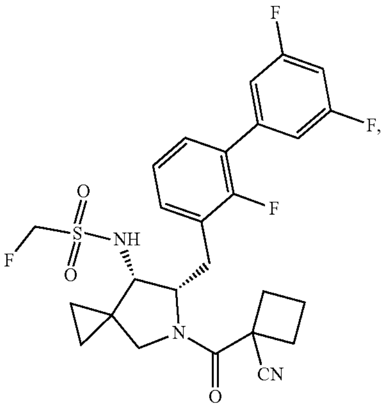

-continued
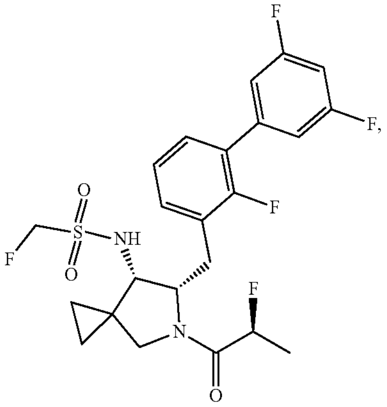
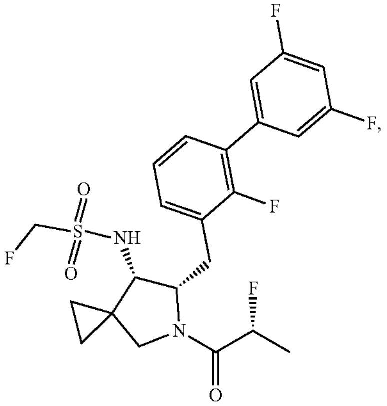
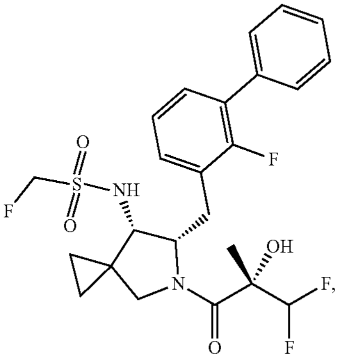
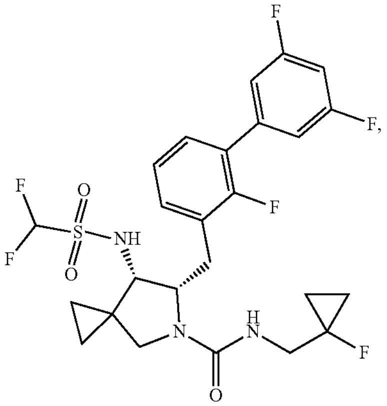
-continued
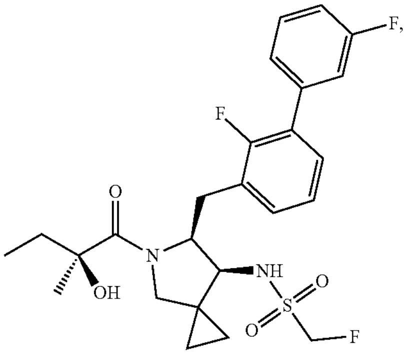
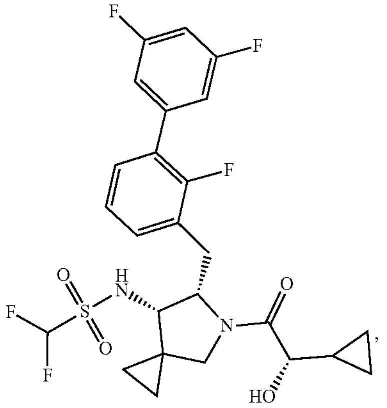
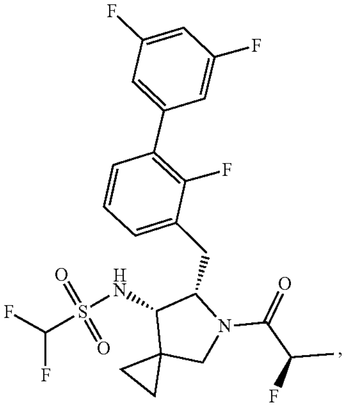
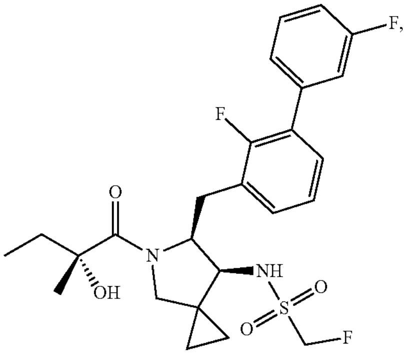

-continued
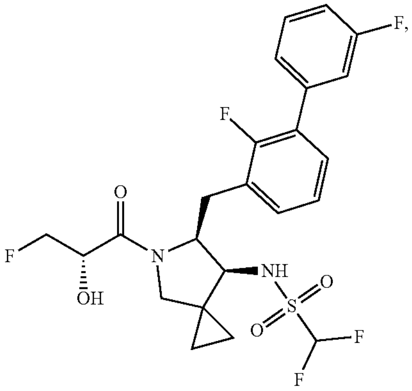
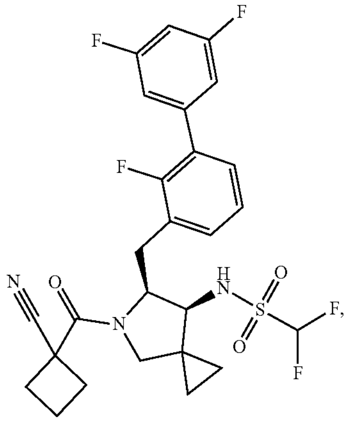
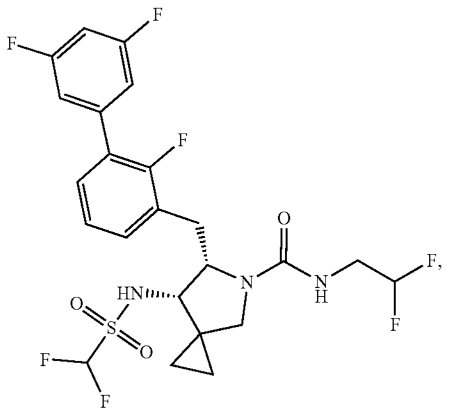
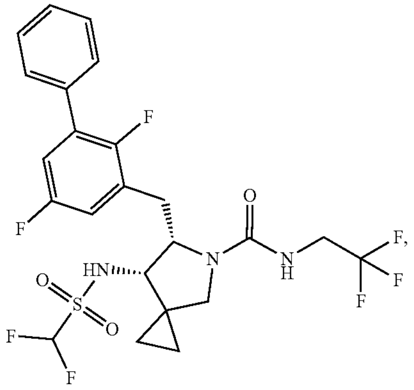
-continued
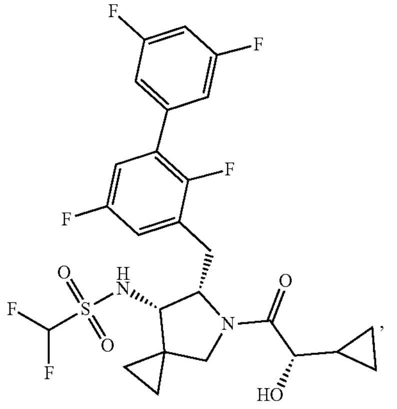
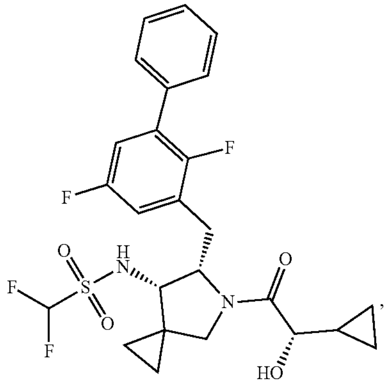
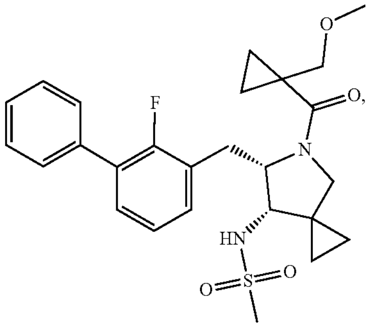
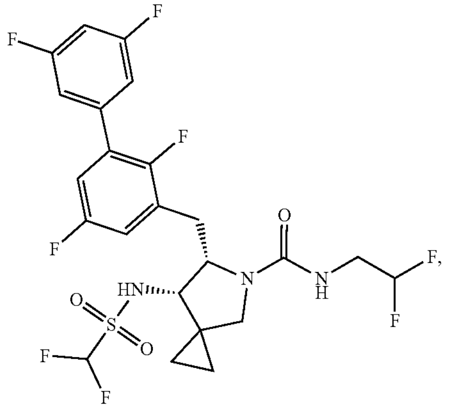

-continued
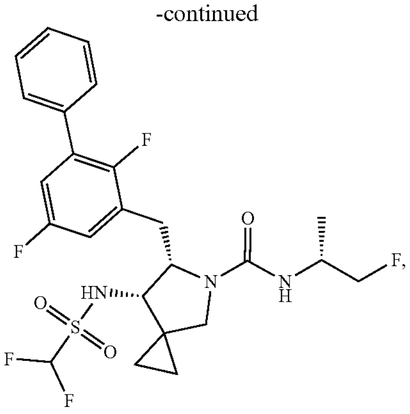
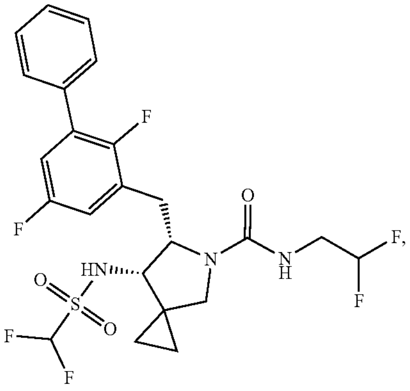
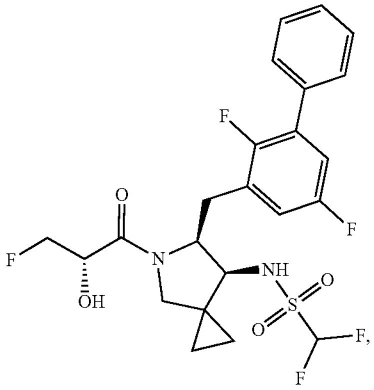
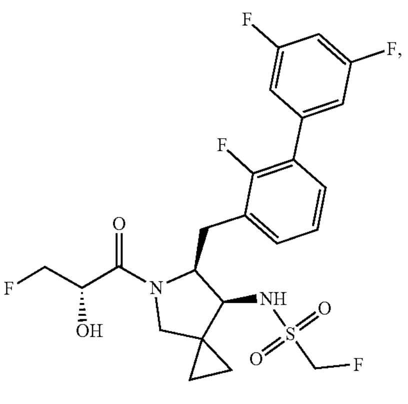
-continued
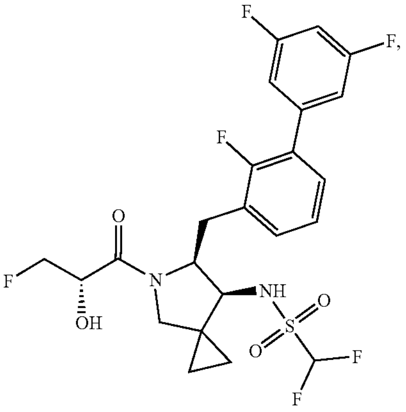
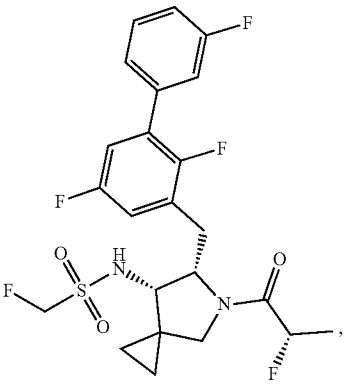
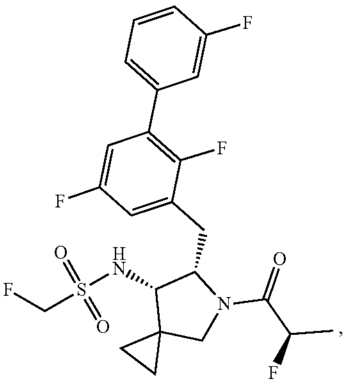
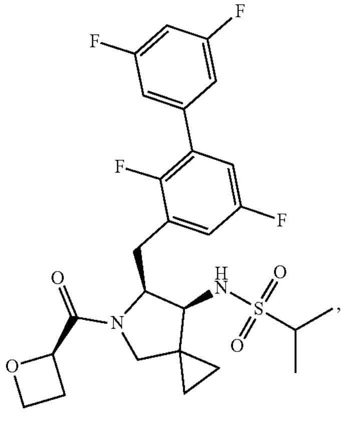

-continued
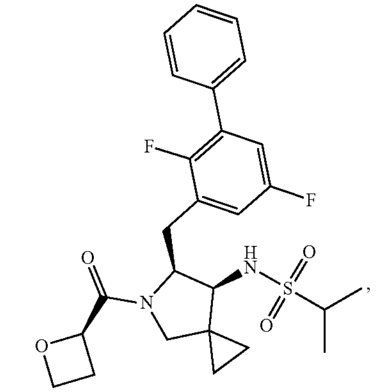
,
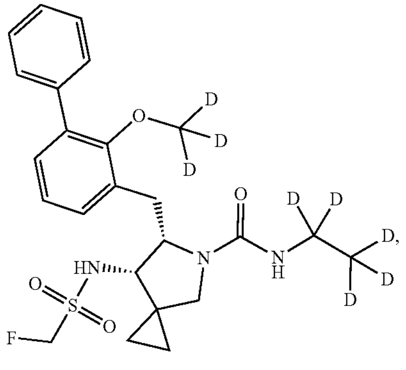
,
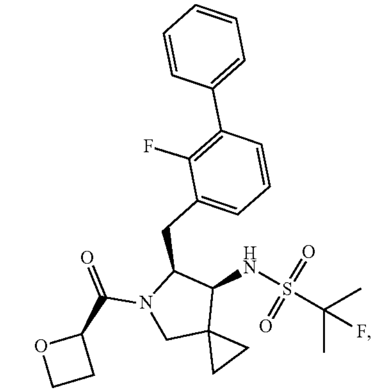
,
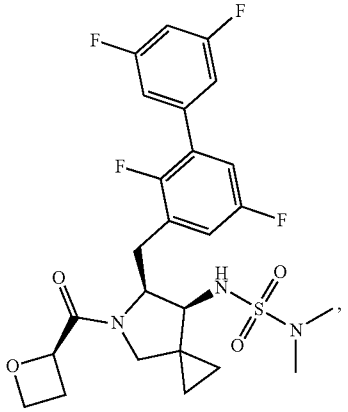
,
-continued
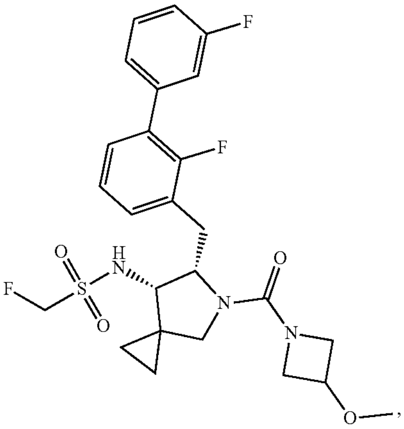
,
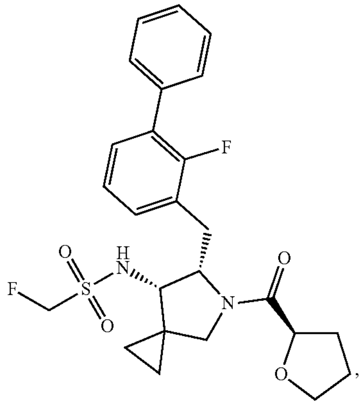
,
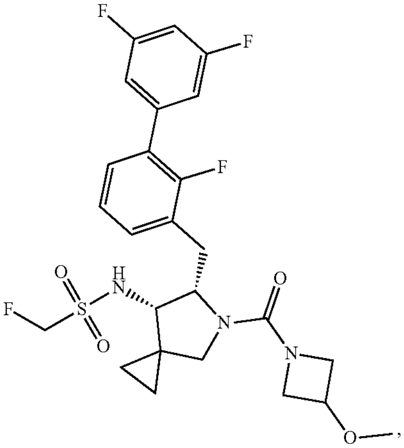
,
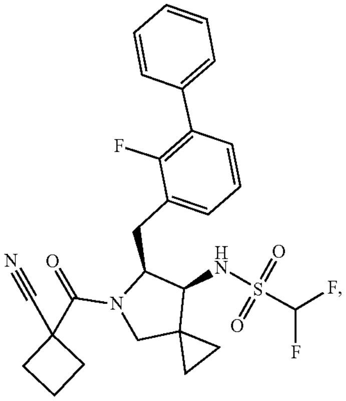
, -continued
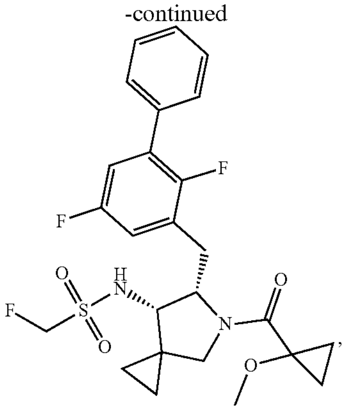
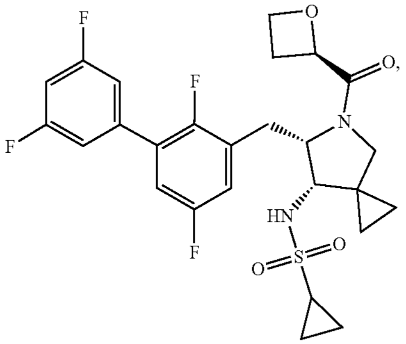
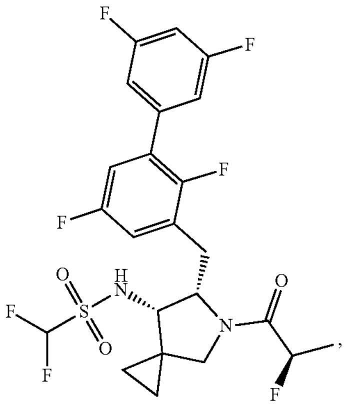
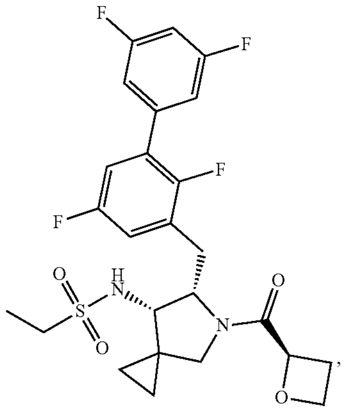
-continued
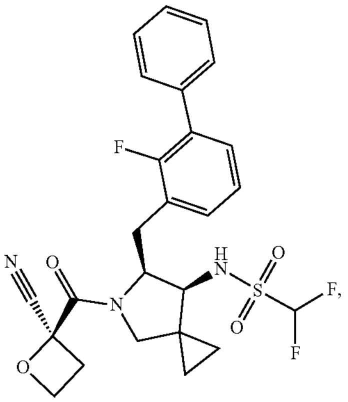 [SMILES: N#C[C@]1(C(=O)N2CC3(CC3)[C@H](NS(=O)(=O)C(F)F)[C@@H]2Cc2cccc(-c3ccccc3)c2F)CCO1]
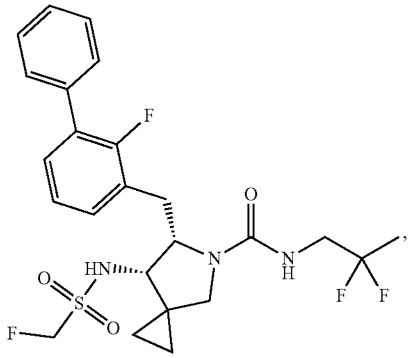
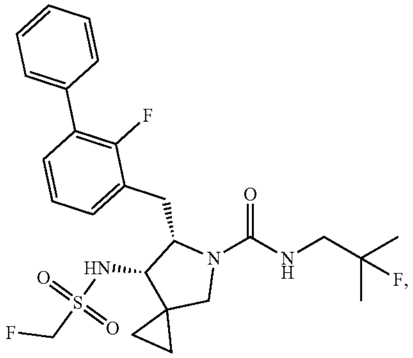
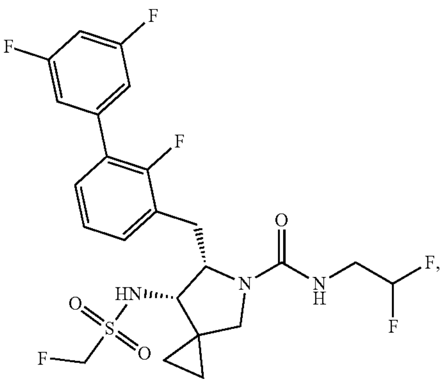

-continued
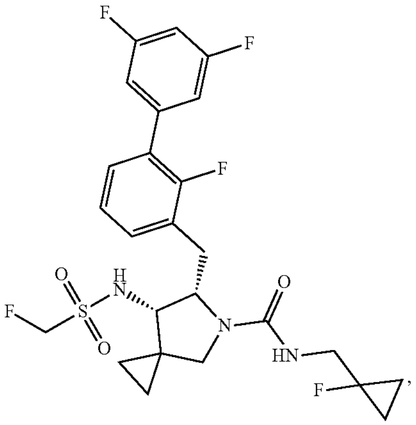
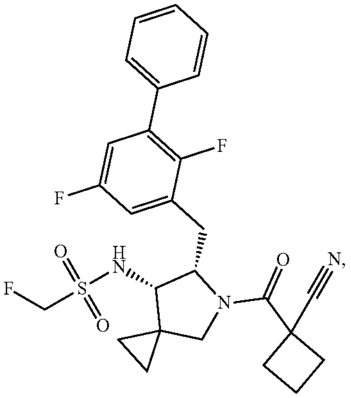
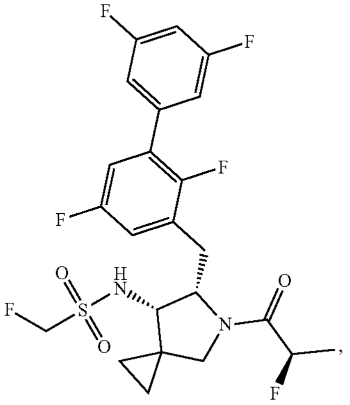
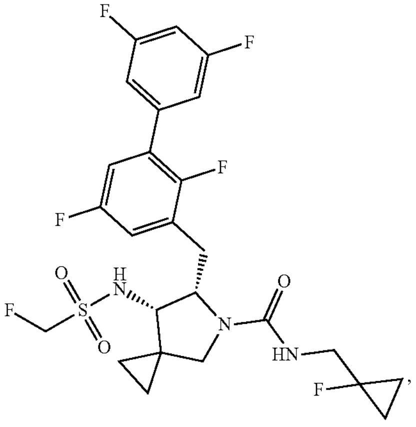
-continued
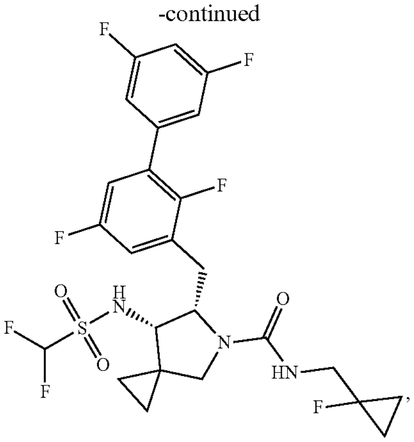
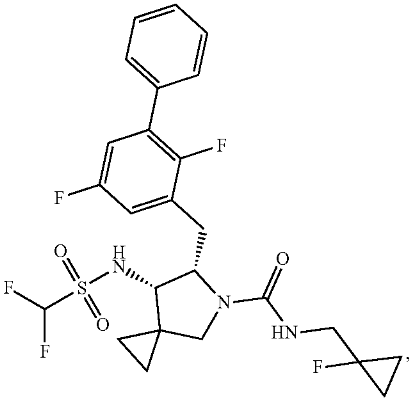
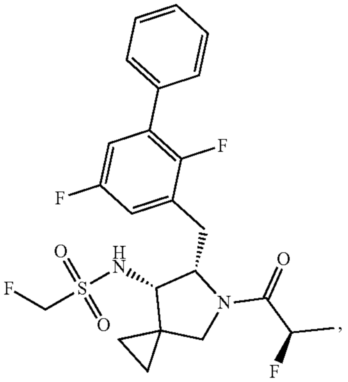
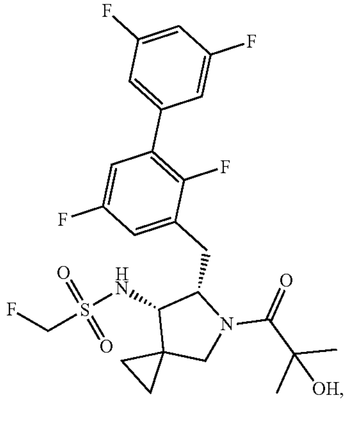
and -continued

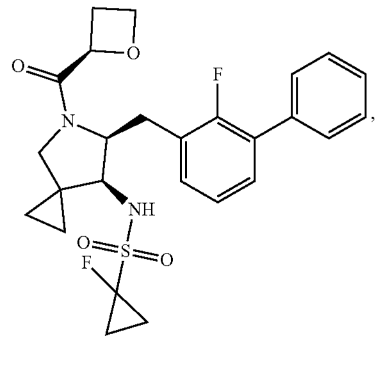

or a pharmaceutically acceptable salt of any one thereof.

16. The compound of claim 1, wherein the compound is selected from:

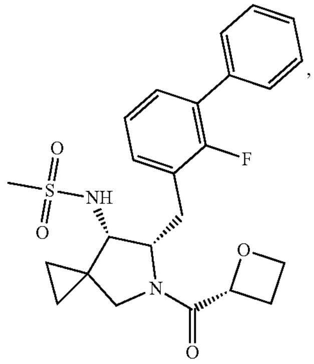

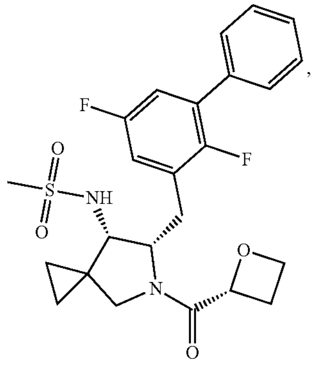

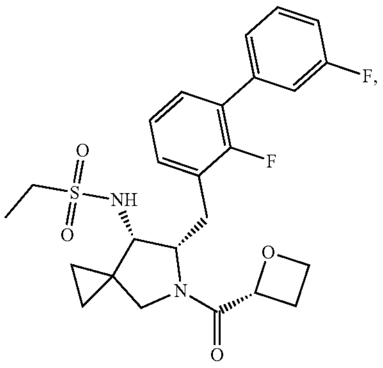

-continued

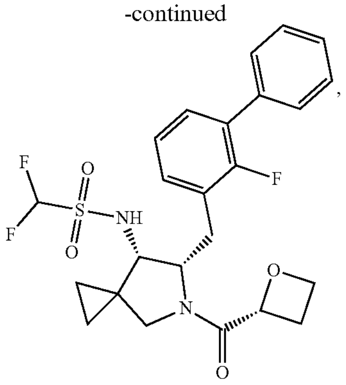

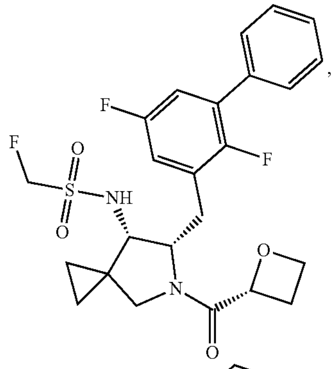

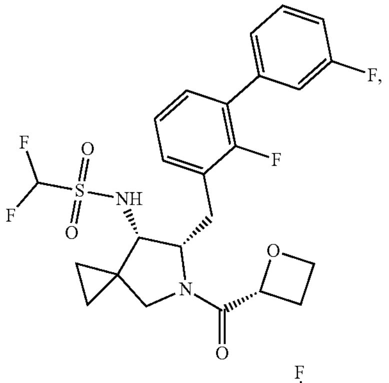

and

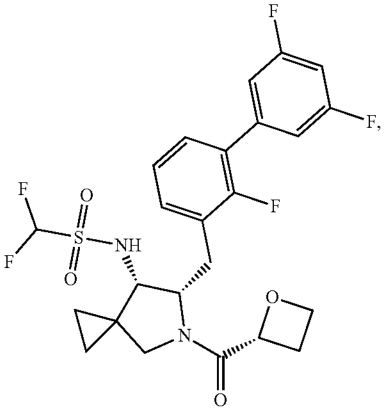

or a pharmaceutically acceptable salt of any one thereof.

17. A pharmaceutical composition comprising the compound of claim 1 or a pharmaceutically acceptable salt thereof, and a pharmaceutically acceptable diluent or carrier.

18. A method of treating a disease or disorder in a subject in need thereof, comprising administering to the subject a therapeutically effective amount of the compound of claim 1, or a pharmaceutically acceptable salt thereof, wherein the disease or disorder is narcolepsy, a hypersomnia disorder, a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or facilitating emergence from anesthesia.

19. The method, of claim 18, wherein the disease or disorder is narcolepsy, idiopathic hypersomnia, or sleep apnea.

20. A method of treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of the compound of claim 1, or a pharmaceutically acceptable salt thereof.

* * * * *